United States Patent
Tozawa et al.

(10) Patent No.: US 8,026,370 B2
(45) Date of Patent: Sep. 27, 2011

(54) CARBOXYLIC ACID DERIVATIVE CONTAINING THIAZOLE RING AND PHARMACEUTICAL USE THEREOF

(75) Inventors: Takashi Tozawa, Tokyo (JP); Osamu Tsuruta, Tokyo (JP); Hiroshi Kitajima, Tokyo (JP); Yoshiyuki Aoki, Tokyo (JP); Naoko Ando, Tokyo (JP); Hiroki Tamakawa, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 785 days.

(21) Appl. No.: 11/667,006

(22) PCT Filed: Nov. 4, 2005

(86) PCT No.: PCT/JP2005/020262
§ 371 (c)(1),
(2), (4) Date: Nov. 15, 2007

(87) PCT Pub. No.: WO2006/049232
PCT Pub. Date: May 11, 2006

(65) Prior Publication Data
US 2008/0167307 A1     Jul. 10, 2008

(30) Foreign Application Priority Data

Nov. 4, 2004 (JP) ................................. 2004-321347

(51) Int. Cl.
- A61K 31/426 (2006.01)
- A61K 31/427 (2006.01)
- C07D 277/36 (2006.01)
- C07D 417/12 (2006.01)

(52) U.S. Cl. ........ 548/187; 544/133; 544/238; 544/331; 544/405; 546/269.7; 514/236.8; 514/252.01; 514/255.05; 514/275; 514/342; 514/369

(58) Field of Classification Search .................... 548/187
See application file for complete search history.

(56) References Cited

U.S. PATENT DOCUMENTS

| | | | | |
|---|---|---|---|---|
| 4,762,848 A | * | 8/1988 | Scheunemann et al. | ...... 514/369 |
| 5,185,354 A | * | 2/1993 | Natsume et al. | ............. 514/369 |

FOREIGN PATENT DOCUMENTS

| | | |
|---|---|---|
| WO | 97 20829 | 6/1997 |
| WO | WO 98/27074 | 6/1998 |
| WO | WO-98/27075 A1 * | 6/1998 |
| WO | 99 18066 | 4/1999 |
| WO | 02 076959 | 10/2002 |
| WO | 02 096880 | 12/2002 |
| WO | 2005 077962 | 8/2005 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Adams, Mayo Clinic Proceedings, Jan. 2009, 84(1), pp. 43-51.*
K. Fleischmann, et al., "Immunomodulation by the New Synthetic Thiazole Derivative Tiprotimod", Arzneimittel-Forschung, vol. 39, No. 7, pp. 743-746, 1989.
G. Swain, "Thiazole Analogues of Dethiobiotin", Journal of the Chemical Society, pp. 2898-2901, 1949.
Ellen Aasum, et al., "Cardiac function and metabolism in Type 2 diabetic mice after treatment with BM 17.0744, a novel PPAR-αactivator", Am J Physiol Heart Circ Physiol, vol. 283, May 9, 2002 pp. H949-H957.
Peter J. Brown, et al., "A Ureido Thioisobutyric Acid (GW9578) Is a subtype-Selective PPARαAgonist with Potent Lipid-Lowering Activity", J. Med. Chem., vol. 42, pp. 3785-3788 , 1999.
Yanping Xu, et al., "Design and Synthesis of a Potent and Selective Triazolone-Based Peroxisome Proliferator-Activated Receptor α Agonist", J. Med. Chem., vol. 46, 2003, pp. 5121-5124.
Peter J. Brown, et al., "Identification of a Subtype Selective Human PPARα Agonist Through Parallel-Array Synthesis", Biorganic & Medicinal Chemistry Letters, no. 11, 2001, pp. 1225-1227.
Hiroyuki Miyachi, et al., "Enantio-Dependent Binding and Transactivation of Optically Active Phenylpropanoic Acid Derivatives at Human Peroxisome Proliferator-Activated Receptor Alpha", Biorganic & Medicinal Chemistry Letters, No. 12, 2002, pp. 333-335.

* cited by examiner

Primary Examiner — Laura L. Stockton
(74) Attorney, Agent, or Firm — Oblon, Spivak, McClelland, Maier & Neustadt, L.L.P.

(57) ABSTRACT

According to the present invention, a compound represented by the following formula (I) having a superior PPAR$_\alpha$ agonist action and concurrently showing a hypolipidemic action can be provided, and further, a compound useful as a synthetic intermediate for the compound can be provided.

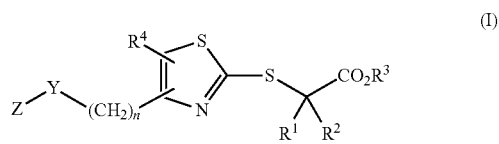

(I)

25 Claims, No Drawings

CARBOXYLIC ACID DERIVATIVE CONTAINING THIAZOLE RING AND PHARMACEUTICAL USE THEREOF

The present application is a National Stage (371) of PCT/JP05/20262, filed on Nov. 4, 2005, which claims priority to JP 2004-321347, filed on Nov. 4, 2004.

TECHNICAL FIELD

The present invention relates to a novel carboxylic acid derivative containing a thiazole ring and a pharmaceutical agent containing the derivative as an active ingredient.

BACKGROUND ART

Peroxisome proliferator-activated receptor (PPAR) is a nuclear receptor cloned in 1990 as a receptor responsive to peroxisome proliferator, forms a heterodimer with other nuclear receptor, retinoid X receptor (RXR), and activates various target genes as a transcription factor. PPAR comprises three kinds of subtypes (PPAR$_\alpha$, $\beta(\delta)$, $\gamma$), and it has been clarified that fibrate, which is a therapeutic drug for hyperlipidemia, acts as a ligand for PPAR$_\alpha$, and a thiazolidine derivative, which is an insulin sensitizer, acts as a ligand for PPAR$_\gamma$.

Fibrate is a pharmaceutical agent widely used as a therapeutic drug for hyperlipidemia, and clofibrate, aluminum clofibrate, simfibrate, clinofibrate and the like have been heretofore used. At present, bezafibrate (Bezatol SR (registered trademark), Bezalip (registered trademark)) and fenofibrate (lipantil (registered trademark)), which are called the second generation, have been generally used.

Fibrate is known to regulate expression of genes (acyl CoA synthase, lipoprotein lipase, fatty acid transport protein and the like) relating to the metabolism of fatty acid and apolipoprotein (AI, AII, AV, CIII) genes involved in triglyceride (TG) and cholesterol metabolism, by activation of PPAR$_\alpha$, decreases TG and LDL cholesterol and increases HDL cholesterol. Thus, fibrate is known to be highly effective as a therapeutic drug for hyperlipidemia.

However, since conventional fibrate shows a weak PPAR$_\alpha$ agonist activity (EC$_{50}$) of a $_\mu$mol/L order (not less than 30 $_\mu$mol/L), the dose needs to be as high as 200-1500 mg/day. In addition, various side effects such as digestive symptoms such as gastric distress, feeling of sickness and the like, skin symptoms such as anthema and the like, liver dysfunction and pancreatitis have been reported (foregoing from lipantil (registered trademark) package insert), and there is a room for further improvement as a pharmaceutical agent having a PPAR$_\alpha$ agonist action.

From the above, a pharmaceutical use as a compound superior in the pharmacological action based on PPAR$_\alpha$ activation (TG lowering action, LDL-C lowering action, HDL-C increasing action, anti-atherogenic action and the like) is expected by creating a compound capable of specifically activating PPAR$_\alpha$ than conventional fibrates.

Given such background, various carboxylic acid derivatives have been reported in recent years with regard to PPAR$_\alpha$ agonists. For example, patent reference 1, non-patent reference 1 and non-patent reference 2 have reported (phenylthio)acetic acid derivatives, patent reference 2 and non-patent reference 3 have reported 3-phenylpropionic acid derivatives, patent reference 3 and non-patent reference 4 have reported phenoxyacetic acid derivatives, patent reference 4 has reported phenoxyacetic acid derivatives, patent reference 5 and non-patent reference 5 have reported 2,2-dichloroalkane carboxylic acid derivatives, patent reference 6 has reported 1,3-dioxane-2-carboxylic acid derivatives, and patent reference 7 has reported phenoxyacetic acid derivatives, but no description of (1,3-thiazol-2-yl)thioacetic acid derivatives like the compound of the present invention is provided.

patent reference 1: WO00/23407
patent reference 2: WO00/75103
patent reference 3: WO02/38553
patent reference 4: WO02/28821
patent reference 5: WO96/15784
patent reference 6: WO01/90087
patent reference 7: WO02/096894
non-patent reference 1: J. Med. Chem., 42, 3785 (1999)
non-patent reference 2: Bioorg. Med. Chem. Lett., 11, 1225 (2001)
non-patent reference 3: Bioorg. Med. Chem. Lett., 12, 333 (2002)
non-patent reference 4: J. Med. Chem., 46, 5121 (2003)
non-patent reference 5: Am. J. Physiol., 283 (3, Pt. 2), H949 (2002)

DISCLOSURE OF THE INVENTION

Problems to be Solved by the Invention

It is an object of the present invention to provide a compound having a PPAR$_\alpha$ agonist action, which is useful as an agent for the prophylaxis and/or treatment of hyperlipidemia, and a compound useful as an intermediate therefor.

Means of Solving the Problems

In an attempt to develop a drug useful as an agent for the prophylaxis and/or treatment of hyperlipidemia, the present inventors took note of the role of PPAR$_\alpha$ relating to the lipid metabolism and conducted intensive studies. As a result, a compound represented by the following formula (I) has a superior PPAR$_\alpha$ agonist action and a lipid-lowering action, and found a compound useful as a synthetic intermediate for the compound, which resulted in the completion of the present invention.

Accordingly, the present invention provides the following.
(1) A carboxylic acid derivative containing a thiazole ring represented by a following formula (I):

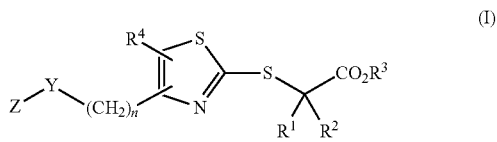

[wherein R$^1$ and R$^2$ are the same or different and each is a hydrogen atom or an alkyl group, or R$^1$ and R$^2$ are bonded to each other to form a cycloalkyl group;
R$^3$ is a hydrogen atom or an alkyl group;
R$^4$ is a hydrogen atom, an alkyl group or an aryl group;
Y is an oxygen atom, a sulfur atom, —NR$^5$—, —CONR$^5$—, —NR$^5$CO— or —NHCONR$^5$— (wherein R$^5$ is a hydrogen atom, an alkyl group, a cycloalkylalkyl group, an aryl group, an arylalkyl group, an arylalkenyl group, an aryloxyalkyl group, a heteroaryl group or a heteroarylalkyl group); and
Z is a cycloalkyl group, an aryl group, an arylalkyl group, an arylalkenyl group, an aryloxyalkyl group, a heteroaryl group or a heteroarylalkyl group, wherein, in the aforementioned groups, an alkyl group, a cycloalkyl group, a cycloalkylalkyl group, an aryl group, an arylalkyl group, an arylalkenyl group, an aryloxyalkyl group, a heteroaryl group and a heteroarylalkyl group each optionally have substituent], or a pharmaceutically acceptable salt thereof or a hydrate thereof or a solvate thereof.

(2) A carboxylic acid derivative containing the thiazole ring of the above-mentioned 1, which is represented by the following formula (I'):

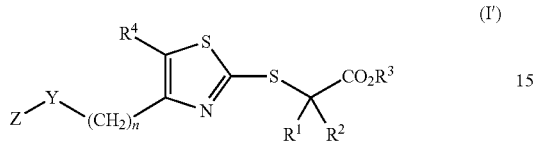

(I')

[wherein $R^1$, $R^2$, $R^3$, $R^4$, n, Y and Z are as defined above], or a pharmaceutically acceptable salt thereof or a hydrate thereof or a solvate thereof.

(3) A carboxylic acid derivative containing the thiazole ring of the above-mentioned 1 or 2, wherein, in the formula (I), n is an integer of 1 to 3, Y is an oxygen atom, a sulfur atom, —$NR^6$—, —$CONR^6$—, —$NR^6CO$— or —$NHCONR^6$— (wherein $R^6$ is a hydrogen atom, an alkyl group, a cycloalkylalkyl group, an arylalkyl group, an arylalkenyl group, an aryloxyalkyl group or a heteroarylalkyl group, wherein, in the aforementioned groups, an alkyl group, an arylalkyl group, an arylalkenyl group, an aryloxyalkyl group and a heteroarylalkyl group each optionally have substituent), and Z is an optionally substituted cycloalkyl group, an optionally substituted aryl group, an optionally substituted arylalkyl group or an optionally substituted heteroaryl group, or a pharmaceutically acceptable salt thereof or a hydrate thereof or a solvate thereof.

(4) A carboxylic acid derivative containing the thiazole ring of any one of the above-mentioned 1 to 3, wherein, in the formula (I), Y is an oxygen atom, a sulfur atom or —$NR^7$— [wherein $R^7$ is a hydrogen atom, an alkyl group or —$CH_2$—W (wherein W is an aryl group or a heteroaryl group), wherein, in the aforementioned groups, an alkyl group, an aryl group and a heteroaryl group each optionally have substituent], and Z is represented by a substituent selected from the following formula (II):

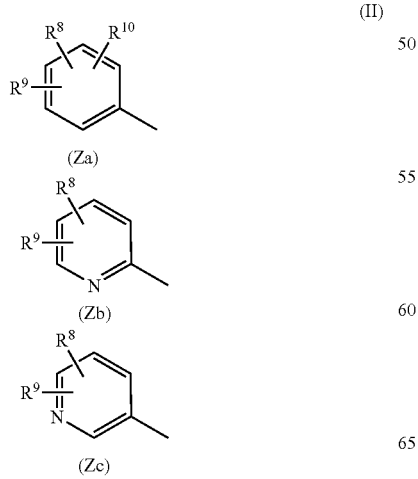

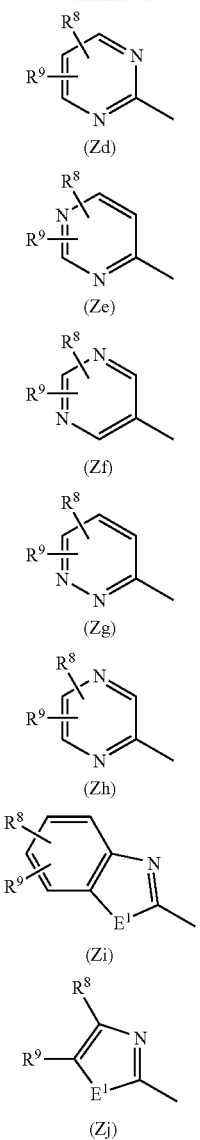

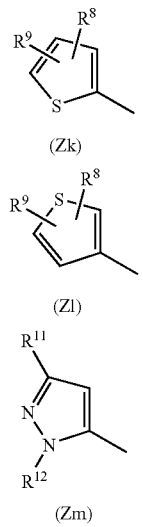

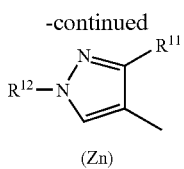

(Zn)

[wherein $R^8$, $R^9$ and $R^{10}$ are the same or different and each is a hydrogen atom, an alkyl group, an aryl group, a heteroaryl group, a halogen atom, a haloalkyl group, a haloalkyloxy group, a cyano group, a nitro group, —$NR^{13}R^{14}$, —$NR^{15}COR^{16}$, —$CONR^{17}R^{18}$ (wherein $R^{13}$, $R^{14}$, $R^{15}$, $R^{16}$, $R^{17}$ and $R^{18}$ are the same or different and each is independently a hydrogen atom, an alkyl group, a cycloalkyl group, an aryl group, an arylalkyl group, a heteroaryl group or a heteroarylalkyl group, or $R^{13}$ and $R^{14}$, and $R^{15}$ and $R^{16}$ are bonded to each other to form a heterocycle optionally having a carbon atom and a hetero atom, —$OR^{19}$, —$COR^{20}$ or —$C\equiv CR^{21}$ (wherein $R^{19}$, $R^{20}$ and $R^{21}$ are each independently a hydrogen atom, an alkyl group, a cycloalkyl group, an aryl group, an arylalkyl group, a heteroaryl group or a heteroarylalkyl group);
$R^{11}$ is a hydrogen atom, an alkyl group, a cycloalkyl group, an aryl group, a heteroaryl group, a halogen atom, a haloalkyl group, a cyano group or a nitro group;
$R^{12}$ is a hydrogen atom, an alkyl group, a cycloalkyl group, a cycloalkylalkyl group, an aryl group, an arylalkyl group, a heteroaryl group or a heteroarylalkyl group;
$E^1$ is an oxygen atom, a sulfur atom or —$NR^{22}$— (wherein $R^{22}$ is a hydrogen atom, an alkyl group, a cycloalkyl group, a cycloalkylalkyl group, an aryl group, an arylalkyl group or a heteroarylalkyl group),
wherein, in the aforementioned groups, an alkyl group, a cycloalkyl group, a cycloalkylalkyl group, an aryl group, an arylalkyl group, a heteroaryl group, a heteroarylalkyl group and a heterocycle each optionally have substituent], or a pharmaceutically acceptable salt thereof or a hydrate thereof or a solvate thereof.
(5) A carboxylic acid derivative containing the thiazole ring of any one of the above-mentioned 1 to 4, wherein, in the formula (I), Y is an oxygen atom, a sulfur atom or —$NR^{23}$— {wherein $R^{23}$ is a hydrogen atom, an optionally substituted alkyl group, or a substituent selected from the following formula (III):

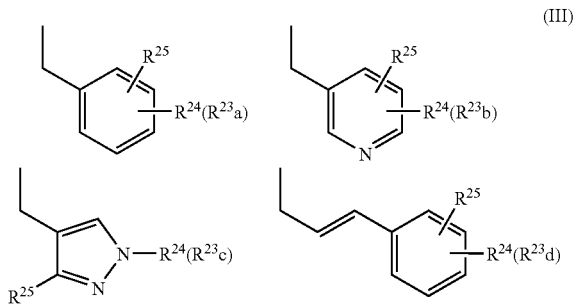

[wherein $R^{24}$ and $R^{25}$ are the same or different and each is a hydrogen atom, an alkyl group, a cycloalkyl group, an aryl group, an arylcarbonyl group, a heteroaryl group, a halogen atom, a haloalkyl group, a haloalkyloxy group, —$NR^{26}R^{27}$, —$NR^{28}COR^{29}$, —$CONR^{30}R^{31}$ (wherein $R^{26}$, $R^{27}$, $R^{28}$, $R^{30}$ and $R^{31}$ are the same or different and each is independently a hydrogen atom, an alkyl group, an aryl group or a heteroaryl group, or $R^{26}$ and $R^{27}$, and $R^{30}$ and $R^{31}$ are bonded to each other to form a heterocycle optionally having a carbon atom and a hetero atom) or —$OR^{32}$ (wherein $R^{32}$ is a hydrogen atom, an alkyl group, a cycloalkyl group, an aryl group, an arylalkyl group, a heteroaryl group or a heteroarylalkyl group), wherein, in the aforementioned groups, an alkyl group, a cycloalkyl group, an aryl group, an arylalkyl group, a heteroaryl group, a heteroarylalkyl group and a heterocycle each optionally have substituent]}, and Z is a substituent selected from the following formula (IV):

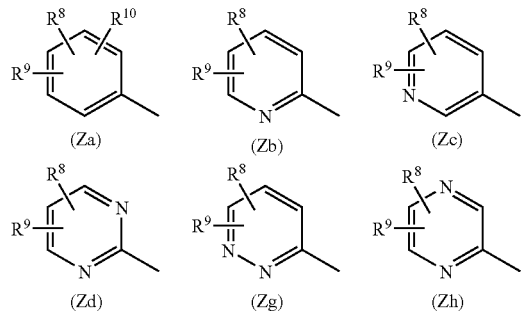

[wherein $R^8$, $R^9$ and $R^{10}$ are as defined above], or a pharmaceutically acceptable salt thereof or a hydrate thereof or a solvate thereof.
(6) A carboxylic acid derivative containing the thiazole ring of any one of the above-mentioned 1 to 5, which is represented by a substituent selected from
(34) 2-[(4-{2-[(4'-fluorobiphenyl-4-yl)oxy]ethyl}-1,3-thiazol-2-yl)thio]-2-methylpropionic acid
(38) 2-[(4-{2-[(4'-chlorobiphenyl-4-yl)oxy]ethyl}-1,3-thiazol-2-yl)thio]-2-methylpropionic acid
(68) 2-[(4-{2-[(3'-fluorobiphenyl-4-yl)oxy]ethyl}-1,3-thiazol-2-yl)thio]-2-methylpropionic acid
(76) 2-[(4-{2-[(4'-fluorobiphenyl-4-yl)thio]ethyl}-1,3-thiazol-2-yl)thio]-2-methylpropionic acid
(79) 2-[(4-{2-[(3,4'-difluorobiphenyl-4-yl)oxy]ethyl}-1,3-thiazol-2-yl)thio]-2-methylpropionic acid
(100) 2-{[4-(2-{[5-(4-fluorophenyl)pyridin-2-yl]oxy}ethyl)-1,3-thiazol-2-yl]thio-2-methylpropionic acid
(102) 2-methyl-2-({4-[2-({5-[4-(trifluoromethyl)phenyl]pyridin-2-yl}oxy)ethyl]-1,3-thiazol-2-yl}thio)propionic acid
(103) 2-methyl-2-({4-[2-({5-[3-(trifluoromethyl)phenyl]pyridin-2-yl}oxy)ethyl]-1,3-thiazol-2-yl}thio)propionic acid
(104) 2-methyl-2-({4-[2-({5-[4-(trifluoromethoxy)phenyl]pyridin-2-yl}oxy)ethyl]-1,3-thiazol-2-yl}thio)propionic acid
(106) 2-{[4-(2-{[5-(4-chlorophenyl)pyridin-2-yl]oxy}ethyl)-1,3-thiazol-2-yl]thio}-2-methylpropionic acid
(107) 2-{[4-(2-{[5-(3-chlorophenyl)pyridin-2-yl]oxy}ethyl)-1,3-thiazol-2-yl]thio}-2-methylpropionic acid
(108) 2-{[4-(2-{[5-(3,4-dichlorophenyl)pyridin-2-yl]oxy}ethyl)-1,3-thiazol-2-yl]thio}-2-methylpropionic acid
(109) 2-{[4-(2-{[5-(3-chloro-4-fluorophenyl)pyridin-2-yl]oxy}ethyl)-1,3-thiazol-2-yl]thio}-2-methylpropionic acid
(152) 2-methyl-2-{[4-({[4'-(trifluoromethyl)biphenyl-4-yl]methoxy}methyl)-1,3-thiazol-2-yl]thio}propionic acid
(162) 2-methyl-2-({4-[2-({5-[4-(trifluoromethoxy)phenyl]pyrimidin-2-yl}amino)ethyl]-1,3-thiazol-2-yl}thio)propionic acid (220) 2-{[4-(2-{[6-(4-chloro-2-fluorophenyl)pyridazin-3-yl]amino}ethyl)-1,3-thiazol-2-yl]thio}-2-methylpropionic acid
(224) 2-({4-[2-({6-[2-fluoro-4-(trifluoromethyl)phenyl]pyridazin-3-yl}amino)ethyl]-1,3-thiazol-2-yl}thio)-2-methylpropionic acid
(226) 2-{[4-(2-{[5-(4-chlorophenyl)pyrazin-2-yl]amino}ethyl)-1,3-thiazol-2-yl]thio}-2-methylpropionic acid
(227) 2-[(4-{2-[[5-(4-chlorophenyl)pyrazin-2-yl](methyl)amino]ethyl}-1,3-thiazol-2-yl)thio]-2-methylpropionic acid
(229) 2-methyl-2-({4-[2-(methyl{5-[4-(trifluoromethyl)phenyl]pyrazin-2-yl}amino)ethyl]-1,3-thiazol-2-yl}thio)propionic acid
(231) 2-methyl-2-({4-[2-(methyl{5-[4-(trifluoromethoxy)phenyl]pyrazin-2-yl}amino)ethyl]-1,3-thiazol-2-yl}thio)propionic acid
(232) 2-({4-[2-({5-[2-fluoro-4-(trifluoromethyl)phenyl]pyrazin-2-yl}amino)ethyl]-1,3-thiazol-2-yl}thio)-2-methylpropionic acid
(243) 2-methyl-2-({4-[2-({5-[4-(trifluoromethyl)phenyl]pyridin-2-yl}amino)ethyl]-1,3-thiazol-2-yl}thio)propionic acid
(260) 2-{[4-(2-{[6-(4-chlorophenyl)pyridin-3-yl]amino}ethyl)-1,3-thiazol-2-yl]thio}-2-methylpropionic acid
(261) 2-methyl-2-({4-[2-({6-[4-(trifluoromethyl)phenyl]pyridin-3-yl}amino)ethyl]-1,3-thiazol-2-yl}thio)propionic acid
(265) 2-[(4-{2-[(5-ethylpyrimidin-2-yl)(heptyl)amino]ethyl}-1,3-thiazol-2-yl)thio]-2-methylpropionic acid
(267) 2-[(4-{2-[heptyl(5-propylpyrimidin-2-yl)amino]ethyl}-1,3-thiazol-2-yl)thio]-2-methylpropionic acid
(319) 2-[(4-{2-[3-(2,4-difluorophenyl)-1-heptylureido]ethyl}-1,3-thiazol-2-yl)thio]-2-methylpropionic acid
(320) 2-({4-[2-(3-cyclohexyl-1-heptylureido)ethyl]-1,3-thiazol-2-yl}thio)-2-methylpropionic acid
(326) 2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid
(329) 2-[(4-{2-[(5-ethylpyrimidin-2-yl)(hexyl)amino]ethyl}-1,3-thiazol-2-yl)thio]-2-methylpropionic acid
(346) 2-{[4-(2-{(5-ethylpyrimidin-2-yl)[(2E)-3-phenylprop-2-en-1-yl]amino}ethyl)-1,3-thiazol-2-yl]thio}-2-methylpropionic acid
(379) 2-[(4-{2-[(3-butoxypropyl)(5-ethylpyrimidin-2-yl)amino]ethyl}-1,3-thiazol-2-yl)thio]-2-methylpropionic acid
(430) 2-methyl-2-[(4-{2-[[(1-phenyl-1H-pyrazol-4-yl)methyl](5-propylpyrimidin-2-yl)amino]ethyl}-1,3-thiazol-2-yl)thio]propionic acid
(442) 2-[(4-{2-[heptyl(5-morpholin-4-ylpyrimidin-2-yl)amino]ethyl}-1,3-thiazol-2-yl)thio]-2-methylpropionic acid
(449) 2-[(4-{2-[(3-ethyl-1H-pyrazol-5-yl)(heptyl)amino]ethyl}-1,3-thiazol-2-yl)thio]-2-methylpropionic acid
(450) 2-[(4-{2-[heptyl(3-propyl-1H-pyrazol-5-yl)amino]ethyl}-1,3-thiazol-2-yl)thio]-2-methylpropionic acid,
or a pharmaceutically acceptable salt thereof or a hydrate thereof or a solvate thereof.

(7) A carboxylic acid derivative containing the thiazole ring of the above-mentioned 1, wherein, in the formula (I), Y is an oxygen atom and Z is an aryl group or a heteroaryl group, or a pharmaceutically acceptable salt thereof or a hydrate thereof or a solvate thereof.

(8) A carboxylic acid derivative containing the thiazole ring of the above-mentioned 1 or 7, wherein, in the formula (I), Y is an oxygen atom and Z is an aryl group, or a pharmaceutically acceptable salt thereof or a hydrate thereof or a solvate thereof.

(9) A carboxylic acid derivative containing the thiazole ring of any one of the above-mentioned 1, 7 and 8, which is represented by a substituent selected from
(34) 2-[(4-{2-[(4'-fluorobiphenyl-4-yl)oxy]ethyl}-1,3-thiazol-2-yl)thio]-2-methylpropionic acid
(38) 2-[(4-{2-[(4'-chlorobiphenyl-4-yl)oxy]ethyl}-1,3-thiazol-2-yl)thio]-2-methylpropionic acid
(68) 2-[(4-{2-[(3'-fluorobiphenyl-4-yl)oxy]ethyl}-1,3-thiazol-2-yl)thio]-2-methylpropionic acid
(76) 2-[(4-{2-[(4'-fluorobiphenyl-4-yl)thio]ethyl}-1,3-thiazol-2-yl)thio]-2-methylpropionic acid
(79) 2-[(4-{2-[(3,4'-difluorobiphenyl-4-yl)oxy]ethyl}-1,3-thiazol-2-yl)thio]-2-methylpropionic acid
(100) 2-{[4-(2-{[5-(4-fluorophenyl)pyridin-2-yl]oxy}ethyl)-1,3-thiazol-2-yl]thio-2-methylpropionic acid
(102) 2-methyl-2-({4-[2-({5-[4-(trifluoromethyl)phenyl]pyridin-2-yl}oxy)ethyl]-1,3-thiazol-2-yl}thio)propionic acid
(103) 2-methyl-2-({4-[2-({5-[3-(trifluoromethyl)phenyl]pyridin-2-yl}oxy)ethyl]-1,3-thiazol-2-yl}thio)propionic acid
(104) 2-methyl-2-({4-[2-({5-[4-(trifluoromethoxy)phenyl]pyridin-2-yl}oxy)ethyl]-1,3-thiazol-2-yl}thio)propionic acid
(106) 2-{[4-(2-{[5-(4-chlorophenyl)pyridin-2-yl]oxy}ethyl)-1,3-thiazol-2-yl]thio}-2-methylpropionic acid
(107) 2-{[4-(2-{[5-(3-chlorophenyl)pyridin-2-yl]oxy}ethyl)-1,3-thiazol-2-yl]thio}-2-methylpropionic acid
(108) 2-{[4-(2-{[5-(3,4-dichlorophenyl)pyridin-2-yl]oxy}ethyl)-1,3-thiazol-2-yl]thio}-2-methylpropionic acid
(109) 2-{[4-(2-{[5-(3-chloro-4-fluorophenyl)pyridin-2-yl]oxy}ethyl)-1,3-thiazol-2-yl]thio}-2-methylpropionic acid
(152) 2-methyl-2-{[4-({[4'-(trifluoromethyl)biphenyl-4-yl]methoxy}methyl)-1,3-thiazol-2-yl]thio}propionic acid
(162) 2-methyl-2-({4-[2-({5-[4-(trifluoromethoxy)phenyl]pyrimidin-2-yl}amino)ethyl]-1,3-thiazol-2-yl}thio)propionic acid
(220) 2-{[4-(2-{[6-(4-chloro-2-fluorophenyl)pyridazin-3-yl]amino}ethyl)-1,3-thiazol-2-yl]thio}-2-methylpropionic acid
(224) 2-({4-[2-({6-[2-fluoro-4-(trifluoromethyl)phenyl]pyridazin-3-yl}amino)ethyl]-1,3-thiazol-2-yl}thio)-2-methylpropionic acid,
or a pharmaceutically acceptable salt thereof or a hydrate thereof or a solvate thereof.

(10) A carboxylic acid derivative containing the thiazole ring of the above-mentioned 1, wherein, in the formula (I), Y is —$NR^{5a}$— (wherein $R^{5a}$ is an alkyl group having 4 to 10 carbon atoms), and Z is a heteroaryl group, or a pharmaceutically acceptable salt thereof or a hydrate thereof or a solvate thereof.

(11) A carboxylic acid derivative containing the thiazole ring of the above-mentioned 1 or 10, wherein, in the formula (I), Y is —$NR^{5b}$— (wherein $R^{5b}$ is alkyl group having 6 to 9 carbon atoms), and Z is a heteroaryl group, or a pharmaceutically acceptable salt thereof or a hydrate thereof or a solvate thereof.

(12) A carboxylic acid derivative containing the thiazole ring of any one of the above-mentioned 1, 10 and 11, which is represented by a substituent selected from
(265) 2-[(4-{2-[(5-ethylpyrimidin-2-yl)(heptyl)amino]ethyl}-1,3-thiazol-2-yl)thio]-2-methylpropionic acid (267) 2-[(4-{2-[heptyl(5-propylpyrimidin-2-yl)amino]ethyl}-1,3-thiazol-2-yl)thio]-2-methylpropionic acid
(329) 2-[(4-{2-[(5-ethylpyrimidin-2-yl)(hexyl)amino]ethyl}-1,3-thiazol-2-yl)thio]-2-methylpropionic acid
(442) 2-[(4-{2-[heptyl(5-morpholin-4-ylpyrimidin-2-yl)amino]ethyl}-1,3-thiazol-2-yl)thio]-2-methylpropionic acid
(449) 2-[(4-{2-[(3-ethyl-1H-pyrazol-5-yl)(heptyl)amino]ethyl}-1,3-thiazol-2-yl)thio]-2-methylpropionic acid
(450) 2-[(4-{2-[heptyl(3-propyl-1H-pyrazol-5-yl)amino]ethyl}-1,3-thiazol-2-yl)thio]-2-methylpropionic acid,
or a pharmaceutically acceptable salt thereof or a hydrate thereof or a solvate thereof.
(13) A carboxylic acid derivative containing the thiazole ring of the above-mentioned 1, wherein, in the formula (I), Y is —NR$^{5c}$— (wherein R$^{5c}$ is an arylalkyl group or an heteroarylalkyl group), and Z is a heteroaryl group, or a pharmaceutically acceptable salt thereof or a hydrate thereof or a solvate thereof.
(14) A carboxylic acid derivative containing the thiazole ring of the above-mentioned 1 or 13, wherein, in the formula (I), Y is —NR$^{5d}$— (wherein R$^{5d}$ is a heteroarylalkyl group), and Z is a heteroaryl group, or a pharmaceutically acceptable salt thereof or a hydrate thereof or a solvate thereof.
(15) A carboxylic acid derivative containing the thiazole ring of the above-mentioned 13 or 14, which is represented by a substituent selected from
(326) 2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid
(430) 2-methyl-2-[(4-{2-[[(1-phenyl-1H-pyrazol-4-yl)methyl](5-propylpyrimidin-2-yl)amino]ethyl}-1,3-thiazol-2-yl)thio]propionic acid,
or a pharmaceutically acceptable salt thereof or a hydrate thereof or a solvate thereof.
(16) A carboxylic acid derivative containing a thiazole ring represented by
(34) 2-[(4-{2-[(4'-fluorobiphenyl-4-yl)oxy]ethyl}-1,3-thiazol-2-yl)thio]-2-methylpropionic acid,
or a pharmaceutically acceptable salt thereof or a hydrate thereof or a solvate thereof.
(17) A carboxylic acid derivative containing a thiazole ring represented by
(442) 2-[(4-{2-[heptyl(5-morpholin-4-ylpyrimidin-2-yl)amino]ethyl}-1,3-thiazol-2-yl)thio]-2-methylpropionic acid,
or a pharmaceutically acceptable salt thereof or a hydrate thereof or a solvate thereof.
(18) A carboxylic acid derivative containing a thiazole ring represented by
(326) 2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid,
or a pharmaceutically acceptable salt thereof or a hydrate thereof or a solvate thereof.
(19) A compound represented by the following formula (V):

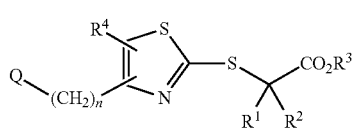

(V)

[wherein R$^1$, R$^2$, R$^3$, R$^4$ and n are as defined above;

Q is —CO$_2$R$^{33}$ (wherein R$^{33}$ is a hydrogen atom or an alkyl group), a hydroxyl group, a halogen atom, —OSO$_2$R$^{34}$ (wherein R$^{34}$ is an alkyl group, an aryl group or a haloalkyl group), —N$_3$, —NR$^{35}$R$^{36}$ (wherein R$^{35}$ and R$^{36}$ are the same or different and each is a hydrogen atom, an alkyl group, an arylalkyl group or a heteroarylalkyl group), —NHCO$_2$R$^{37}$ (wherein R$^{37}$ is an alkyl group, an arylalkyl group or a heteroarylalkyl group) or the following formula (VI)

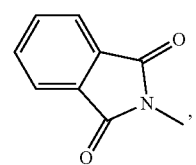

(VI)

wherein, in the aforementioned groups, an alkyl group, an aryl group, an arylalkyl group and a heteroarylalkyl group each optionally have substituent], provided that a compound represented by the following formula (VII) is excluded:

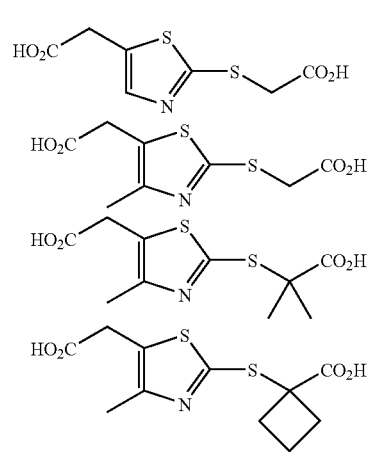

(VII)

(20) A prophylactic and/or therapeutic drug for hyperlipidemia, which comprises, as an active ingredient, a carboxylic acid derivative containing the thiazole ring of any one of the above-mentioned 1 to 18, or a pharmaceutically acceptable salt thereof or a hydrate thereof or a solvate thereof.
(21) A prophylactic and/or therapeutic drug for arteriosclerosis, which comprises, as an active ingredient, a carboxylic acid derivative containing the thiazole ring of any one of the above-mentioned 1 to 18, or a pharmaceutically acceptable salt thereof or a hydrate thereof or a solvate thereof.
(22) A prophylactic and/or therapeutic drug for an ischemic cardiac disease, which comprises, as an active ingredient, a carboxylic acid derivative containing the thiazole ring of any one of the above-mentioned 1 to 18, or a pharmaceutically acceptable salt thereof or a hydrate thereof or a solvate thereof.

Effect of the Invention

According to the present invention, a compound having a PPAR$_\alpha$ agonist action which is useful as an agent for the prophylaxis and/or treatment of hyperlipidemia and a compound useful as an intermediate therefor can be provided.

BEST MODE FOR EMBODYING THE INVENTION

The present invention is explained in detail in the following.

Specific examples of each group in the above-mentioned formula (I) are the following.

As an alkyl group represented by $R^1$ or $R^2$, a linear or branched chain alkyl having 1 to 15 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl and the like can be mentioned. Preferably, methyl, ethyl, propyl, isopropyl, butyl, isobutyl, sec-butyl, tert-butyl and pentyl, more preferably methyl and ethyl can be mentioned.

As the cycloalkyl group for $R^1$ or $R^2$, one having 3 to 7 carbon atoms, for example, cyclopropyl, cyclobutyl, cyclopentyl, cyclohexyl, cycloheptyl and the like can be mentioned. Preferably, cyclopropyl, cyclobutyl, cyclopentyl and cyclohexyl, more preferably cyclopropyl and cyclobutyl can be mentioned.

As the alkyl group for $R^3$, those defined for the alkyl group for $R^1$, preferably, methyl, ethyl, propyl, isopropyl, butyl, isobutyl, sec-butyl, tert-butyl and pentyl, more preferably, methyl and ethyl can be mentioned.

The alkyl group for $R^4$ is as defined for the alkyl group for $R^1$, and preferably, methyl, ethyl, propyl, isopropyl, butyl, isobutyl, sec-butyl and tert-butyl, more preferably methyl can be mentioned.

As the aryl group for $R^4$, an aryl group having 6 to 14 carbon atoms, for example, phenyl, naphthyl, or ortho-fused bicyclic group having 8 to 10 ring atoms wherein at least one ring is an aromatic ring (e.g., indenyl etc.) and the like can be mentioned.

The alkyl group for $R^5$ is as defined for the alkyl group for $R^1$, and preferably, an alkyl group having 5 to 9 carbon atoms, more preferably an alkyl group having 6 to 8 carbon atoms, can be mentioned.

In the cycloalkylalkyl group for $R^5$, the cycloalkyl moiety is the same as the cycloalkyl group for $R^1$, and the alkyl moiety is a linear or branched chain having 1 to 8 carbon atoms and, for example, cyclopropylmethyl, 2-cyclobutylethyl, 3-cyclopentylpropyl, cyclohexylmethyl, 2-cyclohexylethyl, cycloheptylmethyl and the like can be mentioned.

The aryl group for $R^5$ is as defined for the aryl group for $R^4$.

In the arylalkyl group for $R^5$, the aryl moiety is the same as the aryl group for $R^4$, and the alkyl moiety is a linear or branched chain having 1 to 8 carbon atoms and, for example, benzyl, benzhydryl, 1-phenylethyl, 2-phenylethyl, phenylpropyl, phenylbutyl, phenylpentyl, phenylhexyl, naphthylmethyl, naphthylethyl and the like can be mentioned. Preferably, the above-mentioned $R^{23}a$ can be mentioned.

In the arylalkenyl group for $R^5$, the aryl group for $R^4$ is bonded to the alkenyl group having 2 to 6 carbon atoms and, for example, 1-phenylethenyl, 2-phenylethenyl, 1-phenyl-1-propenyl, 2-phenyl-1-propenyl, 3-phenyl-1-propenyl, 1-phenyl-2-propenyl, 2-phenyl-2-propenyl, 3-phenyl-2-propenyl, 1-phenyl-1-butenyl, 2-phenyl-1-butenyl, 3-phenyl-2-butenyl, 4-phenyl-2-butenyl, 3-phenyl-2-propenyl, 2-phenyl-1-pentenyl, 2-phenyl-3-pentenyl, 2-phenyl-1-hexenyl and the like can be mentioned. Preferably, the above-mentioned $R^{23}d$ can be mentioned.

In the aryloxyalkyl group for $R^5$, an aryl group same as the aryl group for $R^4$ is bonded to a linear or branched chain alkyl group having 1 to 8 carbon atoms via an oxygen atom and, for example, (phenyloxy)methyl group, (1-naphthyloxy)methyl group, (2-naphthyloxy)methyl group, 1-(phenyloxy)ethyl group, 2-(phenyloxy)ethyl group, 1-(1-naphthyloxy)ethyl group, 2-(1-naphthyloxy)ethyl group, 1-(phenyloxy)propyl group, 2-(phenyloxy)propyl group, 3-(phenyloxy)propyl group, 4-(phenyloxy)butyl group, 5-(phenyloxy)pentyl group, 6-(phenyloxy)hexyl group and the like can be mentioned.

As the heteroaryl group for $R^5$, a 5- or 6-membered ring group having carbon and 1 to 4 hetero atoms (oxygen, sulfur or nitrogen), or ortho-fused bicyclic heteroaryl having 8 to 10 ring atoms induced therefrom, particularly benz derivative, or those introduced by fusing propenylene, trimethylene or tetramethylene group therewith, their stable N-oxides and the like can be mentioned. For example, pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, benzoxazolyl, benzisoxazolyl, benzothiazolyl, benzisothiazolyl, benzimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indolinyl, indazolyl, isoquinolyl, quinolyl, phthalazinyl, quinoxalinyl, quinazolinyl, cinnolinyl, 2,1,3-benzoxadiazolyl, benzoxazinyl and the like can be mentioned.

In the heteroarylalkyl group for $R^5$, the heteroaryl moiety is the same as the heteroaryl group for $R^5$, and the alkyl moiety may be a linear or branched chain having 1 to 3 carbon atoms and, for example, 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl, 4-imidazolylmethyl and the like can be mentioned. Preferably, the above-mentioned $R^{23}b$ and $R^{23}c$ can be mentioned.

When R5 is an arylalkyl group, an arylalkenyl group or a heteroarylalkyl group, particularly preferably, it shows a substituent selected from the above-mentioned formula (III).

The cycloalkyl group for Z is as defined for the cycloalkyl group for $R^1$, and preferably, cyclohexyl can be mentioned.

The aryl group for Z is as defined for the aryl group for $R^5$, and phenyl or naphthyl is preferable.

The arylalkyl group for Z is as defined for the arylalkyl group for $R^5$, and benzyl or naphthylmethyl is preferable.

The arylalkenyl group for Z is as defined for the arylalkenyl group for $R^5$.

The aryloxyalkyl group for Z is as defined for the aryloxyalkyl group for $R^5$.

The heteroaryl group for Z is as defined for the heteroaryl group for $R^5$.

The heteroarylalkyl group for Z is as defined for the heteroarylalkyl group for $R^5$.

When Z is an aryl group or a heteroaryl group, it particularly preferably shows a substituent selected from the above-mentioned formula (II).

As the halogen atom for $R^8$, $R^9$ or $R^{10}$, a fluorine atom, a chlorine atom, a bromine atom and an iodine atom can be mentioned, with preference given to a fluorine atom, a chlorine atom and a bromine atom.

As the haloalkyl group for $R^8$, $R^9$ or $R^{10}$, an alkyl group same as the alkyl group for $R^1$ wherein the aforementioned halogen atom is substituted can be mentioned and, for example, fluoromethyl, difluoromethyl, trifluoromethyl, chloromethyl, 2,2,2-trifluoroethyl, pentafluoroethyl and the like can be mentioned.

As the haloalkyloxy group for $R^8$, $R^9$ or $R^{10}$, an alkyloxy group wherein the aforementioned halogen atom is substituted can be mentioned and, for example, trifluoromethyloxy, 2,2,2-trifluoroethyloxy, difluoromethyloxy and the like can be mentioned.

As the heterocycle shown by $R^{13}$ and $R^{14}$ or $R^{15}$ and $R^{16}$, a nonaromatic heterocyclic group having 2 to 10 carbon atoms containing, as a ring constituent atom besides carbon atom, 1 to 3 hetero atoms selected from oxygen atom, sulfur atom and nitrogen atom can be mentioned. For example, azetidinyl, pyrrolidinyl, piperidino, piperazino, morpholino, 1,2,5,6-tetrahydropyridyl, thiomorpholino, oxothiomorpholino, dioxothiomorpholino, 3-azaspiro[5,5]undecyl, 1,3,8-triazaspiro[4,5]decyl and the like can be mentioned.

As the arylcarbonyl group for $R^{24}$ or $R^{25}$, that wherein the aryl moiety is the same as the aryl group for $R^4$, for example, benzoyl, 1-naphthoyl and the like can be mentioned.

Of the aforementioned substituents, an alkyl group, a cycloalkyl group, a cycloalkylalkyl group, an aryl group, an arylalkyl group, an arylalkenyl group, an aryloxyalkyl group, a heteroaryl group, a heteroarylalkyl group and a heterocycle each optionally have 1 to 3 substituents at substitutable positions. As such substituent, for example, an alkyl group, an alkyloxy group, a halogen atom, a haloalkyl group, a haloalkoxy group, an aryl group and a heteroaryl group can be mentioned. The substituents recited here are as defined above.

Pharmaceutically acceptable salt of the compound of the formula (I) includes any salt, and salts with inorganic acids such as hydrochloric acid, hydrobromic acid and the like, salts with organic acids, salts with alkali metals, salts with organic bases or salts with amino acids can be mentioned.

In the present invention, the aforementioned compound of the formula (I) and a salt thereof include solvates (e.g., hydrate) and prodrugs metabolized in living organisms to be converted to the aforementioned carboxylic acid of the formula (I) or a salt thereof.

Compounds (I) of the present invention can be synthesized, for example, by the following methods, but the production method thereof is not limited thereto.

Of the compounds of the formula (I), compounds of the formulas (I-2) and (I-4) wherein the bonding pattern of Y part is an oxygen atom can be produced, for example, by the following methods (production methods 1, 2). Compounds wherein the bonding pattern of Y part is a nitrogen atom can also be produced by similar methods (production methods 1, 2).

[Production Method 1]

By reacting alcohol represented by the formula (II-1) (synthetic method is mentioned later) and a compound having a leaving group represented by the formula (III-1) in the presence of a base, an ether compound represented by the formula (I-1) can be obtained (step 1). Alternatively, by reacting a compound having a leaving group on an alkyl chain represented by the formula (II-2) (synthetic method is mentioned later) with an alcohol derivative represented by the formula (III-2) in the presence of a base, an ether compound represented by the formula (I-1) can be obtained (step 2). Moreover, the present compound can be converted to carboxylic acid compound (I-2) (step 3) by de-esterification. Compound (III-1) and compound (III-2), which are starting compounds, can be generally synthesized easily by a known method.

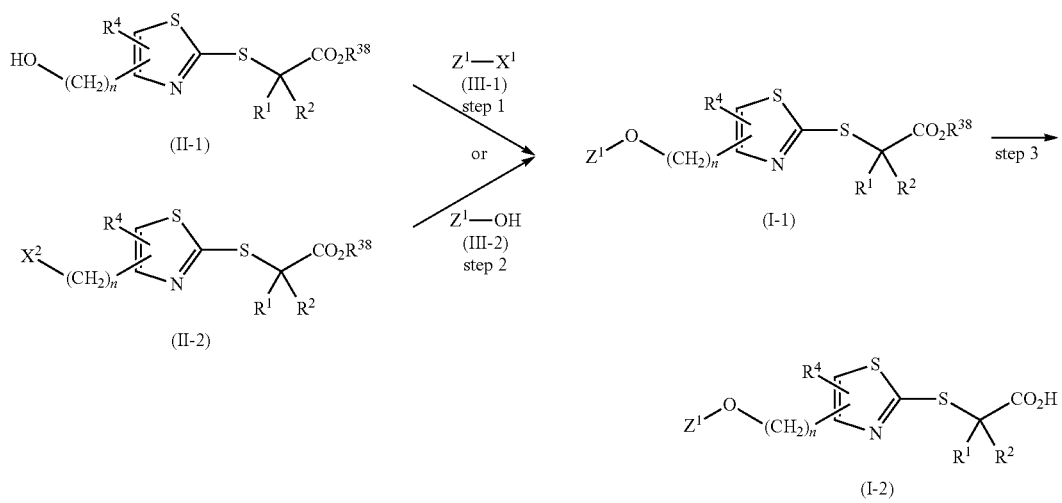

[wherein $R^1$, $R^2$, $R^4$ and n are as defined above, $R^{38}$ is an alkyl group, $Z^1$ is an aryl group, a heteroaryl group, an arylalkyl group, a heteroarylalkyl group or a cycloalkyl group, $X^1$ is —$SO_2R^{39}$ (wherein $R^{39}$ is an alkyl group or an aryl group) or a halogen atom, $X^2$ is —$OSO_2R^{40}$ (wherein $R^{40}$ is an alkyl group, a haloalkyl group or an aryl group) or a halogen atom.]

Step 1 and step 2 are generally performed in the presence of a base in a solvent that does not adversely influence the reaction. As the base, for example, alkali metal carbonates such as potassium carbonate, sodium carbonate, cesium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, N,N-dimethylaniline, 4-dimethylaminopyridine, 1,8-diazabicyclo[5.4.0]undec-7-en and the like, and the like are used. The amount of the base to be used is preferably 1 to 5 molar equivalents relative to compound (II-1) or compound (II-2). The reaction temperature is generally −50° C. to 200° C., preferably −10° C. to 100° C. As a solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, and the like are used. These solvents may be used in a mixture in an appropriate ratio.

Step 3 is generally performed in the presence of an acid or base in an aqueous solvent. As the acid, for example, formic acid, hydrochloric acid, sulfuric acid, acetic acid, hydrobromic acid, trifluoroacetic acid and the like are used. As the base, for example, alkali metal carbonates such as potassium carbonate, sodium carbonate and the like, alkali metal alkoxides such as sodium methoxide, sodium ethoxide and the like, alkali metal hydroxides such as potassium hydroxide, sodium hydroxide, lithium hydroxide and the like, and the like are used. The acid or base is generally used in an excess amount relative to compound (I-1). Preferably, the amount of the acid to be used is 2 to 100 equivalent amount relative to compound (I-1) and the amount of the base to be used is 1.2 to 5 equivalent amount relative to compound (I-1). As the aqueous solvent, for example, a mixed solvent of one or more kinds of solvents selected from alcohols such as methanol, ethanol and the like, ethers such as tetrahydrofuran, dioxane and the like, dimethyl sulfoxide, acetone and the like and water, and the like are used. When $R^{38}$ is a tert-butyl group, acid decomposition can be performed in addition to the above-mentioned reaction in an aqueous solvent. As the acid, for example, formic acid, hydrochloric acid, sulfuric acid, acetic acid, hydrobromic acid, trifluoroacetic acid, methanesulfonic acid, paratoluenesulfonic acid and the like are used. In this case, solvents may be mixed in an appropriate ratio. As the solvent, for example, halogenated hydrocarbons such as chloroform, dichloromethane, dichloroethane and the like, and the like are used. The base is generally used in an excess amount relative to compound (I-1). Preferably, the amount of the acid to be used is 2 to 100 equivalent amount relative to compound (I-1). The reaction temperature is generally −20 to 150° C., preferably −10 to 100° C.

[Production Method 2]

By reacting an alcohol represented by the formula (II-1) (synthetic method is mentioned later) and aryl alcohol represented by the formula (III-3) or heteroaryl alcohol in the presence of phosphines and an azodicarboxylic acid derivative, an ether compound represented by the formula (I-3) can be obtained (step 4). The present compound can be converted to a carboxylic acid compound (I-4) (step 5) by de-esterification. Compound (III-3), which is a starting compound, can be generally synthesized easily by a known method.

[wherein $R^1$, $R^2$, $R^4$ and n are as defined above, $R^{41}$ is an alkyl group or resin, and $Z^2$ is an aryl group or a heteroaryl group.]

Step 4 is generally performed in the presence of phosphines and azodicarboxylic acid derivative, in a solvent that does not adversely influence the reaction. As the phosphines, for example, triphenylphosphine, tributylphosphine and the like are used and, as the azodicarboxylic acid derivative, for example, diethyl azodicarboxylate, diisopropyl azodicarboxylate, azodicarbonyl dipiperazine and the like are used. The amount of phosphines and azodicarboxylic acid derivative to be used is preferably 1 to 5 molar equivalents relative to compound (II-1). The reaction temperature is generally −50° C. to 150° C., preferably −10° C. to 100° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide and the like, sulfoxides such as dimethyl sulfoxide and the like, and the like are used. These solvents may be used in a mixture in an appropriate ratio.

When $R^{41}$ is an alkyl group, step 5 is generally performed in the same manner as in step 3. When $R^{41}$ is a resin, step 5 is generally performed in the same manner as in step 3, generally using an excess amount of aqueous or nonaqueous trifluoroacetic acid, where solvents that do not adversely influence the reaction may be used in a mixture in an appropriate ratio. As the solvent that does not influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like are used. The reaction temperature is generally −20 to 150° C., preferably −10° C. to 60° C.

Of the compounds of the formula (I), compounds of the formulas (I-6) and (I-8) wherein the bonding pattern of Y part is an amide structure can be produced, for example, by the following methods (Production Methods 3, 4).

[Production Method 3]

By reacting primary amine represented by the formula (II-3) (synthetic method is mentioned later) and carboxylic acid represented by the formula (III-4) in the presence of a condensing agent, or carboxylic acid chloride represented by the formula (III-5) in the presence of a base, an amide compound represented by the formula (I-5) can be obtained (step 6). Then the compound can be converted to carboxylic acid compound (I-6) (step 7) by de-esterification. Compound (III-4), compound (III-5), which are starting compounds, can be generally synthesized easily by a known method.

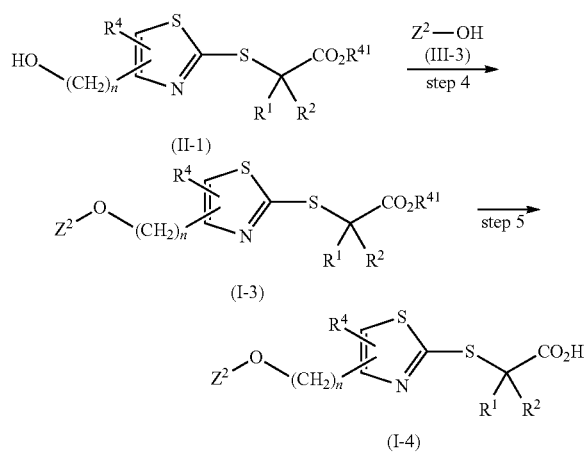

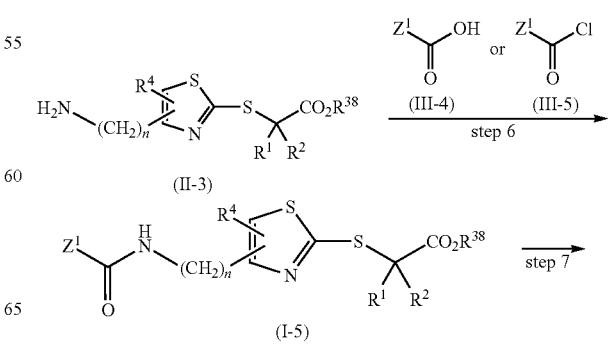

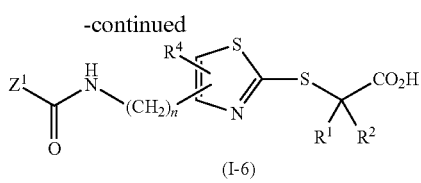

(I-6)

[wherein $R^1$, $R^2$, $R^4$, $R^{38}$, n and $Z^1$ are as defined above.]

When carboxylic acid compound (III-4) is used, step 6 is generally performed in the presence of a condensing agent that activates carboxylic acid, in a solvent that does not adversely influence the reaction. As the condensing agent, for example, dicyclohexylcarbodiimide (DCC), N-(3-dimethylaminopropyl)-N'-ethylcarbodiimide (EDC) or hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytris(pyrrolidino)phosphonium hexafluorophosphate (PyBOP), diphenylphosphoryl azide (DPPA), isobutyl chloroformate, diethylacetyl chloride, trimethylacetyl chloride and the like can be mentioned. These condensing agents are used alone, or in combination with an additive such as N-hydroxysuccinimide (HONSu), hydroxybenzotriazole (HOBT), 3-hydroxy-4-oxo-3,4-dihydro-1,2,3-benzotriazine (HOOBT), or 4-dimethylaminopyridine (DMAP) and the like. The amount of the condensing agent and the additive to be used is preferably 1 to 5 molar equivalents relative to compound (II-3). The reaction temperature is generally −30° C. to 80° C., preferably −10° C. to 50° C. As a solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, and the like are used. These solvents may be used in a mixture in an appropriate ratio. When a carboxylic acid chloride compound (III-5) is used, step 6 is generally performed in the presence of a base, in a solvent that does not adversely influence the reaction. As the base, for example, alkali metal carbonates such as potassium carbonate, sodium carbonate, cesium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, N,N-dimethylaniline, 4-dimethylaminopyridine, 1,8-diazabicyclo[5.4.0]undec-7-en and the like, and the like are used. The amount of the base to be used is preferably 1 to 5 molar equivalents relative to compound (II-3). The reaction temperature is generally −50° C. to 100° C., preferably −10° C. to 50° C. As a solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, and the like are used. These solvents may be used in a mixture in an appropriate ratio.

Step 7 can be performed according to a method similar to that of step 3.

[Production Method 4]

By reacting carboxylic acid represented by the formula (II-4) (synthetic method is mentioned later) and amine represented by the formula (III-6) in the presence of a condensing agent as in Production Method 3, the amide compound represented by the formula (I-7) can be obtained (step 8). Subsequently, the compound can be converted to carboxylic acid compound (I-8) (step 9) by de-esterification. Compound (III-6), which is a starting compound, can be generally synthesized easily by a known method.

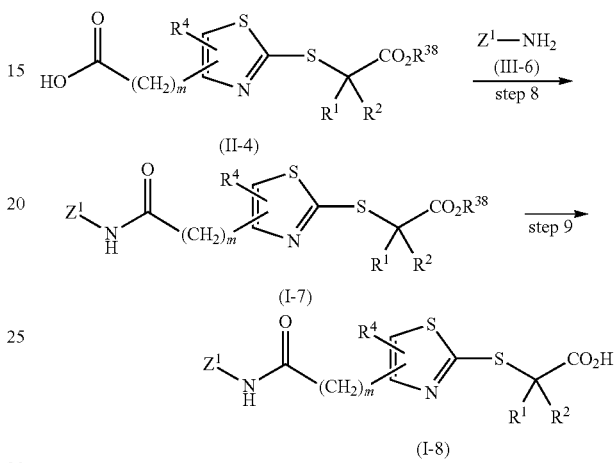

[wherein $R^1$, $R^2$, $R^4$, $R^{38}$, $Z^1$ are as defined above, and m is an integer of 0 to 4.]

Step 8 can be performed according to a method similar to that of step 6.

Step 9 can be performed according to a method similar to that of step 3.

Of the compounds of the formula (I), a compound of the formula (I-10) wherein the bonding pattern of Y part is —NH— can be produced, for example, by the following methods (production methods 5, 6).

[Production Method 5]

By reacting primary amine represented by the formula (II-3) (synthetic method is mentioned later) and a compound having a leaving group represented by the formula (III-1) in the presence of a base, the secondary amine compound represented by the formula (I-9) can be obtained (step 10). Moreover, the present compound can be converted to carboxylic acid compound (I-10) (step 11) by de-esterification. Compound (III-1), which is a starting compound, can be generally synthesized easily by a known method.

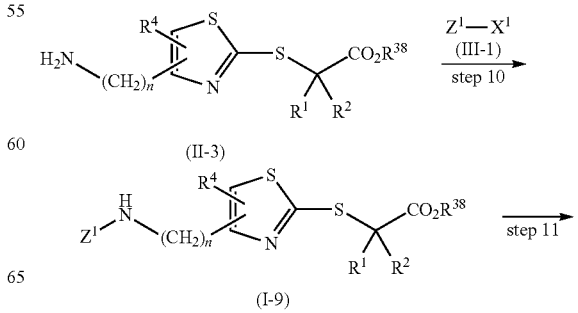

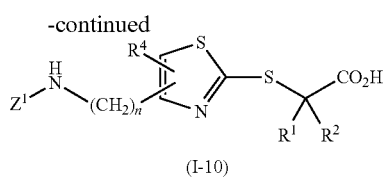

(I-10)

wherein $R^1$, $R^2$, $R^4$, $R^{38}$, n, $Z^1$ and $X^1$ are as defined above.]

Step 10 can be performed according to a method similar to that of step 1.

Step 11 can be performed according to a method similar to that of step 3.

[Production Method 6]

By reacting the amide compound represented by the formula (I-7), which is synthesized in Production Method 4, in the presence of a reducing agent, the secondary amine compound represented by the formula (I-9) can be obtained (step 12). Then, the compound can be converted to carboxylic acid compound (I-10) (step 13) by de-esterification.

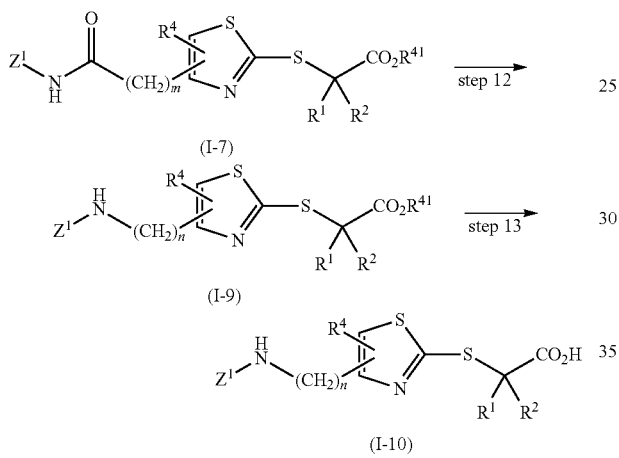

[wherein $R^1$, $R^2$, $R^3$, $R^{41}$, $Z^1$, n and m are as defined above, and n and m show the relationship of n=m+1.]

Step 12 is generally performed in the presence of a reducing agent, in a solvent that does not adversely influence the reaction. As the reducing agent, for example, borane-tetrahydrofuran complex, borane-methylsulfide complex, diborane, tetrabutylammonium tetrahydroborate, sodium tetrahydroborate in the presence of a Lewis acid and the like are used. The amount of the reducing agent to be used is preferably 1 to 5 molar equivalents relative to compound (I-7). The reaction temperature is generally −50° C. to 150° C., preferably −10° C. to 100° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, and the like are used. These solvents may be used in a mixture in an appropriate ratio.

Step 13 can be performed according to a method similar to that of step 5.

Of the compounds of the formula (I), a compound of the formula (I-12) wherein the bonding pattern of Y part is —$NR^{42}$— (wherein $R^{42}$ is an alkyl group, an arylalkyl group, an arylalkenyl group, an aryloxyalkyl group, a heteroarylalkyl group, each of which optionally has substituent) can be produced, for example, by the following methods (production methods 7 to 9).

[Production Method 7]

By reacting secondary amine represented by the formula (I-9), which is synthesized in production methods 5 or 6, and a compound having a leaving group, which is represented by the formula (III-7), in the presence of a base, a tertiary amine compound represented by the formula (I-11) can be obtained (step 14). Alternatively, after reaction of the secondary amine with the ketone compound represented by the formula (III-8) in the presence of a reducing agent, a tertiary amine compound represented by the formula (I-11) can be obtained (step 15). Furthermore, the present compound can be converted to carboxylic acid compound (I-12) (step 16) by de-esterification. Compound (III-7), compound (III-8), which are starting compounds, can be generally synthesized easily by a known method.

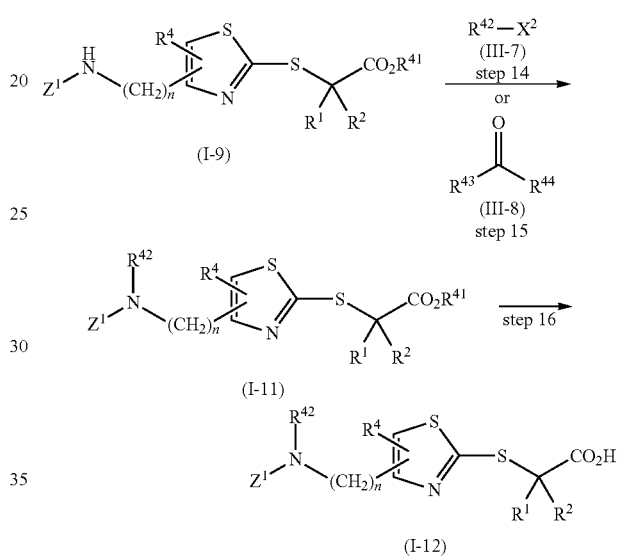

[wherein $R^1$, $R^2$, $R^3$, $R^4$, $R^{41}$, $R^{42}$, n, $Z^1$ and $X^2$ are as defined above, $R^{43}$ and $R^{44}$ are the same or different and each independently is a hydrogen atom, an alkyl group, a cycloalkyl group, a cycloalkylalkyl group, an aryl group, an arylalkyl group, a heteroaryl group or a heteroarylalkyl group.]

Step 14 can be performed according to a method similar to that of step 1.

Step 15 is generally performed in the presence of a reducing agent, in a solvent that does not adversely influence the reaction. As the reducing agent, for example, sodium tetrahydroborate, sodium cyanotetrahydroborate, sodium triacetoxytetrahydroborate and the like can be mentioned. The reaction temperature is generally 0° C. to 100° C. As the solvent that does not adversely influence the reaction, ethers such as tetrahydrofuran, dioxane and the like, halogenated hydrocarbons such as chloroform, dichloromethane, dichloroethane and the like, alcohols such as methanol, ethanol and the like, nitriles such as acetonitrile and the like and the like are used. These solvents may be used in a mixture in an appropriate ratio. Where necessary, acidic catalyst, for example, acetic acid, p-toluenesulfonic acid, boron trifluoride-diethyl ether complex and the like may be used.

Step 16 can be performed according to a method similar to that of step 5.

[Production Method 8]

By reacting carboxylic acid represented by the formula (II-4) (synthetic method is mentioned later) and an amine derivative represented by the formula (III-9) in the same manner as in Production Method 3 in the presence of a condensing agent, the amide compound represented by the formula (I-13) can be obtained (step 17). Then by reacting the amide compound in the presence of a reducing agent, the secondary amine compound represented by the formula (I-15) can be obtained (step 19). Alternatively, by performing condensation reaction, reduction reaction in the same manner as in step 17 and step 19 using primary amine represented by the formula (II-3) (synthetic method is mentioned later) and carboxylic acid derivative represented by the formula (III-10), the secondary amine compound represented by carboxylic acid represented by the formula (I-15) can be obtained (step 18, step 19). Then by reacting the present compound and a compound having a leaving group, which is represented by the formula (I-11) in the presence of a base, the tertiary amine compound represented by the formula (III-1) can be obtained (step 20). Finally, the compound can be converted to carboxylic acid compound (I-12) (step 21) by de-esterification. Compound (III-1), (III-9), (III-10), which are starting compounds, can be generally synthesized easily by a known method.

[wherein $R^1$, $R^2$, $R^4$, $R^{41}$, $R^{42}$, $Z^1$, $X^1$, n and m are as defined above, $R^{45}$ is an alkyl group, a cycloalkyl group, a cycloalkylalkyl group, an aryl group, an arylalkyl group, a heteroaryl group or a heteroarylalkyl group and n and m show the relationship of n=m+1.]

Step 17 can be performed according to a method similar to that of step 6.

Step 18 can be performed according to a method similar to that of step 6.

Step 19 can be performed according to a method similar to that of step 12.

Step 20 can be performed according to a method similar to that of step 1.

Step 21 can be performed according to a method similar to that of step 5.

[Production Method 9]

By reacting a compound having an amino group, which is represented by the formula (III-6), in the presence of a base, a sulfonamide compound represented by the formula (III-11) can be obtained (step 22). By reacting the present compound

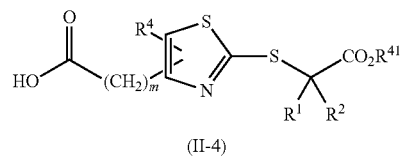

(II-4)

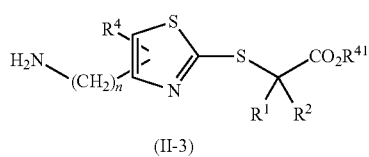

(II-3)

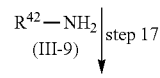

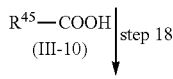

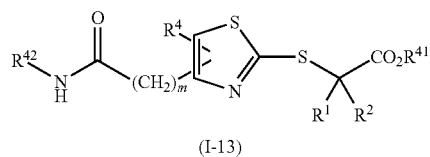

(I-13)

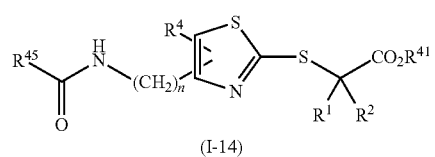

(I-14)

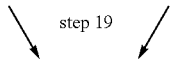

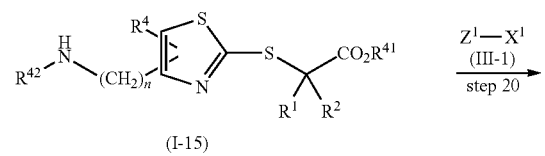

(I-15)

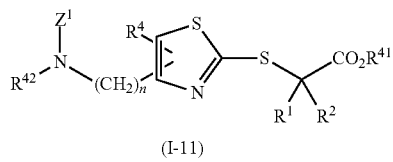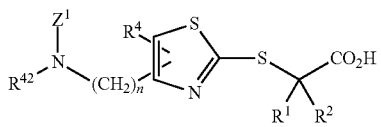

(I-11) (I-12)

and alcohol represented by the formula (II-1) (synthetic method is mentioned later) in the presence of phosphines and azodicarboxylic acid derivative, a sulfonamide compound represented by the formula (I-16) can be obtained (step 23). Moreover, by reacting the present compound and a compound having a thiol group, which is represented by the formula (III-12), in the presence of a base, a secondary amine compound represented by the formula (I-9) can be obtained (step 24). Furthermore, by an operation similar to that in Production Method 7 using the present compound and the formula (III-7) or the formula (III-8), a carboxylic acid compound (I-12) can be obtained (step 25 to step 27). Compounds (III-6), (III-7), (III-8), (III-12), which are starting compounds, can be generally synthesized easily by a known method.

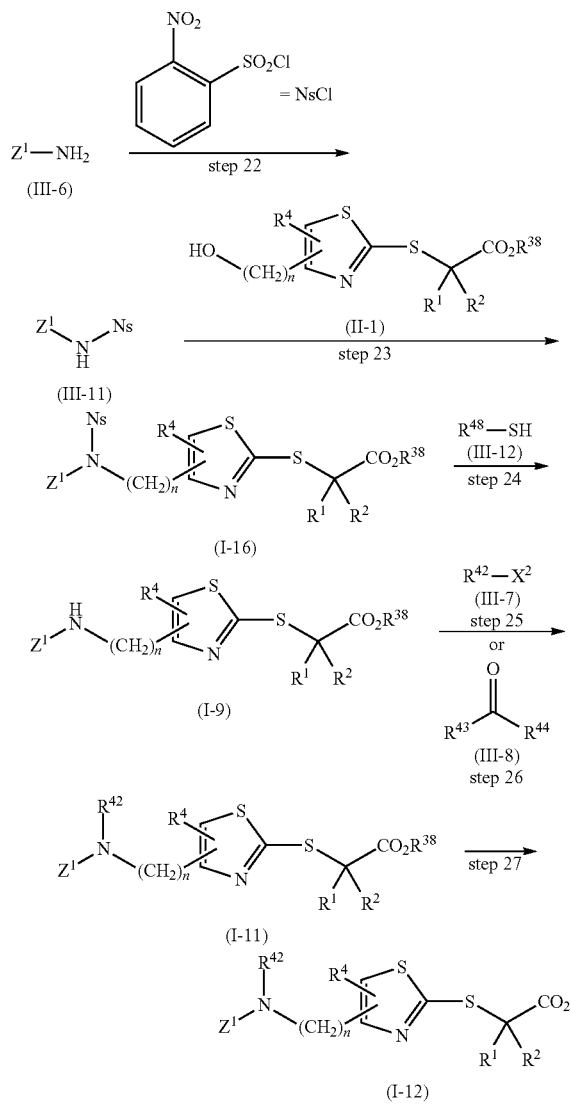

[wherein $R^1$, $R^2$, $R^4$, $R^{38}$, $R^{42}$, $R^{43}$, $R^{44}$, $Z^1$, $X^2$ and n are as defined above, and $R^{46}$ is an alkyl group or an aryl group.]

In step 22 to step 24, a secondary amine compound represented by the formula (I-9) can be obtained by 2-nitrobenzenesulfonylation, Mitsunobu reaction and di-2-nitrobenzenesulfonylation by reference to the methods described in non-patent references [Tetrahedron Lett., 36, 6373 (1995) and Tetrahedron Lett., 33, 5831 (1997)] and the like.

Step 22 can be generally performed using 2-nitrobenzenesulfonyl chloride and according to a method similar to that of step 1.

Step 23 can be performed according to a method similar to that of step 4.

Step 24 can be generally performed using benzenethiol and according to a method similar to that of step 1.

Step 25 can be performed according to a method similar to that of step 1.

Step 26 can be performed according to a method similar to that of step 15.

Step 27 can be performed according to a method similar to that of step 3.

Of the compounds of the formula (I), a compound of the formula (I-18) wherein the bonding pattern of Y part is —$CONR^{42}$— (wherein $R^{42}$ is as defined above) can be produced from a secondary amine compound represented by the formula (I-15), which is synthesized by Production Method 8, and, for example, by the following method (Production Method 10).

[Production Method 10]

In the same manner as in Production Method 3, by reacting secondary amine represented by the formula (I-15), which is synthesized by Production Method 8, and a carboxylic acid compound represented by the formula (III-4) in the presence of a condensing agent or carboxylic acid chloride represented by the formula (III-5) in the presence of a base, an amide compound represented by the formula (I-17) can be obtained (step 28). The present compound can be converted to carboxylic acid compound (I-18) (step 29) by de-esterification. Compound (III-4), compound (III-5), which are starting compounds, can be generally synthesized easily by a known method.

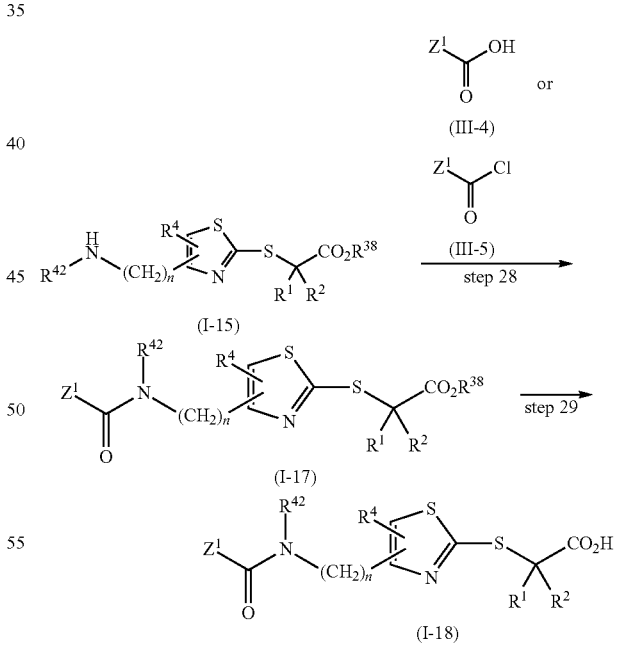

[wherein $R^1$, $R^2$, $R^4$, $R^{38}$, $R^{42}$, n and $Z^1$ are as defined above.]

Step 28 can be performed according to a method similar to that of step 6.

Step 29 can be performed according to a method similar to that of step 3.

Of the compounds of the formula (I), a compound of the formula (I-20) wherein the bonding pattern of Y part is —NH- CONR$^{42}$— (wherein R$^{42}$ are as defined above) can be produced from a secondary amine compound represented by the formula (I-15), which is synthesized by Production Method 8, for example, by the following method (Production Method 11).

[Production Method 11]

By reacting secondary amine represented by the formula (I-15), which is synthesized in Production Method 8, and isocyanate represented by the formula (III-13), a urea compound represented by the formula (I-19) can be obtained (step 30). The present compound can be converted to carboxylic acid compound (I-20) (step 31) by de-esterification. Compound (III-13), which is a starting compound, can be generally synthesized easily by a known method.

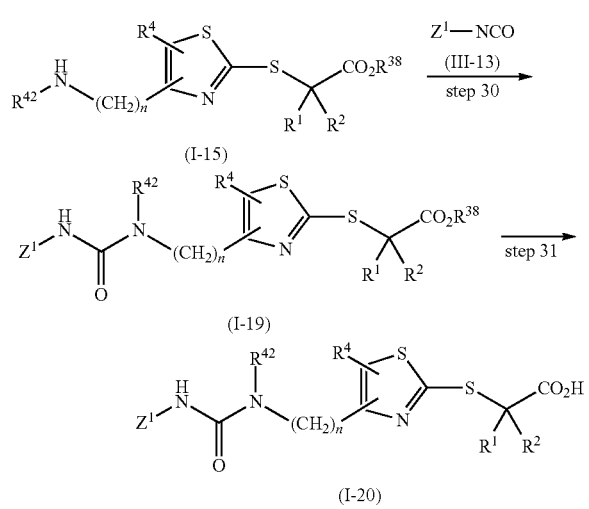

[wherein R$^1$, R$^2$, R$^4$, R$^{38}$, R$^{42}$, n and Z$^1$ are as defined above.]

Step 30 can be generally performed in a solvent that does not adversely influence the reaction. The amount of isocyanate (III-13) to be used is preferably 1 to 5 molar equivalents relative to compound (I-15). The reaction temperature is generally −30° C. to 100° C., preferably −10° C. to 50° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, and the like are used. These solvents may be used in a mixture in an appropriate ratio.

Step 31 can be performed according to a method similar to that of step 3.

Of the compounds of the formula (I), compounds of the formula (I-23), the formula (I-26) and the formula (I-30), wherein Z is an aryl group, a heteroaryl group, an arylalkyl group or a heteroarylalkyl group, wherein the aryl group or the heteroaryl group has an aryl group or a heteroaryl group on its ring, can be produced by the methods shown by Production Methods 1 to 12, as well as, for example, the following methods (Production Methods 12 to 14).

[Production Method 12]

By reacting the compound of formula (I) wherein Z is an aryl group, a heteroaryl group, an arylalkyl group or a heteroarylalkyl group, wherein the aryl group or the heteroaryl group has, on its ring, a leaving group such as a halogen atom, a trifluoromethanesulfonyloxy group and the like [represented by the formula (I-21)] and a boron compound represented by the formula (III-14) or a tin compound represented by the formula (III-15) in the presence of a metal catalyst, a compound represented by the formula (I-22), into which an aryl group or a heteroaryl group has been introduced, can be obtained (step 32). The present compound can be converted to carboxylic acid compound (I-23) by de-esterification (step 33). Compound (III-14), (III-15), which are starting compounds, can be generally synthesized easily by a known method.

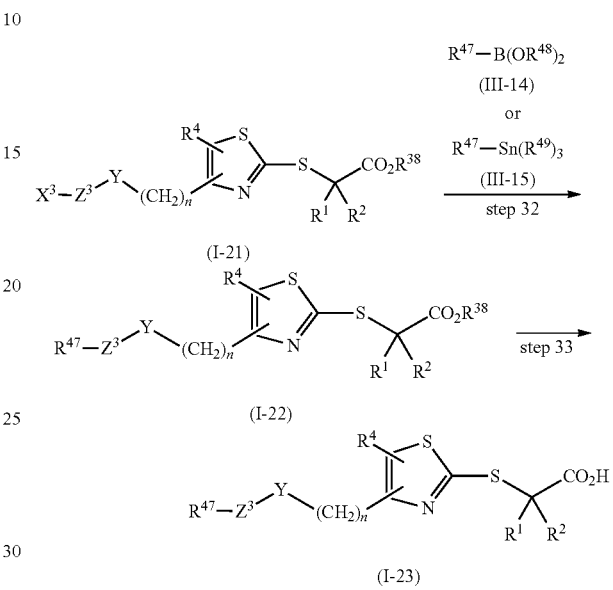

[wherein R$^1$, R$^2$, R$^3$, R$^4$, R$^{38}$, n and Y are as defined above, Z$^3$ is an aryl group, a heteroaryl group, an arylalkyl group or a heteroarylalkyl group, X$^3$ is a halogen atom or a trifluoromethanesulfonyloxy group, R$^{47}$ is an aryl group or a heteroaryl group, R$^{48}$ is a hydrogen atom or an alkyl group, or two R$^{48}$ form, in combination, an orthophenylene group, an ethylene group, a 1,1,2,2-tetramethylethylene group, or a 1,3-propylene group, and R$^{49}$ is an alkyl group.]

Step 32 is generally performed in the presence of a metal catalyst, in a solvent that does not adversely influence the reaction. In this case, a base may be added. As the metal catalyst, for example, zero-valent palladium, divalent palladium, zero-valent nickel and the like can be mentioned. As the zero-valent palladium catalyst, for example, tetrakis(triphenylphosphine)palladium, tris(dibenzylideneacetone)dipalladium and the like can be mentioned; as the divalent palladium catalyst, for example, acetic acid palladium, dichlorobis(triphenylphosphine)palladium and the like can be mentioned; and as the zero-valent nickel catalyst, for example, 1,1'-bis(diphenylphosphino)ferrocene nickel and the like can be mentioned. A monodentate ligand such as triphenylphosphine, tris(o-tolyl)phosphine and the like, a bidentate ligand such as diphenylphosphinopropane, diphenylphosphinobutane and the like, and the like may also be added. As the base, for example, alkali metal hydrogen carbonate salts such as sodium hydrogen carbonate and the like, alkali metal carbonates such as sodium carbonate, potassium carbonate and the like, alkali metal phosphates such as tripotassium phosphate and the like, and the like can be mentioned. For reaction with R$^{47}$—Sn(R$^{49}$)$_3$ (III-15), however, use of a base is not necessary. The amount of the metal catalyst to be used is, for example, 0.01 to 1 molar equivalents, preferably 0.05 to 0.5 molar equivalents, relative to compound (I-21). The amount of the base to be used is, for example, 1 to 20 molar equivalents, preferably 1 to 10 molar equivalents, relative to compound (I-21). The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene and the like, amides such as N,N-dimethylformamide, N-methyl-2-pyrrolidone and the like, alcohols such as methanol, ethanol and the like, water and the like are used. These solvents may be used in a mixture in an appropriate ratio. A reaction with $R^{47}$—Sn $(R^{49})_3$ (III-15) is preferably carried out in a non-aqueous solvent. The amount of $R^{47}$—B(OR$^{48}$)$_3$ (III-14) or $R^{47}$—Sn $(R^{49})_3$ (III-15) to be used is, for example, 1 to 5 molar equivalents, preferably 1 to 3 molar equivalents, relative to compound (I-21).

Step 33 can be performed according to a method similar to that of step 3.

[Production Method 13]

By reacting alcohol represented by the formula (I-1) (synthetic method is mentioned later) and aryl alcohol or heteroaryl alcohol having a boric acid ester group on Z, which is represented by the formula (III-16), using phosphines and azodicarboxylic acid derivative, an ether compound represented by the formula (I-24) can be obtained (step 34). Then, by reacting the present compound and a compound having a leaving group, which is represented by the formula (III-17) in the presence of a metal catalyst, a compound represented by the formula (I-25), into which an aryl group or a heteroaryl group has been introduced, can be obtained (step 35). The present compound can be converted to carboxylic acid compound (I-26) by de-esterification (step 36).

Compound (III-16), (III-17), which are starting compounds, can be generally synthesized easily by a known method.

Step 34 can be performed according to a method similar to that of step 4.

Step 35 can be performed according to a method similar to that of step 32.

Step 36 can be performed according to a method similar to that of step 3.

[Production Method 14]

By reacting a compound [represented by the formula (I-27)] having a halogen atom on $Z^1$ of a compound represented by the formula (I-16), which is synthesized by Production Method 9, and a boric acid compound represented by the formula (III-14) in the presence of a metal catalyst, a compound represented by the formula (I-28), into which an aryl group or a heteroaryl group has been introduced, can be obtained (step 37). Moreover, by reacting the present compound and a compound having a thiol group which is represented by the formula (III-12) in the presence of a base, a secondary amine compound represented by the formula (I-29) can be obtained (step 38). Furthermore, the present compound can be converted to carboxylic acid compound (I-30) by de-esterification (step 39). Compounds (III-12), (III-14), which are starting compounds, can be generally synthesized easily by a known method.

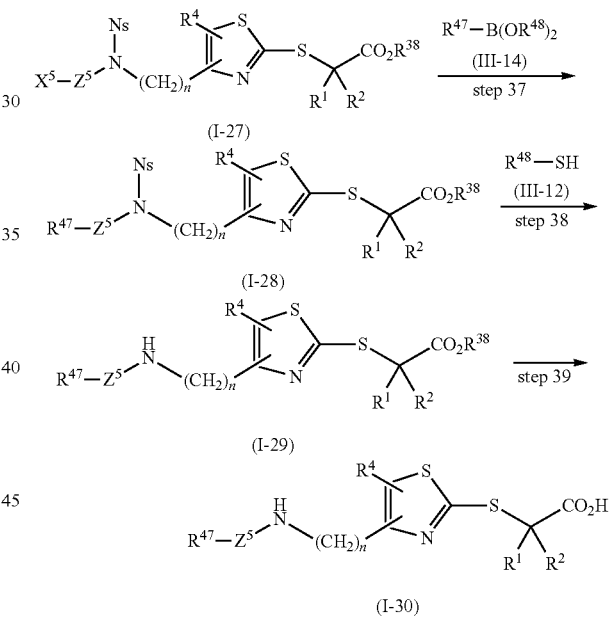

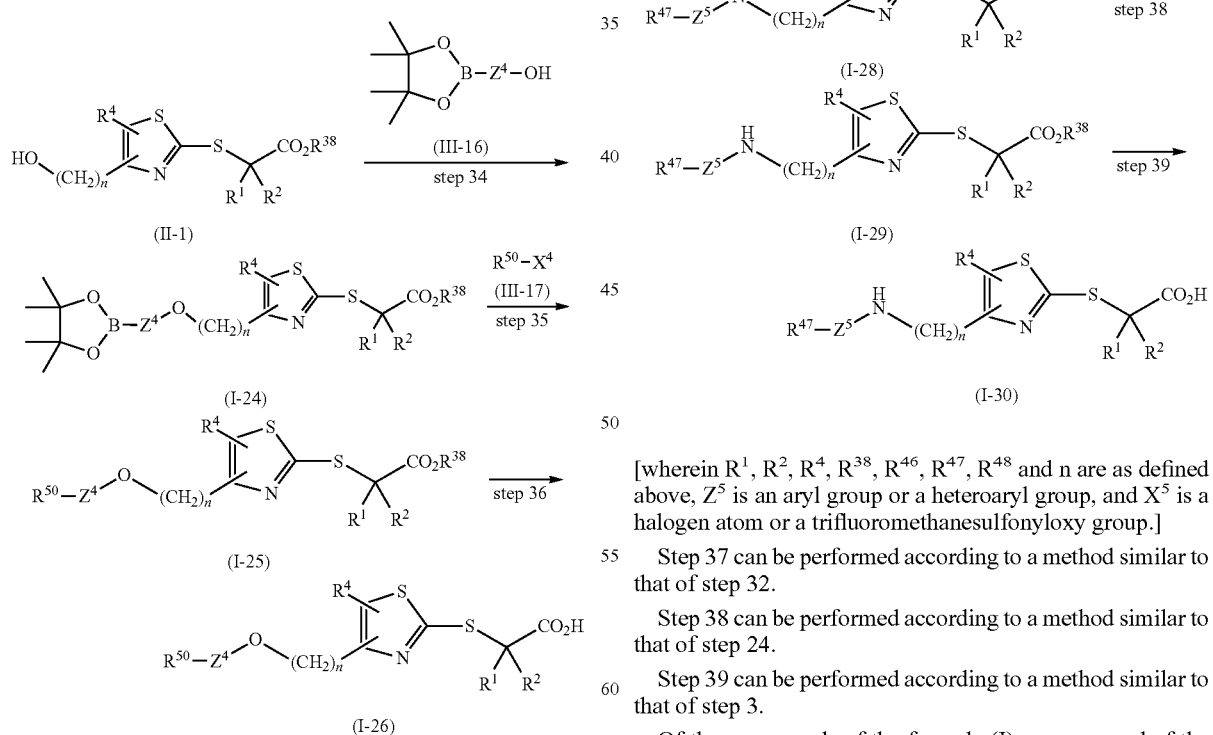

[wherein $R^1$, $R^2$, $R^4$, $R^{38}$ and n are as defined above, $Z^4$ is an aryl group or a heteroaryl group, $X^4$ is a halogen atom or a trifluoromethanesulfonyloxy group, and $R^{50}$ is an aryl group or a heteroaryl group.]

[wherein $R^1$, $R^2$, $R^4$, $R^{38}$, $R^{46}$, $R^{47}$, $R^{48}$ and n are as defined above, $Z^5$ is an aryl group or a heteroaryl group, and $X^5$ is a halogen atom or a trifluoromethanesulfonyloxy group.]

Step 37 can be performed according to a method similar to that of step 32.

Step 38 can be performed according to a method similar to that of step 24.

Step 39 can be performed according to a method similar to that of step 3.

Of the compounds of the formula (I), a compound of the formula (I-32) wherein Z is an aryl group, a heteroaryl group, an arylalkyl group or a heteroarylalkyl group, wherein the aryl group or heteroaryl group has an amino group on its ring, can be produced by the methods shown in Production Methods 1 to 12, as well as by, for example, the following method (Production Method 15).

[Production Method 15]

By reacting a compound having a leaving group, which is represented by the formula (I-21) and an amine compound represented by the formula (III-18) in the presence of a metal catalyst and a base, a compound represented by the formula (I-31), into which an amino group has been introduce, can be obtained (step 40). The present compound can be converted to carboxylic acid compound (I-32) by de-esterification (step 41). Compound (III-18), which is a starting compound, can be generally synthesized easily by a known method.

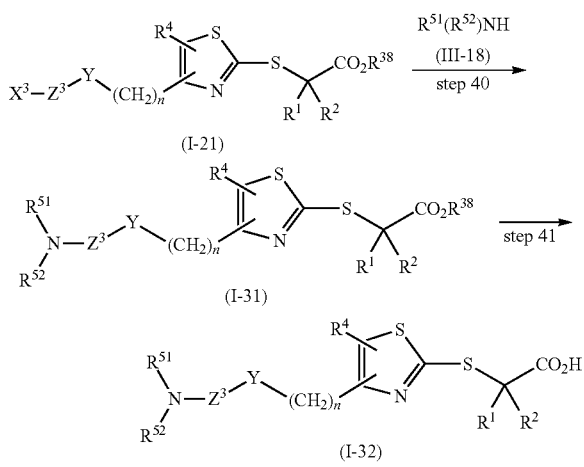

[wherein $R^1$, $R^2$, $R^4$, $R^{38}$, n, Y, $Z^3$ and $X^3$ are as defined above, $R^{51}$ and $R^{52}$ are the same or different and each independently is a hydrogen atom, an alkyl group, a cycloalkyl group, or $R^{51}$ and $R^{52}$ are bonded to each other to form a heterocycle optionally having a carbon atom and a hetero atom.]

In step 40, an amine compound represented by the formula (I-31) can be obtained by amination reaction by reference to the methods described in non-patent reference [J. Org. Chem., 65, 1158 (2000)] and the like. Generally, the reaction is carried out in the presence of a metal catalyst, a metal ligand and a base, in a solvent that does not adversely influence the reaction. As the metal catalyst, for example, tris(dibenzylideneacetone)dipalladium, acetic acid palladium and the like can be mentioned. As the metal ligand, for example, 2-(di-tert-butylphosphino)biphenyl and the like can be mentioned. As the base, for example, cesium carbonate, tripotassium phosphate, sodium tertiary butoxide and the like can be mentioned. The amount of the metal catalyst to be used is, relative to compound (I-21), for example, 0.01 to 1 molar equivalents, preferably 0.05 to 0.5 molar equivalents. The amount of the base to be used is, for example, 1 to 5 molar equivalents, preferably 1 to 2 molar equivalents, relative to compound (I-21). The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene and the like, alcohols such as methanol, ethanol and the like and the like are used. These solvents may be used in a mixture in an appropriate ratio. The amount of $R^{51}(R^{52})NH$ (III-18) to be used is, for example, 1 to 5 molar equivalents, preferably 1 to 3 molar equivalents, relative to compound (I-21).

Step 41 can be performed according to a method similar to that of step 3.

Of the compounds of the formula (I), a compound of the formula (I-34) wherein Z is an aryl group, a heteroaryl group, an arylalkyl group or a heteroarylalkyl group, wherein the aryl group or heteroaryl group has an alkynyl group on its ring, can be produced by the methods shown in Production Methods 1 to 12, as well as by, for example, the following method (Production Method 16).

[Production Method 16]

By reacting a compound having a leaving group, which is represented by the formula (I-21), and a compound represented by the formula (III-19) in the presence of a metal catalyst and a base, a compound represented by the formula (I-33), into which an alkynyl group has been introduced, can be obtained (step 42). The present compound can be converted to carboxylic acid compound (I-34) (step 43) by de-esterification. Compound (III-19), which is a starting compound, can be generally synthesized easily by a known method.

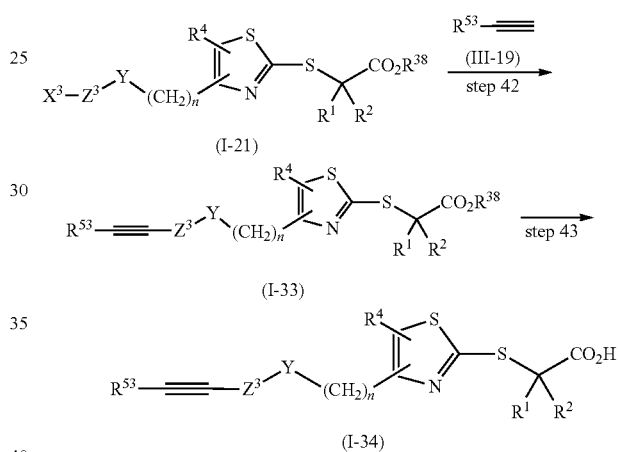

[wherein $R^1$, $R^2$, $R^4$, $R^{38}$, n, Y, $Z^3$ and $X^3$ are as defined above, and $R^{53}$ is an aryl group or a heteroaryl group.]

In step 42, a compound represented by the formula (I-33), into which an alkynyl group has been introduced, can be obtained by alkynylation reaction by reference to the methods described in non-patent reference [Comprehensive Organic Synthesis, Pergamon Press, New York, 3, 521 (1991)] and the like. Generally, the reaction is carried out in the presence of a metal catalyst and a base in a solvent that does not adversely influence the reaction. As the metal catalyst, for example, dichlorobis(triphenylphosphine)palladium and the like can be mentioned. As the base, for example, triethylamine, N,N-diisopropylethylamine, N-methylmorpholine, pyridine and the like can be mentioned. As an additive, a catalytic amount of copper iodide (I) is preferably added. The amount of the metal catalyst to be used is, for example, 0.01 to 1 molar equivalents, preferably 0.05 to 0.5 molar equivalents, relative to compound (I-21). The amount of the base to be used is, for example, 1 to 50 molar equivalents, preferably 10 to 20 molar equivalents, relative to compound (I-21). The reaction temperature is generally from 0° C. to the refluxing temperature of the solvent. As the solvent that does not adversely influence the reaction, ethers such as tetrahydrofuran, dioxane and the like, amides such as N,N-dimethylformamide, N-methyl-2-pyrrolidone and the like, and the like are used. These solvents may be used in a mixture in an appropriate ratio. The amount of the alkynyl compound (III-19) to be used is, for example, 1 to 5 molar equivalents, preferably 1 to 3 molar equivalents, relative to compound (I-21).

Step 43 can be performed according to a method similar to that of step 3.

Of the compounds of the formula (I), compounds of the formula (I-38) and the formula (I-41), wherein Z is a thiazole group or a pyrazole group, and Y is a nitrogen atom can be produced by the methods shown in Production Methods 5 to 11, as well as be produced by, for example, the following methods (Production Methods 17, 18).

[Production Method 17]

By reacting a primary amine compound represented by the formula (II-3) or a secondary amine compound represented by the formula (I-15), which is synthesized by Production Method 8 [represented by the formula (I-35)] and diketene, β-ketocarboxylic acid represented by the formula (III-20) or β-ketoester represented by the formula (III-21), a β-ketoamide compound represented by the formula (I-36) can be obtained (step 44). Moreover, by reacting the present compound and a compound having a hydrazide group, which is represented by the formula (III-22), to give a hydrazone compound, and by using a suitable dehydrating agent, or by dehydrogen sulphide reaction using a suitable sulphating agent in a reaction system via a thioamide compound in the presence of a base, a compound represented by the formula (I-37) wherein Z is a pyrazole ring can be obtained (step 45). The present compound can be converted to carboxylic acid compound (I-38) by de-esterification (step 46). Compounds (III-20), (III-21), (III-22), which are starting compounds, can be generally synthesized easily by a known method.

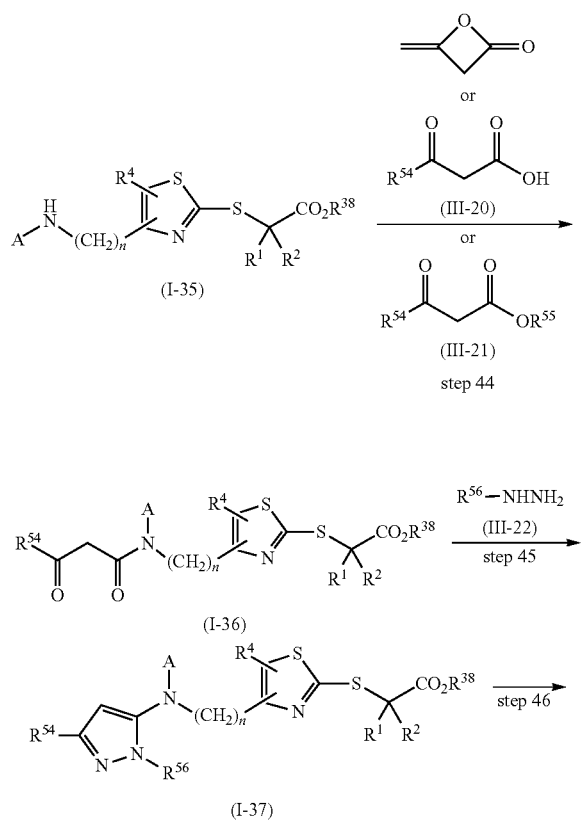

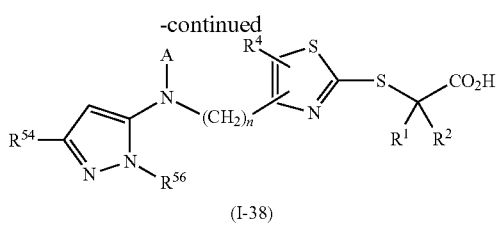

(I-38)

[wherein $R^1$, $R^2$, $R^4$, $R^{38}$ and n are as defined above, A is a hydrogen atom or $R^{42}$ (wherein $R^{42}$ are as defined above), $R^{54}$ is an alkyl group or an aryl group, $R^{55}$ is an alkyl group, $R^{56}$ is an alkyl group or an aryl group.]

When diketene is used as a reaction reagent, step 44 is performed in a solvent that does not adversely influence the reaction. The reaction temperature is generally from 0° C. to room temperature. As the solvent that does not adversely influence the reaction, ethers such as tetrahydrofuran, dioxane and the like, aromatic hydrocarbons such as benzene, toluene and the like, amides such as N,N-dimethylformamide and the like, and the like are used. These solvents may be used in a mixture in an appropriate ratio. When β-ketocarboxylic acid is used as a reaction reagent, step 44 is performed in the same manner as in step 6. When β-ketoester is used as a reaction reagent, step 44 is performed in a solvent that does not adversely influence the reaction. The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene, xylene and the like, and the like are used. These solvents may be used in a mixture in an appropriate ratio.

The hydrazonation step of step 45 is generally performed in a solvent that does not adversely influence the reaction. In this case, an acid or a base catalyst may be co-present. As the acid catalyst, for example, acetic acid, hydrochloric acid, p-toluenesulfonic acid and the like are used. As the base catalyst, for example, sodium methoxide, piperidine and the like are used. The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene and the like, alcohols such as methanol, ethanol and the like and the like are used. These solvents may be used in a mixture in an appropriate ratio. The subsequent cyclization step is generally performed in the presence of a suitable dehydrating agent in a solvent that does not adversely influence the reaction. As the dehydrating agent, for example, phosphorus oxychloride and the like are used. The amount of the dehydrating agent to be used is preferably 1 to 2 equivalent amounts relative to compound (I-36). The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene, xylene and the like and the like are used. These solvents may be used in a mixture in an appropriate ratio. When a sulphating agent is used, the reaction is generally carried out in the presence of a base, in a solvent that does not adversely influence the reaction. As the sulphating agent, for example, diphosphorus pentasulfide, Lawesson's reagent and the like are used. The amount of the sulphating agent to be used is preferably 1 to 2 equivalent amounts, relative to compound (I-36). As the base, for example, alkali metal carbonates such as potassium carbonate, sodium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, N,N-dimethylaniline, 1,8-diazabicyclo[5.4.0]undec-7-en and the like and the like are used. The amount of the base to be used is preferably 1 to 5 molar equivalents relative to compound (I-36). The reaction is generally carried out at 0° C. to the refluxing temperature of the solvent. As the solvent that does not adversely influence the reaction, ethers such as tetrahydrofuran, dioxane and the like, aromatic hydrocarbons such as benzene, toluene, xylene and the like and the like are used. These solvents may be used in a mixture in an appropriate ratio.

Step 46 can be performed according to a method similar to that of step 3.

[Production Method 18]

A secondary amine compound represented by the formula (I-15), which is synthesized by Production Method 8, is converted to a thiourea compound represented by the formula (I-39) (step 47), and this compound is reacted with $\alpha$-haloketone represented by the formula (III-23) to give a thiazole compound represented by the formula (I-40) (step 48). The present compound can be converted to a carboxylic acid compound (I-41) by de-esterification (step 49). Compound (III-23), which is a starting compound, can be generally synthesized easily by a known method.

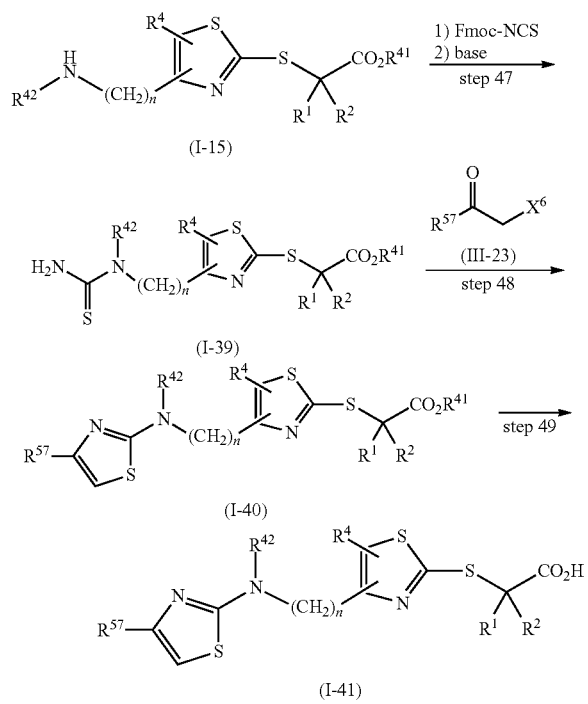

[wherein $R^1$, $R^2$, $R^4$, $R^{41}$, $R^{42}$ and n are as defined above, $R^{57}$ is an alkyl group, a haloalkyl group, an aryl group, a heteroaryl group, $X^6$ is a halogen atom and Fmoc is a 9H-fluorene-9-ylmethyloxycarbonyl group.]

In step 47, by reaction with 9H-fluorene-9-ylmethyloxycarbonyl-isothiocyanate (Fmoc-NCS), a 9H-fluorene-9-ylmethyloxycarbonyl-ureide derivative is obtained, and is treated with a base to give a thiourea compound represented by the formula (I-39). The reaction with Fmoc-NCS is generally carried out in a solvent that does not influence the reaction. The amount of the Fmoc-NCS to be used is preferably 1 to 5 molar equivalents relative to compound (I-15). The reaction temperature is generally −30° C. to 100° C., preferably −10° C. to 50° C. As the solvent that does not adversely influence the reaction, ethers such as diethyl ether, tetrahydrofuran, dioxane and the like, halogenated hydrocarbons such as chloroform, dichloromethane, dichloroethane and the like, amides such as N,N-dimethylformamide, N-methyl-2-pyrrolidone and the like, hydrocarbons such as hexane, benzene, toluene and the like, and the like are used. These solvents may be used in a mixture in an appropriate ratio. The subsequent base treatment step is generally performed in a solvent that does not influence the reaction. As the base, for example, amines such as triethylamine, N,N-diisopropylethylamine, N-methylmorpholine, morpholine, piperidine, 1,8-diazabicyclo[5.4.0]undec-7-en and the like, and the like are used. The amount of the base to be used is preferably 1 to 5 molar equivalents relative to the 9H-fluorene-9-ylmethyloxycarbonylureido derivative obtained earlier. The reaction temperature is generally −30° C. to 100° C., preferably −10° C. to 50° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, alcohols such as methanol, ethanol and the like and the like are used. These solvents may be used in a mixture in an appropriate ratio.

Step 48 is generally performed in a solvent that does not adversely influence the reaction. The amount of the $\alpha$-haloketone (III-23) to be used is preferably 1 to 5 molar equivalents relative to compound (I-39). The reaction temperature is generally −30° C. to 200° C., preferably 0° C. to 150° C. As the solvent that does not adversely influence the reaction, ethers such as tetrahydrofuran, dioxane and the like, aromatic hydrocarbons such as benzene, toluene, xylene and the like, alcohols such as methanol, ethanol, isopropanol and the like, and the like are used. These solvents may be used in a mixture in an appropriate ratio.

Step 49 can be performed according to a method similar to that of step 5.

The following show representative production methods of starting compounds.

The compounds represented by the formulas (II-1), (II-2), (II-3), (II-4) used in the above-mentioned production methods can be produced, for example, by the methods shown in starting compound Production Methods 2 to 5 and using the formula (VI-1) or the formula (VI-1) having a thiol group shown below (obtained by starting compound Production Method 1) as a starting material.

[Starting Compound Production Method 1]

By reacting dithiocarbamate (IV) and an $\alpha$-haloketone compound having an ester group in the structure represented by the formula (V-1) or (V-2), a thiazole compound represented by the formula (VI-1) or (VI-2) can be obtained (step 50). Compounds (IV), (V-1) and (V-2), which are starting compounds, can be generally synthesized easily by a known method.

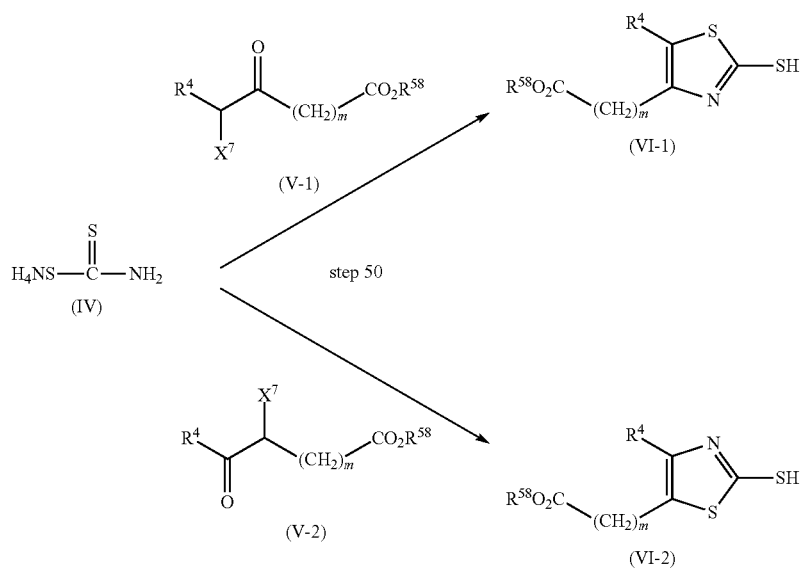

[wherein $R^4$ and m are as defined above, $R^{58}$ is an alkyl group and $X^7$ is a halogen atom.]

Step 50 is generally performed in a solvent that does not adversely influence the reaction and under heating. The amount of the dithiocarbamate (IV) to be used is preferably 1 to 5 molar equivalents relative to $_\alpha$-haloketone (V-1) or (V-2). The reaction temperature is generally −30° C. to 200° C., preferably 0° C. to 150° C. As the solvent that does not adversely influence the reaction, ethers such as tetrahydrofuran, dioxane and the like, aromatic hydrocarbons such as benzene, toluene, xylene and the like, alcohols such as methanol, ethanol, isopropanol and the like, and the like are used. These solvents may be used in a mixture in an appropriate ratio.

the above-mentioned starting compound by, for example, the following two kinds of methods. The first is a method (step 52) comprising reacting an $_\alpha$-haloester compound represented by the formula (VII) in the presence of a base to give a diester compound represented by the formula (II-5) (step 51), and converting the present compound to monocarboxylic acid compound (II-4) by mono-de-esterification. The second is a method (step 54) comprising de-esterifying a thiazole compound represented by the formula (VI-3) to give a carboxylic acid compound (VI-4) (step 53), and reacting an $_\alpha$-haloester compound represented by the formula (VII) in the presence of a base to convert the compound to carboxylic acid compound (II-4) (step 54). The $_\alpha$-haloester compound (VII), which is a starting compound, can be generally synthesized easily by a known method.

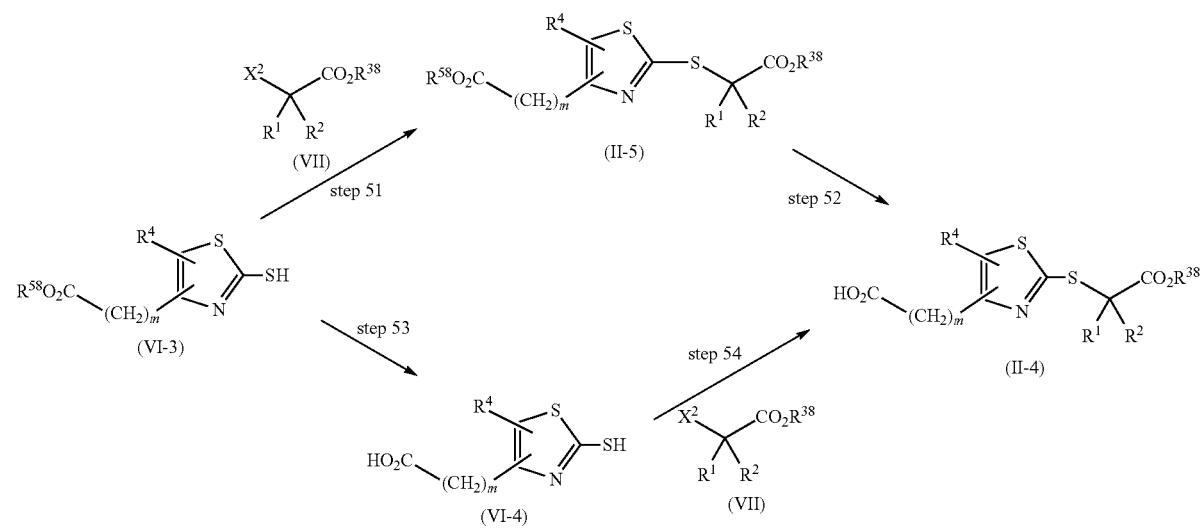

[Starting Compound Production Method 2]

A carboxylic acid compound represented by the formula (II-4) can be produced from a thiazole compound represented by the formula (VI-3) synthesized by Production Method 1 of

[wherein $R^1$, $R^2R^4$, $R^{38}$, $R^{58}$, $X^2$ and m are as defined above.]

Step 51 is generally performed in the presence of a base, in a solvent that does not adversely influence the reaction. As the base, for example, alkali metal carbonates such as potassium carbonate, sodium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, piperidine, pyrrolidine, N-methylmorpholine, pyridine, N,N-dimethylaniline, 1,8-diazabicyclo[5.4.0]undec-7-en and the like, and the like are used. The amount of the base to be used is preferably 1 to 5 molar equivalents relative to compound (VI-3). The amount of the α-haloester (VII) to be used is preferably 1 to 3 molar equivalents relative to compound (VI-3). The reaction temperature is generally −50° C. to 200° C., preferably −10° C. to 100° C. As a solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, alcohols such as methanol, ethanol and the like, water and the like are used. These solvents may be used in a mixture in an appropriate ratio.

Step 52 is generally performed in the presence of a base, in an aqueous solvent. As the base, for example, alkali metal carbonates such as potassium carbonate, sodium carbonate and the like, alkali metal alkoxides such as sodium methoxide, sodium ethoxide and the like, alkali metal hydroxides such as potassium hydroxide, sodium hydroxide, lithium hydroxide and the like, and, the like are used. The amount of the base to be used is generally an excess amount, preferably 1 to 5 equivalent amounts, relative to compound (II-5). As the aqueous solvent, for example, a mixed solvent of one or more kinds of solvents selected from alcohols such as methanol, ethanol and the like, ethers such as tetrahydrofuran, dioxane and the like, dimethyl sulfoxide, acetone and the like and water, and the like are used. The reaction temperature is generally −20° C. to 150° C., preferably −10° C. to 100° C.

Step 53 can be performed according to a method similar to that of step 52.

Step 54 can be performed according to a method similar to that of step 51.

[Starting Compound Production Method 3]

An alcohol compound represented by the formula (II-1) can be produced by reacting a carboxylic acid compound represented by the formula (II-4), which is synthesized in the above-mentioned starting compound Production Method 2, in the presence of a reducing agent (step 55).

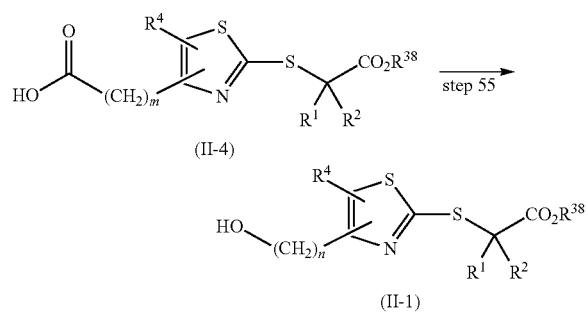

[wherein $R^1$, $R^2$, $R^4$, $R^{38}$, n and m are as defined above, and n and m show the relationship of n=m+1.]

Step 55 can be performed according to a method similar to that of step 12.

[Starting Compound Production Method 4]

A compound having a leaving group, which is represented by the formula (II-2), can be produced by sulfonylating or halogenating an alcohol compound represented by the formula (II-1) synthesized in the above-mentioned starting compound Production Method 3 (step 56).

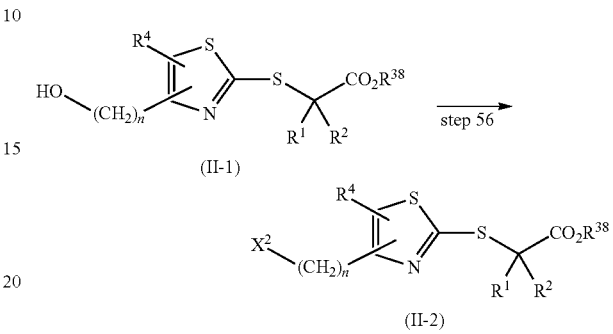

[wherein $R^1$, $R^2$, $R^4$, $R^{38}$, $X^2$ and n are as defined above.]

In step 56, sulfonic acid ester can be generally obtained by reacting the compound such as methanesulfonyl chloride, p-toluenesulfonyl chloride, trifluoromethanesulfonyl chloride and the like in the presence of a base in a solvent that does not adversely influence the reaction. As the base, for example, alkali metal carbonates such as potassium carbonate, sodium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, N,N-dimethylaniline, 4-dimethylaminopyridine, 1,8-diazabicyclo[5.4.0]undec-7-en and the like, and the like are used. The amount of the sulfonyl chloride to be used is preferably 1 to 5 molar equivalents relative to compound (II-1). The amount of the base to be used is preferably 1 to 5 molar equivalents relative to compound (II-1). The reaction temperature is generally −50° C. to 200° C., preferably −30° C. to 80° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, and the like are used. These solvents may be used in a mixture in an appropriate ratio. The thus-obtained sulfonic acid ester can be converted to a halogen compound using various halogenating agents. For chlorination, for example, lithium chloride, pyridine hydrochloride and the like are reacted and, for bromination, for example, hydrobromic acid, sodium bromide, calcium bromide and the like are reacted, in a solvent that does not adversely influence the reaction to give the corresponding halogen compound. As the solvent that does not adversely influence the reaction, alcohols such as methanol, ethanol and the like, amides such as N,N-dimethylformamide, N-methyl-2-pyrrolidone and the like, sulfoxides such as dimethyl sulfoxide and the like, and the like are used.

[Starting Compound Production Method 5]

The primary amine compound represented by the formula (II-3) can be produced from an alcohol compound represented by the formula (II-1), which is synthesized by the above-mentioned starting compound Production Method 3. There are a number of known methods for converting an alcohol compound to a primary amine compound and, for example, the method described in non-patent reference [Comprehensive Organic Transformation, VCH Publishers, Inc. 1989] can be referred to. For example, a hydroxyl group of an alcohol compound is, for example, sulfonylated or halogenated to give a compound having a leaving group and, for example, reacted with potassium phthalimide, hexamethyltetramine, sodium azide, sodium diformylimide, di-tert-butyliminodicarboxylic acid and the like to give a compound, into which a nitrogen atom has been introduced, can be obtained. Then the compound can be converted to a primary amine compound by appropriately performing hydrolysis, reduction and the like. In the following, one example of the production method of the primary amine compound represented by the formula (II-3) via the formula (II-2) synthesized in Production Method 4 is shown. By reacting a compound having a leaving group and synthesized in Production Method 4, which is represented by the formula (II-2), with potassium phthalimide, a compound (II-7), into which a nitrogen atom has been introduced, can be obtained (step 57). Subsequently, the compound is deprotected to give a primary amine compound (II-3) (step 58).

erally 0° C. to 120° C. As the solvent that does not adversely influence the reaction, alcohols such as methanol, ethanol and the like, and the like are used.

Of the primary amine compounds represented by the formula (II-3), a primary amine compound represented by the formula (II-8) can also be produced by the above-mentioned starting compound Production Method 5, as well as by, for example, the following method.

[Starting Compound Production Method 6]

By reacting a ketone compound having a leaving group in the structure represented by the formula (V-3) with potassium phthalimide, a compound, into which a nitrogen atom has been introduced, and which is represented by the formula (VI-5), can be obtained (step 59). Subsequently, the compound is subjected to a bromination reaction to give an $\alpha$-bromoketone compound represented by the formula (VI-6) (step 60). Furthermore, by reacting the compound with dithiocarbamate represented by (IV), a thiazole compound represented by the formula (VI-7) can be obtained (step 61). Moreover, by reacting the compound with an $\alpha$-haloester compound represented by the formula (VII) in the presence of a base, an ester compound represented by the formula (II-7) is obtained (step 62), which is deprotected to give a primary amine compound (II-8) (step 63). Compounds (IV), (V-3) or (VII), which are starting compounds, can be generally synthesized easily by a known method.

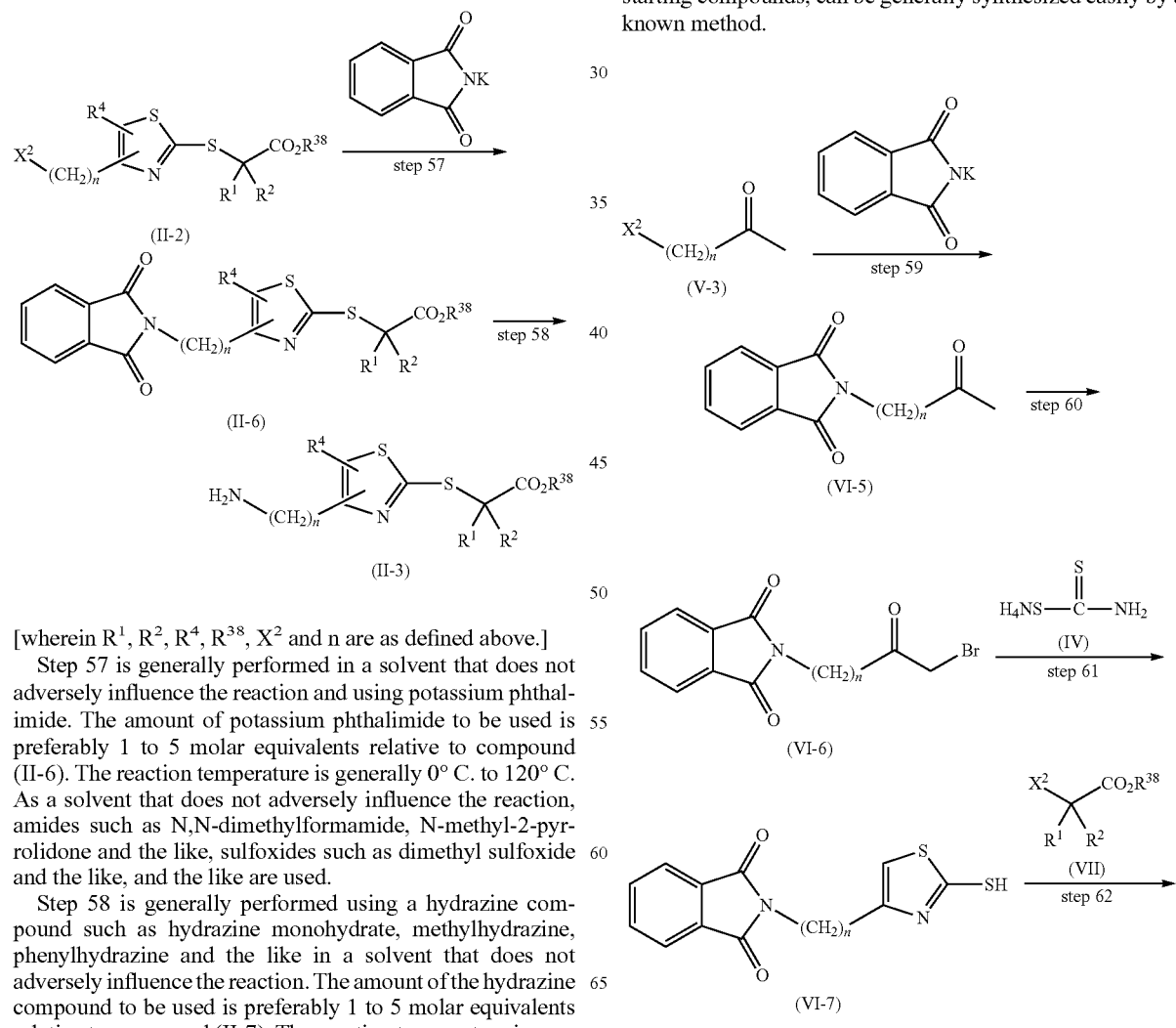

[wherein $R^1$, $R^2$, $R^4$, $R^{38}$, $X^2$ and n are as defined above.]

Step 57 is generally performed in a solvent that does not adversely influence the reaction and using potassium phthalimide. The amount of potassium phthalimide to be used is preferably 1 to 5 molar equivalents relative to compound (II-6). The reaction temperature is generally 0° C. to 120° C. As a solvent that does not adversely influence the reaction, amides such as N,N-dimethylformamide, N-methyl-2-pyrrolidone and the like, sulfoxides such as dimethyl sulfoxide and the like, and the like are used.

Step 58 is generally performed using a hydrazine compound such as hydrazine monohydrate, methylhydrazine, phenylhydrazine and the like in a solvent that does not adversely influence the reaction. The amount of the hydrazine compound to be used is preferably 1 to 5 molar equivalents relative to compound (II-7). The reaction temperature is gen- -continued

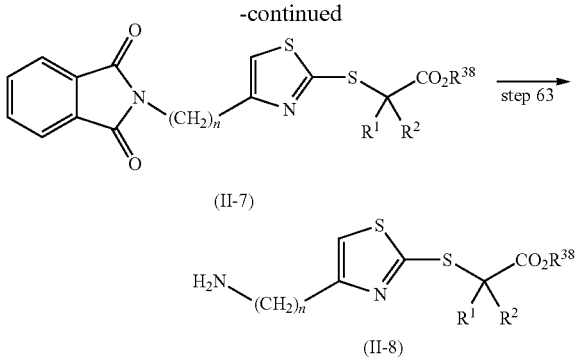

(II-7)

(II-8)

[wherein $R^1$, $R^2$, $R^{38}$, n and $X^2$ are as defined above.]

Step 59 can be performed according to a method similar to that of step 57.

Step 60 is generally performed using a suitable brominating agent in a solvent that does not adversely influence the reaction. As the brominating agent, bromine, pyridinium bromide perbromide, benzyltrimethylammonium tribromide, phenyltrimethylammonium tribromide and the like can be mentioned. The amount of the brominating agent to be used is preferably 1 to 5 molar equivalents relative to compound (IV-5). The reaction temperature is generally 0° C. to 120° C. As the solvent that does not adversely influence the reaction, ethers such as tetrahydrofuran, dioxane and the like, alcohols such as methanol, ethanol and the like, acetic acid and the like are used.

Step 61 can be performed according to a method similar to that of step 50.

Step 62 can be performed according to a method similar to that of step 51.

Step 63 can be performed according to a method similar to that of step 58.

The thus-produced carboxylic acid derivative containing a thiazole ring of the formula (I) of the present invention can be recovered at any purity by appropriately applying a known separation and purification means, for example, concentration, extraction, chromatography, reprecipitation, recrystallization and the like.

Where necessary, the thus-obtained compound of the formula (I) can be converted to a salt thereof by treating with an inorganic acid such as hydrochloric acid, hydrobromic acid and the like, organic acid such as trifluoroacetic acid, acetic acid, methanesulfonic acid, benzenesulfonic acid and the like, alkali metal such as sodium, potassium, calcium and the like, organic base such as dicyclohexylamine and the like, amino acid such as lysine, arginine and the like.

The compound of the formula (I) of the present invention is useful as an agent for the prophylaxis and/or treatment of hyperlipidemia, which is effective and highly safe for the prophylaxis of arteriosclerotic diseases, particularly coronary arteriosclerosis.

When compound (I) of the present invention or an acid addition salt thereof is used as the aforementioned pharmaceutical agent, it can be orally or parenterally administered as it is or in the form of a powder, granule, tablet, capsule, injection and the like by appropriately admixing with a pharmacologically acceptable carrier, excipient, diluent and the like. The above-mentioned preparation contains an effective amount of compound (I) or a pharmacologically acceptable salt thereof.

The dose of compound (I) or a pharmacologically acceptable salt thereof varies depending on the administration route, target disease, symptom, body weight and age of patient, and compounds to be used, but can be appropriately determined according to the administration object. Generally, for an oral administration to an adult, 0.01 to 1000 mg/kg body weight/day, preferably 0.05 to 500 mg/kg body weight/day, is preferably administered at once or in several portions a day.

The compound of the present invention (I) can be administered to a single subject simultaneously with other antihyperlipemia agent and the like, or in a staggered manner. As antihyperlipemia agent, statin compounds that are cholesterol synthase inhibitors, squalene synthase inhibitors, fibrate compounds having a triglyceride lowering action, and the like can be mentioned. When the compound of the present invention is used in combination with multiple agents, the mixing ratio thereof can be appropriately determined according to the administration subject, age and body weight of administration subject, symptom, administration time, dosage form, administration method, combination and the like.

EXAMPLES

The present invention is explained in detail in the following by referring to Examples, which are not to be construed as limitative.

The chemical shift of $^1$H-NMR is shown by parts per million (ppm) of relative delta (δ) value, using tetramethylsilane (TMS) as the internal standard. The coupling constant is shown in hertz (Hz), and the obvious multiplicity is shown by s (singlet), d (doublet), t (triplet), q (quartet), quint (quintet), m (multiplet), dd (doublet of doublets), td (triplet of doublets), brs (broad singlet) and the like. Column chromatography was performed using silica gel manufactured by Fuji-Silysia Chemical Ltd.

Example 1

(2-mercapto-1,3-thiazol-4-yl)acetic acid ethyl ester

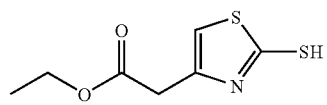

An ammonium salt (102 g) of dithiocarbamic acid was dissolved in ethanol (700 mL), and a solution of 4-chloro-3-oxobutanoic acid ethyl ester (152 g) in ethanol (200 mL) was added dropwise under ice-cooling over 30 min. The temperature was gradually raised, and the mixture was heated under reflux for 2 hr. The reaction solution was concentrated under reduced pressure, water (1 L) was added thereto, and the precipitated solid was collected by filtration. This solid was dissolved in ethyl acetate (4 L), and the mixture was washed with water (2 L) and dried over anhydrous magnesium sulfate. The solvent was evaporated under reduced pressure. Diethyl ether (500 mL) was added to the obtained solid, and the solid was washed by suspending and collected by filtration to give the title compound (165 g) as a slightly yellow solid.

¹H-NMR (CDCl₃, 300 MHz) δ: 1.31 (3H, t, J=7.2 Hz), 3.59 (2H, s), 4.23 (2H, q, J=7.2 Hz) 6.46 (1H, s).

Example 2

2-{[4-(2-ethoxy-2-oxoethyl)-1,3-thiazol-2-yl]thio}-2-methylpropionic acid tert-butyl ester

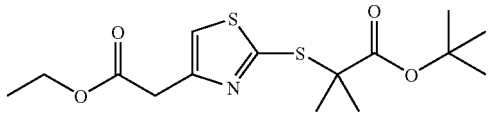

(2-Mercapto-1,3-thiazol-4-yl)acetic acid ethyl ester (88.6 g) synthesized in Example 1 and tert-butyl 2-bromo-2-methylpropionate (105.3 g) were dissolved in N,N-dimethylformamide (700 mL), potassium carbonate (66.3 g) was added, and the mixture was stirred at room temperature for 8 hr. Water (1 L) was added to the reaction mixture, and the mixture was extracted with ethyl acetate (1 L). The organic layer was washed with saturated brine, and dried over hydrous magnesium sulfate. The solvent was evaporated under reduced pressure to give the title compound (150 g) as a slightly brown oil. The present compound was used in the next step without particular purification.

¹H-NMR (CDCl₃, 300 MHz) δ: 1.27 (3H, t, J=7.2 Hz), 1.44 (9H, s), 1.57 (6H, s), 3.83 (2H, s), 4.18 (2H, q, J=7.2 Hz) 7.27 (1H, s).

Example 3

{2-[(2-tert-butoxy-1,1-dimethyl-2-oxoethyl)thio]-1,3-thiazol-4-yl}acetic acid

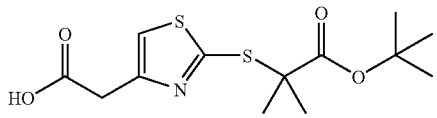

2-{[4-(2-Ethoxy-2-oxoethyl)-1,3-thiazol-2-yl]thio}-2-methylpropionic acid tert-butyl ester (150 g) synthesized in Example 2 was dissolved in methanol (700 mL), a 1N aqueous sodium hydroxide solution (448 mL) was added at room temperature, and the mixture was stirred for 3 hr. The reaction solution was concentrated under reduced pressure, an aqueous 10% citric acid solution (1 L) was added, and the mixture was extracted with ethyl acetate (1 L). The organic layer was washed three times with water (500 mL) and dried over anhydrous magnesium sulfate. The solvent was evaporated under reduced pressure to give the title compound (123 g) as a slightly yellow solid.

¹H-NMR (CDCl₃, 300 MHz) δ: 1.44 (9H, s), 1.59 (6H, s), 3.86 (2H, s) 7.22 (1H, s).

Example 4

2-{[4-(2-hydroxyethyl)-1,3-thiazol-2-yl]thio}-2-methylpropionic acid tert-butyl ester

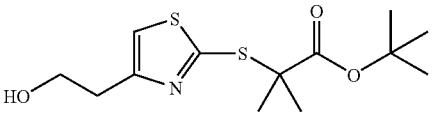

{2-[(2-tert-Butoxy-1,1-dimethyl-2-oxoethyl)thio]-1,3-thiazol-4-yl}acetic acid (127 g) synthesized in Example 3 was added to 1M-borane/tetrahydrofuran complex (800 mL) under ice-cooling, and the mixture was stirred at room temperature for 8 hr. The reaction mixture was ice-cooled, methanol (400 mL) was added dropwise. After warming to room temperature, the mixture was stirred for 1 hr. Then, saturated aqueous ammonia chloride (300 mL) was added, and the mixture was stirred at room temperature for 1 hr. The reaction mixture was concentrated under reduced pressure, poured into water, and the mixture was extracted with ethyl acetate. The organic layer was washed with saturated brine and dried over anhydrous sodium sulfate. The solvent was evaporated under reduced pressure and the residue was purified by silica gel chromatography (elution solvent; hexane:ethyl acetate=1:1) to give the title compound (110 g) as a slightly yellow oil.

¹H-NMR (CDCl₃, 300 MHz) δ: 1.43 (9H, s), 1.59 (6H, s), 2.98 (2H, t, J=5.7 Hz), 3.04-3.10 (1H, m), 3.92-3.97 (2H, m), 7.02 (1H, s)

Example 5

2-methyl-2-[(4-{2-[(methylsulfonyl)oxy]ethyl}-1,3-thiazol-2-yl)thio]propionic acid tert-butyl ester

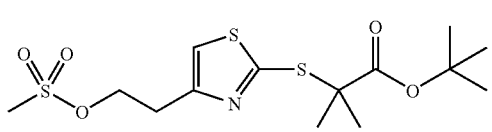

2-{[4-(2-Hydroxyethyl)-1,3-thiazol-2-yl]thio}-2-methylpropionic acid tert-butyl ester (98 g) synthesized in Example 4 and triethylamine (50 mL) were dissolved in dichloromethane (800 mL), methanesulfonyl chloride (38.8 g) was added dropwise under ice-cooling, and the mixture was stirred for 2 hr at 0° C. Water was added to the reaction mixture, and the organic layer was partitioned. The organic layer was washed with saturated brine and dried over anhydrous sodium sulfate, and the solvent was evaporated. The title compound was quantitatively obtained as a crude brown oil and used as it was for the next step.

$^1$H-NMR (CDCl$_3$, 300 MHz) δ: 1.44 (9H, s), 1.58 (6H, s), 2.95 (3H, s), 3.20 (2H, t, J=6.5 Hz), 4.56 (2H, t, J=6.5 Hz), 7.14 (1H, s).

Example 6

2-methyl-2-{[4-(2-phthalimidoethyl)-1,3-thiazol-2-yl]thio}propionic acid tert-butyl ester

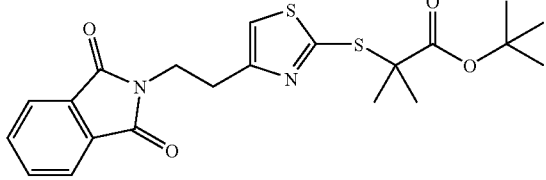

2-Methyl-2-[(4-{2-[(methylsulfonyl)oxy]ethyl}-1,3-thiazol-2-yl)thio]propionic acid tert-butyl ester (123 g) synthesized in Example 5 was dissolved in N,N-dimethylformamide (800 mL), potassium phthalimide (59.7 g) was added thereto and the mixture was stirred for 2 hr at 85° C. Water was added to the reaction mixture, and the mixture was extracted with ethyl acetate. The organic layer was washed with saturated brine and dried over anhydrous sodium sulfate. The solvent was evaporated under reduced pressure and the residue was purified by silica gel chromatography (elution solvent; hexane:ethyl acetate=3:1) to give the title compound (136 g) as a slightly yellow oil.

$^1$H-NMR (CDCl$_3$, 300 MHz) δ: 1.44 (9H, s), 1.55 (6H, s), 3.17 (2H, t, J=7.3 Hz), 4.56 (2H, t, J=7.3 Hz), 7.07 (1H, s), 7.69-7.72 (2H, m), 7.81-7.84 (2H, m).

Example 7

2-{[4-(2-aminoethyl)-1,3-thiazol-2-yl]thio}-2-methylpropionic acid tert-butyl ester

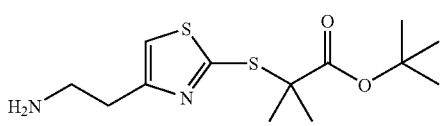

2-Methyl-2-{[4-(2-phthalimidoethyl)-1,3-thiazol-2-yl]thio}propionic acid tert-butyl ester (136 g) synthesized in Example 6 was dissolved in ethanol (800 mL), hydrazine monohydrate (47.2 g) was added, and the mixture was refluxed for 4 hr. White precipitate was filtered off from the reaction mixture, and the filtrate was concentrated under reduced pressure. Water was added thereto, and the mixture was extracted with dichloroethane. The organic layer was washed with saturated brine and dried over anhydrous sodium sulfate. The solvent was evaporated under reduced pressure to give the title compound (77.6 g) as a brown oil.

$^1$H-NMR (CDCl$_3$, 300 MHz) δ: 1.43 (9H, s), 1.58 (6H, s), 2.89 (2H, t, J=6.6 Hz), 3.06 (2H, t, J=6.6 Hz), 7.03 (1H, s).

Example 8

2-[(2-tert-butoxy-1,1-dimethyl-2-oxoethyl)thio]-1,3-thiazole-4-carboxylic acid ethyl ester

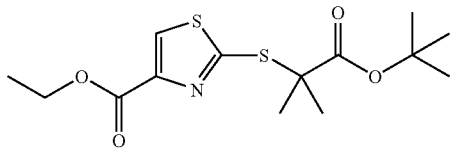

The title compound was obtained using 3-bromo-2-oxopropionic acid as a starting material and by operations similar to those of Example 1 and Example 2.

$^1$H-NMR (CDCl$_3$, 300 MHz) δ: 1.39 (3H, t, J=7.5 Hz), 1.42 (9H, s), 1.61 (6H, s), 4.40 (2H, q, J=7.5 Hz), 8.21 (1H, s).

Example 9

2-[(2-tert-butoxy-1,1-dimethyl-2-oxoethyl)thio]-1,3-thiazole-4-carboxylic acid

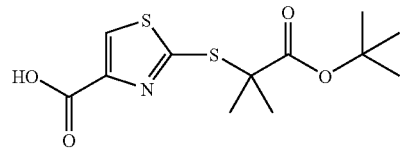

The title compound was obtained using 2-[(2-tert-butoxy-1,1-dimethyl-2-oxoethyl)thio]-1,3-thiazole-4-carboxylic acid ethyl ester synthesized in Example 8 as a starting material and by an operation similar to that of Example 2.

$^1$H-NMR (CDCl$_3$, 300 MHz) δ: 1.43 (9H, s), 1.64 (6H, s), 8.26 (1H, s).

Example 10

2-{[4-(hydroxymethyl)-1,3-thiazol-2-yl]thio}-2-methylpropionic acid tert-butyl ester

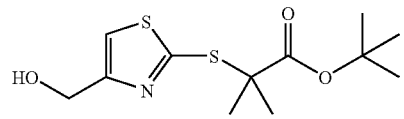

The title compound was obtained using 2-[(2-tert-butoxy-1,1-dimethyl-2-oxoethyl)thio]-1,3-thiazole-4-carboxylic acid synthesized in Example 9 as a starting material and by an operation similar to that of Example 3.

¹H-NMR (CDCl₃, 300 MHz) δ: 1.43 (9H, s), 1.58 (6H, s), 4.75 (2H, s), 7.26 (1H, s).

Example 11

2-methyl-2-[(4-{[(methylsulfonyl)oxy]methyl}-1,3-thiazol-2-yl)thio]propionic acid tert-butyl ester

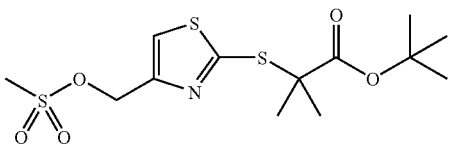

The title compound was obtained using 2-{[4-(hydroxymethyl)-1,3-thiazol-2-yl]thio}-2-methylpropionic acid tert-butyl ester synthesized in Example 10 as a starting material and by an operation similar to that of Example 4.

¹H-NMR (CDCl₃, 300 MHz) δ: 1.43 (9H, s), 1.60 (6H, s), 3.04 (3H, s), 5.30 (2H, s), 7.46 (1H, s).

Example 12

2-methyl-2-{[4-(phthalimidomethyl)-1,3-thiazol-2-yl]thio}propionic acid tert-butyl ester

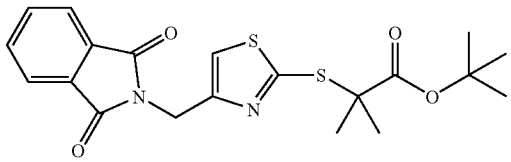

The title compound was obtained using 2-methyl-2-[(4-{[(methylsulfonyl)oxy]methyl}-1,3-thiazol-2-yl)thio]propionic acid tert-butyl ester synthesized in Example 11 as a starting material and by an operation similar to that of Example 5.

¹H-NMR (CDCl₃, 300 MHz) δ: 1.38 (9H, s), 1.56 (6H, s), 4.99 (2H, s), 7.18 (1H, s), 7.71-7.75 (2H, m), 7.85-7.89 (2H, m).

Example 13

2-{[4-(aminomethyl)-1,3-thiazol-2-yl]thio}-2-methylpropionic acid tert-butyl ester

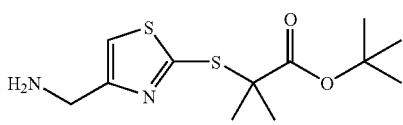

The title compound was obtained using 2-methyl-2-{[4-(phthalimidomethyl)-1,3-thiazol-2-yl]thio}propionic acid tert-butyl ester synthesized in Example 12 as a starting material and by an operation similar to that of Example 6.

¹H-NMR (CDCl₃, 300 MHz) δ: 1.44 (9H, s), 1.59 (6H, s), 3.95 (2H, s), 7.13 (1H, s).

Example 14

2-{[4-(2-ethoxy-2-oxoethyl)-5-methyl-1,3-thiazol-2-yl]thio}-2-methylpropionic acid tert-butyl ester

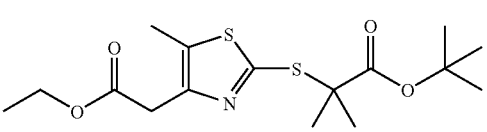

The title compound was obtained using 4-bromo-3-oxopentanoic acid ethyl ester as a starting material and by operations similar to those of Example 1 and Example 2.

¹H-NMR (CDCl₃, 300 MHz) δ: 1.23 (3H, t, J=7.3 Hz), 1.44 (9H, s), 1.53 (6H, s), 2.38 (3H, s), 3.72 (2H, s), 4.13 (2H, q, J=7.3 Hz).

Example 15

{2-[(2-tert-butoxy-1,1-dimethyl-2-oxoethyl)thio]-5-methyl-1,3-thiazol-4-yl}acetic acid

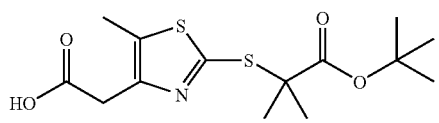

The title compound was obtained using 2-{[4-(2-ethoxy-2-oxoethyl)-5-methyl-1,3-thiazol-2-yl]thio}-2-methylpropionic acid tert-butyl ester synthesized in Example 14 as a starting material and by an operation similar to that of Example 2.

¹H-NMR (CDCl₃, 300 MHz) δ: 1.44 (9H, s), 1.56 (6H, s), 2.38 (3H, s), 3.75 (2H, s).

Example 16

2-{[4-(2-hydroxyethyl)-5-methyl-1,3-thiazol-2-yl]thio}-2-methylpropionic acid tert-butyl ester

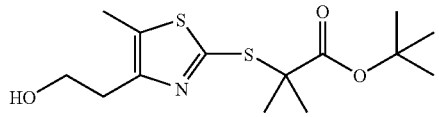

The title compound was obtained using {2-[(2-tert-butoxy-1,1-dimethyl-2-oxoethyl)thio]-5-methyl-1,3-thiazol-4-yl}acetic acid synthesized in Example 15 as a starting material and by an operation similar to that of Example 3.

¹H-NMR (CDCl₃, 300 MHz) δ: 1.44 (9H, s), 1.55 (6H, s), 2.35 (3H, s), 2.84 (2H, t, J=5.6 Hz), 3.41-3.47 (1H, m), 3.90-3.97 (2H, m).

Example 17

2-methyl-2-[(5-methyl-4-{2-[(methylsulfonyl)oxy]ethyl}-1,3-thiazol-2-yl)thio]propionic acid tert-butyl ester

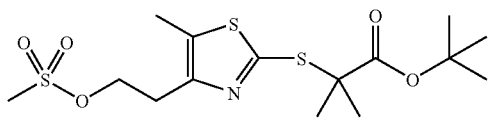

The title compound was obtained using 2-{[4-(2-hydroxyethyl)-5-methyl-1,3-thiazol-2-yl]thio}-2-methylpropionic acid tert-butyl ester synthesized in Example 16 as a starting material and by an operation similar to that of Example 4.

¹H-NMR (CDCl₃, 300 MHz) δ: 1.45 (9H, s), 1.55 (6H, s), 2.39 (3H, s), 2.93 (3H, s), 3.09 (2H, t, J=6.6 Hz), 4.53 (2H, t, J=6.6 Hz).

Example 18

2-methyl-2-{[5-methyl-4-(phthalimidoethyl)-1,3-thiazol-2-yl]thio}propionic acid tert-butyl ester

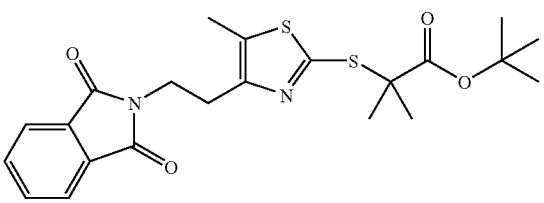

The title compound was obtained using 2-methyl-2-[(5-methyl-4-{2-[(methylsulfonyl)oxy]ethyl}-1,3-thiazol-2-yl)thio]propionic acid tert-butyl ester synthesized in Example 17 as a starting material and by an operation similar to that of Example 5.

¹H-NMR (CDCl₃, 300 MHz) δ: 1.45 (9H, s), 1.50 (6H, s), 2.34 (3H, s), 3.05 (2H, t, J=7.5 Hz), 4.00 (2H, t, J=7.5 Hz), 7.68-7.72 (2H, m), 7.79-7.84 (2H, m).

Example 19

2-{[4-(2-aminoethyl)-5-methyl-1,3-thiazol-2-yl]thio}-2-methylpropionic acid tert-butyl ester

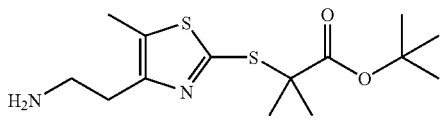

The title compound was obtained using 2-methyl-2-{[5-methyl-4-(phthalimidoethyl)-1,3-thiazol-2-yl]thio}propionic acid tert-butyl ester synthesized in Example 18 as a starting material and by an operation similar to that of Example 6.

¹H-NMR (CDCl₃, 300 MHz) δ: 1.45 (9H, s), 1.55 (6H, s), 2.37 (3H, s), 2.79 (2H, t, J=6.6 Hz), 3.04 (2H, t, J=6.6 Hz).

Example 20

{2-[(2-tert-butoxy-1,1-dimethyl-2-oxoethyl)thio]-4-methyl-1,3-thiazol-5-yl}acetic acid

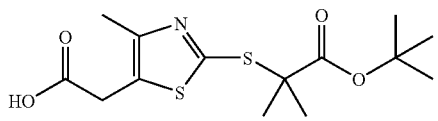

Commercially available (2-mercapto-4-methyl-1,3-thiazol-5-yl)acetic acid (15 g) was dissolved in methanol (360 mL) and 1N aqueous sodium hydroxide solution (174 mL), 2-bromo-2-methylpropionic acid tert-butyl ester (19.4 g) was added, and the mixture was stirred at 60° C. for 6 hr. The reaction mixture was concentrated, the residue was dissolved in water, and the mixture was acidified with 10% aqueous citric acid solution. The precipitated solid was collected by filtration, and dried under reduced pressure to give the title compound (25 g) as a white solid.

¹H-NMR (CDCl₃, 300 MHz) δ: 1.43 (9H, s), 1.56 (6H, s), 2.37 (3H, s), 3.77 (2H, s).

Example 21

2-{[5-(2-hydroxyethyl)-4-methyl-1,3-thiazol-2-yl]thio}-2-methylpropionic acid tert-butyl ester

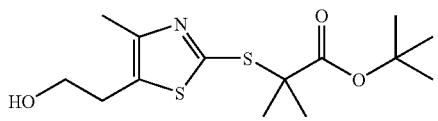

The title compound was obtained using {2-[(2-tert-butoxy-1,1-dimethyl-2-oxoethyl)thio]-4-methyl-1,3-thiazol-5-yl}acetic acid synthesized in Example 20 as a starting material and by an operation similar to that of Example 3.

¹H-NMR (CDCl₃, 300 MHz) δ: 1.44 (9H, s), 1.56 (6H, s), 2.37 (3H, s), 2.97 (2H, t, J=6.3 Hz), 3.79-3.84 (2H, m).

Example 22

2-methyl-2-[(4-methyl-5-{2-[(methylsulfonyl)oxy]ethyl}-1,3-thiazol-2-yl)thio]propionic acid tert-butyl ester

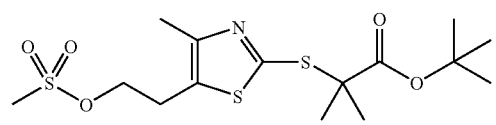

The title compound was obtained using 2-{[5-(2-hydroxyethyl)-4-methyl-1,3-thiazol-2-yl]thio}-2-methylpropionic acid tert-butyl ester synthesized in Example 21 as a starting material and by an operation similar to that of Example 4.

¹H-NMR (CDCl₃, 300 MHz) δ: 1.45 (9H, s), 1.56 (6H, s), 2.38 (3H, s), 2.98 (3H, s), 3.18 (2H, t, J=6.6 Hz), 4.34 (2H, t, J=6.6 Hz).

Example 23

2-methyl-2-{[4-methyl-5-(phthalimidoethyl)-1,3-thiazol-2-yl]thio}propionic acid tert-butyl ester

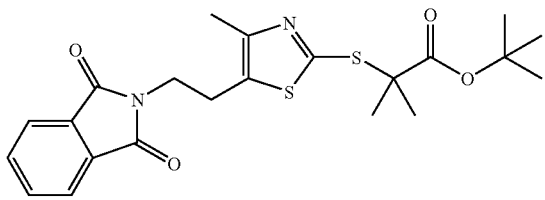

The title compound was obtained using 2-methyl-2-[(4-methyl-5-{2-[(methylsulfonyl)oxy]ethyl}-1,3-thiazol-2-yl)thio]propionic acid tert-butyl ester synthesized in Example 22 as a starting material and by an operation similar to that of Example 5.

¹H-NMR (CDCl₃, 300 MHz) δ: 1.42 (9H, s), 1.52 (6H, s), 2.35 (3H, s), 3.12 (2H, t, J=7.5 Hz), 3.89 (2H, t, J=7.5 Hz), 7.71-7.75 (2H, m), 7.82-7.85 (2H, m).

Example 24

2-{[5-(2-aminoethyl)-4-methyl-1,3-thiazol-2-yl]thio}-2-methylpropionic acid tert-butyl ester

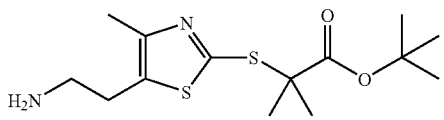

The title compound was obtained using 2-methyl-2-{[4-methyl-5-(phthalimidoethyl)-1,3-thiazol-2-yl]thio}propionic acid tert-butyl ester synthesized in Example 23 as a starting material and by an operation similar to that of Example 6.

¹H-NMR (CDCl₃, 300 MHz) δ: 1.44 (9H, s), 1.56 (6H, s), 2.36 (3H, s), 2.82-2.87 (2H, m), 2.91-2.97 (2H, m).

Example 25

2-[(2-tert-butoxy-1,1-dimethyl-2-oxoethyl)thio]-4-methyl-1,3-thiazole-5-carboxylic acid ethyl ester

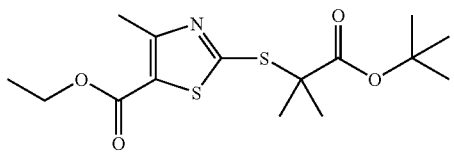

The title compound was obtained using 2-chloro-3-oxobutanoic acid ethyl ester as a starting material and by operations similar to those of Example 1 and Example 2.

¹H-NMR (CDCl₃, 300 MHz) δ: 1.35 (3H, t, J=7.2 Hz), 1.44 (9H, s), 1.64 (6H, s), 2.68 (3H, s), 4.31 (2H, q, J=7.2 Hz).

Example 26

2-[(2-tert-butoxy-1,1-dimethyl-2-oxoethyl)thio]-4-methyl-1,3-thiazole-5-carboxylic acid

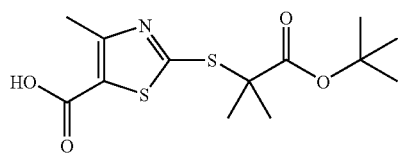

The title compound was obtained using 2-[(2-tert-butoxy-1,1-dimethyl-2-oxoethyl)thio]-4-methyl-1,3-thiazole-5-carboxylic acid ethyl ester synthesized in Example 25 as a starting material and by an operation similar to that of Example 2.

¹H-NMR (CDCl₃, 300 MHz) δ: 1.43 (9H, s), 1.67 (6H, s), 2.68 (3H, s).

Example 27

2-{[5-(hydroxymethyl)-4-methyl-1,3-thiazol-2-yl]thio}-2-methylpropionic acid tert-butyl ester

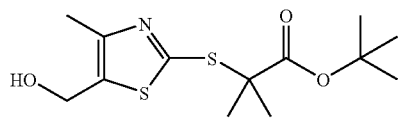

The title compound was obtained using 2-[(2-tert-butoxy-1,1-dimethyl-2-oxoethyl)thio]-4-methyl-1,3-thiazole-5-carboxylic acid synthesized in Example 26 as a starting material and by an operation similar to that of Example 3.

¹H-NMR (CDCl₃, 300 MHz) δ: 1.45 (9H, s), 1.57 (6H, s), 2.39 (3H, s), 4.77 (2H, s).

Example 28

2-{[4-(chloromethyl)-5-methyl-1,3-thiazol-2-yl]thio}-2-methylpropionic acid tert-butyl ester

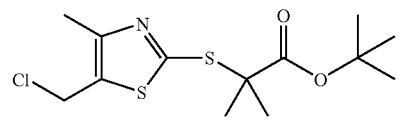

The title compound was obtained using 2-{[5-(hydroxymethyl)-4-methyl-1,3-thiazol-2-yl]thio}-2-methylpropionic acid tert-butyl ester synthesized in Example 27 as a starting material and by an operation similar to that of Example 4.

$^1$H-NMR (CDCl$_3$, 300 MHz) δ: 1.43 (9H, s), 1.59 (6H, s), 2.41 (3H, s), 4.70 (2H, s).

Example 29

2-methyl-2-{[4-methyl-5-(phthalimidomethyl)-1,3-thiazol-2-yl]thio}propionic acid tert-butyl ester

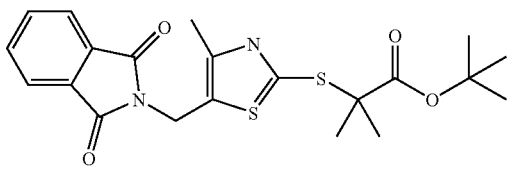

The title compound was obtained using 2-{[4-(chloromethyl)-5-methyl-1,3-thiazol-2-yl]thio}-2-methylpropionic acid tert-butyl ester synthesized in Example 28 as a starting material and by an operation similar to that of Example 5.

$^1$H-NMR (CDCl$_3$, 300 MHz) δ: 1.37 (9H, s), 1.56 (6H, s), 2.56 (3H, s), 4.92 (2H, s), 7.71-7.76 (2H, m), 7.82-7.87 (2H, m).

Example 30

2-{[5-(aminomethyl)-4-methyl-1,3-thiazol-2-yl]thio}-2-methylpropionic acid tert-butyl ester

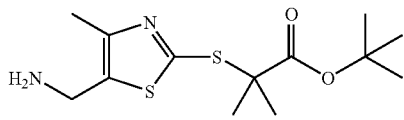

The title compound was obtained using 2-methyl-2-{[4-methyl-5-(phthalimidomethyl)-1,3-thiazol-2-yl]thio}propionic acid tert-butyl ester synthesized in Example 29 as a starting material and by an operation similar to that of Example 6.

$^1$H-NMR (CDCl$_3$, 300 MHz) δ: 1.45 (9H, s), 1.56 (6H, s), 2.35 (3H, s), 3.96 (2H, s).

Example 31

2-mercapto-4-(3-phthalimidopropyl)-1,3-thiazole

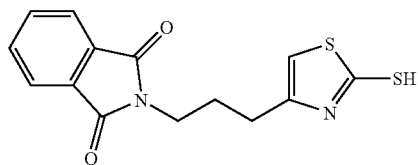

2-(5-Bromo-4-oxopentyl)-isoindoline-1,3-dione (17.8 g) synthesized using 1-chloro-4-oxopentane and potassium phthalimide as starting materials and in reference to non-patent reference [Pharmazie, 47, 86 (1992)] and the like and ammonium dithiocarbamate (6.96 g) were suspended in ethanol (250 mL), and the suspension was refluxed for 6 hr. The precipitated crystals were collected by filtration and washed with ethanol to give the title compound (10.1 g) as white crystals.

$^1$H-NMR (DMSO-d$_6$, 270 MHz) δ: 1.80-2.00 (2H, m), 3.25-3.50 (2H, m), 3.60 (2H, t, J=6.8 Hz), 6.60 (1H, s), 7.76-7.90 (4H, m), 13.10 (1H, s).

Example 32

2-methyl-2-{[4-(3-phthalimidopropyl)-1,3-thiazol-2-yl]thio}propionic acid tert-butyl ester

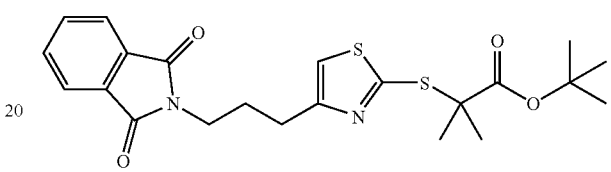

2-Mercapto-4-(3-phthalimidopropyl)-1,3-thiazole (22.6 g) obtained in Example 31 was dissolved in N,N-dimethylformamide (200 mL), potassium carbonate (11.3 g) and 2-bromo-2-methylpropionic acid tert-butyl ester (17.4 g) were added, and the mixture was stirred at room temperature for 14 hr. The reaction mixture was concentrated under reduced pressure, ethyl acetate and water were added, and the mixture was stirred. The organic layer was dried over magnesium sulfate and evaporated under reduced pressure. The residue was purified by silica gel chromatography (elution solvent; hexane:ethyl acetate=7:3) to give the title compound (32.0 g) as a colorless oil.

$^1$H-NMR (CDCl$_3$, 270 MHz) δ: 1.42 (9H, s), 1.52 (6H, s), 2.03-2.20 (2H, m), 2.82 (2H, t, J=7.8 Hz), 3.76 (2H, t, J=7.8 Hz), 7.06 (1H, s), 7.67-7.91 (4H, m), 13.10 (1H, s).

Example 33

2-{[4-(3-aminopropyl)-1,3-thiazol-2-yl]thio}-2-methylpropionic acid tert-butyl ester

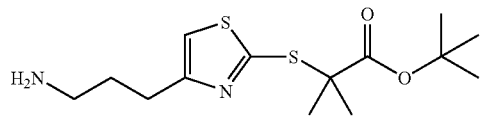

2-Methyl-2-{[4-(3-phthalimidopropyl)-1,3-thiazol-2-yl]thio}propionic acid tert-butyl ester (31.1 g) obtained in Example 32 was dissolved in ethanol (400 mL), hydrazine monohydrate (10 mL) was added, and the mixture was refluxed for 2 hr. The precipitated solid was removed by filtration, and the filtrate was concentrated under reduced pressure. Water and dichloromethane were added to the residue, and the organic layer was washed with water, and dried over magnesium sulfate. The solvent was concentrated under reduced pressure to give the title compound (20.1 g). The obtained compound was used in the next reaction without purification.

¹H-NMR (CDCl₃, 270 MHz) δ: 1.43 (9H, s), 1.57 (6H, s), 1.78-1.93 (2H, m), 2.74 (2H, t, J=7.6 Hz), 2.81 (2H, t, J=7.6 Hz), 6.97 (1H, s).

Example 34

2-[(4-{2-[(4'-fluorobiphenyl-4-yl)oxy]ethyl}-1,3-thiazol-2-yl)thio]-2-methylpropionic acid Example 34-1

2-[(4-{2-[(4'-fluorobiphenyl-4-yl)oxy]ethyl}-1,3-thiazol-2-yl)thio]-2-methylpropionic acid tert-butyl ester

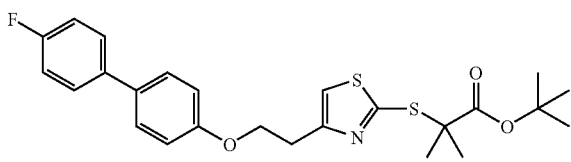

2-{[4-(2-Hydroxyethyl)-1,3-thiazol-2-yl]thio}-2-methylpropionic acid tert-butyl ester (451 mg) synthesized in Example 4 and 4'-fluorobiphenyl-4-ol (280 mg) were dissolved in tetrahydrofuran (10 mL), triphenylphosphine (430 mg) and diisopropyl azodicarboxylate (40% toluene solution, 0.88 ml) were added under ice-cooling, and the mixture was stirred at room temperature for 17 hr. The reaction mixture was concentrated under reduced pressure, and hexane (about 10 mL) was added. The precipitated crystals were removed by filtration, and the solvent of the filtrate was evaporated under reduced pressure. The residue was purified by silica gel chromatography (elution solvent; hexane:ethyl acetate=4:1) to give the title compound (390 mg) as a colorless oil.

¹H-NMR (DMSO, 300 MHz) δ: 1.33 (9H, s), 1.51 (6H, s), 3.18 (2H, t, J=6.6 Hz), 4.33 (2H, t, J=6.6 Hz), 7.01 (2H, d, J=9 Hz), 7.25 (2H, t, J=9 Hz), 7.56 (2H, d, J=9 Hz), 7.57 (1H, s), 7.61-7.66 (2H, m).
MS: 474 (M⁺+1).

Example 34-2

2-[(4-{2-[(4'-fluorobiphenyl-4-yl)oxy]ethyl}-1,3-thiazol-2-yl)thio]-2-methylpropionic acid

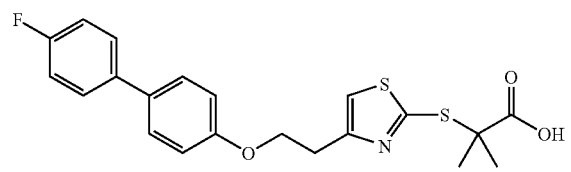

2-[(4-{2-[(4'-Fluorobiphenyl-4-yl)oxy]ethyl}-1,3-thiazol-2-yl)thio]-2-methylpropionic acid tert-butyl ester (351 mg) obtained in Example 34-1 was dissolved in dichloromethane (2 ml), trifluoroacetic acid (1 ml) was added, and the mixture was stirred at room temperature for 12 hr. The reaction mixture was concentrated under reduced pressure, and the residue was purified by silica gel chromatography (elution solvent; hexane:ethyl acetate=1:1) to give the title compound (293 mg) as a white solid.

¹H-NMR (DMSO-d₆, 300 MHz) δ: 1.51 (6H, s), 3.19 (2H, t, J=6.6 Hz), 4.33 (2H, t, J=6.6 Hz), 7.03 (2H, d, J=9.0 Hz), 7.25 (2H, t, J=9.0 Hz), 7.57 (2H, d, J=9.0 Hz), 7.58 (1H, s), 7.64 (2H, dd, J=5.7 Hz, 9.0 Hz), 12.94 (1H, brs).
MS: 418 (M⁺+1).

Example 35

2-[(4-{2-[(4'-fluorobiphenyl-4-yl)oxy]ethyl}-5-methyl-1,3-thiazol-2-yl)thio]-2-methylpropionic acid

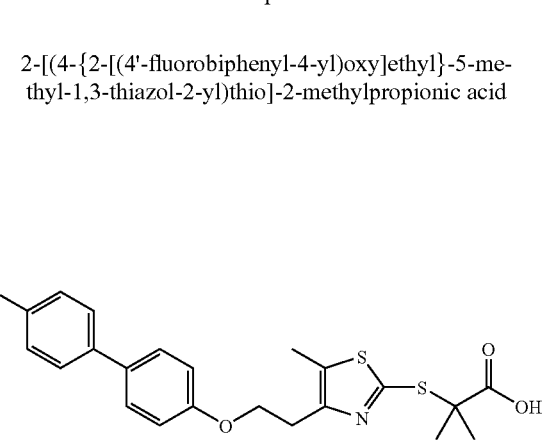

The title compound was obtained using 2-{[4-(2-hydroxyethyl)-5-methyl-1,3-thiazol-2-yl]thio}-2-methylpropionic acid tert-butyl ester synthesized in Example 16 and 4'-fluorobiphenyl-4-ol as starting materials and by an operation similar to that of Example 34.

¹H-NMR (CDCl₃, 300 MHz) δ: 1.61 (6H, s), 2.49 (3H, s), 3.22 (2H, t, J=6.0 Hz), 4.29 (2H, t, J=6.0 Hz), 6.91 (2H, d, J=7.0 Hz), 7.06-7.12 (2H, m), 7.42-7.49 (4H, m).
MS: 432 (M⁺+1).

Example 36

2-[(5-{2-[(4'-fluorobiphenyl-4-yl)oxy]ethyl}-4-methyl-1,3-thiazol-2-yl)thio]-2-methylpropionic acid The title compound was obtained using 2-{[5-(2-hydroxyethyl)-4-methyl-1,3-thiazol-2-yl]thio}-2-methylpropionic acid tert-butyl ester synthesized in Example 21 and 4'-fluorobiphenyl-4-ol as starting materials and by an operation similar to that of Example 34.

¹H-NMR (CDCl₃, 300 MHz) δ: 1.63 (6H, s), 2.43 (3H, s), 3.21 (2H, t, J=6.0 Hz), 4.18 (2H, t, J=6.0 Hz), 6.96 (2H, d, J=6.9 Hz), 7.07-7.13 (2H, m), 7.26-7.51 (4H, m)
MS: 432 (M⁺+1). .

Example 37

2-[(4-{[(4'-fluorobiphenyl-4-yl)oxy]methyl}-1,3-thiazol-2-yl)thio]-2-methylpropionic acid

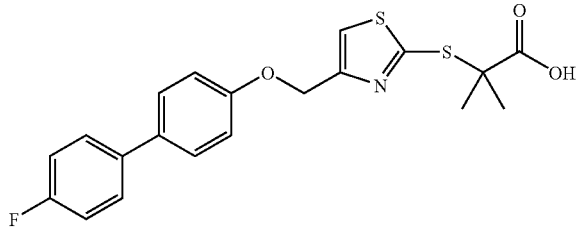

The title compound was obtained using 2-{[4-(hydroxymethyl)-1,3-thiazol-2-yl]thio}-2-methylpropionic acid tert-butyl ester synthesized in Example 10 and 4'-fluorobiphenyl-4-ol as starting materials and by an operation similar to that of Example 34.

$^1$H-NMR (CDCl$_3$, 300 MHz) δ: 1.65 (6H, s), 5.25 (2H, s) 7.00-7.13 (5H, m), 7.46-7.51 (4H, m).
MS: 404 (M$^+$+1).

Example 38

2-[(4-{2-[(4'-chlorobiphenyl-4-yl)oxy]ethyl}-1,3-thiazol-2-yl)thio]-2-methylpropionic acid

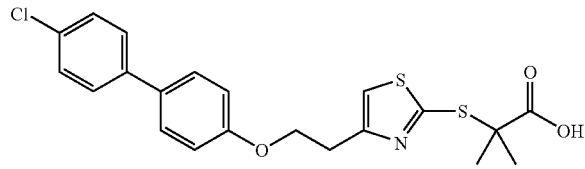

The title compound was obtained using 2-{[4-(2-hydroxyethyl)-1,3-thiazol-2-yl]thio}-2-methylpropionic acid tert-butyl ester synthesized in Example 4 and 4'-chlorobiphenyl-4-ol as starting materials and by an operation similar to that of Example 34.

$^1$H-NMR (DMSO-d$_6$, 300 MHz) δ: 1.51 (6H, s), 3.19 (2H, t, J=6.6 Hz), 4.34 (2H, t, J=6.6 Hz), 7.03 (2H, d, J=8.7 Hz), 7.47 (2H, t, J=8.4 Hz), 7.58 (1H, s), 7.60 (2H, d, J=8.4 Hz), 7.64 (2H, dd, J=5.7 Hz, 8.7 Hz), 12.92 (1H, brs).
MS: 434 (M$^+$+1).

Example 39

2-[(4-{2-[(4'-methoxybiphenyl-4-yl)oxy]ethyl}-1,3-thiazol-2-yl)thio]-2-methylpropionic acid

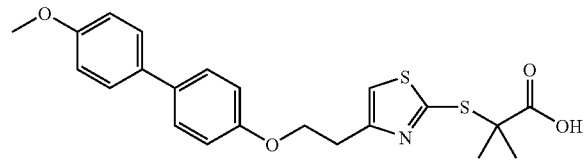

The title compound was obtained using 2-{[4-(2-hydroxyethyl)-1,3-thiazol-2-yl]thio}-2-methylpropionic acid tert-butyl ester synthesized in Example 4 and 4'-methoxybiphenyl-4-ol as starting materials and by an operation similar to that of Example 34.

$^1$H-NMR (DMSO-d$_6$, 300 MHz) δ: 1.51 (6H, s), 3.18 (2H, t, J=6.6 Hz), 3.27 (3H, s), 4.32 (2H, t, J=6.6 Hz), 6.97 (4H, m), 7.52 (4H, m), 7.58 (1H, s), 12.92 (1H, s).
MS: 430 (M$^+$+1).

Example 40

2-[(4-{2-[(4'-cyanobiphenyl-4-yl)oxy]ethyl}-1,3-thiazol-2-yl)thio]-2-methylpropionic acid

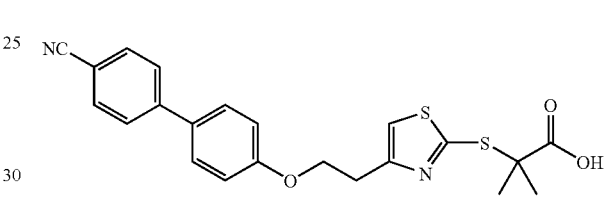

The title compound was obtained using 2-{[4-(2-hydroxyethyl)-1,3-thiazol-2-yl]thio}-2-methylpropionic acid tert-butyl ester synthesized in Example 4 and 4'-hydroxybiphenyl-4-carbonitrile as starting materials and by an operation similar to that of Example 34.

$^1$H-NMR (DMSO-d$_6$, 300 MHz) δ: 1.51 (6H, s), 3.19 (2H, t, J=6.6 Hz), 4.36 (2H, t, J=6.6 Hz), 7.04 (2H, d, J=8.4 Hz), 7.58 (1H, s), 7.71 (2H, t, J=8.4 Hz), 7.83 (2H, d, J=8.7 Hz), 7.88 (2H, d, J=8.7 Hz), 12.90 (1H, s).
MS: 425 (M$^+$+1).

Example 41

2-[(4-{2-[4-(4-chlorobenzoyl)phenoxy]ethyl}-1,3-thiazol-2-yl)thio]-2-methylpropionic acid

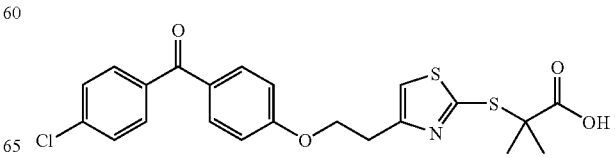

The title compound was obtained using 2-{[4-(2-hydroxyethyl)-1,3-thiazol-2-yl]thio}-2-methylpropionic acid tert-butyl ester synthesized in Example 4 and 4-chloro-4'-hydroxybenzophenone as starting materials and by an operation similar to that of Example 34.

$^1$H-NMR (DMSO-$d_6$, 300 MHz) δ: 1.51 (6H, s), 3.21 (2H, t, J=6.6 Hz), 4.41 (2H, t, J=6.6 Hz), 7.10 (2H, d, J=8.7 Hz), 7.58 (1H, s), 7.62 (2H, t, J=8.7 Hz), 7.69-7.75 (4H, m), 12.98 (1H, brs).

MS: 462 (M$^+$+1).

Example 42

2-({4-[2-(4-benzoylphenoxy)ethyl]-1,3-thiazol-2-yl}thio)-2-methylpropionic acid

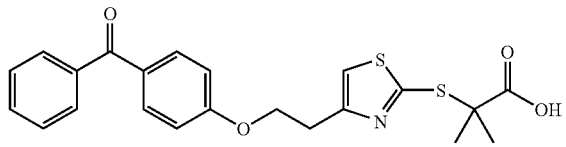

The title compound was obtained using 2-{[4-(2-hydroxyethyl)-1,3-thiazol-2-yl]thio}-2-methylpropionic acid tert-butyl ester synthesized in Example 4 and (4-hydroxyphenyl)(phenyl)methanone as starting materials and by an operation similar to that of Example 34.

$^1$H-NMR (DMSO-$d_6$, 300 MHz) δ: 1.50 (6H, s), 3.21 (2H, t, J=6.6 Hz), 4.41 (2H, t, J=6.6 Hz), 7.04 (2H, d, J=8.7 Hz), 7.50-7.58 (3H, m), 7.60-7.75 (5H, m), 12.91 (1H, brs).

MS: 428 (M$^+$+1).

Example 43

2-methyl-2-[(4-{2-[4-(trifluoromethyl)phenoxy]ethyl}-1,3-thiazol-2-yl)thio]propionic acid

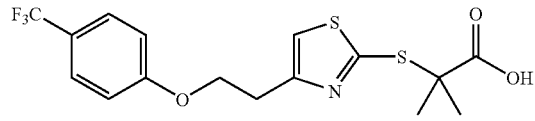

The title compound was obtained using 2-{[4-(2-hydroxyethyl)-1,3-thiazol-2-yl]thio}-2-methylpropionic acid tert-butyl ester synthesized in Example 4 and 4-(trifluoromethyl)phenol as starting materials and by an operation similar to that of Example 34.

$^1$H-NMR (CDCl$_3$, 300 MHz) δ: 1.61 (6H, s), 3.26 (2H, t, J=6.1 Hz), 4.27 (2H, t, J=6.1 Hz), 6.87 (2H, d, J=9.1 Hz), 7.12 (2H, d, J=9.1 Hz), 7.26 (1H, s).

MS: 392 (M$^+$+1).

Example 44

2-methyl-2-[(4-{2-[4-(trifluoromethoxy)phenoxy]ethyl}-1,3-thiazol-2-yl)thio]propionic acid

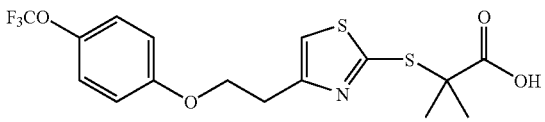

The title compound was obtained using 2-{[4-(2-hydroxyethyl)-1,3-thiazol-2-yl]thio}-2-methylpropionic acid tert-butyl ester synthesized in Example 4 and 4-(trifluoromethoxy)phenol as starting materials and by an operation similar to that of Example 34.

$^1$H-NMR (CDCl$_3$, 300 MHz) δ: 1.63 (6H, s), 3.31 (2H, t, J=6.1 Hz), 4.34 (2H, t, J=6.1 Hz), 6.97 (2H, d, J=8.6 Hz), 7.16 (1H, s), 7.55 (2H, d, J=8.6 Hz).

MS: 408 (M$^+$+1).

Example 45

2-methyl-2-({4-[2-(4-phenoxyphenoxy)ethyl]-1,3-thiazol-2-yl}thio)propionic acid

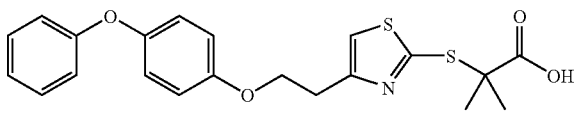

The title compound was obtained using 2-{[4-(2-hydroxyethyl)-1,3-thiazol-2-yl]thio}-2-methylpropionic acid tert-butyl ester synthesized in Example 4 and 4-phenoxyphenol as starting materials and by an operation similar to that of Example 34.

$^1$H-NMR (DMSO-$d_6$, 300 MHz) δ: 1.51 (6H, s), 3.16 (2H, t, J=6.6 Hz), 4.27 (2H, t, J=6.6 Hz), 6.91 (2H, d, J=9.0 Hz), 6.97 (4H, s), 7.06 (1H, t, J=9.0 Hz), 7.34 (2H, d, J=9.0 Hz), 7.56 (1H, s), 12.90 (1H, s).

MS: 416 (M$^+$+1).

Example 46

2-methyl-2-({4-[2-(4-(4-trifluoromethylphenoxy)phenoxy)]ethyl}-1,3-thiazol-2-yl)thio)propionic acid

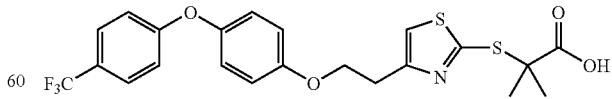

The title compound was obtained using 2-{[4-(2-hydroxyethyl)-1,3-thiazol-2-yl]thio}-2-methylpropionic acid tert-butyl ester synthesized in Example 4 and 4-(4-trifluoromethylphenoxy)phenol as starting materials and by an operation similar to that of Example 34.

$^1$H-NMR (DMSO-d$_6$, 300 MHz) δ: 1.51 (6H, s), 3.18 (2H, t, J=6.6 Hz), 4.32 (2H, t, J=6.6 Hz), 7.05 (6H, m), 6.97 (4H, s), 7.57 (1H, s), 7.69 (2H, d, J=8.8 Hz), 12.90 (1H, s).
MS: 484 (M$^+$+1).

Example 47

2-[(4-{2-[4-(4-fluorophenoxy)phenoxy]ethyl}-1,3-thiazol-2-yl)thio]-2-methylpropionic acid

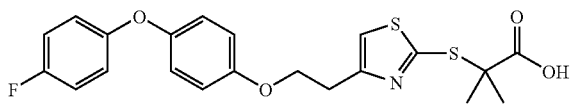

The title compound was obtained using 2-{[4-(2-hydroxyethyl)-1,3-thiazol-2-yl]thio}-2-methylpropionic acid tert-butyl ester synthesized in Example 4 and 4-(4-fluorophenoxy)phenol as starting materials and by an operation similar to that of Example 34.

$^1$H-NMR (CDCl$_3$, 300 MHz) δ: 1.62 (6H, s), 3.25 (2H, t, J=6.2 Hz), 4.27 (2H, t, J=6.2 Hz), 6.83-7.01 (8H, m), 7.11 (1H, s).
MS: 434 (M$^+$+1).

Example 48

2-methyl-2-({4-[2-(4-phenoxy-2-propylphenoxy)ethyl]-1,3-thiazol-2-yl}thio)propionic acid

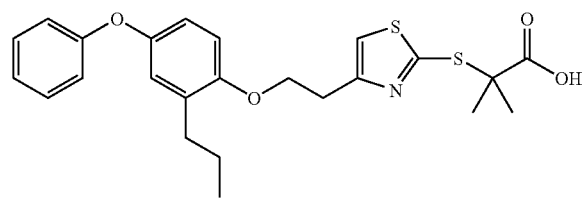

The title compound was obtained using 2-{[4-(2-hydroxyethyl)-1,3-thiazol-2-yl]thio}-2-methylpropionic acid tert-butyl ester synthesized in Example 4 and 4-phenoxy-2-propylphenol synthesized in reference to non-patent reference [Bioorg. Med. Chem. Lett. 13, 2795 (2003)] and the like as starting materials and by an operation similar to that of Example 34.

$^1$H-NMR (CDCl$_3$, 300 MHz) δ: 0.86 (3H, t, J=7.2 Hz), 1.41-1.49 (2H, m), 1.61 (6H, s), 2.44 (2H, t, J=7.5 Hz), 3.28 (2H, t, J=6.3 Hz), 4.29 (2H, t, J=6.3 Hz), 6.80-6.83 (3H, m), 6.92 (2H, d, J=7.5 Hz), 7.03 (1H, d, J=7.5 Hz), 7.10 (1H, s), 7.26-7.31 (2H, m).
MS: 458 (M$^+$+1).

Example 49

2-[(4-{2-[4-(4-fluorophenoxy)-2-propylphenoxy]ethyl}-1,3-thiazol-2-yl)thio]-2-methylpropionic acid

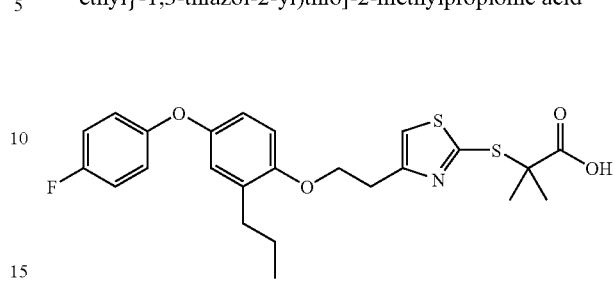

The title compound was obtained using 2-{[4-(2-hydroxyethyl)-1,3-thiazol-2-yl]thio}-2-methylpropionic acid tert-butyl ester synthesized in Example 4 and 4-(4-fluorophenoxy)-2-propylphenol synthesized in reference to non-patent reference [Bioorg. Med. Chem. Lett. 13, 2795 (2003)] and the like as starting materials, and by an operation similar to that of Example 34.

$^1$H-NMR (CDCl$_3$, 300 MHz) δ: 0.85 (3H, t, J=7.3 Hz), 1.40-1.48 (2H, m), 1.61 (6H, s), 2.43 (2H, t, J=7.4 Hz), 3.27 (2H, t, J=6.1 Hz), 4.28 (2H, t, J=6.1 Hz), 6.77-7.01 (7H, m), 7.11 (1H, s).
MS: 476 (M$^+$+1).

Example 50

2-{[4-(2-{4-[(4-chlorobenzyl)oxy]phenoxy}ethyl)-1,3-thiazol-2-yl]thio}-2-methylpropionic acid Example 50-1 benzoic acid 4-(2-{2-[(2-tert-butoxy-1,1-dimethyl-2-oxyethyl)thio]-1,3-thiazol-4-yl}ethoxy)phenyl ester

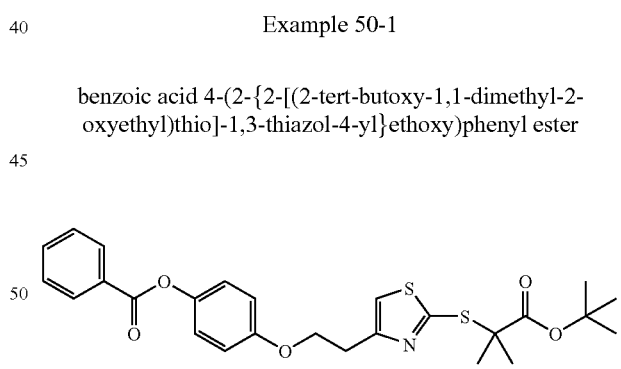

2-{[4-(2-Hydroxyethyl)-1,3-thiazol-2-yl]thio}-2-methylpropionic acid tert-butyl ester (6.0 g) synthesized in Example 4 and benzoic acid 4-hydroxyphenylester (4.24 g) were dissolved in tetrahydrofuran (60 mL), triphenylphosphine (5.19 g) and diethyl diazodicarboxylate (3.45 g) were added under ice-cooling, and the mixture was stirred at room temperature for 8 hr. The reaction mixture was concentrated under reduced pressure, the residue was purified by silica gel chromatography (elution solvent; hexane:ethyl acetate=5:1) to give the title compound (7.7 g) as a white solid.

$^1$H-NMR (CDCl$_3$, 300 MHz) δ: 1.42 (9H, s), 1.58 (6H, s), 3.25 (2H, t, J=6.6 Hz), 4.31 (2H, t, J=6.6 Hz), 6.93 (2H, d,

J=9.0 Hz), 7.09-7.13 (3H, m), 7.50 (2H, t, J=7.6 Hz), 7.63 (1H, t, J=7.5 Hz), 8.19 (2H, d, J=7.2 Hz).

Example 50-2

2-({4-[2-(4-hydroxyphenoxy)ethyl]-1,3-thiazol-2-yl}thio)-2-methylpropionic acid tert-butyl ester

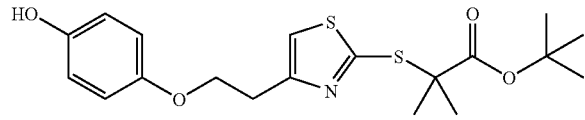

Benzoic acid 4-(2-{2-[(2-tert-butoxy-1,1-dimethyl-2-oxy-ethyl)thio]-1,3-thiazol-4-yl}ethoxy)phenyl ester (7.7 g) obtained in Example 50-1 was dissolved in methanol (20 mL) and tetrahydrofuran (20 mL), 1 mol/L aqueous sodium hydroxide solution (18.5 ml) was added, and the mixture was stirred at room temperature for 30 min. The reaction mixture was concentrated under reduced pressure, aqueous 10% citric acid solution was added, and the mixture was extracted with ethyl acetate. The organic layer was washed with saturated brine and dried over anhydrous sodium sulfate. The solvent was evaporated under reduced pressure and the residue was purified by silica gel chromatography (elution solvent; hexane:ethyl acetate=4:1 to 2:1) to give the title compound (6.3 g) as a white solid.

$^1$H-NMR (CDCl$_3$, 300 MHz) δ: 1.42 (9H, s), 1.57 (6H, s), 3.21 (2H, t, J=6.6 Hz), 4.22 (2H, t, J=6.6 Hz), 6.75 (4H, s), 7.13 (1H, s).

Example 50-3

2-{[4-(2-{4-[(4-chlorobenzyl)oxy]phenoxy}ethyl)-1,3-thiazol-2-yl]thio}-2-methylpropionic acid tert-butyl ester

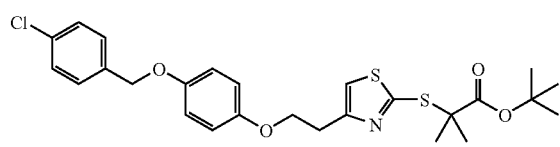

2-({4-[2-(4-Hydroxyphenoxy)ethyl]-1,3-thiazol-2-yl}thio)-2-methylpropionic acid tert-butyl ester (600 mg) obtained in Example 50-2 and 4-chlorobenzylbromide (312 mg) were dissolved in acetone (10 mL), potassium carbonate (210 mg) was added, and the mixture was refluxed for 6 hr. The reaction mixture was concentrated under reduced pressure, water was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (420 mg) as a colorless oil.

$^1$H-NMR (CDCl$_3$, 300 MHz) δ: 1.42 (9H, s), 1.57 (6H, s), 3.21 (2H, t, J=6.6 Hz), 4.25 (2H, t, J=6.6 Hz), 4.97 (2H, s), 6.80-6.88 (4H, m), 7.11 (1H, s), 7.34 (4H, s).

Example 50-4

2-{[4-(2-{4-[(4-chlorobenzyl)oxy]phenoxy}ethyl)-1,3-thiazol-2-yl]thio}-2-methylpropionic acid

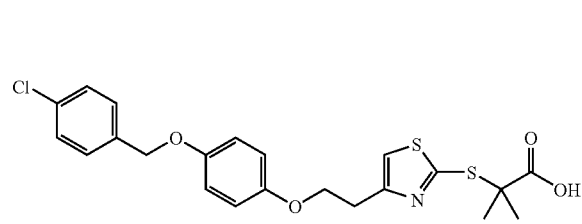

2-{[4-(2-{4-[(4-Chlorobenzyl)oxy]phenoxy}ethyl)-1,3-thiazol-2-yl]thio}-2-methylpropionic acid tert-butyl ester (420 mg) obtained in Example 50-3 was dissolved in dichloromethane (10 mL), trifluoroacetic acid (4 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (260 mg) as a white solid.

$^1$H-NMR (CDCl$_3$, 300 MHz) δ: 1.61 (6H, s), 3.23 (2H, t, J=6.0 Hz), 4.24 (2H, t, J=6.0 Hz), 4.97 (2H, s), 6.97-6.88 (4H, m), 7.10 (1H, s), 7.34 (4H, s).

MS: 464 (M$^+$+1).

Example 51

2-[(4-{2-[4-(benzyloxy)phenoxy]ethyl}-1,3-thiazol-2-yl)thio]-2-methylpropionic acid

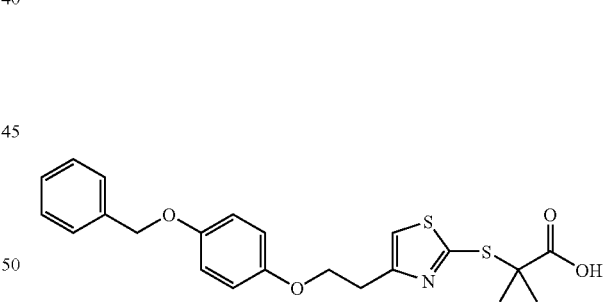

The title compound was obtained using 2-({4-[2-(4-hydroxyphenoxy)ethyl]-1,3-thiazol-2-yl}thio)-2-methylpropionic acid tert-butyl ester synthesized in Example 50-2 and benzyl bromide as starting materials and by operations similar to those of Example 50-3 and Example 50-4.

$^1$H-NMR (CDCl$_3$, 300 MHz) δ: 1.61 (6H, s), 3.22 (2H, t, J=6.0 Hz), 4.24 (2H, t, J=6.0 Hz), 5.01 (2H, s), 6.81 (2H, d, J=9.0 Hz), 6.88 (2H, d, J=9.0 Hz), 7.09 (1H, s), 7.30-7.43 (5H, m).

MS: 430 (M$^+$+1).

Example 52

2-{[4-(2-{4-[(4-fluorobenzyl)oxy]phenoxy}ethyl)-1,3-thiazol-2-yl]thio}-2-methylpropionic acid

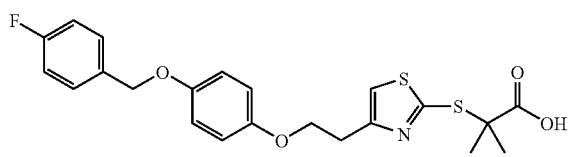

The title compound was obtained using 2-({4-[2-(4-hydroxyphenoxy)ethyl]-1,3-thiazol-2-yl}thio)-2-methylpropionic acid tert-butyl ester synthesized in Example 50-2 and 4-fluorobenzylbromide as starting materials and by operations similar to those of Example 50-3 and Example 50-4.

$^1$H-NMR (CDCl$_3$, 300 MHz) δ: 1.63 (6H, s), 3.28 (2H, t, J=6.0 Hz), 4.24 (2H, t, J=6.0 Hz), 4.97 (2H, s), 6.81 (2H, d, J=9.0 Hz), 6.87 (2H, d, J=9.0 Hz), 7.02-7.08 (3H, m), 7.35-7.40 (2H, m).

MS: 448 (M$^+$+1).

Example 53

2-methyl-2-({4-[2-(4-{[4-(trifluoromethyl)benzyl]oxy}phenoxy)ethyl]-1,3-thiazol-2-yl}thio)propionic acid

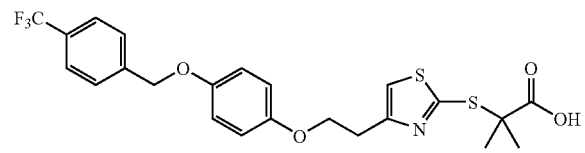

The title compound was obtained using 2-({4-[2-(4-hydroxyphenoxy)ethyl]-1,3-thiazol-2-yl}thio)-2-methylpropionic acid tert-butyl ester synthesized in Example 50-2 and 4-(trifluoromethyl)benzyl bromide as starting materials and by operations similar to those of Example 50-3 and Example 50-4.

$^1$H-NMR (CDCl$_3$, 300 MHz) δ: 1.61 (6H, s), 3.23 (2H, t, J=6.0 Hz), 4.24 (2H, t, J=6.0 Hz), 5.07 (2H, s), 6.81 (2H, d, J=9.0 Hz), 6.88 (2H, d, J=9.0 Hz), 7.09 (1H, s), 7.53 (2H, d, J=8.1 Hz), 7.63 (2H, d, J=8.1 Hz).

MS: 498 (M$^+$+1).

Example 54

2-[(4-{2-[4-(benzoylamino)phenoxy]ethyl}-1,3-thiazol-2-yl)thio]-2-methylpropionic acid

Example 54-1

2-[(4-{2-[4-(benzoylamino)phenoxy]ethyl}-1,3-thiazol-2-yl)thio]-2-methylpropionic acid tert-butyl ester 2-{[4-(2-Hydroxyethyl)-1,3-thiazol-2-yl]thio}-2-methylpropionic acid tert-butyl ester (1.0 g) synthesized in Example 4 and N-(4-hydroxyphenyl)benzamide (703 mg) were dissolved in tetrahydrofuran (10 mL), triphenylphosphine (866 mg) and diethyl diazodicarboxylate (575 mg) were added thereto under ice-cooling, and the mixture was stirred at room temperature for 8 hr. The reaction mixture was concentrated under reduced pressure, and the residue was purified by silica gel chromatography (elution solvent; hexane:ethyl acetate=2:1) to give the title compound (1.1 g) as a white solid.

$^1$H-NMR (CDCl$_3$, 300 MHz) δ: 1.42 (9H, s), 1.58 (6H, s), 3.25 (2H, t, J=6.0 Hz), 4.30 (2H, t, J=6.0 Hz), 6.91 (2H, d, J=9.0 Hz), 7.13 (1H, s), 7.45-7.55 (5H, m), 7.74 (1H, s), 7.86 (2H, d, J=7.0 Hz).

Example 54-2

2-[(4-{2-[4-(benzoylamino)phenoxy]ethyl}-1,3-thiazol-2-yl)thio]-2-methylpropionic acid 2-[(4-{2-[4-(Benzoylamino)phenoxy]ethyl}-1,3-thiazol-2-yl)thio]-2-methylpropionic acid tert-butyl ester (550 mg) obtained in Example 54-1 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (350 mg) as a white solid.

$^1$H-NMR (CDCl$_3$, 300 MHz) δ: 1.62 (6H, s), 3.26 (2H, t, J=6.0 Hz), 4.30 (2H, t, J=6.0 Hz), 6.89 (2H, d, J=9.0 Hz), 7.11 (1H, s), 7.45-7.55 (5H, m), 7.80-7.87 (3H, m).

MS: 443 (M$^+$+1).

Example 55

2-{[4-(2-{4-[benzoyl(methyl)amino]phenoxy}ethyl)-1,3-thiazol-2-yl]thio}-2-methylpropionic acid

Example 55-1

2-{[4-(2-{4-[benzoyl(methyl)amino]phenoxy}ethyl)-1,3-thiazol-2-yl]thio}-2-methylpropionic acid tert-butyl ester

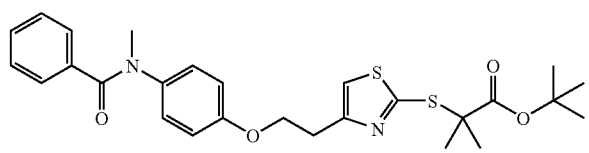

2-[(4-{2-[4-(Benzoylamino)phenoxy]ethyl}-1,3-thiazol-2-yl)thio]-2-methylpropionic acid tert-butyl ester (500 mg) synthesized in Example 54-1 and methyl iodide (170 mg) were dissolved in N,N-dimethylformamide (6 mL), potassium tert-butoxide (135 mg) was added, and the mixture was stirred at room temperature for 1 hr. Water was added to the reaction mixture, the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1) to give the title compound (290 mg) as a colorless oil.

$^1$H-NMR (CDCl$_3$, 300 MHz) δ: 1.40 (9H, s), 1.56 (6H, s), 3.18 (2H, t, J=6.0 Hz), 3.44 (3H, s), 4.21 (2H, t, J=6.0 Hz), 6.71 (2H, d, J=8.6 Hz), 6.93 (2H, d, J=8.6 Hz), 7.08 (1H, s), 7.12-7.21 (3H, m), 7.28 (2H, d, J=8.1 Hz).

Example 55-2

2-{[4-(2-{4-[benzoyl(methyl)amino]phenoxy}ethyl)-1,3-thiazol-2-yl]thio}-2-methylpropionic acid

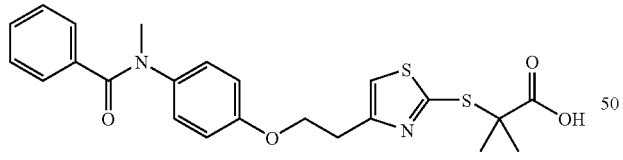

2-{[4-(2-{4-[Benzoyl(methyl)amino]phenoxy}ethyl)-1,3-thiazol-2-yl]thio}-2-methylpropionic acid tert-butyl ester (290 mg) obtained in Example 55-1 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (170 mg) as a colorless oil.

$^1$H-NMR (CDCl$_3$, 300 MHz) δ: 1.59 (6H, s), 3.22 (2H, t, J=6.1 Hz), 3.45 (3H, s), 4.21 (2H, t, J=6.1 Hz), 6.72 (2H, d, J=8.7 Hz), 6.94 (2H, d, J=8.7 Hz), 7.07 (1H, s), 7.14-7.29 (5H, m)

MS: 457 (M$^+$+1).

Example 56

2-{[4-(2-{4-[(4-fluorobenzoyl)amino]phenoxy}ethyl)-1,3-thiazol-2-yl]thio}-2-methylpropionic acid

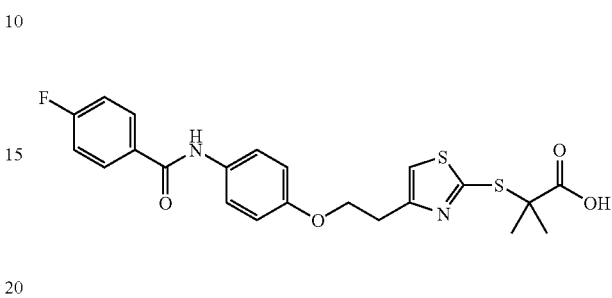

The title compound was obtained using 2-{[4-(2-hydroxyethyl)-1,3-thiazol-2-yl]thio}-2-methylpropionic acid tert-butyl ester synthesized in Example 4 and 4-fluoro-N-(4-hydroxyphenyl)benzamide as starting materials and by an operation similar to that of Example 54.

$^1$H-NMR (CDCl$_3$, 300 MHz) δ: 1.61 (6H, s), 3.25 (2H, t, J=6.1 Hz), 4.29 (2H, t, J=6.1 Hz), 6.87 (2H, d, J=9.0 Hz), 7.10-7.17 (3H, m), 7.49 (2H, d, J=8.9 Hz), 7.80 (1H, s), 7.85-7.89 (2H, m).

MS: 461 (M$^+$+1).

Example 57

2-{[4-(2-{4-[(4-chlorobenzoyl)amino]phenoxy}ethyl)-1,3-thiazol-2-yl]thio}-2-methylpropionic acid

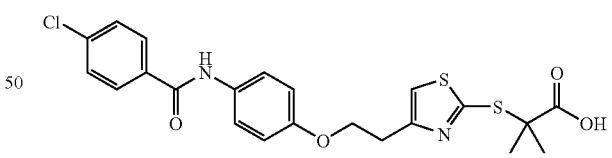

The title compound was obtained using 2-{[4-(2-hydroxyethyl)-1,3-thiazol-2-yl]thio}-2-methylpropionic acid tert-butyl ester synthesized in Example 4 and 4-chloro-N-(4-hydroxyphenyl)benzamide as starting materials and by an operation similar to that of Example 54.

$^1$H-NMR (CDCl$_3$, 300 MHz) δ: 1.62 (6H, s), 3.27 (2H, t, J=6.0 Hz), 4.30 (2H, t, J=6.1 Hz), 6.90 (2H, d, J=9.0 Hz), 7.11 (1H, s), 7.44-7.51 (4H, m), 7.74 (1H, s), 7.80 (2H, d, J=8.1 Hz).

MS: 477 (M$^+$+1).

Example 58

2-{[4-(2-{4-[(4-fluorobenzoyl)(methyl)amino]phenoxy}ethyl)-1,3-thiazol-2-yl]thio}-2-methylpropionic acid

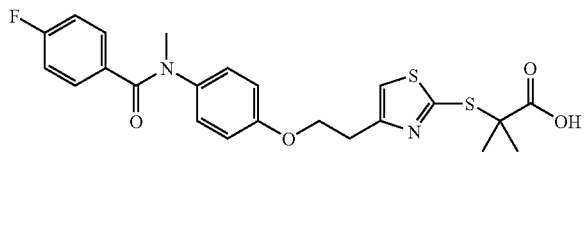

The title compound was obtained using 2-{[4-(2-{4-[(4-fluorobenzoyl)amino]phenoxy}ethyl)-1,3-thiazol-2-yl]thio}-2-methylpropionic acid tert-butyl ester, which is an intermediate synthesized in Example 56, as a starting material and by an operation similar to that of Example 55.

$^1$H-NMR (CDCl$_3$, 300 MHz) δ: 1.61 (6H, s), 3.24 (2H, t, J=6.2 Hz), 3.44 (3H, s), 4.23 (2H, t, J=6.2 Hz), 6.75 (2H, d, J=8.8 Hz), 6.93 (2H, d, J=8.8 Hz), 7.08 (1H, s), 7.14 (2H, d, J=8.4 Hz), 7.22 (2H, d, J=8.4 Hz).

MS: 475 (M$^+$+1).

Example 59

2-{[4-(2-{4-[(4-chlorobenzoyl)(methyl)amino]phenoxy}ethyl)-1,3-thiazol-2-yl]thio}-2-methylpropionic acid

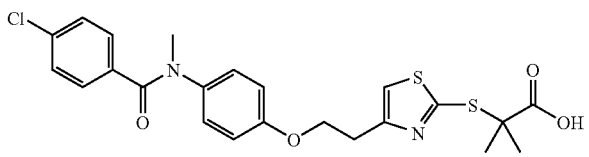

The title compound was obtained using 2-{[4-(2-{4-[(4-chlorobenzoyl)amino]phenoxy}ethyl)-1,3-thiazol-2-yl]thio}-2-methylpropionic acid tert-butyl ester, which is an intermediate synthesized in Example 57, as a starting material and by an operation similar to that of Example 55.

$^1$H-NMR (CDCl$_3$, 300 MHz) δ: 1.60 (6H, s), 3.23 (2H, t, J=6.1 Hz), 3.44 (3H, s), 4.23 (2H, t, J=6.1 Hz), 6.75 (2H, d, J=8.9 Hz), 6.85 (2H, d, J=8.7 Hz), 6.93 (2H, d, J=8.9 Hz), 7.08 (1H, s), 7.28-7.31 (2H, m).

MS: 491 (M$^+$+1).

Example 60

2-[(4-{2-[4-(anilinocarbonyl)phenoxy]ethyl}-1,3-thiazol-2-yl)thio]-2-methylpropionic acid

Example 60-1

4-(2-{2-[(2-tert-butoxy-1,1-dimethyl-2-oxoethyl)thio]-1,3-thiazol-4-yl}ethoxy)benzoic acid methyl ester

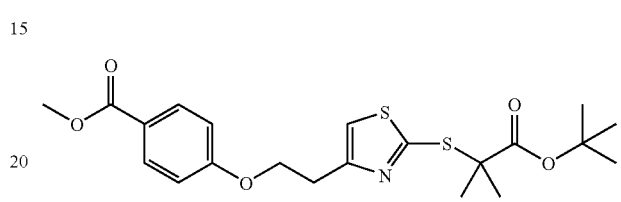

2-{[4-(2-Hydroxyethyl)-1,3-thiazol-2-yl]thio}-2-methylpropionic acid tert-butyl ester (7.0 g) synthesized in Example 4 and 4-hydroxybenzoic acid methyl ester (3.5 g) were dissolved in tetrahydrofuran (100 mL), triphenylphosphine (6.06 g) and diethyl diazodicarboxylate (4.0 g) were added under ice-cooling, and the mixture was stirred at room temperature for 8 hr. The reaction mixture was concentrated under reduced pressure, and the residue was purified by silica gel chromatography (elution solvent; hexane:ethyl acetate=4:1) to give the title compound (7.0 g) as a colorless oil.

$^1$H-NMR (CDCl$_3$, 300 MHz) δ: 1.41 (9H, s), 1.57 (6H, s), 3.26 (2H, t, J=6.6 Hz), 3.88 (3H, s), 4.36 (2H, t, J=6.6 Hz), 6.90 (2H, d, J=8.1 Hz), 7.12 (1H, s), 7.97 (2H, d, J=8.1 Hz).

Example 60-2

4-(2-{2-[(2-tert-butoxy-1,1-dimethyl-2-oxoethyl)thio]-1,3-thiazol-4-yl}ethoxy)benzoic acid

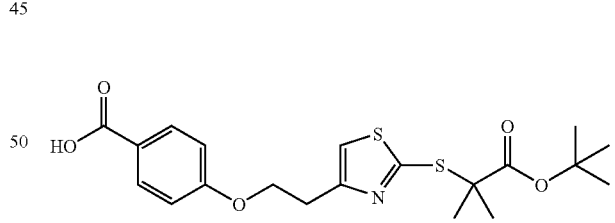

4-(2-{2-[(2-tert-Butoxy-1,1-dimethyl-2-oxoethyl)thio]-1,3-thiazol-4-yl}ethoxy)benzoic acid methyl ester (7.0 g) obtained in Example 60-1 was dissolved in methanol (50 mL) and tetrahydrofuran (30 mL), 1 mol/L aqueous sodium hydroxide solution (24 ml) was added, and the mixture was stirred at 60° C. for 2 hr. The reaction mixture was concentrated under reduced pressure, aqueous 10% citric acid solution was added, and the mixture was extracted with ethyl acetate. The organic layer was washed with saturated brine and dried over anhydrous sodium sulfate. The solvent was evaporated under reduced pressure to give the title compound (6.8 g) as a white solid.

¹H-NMR (CDCl₃, 300 MHz) δ: 1.41 (9H, s), 1.58 (6H, s), 3.27 (2H, t, J=6.6 Hz), 4.38 (2H, t, J=6.6 Hz), 6.93 (2H, d, J=8.1 Hz), 7.14 (1H, s), 8.03 (2H, d, J=8.1 Hz).

Example 60-3

2-[(4-{2-[4-(anilinocarbonyl)phenoxy]ethyl}-1,3-thiazol-2-yl)thio]-2-methylpropionic acid tert-butyl ester

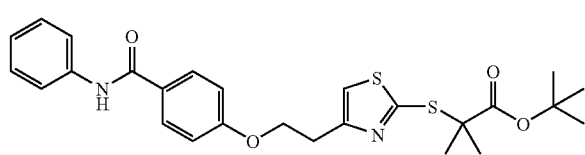

4-(2-{2-[(2-tert-Butoxy-1,1-dimethyl-2-oxoethyl)thio]-1,3-thiazol-4-yl}ethoxy)benzoic acid (500 mg) obtained in Example 60-2 and aniline (132 mg) were dissolved in dichloromethane (6 mL), N-(3-dimethylaminopropyl)-N'-ethylcarbodiimide (EDC) hydrochloride (339 mg) and 4-dimethylaminopyridine (DMAP) (217 mg) were successively added, and the mixture was stirred at room temperature for 6 hr. The reaction mixture was concentrated under reduced pressure, and the residue was purified by silica gel chromatography (elution solvent; hexane:ethyl acetate=2:1) to give the title compound (480 mg) as a white solid.

¹H-NMR (CDCl₃, 300 MHz) δ: 1.42 (9H, s), 1.58 (6H, s), 3.27 (2H, t, J=6.6 Hz), 4.37 (2H, t, J=6.6 Hz), 6.96 (2H, d, J=8.9 Hz), 7.12-7.16 (2H, m), 7.36 (2H, t, J=8.1 Hz), 7.62 (2H, d, J=8.1 Hz), 7.74 (1H, s), 7.82 (2H, d, J=8.9 Hz).

Example 60-4

2-[(4-{2-[4-(anilinocarbonyl)phenoxy]ethyl}-1,3-thiazol-2-yl)thio]-2-methylpropionic acid

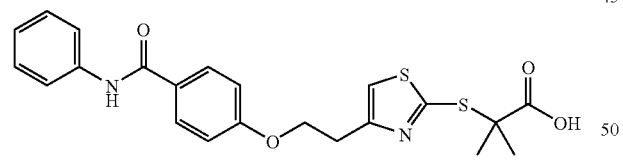

2-[(4-{2-[4-(Anilinocarbonyl)phenoxy]ethyl}-1,3-thiazol-2-yl)thio]-2-methylpropionic acid tert-butyl ester (480 mg) obtained in Example 60-3 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (400 mg) as a white solid.

¹H-NMR (CDCl₃, 300 MHz) δ: 1.61 (6H, s), 3.28 (2H, t, J=6.2 Hz), 4.35 (2H, t, J=6.2 Hz), 6.94 (2H, d, J=8.8 Hz), 7.10-7.16 (2H, m), 7.36 (2H, t, J=7.8 Hz), 7.63 (2H, d, J=7.8 Hz), 7.81 (2H, d, J=8.8 Hz), 7.87 (1H, s)

MS: 443 (M⁺+1).

Example 61

2-methyl-2-({4-[2-(4-{[methyl(phenyl)amino]carbonyl}phenoxy)ethyl]-1,3-thiazol-2-yl}thio)propionic acid

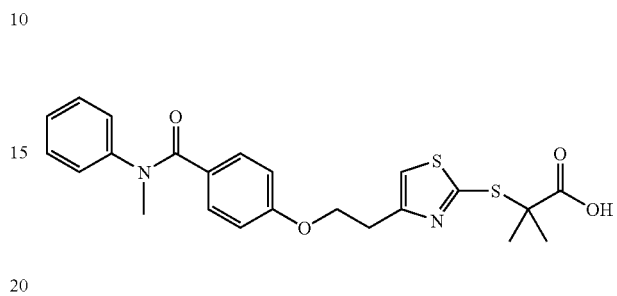

The title compound was obtained using 4-(2-{2-[(2-tert-butoxy-1,1-dimethyl-2-oxoethyl)thio]-1,3-thiazol-4-yl}ethoxy)benzoic acid synthesized in Example 60-2 and N-methylaniline as starting materials and by operations similar to those of Example 60-3 and Example 60-4.

¹H-NMR (CDCl₃, 300 MHz) δ: 1.59 (6H, s), 3.20 (2H, t, J=6.0 Hz), 3.48 (3H, s), 4.22 (2H, t, J=6.0 Hz), 6.64 (2H, d, J=8.7 Hz), 7.01-7.26 (8H, m).

MS: 457 (M⁺+1).

Example 62

2-({4-[2-(4-{[(4-fluorophenyl)amino]carbonyl}phenoxy)ethyl]-1,3-thiazol-2-yl}thio)-2-methylpropionic acid

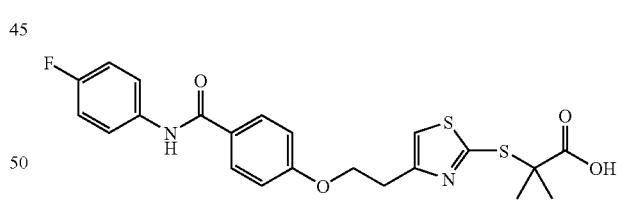

The title compound was obtained using 4-(2-{2-[(2-tert-butoxy-1,1-dimethyl-2-oxoethyl)thio]-1,3-thiazol-4-yl}ethoxy)benzoic acid synthesized in Example 60-2 and (4-fluorophenyl)aniline as starting materials and by operations similar to those of Example 60-3 and Example 60-4.

¹H-NMR (CDCl₃, 300 MHz) δ: 1.61 (6H, s), 3.28 (2H, t, J=6.3 Hz), 4.35 (2H, t, J=6.3 Hz), 6.94 (2H, d, J=8.7 Hz), 7.05 (2H, t, J=8.7 Hz), 7.11 (1H, s), 7.56-7.61 (2H, m), 7.80 (2H, d, J=8.7 Hz), 7.88 (1H, s).

MS: 461 (M⁺+1).

Example 63

2-{[4-(2-{4-[(benzylamino)carbonyl]phenoxy}ethyl)-1,3-thiazol-2-yl]thio}-2-methylpropionic acid

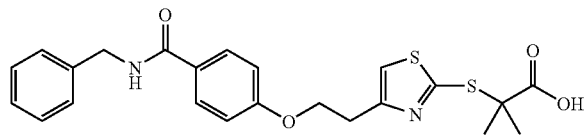

The title compound was obtained using 4-(2-{2-[(2-tert-butoxy-1,1-dimethyl-2-oxoethyl)thio]-1,3-thiazol-4-yl}ethoxy)benzoic acid synthesized in Example 60-2 and benzylamine as starting materials and by operations similar to those of Example 60-3 and Example 60-4.

$^1$H-NMR (CDCl$_3$, 300 MHz) δ: 1.60 (6H, s), 3.26 (2H, t, J=6.1 Hz), 4.32 (2H, t, J=6.1 Hz), 4.63 (2H, d, J=5.5 Hz), 6.37-6.39 (1H, m), 6.90 (2H, d, J=8.9 Hz), 7.09 (1H, s), 7.27-7.37 (5H, m), 7.73 (2H, d, J=8.9 Hz).
MS: 457 (M$^+$+1).

Example 64

2-({4-[2-(4-{[(4-fluorobenzyl)amino]carbonyl}phenoxy)ethyl]-1,3-thiazol-2-yl}thio)-2-methylpropionic acid

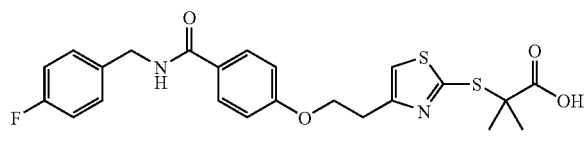

The title compound was obtained using 4-(2-{2-[(2-tert-butoxy-1,1-dimethyl-2-oxoethyl)thio]-1,3-thiazol-4-yl}ethoxy)benzoic acid synthesized in Example 60-2 and (4-fluorobenzyl)amine as starting materials and by operations similar to those of Example 60-3 and Example 60-4.

$^1$H-NMR (CDCl$_3$, 300 MHz) δ: 1.60 (6H, s), 3.26 (2H, t, J=6.1 Hz), 4.32 (2H, t, J=6.1 Hz), 4.58 (2H, d, J=5.8 Hz), 6.45-6.48 (1H, m), 6.89 (2H, d, J=8.9 Hz), 7.01 (2H, t, J=8.8 Hz), 7.10 (1H, s), 7.28-7.33 (2H, m), 7.72 (2H, d, J=8.9 Hz).
MS: 475 (M$^+$+1).

Example 65

2-methyl-2-[(4-{2-[4-({[4-(trifluoromethyl)benzyl]amino}carbonyl)phenoxy]ethyl}-1,3-thiazol-2-yl)thio]propionic acid

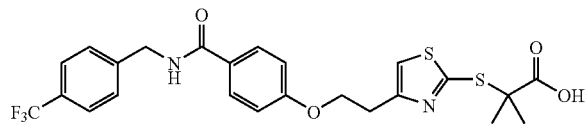

The title compound was obtained using 4-(2-{2-[(2-tert-butoxy-1,1-dimethyl-2-oxoethyl)thio]-1,3-thiazol-4-yl}ethoxy)benzoic acid synthesized in Example 60-2 and [4-(trifluoromethyl)benzyl]amine as starting materials and by operations similar to those of Example 60-3 and Example 60-4.

$^1$H-NMR (CDCl$_3$, 300 MHz) δ: 1.61 (6H, s), 3.28 (2H, t, J=6.0 Hz), 4.34 (2H, t, J=6.1 Hz), 4.69 (2H, d, J=6.0 Hz), 6.39-6.42 (1H, m), 6.92 (2H, d, J=8.7 Hz), 7.09 (1H, s), 7.46 (2H, d, J=8.1 Hz), 7.60 (2H, d, J=8.1 Hz), 7.74 (2H, d, J=8.7 Hz).
MS: 525 (M$^+$+1).

Example 66

2-methyl-2-[(4-{2-[4-(morpholin-4-ylcarbonyl)phenoxy]ethyl}-1,3-thiazol-2-yl)thio]propionic acid

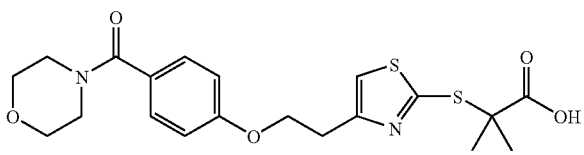

The title compound was obtained using 4-(2-{2-[(2 tert-butoxy-1,1-dimethyl-2-oxoethyl)thio]-1,3-thiazol-4-yl}ethoxy)benzoic acid synthesized in Example 60-2 and morpholine as starting materials and by operations similar to those of Example 60-3 and Example 60-4.

$^1$H-NMR (CDCl$_3$, 300 MHz) δ: 1.62 (6H, s), 3.27 (2H, t, J=6.0 Hz), 3.50-3.78 (8H, m), 4.33 (2H, t, J=6.0 Hz), 6.90 (2H, d, J=8.7 Hz), 7.09 (1H, s), 7.36 (2H, d, J=8.7 Hz).
MS: 437 (M$^+$+1).

Example 67

2-({4-[2-(4-bromophenoxy)ethyl]-1,3-thiazol-2-yl}thio)-2-methylpropionic acid

Example 67-1

2-({4-[2-(4-bromophenoxy)ethyl]-1,3-thiazol-2-yl}thio)-2-methylpropionic acid tert-butyl ester

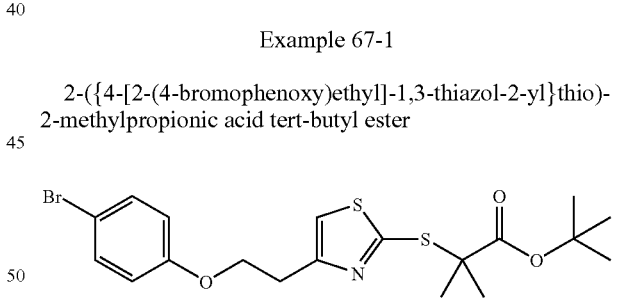

2-{[4-(2-Hydroxyethyl)-1,3-thiazol-2-yl]thio}-2-methylpropionic acid tert-butyl ester (3.077 g) synthesized in Example 4 and 4-bromophenol (1.75 g) were dissolved in tetrahydrofuran (50 mL), triphenylphosphine (3.20 g) and diisopropyl diazodicarboxylate (40% toluene solution, 6.54 ml) were added under ice-cooling, and the mixture was stirred at room temperature for 12 hr. The reaction mixture was concentrated under reduced pressure, and the residue was purified by silica gel chromatography (elution solvent; hexane:ethyl acetate=10:1 to 5:1) to give the title compound (3.45 g) as a colorless oil.

$^1$H-NMR (CDCl$_3$, 300 MHz) δ: 1.44 (9H, s), 1.57 (6H, s), 3.22 (2H, t, J=6.6 Hz), 4.27 (2H, t, J=6.6 Hz), 6.77 (2H, d, J=8.7 Hz), 7.10 (1H, s), 7.35 (2H, d, J=8.7 Hz).
MS: 458 (M$^+$+1).

Example 67-2

2-({4-[2-(4-bromophenoxy)ethyl]-1,3-thiazol-2-yl}thio)-2-methylpropionic acid

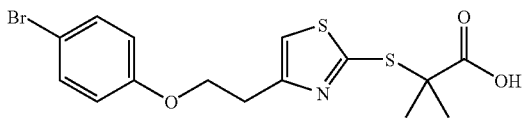

The title compound was obtained using 2-({4-[2-(4-bromophenoxy)ethyl]-1,3-thiazol-2-yl}thio)-2-methylpropionic acid tert-butyl ester obtained in Example 67-1 as a starting material and by an operation similar to that of Example 34-2.

$^1$H-NMR (DMSO-d$_6$, 300 MHz) δ: 1.50 (6H, s), 3.15 (2H, t, J=6.6 Hz), 4.28 (2H, t, J=6.6 Hz), 6.91 (2H, d, J=8.7 Hz), 7.43 (2H, d, J=87 Hz), 7.56 (1H, s), 12.93 (1H, s).

MS: 404 (M$^+$+1).

Example 68

2-[(4-{2-[(3'-fluorobiphenyl-4-yl)oxy]ethyl}-1,3-thiazol-2-yl)thio]-2-methylpropionic acid

Example 68-1

2-[(4-{2-[(3'-fluorobiphenyl-4-yl)oxy]ethyl}-1,3-thiazol-2-yl)thio]-2-methylpropionic acid tert-butyl ester

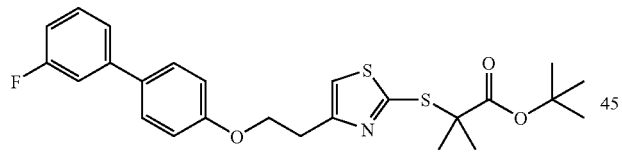

Under nitrogen atmosphere, 2-({4-[2-(4-bromophenoxy)ethyl]-1,3-thiazol-2-yl}thio)-2-methylpropionic acid tert-butyl ester (447 mg) synthesized in Example 67-1 and 3-fluorophenylboric acid (273 mg) were dissolved in tetrahydrofuran (10 mL) and sodium hydrogen carbonate (1 mol/l, 10 mL), tetrakis(triphenylphosphine)palladium (231 mg) was added, and the mixture was refluxed for 6.5 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1) to give the title compound (296 mg) as a pale-yellow oil.

$^1$H-NMR (DMSO-d$_6$, 300 MHz) δ: 1.33 (9H, s), 1.51 (6H, s,), 3.18 (2H, t, J=6.6 Hz), 7.02 (2H, d, J=8.7 Hz), 7.13 (1H, m), 7.43-7.48 (3H, m), 7.58 (1H, s), 7.64 (2H, d, J=8.7 Hz).

MS: 474 (M$^+$+1).

Example 68-2

2-[(4-{2-[(3'-fluorobiphenyl-4-yl)oxy]ethyl}-1,3-thiazol-2-yl)thio]-2-methylpropionic acid

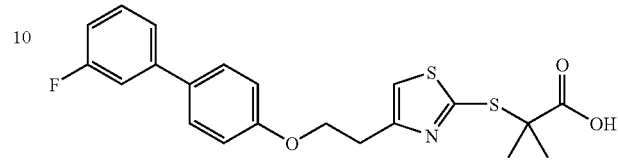

2-[(4-{2-[(3'-Fluorobiphenyl-4-yl)oxy]ethyl}-1,3-thiazol-2-yl)thio]-2-methylpropionic acid tert-butyl ester obtained in Example 68-1 was dissolved in dichloromethane (2 mL), trifluoroacetic acid (1 mL) was added, and the mixture was stirred at room temperature for 12 hr. The reaction mixture was concentrated under reduced pressure, and the residue was purified by silica gel chromatography (elution solvent; hexane:ethyl acetate=2:1) to give the title compound (151 mg) as a white solid.

$^1$H-NMR (DMSO-d$_6$, 300 MHz) δ: 1.51 (6H, s), 3.19 (2H, t, J=6.6 Hz), 4.34 (2H, t, J=6.6 Hz), 7.04 (2H, d, J=8.7 Hz), 7.12 (1H, m), 7.43-7.48 (2H, m), 7.58 (1H, s), 7.64 (2H, d, J=8.7 Hz), 12.93 (1H, brs).

MS: 418 (M$^+$+1).

Example 69

2-methyl-2-{[4-(2-{[4'-(trifluoromethyl)biphenyl-4-yl]oxy}ethyl)-1,3-thiazol-2-yl]thio}propionic acid

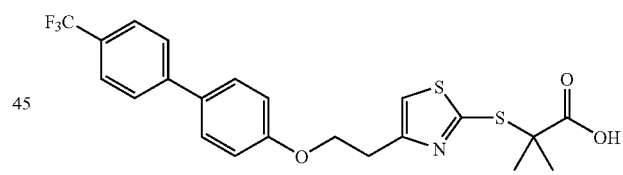

The title compound was obtained using 2-({4-[2-(4-bromophenoxy)ethyl]-1,3-thiazol-2-yl}thio)-2-methylpropionic acid tert-butyl ester synthesized in Example 67-1 and 4-(trifluoromethyl)phenylboric acid as starting materials and by an operation similar to that of Example 68.

$^1$H-NMR (DMSO-d$_6$, 300 MHz) δ: 1.51 (6H, s), 3.20 (2H, t, J=6.6 Hz), 4.36 (2H, t, J=6.6 Hz), 7.07 (2H, d, J=9.0 Hz), 7.59 (1H, s), 7.69 (2H, t, J=9.0 Hz), 7.77 (2H, d, J=8.4 Hz), 7.85 (2H, d, J=8.4 Hz), 12.94 (1H, brs).

Example 70

2-methyl-2-{[4-(2-{[3'-(trifluoromethyl)biphenyl-4-yl]oxy}ethyl)-1,3-thiazol-2-yl]thio}propionic acid

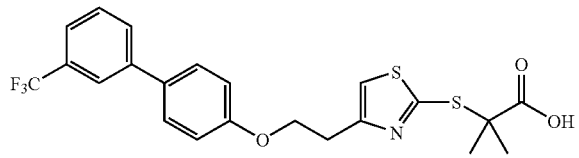

The title compound was obtained using 2-({4-[2-(4-bromophenoxy)ethyl]-1,3-thiazol-2-yl}thio)-2-methylpropionic acid tert-butyl ester synthesized in Example 67-1 and 3-(trifluoromethyl)phenylboric acid as starting materials and by an operation similar to that of Example 68.

$^1$H-NMR (DMSO-$d_6$, 300 MHz) δ: 1.51 (6H, s), 3.20 (2H, t, J=6.6 Hz), 4.35 (2H, t, J=6.6 Hz), 7.06 (2H, d, J=8.4 Hz), 7.58 (1H, s), 7.65-7.70 (4H, m), 7.90-7.95 (2H, m), 12.95 (1H, brs).

MS: 468 (M$^+$+1).

Example 71

2-methyl-2-{[4-(2-{[4'-(trifluoromethoxy)biphenyl-4-yl]oxy}ethyl)-1,3-thiazol-2-yl]thio}propionic acid

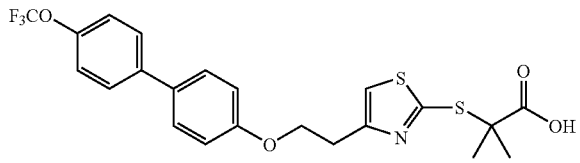

The title compound was obtained using 2-({4-[2-(4-bromophenoxy)ethyl]-1,3-thiazol-2-yl}thio)-2-methylpropionic acid tert-butyl ester synthesized in Example 67-1 and 4-(trifluoromethoxy)phenylboric acid as starting materials and by an operation similar to that of Example 68.

$^1$H-NMR (DMSO-$d_6$, 300 MHz) δ: 1.51 (6H, s), 3.19 (2H, t, J=6.6 Hz), 4.34 (2H, t, J=6.6 Hz), 7.05 (2H, d, J=8.4 Hz), 7.41 (2H, d, J=8.4 Hz), 7.58 (1H, s), 7.62 (2H, d, J=8.7 Hz), 7.73 (2H, d, J=8.7 Hz), 12.95 (1H, brs).

MS: 484 (M$^+$+1).

Example 72

2-methyl-2-{[4-(2-{[3'-(trifluoromethoxy)biphenyl-4-yl]oxy}ethyl)-1,3-thiazol-2-yl]thio}propionic acid

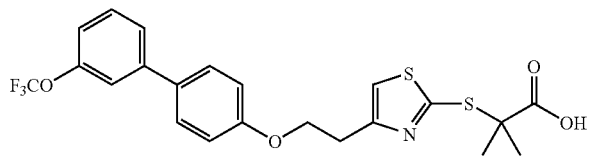

The title compound was obtained using 2-({4-[2-(4-bromophenoxy)ethyl]-1,3-thiazol-2-yl}thio)-2-methylpropionic acid tert-butyl ester synthesized in Example 67-1 and 3-(trifluoromethoxy)phenylboric acid as starting materials and by an operation similar to that of Example 68.

$^1$H-NMR (DMSO-$d_6$, 300 MHz) δ: 1.51 (6H, s), 3.19 (2H, t, J=6.6 Hz), 4.35 (2H, t, J=6.6 Hz), 7.05 (2H, d, J=8-7 Hz), 7.30 (1H, d, J=8.4 Hz), 7.53-7.58 (3H, m), 7.63-7.69 (3H, m), 12.95 (1H, brs).

MS: 484 (M$^+$+1).

Example 73

2-{[4-(2-{[4'-(acetylamino)biphenyl-4-yl]oxy}ethyl)-1,3-thiazol-2-yl]thio}-2-methylpropionic acid

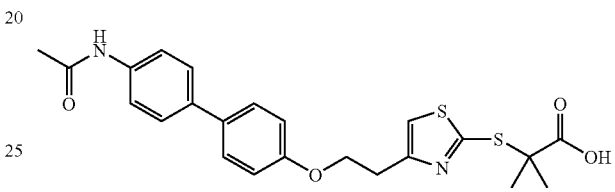

The title compound was obtained using 2-({4-[2-(4-bromophenoxy)ethyl]-1,3-thiazol-2-yl}thio)-2-methylpropionic acid tert-butyl ester synthesized in Example 67-1 and [4-(acetylamino)phenyl]boric acid as starting materials and by an operation similar to that of Example 68.

$^1$H-NMR (DMSO-$d_6$, 300 MHz) δ: 1.51 (6H, s), 2.05 (3H, s), 3.18 (2H, t, J=6.6 Hz), 4.32 (2H, t, J=6.6 Hz), 7.00 (2H, d, J=8.7 Hz), 7.52-7.58 (5H, m), 7.63 (2H, d, J=8.7 Hz), 9.98 (1H, s), 12.93 (1H, s).

MS: 457 (M$^+$+1).

Example 74

2-{[4-(2-{[4'-(dimethylamino)biphenyl-4-yl]oxy}ethyl)-1,3-thiazol-2-yl]thio}-2-methylpropionic acid

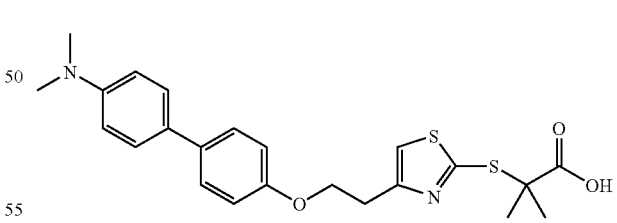

The title compound was obtained using 2-({4-[2-(4-bromophenoxy)ethyl]-1,3-thiazol-2-yl}thio)-2-methylpropionic acid tert-butyl ester synthesized in Example 67-1 and [4-(dimethylamino)phenyl]boric acid as starting materials and by an operation similar to that of Example 68.

$^1$H-NMR (DMSO-$d_6$, 300 MHz) δ: 1.52 (6H, s), 2.91 (6H, s), 3.17 (2H, t, J=6.6 Hz), 4.30 (2H, t, J=6.6 Hz), 6.77 (2H, d, J=8.7 Hz), 6.96 (2H, d, J=8.7 Hz), 7.42-7.57 (4H, m), 7.63 (1H, s), 12.92 (1H, s).

MS: 443 (M$^+$+1).

Example 75

2-methyl-2-[(4-{2-[4-(5-methyl-2-thienyl)phenoxy]ethyl}-1,3-thiazol-2-yl)thio]propionic acid

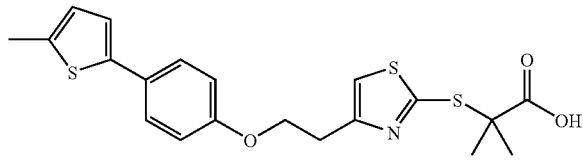

The title compound was obtained using 2-({4-[2-(4-bromophenoxy)ethyl]-1,3-thiazol-2-yl}thio)-2-methylpropionic acid tert-butyl ester synthesized in Example 67-1 and 5-methyl-2-thiopheneboronic acid as starting materials and by an operation similar to that of Example 68.

$^1$H-NMR (DMSO-$d_6$, 300 MHz) δ: 1.50 (6H, s), 2.44 (3H, s), 3.17 (2H, t, J=6.6 Hz), 4.30 (2H, t, J=6.6 Hz), 6.77 (1H, d, J=3.9 Hz), 6.96 (2H, d, J=8.4 Hz), 7.15 (1H, d, J=3.6 Hz), 7.48 (2H, d, J=8.4 Hz), 7.57 (1H, s), 12.92 (1H, s).

MS: 420 (M$^+$+1).

Example 76

2-[(4-{2-[(4'-fluorobiphenyl-4-yl)thio]ethyl}-1,3-thiazol-2-yl)thio]-2-methylpropionic acid

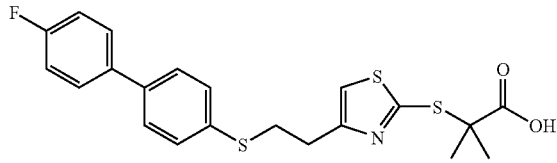

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-bromobenzenethiol as starting materials, followed by an operation similar to of Example 68 and using 4-fluorophenylboric acid.

$^1$H-NMR (DMSO-$d_6$, 300 MHz) δ: 1.52 (6H, s), 3.02 (2H, t, J=7.2 Hz), 3.33 (2H, t, J=7.2 Hz), 7.29 (2H, t, J=9.0 Hz), 7.43 (2H, d, J=8.4 Hz), 7.53 (1H, s), 7.61 (2H, d, J=8.4 Hz), 7.70 (2H, m), 12.91 (1H, s).

MS: 434 (M$^+$+1).

Example 77

2-[(4-{2-[(4'-fluorobiphenyl-3-yl)oxy]ethyl}-1,3-thiazol-2-yl)thio]-2-methylpropionic acid

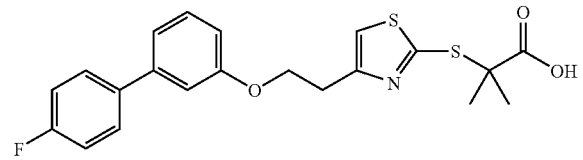

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 3-bromophenol as starting materials, followed by an operation similar to that of Example 68 and using 4-fluorophenylboric acid.

$^1$H-NMR (DMSO-$d_6$, 300 MHz) δ: 1.50 (6H, s), 3.19 (2H, t, J=6.6 Hz), 4.37 (2H, t, J=6.6 Hz), 6.94 (1H, dd, J=2.1, 7.8 Hz), 7.18 (1H, s), 7.20 (1H, d, J=7.8 Hz), 7.27 (2H, t, J=8.7 Hz), 7.36 (1H, t, J=7.8 Hz), 7.59 (1H, s), 7.71 (2H, m), 12.92 (1H, s).

MS: 418 (M$^+$+1).

Example 78

2-[(4-{2-[(4'-chloro-3-fluorobiphenyl-4-yl)oxy]ethyl}-1,3-thiazol-2-yl)thio]-2-methylpropionic acid

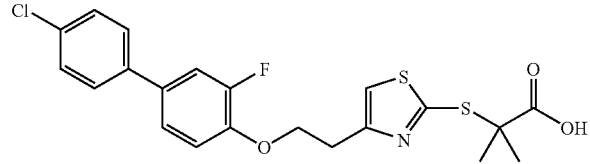

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-bromo-2-fluorophenol as starting materials, followed by an operation similar to that of Example 68 and using 4-chlorophenylboric acid.

$^1$H-NMR (CDCl$_3$, 300 MHz) δ: 1.63 (6H, s), 3.36 (2H, t, J=6.0 Hz), 4.39 (2H, t, J=6.0 Hz), 7.03 (1H, d, J=8.4 Hz), 7.22-7.45 (7H, m).

MS: 452 (M$^+$+1).

Example 79

2-[(4-{2-[(3,4'-difluorobiphenyl-4-yl)oxy]ethyl}-1,3-thiazol-2-yl)thio]-2-methylpropionic acid

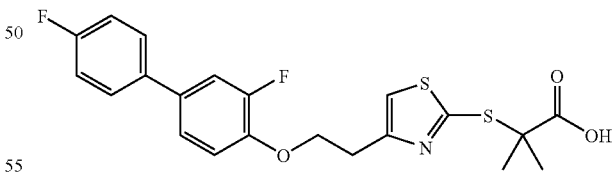

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-bromo-2-fluorophenol as starting materials, followed by an operation similar to that of Example 68 and using 4-fluorophenylboric acid.

$^1$H-NMR (CDCl$_3$, 300 MHz) δ: 1.63 (6H, s), 3.33 (2H, t, J=6.0 Hz), 4.40 (2H, t, J=6.0 Hz), 7.02-7.14 (3H, m) 7.21-7.26 (3H, m), 7.44-7.49 (2H, m).

MS: 436 (M$^+$+1).

Example 80

2-[(4-{2-[(4'-chloro-3-methoxybiphenyl-4-yl)oxy]ethyl}-1,3-thiazol-2-yl)thio]-2-methylpropionic acid

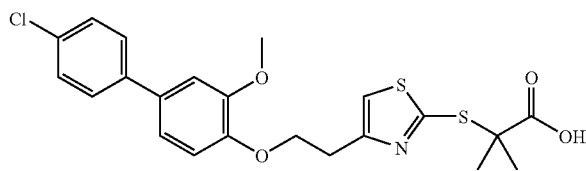

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-bromo-2-methoxyphenol as starting materials, followed by an operation similar to that of Example 68 and using 4-chlorophenylboric acid.

$^1$H-NMR (CDCl$_3$, 300 MHz) δ: 1.63 (6H, s), 3.35 (2H, t, J=6.2 Hz), 3.90 (3H, t), 4.37 (2H, t, J=6.2 Hz), 6.95 (1H, d, J=8.3 Hz), 7.05-7.11 (2H, m), 7.33-7.40 (3H, m), 7.47 (2H, d, J=8.7 Hz).

MS: 464 (M$^+$+1).

Example 81

2-[(4-{2-[(4'-fluoro-3-methoxybiphenyl-4-yl)oxy]ethyl}-1,3-thiazol-2-yl)thio]-2-methylpropionic acid

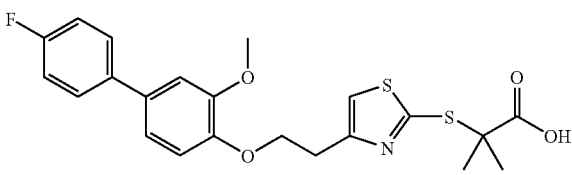

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-bromo-2-methoxyphenol as starting materials, followed by an operation similar to that of Example 68 and using 4-fluorophenylboric acid.

$^1$H-NMR (CDCl$_3$, 300 MHz) δ: 1.63 (6H, s), 3.35 (2H, t, J=6.0 Hz), 3.90 (3H, s), 4.38 (2H, t, J=6.0 Hz), 6.93-7.13 (5H, m), 7.32 (1H, s), 7.46-7.51 (2H, m).

MS: 448 (M$^+$+1).

Example 82

2-[(4-{2-[(4'-chloro-3-methylbiphenyl-4-yl)oxy]ethyl}-1,3-thiazol-2-yl)thio]-2-methylpropionic acid

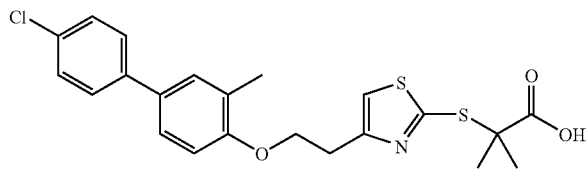

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-iodo-2-methylphenol as starting materials, followed by an operation similar to that of Example 68 and using 4-chlorophenylboric acid.

$^1$H-NMR (CDCl$_3$, 300 MHz) δ: 1.61 (6H, s), 2.18 (3H, s), 3.31 (2H, t, J=6.0 Hz), 4.34 (2H, t, J=6.0 Hz), 6.88 (1H, d, J=7.8 Hz), 7.13 (1H, s), 7.31-7.38 (4H, m), 7.45 (2H, d, J=8.7 Hz).

MS: 448 (M$^+$+1).

Example 83

2-[(4-{2-[(4'-fluoro-3-methylbiphenyl-4-yl)oxy]ethyl}-1,3-thiazol-2-yl)thio]-2-methylpropionic acid

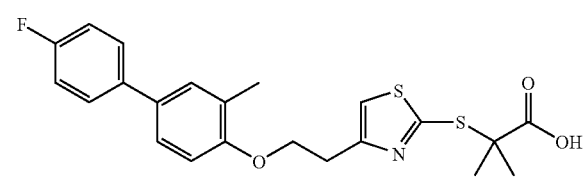

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 4-iodo-2-methylphenol as starting materials, followed by an operation similar to that of Example 68 and using 4-fluorophenylboric acid.

$^1$H-NMR (CDCl$_3$, 300 MHz) δ: 1.61 (6H, s), 2.18 (3H, s), 3.32 (2H, t, J=6.0 Hz), 4.34 (2H, t, J=6.0 Hz), 6.88 (1H, d, J=8.1 Hz), 7.08 (2H, t, J=8.7 Hz), 7.16 (1H, s), 7.29-7.33 (2H, m), 7.44-7.50 (2H, m).

MS: 432 (M$^+$+1).

Example 84

2-[(4-{2-[(3-cyano-4'-fluorobiphenyl-4-yl)oxy]ethyl}-1,3-thiazol-2-yl)thio]-2-methylpropionic acid

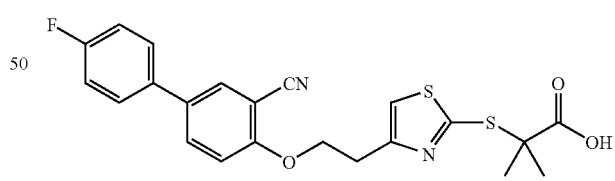

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 5-bromo-2-hydroxybenzonitrile as starting materials, followed by an operation similar to that of Example 68 and using 4-fluorophenylboric acid.

$^1$H-NMR (CDCl$_3$, 300 MHz) δ: 1.61 (6H, s), 3.36 (2H, t, J=6.0 Hz), 4.43 (2H, t, J=6.0 Hz), 7.03-7.06 (1H, m), 7.10-7.16 (2H, m), 7.30 (1H, s), 7.42-7.47 (2H, m), 7.67-7.70 (2H, m).

MS: 423 (M$^+$+1).

Example 85

2-[(4-{2-[(4'-chloro-3-cyanobiphenyl-4-yl)oxy]ethyl}-1,3-thiazol-2-yl)thio]-2-methylpropionic acid

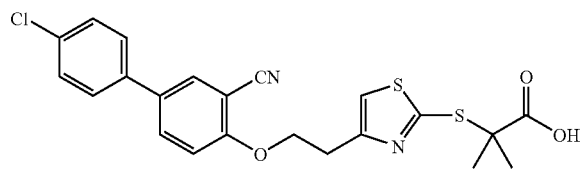

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 5-bromo-2-hydroxybenzonitrile as starting materials, followed by an operation similar to that of Example 68 and using 4-chlorophenylboric acid.

¹H-NMR (CDCl₃, 300 MHz) δ: 1.61 (6H, s), 3.36 (2H, t, J=6.0 Hz), 4.43 (2H, t, J=6.0 Hz), 7.03-7.07 (1H, m), 7.30 (1H, s), 7.42 (4H, s), 7.68-7.72 (2H, m).

MS: 459 (M⁺+1).

Example 86

2-{[4-(2-{[5-(4-chlorophenyl)-3-methylpyridin-2-yl]oxy}ethyl)-1,3-thiazol-2-yl]thio}-2-methylpropionic acid

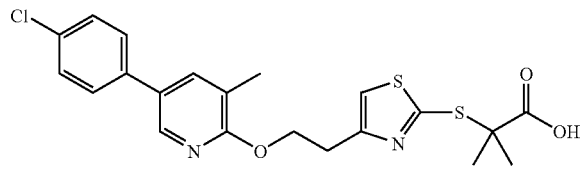

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 5-bromo-3-methylpyridin-2-ol as starting materials, followed by an operation similar to that of Example 68 and using 4-chlorophenylboric acid.

¹H-NMR (CDCl₃, 300 MHz) δ: 1.64 (6H, s), 2.18 (3H, s), 3.31 (2H, t, J=6.0 Hz), 4.70 (2H, t, J=6.0 Hz), 7.08 (1H, s), 7.37-7.45 (4H, m), 7.56 (1H, s), 8.15 (1H, s).

MS: 449 (M⁺+1).

Example 87

2-{[4-(2-{[5-(4-fluorophenyl)-3-methylpyridin-2-yl]oxy}ethyl)-1,3-thiazol-2-yl]thio}-2-methylpropionic acid

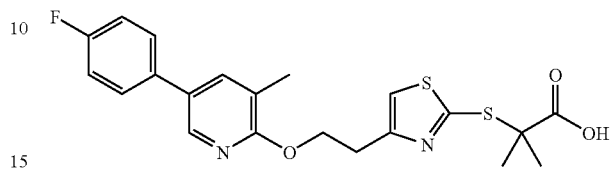

The title compound was obtained by an operation similar to that of Example 67-1 and using 2-{[4-(2-hydroxyethyl)-1,3-thiazol-2-yl]thio}-2-methylpropionic acid tert-butyl ester synthesized in Example 4 and 5-bromo-3-methylpyridin-2-ol as starting materials, followed by an operation similar to that of Example 68 and using 4-fluorophenylboric acid.

¹H-NMR (CDCl₃, 300 MHz) δ: 1.64 (6H, s), 2.18 (3H, s), 3.31 (2H, t, J=6.6 Hz), 4.70 (2H, t, J=6.6 Hz), 7.08-7.15 (3H, m), 7.43-7.48 (2H, m), 7.55 (1H, s), 8.13 (1H, s).

MS: 433 (M⁺+1).

Example 88

2-{[4-(2-{[6-(4-fluorophenyl)pyridin-3-yl]oxy}ethyl)-1,3-thiazol-2-yl]thio}-2-methylpropionic acid hydrochloride

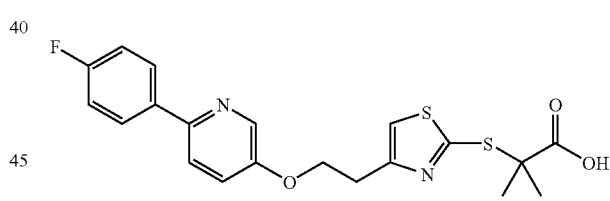

A compound obtained by an operation similar to that of Example 67-1 and using 2-{[4-(2-hydroxyethyl)-1,3-thiazol-2-yl]thio}-2-methylpropionic acid tert-butyl ester synthesized in Example 4 and 2-chloro-5-hydroxypyridine synthesized in reference to patent reference [WO9825920] as starting materials, followed by an operation similar to that of Example 68 and using 4-fluorophenylboric acid was dissolved in diethyl ether and the solution was reacted with 4 mol/L hydrochloric acid-ethyl acetate to give the title compound.

¹H-NMR (DMSO-d₆, 300 MHz) δ: 1.50 (6H, s), 3.22 (2H, t, J=6.6 Hz), 4.45 (2H, t, J=6.6 Hz), 7.28-7.34 (2H, m), 7.58-7.62 (2H, m), 7.96 (1H, d, J=8.7 Hz), 8.03-8.08 (2H, m), 8.39 (1H, d, J=3.0 Hz).

MS: 419 (M⁺+1).

Example 89

2-{[4-(2-{[6-(4-chlorophenyl)pyridin-3-yl]oxy}ethyl)-1,3-thiazol-2-yl]thio}-2-methylpropionic acid hydrochloride

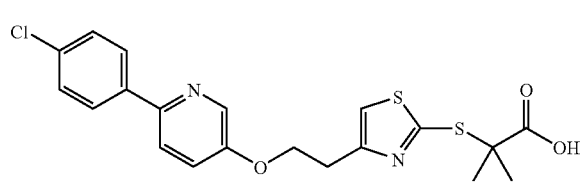

A compound obtained by an operation similar to that of Example 67-1 and using 2-{[4-(2-hydroxyethyl)-1,3-thiazol-2-yl]thio}-2-methylpropionic acid tert-butyl ester synthesized in Example 4 and 2-chloro-5-hydroxypyridine synthesized in reference to patent reference [WO9825920] as starting materials, followed by an operation similar to that of Example 68 and using 4-chlorophenylboric acid was dissolved in diethyl ether and the solution was reacted with 4 mol/L hydrochloric acid-ethyl acetate to give the title compound.

$^1$H-NMR (DMSO-$d_6$, 300 MHz) δ: 1.50 (6H, s), 3.22 (2H, t, J=6.4 Hz), 4.45 (2H, t, J=6.4 Hz), 7.53 (2H, d, J=8.6 Hz) 7.58-7.62 (2H, m), 7.98 (1H, d, J=8.9 Hz), 8.03 (2H, d, J=8.7 Hz), 8.39 (1H, d, J=2.9 Hz).

MS: 435 (M$^+$+1).

Example 90

2-[(4-{[(4'-chlorobiphenyl-3-yl)oxy]methyl}-1,3-thiazol-2-yl)thio]-2-methylpropionic acid

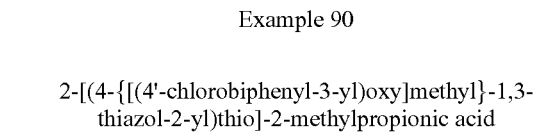

The title compound was obtained by an operation similar to that of Example 67-1 and using 2-{[4-(hydroxymethyl)-1,3-thiazol-2-yl]thio}-2-methylpropionic acid tert-butyl ester synthesized in Example 10 and 3-bromophenol as starting materials, followed by an operation similar to that of Example 68 and using 4-chlorophenylboric acid.

$^1$H-NMR (CDCl$_3$, 300 MHz) δ: 1.64 (6H, s), 5.26 (2H, s), 6.95-7.52 (9H, m).

MS: 420 (M$^+$+1).

Example 91

2-[(4-{[(4'-fluorobiphenyl-3-yl)oxy]methyl}-1,3-thiazol-2-yl)thio]-2-methylpropionic acid

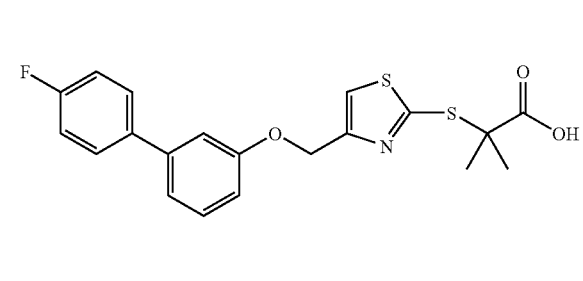

The title compound was obtained by an operation similar to that of Example 67-1 and using 2-{[4-(hydroxymethyl)-1,3-thiazol-2-yl]thio}-2-methylpropionic acid tert-butyl ester synthesized in Example 10 and 3-bromophenol as starting materials, followed by an operation similar to that of Example 68 and using 4-fluorophenylboric acid.

$^1$H-NMR (CDCl$_3$, 300 MHz) δ: 1.64 (6H, s), 5.26 (2H, s) 6.90-6.97 (1H, m), 7.08-7.19 (4H, m), 7.33-7.39 (2H, m), 7.50-7.55 (2H, m).

MS: 404 (M$^+$+1).

Example 92

2-{[4-(2-{[4'-fluoro-3-(methoxycarbonyl)biphenyl-4-yl]oxy}ethyl)-1,3-thiazol-2-yl]thio}-2-methylpropionic acid

Example 92-1

2-(2-{2-[(2-tert-butoxy-1,1-dimethyl-2-oxoethyl)thio]-1,3-thiazol-4-yl}ethoxy)-5-iodobenzoic acid methyl ester

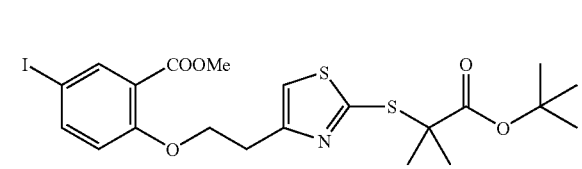

2-{[4-(2-Hydroxyethyl)-1,3-thiazol-2-yl]thio}-2-methylpropionic acid tert-butyl ester (8.0 g) synthesized in Example 4 and 5-iodosalicylic acid methyl ester (7.3 g) were dissolved in tetrahydrofuran (130 mL), triphenylphosphine (9.0 g) and diethyl diazodicarboxylate (14.9 g) were added under ice-cooling, and the mixture was stirred at room temperature for 8 hr. The reaction mixture was concentrated under reduced pressure, and the residue was purified by silica gel chromatography (elution solvent; hexane:ethyl acetate=10:1 to 5:1) to give the title compound (14.3 g) as a colorless oil.

$^1$H-NMR (CDCl$_3$, 300 MHz) δ: 1.41 (9H, s), 1.56 (6H, s), 3.28 (2H, t, J=6.6 Hz), 3.85 (3H, s), 4.32 (2H, t, J=6.6 Hz), 6.75 (1H, d, J=8.7 Hz), 7.29 (1H, s), 7.70 (1H, dd, J=2.4, 8.7 Hz) 8.05 (1H, d, J=2.4 Hz)

Example 92-2

4-(2-{2-[(2-tert-butoxy-1,1-dimethyl-2-oxoethyl)thio]-1,3-thiazol-4-yl}ethoxy)-4'-fluoro-biphenyl-3-carboxylic acid methyl ester

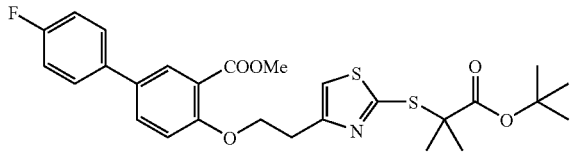

Under nitrogen atmosphere, 2-(2-{2-[(2-tert-butoxy-1,1-dimethyl-2-oxoethyl)thio]-1,3-thiazol-4-yl}ethoxy)-5-iodo-benzoic acid methyl ester (5.0 g) synthesized in Example 92-1 and 4-fluorophenylboric acid (1.5 g) were dissolved in dioxane (40 mL) and aqueous sodium carbonate solution (2 mol/L, 20 mL), tetrakis(triphenylphosphine)palladium (0.51 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (2.7 g) as a colorless oil.

$^1$H-NMR (CDCl$_3$, 300 MHz) δ: 1.42 (9H, s), 1.56 (6H, s), 3.32 (2H, t, J=6.3 Hz), 3.89 (3H, s), 4.39 (2H, t, J=6.3 Hz), 7.03-7.14 (3H, m), 7.33 (1H, s), 7.48-7.53 (2H, m), 7.60-7.63 (1H, m), 7.96 (1H, d, J=2.6 Hz)

Example 92-3

2-{[4-(2-{[4'-fluoro-3-(methoxycarbonyl)biphenyl-4-yl]oxy}ethyl)-1,3-thiazol-2-yl]thio}-2-methylpropionic acid

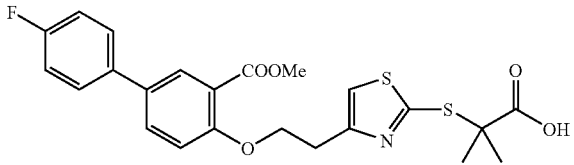

4-(2-{2-[(2-tert-Butoxy-1,1-dimethyl-2-oxoethyl)thio]-1,3-thiazol-4-yl}ethoxy)-4'-fluoro-biphenyl-3-carboxylic acid methyl ester (250 mg) obtained in Example 92-2 was dissolved in dichloromethane (2 mL), trifluoroacetic acid (2 mL) was added, the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (175 mg) as a colorless oil.

$^1$H-NMR (CDCl$_3$, 300 MHz) δ: 1.61 (6H, s), 3.34 (2H, t, J=6.0 Hz), 3.87 (3H, s), 4.40 (2H, t, J=6.0 Hz), 7.03-7.14 (3H, m), 7.38 (1H, s), 7.48-7.52 (2H, m), 7.63 (1H, dd, J=2.4, 8.4 Hz), 7.95 (1H, d, J=2.4 Hz)

MS: 476 (M$^+$+1).

Example 93

2-{[4-(2-{[4'-fluoro-3-(morpholin-4-ylcarbonyl)biphenyl-4-yl]oxy}ethyl)-1,3-thiazol-2-yl]thio}-2-methylpropionic acid Example 93-1

4'-fluoro-4-(2-{2-[(2-tert-butoxy-1,1-dimethyl-2-oxoethyl)thio]-1,3-thiazol-4-yl}ethoxy)biphenyl-3-carboxylic acid

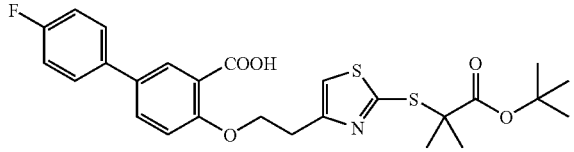

4-(2-{2-[(2-tert-Butoxy-1,1-dimethyl-2-oxoethyl)thio]-1,3-thiazol-4-yl}ethoxy)-4'-fluoro-biphenyl-3-carboxylic acid methyl ester (1.6 g) synthesized in Example 92-2 was dissolved in methanol (15 mL) and tetrahydrofuran (20 mL), aqueous sodium hydroxide solution (1 mol/L, 15 ml) was added, and the mixture was stirred at room temperature overnight. The reaction mixture was concentrated under reduced pressure, aqueous 10% citric acid solution was added, and the mixture was extracted with ethyl acetate. The organic layer was washed with saturated brine, and dried over anhydrous sodium sulfate. The solvent was evaporated under reduced pressure to give the title compound (1.3 g) as an oil.

$^1$H-NMR (CDCl$_3$, 300 MHz) δ: 1.41 (9H, s), 1.56 (6H, s), 3.34 (2H, t, J=6.1 Hz), 4.63 (2H, t, J=6.1 Hz), 7.09-7.18 (4H, m), 7.51-7.55 (2H, m), 7.45 (1H, dd, J=2.4, 8.6 Hz), 8.33 (1H, d, J=2.5 Hz).

Example 93-2

2-{[4-(2-{[4'-fluoro-3-(morpholin-4-ylcarbonyl)biphenyl-4-yl]oxy}ethyl)-1,3-thiazol-2-yl]thio}-2-methylpropionic acid tert-butyl ester

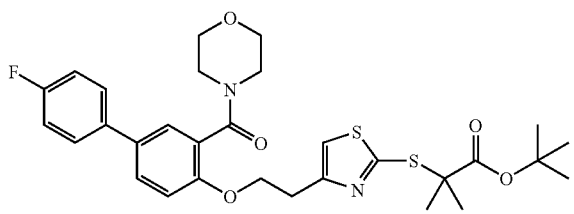

4'-Fluoro-4-(2-{2-[(2-tert-butyl-1,1-dimethyl-2-oxoethyl)thio]-1,3-thiazol-4-yl}ethoxy)biphenyl-3-carboxylic acid (170 mg) obtained in Example 93-1 and morpholine (43 mg) were dissolved in dichloromethane (2 mL), N-(3-dimethylaminopropyl)-N'-ethylcarbodiimide (EDC) hydrochloride (94 mg) and 1-hydroxybenztriazole (HOBt) monohydrate (75 mg) were successively added, and the mixture was stirred at room temperature for 6 hr. The reaction mixture was concentrated under reduced pressure, and the residue was purified by silica gel chromatography (elution solvent; hexane:ethyl acetate=2:1) to give the title compound (180 mg) as a colorless oil.

¹H-NMR (CDCl₃, 300 MHz) δ: 1.44 (9H, s), 1.58 (6H, s), 3.13-3.27 (4H, m), 3.49-3.53 (2H, m), 3.68-3.90 (4H, m), 4.10-4.40 (2H, m), 7.00 (1H, d, J=8.7 Hz), 7.07-7.14 (3H, m), 7.43 (1H, d, J=2.4 Hz), 7.46-7.52 (3H, m).

Example 93-3

2-{[4-(2-{[4'-fluoro-3-(morpholin-4-ylcarbonyl)biphenyl-4-yl]oxy}ethyl)-1,3-thiazol-2-yl]thio}-2-methylpropionic acid

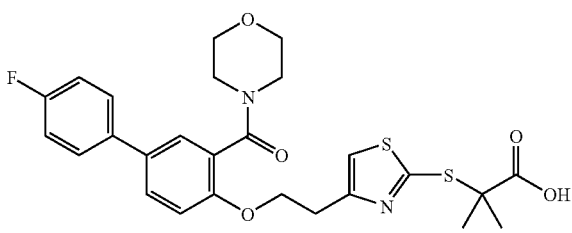

2-{[4-(2-{[4'-Fluoro-3-(morpholin-4-ylcarbonyl)biphenyl-4-yl]oxy}ethyl)-1,3-thiazol-2-yl]thio}-2-methylpropionic acid tert-butyl ester (180 mg) obtained in Example 93-2 was dissolved in dichloromethane (2 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (120 mg) as a colorless oil.

¹H-NMR (CDCl₃, 300 MHz) δ: 1.64-1.66 (6H, m), 3.14-3.28 (4H, m), 3.51-3.55 (2H, m), 3.67-3.83 (4H, m), 4.37-4.45 (2H, m), 7.00 (1H, d, J=8.7 Hz), 7.07-7.13 (3H, m), 7.40 (1H, d, J=2.1 Hz), 7.46-7.54 (3H, m).

MS: 531 (M⁺+1).

Example 94

2-({4-[2-({3-[(dimethylamino)carbonyl]-4'-fluorobiphenyl-4-yl}oxy)ethyl]-1,3-thiazol-2-yl}thio)-2-methylpropionic acid

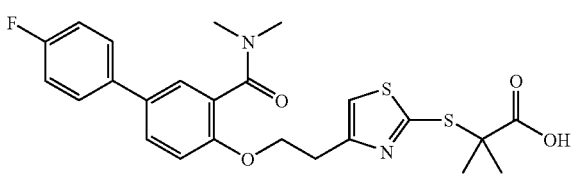

The title compound was obtained using 4'-fluoro-4-(2-{2-[(2-tert-butyl-1,1-dimethyl-2-oxoethyl)thio]-1,3-thiazol-4-yl}ethoxy)biphenyl-3-carboxylic acid obtained in Example 93-1 and dimethylamine hydrochloride as starting materials and by operations similar to those of Example 93-2 and Example 93-3.

¹H-NMR (CDCl₃, 300 MHz) δ: 1.63 (6H, s), 2.77 (3H, s), 3.07 (3H, s), 3.24 (2H, t, J=5.8 Hz), 4.38 (2H, brs), 6.98 (1H, d, J=8.9 Hz), 7.06-7.12 (3H, m), 7.39 (1H, d, J=2.3 Hz), 7.45-7.51 (3H, m)

MS: 489 (M⁺+1).

Example 95

2-({4-[2-({4'-fluoro-3-[(methylamino)carbonyl]biphenyl-4-yl}oxy)ethyl]-1,3-thiazol-2-yl}thio)-2-methylpropionic acid

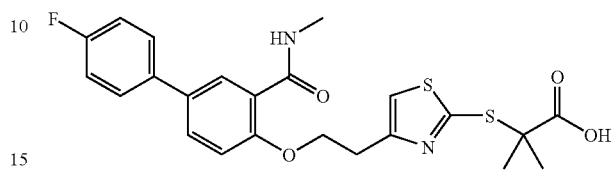

The title compound was obtained using 4'-fluoro-4-(2-{2-[(2-tert-butyl-1,1-dimethyl-2-oxoethyl)thio]-1,3-thiazol-4-yl}ethoxy)biphenyl-3-carboxylic acid obtained in Example 93-1 and methylamine hydrochloride as starting materials and by operations similar to those of Example 93-2 and Example 93-3.

¹H-NMR (CDCl₃, 300 MHz) δ: 1.59 (6H, s), 2.91-2.92 (3H, m), 3.34 (2H, t, J=6.0 Hz), 4.54 (2H, t, J=6.0 Hz), 7.02-7.13 (4H, m), 7.51-7.61 (4H, m) 8.35 (1H, d, J=2.4 Hz).

MS: 475 (M⁺+1).

Example 96

2-{[4-(2-{[3-(aminocarbonyl)-4'-fluorobiphenyl-4-yl]oxy}ethyl)-1,3-thiazol-2-yl]thio}-2-methylpropionic acid

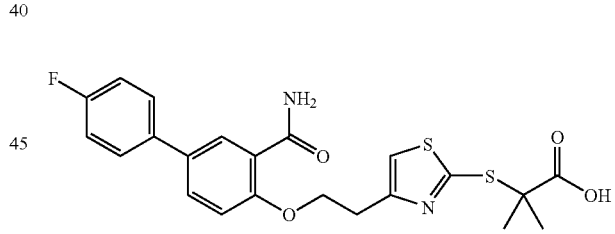

The title compound was obtained using 4'-fluoro-4-(2-{2-[(2-tert-butyl-1,1-dimethyl-2-oxoethyl)thio]-1,3-thiazol-4-yl}ethoxy)biphenyl-3-carboxylic acid obtained in Example 93-1 and ammonium acetate as starting materials and by operations similar to those of Example 93-2 and Example 93-3.

¹H-NMR (CDCl₃, 300 MHz) δ: 1.63 (6H, s), 3.31 (2H, t, J=6.3 Hz), 4.49 (2H, t, J=6.3 Hz), 6.89 (1H, brs), 6.99 (1H, d, J=8.4 Hz), 7.06 (2H, t, J=8.4 Hz) 7.11 (1H, s), 7.43-7.48 (2H, m), 7.53 (1H, dd, J=2.7, 8.7 Hz), 7.85 (1H, brs), 8.29 (1H, d, J=2.4 Hz).

MS: 461 (M⁺+1).

Example 97

2-[(4-{2-[(4'-fluoro-3-nitrobiphenyl-4-yl)oxy]ethyl}-1,3-thiazol-2-yl)thio]-2-methylpropionic acid

Example 97-1

2-({4-[2-(4-bromo-3-nitrophenoxy)ethyl]-1,3-thiazol-2-yl}thio)-2-methylpropionic acid tert-butyl ester

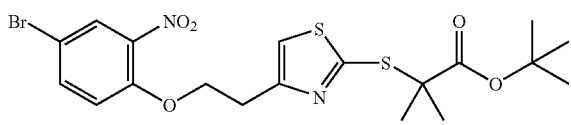

2-{[4-(2-Hydroxyethyl)-1,3-thiazol-2-yl]thio}-2-methylpropionic acid tert-butyl ester (5.0 g) synthesized in Example 4 and 4-bromo-2-nitrophenol (3.6 g) were dissolved in tetrahydrofuran (82 mL), triphenylphosphine (5.6 g) and diethyl diazodicarboxylate (9.3 g) were added under ice-cooling, and the mixture was stirred at room temperature for 8 hr. The reaction mixture was concentrated under reduced pressure, and the residue was purified by silica gel chromatography (elution solvent; hexane:ethyl acetate=5:1 to 3:1) to give the title compound (8.0 g) as a colorless oil.

$^1$H-NMR (CDCl$_3$, 300 MHz) δ: 1.41 (9H, s), 1.56 (6H, s), 3.28 (2H, t, J=6.3 Hz), 4.40 (2H, t, J=6.3 Hz), 6.99 (1H, d, J=9.0 Hz), 7.22 (1H, s), 7.61 (1H, dd, J=2.5, 9.0 Hz), 8.00 (1H, d, J=2.5 Hz).

Example 97-2

2-[(4-{2-[(4'-fluoro-3-nitrobiphenyl-4-yl)oxy]ethyl}-1,3-thiazol-2-yl)thio]-2-methylpropionic acid tert-butyl ester

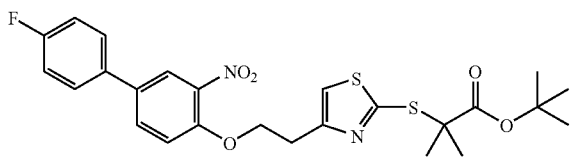

Under nitrogen atmosphere, 2-({4-[2-(4-bromo-3-nitrophenoxy)ethyl]-1,3-thiazol-2-yl}thio)-2-methylpropionic acid tert-butyl ester (4.0 g) synthesized in Example 97-1 and 4-fluorophenylboric acid (1.33 g) were dissolved in dioxane (40 mL) and aqueous sodium carbonate solution (2 mol/L, 20 mL), tetrakis(triphenylphosphine)palladium (0.46 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1 to 2:1) to give the title compound (4.3 g) as a colorless oil.

$^1$H-NMR (CDCl$_3$, 300 MHz) δ: 1.41 (9H, s), 1.58 (6H, s), 3.32 (2H, t, J=6.3 Hz), 4.46 (2H, t, J=6.3 Hz), 7.11-7.17 (3H, m), 7.27 (1H, s), 7.48-7.52 (2H, m), 7.68 (1H, dd, J=2.4, 8.7 Hz), 8.00 (1H, d, J=2.4 Hz).

Example 97-3

2-[(4-{2-[(4'-fluoro-3-nitrobiphenyl-4-yl)oxy]ethyl}-1,3-thiazol-2-yl)thio]-2-methylpropionic acid

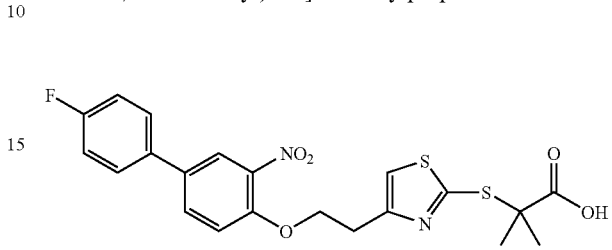

2-[(4-{2-[(4'-Fluoro-3-nitrobiphenyl-4-yl)oxy]ethyl}-1,3-thiazol-2-yl)thio]-2-methylpropionic acid tert-butyl ester (300 mg) obtained in Example 97-2 was dissolved in dichloromethane (2 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (167 mg) as a white solid.

$^1$H-NMR (CDCl$_3$, 300 MHz) δ: 1.60 (6H, s), 3.34 (2H, t, J=6.0 Hz), 4.46 (2H, t, J=6.0 Hz), 7.11-7.17 (3H, m), 7.27 (1H, s), 7.47-7.52 (2H, m), 7.70 (1H, dd, J=2.4, 9.0 Hz), 7.99 (1H, d, J=2.4 Hz).

MS: 463 (M$^+$+1).

Example 98

2-[(4-{2-[(3-amino-4'-fluorobiphenyl-4-yl)oxy]ethyl}-1,3-thiazol-2-yl)thio]-2-methylpropionic acid

Example 98-1

2-[(4-{2-[(3-amino-4'-fluorobiphenyl-4-yl)oxy]ethyl}-1,3-thiazol-2-yl)thio]-2-methylpropionic acid tert-butyl ester

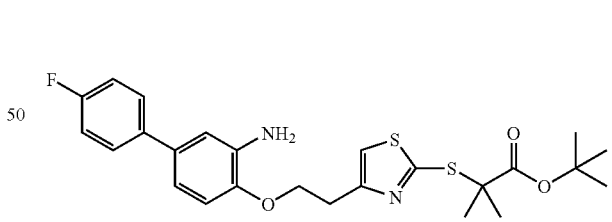

2-[(4-{2-[(4'-Fluoro-3-nitrobiphenyl-4-yl)oxy]ethyl}-1,3-thiazol-2-yl)thio]-2-methylpropionic acid tert-butyl ester (2.0 g) obtained in Example 97-2 was dissolved in methanol (20 mL), a catalytic amount of iron chloride (III) (62 mg), activated carbon (1.0 g) and hydrazine monohydrate (580 mg) were successively added, and the mixture was heated under reflux for 3 hr. The mixture was filtered through celite, methanol was evaporated under reduced pressure, and the residue was extracted with ethyl acetate. The organic layer was washed with water and saturated brine, and dried over anhydrous sodium sulfate. The solvent was evaporated under reduced pressure to give the title compound (1.5 g).

¹H-NMR (CDCl₃, 300 MHz) δ: 1.43 (9H, s), 1.58 (6H, s), 3.29 (2H, t, J=6.3 Hz), 3.84 (2H, brs), 4.38 (2H, t, J=6.3 Hz), 6.86-6.89 (3H, m), 7.04-7.14 (3H, m), 7.44-7.48 (2H, m).

Example 98-2

2-[(4-{2-[(3-amino-4'-fluorobiphenyl-4-yl)oxy]ethyl}-1,3-thiazol-2-yl)thio]-2-methylpropionic acid

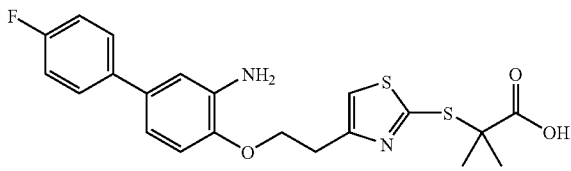

2-[(4-{2-[(3-Amino-4'-fluorobiphenyl-4-yl)oxy]ethyl}-1,3-thiazol-2-yl)thio]-2-methylpropionic acid tert-butyl ester (230 mg) obtained in Example 98-1 was dissolved in dichloromethane (2 mL), trifluoroacetic acid (2 mL) was added, and the mixture was stirred at room temperature for 12 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=2:1 to 1:1) to give the title compound (148 mg) as a white solid.

¹H-NMR (CDCl₃, 300 MHz) δ: 1.62 (6H, s), 3.31 (2H, t, J=6.0 Hz), 4.36 (2H, t, J=6.0 Hz), 6.82-6.92 (3H, m), 7.04-7.11 (3H, m), 7.42-7.47 (2H, m).

MS: 433 (M⁺+1).

Example 99

2-{[4-(2-{[3-(acetylamino)-4'-fluorobiphenyl-4-yl]oxy}ethyl)-1,3-thiazol-2-yl]thio}-2-methylpropionic acid

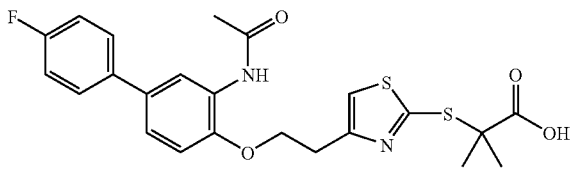

2-[(4-{2-[(3-Amino-4'-fluorobiphenyl-4-yl)oxy]ethyl}-1,3-thiazol-2-yl)thio]-2-methylpropionic acid tert-butyl ester (300 mg) obtained in Example 98-1 was dissolved in dichloromethane (3 mL), and triethylamine (0.13 mL) and acetyl chloride (72 mg) were added under ice-cooling. After 1 hr, water was added to the reaction mixture, and the organic layer was washed with saturated brine and dried over anhydrous sodium sulfate. The solvent was evaporated under reduced pressure, and the residue was purified by silica gel chromatography (elution solvent; hexane:ethyl acetate=2:1) to give the N-acetylated compound (260 mg) as a white solid. Then, the title compound was obtained by an operation similar to that of Example 98-2.

¹H-NMR (CDCl₃, 300 MHz) δ: 1.62 (6H, s), 2.22 (3H, s), 3.32 (2H, t, J=5.7 Hz), 4.42 (2H, t, J=5.7 Hz), 6.93 (1H, d, J=8.4 Hz), 7.05-7.11 (3H, m), 7.18-7.21 (1H, m), 7.49-7.54 (2H, m), 7.83 (1H, brs), 8.54 (1H, brs).

MS: 475 (M⁺+1).

Example 100

2-{[4-(2-[5-(4-fluorophenyl)pyridin-2-yl]oxy}ethyl)-1,3-thiazol-2-yl]thio-2-methylpropionic acid Example 100-1

2-[(4-{2-[(5-bromopyridin-2-yl)oxy]ethyl}-1,3-thiazol-2-yl)thio]-2-methylpropionic acid tert-butyl ester

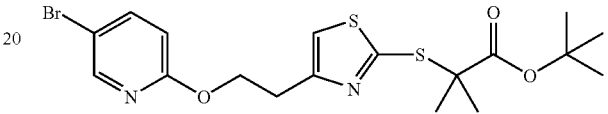

2-{[4-(2-Hydroxyethyl)-1,3-thiazol-2-yl]thio}-2-methylpropionic acid tert-butyl ester (2.12 g) synthesized in Example 4 and 5-bromopyridin-2-ol (1.22 g) were dissolved in tetrahydrofuran (20 mL), triphenylphosphine (2.02 g) and diisopropyl diazodicarboxylate (40% toluene solution, 4.14 ml) were added under ice-cooling, and the mixture was stirred at room temperature for 12 hr. The reaction mixture was concentrated under reduced pressure, and hexane (about 10 mL) was added. The precipitated crystals were removed by filtration, and the solvent of the filtrate was evaporated under reduced pressure. The residue was purified by silica gel chromatography (elution solvent; hexane:ethyl acetate=5:1) to give the title compound (1.84 g) as a pale-yellow oil.

¹H-NMR (DMSO-d₆, 300 MHz) δ: 1.32 (9H, s), 1.50 (6H, s), 3.15 (2H, t, J=6.6 Hz), 4.54 (2H, t, J=6.6 Hz), 6.77 (1H, d, J=8.8 Hz), 7.54 (1H, s), 7.88 (1H, dd, J=2.5 Hz, 8.8 Hz), 8.27 (1H, d, J=2.5 Hz).

Example 100-2

2-{[4-(2-{[5-(4-fluorophenyl)pyridin-2-yl]oxy}ethyl)-1,3-thiazol-2-yl]thio}-2-methylpropionic acid tert-butyl ester

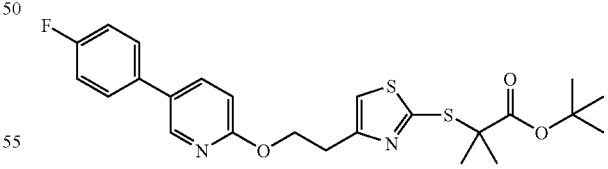

Under nitrogen atmosphere, 2-[(4-{2-[(5-bromopyridin-2-yl)oxy]ethyl}-1,3-thiazol-2-yl)thio]-2-methylpropionic acid tert-butyl ester (486 mg) synthesized in Example 100-1 and 4-fluorophenylboric acid (297 mg) were dissolved in tetrahydrofuran (10 mL) and sodium hydrogen carbonate (1 mol/l, 10 mL), tetrakis(triphenylphosphine)palladium (245 mg) was added, and the mixture was refluxed for 4.5 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (304 mg) as a pale-yellow oil.

$^1$H-NMR (DMSO-d$_6$, 300 MHz) δ: 1.36 (9H, s), 1.51 (6H, s), 3.19 (2H, t, J=6.6 Hz), 4.61 (2H, t, J=6.6 Hz), 6.85 (1H, d, J=8.7 Hz), 7.29 (2H, t, J=9.0 Hz), 7.56 (1H, s), 7.70 (2H, dd, J=5.4 Hz, 9 Hz), 7.98 (1H, dd, J=2.7 Hz, 8.7 Hz), 8.45 (1H, d, J=2.7 Hz).

Example 100-3

2-{[4-(2-{[5-(4-fluorophenyl)pyridin-2-yl]oxy}ethyl)-1,3-thiazol-2-yl]thio}-2-methylpropionic acid

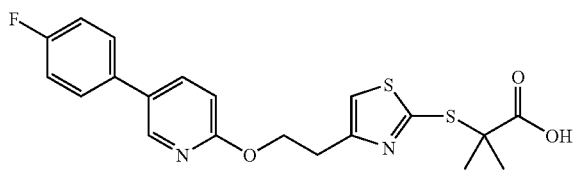

2-{[4-(2-{[5-(4-Fluorophenyl)pyridin-2-yl]oxy}ethyl)-1,3-thiazol-2-yl]thio}-2-methylpropionic acid tert-butyl ester obtained in Example 100-2 was dissolved in dichloromethane (2 ml), trifluoroacetic acid (1 ml) was added, and the mixture was stirred at room temperature for 12 hr. The reaction mixture was concentrated under reduced pressure, and the residue was purified by silica gel chromatography (elution solvent; hexane:ethyl acetate=5:1 to 2:1) to give the title compound (201 mg) as a white solid.

$^1$H-NMR (DMSO-d$_6$, 300 MHz) δ: 1.51 (6H, s), 3.19 (2H, t, J=6.6 Hz), 4.61 (2H, t, J=6.6 Hz), 6.86 (1H, d, J=8.7 Hz), 7.29 (2H, t, J=9.0 Hz), 7.56 (1H, s), 7.70 (2H, m), 7.98 (1H, dd, J=2.7 Hz, 8.7 Hz), 8.46 (1H, d, J=2.7 Hz), 12.91 (1H, s).

MS: 419 (M$^+$+1).

Example 101

2-{[4-(2-{[5-(3-fluorophenyl)pyridin-2-yl]oxy}ethyl)-1,3-thiazol-2-yl]thio}-2-methylpropionic acid

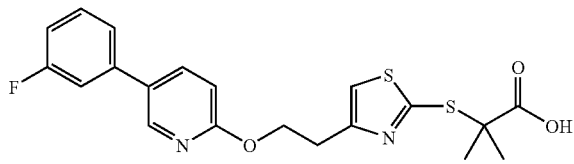

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3-fluorophenylboric acid as starting materials and by operations similar to those of Example 100-2 and Example 100-3.

$^1$H-NMR (DMSO-d$_6$, 300 MHz) δ: 1.50 (6H, s), 3.20 (2H, t, J=6.6 Hz), 4.62 (2H, t, J=6.6 Hz), 6.88 (1H, d, J=8.7 Hz), 7.18 (1H, m), 7.51 (2H, m), 7.56 (1H, s), 8.05 (1H, dd, J=2.7 Hz, 6.3 Hz), 8.53 (1H, d, J=2.7 Hz), 12.91 (1H, s).

MS: 419 (M$^+$+1).

Example 102

2-methyl-2-({4-[2-({5-[4-(trifluoromethyl)phenyl]pyridin-2-yl}oxy)ethyl]-1,3-thiazol-2-yl}thio)propionic acid hydrochloride

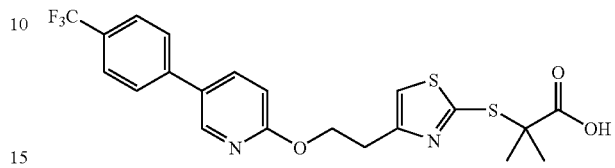

A compound obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 4-(trifluoromethyl)phenylboric acid as starting materials by operations similar to those of Example 100-2 and Example 100-3 was reacted with 4 mol/L hydrochloric acid-ethyl acetate to give the title compound.

$^1$H-NMR (DMSO-d$_6$, 300 MHz) δ: 1.50 (6H, s), 3.21 (2H, t, J=6.6 Hz), 4.64 (2H, t, J=6.6 Hz), 6.92 (1H, d, J=8.7 Hz), 7.58 (1H, s), 7.81 (2H, t, J=8.4 Hz), 7.91 (2H, d, J=8.4 Hz), 8.10 (1H, dd, J=2.7 Hz, 8.7 Hz), 8.57 (1H, d, J=2.7 Hz).

MS: 469 (M$^+$+1).

Example 103

2-methyl-2-({4-[2-({5-[3-(trifluoromethyl)phenyl]pyridin-2-yl}oxy)ethyl]-1,3-thiazol-2-yl}thio)propionic acid

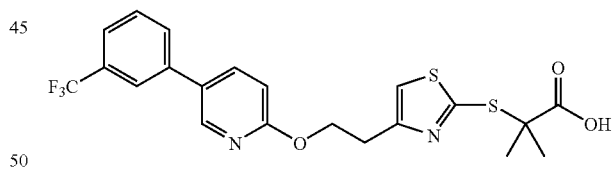

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3-(trifluoromethyl)phenylboric acid as starting materials and by operations similar to those of Example 100-2 and Example 100-3.

$^1$H-NMR (DMSO-d$_6$, 300 MHz) δ: 1.50 (6H, s), 3.21 (2H, t, J=6.6 Hz), 4.63 (2H, t, J=6.6 Hz), 6.90 (2H, d, J=8.7 Hz), 7.57 (1H, s), 7.61-7.74 (2H, m), 7.98-8.00 (2H, m), 8.11 (1H, dd, J=2.4 Hz, 8.4 Hz), 8.57 (1H, d, J=2.4 Hz), 12.93 (1H, brs).

MS: 469 (M$^+$+1).

Example 104

2-methyl-2-({4-[2-({5-[4-(trifluoromethoxy)phenyl]pyridin-2-yl}oxy)ethyl]-1,3-thiazol-2-yl}thio)propionic acid

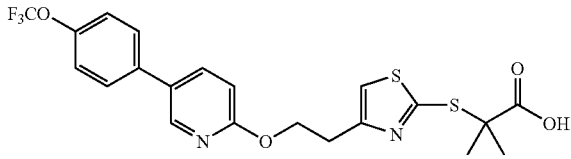

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 4-(trifluoromethoxy)phenylboric acid as starting materials and by operations similar to those of Example 100-2 and Example 100-3.

$^1$H-NMR (DMSO-d$_6$, 300 MHz) δ: 1.50 (6H, s), 3.18 (2H, t, J=6.6 Hz), 4.62 (2H, t, J=6.6 Hz), 6.89 (1H, d, J=8.4 Hz), 7.46 (2H, d, J=8.4 Hz), 7.57 (1H, s), 7.79 (2H, d, J=8.7 Hz), 8.03 (1H, dd, J=2.7 Hz, 8.4 Hz), 8.50 (1H, d, J=2.7 Hz), 12.95 (1H, brs).

MS: 485 (M$^+$+1).

Example 105

2-methyl-2-({4-[2-({5-[3-(trifluoromethoxy)phenyl]pyridin-2-yl}oxy)ethyl]-1,3-thiazol-2-yl}thio)propionic acid

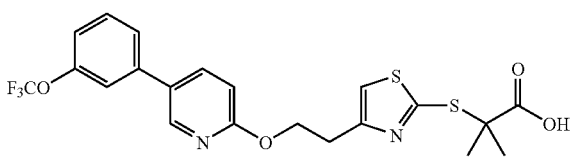

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3-(trifluoromethoxy)phenylboric acid as starting materials and by operations similar to those of Example 100-2 and Example 100-3.

$^1$H-NMR (DMSO-d$_6$, 300 MHz) δ: 1.50 (6H, s), 3.20 (2H, t, J=6.6 Hz), 4.62 (2H, t, J=6.6 Hz), 6.89 (2H, d, J=8.4 Hz), 7.36 (1H, s), 7.56-7.62 (2H, m), 7.67 (1H, s), 7.72 (1H, d, J=8.1 Hz), 8.07 (1H, dd, J=2.1 Hz, 9.0 Hz), 8.54 (1H, d, J=2.7 Hz), 12.93 (1H, brs).

MS: 485 (M$^+$+1).

Example 106

2-{[4-(2-{[5-(4-chlorophenyl)pyridin-2-yl]oxy}ethyl)-1,3-thiazol-2-yl]thio}-2-methylpropionic acid

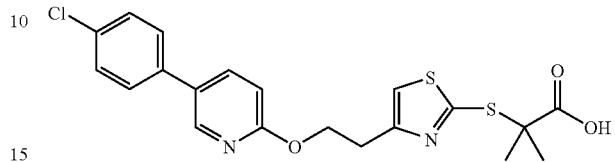

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 4-chlorophenylboric acid as starting materials and by operations similar to those of Example 100-2 and Example 100-3.

$^1$H-NMR (DMSO-d$_6$, 300 MHz) δ: 1.50 (6H, s), 3.19 (2H, t, J=6.6 Hz), 4.61 (2H, t, J=6.6 Hz), 6.88 (1H, d, J=8.7 Hz), 7.52 (2H, d, J=8.7 Hz), 7.57 (1H, s), 7.70 (2H, d, J=8.7 Hz), 8.05 (1H, dd, J=2.7 Hz, 8.7 Hz), 8.50 (1H, d, J=2.7 Hz), 12.95 (1H, s).

MS: 435 (M$^+$+1).

Example 107

2-{[4-(2-{[5-(3-chlorophenyl)pyridin-2-yl]oxy}ethyl)-1,3-thiazol-2-yl]thio}-2-methylpropionic acid

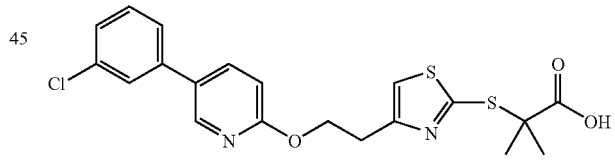

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3-chlorophenylboric acid as starting materials and by operations similar to those of Example 100-2 and Example 100-3.

$^1$H-NMR (DMSO-d$_6$, 300 MHz) δ: 1.50 (6H, s), 3.20 (2H, t, J=6.6 Hz), 4.62 (2H, t, J=6.6 Hz), 6.88 (1H, d, J=8.4 Hz), 7.43-7.52 (2H, m), 7.57 (1H, s), 7.64 (1H, d, J=7.5 Hz), 7.75 (1H, s), 8.05 (1H, dd, J=2.7 Hz, 8.4 Hz), 8.52 (1H, d, J=2.7 Hz), 12.95 (1H, s).

MS: 435 (M$^+$+1).

Example 108

2-{[4-(2-{[5-(3,4-dichlorophenyl)pyridin-2-yl]oxy}ethyl)-1,3-thiazol-2-yl]thio}-2-methylpropionic acid

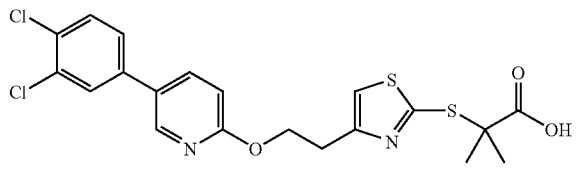

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3,4-dichlorophenylboric acid as starting materials and by operations similar to those of Example 100-2 and Example 100-3.

$^1$H-NMR (DMSO-$d_6$, 300 MHz) δ: 1.50 (6H, s), 3.19 (2H, t, J=6.6 Hz), 4.62 (2H, t, J=6.6 Hz), 6.88 (2H, d, J=8.7 Hz), 7.56 (1H, s), 7.67 (2H, d, J=8.4 Hz), 7.72 (2H, d, J=8.4 Hz), 7.97 (1H, s), 8.07 (1H, dd, J=2.7 Hz, 8.7 Hz), 8.55 (1H, d, J=2.7 Hz), 12.95 (1H, s).

MS: 469 (M$^+$+1).

Example 109

2-{[4-(2-{[5-(3-chloro-4-fluorophenyl)pyridin-2-yl]oxy}ethyl)-1,3-thiazol-2-yl]thio}-2-methylpropionic acid

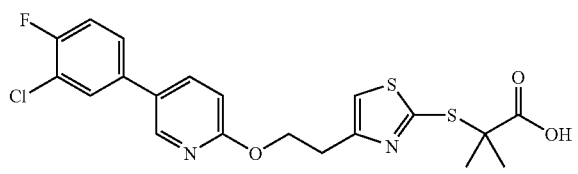

The title compound was obtained using 2-[(4-{2-[(5-bromopyridin-2-yl)oxy]ethyl}-1,3-thiazol-2-yl)thio]-2-methylpropionic acid tert-butyl ester synthesized in Example 100-1 and 3-chloro-4-fluorophenylboric acid as starting materials and by operations similar to those of Example 100-2 and Example 100-3.

$^1$H-NMR (DMSO-$d_6$, 300 MHz) δ: 1.50 (6H, s), 3.20 (2H, t, J=6.6 Hz), 4.62 (2H, t, J=6.6 Hz), 6.87 (2H, d, J=8.4 Hz), 7.51 (1H, t, J=9.0 Hz), 7.66 (1H, s), 7.69 (1H, m), 7.91 (1H, dd, J=2.4 Hz, 7.2 Hz), 8.07 (1H, dd, J=2.7 Hz, 8.7 Hz), 8.51 (1H, d, J=2.4 Hz), 12.93 (1H, s).

MS: 453 (M$^+$+1).

Example 110

2-methyl-2-({4-[2-({5-[4-(trifluoromethoxy)phenyl]pyrimidin-2-yl}oxy)ethyl]-1,3-thiazol-2-yl}thio)propionic acid

Example 110-1

2-[(4-{2-[(5-bromopyrimidin-2-yl)oxy]ethyl}-1,3-thiazol-2-yl)thio]-2-methylpropionic acid tert-butyl ester

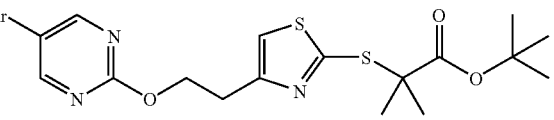

2-{[4-(2-Hydroxyethyl)-1,3-thiazol-2-yl]thio}-2-methylpropionic acid tert-butyl ester (7.84 g) synthesized in Example 4 and 5-bromo-2-chloropyrimidine (5.0 g) were dissolved in N,N-dimethylformamide (70 mL), potassium tert-butoxide (3.47 g) was added, and the mixture was stirred at room temperature for 4 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (6.0 g) as a colorless oil.

$^1$H-NMR (CDCl$_3$, 300 MHz) δ: 1.42 (9H, s), 1.57 (6H, s), 3.28 (2H, t, J=6.6 Hz), 4.67 (2H, t, J=6.6 Hz), 7.14 (1H, s), 8.51 (2H, s).

Example 110-2

2-methyl-2-({4-[2-({5-[4-(trifluoromethoxy)phenyl]pyrimidin-2-yl}oxy)ethyl]-1,3-thiazol-2-yl}thio)propionic acid tert-butyl ester

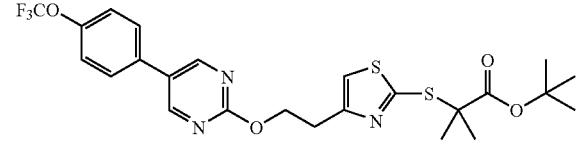

Under nitrogen atmosphere, 2-[(4-{2-[(5-bromopyrimidin-2-yl)oxy]ethyl}-1,3-thiazol-2-yl)thio]-2-methylpropionic acid tert-butyl ester (600 mg) synthesized in Example 110-1 and 4-trifluoromethoxyphenylboric acid (400 mg) were dissolved in dioxane (6 mL) and aqueous sodium carbonate solution (2 mol/L, 3 mL), tetrakis(triphenylphosphine)palladium (75 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1) to give the title compound (600 mg) as a colorless oil.

¹H-NMR (CDCl₃, 300 MHz) δ: 1.43 (9H, s), 1.58 (6H, s), 3.32 (2H, t, J=6.7 Hz), 4.75 (2H, t, J=6.7 Hz), 7.18 (1H, s), 7.33 (2H, d, J=8.7 Hz), 7.54 (2H, d, J=8.7 Hz), 8.68 (2H, s).

Example 110-3

2-methyl-2-({4-[2-({5-[4-(trifluoromethoxy)phenyl]pyrimidin-2-yl}oxy)ethyl]-1,3-thiazol-2-yl}thio)propionic acid

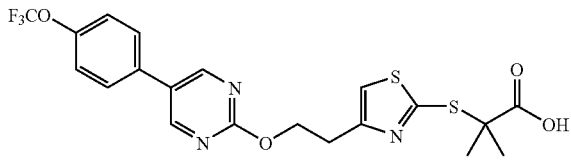

2-Methyl-2-({4-[2-({5-[4-(trifluoromethoxy)phenyl]pyrimidin-2-yl}oxy)ethyl]-1,3-thiazol-2-yl}thio)propionic acid tert-butyl ester (600 mg) obtained in Example 110-2 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (350 mg) as a white solid.

¹H-NMR (CDCl₃, 300 MHz) δ: 1.65 (6H, s), 3.32 (2H, t, J=6.2 Hz), 4.75 (2H, t, J=6.2 Hz), 7.13 (1H, s), 7.35 (2H, d, J=8.7 Hz), 7.53 (2H, d, J=8.7 Hz), 8.69 (2H, s).

MS: 486 (M⁺+1).

Example 111

2-{[4-(2-{[5-(4-chlorophenyl)pyrimidin-2-yl]oxy}ethyl)-1,3-thiazol-2-yl]thio}-2-methylpropionic acid

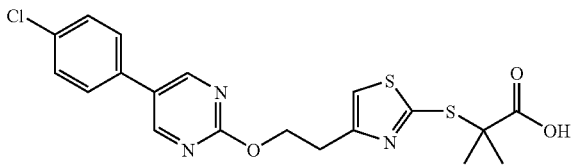

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4-chlorophenylboric acid as starting materials and by operations similar to those of Example 110-2 and Example 110-3.

¹H-NMR (CDCl₃, 300 MHz) δ: 1.65 (6H, s), 3.32 (2H, t, J=6.1 Hz), 4.74 (2H, t, J=6.1 Hz), 7.13 (1H, s), 7.45 (4H, s), 8.68 (2H, s).

MS: 436 (M⁺+1).

Example 112

2-{[4-(2-{[5-(3-chlorophenyl)pyrimidin-2-yl]oxy}ethyl)-1,3-thiazol-2-yl]thio}-2-methylpropionic acid The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 3-chlorophenylboric acid as starting materials and by operations similar to those of Example 110-2 and Example 110-3.

¹H-NMR (CDCl₃, 300 MHz) δ: 1.66 (6H, s), 3.32 (2H, t, J=6.0 Hz), 4.74 (2H, t, J=6.0 Hz), 7.13 (1H, s), 7.38 (3H, s), 7.50 (1H, s), 8.69 (2H, s).

MS: 436 (M⁺+1).

Example 113

2-methyl-2-({4-[2-({5-[4-(trifluoromethyl)phenyl]pyrimidin-2-yl}oxy)ethyl]-1,3-thiazol-2-yl}thio)propionic acid

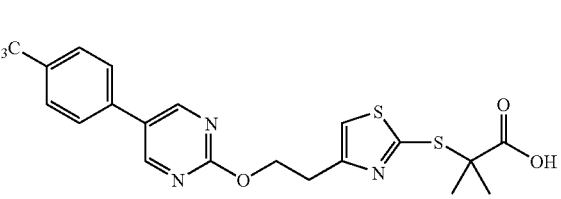

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4-(trifluoromethyl)phenylboric acid as starting materials and by operations similar to those of Example 110-2 and Example 110-3.

¹H-NMR (CDCl₃, 300 MHz) δ: 1.65 (6H, s), 3.33 (2H, t, J=6.0 Hz), 4.76 (2H, t, J=6.0 Hz), 7.14 (1H, s), 7.63 (2H, d, J=8.4 Hz), 7.75 (2H, d, J=8.4 Hz), 8.74 (2H, s).

MS: 470 (M⁺+1).

Example 114

2-methyl-2-({4-[2-({5-[3-(trifluoromethyl)phenyl]pyrimidin-2-yl}oxy)ethyl]-1,3-thiazol-2-yl}thio)propionic acid

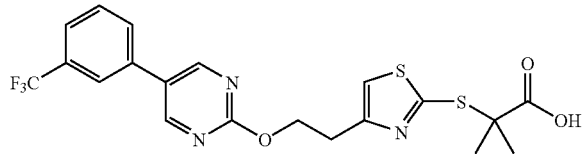

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 3-(trifluoromethyl)phenylboric acid as starting materials and by operations similar to those of Example 110-2 and Example 110-3.

$^1$H-NMR (CDCl$_3$, 300 MHz) δ: 1.66 (6H, s), 3.33 (2H, t, J=6.0 Hz), 4.76 (2H, t, J=6.0 Hz), 7.14 (1H, s), 7.59-7.75 (4H, m), 8.73 (2H, s).

MS: 470 (M$^+$+1).

Example 115

2-{[4-(2-{[5-(3-chloro-4-fluorophenyl)pyrimidin-2-yl]oxy}ethyl)-1,3-thiazol-2-yl]thio}-2-methylpropionic acid

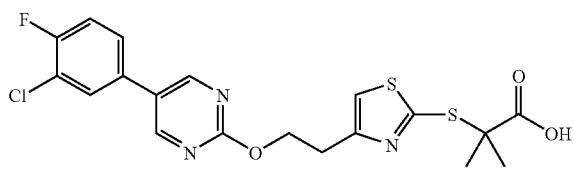

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 3-chloro-4-fluorophenylboric acid as starting materials and by operations similar to those of Example 110-2 and Example 110-3.

$^1$H-NMR (CDCl$_3$, 300 MHz) δ: 1.65 (6H, s), 3.32 (2H, t, J=6.3 Hz), 4.74 (2H, t, J=6.2 Hz), 7.13 (1H, s), 7.23-7.39 (2H, m), 7.53-7.56 (1H, m), 8.66 (2H, s).

MS: 454 (M$^+$+1).

Example 116

2-{[4-(2-{[5-(3,4-dichlorophenyl)pyrimidin-2-yl]oxy}ethyl)-1,3-thiazol-2-yl]thio}-2-methylpropionic acid

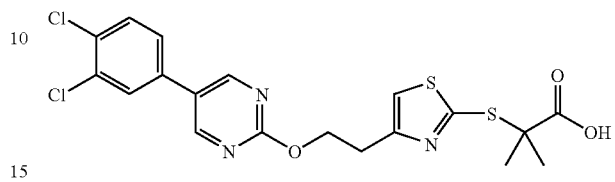

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 3,4-dichlorophenylboric acid as starting materials and by operations similar to those of Example 110-2 and Example 110-3.

$^1$H-NMR (CDCl$_3$, 300 MHz) δ: 1.65 (6H, s), 3.32 (2H, t, J=6.0 Hz), 4.75 (2H, t, J=6.0 Hz), 7.13 (1H, s), 7.34 (1H, dd, J=2.1, 8.4 Hz), 7.56 (1H, d, J=8.4 Hz), 7.60 (1H, d, J=2.1 Hz), 8.68 (2H, s).

MS: 470 (M$^+$+1).

Example 117

2-methyl-2-({4-[2-({5-[4-(2,2,2-trifluoroethoxy)phenyl]pyrimidin-2-yl}oxy)ethyl]-1,3-thiazol-2-yl}thio)propionic acid

Reference Example 1

4,4,5,5-tetramethyl-2-[4-(2,2,2-trifluoroethoxy)phenyl]-1,3,2-dioxabororane

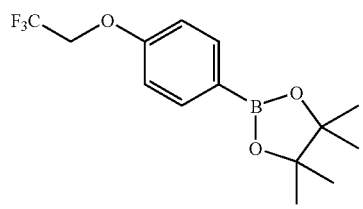

Trifluoromethanesulfonate 2,2,2-trifluoroethyl ester (5.0 g) and 4-(4,4,5,5-tetramethyl-1,3,2-dioxabororan-2-yl)phenol (5.0 g) were dissolved in N,N-dimethylformamide (50 mL), potassium carbonate (1.86 g) was added, and the mixture was stirred at 50° C. for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (2.6 g) as a colorless oil.

$^1$H-NMR (CDCl$_3$, 300 MHz) δ: 1.34 (12H, s), 4.37 (2H, q, J=8.1 Hz), 6.93 (2H, d, J=8.7 Hz), 7.78 (2H, d, J=8.7 Hz).

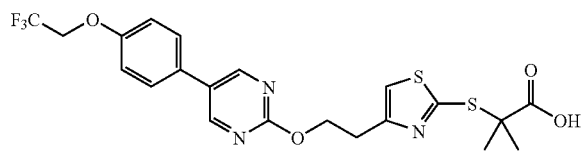

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4,4,5,5-tetramethyl-2-[4-(2,2,2-trifluoroethoxy)phenyl]-1,3,2-dioxabororane synthesized in Reference Example 1 as starting materials and by operations similar to those of Example 110-2 and Example 110-3.

$^{1}$H-NMR (CDCl$_{3}$, 300 MHz) δ: 1.65 (6H, s), 3.31 (2H, t, J=6.0 Hz), 4.40 (2H, q, J=8.4 Hz), 4.73 (2H, t, J=6.0 Hz), 7.06 (2H, d, J=8.7 Hz), 7.13 (1H, s), 7.47 (2H, d, J=8.7 Hz), 8.66 (2H, s).

MS: 500 (M$^{+}$+1).

Example 118

2-methyl-2-({4-[2-({5-[3-(2,2,2-trifluoroethoxy)phenyl]pyrimidin-2-yl}oxy)ethyl]-1,3-thiazol-2-yl}thio)propionic acid

Reference Example 2

4,4,5,5-tetramethyl-2-[3-(2,2,2-trifluoroethoxy)phenyl]-1,3,2-dioxabororane

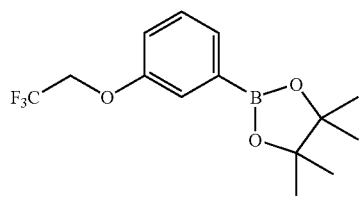

The title compound was obtained using trifluoromethanesulfonate 2,2,2-trifluoroethylester and 3-(4,4,5,5-tetramethyl-1,3,2-dioxabororan-2-yl)phenol as starting materials and by an operation similar to that of Reference Example 1.

$^{1}$H-NMR (CDCl$_{3}$, 300 MHz) δ: 1.37 (12H, s), 4.38 (2H, q, J=8.1 Hz), 7.04-7.08 (1H, m), 7.30-7.36 (2H, m), 7.48-7.51 (1H, m).

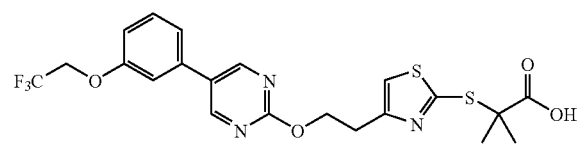

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4,4,5,5-tetramethyl-2-[3-(2,2,2-trifluoroethoxy)phenyl]-1,3,2-dioxabororane synthesized in Reference Example 2 as starting materials and by operations similar to those of Example 110-2 and Example 110-3.

$^{1}$H-NMR (CDCl$_{3}$, 300 MHz) δ: 1.65 (6H, s), 3.32 (2H, t, J=6.0 Hz), 4.42 (2H, q, J=8.4 Hz), 4.74 (2H, t, J=6.0 Hz), 6.96-7.20 (4H, m), 7.44 (1H, t, J=8.1 Hz), 8.69 (2H, s).

MS: 500 (M$^{+}$+1).

Example 119

2-methyl-2-{[4-(2-{[5-(4-propylphenyl)pyrimidin-2-yl]oxy}ethyl)-1,3-thiazol-2-yl]thio}propionic acid

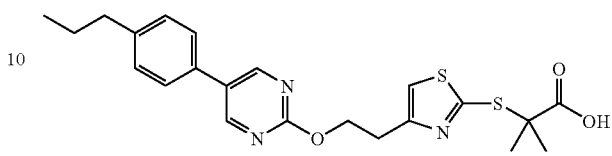

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4-propylphenylboric acid as starting materials and by operations similar to those of Example 110-2 and Example 110-3.

$^{1}$H-NMR (CDCl$_{3}$, 300 MHz) δ: 0.96 (3H, t, J=7.3 Hz), 1.60-1.71 (8H, m), 2.63 (2H, t, J=7.3 Hz), 3.31 (2H, t, J=6.1 Hz), 4.72 (2H, t, J=6.1 Hz), 7.13 (1H, s), 7.28 (2H, d, J=8.4 Hz), 7.41 (2H, d, J=8.4 Hz), 8.68 (2H, s).

MS: 444 (M$^{+}$+1).

Example 120

2-methyl-2-{[4-(2-{[5-(4-isopropylphenyl)pyrimidin-2-yl]oxy}ethyl)-1,3-thiazol-2-yl]thio}propionic acid

The title compound was obtained using 2-[(4-{2-[(5-bromopyrimidin-2-yl)oxy]ethyl}-1,3-thiazol-2-yl)thio]-2-methylpropionic acid tert-butyl ester synthesized in Example 110-1 and 4-isopropylphenylboric acid as starting materials and by operations similar to those of Example 110-2 and Example 110-3.

$^{1}$H-NMR (CDCl$_{3}$, 300 MHz) δ: 1.28 (6H, d, J=6.9 Hz), 1.65 (6H, s), 2.91-3.01 (1H, m), 3.31 (2H, t, J=6.1 Hz), 4.72 (2H, t, J=6.1 Hz), 7.13 (1H, s), 7.34 (2H, d, J=8.2 Hz), 7.43 (2H, d, J=8.2 Hz), 8.68 (2H, s).

MS: 444 (M$^{+}$+1).

Example 121

2-{[4-(2-{[3-cyano-5-(4-fluorophenyl)pyridin-2-yl]oxy}ethyl)-1,3-thiazol-2-yl]thio}-2-methylpropionic acid

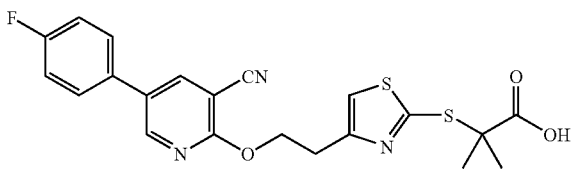

The title compound was obtained by an operation similar to that of Example 110-1 and using 2-{[4-(2-hydroxyethyl)-1,3-thiazol-2-yl]thio}-2-methylpropionic acid tert-butyl ester synthesized in Example 4 and 5-bromo-2-chloronicotinonitrile synthesized in reference to patent reference [WO0224694] and the like as starting materials, followed by operations similar to those of Example 110-2 and Example 110-3 and using 4-fluorophenylboric acid.

$^1$H-NMR (CDCl$_3$, 300 MHz) δ: 1.64 (6H, s), 3.35 (2H, t, J=6.3 Hz), 4.79 (2H, t, J=6.3 Hz), 7.14-7.20 (3H, m), 7.42-7.48 (2H, m), 8.00 (1H, d, J=2.7 Hz), 8.49 (1H, d, J=2.4 Hz).

MS: 444 (M$^+$+1).

Example 122

2-{[4-(2-{[5-(4-chlorophenyl)-3-cyanopyridin-2-yl]oxy}ethyl)-1,3-thiazol-2-yl]thio}-2-methylpropionic acid

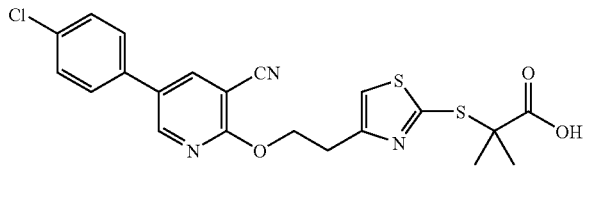

The title compound was obtained by an operation similar to that of Example 110-1 and using 2-{[4-(2-hydroxyethyl)-1,3-thiazol-2-yl]thio}-2-methylpropionic acid tert-butyl ester synthesized in Example 4 and 5-bromo-2-chloronicotinonitrile synthesized in reference to patent reference [WO0224694] and the like as starting materials, followed by operations similar to those of Example 110-2 and Example 110-3 and using 4-chlorophenylboric acid.

$^1$H-NMR (CDCl$_3$, 300 MHz) δ: 1.64 (6H, s), 3.35 (2H, t, J=6.3 Hz), 4.79 (2H, t, J=6.3 Hz), 7.20 (1H, s), 7.40-7.48 (4H, m), 8.01 (1H, d, J=2.4 Hz), 8.51 (1H, d, J=2.7 Hz).

MS: 460 (M$^+$+1).

Example 123

2-{[4-(2-{[6-(4-fluorophenyl)pyridazin-3-yl]oxy}ethyl)-1,3-thiazol-2-yl]thio}-2-methylpropionic acid

Example 123-1

2-[(4-{2-[(6-chloropyridazin-3-yl)oxy]ethyl}-1,3-thiazol-2-yl)thio]-2-methylpropionic acid tert-butyl ester

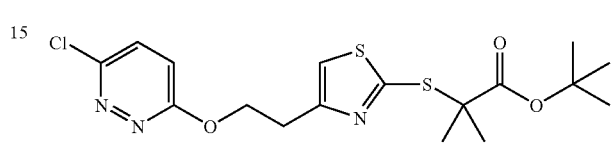

2-{[4-(2-Hydroxyethyl)-1,3-thiazol-2-yl]thio}-2-methylpropionic acid tert-butyl ester (2.0 g) synthesized in Example 4 and 3,6-dichloropyridazine (1.2 g) were dissolved in N,N-dimethylformamide (30 mL), potassium tert-butoxide (0.9 g) was added, and the mixture was stirred at room temperature for 4 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (1.7 g) as a colorless oil.

$^1$H-NMR (CDCl$_3$, 300 MHz) δ: 1.42 (9H, s), 1.58 (6H, s), 3.30 (2H, t, J=6.6 Hz), 4.83 (2H, t, J=6.6 Hz), 6.92 (1H, d, J=9.0 Hz), 7.09 (1H, s), 7.36 (1H, d, J=9.6 Hz).

Example 123-2

2-{[4-(2-{[6-(4-fluorophenyl)pyridazin-3-yl]oxy}ethyl)-1,3-thiazol-2-yl]thio}-2-methylpropionic acid tert-butyl ester

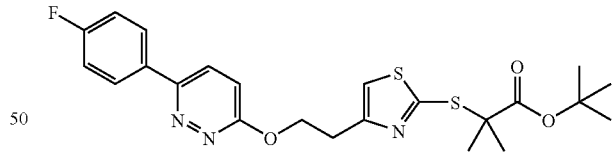

Under nitrogen atmosphere, 2-[(4-{2-[(6-chloropyridazin-3-yl)oxy]ethyl}-1,3-thiazol-2-yl)thio]-2-methylpropionic acid tert-butyl ester (500 mg) synthesized in Example 123-1 and 4-fluorophenylboric acid (292 mg) were dissolved in dioxane (6 mL) and aqueous sodium carbonate solution (2 mol/L, 3 mL), tetrakis(triphenylphosphine)palladium (80 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1) to give the title compound (400 mg) as a white solid.

¹H-NMR (CDCl₃, 300 MHz) δ: 1.43 (9H, s), 1.58 (6H, s), 3.35 (2H, t, J=6.6 Hz), 4.91 (2H, t, J=6.6 Hz), 7.02 (1H, d, J=9.3 Hz), 7.12-7.18 (3H, m), 7.74 (1H, d, J=9.3 Hz), 7.97-8.02 (2H, m).

Example 123-3

2-{[4-(2-{[6-(4-fluorophenyl)pyridazin-3-yl]oxy}ethyl)-1,3-thiazol-2-yl]thio}-2-methylpropionic acid

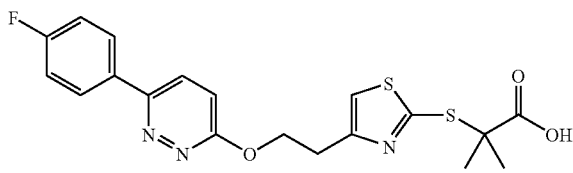

2-{[4-(2-{[6-(4-Fluorophenyl)pyridazin-3-yl]oxy}ethyl)-1,3-thiazol-2-yl]thio}-2-methylpropionic acid tert-butyl ester (400 mg) obtained in Example 123-2 was dissolved in dichloromethane (2 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (290 mg) as a white solid.

¹H-NMR (CDCl₃, 300 MHz) δ: 1.65 (6H, s), 3.36 (2H, t, J=6.1 Hz), 4.89 (2H, t, J=6.1 Hz), 7.08-7.22 (4H, m), 7.77 (1H, d, J=9.0 Hz), 7.96-8.01 (2H, m).

MS: 420 (M⁺+1).

Example 124

2-{[4-(2-{[6-(4-chlorophenyl)pyridazin-3-yl]oxy}ethyl)-1,3-thiazol-2-yl]thio}-2-methylpropionic acid

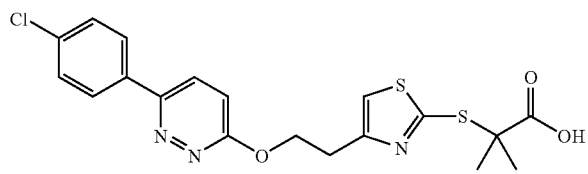

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 4-chlorophenylboric acid as starting materials and by operations similar to those of Example 123-2 and Example 123-3.

¹H-NMR (CDCl₃, 300 MHz) δ: 1.65 (6H, s), 3.36 (2H, t, J=6.0 Hz), 4.89 (2H, t, J=6.0 Hz), 7.08 (1H, s), 7.14 (1H, d, J=9.3 Hz), 7.46-7.50 (2H, m), 7.78 (1H, d, J=9.3 Hz), 7.92-7.96 (2H, m).

MS: 436 (M⁺+1).

Example 125

2-methyl-2-({4-[2-({6-[4-(trifluoromethyl)phenyl]pyridazin-3-yl}oxy)ethyl]-1,3-thiazol-2-yl}thio)propionic acid

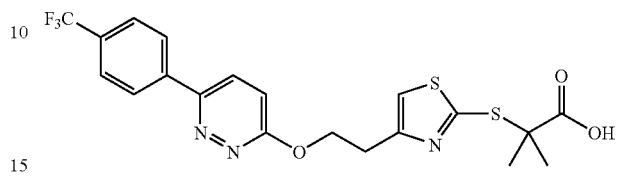

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 4-(trifluoromethyl)phenylboric acid as starting materials and by operations similar to those of Example 123-2 and Example 123-3.

¹H-NMR (CDCl₃, 300 MHz) δ: 1.65 (6H, s), 3.37 (2H, t, J=6.3 Hz), 4.91 (2H, t, J=6.3 Hz), 7.09 (1H, s), 7.19 (1H, d, J=9.3 Hz), 7.76 (2H, d, J=8.1 Hz), 7.84 (1H, d, J=9.0 Hz), 8.12 (2H, d, J=8.4 Hz).

MS: 470 (M⁺+1).

Example 126

2-methyl-2-({4-[2-({6-[4-(trifluoromethoxy)phenyl]pyridazin-3-yl}oxy)ethyl]-1,3-thiazol-2-yl}thio)propionic acid

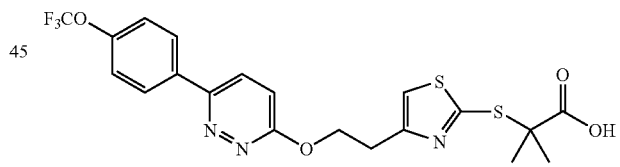

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 4-(trifluoromethoxy)phenylboric acid as starting materials and by operations similar to those of Example 123-2 and Example 123-2.

¹H-NMR (CDCl₃, 300 MHz) δ: 1.65 (6H, s), 3.37 (2H, t, J=6.2 Hz), 4.90 (2H, t, J=6.2 Hz), 7.08 (1H, s), 7.16 (1H, d, J=9.5 Hz), 7.35 (2H, brd, J=8.4 Hz), 7.79 (1H, d, J=9.1 Hz), 8.02-8.05 (2H, m).

MS: 486 (M⁺+1).

Example 127

2-methyl-2-{[4-(2-{4-[5-(trifluoromethyl)pyridin-2-yl]phenoxy}ethyl)-1,3-thiazol-2-yl]thio}propionic acid

Example 127-1

2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester

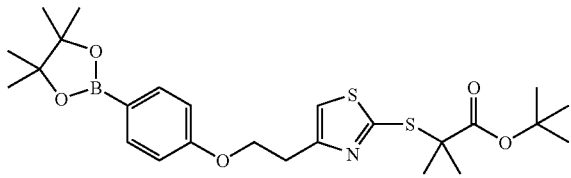

2-{[4-(2-Hydroxyethyl)-1,3-thiazol-2-yl]thio}-2-methylpropionic acid tert-butyl ester (6.89 g) synthesized in Example 4 and 4-(4,4,5,5-tetramethyl-1,3,2-dioxabororan-2-yl)phenol (5.0 g) were dissolved in tetrahydrofuran (100 mL), triphenylphosphine (5.95 g) and diethyl diazodicarboxylate (3.95 g) were added under ice-cooling, and the mixture was stirred at room temperature for 8 hr. The reaction mixture was concentrated under reduced pressure, and the residue was purified by silica gel chromatography (elution solvent; hexane:ethyl acetate=5:1) to give the title compound (9.1 g) as a colorless oil.

$^1$H-NMR (CDCl$_3$, 300 MHz) δ: 1.33 (12H, s), 1.41 (9H, s), 1.57 (6H, s), 3.25 (2H, t, J=6.6 Hz), 4.32 (2H, t, J=6.6 Hz), 6.88 (2H, d, J=8.4 Hz), 7.12 (1H, s), 7.73 (2H, d, J=8.4 Hz).

Example 127-2

2-methyl-2-{[4-(2-{4-[5-(trifluoromethyl)pyridin-2-yl]phenoxy}ethyl)-1,3-thiazol-2-yl]thio}propionic acid tert-butyl ester

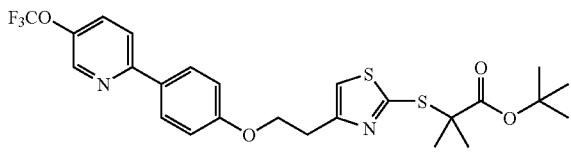

Under nitrogen atmosphere, 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester (700 mg) synthesized in Example 127-1 and 2-bromo-5-(trifluoromethyl)pyridine (313 mg) were dissolved in dioxane (6 mL) and aqueous sodium carbonate solution (2 mol/L, 3 mL), tetrakis(triphenylphosphine)palladium (80 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (650 mg) as a colorless oil.

$^1$H-NMR (CDCl$_3$, 300 MHz) δ: 1.42 (9H, s), 1.58 (6H, s), 3.28 (2H, t, J=6.6 Hz), 4.38 (2H, t, J=6.6 Hz), 7.00 (2H, d, J=8.7 Hz), 7.15 (1H, s), 7.78 (1H, d, J=8.7 Hz), 7.91-7.95 (1H, m), 7.99 (2H, d, J=8.7 Hz), 8.89 (1H, s).

Example 127-3

2-methyl-2-{[4-(2-{4-[5-(trifluoromethyl)pyridin-2-yl]phenoxy}ethyl)-1,3-thiazol-2-yl]thio}propionic acid

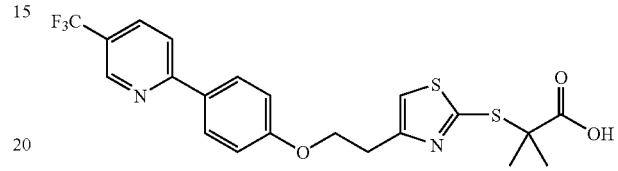

2-Methyl-2-{[4-(2-{4-[5-(trifluoromethyl)pyridin-2-yl]phenoxy}ethyl)-1,3-thiazol-2-yl]thio}propionic acid tert-butyl ester (650 mg) obtained in Example 127-2 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (340 mg) as a white solid.

$^1$H-NMR (CDCl$_3$, 300 MHz) δ: 1.62 (6H, s), 3.30 (2H, t, J=6.2 Hz), 4.37 (2H, t, J=6.2 Hz), 7.00 (2H, d, J=8.9 Hz), 7.12 (1H, s), 7.77 (1H, d, J=8.3 Hz), 7.93-7.98 (3H, m), 8.91 (1H, s).

MS: 469 (M$^+$+1).

Example 128

2-methyl-2-{[4-(2-{4-[6-(trifluoromethyl)pyridin-2-yl]phenoxy}ethyl)-1,3-thiazol-2-yl]thio}propionic acid

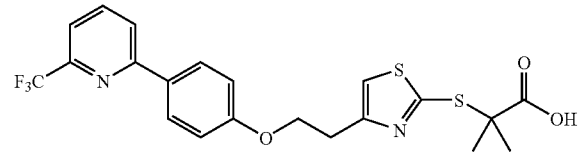

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-chloro-6-(trifluoromethyl)pyridine as starting materials and by operations similar to those of Example 127-2 and Example 127-3.

$^1$H-NMR (CDCl$_3$, 300 MHz) δ: 1.62 (6H, s), 3.30 (2H, t, J=6.0 Hz), 4.36 (2H, t, J=6.0 Hz), 6.99 (2H, d, J=9.0 Hz), 7.13 (1H, s), 7.54 (1H, dd, J=1.2, 6.6 Hz), 7.82-7.88 (2H, m), 8.01 (2H, d, J=9.0 Hz).

MS: 469 (M$^+$+1).

Example 129

2-[(4-{2-[4-(5-fluoropyridin-2-yl)phenoxy]ethyl}-1,3-thiazol-2-yl)thio]-2-methylpropionic acid

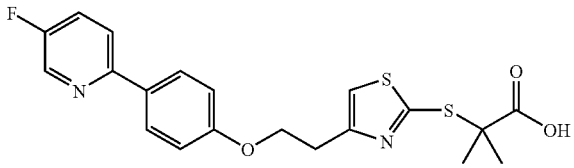

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-bromo-5-fluoropyridine as starting materials and by operations similar to those of Example 127-2 and Example 127-3.

$^1$H-NMR (CDCl$_3$, 300 MHz) δ: 1.62 (6H, s), 3.29 (2H, t, J=6.0 Hz), 4.36 (2H, t, J=6.0 Hz), 6.97 (2H, d, J=9.0 Hz), 7.11 (1H, s), 7.44-7.48 (1H, m), 7.62-7.67 (1H, m), 7.85 (2H, d, J=9.0 Hz), 8.50 (1H, d, J=2.7 Hz).

MS: 419 (M$^+$+1).

Example 130

2-[(4-{2-[4-(5-chloropyridin-2-yl)phenoxy]ethyl}-1,3-thiazol-2-yl)thio]-2-methylpropionic acid

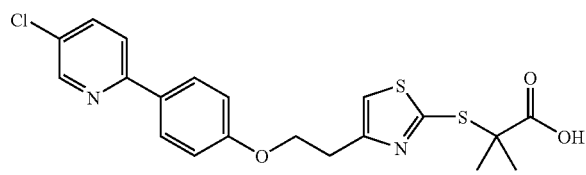

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2,5-dichloropyridine as starting materials and by operations similar to those of Example 127-2 and Example 127-3.

$^1$H-NMR (CDCl$_3$, 300 MHz) δ: 1.61 (6H, s), 3.28 (2H, t, J=6.1 Hz), 4.35 (2H, t, J=6.1 Hz), 6.97 (2H, d, J=8.8 Hz), 7.11 (1H, s), 7.61 (1H, d, J=8.3 Hz), 7.73 (1H, dd, J=2.3, 8.3 Hz), 7.85 (2H, d, J=8.8 Hz), 8.63 (1H, d, J=2.3 Hz).

MS: 435 (M$^+$+1).

Example 131

2-[(4-{2-[4-(5-ethylpyrimidin-2-yl)phenoxy]ethyl}-1,3-thiazol-2-yl)thio]-2-methylpropionic acid

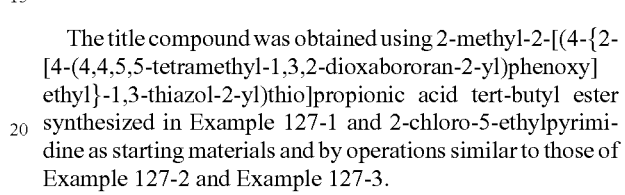

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-chloro-5-ethylpyrimidine as starting materials and by operations similar to those of Example 127-2 and Example 127-3.

$^1$H-NMR (CDCl$_3$, 300 MHz) δ: 1.31 (3H, t, J=7.7 Hz), 1.62 (6H, s), 2.68 (2H, q, J=7.7 Hz), 3.29 (2H, t, J=6.1 Hz), 4.37 (2H, t, J=6.1 Hz), 6.98 (2H, d, J=8.8 Hz), 7.12 (1H, s), 8.31 (2H, d, J=8.8 Hz), 8.66 (2H, s).

MS: 430 (M$^+$+1).

Example 132

2-[(4-{2-[4-(5-propylpyrimidin-2-yl)phenoxy]ethyl}-1,3-thiazol-2-yl)thio]-2-methylpropionic acid

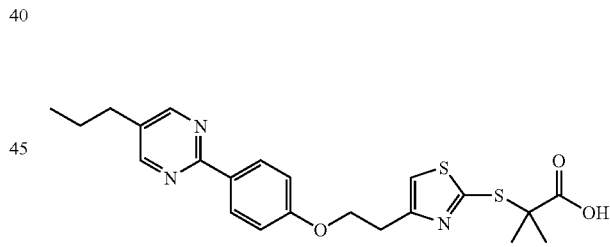

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-chloro-5-propylpyrimidine as starting materials and by operations similar to those of Example 127-2 and Example 127-3.

$^1$H-NMR (CDCl$_3$, 300 MHz) δ: 0.98 (3H, t, J=7.2 Hz), 1.61 (6H, s), 1.62-1.72 (2H, m), 2.59 (2H, t, J=7.4 Hz), 3.29 (2H, t, J=6.0 Hz), 4.37 (2H, t, J=6.0 Hz), 6.97 (2H, d, J=8.9 Hz), 7.11 (1H, s), 8.32 (2H, d, J=8.9 Hz), 8.58 (2H, s).

MS: 444 (M$^+$+1).

Example 133

2-methyl-2-{[4-(2-{4-[4-(trifluoromethyl)pyrimidin-2-yl]phenoxy}ethyl)-1,3-thiazol-2-yl]thio}propionic acid

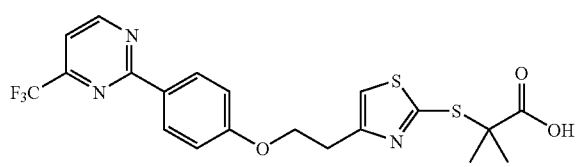

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-chloro-4-(trifluoromethyl)pyrimidine as starting materials and by operations similar to those of Example 127-2 and Example 127-3.

$^1$H-NMR (CDCl$_3$, 300 MHz) δ: 1.62 (6H, s), 3.31 (2H, t, J=6.0 Hz), 4.38 (2H, t, J=6.0 Hz), 6.99 (2H, d, J=9.0 Hz), 7.13 (1H, s), 7.42 (1H, d, J=4.8 Hz), 8.43 (2H, d, J=9.0 Hz), 8.97 (1H, d, J=4.8 Hz).

MS: 470 (M$^+$+1).

Example 134

2-[(4-{2-[4-(1,3-benzoxazol-2-yl)phenoxy]ethyl}-1,3-thiazol-2-yl)thio]-2-methylpropionic acid

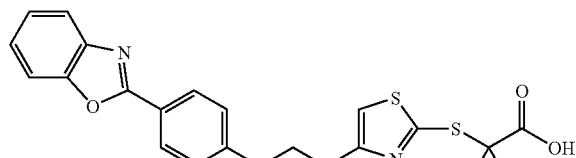

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-chloro-1,3-benzoxazole as starting materials and by operations similar to those of Example 127-2 and Example 127-3.

$^1$H-NMR (CDCl$_3$, 300 MHz) δ: 1.61 (6H, s), 3.30 (2H, t, J=6.2 Hz), 4.37 (2H, t, J=6.2 Hz), 7.01 (2H, d, J=8.7 Hz), 7.12 (1H, s), 7.31-7.34 (2H, m), 7.53-7.57 (1H, m), 7.72-7.76 (1H, m) 8.17 (2H, d, J=8.7 Hz).

MS: 441 (M$^+$+1).

Example 135

2-[(4-{2-[4-(1,3-benzothiazol-2-yl)phenoxy]ethyl}-1,3-thiazol-2-yl)thio]-2-methylpropionic acid

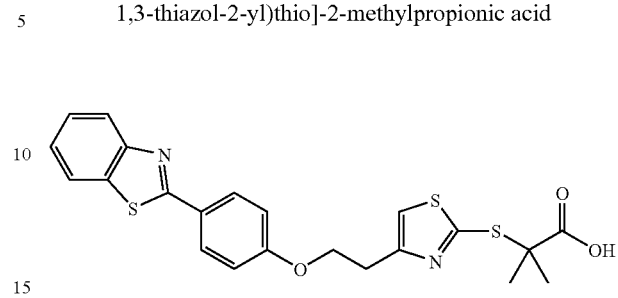

The title compound was obtained using 2-methyl-2-[(4-{2-[4-(4,4,5,5-tetramethyl-1,3,2-dioxabororan-2-yl)phenoxy]ethyl}-1,3-thiazol-2-yl)thio]propionic acid tert-butyl ester synthesized in Example 127-1 and 2-bromo-benzothiazole as starting materials and by operations similar to those of Example 127-2 and Example 127-3.

$^1$H-NMR (CDCl$_3$, 300 MHz) δ: 1.62 (6H, s), 3.28 (2H, t, J=6.2 Hz), 4.34 (2H, t, J=6.2 Hz), 6.97 (2H, d, J=8.7 Hz), 7.11 (1H, s), 7.32-7.38 (1H, m), 7.44-7.50 (1H, m), 7.86 (1H, d, J=8.0 Hz), 7.97-8.05 (3H, m).

MS: 457 (M$^+$+1).

Example 136

2-{[4-(2-{2,6-dimethyl-4-[5-(trifluoromethyl)pyridin-2-yl]phenoxy}ethyl)-1,3-thiazol-2-yl]thio}-2-methylpropionic acid

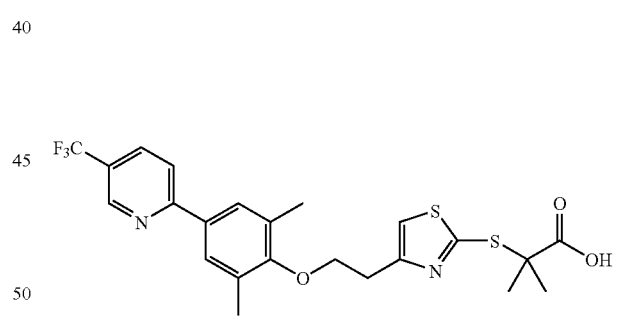

The title compound was obtained using 2-{[4-(2-hydroxyethyl)-1,3-thiazol-2-yl]thio}-2-methylpropionic acid tert-butyl ester synthesized in Example 4 and 2,6-dimethyl-4-(4,4,5,5-tetramethyl-1,3,2-dioxabororan-2-yl)phenol as starting materials and by an operation similar to that of Example 127.

$^1$H-NMR (CDCl$_3$, 300 MHz) δ: 1.67 (6H, s), 2.29 (6H, s), 3.32 (2H, t, J=6.3 Hz), 4.16 (2H, t, J=6.3 Hz), 7.20 (1H, s), 7.66 (2H, s), 7.80 (1H, d, J=8.3 Hz), 7.96-8.00 (1H, m), 8.93 (1H, s).

MS: 497 (M$^+$+1).

Example 137

2-{[4-(2-{2-methoxy-4-[5-(trifluoromethyl)pyridin-2-yl]phenoxy}ethyl)-1,3-thiazol-2-yl]thio}-2-methylpropionic acid

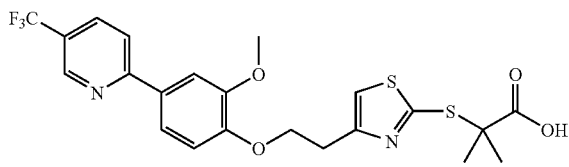

The title compound was obtained using 2-{[4-(2-hydroxyethyl)-1,3-thiazol-2-yl]thio}-2-methylpropionic acid tert-butyl ester synthesized in Example 4 and 2-methoxy-4-(4,4,5,5-tetramethyl-1,3,2-dioxaboroaran-2-yl)phenol as starting materials and by an operation similar to that of Example 127.

$^1$H-NMR (CDCl$_3$, 300 MHz) δ: 1.64 (6H, s), 3.37 (2H, t, J=6.3 Hz), 3.97 (3H, s), 4.44 (2H, t, J=6.3 Hz), 7.00 (1H, d, J=8.4 Hz), 7.23 (1H, s), 7.53 (1H, dd, J=2.0, 8.4 Hz), 7.71 (1H, d, J=2.0 Hz), 7.82 (1H, d, J=8.3 Hz), 7.97 (1H, dd, J=2.0, 8.3 Hz), 8.93 (1H, s).

MS: 499 (M$^+$+1).

Example 138

2-[(4-{2-[4-(5-ethylpyrimidin-2-yl)-2,6-dimethylphenoxy]ethyl}-1,3-thiazol-2-yl)thio]-2-methylpropionic acid

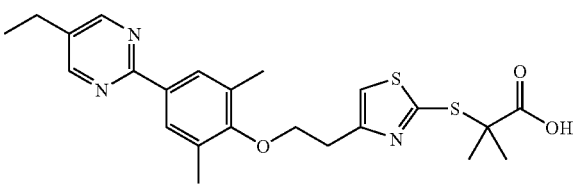

The title compound was obtained by an operation similar to that of Example 127-1 and using 2-{[4-(2-hydroxyethyl)-1,3-thiazol-2-yl]thio}-2-methylpropionic acid tert-butyl ester synthesized in Example 4 and 2,6-dimethyl-4-(4,4,5,5-tetramethyl-1,3,2-dioxaboroaran-2-yl)phenol as starting materials, followed by operations similar to those of Example 127-2 and Example 127-3 and using 2-chloro-5-ethylpyrimidine.

$^1$H-NMR (CDCl$_3$, 300 MHz) δ: 1.30 (3H, t, J=7.6 Hz), 1.65 (6H, s), 2.26 (6H, s), 2.67 (2H, q, J=7.6 Hz), 3.28 (2H, t, J=6.2 Hz), 4.13 (2H, t, J=6.2 Hz), 7.17 (1H, s), 8.01 (2H, s), 8.63 (2H, s).

MS: 458 (M$^+$+1).

Example 139

2-[(4-{2-[4-(5-ethylpyrimidin-2-yl)-2-methoxyphenoxy]ethyl}-1,3-thiazol-2-yl)thio]-2-methylpropionic acid

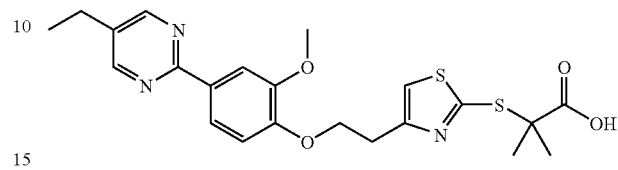

The title compound was obtained by an operation similar to that of Example 127-1 and using 2-{[4-(2-hydroxyethyl)-1,3-thiazol-2-yl]thio}-2-methylpropionic acid tert-butyl ester synthesized in Example 4 and 2-methoxy-4-(4,4,5,5-tetramethyl-1,3,2-dioxaboroaran-2-yl)phenol as starting materials, followed by operations similar to those of Example 127-2 and Example 127-3 and using 2-chloro-5-ethylpyrimidine.

$^1$H-NMR (CDCl$_3$, 300 MHz) δ: 1.30 (3H, t, J=7.6 Hz), 1.62 (6H, s), 2.66 (2H, q, J=7.6 Hz), 3.34 (2H, t, J=6.3 Hz), 3.96 (3H, s), 4.41 (2H, t, J=6.3 Hz), 7.20 (1H, s), 7.95-8.00 (2H, m), 8.61 (2H, s).

MS: 460 (M++1).

Example 140

2-methyl-2-{[4-(2-{2-methyl-4-[5-(trifluoromethyl)pyridin-2-yl]phenoxy}ethyl)-1,3-thiazol-2-yl]thio}propionic acid

Example 140-1

2-({4-[2-(4-iodo-2-methylphenoxy)ethyl]-1,3-thiazol-2-yl}thio)-2-methylpropionic acid tert-butyl ester

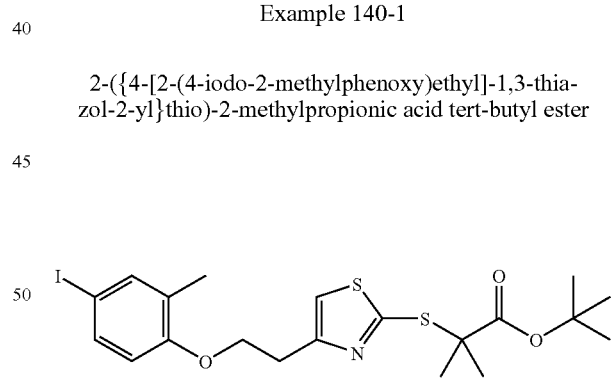

2-{[4-(2-Hydroxyethyl)-1,3-thiazol-2-yl]thio}-2-methylpropionic acid tert-butyl ester (3.89 g) synthesized in Example 4 and 4-iodo-2-methylphenol (3.0 g) were dissolved in tetrahydrofuran (30 mL), triphenylphosphine (3.36 g) and diethyl diazodicarboxylate (2.23 g) were added under ice-cooling, and the mixture was stirred at room temperature for 8 hr. The reaction mixture was concentrated under reduced pressure, and the residue was purified by silica gel chromatography (elution solvent; hexane:ethyl acetate=6:1) to give the title compound (4.4 g) as a colorless oil.

$^1$H-NMR (CDCl$_3$, 300 MHz) δ: 1.41 (9H, s), 1.56 (6H, s), 2.09 (3H, s), 3.24 (2H, t, J=6.6 Hz), 4.25 (2H, t, J=6.6 Hz), 6.58 (1H, d, J=9.3 Hz), 7.10 (1H, s), 7.39-7.42 (2H, m).

Example 140-2

2-methyl-2-[(4-{2-[2-methyl-4-(4,4,5,5-tetramethyl-1,3,2-dioxabororan-2-yl)phenoxy]ethyl}-1,3-thiazol-2-yl)thio]propionic acid tert-butyl ester

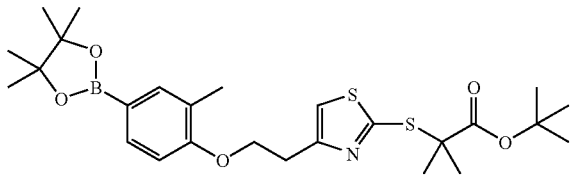

2-({4-[2-(4-Iodo-2-methylphenoxy)ethyl]-1,3-thiazol-2-yl}thio)-2-methylpropionic acid tert-butyl ester (2.40 g) synthesized in Example 140-1 under nitrogen atmosphere, in reference to non-patent reference [J. Org. Chem. 65, 164 (2000)] and the like, 4,4,5,5-tetramethyl-1,3,2-dioxabororane (887 mg) and triethylamine (1.53 g) were dissolved in dioxane (20 mL), [1,1'-bis(diphenylphosphino)ferrocene]dichloropalladium (II) (110 mg) was added, and the mixture was stirred at 80° C. for 2 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=7:1 to 4:1) to give the title compound (800 mg) as a colorless oil.

$^1$H-NMR (CDCl$_3$, 300 MHz) δ: 1.35 (12H, s), 1.42 (9H, s), 1.59 (6H, s), 2.17 (3H, s), 3.29 (2H, t, J=6.5 Hz), 4.34 (2H, t, J=6.5 Hz), 6.84 (1H, d, J=8.1 Hz), 7.14 (1H, s), 7.59 (1H, s), 7.63 (1H, d, J=8.1 Hz).

Example 140-3

2-methyl-2-{[4-(2-{2-methyl-4-[5-(trifluoromethyl)pyridin-2-yl]phenoxy}ethyl)-1,3-thiazol-2-yl]thio}propionic acid

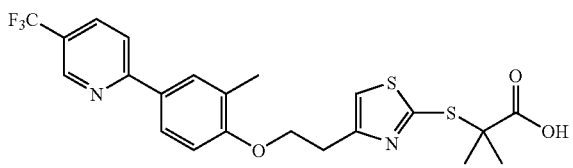

The title compound was obtained using 2-methyl-2-[(4-{2-[2-methyl-4-(4,4,5,5-tetramethyl-1,3,2-dioxabororan-2-yl)phenoxy]ethyl}-1,3-thiazol-2-yl)thio]propionic acid tert-butyl ester synthesized in Example 140-2 and 2-bromo-5-(trifluoromethyl)pyridine and by operations similar to those of Example 127-2 and Example 127-3.

$^1$H-NMR (CDCl$_3$, 300 MHz) δ: 1.60 (6H, s), 2.20 (3H, s), 3.32 (2H, t, J=6.0 Hz), 4.38 (2H, t, J=6.0 Hz), 6.93 (1H, d, J=8.1 Hz), 7.12 (1H, s), 7.75-7.82 (3H, m), 7.94 (1H, d, J=8.3 Hz), 8.89 (1H, s).

MS: 483 (M$^+$+1).

Example 141

2-[(4-{2-[4-(5-ethylpyrimidin-2-yl)-2-methylphenoxy]ethyl}-1,3-thiazol-2-yl)thio]-2-methylpropionic acid

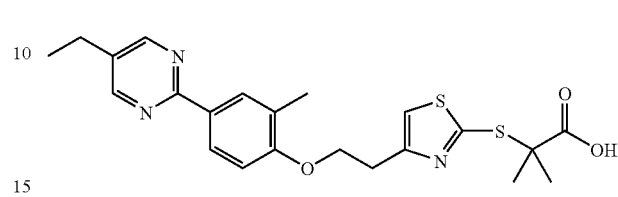

The title compound was obtained using 2-methyl-2-[(4-{2-[2-methyl-4-(4,4,5,5-tetramethyl-1,3,2-dioxabororan-2-yl)phenoxy]ethyl}-1,3-thiazol-2-yl)thio]propionic acid tert-butyl ester synthesized in Example 140-2 and 2-chloro-5-ethylpyrimidine and by operations similar to those of Example 127-2 and Example 127-3.

$^1$H-NMR (CDCl$_3$, 300 MHz) δ: 1.32 (3H, t, J=7.6 Hz), 1.60 (6H, s), 2.63 (3H, s), 2.66 (2H, q, J=7.6 Hz), 3.31 (2H, t, J=6.1 Hz), 4.38 (2H, t, J=6.1 Hz), 6.67 (1H, d, J=8.6 Hz), 7.11 (1H, s), 8.14-8.19 (2H, m), 8.63 (2H, s).

MS: 444 (M$^+$+1).

Example 142

2-{[4-(2-{2-fluoro-4-[5-(trifluoromethyl)pyridin-2-yl]phenoxy}ethyl)-1,3-thiazol-2-yl]thio}-2-methylpropionic acid Example 142-1

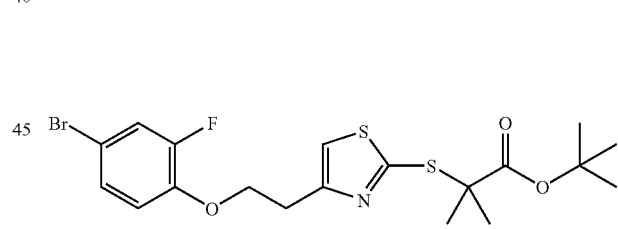

2-({4-[2-(4-bromo-2-fluorophenoxy)ethyl]-1,3-thiazol-2-yl}thio)-2-methylpropionic acid tert-butyl ester 2-{[4-(2-hydroxyethyl)-1,3-thiazol-2-yl]thio}-2-methylpropionic acid tert-butyl ester (3.0 g) synthesized in Example 4 and 4-bromo-2-fluorophenol (1.91 g) were dissolved in tetrahydrofuran (20 mL), triphenylphosphine (2.62 g) and diethyl diazodicarboxylate (1.74 g) were added under ice-cooling, and the mixture was stirred at room temperature for 6 hr. The reaction mixture was concentrated under reduced pressure, and the residue was purified by silica gel chromatography (elution solvent; hexane:ethyl acetate=6:1) to give the title compound (3.2 g) as a colorless oil.

¹H-NMR (CDCl₃, 300 MHz) δ: 1.41 (9H, s), 1.57 (6H, s), 3.26 (2H, t, J=6.6 Hz), 4.33 (2H, t, J=6.6 Hz), 6.85 (1H, t, J=8.5 Hz), 7.14-7.24 (3H, m).

Example 142-2

2-[(4-{2-[2-fluoro-4-(4,4,5,5-tetramethyl-1,3,2-dioxaboroaran-2-yl)phenoxy]ethyl}-1,3-thiazol-2-yl)thio]-2-methylpropionic acid tert-butyl ester

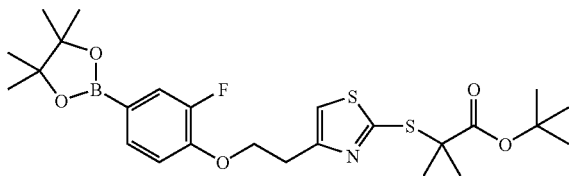

2-({4-[2-(4-Bromo-2-fluorophenoxy)ethyl]-1,3-thiazol-2-yl}thio)-2-methylpropionic acid tert-butyl ester (1.65 g) synthesized in Example 142-1 under nitrogen atmosphere in reference to non-patent reference [J. Org. Chem. 65, 164 (2000)] and the like, 4,4,5,5-tetramethyl-1,3,2-dioxabororane (665 mg) and triethylamine (1.05 g) were dissolved in dioxane (20 mL), dichlorobis(triphenylphosphine)palladium (73 mg) was added thereto, and the mixture was stirred at 100° C. for 3 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=6:1 to 4:1) to give the title compound (440 mg) as a colorless oil.

¹H-NMR (CDCl₃, 300 MHz) δ: 1.35 (12H, s), 1.42 (9H, s), 1.59 (6H, s), 3.30 (2H, t, J=6.7 Hz), 4.39 (2H, t, J=6.7 Hz), 6.97 (1H, t, J=8.1 Hz), 7.20 (1H, s), 7.47-7.53 (2H, m).

Example 142-3

2-{[4-(2-{2-fluoro-4-[5-(trifluoromethyl)pyridin-2-yl]phenoxy}ethyl)-1,3-thiazol-2-yl]thio}-2-methylpropionic acid

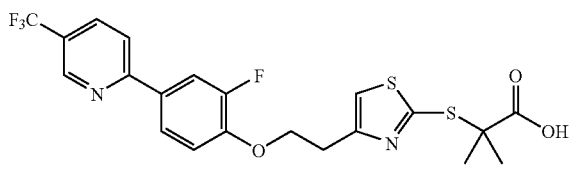

The title compound was obtained using 2-[(4-{2-[2-fluoro-4-(4,4,5,5-tetramethyl-1,3,2-dioxabororan-2-yl)phenoxy]ethyl}-1,3-thiazol-2-yl)thio]-2-methylpropionic acid tert-butyl ester synthesized in Example 142-2 and 2-bromo-5-(trifluoromethyl)pyridine and by operations similar to those of Example 127-2 and Example 127-3.

¹H-NMR (CDCl₃, 300 MHz) δ: 1.62 (6H, s), 3.33 (2H, t, J=6.1 Hz), 4.44 (2H, t, J=6.1 Hz), 7.07 (1H, t, J=8.5 Hz), 7.18 (1H, s), 7.74-7.84 (3H, m), 7.93-7.97 (1H, m), 8.89 (1H, s).

MS: 487 (M⁺+1).

Example 143

2-[(4-{2-[4-(5-ethylpyrimidin-2-yl)-2-fluorophenoxy]ethyl}-1,3-thiazol-2-yl)thio]-2-methylpropionic acid

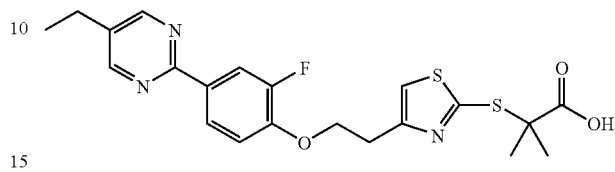

The title compound was obtained using 2-[(4-{2-[2-fluoro-4-(4,4,5,5-tetramethyl-1,3,2-dioxabororan-2-yl)phenoxy]ethyl}-1,3-thiazol-2-yl)thio]-2-methylpropionic acid tert-butyl ester synthesized in Example 142-2 and 2-chloro-5-ethylpyrimidine and by operations similar to those of Example 127-2 and Example 127-3.

¹H-NMR (CDCl₃, 300 MHz) δ: 1.30 (3H, t, J=7.5 Hz), 1.62 (6H, s), 2.67 (2H, q, J=7.5 Hz), 3.33 (2H, t, J=6.1 Hz), 4.43 (2H, t, J=6.1 Hz), 7.04 (1H, t, J=8.6 Hz), 7.18 (1H, s), 8.08-8.10 (1H, m), 8.13 (1H, s), 8.63 (2H, s).

MS: 448 (M⁺+1).

Example 144

2-methyl-2-[(4-{2-[4-(phenylethynyl)phenoxy]ethyl}-1,3-thiazol-2-yl)thio]propionic acid Example 144-1

2-({4-[2-(4-iodophenoxy)ethyl]-1,3-thiazol-2-yl}thio)-2-methylpropionic acid tert-butyl ester

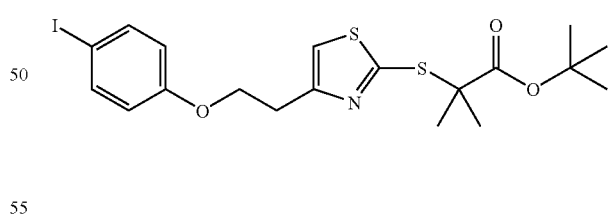

2-{[4-(2-Hydroxyethyl)-1,3-thiazol-2-yl]thio}-2-methylpropionic acid tert-butyl ester (7.0 g) synthesized in Example 4 and 4-iodophenol (5.08 g) were dissolved in tetrahydrofuran (100 mL), triphenylphosphine (6.06 g) and diethyl diazodicarboxylate (4.02 g) were added under ice-cooling, and the mixture was stirred at room temperature for 8 hr. The reaction mixture was concentrated under reduced pressure, and the residue was purified by silica gel chromatography (elution solvent; hexane:ethyl acetate=10:1) to give the title compound (7.5 g) as a colorless oil.

¹H-NMR (CDCl₃, 300 MHz) δ: 1.41 (9H, s), 1.57 (6H, s), 3.22 (2H, t, J=6.6 Hz), 4.26 (2H, t, J=6.6 Hz), 6.67 (2H, d, J=8.7 Hz), 7.10 (1H, s), 7.53 (2H, d, J=8.7 Hz).

Example 144-2

2-({4-[2-(4-iodophenoxy)ethyl]-1,3-thiazol-2-yl}thio)-2-methylpropionic acid methyl ester

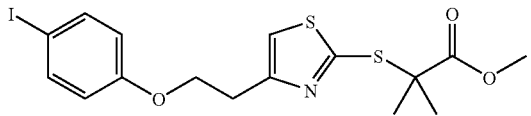

2-({4-[2-(4-Iodophenoxy)ethyl]-1,3-thiazol-2-yl}thio)-2-methylpropionic acid tert-butyl ester (6.0 g) obtained in Example 144-1 was dissolved in dichloromethane (25 mL), trifluoroacetic acid (20 mL) was added, and the mixture was stirred at room temperature for 12 hr. The reaction mixture was concentrated under reduced pressure, and the residue was dissolved in methanol (60 mL). Thionyl chloride (5.63 g) was added under ice-cooling and the mixture was refluxed for 4 hr. The reaction mixture was concentrated under reduced pressure, saturated aqueous sodium hydrogen carbonate solution was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=6:1 to 4:1) to give the title compound (5.2 g) as a colorless oil.

¹H-NMR (CDCl₃, 300 MHz) δ: 1.60 (6H, s), 3.22 (2H, t, J=6.6 Hz), 3.69 (3H, s), 4.27 (2H, t, J=6.6 Hz), 6.68 (2H, d, J=9.0 Hz), 7.10 (1H, s), 7.54 (2H, d, J=9.0 Hz).

Example 144-3

2-methyl-2-[(4-{2-[4-(phenylethynyl)phenoxy]ethyl}-1,3-thiazol-2-yl)thio]propionic acid methyl ester

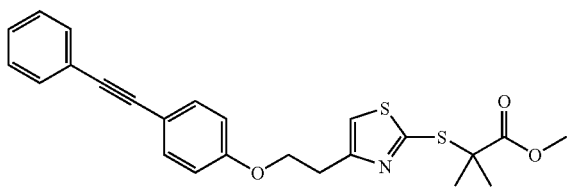

Under nitrogen atmosphere, 2-({4-[2-(4-iodophenoxy)ethyl]-1,3-thiazol-2-yl}thio)-2-methylpropionic acid methyl ester (600 mg) synthesized in Example 144-2 and ethynylbenzene (145 mg) were dissolved in N,N-dimethylformamide (2 mL) and triethylamine (6 mL), dichlorobis(triphenylphosphine)palladium (10 mg) and copper(I) iodide (5 mg) were added, and the mixture was stirred at 60° C. for 1 hr. The reaction mixture was cooled, water was added thereto, and the organic layer was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (400 mg) as a yellow oil.

¹H-NMR (CDCl₃, 300 MHz) δ: 1.61 (6H, s), 3.25 (2H, t, J=6.6 Hz), 3.69 (3H, s), 4.32 (2H, t, J=6.6 Hz), 6.87 (2H, d, J=8.8 Hz), 7.13 (1H, s), 7.31-7.34 (3H, m), 7.43-7.52 (4H, m).

Example 144-4

2-methyl-2-[(4-{2-[4-(phenylethynyl)phenoxy]ethyl}-1,3-thiazol-2-yl)thio]propionic acid

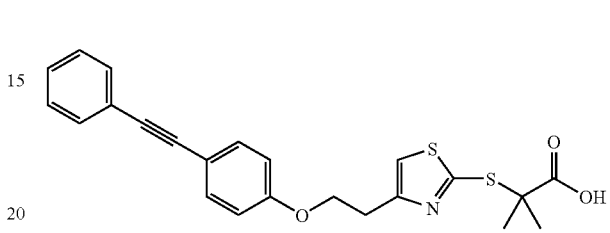

2-Methyl-2-[(4-{2-[4-(phenylethynyl)phenoxy]ethyl}-1,3-thiazol-2-yl)thio]propionic acid methyl ester (400 mg) obtained in Example 144-3 was dissolved in methanol (4 mL) and tetrahydrofuran (4 mL), aqueous sodium hydroxide solution (1 mol/L, 2 mL) was added, and the mixture was stirred at room temperature for 4 hr. The reaction mixture was concentrated under reduced pressure, aqueous 10% citric acid solution was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=1:1 to 0:1) to give the title compound (290 mg) as a slightly yellow oil.

¹H-NMR (CDCl₃, 300 MHz) δ: 1.62 (6H, s), 3.27 (2H, t, J=6.3 Hz), 4.31 (2H, t, J=6.3 Hz), 6.86 (2H, d, J=9.0 Hz), 7.10 (1H, s), 7.31-7.34 (3H, m), 7.43-7.52 (4H, m).
MS: 424 (M⁺+1).

Example 145

2-{[4-(2-{4-[(4-fluorophenyl)ethynyl]phenoxy}ethyl)-1,3-thiazol-2-yl]thio}-2-methylpropionic acid

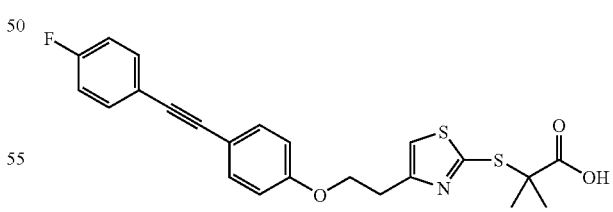

The title compound was obtained using 2-({4-[2-(4-iodophenoxy)ethyl]-1,3-thiazol-2-yl}thio)-2-methylpropionic acid methyl ester synthesized in Example 144-2 and 1-ethynyl-4-fluorobenzene as starting materials and by operations similar to those of Example 144-3 and Example 144-4.

¹H-NMR (CDCl₃, 300 MHz) δ: 1.61 (6H, s), 3.27 (2H, t, J=6.1 Hz), 4.31 (2H, t, J=6.1 Hz), 6.86 (2H, d, J=8.9 Hz), 6.99-7.05 (2H, m), 7.10 (1H, s), 7.41-7.50 (4H, m).
MS: 442 (M⁺+1).

Example 146

2-methyl-2-({4-[2-(4-{[4-(trifluoromethyl)phenyl]ethynyl}phenoxy)ethyl]-1,3-thiazol-2-yl}thio)propionic acid

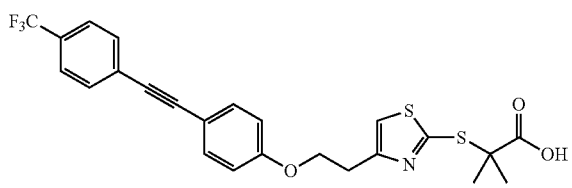

The title compound was obtained using 2-({4-[2-(4-iodophenoxy)ethyl]-1,3-thiazol-2-yl}thio)-2-methylpropionic acid methyl ester synthesized in Example 144-2 and 1-ethynyl-4-(trifluoromethyl)benzene as starting materials and by operations similar to those of Example 144-3 and Example 144-4.

$^1$H-NMR (CDCl$_3$, 300 MHz) δ: 1.62 (6H, s), 3.28 (2H, t, J=6.0 Hz), 4.32 (2H, t, J=6.0 Hz), 6.88 (2H, d, J=8.7 Hz), 7.10 (1H, s), 7.46 (2H, d, J=8.7 Hz), 7.59 (4H, s).

MS: 492 (M$^+$+1).

Example 147

2-methyl-2-({4-[2-(4-{[3-(trifluoromethyl)phenyl]ethynyl}phenoxy)ethyl]-1,3-thiazol-2-yl}thio)propionic acid

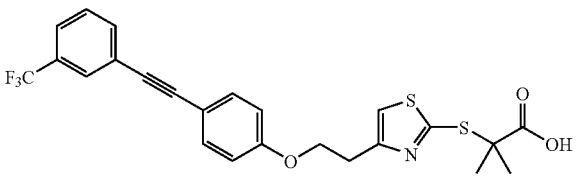

The title compound was obtained using 2-({4-[2-(4-iodophenoxy)ethyl]-1,3-thiazol-2-yl}thio)-2-methylpropionic acid methyl ester synthesized in Example 144-2 and 1-ethynyl-3-(trifluoromethyl)benzene as starting materials and by operations similar to those of Example 144-3 and Example 144-4.

$^1$H-NMR (CDCl$_3$, 300 MHz) δ: 1.62 (6H, s), 3.28 (2H, t, J=6.0 Hz), 4.32 (2H, t, J=6.0 Hz), 6.88 (2H, d, J=8.7 Hz), 7.10 (1H, s) 7.42-7.48 (3H, m), 7.55 (1H, d, J=8.7 Hz), 7.66 (1H, d, J=7.8 Hz), 7.76 (1H, s).

MS: 492 (M$^+$+1).

Example 148

2-methyl-2-[(4-{2-[4-(4-phenylpiperazin-1-yl)phenoxy]ethyl}-1,3-thiazol-2-yl)thio]propionic acid

Example 148-1

2-methyl-2-[(4-{2-[4-(4-phenylpiperazin-1-yl)phenoxy]ethyl}-1,3-thiazol-2-yl)thio]propionic acid tert-butyl ester

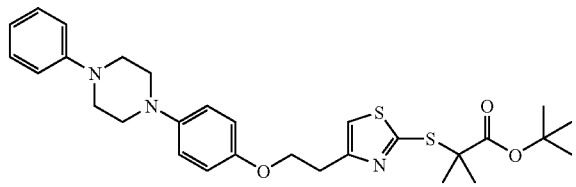

Under nitrogen atmosphere, 2-({4-[2-(4-bromophenoxy)ethyl]-1,3-thiazol-2-yl}thio)-2-methylpropionic acid tert-butyl ester (800 mg) synthesized in Example 67-1 and 1-phenylpiperazine (425 mg) were dissolved in toluene (5 mL), sodium tert-butoxide (185 mg), tris(dibenzylideneacetone)dipalladium (80.1 mg) and 2-(di-tert-butylphosphino)biphenyl (52.2 mg) were added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (490 mg) as a yellow oil.

$^1$H-NMR (CDCl$_3$, 300 MHz) δ: 1.42 (9H, s), 1.58 (6H, s), 3.20-3.25 (6H, m), 3.32-3.36 (4H, m), 4.26 (2H, t, J=6.6 Hz), 6.84-7.00 (7H, m), 7.13 (1H, s), 7.26-7.32 (2H, m).

Example 148-2

2-methyl-2-[(4-{2-[4-(4-phenylpiperazin-1-yl)phenoxy]ethyl}-1,3-thiazol-2-yl)thio]propionic acid

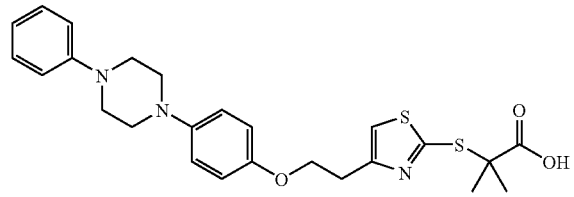

2-Methyl-2-[(4-{2-[4-(4-phenylpiperazin-1-yl)phenoxy]ethyl}-1,3-thiazol-2-yl)thio]propionic acid tert-butyl ester (490 mg) obtained in Example 148-1 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (330 mg) as a white solid.

¹H-NMR (CDCl₃, 300 MHz) δ: 1.62 (6H, s), 3.25 (2H, t, J=6.0 Hz), 3.42-3.60 (8H, m), 4.30 (2H, t, J=6.0 Hz), 6.94 (2H, d, J=9.0 Hz), 7.02-7.09 (4H, m), 7.32-7.38 (4H, m).

MS: 484 (M⁺+1).

Example 149

2-{[4-(2-{4-[4-(4-fluorophenyl)piperazin-1-yl]phenoxy}ethyl)-1,3-thiazol-2-yl]thio}-2-methylpropionic acid

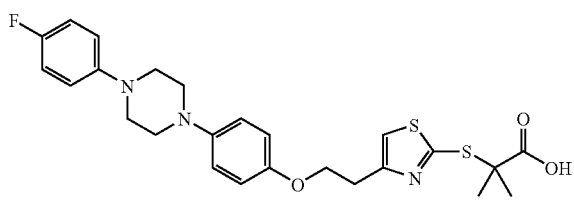

The title compound was obtained using 2-({4-[2-(4-bromophenoxy)ethyl]-1,3-thiazol-2-yl}thio)-2-methylpropionic acid tert-butyl ester synthesized in Example 67-1 and 1-(4-fluorophenyl)piperazine as starting materials and by an operation similar to that of Example 148.

¹H-NMR (CDCl₃, 300 MHz) δ: 1.62 (6H, s), 3.26 (2H, t, J=6.0 Hz), 3.45-3.56 (8H, m), 4.30 (2H, t, J=6.0 Hz), 6.94 (2H, d, J=9.0 Hz), 7.01-7.04 (4H, m), 7.09 (1H, s), 7.33 (2H, d, J=9.0 Hz).

MS: 502 (M⁺+1).

Example 150

2-methyl-2-({4-[2-(4-{4-[4-(trifluoromethyl)phenyl]piperazin-1-yl}phenoxy)ethyl]-1,3-thiazol-2-yl}thio)propionic acid

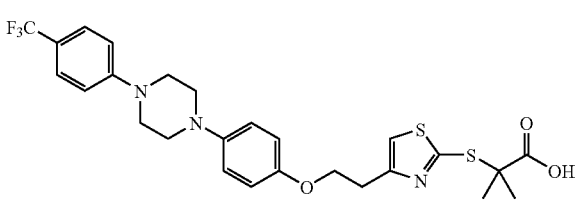

The title compound was obtained using 2-({4-[2-(4-bromophenoxy)ethyl]-1,3-thiazol-2-yl}thio)-2-methylpropionic acid tert-butyl ester synthesized in Example 67-1 and 1-[4-(trifluoromethyl)phenyl]piperazine as starting materials and by an operation similar to that of Example 148.

¹H-NMR (CDCl₃, 300 MHz) δ: 1.64 (6H, s), 3.22-3.27 (6H, m), 3.43-3.52 (4H, m), 4.26 (2H, t, J=6.1 Hz), 6.86 (2H, d, J=8.8 Hz), 6.95-6.99 (4H, m), 7.09 (1H, s), 7.52 (2H, d, J=8.8 Hz).

Example 151

2-methyl-2-[(4-{2-[4-(4-phenylpiperidin-1-yl)phenoxy]ethyl}-1,3-thiazol-2-yl)thio]propionic acid

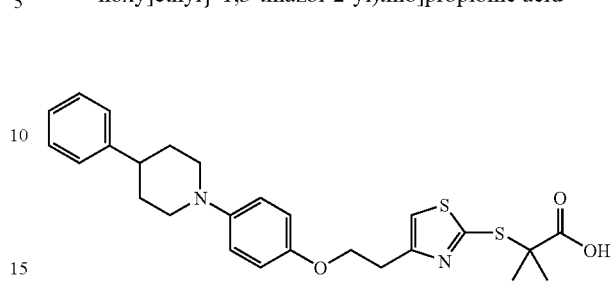

The title compound was obtained using 2-({4-[2-(4-bromophenoxy)ethyl]-1,3-thiazol-2-yl}thio)-2-methylpropionic acid tert-butyl ester synthesized in Example 67-1 and 1-phenylpiperidine as starting materials and by an operation similar to that of Example 148.

¹H-NMR (CDCl₃, 300 MHz) δ: 1.62 (6H, s), 2.04-2.12 (2H, m), 2.45-2.57 (2H, m), 2.77-2.85 (1H, m), 3.24-3.34 (4H, m), 3.76-3.81 (2H, m), 4.31 (2H, t, J=6.0 Hz), 6.97 (2H, d, J=9.0 Hz), 7.09 (1H, s), 7.23-7.38 (5H, m), 7.53 (2H, d, J=9.0 Hz).

MS: 483 (M⁺+1).

Example 152

2-methyl-2-{[4-({[4'-(trifluoromethyl)biphenyl-4-yl]methoxy}methyl)-1,3-thiazol-2-yl]thio}propionic acid Example 152-1

2-[(4-{[(4-bromobenzyl)oxy]methyl}-1,3-thiazol-2-yl)thio]-2-methylpropionic acid tert-butyl ester

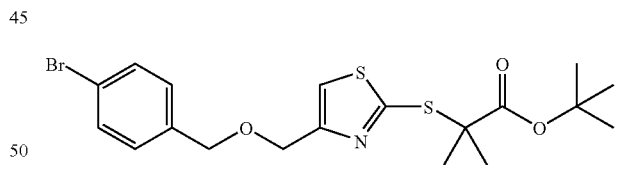

2-{[4-(Hydroxymethyl)-1,3-thiazol-2-yl]thio}-2-methylpropionic acid tert-butyl ester (5.0 g) synthesized in Example 10 and 4-bromobenzylbromide (4.75 g) were dissolved in N,N-dimethylformamide (50 mL), potassium tert-butoxide (2.33 g) was added, and the mixture was stirred at room temperature for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=7:1) to give the title compound (4.5 g) as a colorless oil.

¹H-NMR (CDCl₃, 300 MHz) δ: 1.45 (9H, s), 1.62 (6H, s), 4.61 (2H, s) 4.69 (2H, s), 7.27 (2H, d, J=8.3 Hz), 7.34 (1H, s), 7.50 (2H, d, J=8.3 Hz).

Example 152-2

2-methyl-2-{[4-({[4'-(trifluoromethyl)biphenyl-4-yl]methoxy}methyl)-1,3-thiazol-2-yl]thio}propionic acid tert-butyl ester

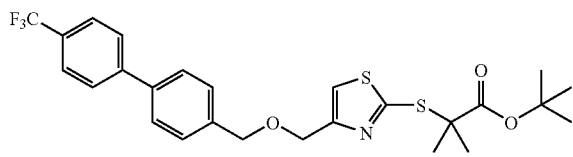

Under nitrogen atmosphere, 2-[(4-{[(4-bromobenzyl)oxy]methyl}-1,3-thiazol-2-yl)thio]-2-methylpropionic acid tert-butyl ester (1.0 g) synthesized in Example 152-1 and 4-(trifluoromethyl)phenylboric acid (621 mg) were dissolved in dioxane (10 mL) and sodium hydrogen carbonate aqueous solution (2 mol/L, 5 mL), tetrakis(triphenylphosphine)palladium (162 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (900 mg) as a colorless oil.

¹H-NMR (CDCl₃, 300 MHz) δ: 1.43 (9H, s), 1.59 (6H, s), 4.69 (2H, s), 4.72 (2H, s), 7.34 (1H, s), 7.47 (2H, d, J=8.2 Hz), 7.59 (2H, d, J=8.2 Hz), 7.69 (4H, s).

Example 152-3

2-methyl-2-{[4-({[4'-(trifluoromethyl)biphenyl-4-yl]methoxy}methyl)-1,3-thiazol-2-yl]thio}propionic acid

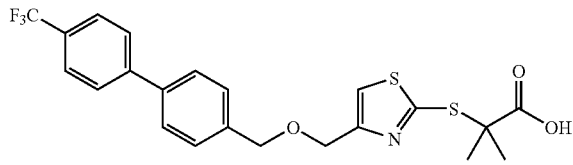

2-Methyl-2-{[4-({[4'-(trifluoromethyl)biphenyl-4-yl]methoxy}methyl)-1,3-thiazol-2-yl]thio}propionic acid tert-butyl ester (900 mg) obtained in Example 152-2 was dissolved in dichloromethane (10 mL), trifluoroacetic acid (4 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (420 mg) as a white solid.

¹H-NMR (CDCl₃, 300 MHz) δ: 1.67 (6H, s), 4.72 (2H, s), 4.72 (2H, s), 7.34 (1H, s), 7.49 (2H, d, J=8.1 Hz), 7.62 (2H, d, J=8.1 Hz), 7.71 (4H, s).

MS: 468 (M⁺+1).

Example 153

2-[(4-{[(4'-fluorobiphenyl-4-yl)methoxy]methyl}-1,3-thiazol-2-yl)thio]-2-methylpropionic acid

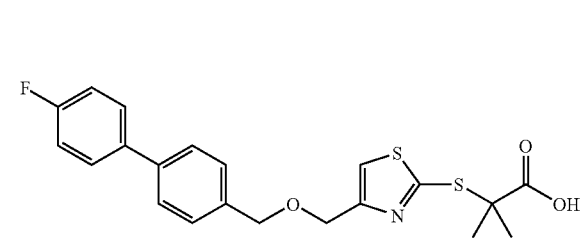

The title compound was obtained using 2-[(4-{[(4-bromobenzyl)oxy]methyl}-1,3-thiazol-2-yl)thio]-2-methylpropionic acid tert-butyl ester synthesized in Example 152-1 and 4-fluorophenylboric acid as starting materials and by operations similar to those of Example 152-2 and Example 152-3.

¹H-NMR (CDCl₃, 300 MHz) δ: 1.65 (6H, s), 4.68 (4H, s), 7.09-7.15 (2H, m), 7.30 (1H, s), 7.43 (2H, d, J=8.1 Hz), 7.51-7.56 (4H, m).

MS: 418 (M⁺+1).

Example 154

2-[(4-{[(4'-chlorobiphenyl-4-yl)methoxy]methyl}-1,3-thiazol-2-yl)thio]-2-methylpropionic acid

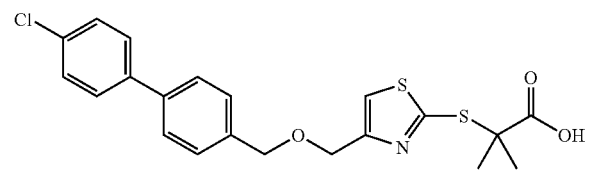

The title compound was obtained using 2-[(4-{[(4-bromobenzyl)oxy]methyl}-1,3-thiazol-2-yl)thio]-2-methylpropionic acid tert-butyl ester synthesized in Example 152-1 and 4-fluorophenylboric acid as starting materials and by operations similar to those of Example 152-2 and Example 152-3.

¹H-NMR (CDCl₃, 300 MHz) δ: 1.68 (6H, s), 4.72 (4H, s), 7.33 (1H, s), 7.42-7.60 (8H, m).

MS: 434 (M⁺+1).

Example 155

2-[(4-{2-[(4'-fluorobiphenyl-4-yl)methoxy]ethyl}-1,3-thiazol-2-yl)thio]-2-methylpropionic acid

Example 155-1

2-{[4-(2-hydroxyethyl)-1,3-thiazol-2-yl]thio}-2-methylpropionic acid ethyl ester

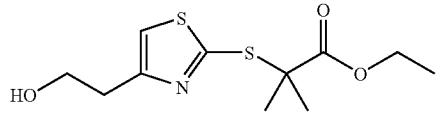

2-{[4-(2-Hydroxyethyl)-1,3-thiazol-2-yl]thio}-2-methylpropionic acid tert-butyl ester (8.4 g) obtained in Example 4 was dissolved in dichloromethane (50 mL), trifluoroacetic acid (50 mL) was added, and the mixture was stirred at room temperature for 12 hr. The reaction mixture was concentrated under reduced pressure, and the residue was dissolved in ethanol (100 mL). Thionyl chloride (8 mL) was added under ice-cooling, and the mixture was refluxed for 4 hr. Under ice-cooling, saturated aqueous sodium hydrogen carbonate solution was added to the reaction mixture, and the solvent was concentrated under reduced pressure. The mixture was extracted with ethyl acetate, and the organic layer was washed with saturated brine and dried over anhydrous sodium sulfate. The solvent was evaporated under reduced pressure, and the residue was purified by silica gel chromatography (elution solvent; hexane:ethyl acetate=1:1) to give the title compound (6.7 g) as a colorless oil.

$^1$H-NMR (CDCl$_3$, 300 MHz) δ: 1.25 (3H, t, J=7.1 Hz), 1.62 (6H, s), 2.97 (2H, t, J=5.6 Hz), 3.95 (2H, t, J=5.6 Hz), 4.18 (2H, q, J=7.1 Hz), 7.02 (1H, s).

Example 155-2

2-[(4-{2-[(4-bromobenzyl)oxy]ethyl}-1,3-thiazol-2-yl)thio]-2-methylpropionic acid ethyl ester

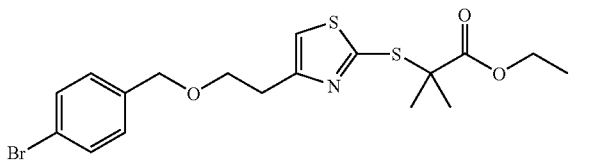

2-{[4-(2-Hydroxyethyl)-1,3-thiazol-2-yl]thio}-2-methylpropionic acid ethyl ester (1.6 g) synthesized in Example 155-1 and 4-bromobenzylbromide (1.7 g) were dissolved in N,N-dimethylformamide (30 mL), potassium tert-butoxide (0.72 g) was added, and the mixture was stirred at room temperature for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 3:1) to give the title compound (1.3 g) as a colorless oil.

$^1$H-NMR (CDCl$_3$, 300 MHz) δ: 1.23 (3H, t, J=7.2 Hz), 1.60 (6H, s), 3.07 (2H, t, J=6.6 Hz), 3.80 (2H, t, J=6.6 Hz), 4.14 (2H, q, J=7.2 Hz), 4.46 (2H, s), 7.07 (1H, s), 7.13-7.19 (2H, m), 7.42-7.47 (2H, m).

Example 155-3

2-[(4-{2-[(4'-fluorobiphenyl-4-yl)methoxy]ethyl}-1,3-thiazol-2-yl)thio]-2-methylpropionic acid ethyl ester

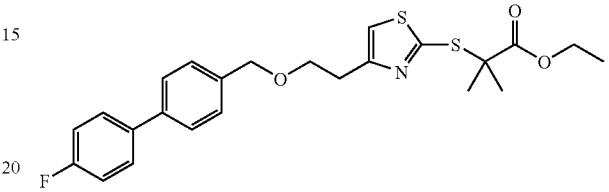

Under nitrogen atmosphere, 2-[(4-{2-[(4-bromobenzyl)oxy]ethyl}-1,3-thiazol-2-yl)thio]-2-methylpropionic acid ethyl ester (0.9 g) synthesized in Example 155-2 and 4-fluorophenylboric acid (425 mg) were dissolved in dioxane (10 mL) and aqueous sodium carbonate solution (2 mol/L, 5 mL), tetrakis(triphenylphosphine)palladium (117 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (400 mg) as a colorless oil.

$^1$H-NMR (CDCl$_3$, 300 MHz) δ: 1.23 (3H, t, J=7.5 Hz), 1.61 (6H, s), 3.10 (2H, t, J=6.3 Hz), 3.84 (2H, t, J=6.3 Hz), 4.30 (2H, q, J=7.5 Hz), 4.56 (2H, s), 7.09-7.15 (3H, m), 7.34-7.37 (2H, m), 7.49-7.55 (4H, m).

Example 155-4

2-[(4-{2-[(4'-fluorobiphenyl-4-yl)methoxy]ethyl}-1,3-thiazol-2-yl)thio]-2-methylpropionic acid

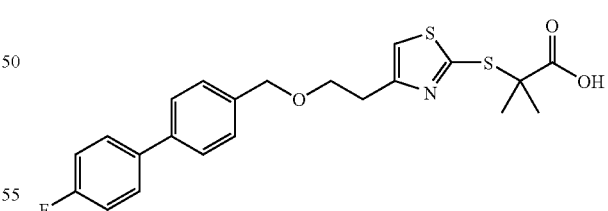

2-[(4-{2-[(4'-Fluorobiphenyl-4-yl)methoxy]ethyl}-1,3-thiazol-2-yl)thio]-2-methylpropionic acid ethyl ester (400 mg) synthesized in Example 155-3 was dissolved in methanol (4 mL) and tetrahydrofuran (4 mL), aqueous sodium hydroxide solution (1 mol/L, 2 mL) was added, and the mixture was stirred at room temperature for 4 hr. The reaction mixture was concentrated under reduced pressure, aqueous 10% citric acid solution was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1 to 1:1) to give the title compound (245 mg) as a white solid.

¹H-NMR (CDCl₃, 300 MHz) δ: 1.61 (6H, s), 3.10 (2H, t, J=6.3 Hz), 3.84 (2H, t, J=6.3 Hz), 4.56 (2H, s), 7.05 (1H, s), 7.09-7.15 (2H, m), 7.34 (2H, d, J=8.1 Hz), 7.49-7.55 (4H, m).

MS: 432 (M⁺+1).

Example 156

2-[(4-{2-[(4'-chlorobiphenyl-4-yl)methoxy]ethyl}-1,3-thiazol-2-yl)thio]-2-methylpropionic acid

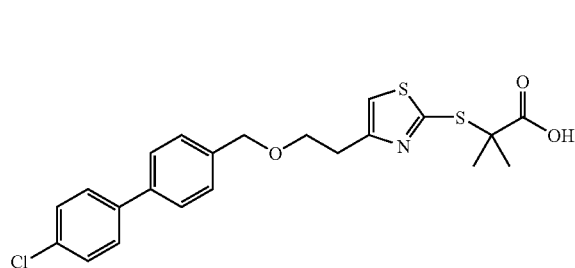

The title compound was obtained using 2-[(4-{2-[(4-bromobenzyl)oxy]ethyl}-1,3-thiazol-2-yl)thio]-2-methylpropionic acid ethyl ester synthesized in Example 155-2 and 4-chlorophenylboric acid as starting materials and by operations similar to those of Example 155-3 and Example 155-4.

¹H-NMR (CDCl₃, 300 MHz) δ: 1.61 (6H, s), 3.10 (2H, t, J=6.2 Hz), 3.85 (2H, t, J=6.2 Hz), 4.56 (2H, s), 7.05 (1H, s), 7.34-7.42 (4H, m), 7.48-7.53 (4H, m).

MS: 448 (M⁺+1).

Example 157

2-methyl-2-{[4-(2-{[4'-(trifluoromethyl)biphenyl-4-yl]methoxy}ethyl)-1,3-thiazol-2-yl]thio}propionic acid

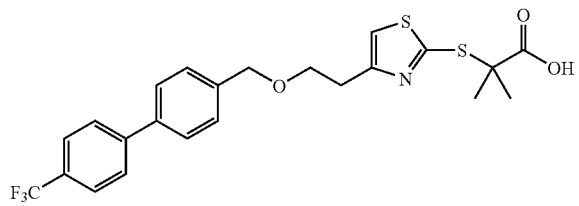

The title compound was obtained using 2-[(4-{2-[(4-bromobenzyl)oxy]ethyl}-1,3-thiazol-2-yl)thio]-2-methylpropionic acid ethyl ester synthesized in Example 155-2 and 4-(trifluoromethyl)phenylboric acid as starting materials and by operations similar to those of Example 155-3 and Example 155-4.

¹H-NMR (CDCl₃, 300 MHz) δ: 1.61 (6H, s), 3.11 (2H, t, J=6.3 Hz), 3.86 (2H, t, J=6.3 Hz), 4.58 (2H, s), 7.05 (1H, s), 7.38 (2H, d, J=8.1 Hz), 7.56 (2H, d, J=8.1 Hz), 7.68 (4H, brs).

MS: 482 (M⁺+1).

Example 158

2-methyl-2-({4-[2-({1-[3-(trifluoromethyl)phenyl]-1H-pyrazol-4-yl}oxy)ethyl]-1,3-thiazol-2-yl}thio) propionic acid Example 158-1

2-methyl-2-({4-[2-({1-[3-(trifluoromethyl)phenyl]-1H-pyrazol-4-yl}oxy)ethyl]-1,3-thiazol-2-yl}thio) propionic acid tert-butyl ester

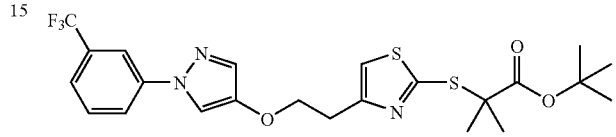

2-Methyl-2-[(4-{2-[(methylsulfonyl)oxy]ethyl}-1,3-thiazol-2-yl)thio]propionic acid tert-butyl ester (1.0 g) synthesized in Example 5 and 1-[3-(trifluoromethyl)phenyl]-1H-pyrazole-4-ol (600 mg) were dissolved in N,N-dimethylformamide (10 mL), potassium carbonate (363 mg) was added, and the mixture was stirred at 85° C. for 3 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 4:1) to give the title compound (400 mg) as a colorless oil.

¹H-NMR (CDCl₃, 300 MHz) δ: 1.43 (9H, s), 1.58 (6H, s), 3.23 (2H, t, J=6.6 Hz), 4.30 (2H, t, J=6.6 Hz), 7.12 (1H, s), 7.47-7.58 (3H, m), 7.66 (1H, s), 7.82 (1H, d, J=8.2 Hz), 7.92 (1H, s).

Example 158-2

2-methyl-2-({4-[2-({1-[3-(trifluoromethyl)phenyl]-1H-pyrazol-4-yl}oxy)ethyl]-1,3-thiazol-2-yl}thio) propionic acid

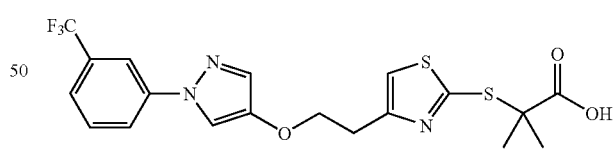

2-Methyl-2-({4-[2-({1-[3-(trifluoromethyl)phenyl]-1H-pyrazol-4-yl}oxy)ethyl]-1,3-thiazol-2-yl}thio)propionic acid tert-butyl ester (400 mg) obtained in Example 158-1 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (290 mg) as a colorless oil.

¹H-NMR (CDCl₃, 300 MHz) δ: 1.63 (6H, s), 3.26 (2H, t, J=6.0 Hz), 4.29 (2H, t, J=6.0 Hz), 7.11 (1H, s), 7.48-7.58 (3H, m), 7.65 (1H, s), 7.80 (1H, d, J=7.8 Hz), 7.92 (1H, s).

MS: 458.

Example 159

2-methyl-2-[(4-{2-[(1-phenyl-1H-pyrazol-4-yl)oxy]ethyl}-1,3-thiazol-2-yl)thio]propionic acid

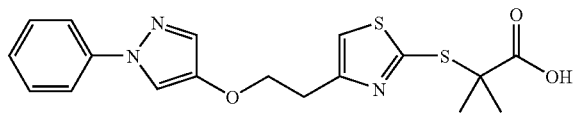

The title compound was obtained using 2-methyl-2-[(4-{2-[(methylsulfonyl)oxy]ethyl}-1,3-thiazol-2-yl)thio]propionic acid tert-butyl ester synthesized in Example 5 and 1-phenyl-1H-pyrazole-4-ol synthesized in reference to non-patent reference [Organic Preparations and Procedures International, 34, 98 (2002)] as starting materials and by an operation similar to that of Example 158.

$^1$H-NMR (CDCl$_3$, 300 MHz) δ: 1.62 (6H, s), 3.24 (2H, t, J=6.1 Hz), 4.28 (2H, t, J=6.1 Hz), 7.11 (1H, s), 7.22-7.27 (1H, m), 7.40-7.45 (3H, m), 7.59-7.62 (3H, m).

MS: 390 (M$^+$+1).

Example 160

2-{[4-(2-{[1-(4-fluorophenyl)-1H-pyrazol-4-yl]oxy}ethyl)-1,3-thiazol-2-yl]thio}-2-methylpropionic acid

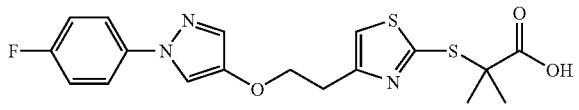

The title compound was obtained using 2-methyl-2-[(4-{2-[(methylsulfonyl)oxy]ethyl}-1,3-thiazol-2-yl)thio]propionic acid tert-butyl ester synthesized in Example 5 and 1-(4-fluorophenyl)-1H-pyrazole-4-ol synthesized in reference to non-patent reference [Organic Preparations and Procedures International, 34, 98 (2002)] as starting materials and by an operation similar to that of Example 158.

$^1$H-NMR (CDCl$_3$, 300 MHz) δ: 1.62 (6H, s), 3.24 (2H, t, J=6.1 Hz), 4.27 (2H, t, J=6.1 Hz), 7.08-7.15 (3H, m), 7.43 (1H, s), 7.54-7.59 (3H, m).

MS: 408 (M$^+$+1).

Example 161

2-{[4-(2-{[1-(4-chlorophenyl)-1H-pyrazol-4-yl]oxy}ethyl)-1,3-thiazol-2-yl]thio}-2-methylpropionic acid

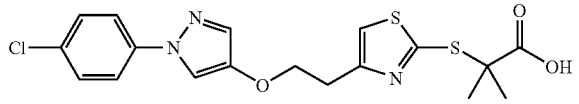

The title compound was obtained using 2-methyl-2-[(4-{2-[(methylsulfonyl)oxy]ethyl}-1,3-thiazol-2-yl)thio]propionic acid tert-butyl ester synthesized in Example 5 and 1-(4-chlorophenyl)-1H-pyrazole-4-ol synthesized in reference to non-patent reference [Organic Preparations and Procedures International, 34, 98 (2002)] as starting materials and by an operation similar to that of Example 158.

$^1$H-NMR (CDCl$_3$, 300 MHz) δ: 1.63 (6H, s), 3.24 (2H, t, J=6.2 Hz), 4.27 (2H, t, J=6.2 Hz), 7.10 (1H, s), 7.39 (2H, t, J=8.8 Hz), 7.44 (1H, s), 7.55-7.57 (3H, m).

MS: 424 (M$^+$+1).

Example 162

2-methyl-2-({4-[2-({5-[4-(trifluoromethoxy)phenyl]pyrimidin-2-yl}amino)ethyl]-1,3-thiazol-2-yl}thio)propionic acid

Example 162-1

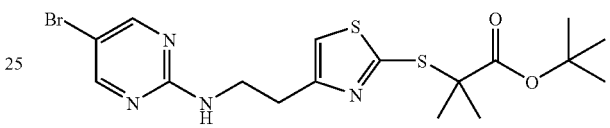

2-{[4-(2-Aminoethyl)-1,3-thiazol-2-yl]thio}-2-methylpropionic acid tert-butyl ester (15.6 g) synthesized in Example 7 and 5-bromo-2-chloropyrimidine (10 g) were dissolved in N-methylpyrrolidone (170 mL), diisopropylethylamine (18.0 mL) was added, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (20 g) as a white solid.

$^1$H-NMR (CDCl$_3$, 300 MHz) δ: 1.44 (9H, s), 1.59 (6H, s), 3.04 (2H, t, J=6.5 Hz), 3.76 (2H, t, J=6.5 Hz), 5.61 (1H, brs), 7.01 (1H, s), 8.26 (2H, s).

MS: 461 (M$^+$+1).

Example 162-2

2-methyl-2-({4-[2-({5-[4-(trifluoromethoxy)phenyl]pyrimidin-2-yl}amino)ethyl]-1,3-thiazol-2-yl}thio)propionic acid tert-butyl ester

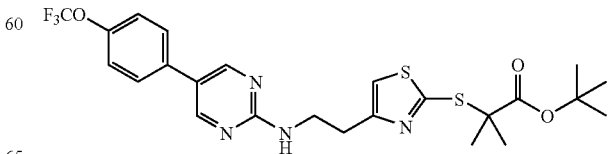

Under nitrogen atmosphere, 2-[(4-{2-[(5-bromopyrimidin-2-yl)amino]ethyl}-1,3-thiazol-2-yl)thio]-2-methylpropionic acid tert-butyl ester (1.0 g) synthesized in Example 162-1 and 4-trifluoromethoxyphenylboric acid (0.54 g) were dissolved in dioxane (10 mL) and 2 mol/L sodium carbonate (5 mL), tetrakis(triphenylphosphine)palladium (0.13 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1 to 1:1) to give the title compound (1.0 g) as a white solid.

$^1$H-NMR (CDCl$_3$, 300 MHz) δ: 1.44 (9H, s), 1.60 (6H, s), 3.10 (2H, t, J=6.3 Hz), 3.83-3.89 (2H, m), 5.61 (1H, brs), 7.04 (1H, s), 7.28-7.30 (2H, m), 7.46-7.50 (2H, m), 8.49 (2H, s).

MS: 541 (M$^+$+1).

Example 162-3

2-methyl-2-({4-[2-({5-[4-(trifluoromethoxy)phenyl]pyrimidin-2-yl}amino)ethyl]-1,3-thiazol-2-yl}thio)propionic acid

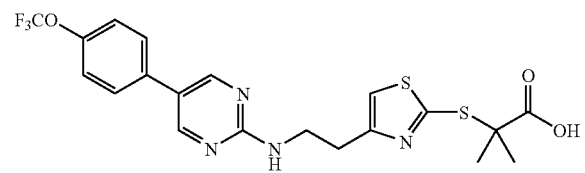

2-Methyl-2-({4-[2-({5-[4-(trifluoromethoxy)phenyl]pyrimidin-2-yl}amino)ethyl]-1,3-thiazol-2-yl}thio)propionic acid tert-butyl ester (370 mg) obtained in Example 162-2 was dissolved in dichloromethane (2 mL), trifluoroacetic acid (2 mL) was added, and the mixture was stirred at room temperature for 12 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=2:1 to 1:1) to give the title compound (297 mg) as a white solid.

$^1$H-NMR (CDCl$_3$, 300 MHz) δ: 1.69 (6H, s), 3.04 (2H, t, J=5.7 Hz), 3.71-3.77 (2H, m), 7.06 (1H, s), 7.28-7.33 (3H, m), 7.45-7.51 (2H, m), 8.49 (2H, brs).

MS: 485 (M$^+$+1).

Example 163

2-methyl-2-({4-[2-(methyl{5-[4-(trifluoromethoxy)phenyl]pyrimidin-2-yl}amino)ethyl]-1,3-thiazol-2-yl}thio)propionic acid Example 163-1

2-methyl-2-({4-[2-(methyl{5-[4-(trifluoromethoxy)phenyl]pyrimidin-2-yl}amino)ethyl]-1,3-thiazol-2-yl}thio)propionic acid tert-butyl ester

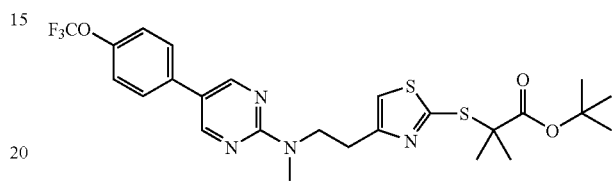

2-Methyl-2-({4-[2-({5-[4-(trifluoromethoxy)phenyl]pyrimidin-2-yl}amino)ethyl]-1,3-thiazol-2-yl}thio)propionic acid tert-butyl ester (620 mg) synthesized in Example 162-2 and methyl iodide (325 mg) were dissolved in N,N-dimethylformamide (6.0 mL), potassium tertiary butoxide (154 mg) was added, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1) to give the title compound (215 mg) as a colorless oil.

$^1$H-NMR (CDCl$_3$, 300 MHz) δ: 1.45 (9H, s), 1.58 (6H, s), 3.09-3.17 (5H, m), 4.03 (2H, t, J=6.9 Hz), 7.03 (1H, s), 7.27-7.30 (2H, m), 7.47-7.50 (2H, m), 8.52 (2H, s).

MS: 555 (M$^+$+1).

Example 163-2

2-methyl-2-({4-[2-(methyl{5-[4-(trifluoromethoxy)phenyl]pyrimidin-2-yl}amino)ethyl]-1,3-thiazol-2-yl}thio)propionic acid

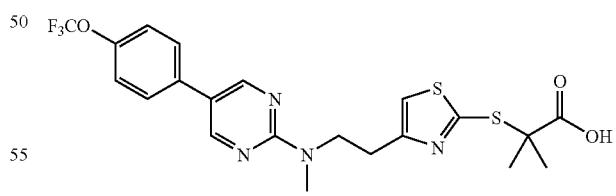

2-Methyl-2-({4-[2-(methyl{5-[4-(trifluoromethoxy)phenyl]pyrimidin-2-yl}amino)ethyl]-1,3-thiazol-2-yl}thio)propionic acid tert-butyl ester (210 mg) obtained in Example 163-1 was dissolved in dichloromethane (2 mL), trifluoroacetic acid (2 mL) was added, and the mixture was stirred at room temperature for 12 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=2:1 to 1:1) to give the title compound (150 mg) as a white solid.

$^1$H-NMR (CDCl$_3$, 300 MHz) δ: 1.66 (6H, s), 3.12-3.17 (5H, m), 4.03 (2H, t, J=7.2 Hz), 6.99 (1H, s), 7.27-7.30 (2H, m), 7.45-7.51 (2H, m), 8.51 (2H, s).

MS: 499 (M$^+$+1).

Example 164

2-methyl-2-({4-[2-({5-[3-(trifluoromethyl)phenyl]pyrimidin-2-yl}amino)ethyl]-1,3-thiazol-2-yl}thio)propionic acid Example 164-1

2-methyl-2-({4-[2-({5-[3-(trifluoromethyl)phenyl]pyrimidin-2-yl}amino)ethyl]-1,3-thiazol-2-yl}thio)propionic acid tert-butyl ester

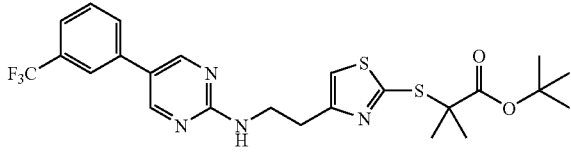

Under nitrogen atmosphere, 2-[(4-{2-[(5-bromopyrimidin-2-yl)amino]ethyl}-1,3-thiazol-2-yl)thio]-2-methylpropionic acid tert-butyl ester (920 mg) synthesized in Example 162-1 and 3-(trifluoromethyl)phenylboric acid (380 mg) were dissolved in dioxane (10 mL) and 2 mol/L sodium carbonate (5 mL), tetrakis(triphenylphosphine)palladium (115 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1 to 2:1) to give the title compound (890 mg) as a white solid.

$^1$H-NMR (CDCl$_3$, 300 MHz) δ: 1.44 (9H, s), 1.59 (6H, s), 3.10 (2H, t, J=6.6 Hz), 3.83-3.90 (2H, m), 5.67 (1H, brs), 7.05 (1H, s), 7.53-7.71 (4H, m), 8.52 (2H, s).

Example 164-2

2-methyl-2-({4-[2-({5-[3-(trifluoromethyl)phenyl]pyrimidin-2-yl}amino)ethyl]-1,3-thiazol-2-yl}thio)propionic acid hydrochloride

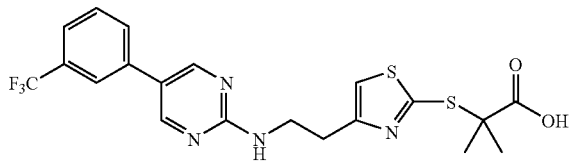

2-Methyl-2-({4-[2-({5-[3-(trifluoromethyl)phenyl]pyrimidin-2-yl}amino)ethyl]-1,3-thiazol-2-yl}thio)propionic acid tert-butyl ester (190 mg) obtained in Example 164-1 was dissolved in dichloromethane (4 mL), trifluoroacetic acid (4 mL) was added, and the mixture was stirred at room temperature for 20 hr. The reaction mixture was concentrated under reduced pressure, and the residue was purified by silica gel chromatography (elution solvent; hexane:ethyl acetate=1:1 to 0:1). The obtained compound was dissolved in diethyl ether (4 mL), 4 mol/L hydrochloric acid-ethyl acetate (0.5 mL) was added, and the mixture was stirred at room temperature for 1 hr. The precipitated solid was collected by filtration to give the title compound (151 mg) as a white solid.

$^1$H-NMR (DMSO-d$_6$, 300 MHz) δ: 1.52 (6H, s), 3.02 (2H, t, J=7.2 Hz), 3.67-3.75 (2H, m), 7.51 (1H, s), 7.67-7.69 (2H, m), 7.96-7.98 (2H, m), 8.75 (2H, s).

MS: 469 (M$^+$+1).

Example 165

2-methyl-2-({4-[2-({5-[4-(trifluoromethyl)phenyl]pyrimidin-2-yl}amino)ethyl]-1,3-thiazol-2-yl}thio)propionic acid

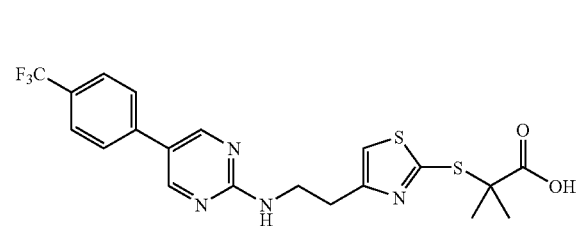

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-trifluoromethylphenylboronic acid as starting materials and by operations similar to those of Example 162-2 and Example 162-3.

$^1$H-NMR (CDCl$_3$, 300 MHz) δ: 1.68 (6H, s), 3.05 (2H, t, J=5.4 Hz), 3.81 (2H, m), 6.91 (1H, s), 7.58 (2H, d, J=8.4 Hz), 7.72 (2H, d, J=8.4 Hz), 7.74 (1H, s), 8.63 (2H, s).

MS: 469 (M$^+$+1).

Example 166

2-{[4-(2-{[5-(4-chlorophenyl)pyrimidin-2-yl]amino}ethyl)-1,3-thiazol-2-yl]thio}-2-methylpropionic acid

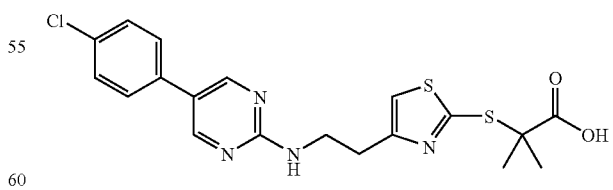

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-chlorophenylboric acid as starting materials and by operations similar to those of Example 162-2 and Example 162-3.

¹H-NMR (CDCl₃, 300 MHz) δ: 1.69 (6H, s), 3.04 (2H, t, J=5.7 Hz), 3.71-3.77 (2H, m), 7.05 (1H, s), 7.28-7.43 (5H, m), 8.49 (2H, brs).

MS: 435 (M⁺+1).

Example 167

2-[(4-{2-[[5-(4-chlorophenyl)pyrimidin-2-yl](isopropyl)amino]ethyl}-1,3-thiazol-2-yl)thio]-2-methylpropionic acid

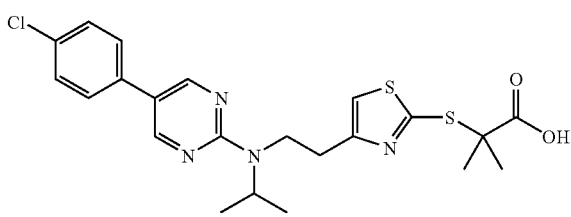

The title compound was obtained by an operation similar to that of Example 162-2 and using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-chlorophenylboric acid as starting materials, followed by an operation similar to that of Example 163 and using isopropyl iodide.

¹H-NMR (CDCl₃, 300 MHz) δ: 1.23 (6H, d, J=6.6 Hz), 1.67 (6H, s), 3.13-3.18 (2H, m), 3.74-3.79 (2H, m), 5.04-5.08 (1H, m), 7.02 (1H, s), 7.41 (4H, s), 8.54 (2H, s).

MS: 477 (M⁺+1).

Example 168

2-({4-[2-(ethyl{5-[4-(trifluoromethyl)phenyl]pyrimidin-2-yl}amino)ethyl]-1,3-thiazol-2-yl}thio)-2-methylpropionic acid

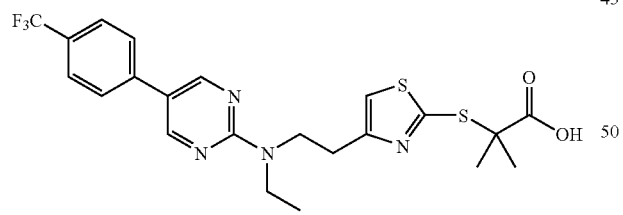

The title compound was obtained by an operation similar to that of Example 162-2 and using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(trifluoromethyl)phenylboric acid as starting materials, followed by an operation similar to that of Example 163 and using ethyl iodide.

¹H-NMR (DMSO-d₆, 300 MHz) δ: 1.10 (3H, t, J=7.1 Hz), 1.52 (6H, s), 3.05-3.07 (2H, m), 3.56-3.58 (2H, m), 3.90-3.92 (2H, m), 7.49 (1H, s), 7.77-7.79 (2H, m), 7.86-7.89 (2H, m), 8.79 (2H, s).

MS: 497 (M⁺+1).

Example 169

2-({4-[2-(ethyl{5-[4-(trifluoromethoxy)phenyl]pyrimidin-2-yl}amino)ethyl]-1,3-thiazol-2-yl}thio)-2-methylpropionic acid

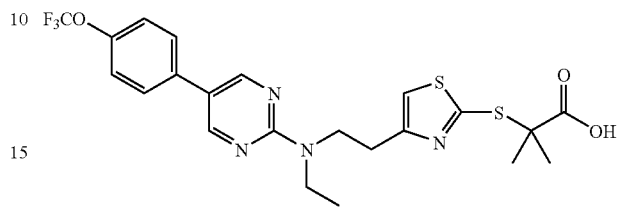

The title compound was obtained by an operation similar to that of Example 162-2 and using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(trifluoromethoxy)phenylboric acid as starting materials, followed by an operation similar to that of Example 1634 and using ethyl iodide.

¹H-NMR (CDCl₃, 300 MHz) δ: 1.19 (3H, t, J=6.9 Hz), 1.66 (6H, s), 3.15 (2H, t, J=6.9 Hz), 3.62 (2H, q, J=6.9 Hz), 3.95 (2H, t, J=6.9 Hz), 7.00 (1H, s), 7.27-7.30 (2H, m), 7.47-7.50 (2H, m), 8.51 (2H, s).

MS: 513 (M⁺+1).

Example 170

2-({4-[2-(isopropyl{5-[4-(trifluoromethoxy)phenyl]pyrimidin-2-yl}amino)ethyl]-1,3-thiazol-2-yl}thio)-2-methylpropionic acid

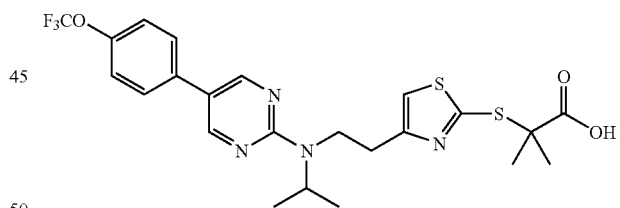

The title compound was obtained by an operation similar to that of Example 162-2 and using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(trifluoromethoxy)phenylboric acid as starting materials, followed by an operation similar to that of Example 163 and using isopropyl iodide.

¹H-NMR (CDCl₃, 300 MHz) δ: 1.24 (6H, d, J=6.9 Hz), 1.68 (6H, s), 3.16 (2H, t, J=7.8 Hz), 3.78 (2H, t, J=7.8 Hz), 5.04-5.09 (1H, m), 7.02 (1H, s), 7.28-7.30 (2H, m), 7.48-7.51 (2H, m), 8.55 (2H, s).

MS: 527 (M⁺+1).

Example 171

2-methyl-2-({4-[2-({5-[4-(2,2,2-trifluoroethoxy)phenyl]pyrimidin-2-yl}amino)ethyl]-1,3-thiazol-2-yl}thio)propionic acid

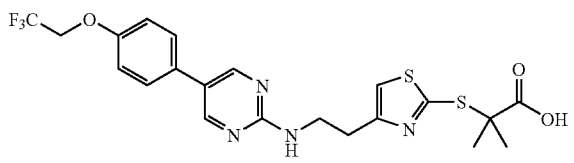

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(2,2,2-trifluoroethoxy)phenylboric acid as starting materials and by operations similar to those of Example 162-2 and Example 162-3.

$^1$H-NMR (CDCl$_3$, 300 MHz) δ: 1.69 (6H, s), 3.04 (2H, t, J=5.7 Hz), 3.71-3.76 (2H, m), 4.39 (2H, q, J=8.1 Hz), 7.01-7.05 (3H, m), 7.38-7.41 (2H, m), 8.46 (2H, brs).

MS: 499 (M$^+$+1).

Example 172

2-methyl-2-({4-[2-({5-[3-(2,2,2-trifluoroethoxy)phenyl]pyrimidin-2-yl}amino)ethyl]-1,3-thiazol-2-yl}thio)propionic acid

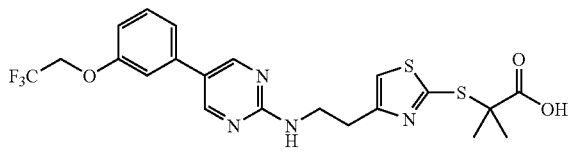

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 3-(2,2,2-trifluoroethoxy)phenylboric acid as starting materials and by operations similar to those of Example 162-2 and Example 162-3.

$^1$H-NMR (CDCl$_3$, 300 MHz) δ: 1.69 (6H, s), 3.04 (2H, t, J=5.7 Hz), 3.71-3.77 (2H, m), 4.40 (2H, q, J=8.1 Hz), 6.90-6.94 (1H, m), 7.03-7.05 (2H, m), 7.13 (1H, d, J=7.2 Hz), 7.29-7.42 (2H, m), 8.51 (2H, brs).

MS: 499 (M$^+$+1).

Example 173

2-methyl-2-{[4-(2-{[5-(4-propylphenyl)pyrimidin-2-yl]amino}ethyl)-1,3-thiazol-2-yl]thio}-propionic acid

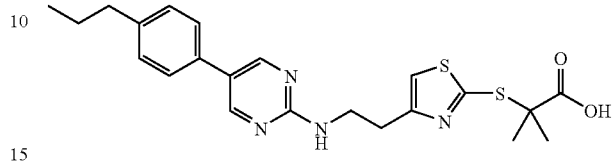

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-propylphenylboric acid as starting materials and by operations similar to those of Example 162-2 and Example 162-3.

$^1$H-NMR (CDCl$_3$, 300 MHz) δ: 0.97 (3H, t, J=7.5 Hz), 1.61-1.71 (8H, m), 2.62 (2H, t, J=7.7 Hz), 3.04 (2H, t, J=5.7 Hz), 3.71-3.77 (2H, m), 7.05 (1H, s), 7.24-7.27 (2H, m), 7.35-7.38 (2H, m), 8.50 (2H, brs).

MS: 443 (M$^+$+1).

Example 174

2-methyl-2-{[4-(2-{[5-(4-propoxyphenyl)pyrimidin-2-yl]amino}ethyl)-1,3-thiazol-2-yl]thio}-propionic acid

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-propoxyphenylboric acid as starting materials and by operations similar to those of Example 162-2 and Example 162-3.

$^1$H-NMR (CDCl$_3$, 300 MHz) δ: 1.05 (3H, t, J=7.5 Hz), 1.69 (6H, s), 1.80-1.87 (2H, m), 3.04 (2H, t, J=5.7 Hz), 3.70-3.76 (2H, m), 3.95 (2H, t, J=6.6 Hz), 6.96-6.98 (2H, m), 7.04 (1H, s), 7.20-7.25 (1H, m), 7.34-7.37 (2H, m), 8.46 (2H, brs).

MS: 459 (M$^+$+1).

Example 175

2-{[4-(2-{[5-(4-isopropylphenyl)pyrimidin-2-yl]amino}ethyl)-1,3-thiazol-2-yl]thio}-2-methylpropionic acid

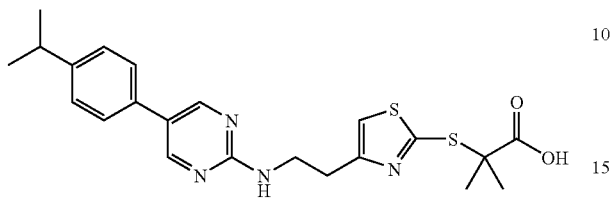

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-isopropylphenylboric acid as starting materials and by operations similar to those of Example 162-2 and Example 162-3.

$^1$H-NMR (CDCl$_3$, 300 MHz) δ: 1.28 (6H, d, J=6.6 Hz), 1.69 (6H, s), 2.88-3.00 (1H, m), 3.04 (2H, t, J=5.7 Hz), 3.71-3.77 (2H, m), 7.05 (1H, s), 7.28-7.32 (2H, m), 7.36-7.40 (2H, m), 8.50 (2H, brs).

MS: 443 (M$^+$+1).

Example 176

2-{[4-(2-{[5-(4-isopropoxyphenyl)pyrimidin-2-yl]amino}ethyl)-1,3-thiazol-2-yl]thio}-2-methylpropionic acid

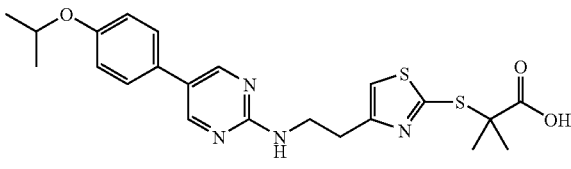

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-isopropoxyphenylboric acid as starting materials and by operations similar to those of Example 162-2 and Example 162-3.

$^1$H-NMR (CDCl$_3$, 300 MHz) δ: 1.36 (6H, d, J=6.0 Hz), 1.69 (6H, s), 3.04 (2H, t, J=5.7 Hz), 3.70-3.76 (2H, m), 4.54-4.62 (1H, m), 6.95 (2H, d, J=8.7 Hz), 7.04 (1H, s), 7.21 (1H, brs), 7.35 (2H, d, J=8.7 Hz), 8.46 (2H, brs).

MS: 459 (M$^+$+1).

Example 177

2-{[4-(2-{[5-(4-chloro-2-fluorophenyl)pyrimidin-2-yl]amino}ethyl)-1,3-thiazol-2-yl]thio}-2-methylpropionic acid Reference Example 3

4-chloro-2-fluorophenylboric acid

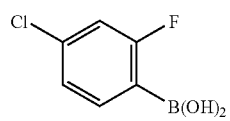

Under nitrogen atmosphere, n-butyllithium (1.6 mol/L-n-hexane, 18.8 mL) was added dropwise at −78° C. to a solution of n-hexane (11 mL) and tetrahydrofuran (30 mL). Then, a solution of 1-bromo-4-chloro-2-fluorobenzene (5.24 g) in n-hexane (15 mL) and tetrahydrofuran (15 mL) was added dropwise. The mixture was stirred at −78° C. for one hour, boric acid trimethyl ester (4.0 mL) in tetrahydrofuran (15 mL) was added dropwise. The mixture was raised to room temperature. After 2 hr, aqueous hydrochloric acid solution (3 mol/L, 120 mL) was added, and the mixture was extracted with diethyl ether (100 mL). The aqueous layer was extracted again with diethyl ether (100 mL), and the combined organic layers were dried over magnesium sulfate. The solvent was evaporated under reduced pressure, n-hexane was added to the residue, and the precipitated solid was collected by filtration to give the title compound (2.0 g) as a white solid.

$^1$H-NMR (CDCl$_3$, 300 MHz) δ: 7.08-7.12 (1H, m), 7.20-7.23 (1H, m), 7.78 (1H, t, J=7.6 Hz).

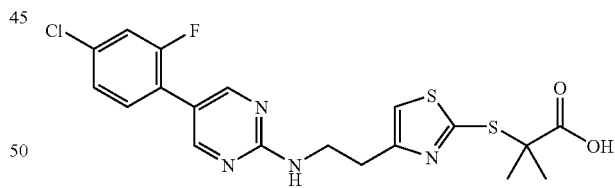

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-chloro-2-fluorophenylboric acid synthesized in Reference Example 3 as starting materials and by operations similar to those of Example 162-2 and Example 162-3.

$^1$H-NMR (CDCl$_3$, 300 MHz) δ: 1.68 (6H, s), 3.04 (2H, t, J=5.7 Hz), 3.71-3.77 (2H, m), 7.05 (1H, s), 7.18-7.34 (3H, m), 8.41-8.46 (2H, m).

MS: 453 (M$^+$+1).

Example 178

2-{[4-(2-{[5-(2,4-dichlorophenyl)pyrimidin-2-yl]amino}ethyl)-1,3-thiazol-2-yl]thio}-2-methylpropionic acid

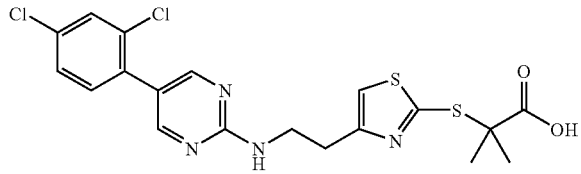

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 2,4-dichlorophenylboric acid as starting materials and by operations similar to those of Example 162-2 and Example 162-3.

$^1$H-NMR (CDCl$_3$, 300 MHz) δ: 1.69 (6H, s), 3.05 (2H, t, J=5.4 Hz), 3.72-3.78 (2H, m), 7.06 (1H, s), 7.21 (1H, d, J=8.1 Hz), 7.31-7.37 (2H, m), 7.51 (1H, d, J=2.1 Hz), 8.21-8.43 (2H, m).

MS: 469 (M$^+$+1).

Example 179

2-[(4-{2-[[5-(2,4-dichlorophenyl)pyrimidin-2-yl](methyl)amino]ethyl}-1,3-thiazol-2-yl)thio]-2-methylpropionic acid

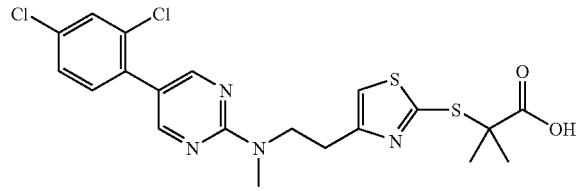

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-2,4-dichlorophenylphenylboric acid as starting materials and by operations similar to those of Example 162-2 and Example 163.

$^1$H-NMR (CDCl$_3$, 300 MHz) δ: 1.65 (6H, s), 3.15 (2H, t, J=6.9 Hz) 3.18 (3H, s), 4.04 (2H, t, J=6.9 Hz), 7.00 (1H, s), 7.24 (1H, d, J=8.4 Hz), 7.32 (1H, dd, J=1.8, 8.4 Hz), 7.50 (1H, d, J=1.8 Hz), 8.39 (2H, s).

MS: 483 (M$^+$+1).

Example 180

2-({4-[2-({5-[2-chloro-4-(trifluoromethyl)phenyl]pyrimidin-2-yl}amino)ethyl]-1,3-thiazol-2-yl}thio)-2-methylpropionic acid

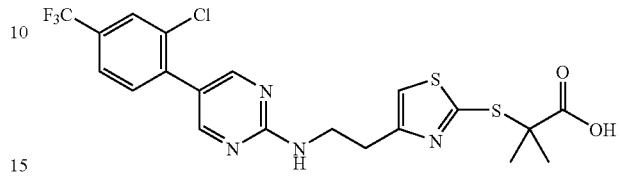

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 2-chloro-4-(trifluoromethyl)phenyl]boric acid synthesized in the same manner as Reference Example 3 from 3-chloro-4-iodobenzotrifluoride as starting materials, and by operations similar to those of Example 162-2 and Example 162-3.

$^1$H-NMR (CDCl$_3$, 300 MHz) δ: 1.69 (6H, s), 3.05 (2H, t, J=5.7 Hz), 3.73-3.79 (2H, m), 7.07 (1H, s), 7.39-7.43 (2H, m), 7.58-7.61 (1H, m), 7.76 (1H, brs), 8.32-8.50 (2H, m).

MS: 503 (M$^+$+1).

Example 181

2-({4-[2-({5-[2-fluoro-4-(trifluoromethyl)phenyl]pyrimidin-2-yl}amino)ethyl]-1,3-thiazol-2-yl}thio)-2-methylpropionic acid

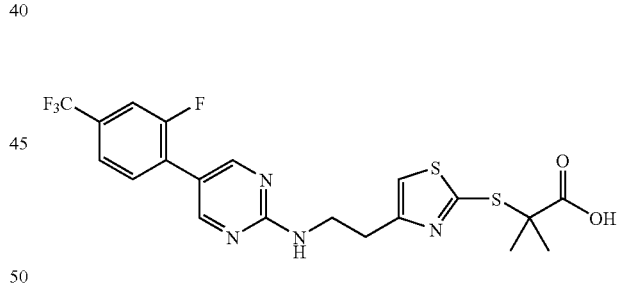

The title compound was obtained using, as starting materials, 2-[(4-{2-[(5-bromopyrimidin-2-yl)amino]ethyl}-1,3-thiazol-2-yl)thio]-2-methylpropionic acid tert-butyl ester synthesized in Example 162-1 and [2-fluoro-4-(trifluoromethyl)phenyl]boric acid synthesized in the same manner as in Reference Example 3 from 4-bromo-3-fluorobenzotrifluoride, and by operations similar to those of Example 162-2 and Example 162-3.

$^1$H-NMR (CDCl$_3$, 300 MHz) δ: 1.68 (6H, s), 3.04 (2H, t, J=5.7 Hz), 3.72-3.78 (2H, m), 7.06 (1H, s), 7.41-7.50 (4H, m), 8.43 (1H, brs), 8.59 (1H, brs),

MS: 487 (M$^+$+1).

Example 182

2-[(4-{2-[{5-[2-fluoro-4-(trifluoromethyl)phenyl]pyrimidin-2-yl}(methyl)amino]ethyl}-1,3-thiazol-2-yl)thio]-2-methylpropionic acid

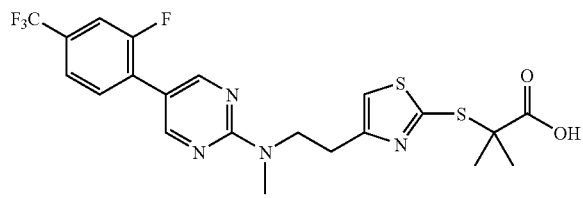

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and [2-fluoro-4-(trifluoromethyl)phenyl]boric acid as starting materials and by operations similar to those of Example 162-2 and Example 163.

$^1$H-NMR (CDCl$_3$, 300 MHz) δ: 1.63 (6H, s), 3.09-3.13 (5H, m), 4.01 (2H, t, J=6.9 Hz), 7.01 (1H, s), 7.38-7.49 (3H, m), 8.53 (2H, s).

MS: 501 (M$^+$+1).

Example 183

2-methyl-2-[(4-{3-[(5-phenylpyrimidin-2-yl)amino]propyl}-1,3-thiazol-2-yl)thio]-propionic acid

Example 183-1

2-[(4-{3-[(5-bromopyrimidin-2-yl)amino]propyl}-1,3-thiazol-2-yl)thio]-2-methylpropionic acid tert-butyl ester

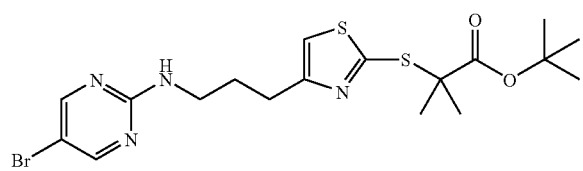

2-{[4-(3-Aminopropyl)-1,3-thiazol-2-yl]thio}-2-methylpropionic acid tert-butyl ester (5.3 g) synthesized in Example 33 and 5-bromo-2-chloropyrimidine (3.24 g) were dissolved in N-methylpyrrolidone (60 mL), diisopropylethylamine (5.8 mL) was added, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (5.65 g) as a colorless oil.

$^1$H-NMR (CDCl$_3$, 300 MHz) δ: 1.43 (9H, s), 1.57 (6H, s), 1.97-2.07 (2H, m), 2.84 (2H, t, J=7.2 Hz), 3.39-3.46 (2H, m), 5.34 (1H, brs), 6.99 (1H, s), 8.26 (2H, s).

Example 183-2

2-methyl-2-[(4-{3-[(5-phenylpyrimidin-2-yl)amino]propyl}-1,3-thiazol-2-yl)thio]-propionic acid

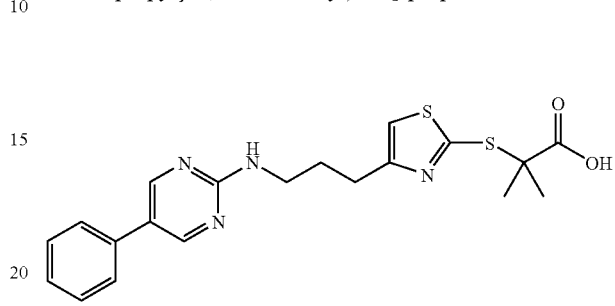

The title compound was obtained using 2-[(4-{3-[(5-bromopyrimidin-2-yl)amino]propyl}-1,3-thiazol-2-yl)thio]-2-methylpropionic acid tert-butyl ester synthesized in Example 183-1 and phenylphenylboric acid as starting materials and by operations similar to those of Example 162-2 and Example 162-3.

$^1$H-NMR (CDCl$_3$, 300 MHz) δ: 1.70 (6H, s), 2.05-2.14 (2H, m), 2.93 (2H, t, J=6.0 Hz), 3.52-3.58 (2H, m), 6.48 (1H, brs), 6.93 (1H, s), 7.34-7.45 (5H, m) 8.51 (2H, s).

MS: 415 (M$^+$+1).

Example 184

2-{[4-(3-{([5-(4-fluorophenyl)pyrimidin-2-yl]amino}propyl)-1,3-thiazol-2-yl]thio}-2-methylpropionic acid

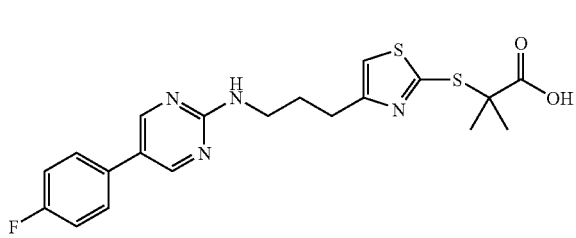

The title compound was obtained using 2-[(4-{3-[(5-bromopyrimidin-2-yl)amino]propyl}-1,3-thiazol-2-yl)thio]-2-methylpropionic acid tert-butyl ester synthesized in Example 183-1 and 4-fluorophenylphenylboric acid as starting materials and by operations similar to those of Example 162-2 and Example 162-3.

$^1$H-NMR (CDCl$_3$, 300 MHz) δ: 1.69 (6H, s), 2.05-2.13 (2H, m), 2.91-2.95 (2H, m), 3.49-3.57 (2H, m), 6.48 (1H, brs), 6.93 (1H, s), 7.10-7.17 (2H, m), 7.38-7.42 (2H, m), 8.46 (2H, s).

MS: 433 (M$^+$+1).

Example 185

2-{[4-(3-{[5-(4-methylphenyl)pyrimidin-2-yl]amino}propyl)-1,3-thiazol-2-yl]thio}-2-methylpropionic acid

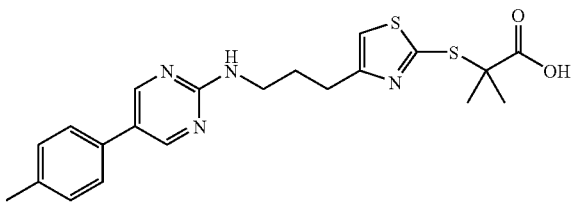

The title compound was obtained using 2-[(4-{3-[(5-bromopyrimidin-2-yl)amino]propyl}-1,3-thiazol-2-yl)thio]-2-methylpropionic acid tert-butyl ester synthesized in Example 183-1 and 4-methylphenylphenylboric acid as starting materials and by operations similar to those of Example 162-2 and Example 162-3.

$^1$H-NMR (CDCl$_3$, 300 MHz) δ: 1.70 (6H, s), 2.05-2.13 (2H, m), 2.39 (3H, s), 2.93 (2H, t, J=6.3 Hz), 3.51-3.57 (2H, m), 6.45-6.47 (1H, m), 6.93 (1H, s), 7.23-7.26 (2H, m), 7.33-7.36 (2H, m), 8.48 (2H, s).

MS: 429 (M$^+$+1).

Example 186

2-methyl-2-({4-[3-({5-[4-(trifluoromethyl)phenyl]pyrimidin-2-yl}amino)propyl]-1,3-thiazol-2-yl}thio)propionic acid

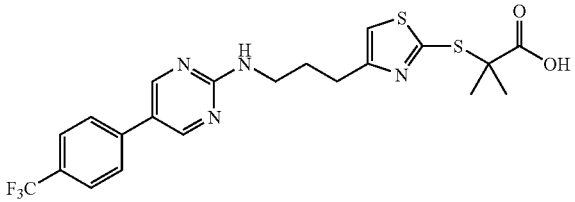

The title compound was obtained using 2-[(4-{3-[(5-bromopyrimidin-2-yl)amino]propyl}-1,3-thiazol-2-yl)thio]-2-methylpropionic acid tert-butyl ester synthesized in Example 183-1 and 4-(trifluoromethyl)phenylphenylboric acid as starting materials and by operations similar to those of Example 162-2 and Example 162-3.

$^1$H-NMR (CDCl$_3$, 300 MHz) δ: 1.69 (6H, s), 2.05-2.14 (2H, m), 2.93 (2H, t, J=6.3 Hz), 3.53-3.59 (2H, m), 6.54-6.56 (1H, m), 6.94 (1H, s), 7.57 (2H, d, J=8.4 Hz), 7.70 (2H, d, J=8.4 Hz), 8.53 (2H, s).

MS: 483 (M$^+$+1).

Example 187

2-methyl-2-{[4-(2-{[5-(4-methylphenyl)pyrimidin-2-yl]amino}ethyl)-1,3-thiazol-2-yl]thio}propionic acid hydrochloride

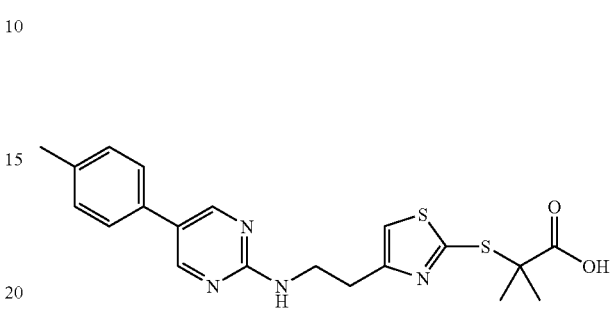

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-methylphenylboronic acid as starting materials and by an operation similar to that of Example 164.

$^1$H-NMR (DMSO-d$_6$, 300 MHz) δ: 1.51 (6H, s), 2.33 (3H, s), 3.02 (2H, t, J=7.2 Hz), 3.68 (2H, t, J=7.2 Hz), 7.27 (2H, d, J=7.8 Hz), 7.54 (2H, d, J=7.8 Hz), 7.53 (1H, s), 8.70 (2H, s).

MS: 415 (M$^+$+1).

Example 188

2-{[4-(2-{[5-(4-fluorophenyl)pyrimidin-2-yl]amino}ethyl)-1,3-thiazol-2-yl]thio}-2-methylpropionic acid hydrochloride

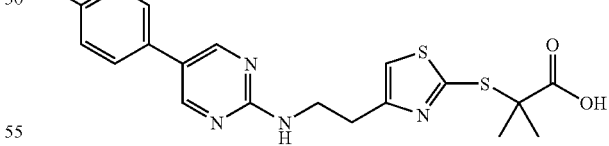

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-fluorophenylboronic acid as starting materials and by an operation similar to that of Example 164.

$^1$H-NMR (DMSO-d$_6$, 300 MHz) δ: 1.51 (6H, s), 3.02 (2H, t, J=7.2 Hz), 3.69 (2H, t, J=7.2 Hz), 7.30 (2H, t, J=9.0 Hz), 7.53 (1H, s), 7.71 (2H, m), 8.70 (2H, s).

MS: 419 (M$^+$+1).

Example 189

2-{[4-(2-{[5-(4-methoxyphenyl)pyrimidin-2-yl]amino}ethyl)-1,3-thiazol-2-yl]thio}-2-methylpropionic acid hydrochloride

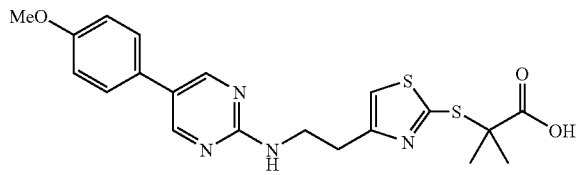

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-methoxyphenylboronic acid as starting materials and by an operation similar to that of Example 164.

$^1$H-NMR (DMSO-d$_6$, 300 MHz) δ: 1.51 (6H, s), 3.02 (2H, t, J=7.2 Hz), 3.68 (2H, t, J=7.2 Hz), 3.79 (3H, s), 7.03 (2H, d, J=8.7 Hz), 7.53 (1H, s), 7.59 (2H, d, J=8.7 Hz), 8.69 (2H, s).

MS: 431 (M$^+$+1).

Example 190

2-methyl-2-({4-[2-(methyl{5-[4-(trifluoromethyl)phenyl]pyrimidin-2-yl}amino)ethyl]-1,3-thiazol-2-yl}thio)propionic acid hydrochloride

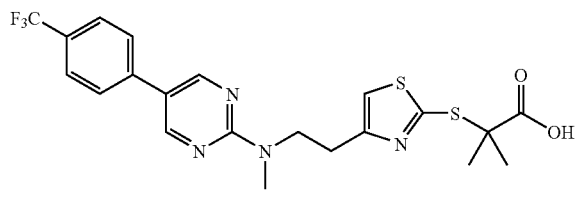

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-trifluoromethylphenylboronic acid as starting materials and by operations similar to those of Example 162-2, Example 163-1 and Example 164-2.

$^1$H-NMR (DMSO-d$_6$, 300 MHz) δ: 1.51 (6H, s), 3.04 (2H, t, J=7.2 Hz), 3.09 (3H, s), 3.98 (2H, t, J=7.2 Hz), 7.50 (1H, s), 7.78 (2H, d, J=8.1 Hz), 7.88 (2H, d, J=8.1 Hz), 8.79 (2H, s).

MS: 483 (M$^+$+1).

Example 191

2-methyl-2-{[4-(2-{[5-(2-naphthyl)pyrimidin-2-yl]amino}ethyl)-1,3-thiazol-2-yl]thio}propionic acid hydrochloride

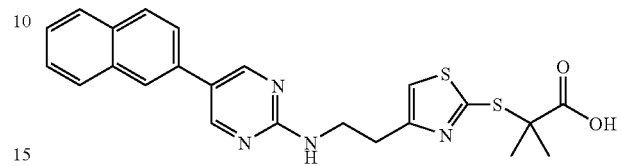

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 2-naphthylboronic acid as starting materials and by an operation similar to that of Example 164.

$^1$H-NMR (DMSO-d$_6$, 300 MHz) δ: 1.52 (6H, s), 3.03 (2H, t, J=7.2 Hz), 7.53 (1H, s), 7.55 (2H, m), 7.83 (1H, d, J=8.3 Hz), 7.94 (2H, m), 8.00 (1H, d, J=8.5 Hz), 8.20 (1H, s), 8.83 (2H, s).

MS: 451 (M$^+$+1).

Example 192

2-{[4-(2-{[5-(4-tert-butylphenyl)pyrimidin-2-yl]amino}ethyl)-1,3-thiazol-2-yl]thio}-2-methylpropionic acid hydrochloride

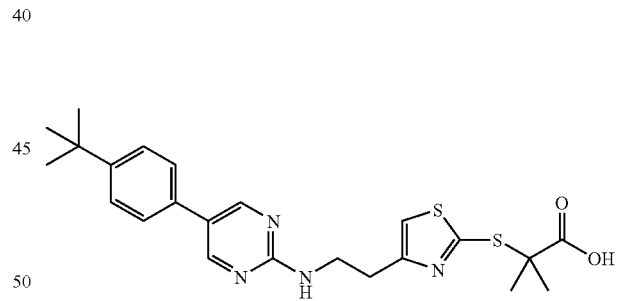

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-tert-butylphenylboronic acid as starting materials and by an operation similar to that of Example 164.

$^1$H-NMR (DMSO-d$_6$, 300 MHz) δ: 1.31 (9H, s), 1.51 (6H, s), 3.03 (2H, t, J=7.2 Hz), 3.71 (2H, t, J=7.2 Hz), 7.48 (2H, d, J=8.4 Hz), 7.54 (1H, s), 7.58 (2H, d, J=8.4 Hz), 8.75 (2H, s).

MS: 457 (M$^+$+1).

Example 193

2-[(4-{2-[[5-(4-chlorophenyl)pyrimidin-2-yl](methyl)amino]ethyl}-1,3-thiazol-2-yl)thio]-2-methylpropionic acid hydrochloride

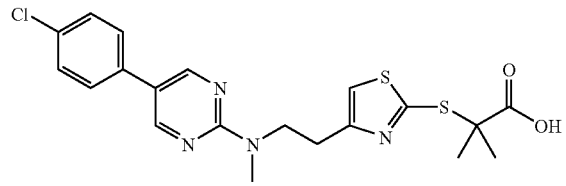

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-chlorophenylboric acid as starting materials and by operations similar to those of Example 162-2, Example 163-1 and Example 164-2.

$^1$H-NMR (DMSO-$d_6$, 300 MHz) δ: 1.51 (6H, s), 3.03-3.07 (5H, m), 3.94-3.99 (2H, m), 7.48-7.51 (3H, m), 7.67 (2H, d, J=8.4 Hz), 8.70 (2H, s).

MS: 449 (M$^+$+1).

Example 194

2-methyl-2-({4-[2-({5-[3-(trifluoromethoxy)phenyl]pyrimidin-2-yl}amino)ethyl]-1,3-thiazol-2-yl}thio)propionic acid hydrochloride

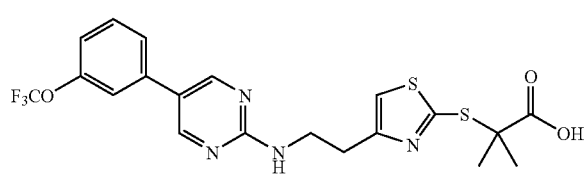

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 3-(trifluoromethoxy)phenylboric acid as starting materials and by an operation similar to that of Example 164.

$^1$H-NMR (DMSO-$d_6$, 300 MHz) δ: 1.51 (6H, s), 3.01 (2H, t, J=7.2 Hz), 3.68 (2H, t, J=7.2 Hz), 7.32-7.34 (1H, m), 7.52 (1H, s), 7.55-7.61 (1H, m), 7.68-7.72 (2H, m), 8.75 (2H, s).

MS: 485 (M$^+$+1).

Example 195

2-methyl-2-({4-[2-(methyl{5-[3-(trifluoromethoxy)phenyl]pyrimidin-2-yl}amino)ethyl]-1,3-thiazol-2-yl}thio)propionic acid hydrochloride

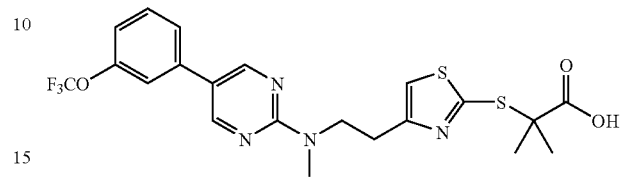

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 3-(trifluoromethoxy)phenylboric acid as starting materials and by operations similar to those of Example 162-2, Example 163-1 and Example 164-2.

$^1$H-NMR (DMSO-$d_6$, 300 MHz) δ: 1.51 (6H, s), 3.04 (2H, t, J=7.0 Hz), 3.09 (3H, s), 3.98 (2H, t, J=7.0 Hz), 7.31-7.34 (1H, m), 7.50 (1H, s), 7.55-7.60 (1H, m), 7.66-7.71 (2H, m), 8.76 (2H, s).

MS: 499 (M$^+$+1).

Example 196

2-[(4-{2-[[5-(4-chlorophenyl)pyrimidin-2-yl](ethyl)amino]ethyl}-1,3-thiazol-2-yl)thio]-2-methylpropionic acid hydrochloride

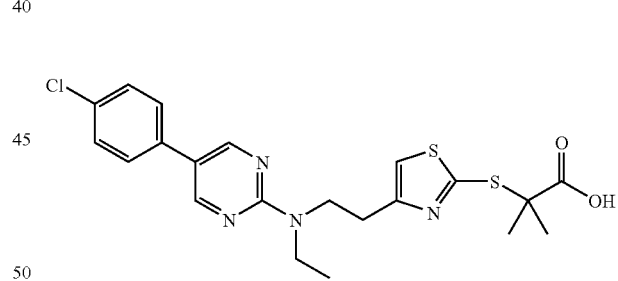

The title compound was obtained by an operation similar to that of Example 1-2 and using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-chlorophenylboric acid, followed by operations similar to those of Example 163-1 and Example 164-2 and using ethyl iodide.

$^1$H-NMR (DMSO-$d_6$, 300 MHz) δ: 1.10 (3H, t, J=6.9 Hz), 1.52 (6H, s), 3.04 (2H, t, J=6.9 Hz), 3.56 (2H, q, J=6.9 Hz), 3.91 (2H, t, J=6.9 Hz), 7.48-7.51 (3H, m), 7.65-7.70 (2H, m), 8.71 (2H, s).

MS: 463 (M$^+$+1).

Example 197

2-{[4-(2-{[5-(3-chloro-4-fluorophenyl)pyrimidin-2-yl]amino}ethyl)-1,3-thiazol-2-yl]thio}-2-methylpropionic acid hydrochloride

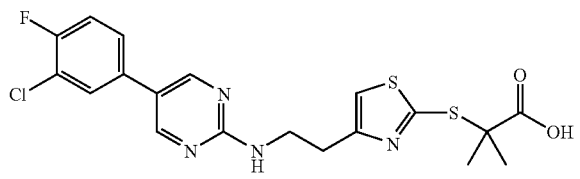

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 3-chloro-4-fluorophenylboric acid as starting materials and by an operation similar to that of Example 164.

$^1$H-NMR (DMSO-$d_6$, 300 MHz) δ: 1.51 (6H, s), 3.00 (2H, t, J=7.2 Hz), 3.64-3.80 (2H, m), 7.46-7.52 (2H, m), 7.64-7.66 (1H, m), 7.89-7.91 (1H, m), 8.69 (2H, s).

MS: 453 (M$^+$+1).

Example 198

2-{[4-(2-{[5-(3,4-dichlorophenyl)pyrimidin-2-yl]amino}ethyl)-1,3-thiazol-2-yl]thio}-2-methylpropionic acid hydrochloride

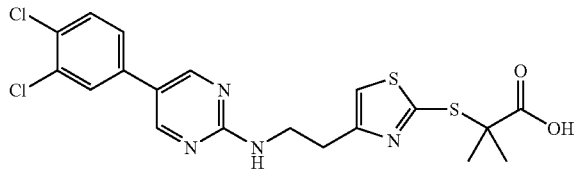

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 3,4-dichlorophenylboric acid as starting materials and by an operation similar to that of Example 164.

$^1$H-NMR (DMSO-$d_6$, 300 MHz) δ: 1.51 (6H, s), 3.00 (2H, t, J=7.2 Hz), 3.67-3.80 (2H, m), 7.51 (1H, s), 7.64-7.71 (2H, m), 7.96 (1H, s), 8.72 (2H, s).

MS: 469 (M$^+$+1).

Example 199

2-methyl-2-[(4-{2-[(5-phenylpyrimidin-2-yl)amino]ethyl}-1,3-thiazol-2-yl)thio]propionic acid trifluoroacetate

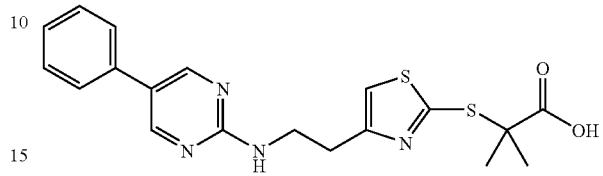

The compound obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and phenylboronic acid as starting materials and by an operation similar to that of Example 162-2 was treated with dichloromethane and trifluoroacetic acid, and the mixture was stirred at room temperature for 12 hr. The reaction mixture was concentrated under reduced pressure, and the obtained solid was triturated and washed with hexane-ethyl acetate to give the title compound as a white solid.

$^1$H-NMR (DMSO-$d_6$, 300 MHz) δ: 1.51 (6H, s), 3.01 (2H, t, J=7.0 Hz), 3.66 (2H, t, J=7.0 Hz), 7.34 (1H, t, J=7.6 Hz), 7.45 (2H, t, J=7.6 Hz), 7.52 (1H, s), 7.63 (2H, d, J=8.0 Hz), 8.68 (2H, s).

MS: 401 (M$^+$+1).

Example 200

2-methyl-2-{[4-(2-{[5-(2-thienyl)pyrimidin-2-yl]amino}ethyl)-1,3-thiazol-2-yl]thio}propionic acid trifluoroacetate

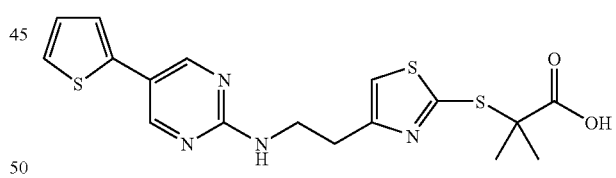

The compound obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 2-thiopheneboronic acid as starting materials and by an operation similar to that of Example 162-2 was treated with dichloromethane and trifluoroacetic acid, and the mixture was stirred at room temperature for 12 hr. The reaction mixture was concentrated under reduced pressure, and the obtained solid was triturate and washed with hexane-ethyl acetate to give the title compound as a white solid.

$^1$H-NMR (DMSO-$d_6$, 300 MHz) δ: 1.51 (6H, s), 2.99 (2H, t, J=7.5 Hz), 3.62 (2H, m), 7.12 (1H, m), 7.39 (1H, d, J=2.7 Hz), 7.49 (1H, d, J=4.5 Hz), 7.50 (1H, s), 7.52 (1H, s), 8.59 (2H, s).

MS: 407 (M$^+$+1).

Example 201

2-methyl-2-({4-[3-({5-[3-(trifluoromethyl)phenyl]pyrimidin-2-yl}amino)propyl]-1,3-thiazol-2-yl}thio)propionic acid hydrochloride

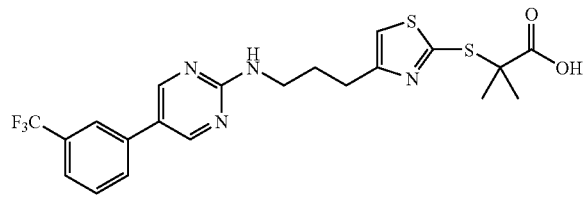

The title compound was obtained using 2-[(4-{3-[(5-bromopyrimidin-2-yl)amino]propyl}-1,3-thiazol-2-yl)thio]-2-ethylpropionic acid tert-butyl ester synthesized in Example 183-1 and 3-(trifluoromethyl)phenylboric acid as starting materials and by an operation similar to that of Example 164.

$^1$H-NMR (DMSO-$d_6$, 300 MHz) δ: 1.51 (6H, s), 1.89-1.99 (2H, m), 2.79 (2H, t, J=7.2 Hz), 3.42 (2H, t, J=7.2 Hz), 7.49 (1H, s), 7.66-7.70 (2H, m), 7.97-8.01 (3H, m), 8.82 (2H, s).

MS: 483 (M$^+$+1).

Example 202

2-methyl-2-({4-[3-(methyl{5-[4-(trifluoromethyl)phenyl]pyrimidin-2-yl}amino)propyl]-1,3-thiazol-2-yl}thio)propionic acid hydrochloride

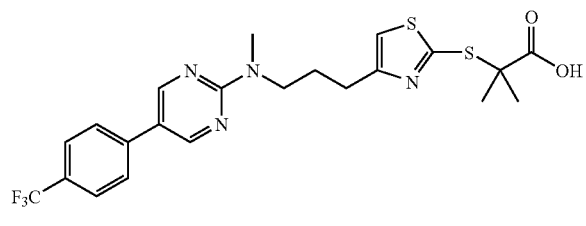

The title compound was obtained using 2-[(4-{3-[(5-bromopyrimidin-2-yl)amino]propyl}-1,3-thiazol-2-yl)thio]-2-methylpropionic acid tert-butyl ester synthesized in Example 183-1 and 4-(trifluoromethyl)phenylboric acid as starting materials and by operations similar to those of Example 162-2, Example 163-1 and Example 164-2.

$^1$H-NMR (DMSO-$d_6$, 300 MHz) δ: 1.51 (6H, s), 1.91-2.03 (2H, m), 2.75 (2H, t, J=7.5 Hz), 3.17 (3H, s), 3.71 (2H, t, J=7.5 Hz), 7.48 (1H, s), 7.78 (2H, d, J=8.4 Hz), 7.88 (2H, d, J=8.4 Hz), 8.79 (2H, s).

MS: 497 (M$^+$+1).

Example 203

2-methyl-2-({4-[({5-[4-(trifluoromethyl)phenyl]pyrimidin-2-yl}amino)methyl]-1,3-thiazol-2-yl}thio)propionic acid hydrochloride

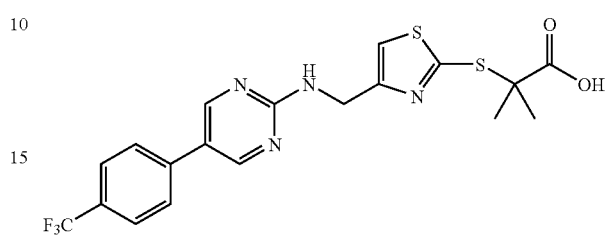

The title compound was obtained by an operation similar to that of Example 162-1 and using 2-{[4-(aminomethyl)-1,3-thiazol-2-yl]thio}-2-methylpropionic acid tert-butyl ester synthesized in Example 13 and 5-bromo-2-chloropyrimidine as starting materials, followed by operations similar to those of Example 162-2 and Example 164-2 and using [4-(trifluoromethyl)phenyl]boric acid.

$^1$H-NMR (DMSO-$d_6$, 300 MHz) δ: 1.51 (6H, s), 4.68 (2H, s), 7.50 (1H, s), 7.79 (2H, d, J=8.1 Hz), 7.89 (2H, d, J=8.1 Hz), 8.79 (2H, s).

MS: 455 (M$^+$+1).

Example 204

2-methyl-2-({4-[(methyl{5-[4-(trifluoromethyl)phenyl]pyrimidin-2-yl}amino)methyl]-1,3-thiazol-2-yl}thio)propionic acid hydrochloride

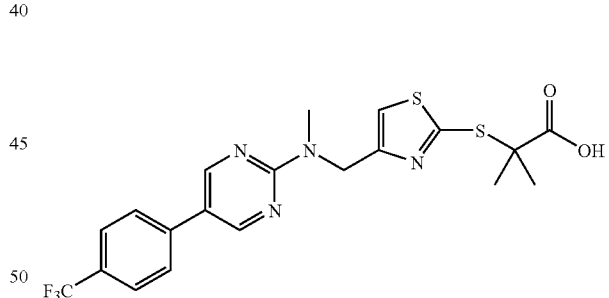

The title compound was obtained by an operation similar to that of Example 162-1 and using 2-{[4-(aminomethyl)-1,3-thiazol-2-yl]thio}-2-methylpropionic acid tert-butyl ester synthesized in Example 13 and 5-bromo-2-chloropyrimidine as starting materials, followed by operations similar to those of Example 162-2, Example 163-1 and Example 164-2 and using [4-(trifluoromethyl)phenyl]boric acid.

$^1$H-NMR (DMSO-$d_6$, 300 MHz) δ: 1.50 (6H, s), 3.24 (3H, s), 4.99 (2H, s), 7.51 (1H, s), 7.79 (2H, d, J=8.1 Hz), 7.89 (2H, d, J=8.1 Hz), 8.82 (2H, s).

MS: 469 (M$^+$+1).

Example 205

2-methyl-2-({4-[({5-[3-(trifluoromethyl)phenyl]pyrimidin-2-yl}amino)methyl]-1,3-thiazol-2-yl}thio)propionic acid hydrochloride

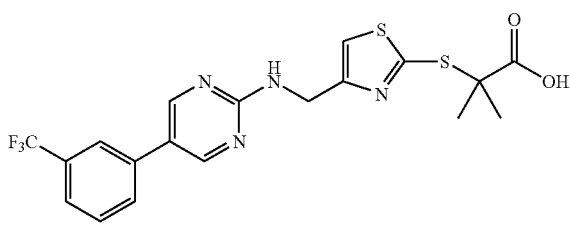

The title compound was obtained by an operation similar to that of Example 162-1 and using 2-{[4-(aminomethyl)-1,3-thiazol-2-yl]thio}-2-methylpropionic acid tert-butyl ester synthesized in Example 13 and 5-bromo-2-chloropyrimidine as starting materials, followed by operations similar to those of Example 162-2 and Example 164-2 and using [3-(trifluoromethyl)phenyl]boric acid.

$^1$H-NMR (DMSO-d$_6$, 300 MHz) δ: 1.51 (6H, s), 4.71 (2H, s), 7.54 (1H, s), 7.62-7.71 (2H, m), 7.96-8.02 (2H, m), 8.86 (2H, s).

MS: 455 (M$^+$+1).

Example 206

2-methyl-2-({5-methyl-4-[2-({5-[4-(trifluoromethyl)phenyl]pyrimidin-2-yl}amino)ethyl]-1,3-thiazol-2-yl}thio)propionic acid hydrochloride

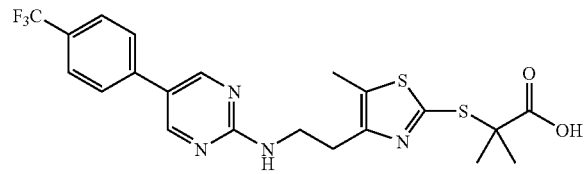

The title compound was obtained by an operation similar to that of Example 162-1 and using 2-{[4-(2-aminoethyl)-5-methyl-1,3-thiazol-2-yl]thio}-2-methylpropionic acid tert-butyl ester synthesized in Example 19 and 5-bromo-2-chloropyrimidine as starting materials, followed by operations similar to those of Example 162-2 and Example 164-2 and using [4-(trifluoromethyl)phenyl]boric acid.

$^1$H-NMR (DMSO-d$_6$, 300 MHz) δ: 1.48 (6H, s), 2.35 (3H, s), 2.89-2.97 (2H, m), 3.62-3.69 (2H, m), 7.80 (2H, d, J=8.4 Hz), 7.90 (2H, d, J=8.4 Hz), 8.83 (2H, s).

MS: 483 (M$^+$+1).

Example 207

2-methyl-2-({5-methyl-4-[2-(methyl{5-[4-(trifluoromethyl)phenyl]pyrimidin-2-yl}amino)ethyl]-1,3-thiazol-2-yl}thio)propionic acid hydrochloride

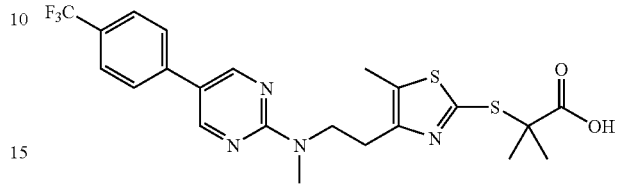

The title compound was obtained by an operation similar to that of Example 162-1 and using 2-{[4-(2-aminoethyl)-5-methyl-1,3-thiazol-2-yl]thio}-2-methylpropionic acid tert-butyl ester synthesized in Example 19 and 5-bromo-2-chloropyrimidine as starting materials, followed by operations similar to those of Example 162-2, Example 163-1 and Example 164-2 and using [4-(trifluoromethyl)phenyl]boric acid.

$^1$H-NMR (DMSO-d$_6$, 300 MHz) δ: 1.48 (6H, s), 2.28 (3H, s), 2.97 (2H, t, J=6.8 Hz), 3.07 (3H, s), 3.92 (2H, d, J=6.8 Hz), 7.79 (2H, d, J=8.2 Hz), 7.89 (2H, d, J=8.2 Hz), 8.80 (2H, s).

MS: 497 (M$^+$+1).

Example 208

2-methyl-2-({5-methyl-4-[2-({5-[3-(trifluoromethyl)phenyl]pyrimidin-2-yl}amino)ethyl]-1,3-thiazol-2-yl}thio)propionic acid hydrochloride

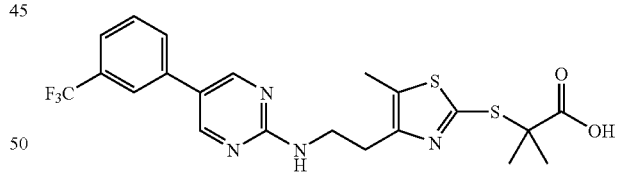

The title compound was obtained by an operation similar to that of Example 162-1 and using 2-{[4-(2-aminoethyl)-5-methyl-1,3-thiazol-2-yl]thio}-2-methylpropionic acid tert-butyl ester synthesized in Example 19 and 5-bromo-2-chloropyrimidine as starting materials, followed by operations similar to those of Example 162-2 and Example 164-2 and using [3-(trifluoromethyl)phenyl]boric acid.

$^1$H-NMR (DMSO-d$_6$, 300 MHz) δ: 1.48 (6H, s), 2.36 (3H, s), 2.90-2.97 (2H, m), 3.63-3.71 (2H, m), 7.67-7.71 (2H, m), 7.98-8.03 (2H, m), 8.86 (2H, s).

MS: 483 (M$^+$+1).

Example 209

2-methyl-2-({4-methyl-5-[2-({5-[4-(trifluoromethyl)phenyl]pyrimidin-2-yl}amino)ethyl]-1,3-thiazol-2-yl}thio)propionic acid hydrochloride

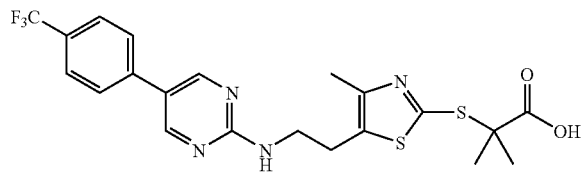

The title compound was obtained by an operation similar to that of Example 162-1 and using 2-{[5-(2-aminoethyl)-4-methyl-1,3-thiazol-2-yl]thio}-2-methylpropionic acid tert-butyl ester synthesized in Example 24 and 5-bromo-2-chloropyrimidine as starting materials, followed by operations similar to those of Example 162-2 and Example 164-2 and using [4-(trifluoromethyl)phenyl]boric acid.

$^1$H-NMR (DMSO-d$_6$, 300 MHz) δ: 1.46 (6H, s), 2.29 (3H, s), 3.04 (2H, t, J=6.8 Hz), 3.52-3.57 (2H, m), 7.78 (2H, d, J=8.1 Hz), 7.88 (2H, d, J=8.1 Hz), 8.76 (2H, s).

MS: 483 (M$^+$+1).

Example 210

2-methyl-2-({4-methyl-5-[2-(methyl{5-[4-(trifluoromethyl)phenyl]pyrimidin-2-yl}amino)ethyl]-1,3-thiazol-2-yl}thio)propionic acid hydrochloride

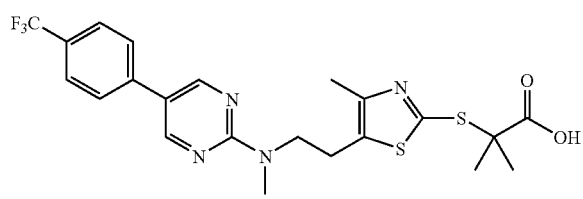

The title compound was obtained by an operation similar to that of Example 162-1 and using 2-{[5-(2-aminoethyl)-4-methyl-1,3-thiazol-2-yl]thio}-2-methylpropionic acid tert-butyl ester synthesized in Example 24 and 5-bromo-2-chloropyrimidine as starting materials, followed by operations similar to those of Example 162-2, Example 163-1 and Example 164-2 and using [4-(trifluoromethyl)phenyl]boric acid.

$^1$H-NMR (DMSO-d$_6$, 300 MHz) δ: 1.43 (6H, s), 2.28 (3H, s), 3.06-3.12 (5H, m), 3.83-3.89 (2H, m), 7.78 (2H, d, J=8.4 Hz), 7.89 (2H, d, J=8.4 Hz), 8.79 (2H, s).

MS: 497 (M$^+$+1).

Example 211

2-methyl-2-({4-methyl-5-[2-({5-[4-(trifluoromethoxy)phenyl]pyrimidin-2-yl}amino)ethyl]-1,3-thiazol-2-yl}thio)propionic acid hydrochloride

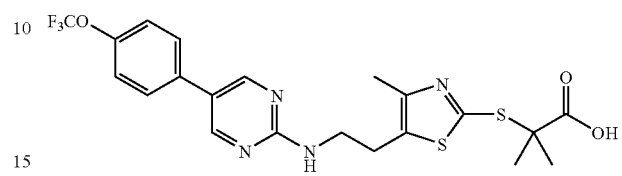

The title compound was obtained by an operation similar to that of Example 162-1 and using 2-{[5-(2-aminoethyl)-4-methyl-1,3-thiazol-2-yl]thio}-2-methylpropionic acid tert-butyl ester synthesized in Example 24 and 5-bromo-2-chloropyrimidine as starting materials, followed by operations similar to those of Example 162-2 and Example 164-2 and using [4-(trifluoromethoxy)phenyl]boric acid.

$^1$H-NMR (DMSO-d$_6$, 300 MHz) δ: 1.46 (6H, s), 2.29 (3H, s), 3.04 (2H, t, J=6.9 Hz), 3.52-3.58 (2H, m), 7.44 (2H, d, J=8.3 Hz), 7.78 (2H, d, J=8.3 Hz), 8.73 (2H, s).

MS: 499 (M$^+$+1).

Example 212

2-methyl-2-({4-methyl-5-[2-(methyl{5-[4-(trifluoromethoxy)phenyl]pyrimidin-2-yl}amino)ethyl]-1,3-thiazol-2-yl}thio)propionic acid hydrochloride

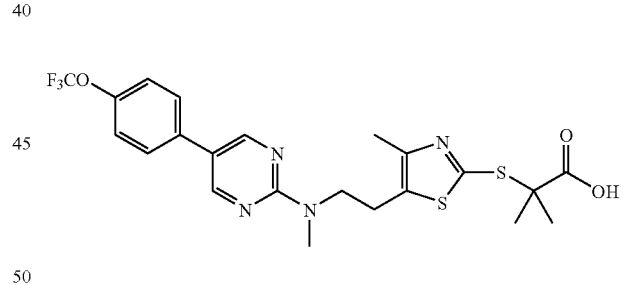

The title compound was obtained by an operation similar to that of Example 162-1 and using 2-{[5-(2-aminoethyl)-4-methyl-1,3-thiazol-2-yl]thio}-2-methylpropionic acid tert-butyl ester synthesized in Example 24 and 5-bromo-2-chloropyrimidine as starting materials, followed by operations similar to those of Example 162-2, Example 163-1 and Example 164-2 and using [4-(trifluoromethoxy)phenyl]boric acid.

$^1$H-NMR (DMSO-d$_6$, 300 MHz) δ: 1.43 (6H, s), 2.27 (3H, s), 3.05-3.10 (5H, m), 3.80-3.86 (2H, m), 7.43 (2H, d, J=8.7 Hz), 7.77 (2H, d, J=8.7 Hz), 8.73 (2H, s).

MS: 513 (M$^+$+1).

Example 213

2-methyl-2-({4-[2-({6-[4-(trifluoromethoxy)phenyl]pyridazin-3-yl}amino)ethyl]-1,3-thiazol-2-yl}thio)propionic acid

Example 213-1

2-[(4-{2-[(6-chloropyridazin-3-yl)amino]ethyl}-1,3-thiazol-2-yl)thio]-2-methylpropionic acid tert-butyl ester

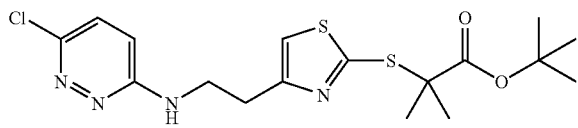

2-{[4-(2-Aminoethyl)-1,3-thiazol-2-yl]thio}-2-methylpropionic acid tert-butyl ester (5.0 g) synthesized in Example 7 and 3,6-dichloropyridazine (4.92 g) were dissolved in N-methylpyrrolidone (25 mL), diisopropylethylamine (4.27 g) was added, and the mixture was heated at 130° C. with stirring for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1 to 1:1) to give the title compound (5.5 g) as a white solid.

$^1$H-NMR (CDCl$_3$, 300 MHz) δ: 1.42 (9H, s), 1.60 (6H, s), 3.04 (2H, t, J=6.0 Hz), 3.80-3.86 (2H, m), 5.76 (1H, brs), 6.94-6.97 (2H, m), 7.09 (1H, d, J=9.0 Hz).

Example 213-2

2-methyl-2-({4-[2-({6-[4-(trifluoromethoxy)phenyl]pyridazin-3-yl}amino)ethyl]-1,3-thiazol-2-yl}thio)propionic acid tert-butyl ester

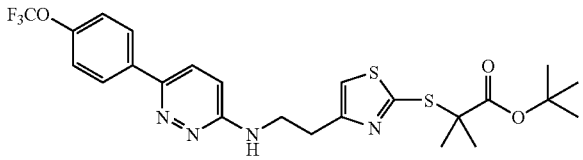

Under nitrogen atmosphere, 2-[(4-{2-[(6-chloropyridazin-3-yl)amino]ethyl}-1,3-thiazol-2-yl)thio]-2-methylpropionic acid tert-butyl ester (500 mg) synthesized in Example 213-1 and 4-trifluoromethoxyphenylboric acid (300 mg) were dissolved in dioxane (6 mL) and 2 mol/L sodium carbonate (3 mL), tetrakis(triphenylphosphine)palladium (70 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:2) to give the title compound (520 mg).

$^1$H-NMR (CDCl$_3$, 300 MHz) δ: 1.44 (9H, s), 1.62 (6H, s), 3.11 (2H, t, J=6.0 Hz), 3.90-3.96 (2H, m), 5.81 (1H, brs), 6.97 (1H, s), 7.07 (1H, d, J=9.3 Hz), 7.30-7.32 (2H, m), 7.55 (1H, d, J=9.3 Hz), 7.97-8.00 (2H, m).

Example 213-3

2-methyl-2-({4-[2-({6-[4-(trifluoromethoxy)phenyl]pyridazin-3-yl}amino)ethyl]-1,3-thiazol-2-yl}thio)propionic acid

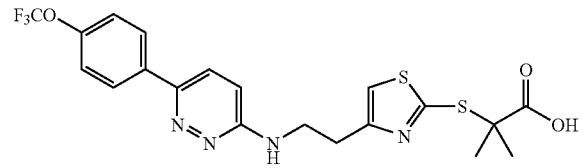

2-Methyl-2-({4-[2-({6-[4-(trifluoromethoxy)phenyl]pyridazin-3-yl}amino)ethyl]-1,3-thiazol-2-yl}thio)propionic acid tert-butyl ester (520 mg) obtained in Example 213-2 was dissolved in dichloromethane (2 mL), trifluoroacetic acid (2 mL) was added, and the mixture was stirred at room temperature for 12 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (233 mg) as a white amorphous.

$^1$H-NMR (CDCl$_3$, 300 MHz) δ: 1.70 (6H, s), 3.08 (2H, t, J=5.9 Hz), 3.54 (2H, brs), 6.96 (1H, d, J=9.4 Hz), 7.03 (1H, s), 7.27-7.31 (2H, m), 7.59 (1H, brs), 7.70 (1H, d, J=9.4 Hz), 7.91-7.95 (2H, m).

MS: 485 (M$^+$+1).

Example 214

2-methyl-2-({4-[2-(methyl{6-[4-(trifluoromethoxy)phenyl]pyridazin-3-yl}amino)ethyl]-1,3-thiazol-2-yl}thio)propionic acid

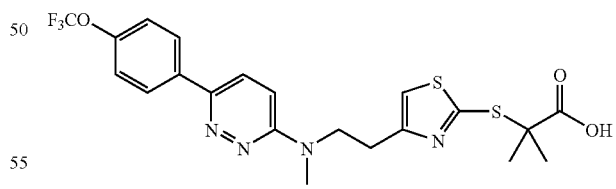

The title compound was obtained using 2-methyl-2-({4-[2-({6-[4-(trifluoromethoxy)phenyl]pyridazin-3-yl}amino)ethyl]-1,3-thiazol-2-yl}thio)propionic acid tert-butyl ester synthesized in Example 213-2 as a starting material and by an operation similar to that of Example 163.

$^1$H-NMR (CDCl$_3$, 300 MHz) δ: 1.64 (6H, s), 3.12 (3H, s), 3.18 (2H, t, J=6.9 Hz), 4.11 (2H, t, J=6.9 Hz), 6.86 (1H, d, J=9.3 Hz), 7.02 (1H, s), 7.29-7.32 (2H, m), 7.62 (1H, d, J=9.3 Hz), 7.99-8.02 (2H, m).

MS: 499 (M$^+$+1).

Example 215

2-{[4-(2-{[6-(4-fluorophenyl)pyridazin-3-yl]amino}ethyl)-1,3-thiazol-2-yl]thio}-2-methylpropionic acid

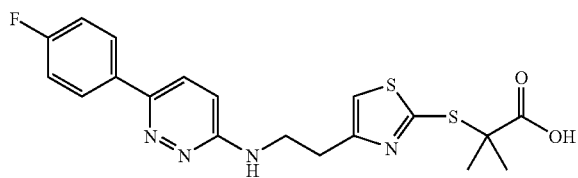

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-fluorophenylboric acid as starting materials and by operations similar to those of Example 213-2 and Example 213-3.

$^1$H-NMR (CDCl$_3$, 300 MHz) δ: 1.70 (6H, s), 3.07 (2H, t, J=5.7 Hz), 3.54 (2H, brs), 6.97 (1H, d, J=9.5 Hz), 7.03 (1H, s), 7.11-7.17 (2H, m), 7.62 (1H, brs), 7.69 (1H, d, J=9.5 Hz), 7.86-7.91 (2H, m).

MS: 419 (M$^+$+1).

Example 216

2-{[4-(2-{[6-(4-chlorophenyl)pyridazin-3-yl]amino}ethyl)-1,3-thiazol-2-yl]thio}-2-methylpropionic acid

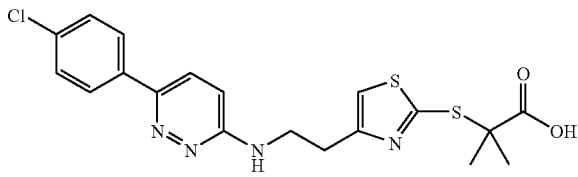

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-chlorophenylboric acid as starting materials and by operations similar to those of Example 213-2 and Example 213-3.

$^1$H-NMR (CDCl$_3$, 300 MHz) δ: 1.69 (6H, s), 3.07 (2H, t, J=6.0 Hz), 3.57-3.61 (2H, m), 7.03 (1H, s), 7.09 (1H, d, J=9.6 Hz), 7.39-7.43 (2H, m), 7.75 (1H, d, J=9.6 Hz), 7.79-7.82 (2H, m).

MS: 435 (M$^+$+1).

Example 217

2-[(4-{2-[[6-(4-chlorophenyl)pyridazin-3-yl](methyl)amino]ethyl}-1,3-thiazol-2-yl)thio]-2-methylpropionic acid

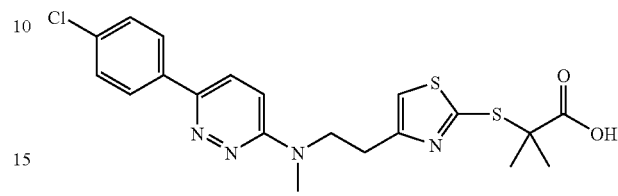

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-chlorophenylboric acid as starting materials and by operations similar to those of Example 213-2 and Example 214.

$^1$H-NMR (CDCl$_3$, 300 MHz) δ: 1.64 (6H, s), 3.12 (3H, s), 3.18 (2H, t, J=6.6 Hz), 4.11 (2H, t, J=6.6 Hz), 6.86 (1H, d, J=9.6 Hz), 7.02 (1H, s), 7.42-7.45 (2H, m), 7.62 (1H, d, J=9.6 Hz), 7.91-7.93 (2H, m).

MS: 449 (M$^+$+1).

Example 218

2-methyl-2-({4-[2-({6-[4-(trifluoromethyl)phenyl]pyridazin-3-yl}amino)ethyl]-1,3-thiazol-2-yl}thio)propionic acid

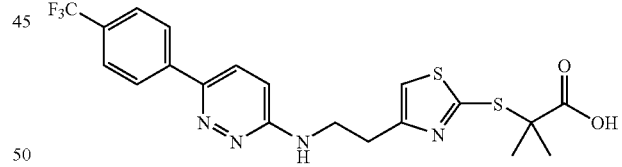

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-(trifluoromethyl)phenylboric acid as starting materials and by operations similar to those of Example 213-2 and Example 213-3.

$^1$H-NMR (CDCl$_3$, 300 MHz) δ: 1.69 (6H, s), 3.11 (2H, t, J=6.0 Hz), 3.61-3.65 (2H, m), 7.06 (1H, s), 7.12 (1H, d, J=9.6 Hz), 7.71 (2H, d, J=8.4 Hz), 7.84 (1H, d, J=9.6 Hz), 8.01 (2H, d, J=8.4 Hz).

MS: 469 (M$^+$+1).

Example 219

2-methyl-2-({4-[2-(methyl{6-[4-(trifluoromethyl)phenyl]pyridazin-3-yl}amino)ethyl]-1,3-thiazol-2-yl}thio)propionic acid

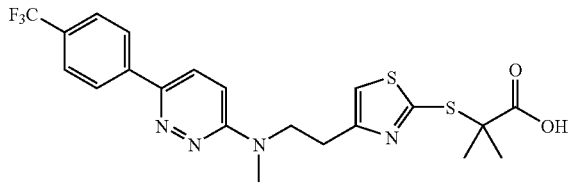

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-(trifluoromethyl)phenylboric acid as starting materials and by operations similar to those of Example 213-2 and Example 214.

$^1$H-NMR (CDCl$_3$, 300 MHz) δ: 1.64 (6H, s), 3.14 (3H, s), 3.19 (2H, t, J=6.9 Hz), 4.13 (2H, t, J=6.9 Hz), 6.84 (1H, d, J=9.3 Hz), 7.03 (1H, s), 7.67-7.74 (3H, m), 8.10 (2H, d, J=7.8 Hz).

MS: 483 (M$^+$+1).

Example 220

2-{[4-(2-{[6-(4-chloro-2-fluorophenyl)pyridazin-3-yl]amino}ethyl)-1,3-thiazol-2-yl]thio}-2-methylpropionic acid

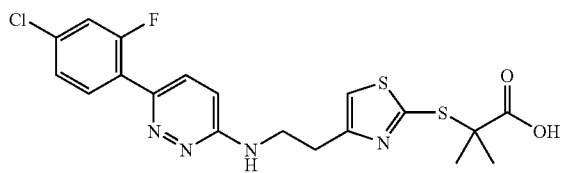

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-chloro-2-fluorophenylboric acid synthesized in Reference Example 3 as starting materials and by operations similar to those of Example 213-2 and Example 213-3.

$^1$H-NMR (CDCl$_3$, 300 MHz) δ: 1.70 (6H, s), 3.08 (2H, t, J=5.7 Hz), 3.52-3.57 (2H, m), 6.92 (1H, d, J=9.6 Hz), 7.04 (1H, s), 7.16-7.24 (2H, m), 7.58 (1H, brs), 7.75-7.79 (1H, m), 7.98-8.04 (1H, m).

MS: 453 (M$^+$+1).

Example 221

2-[(4-{2-[[6-(4-chloro-2-fluorophenyl)pyridazin-3-yl](methyl)amino]ethyl}-1,3-thiazol-2-yl)thio]-2-methylpropionic acid

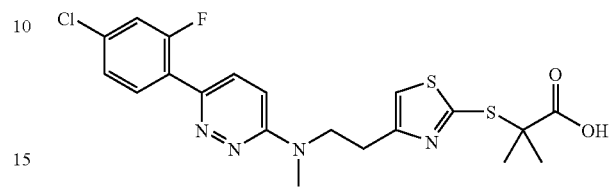

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 4-chloro-2-fluorophenylboric acid synthesized in Reference Example 3 as starting materials and by operations similar to those of Example 213-2 and Example 214.

$^1$H-NMR (CDCl$_3$, 300 MHz) δ: 1.64 (6H, s), 3.11 (3H, s), 3.18 (2H, t, J=6.9 Hz), 4.11 (2H, t, J=6.9 Hz), 6.83 (1H, d, J=9.6 Hz), 7.02 (1H, s), 7.17-7.28 (2H, m), 7.68-7.72 (1H, m), 8.06-8.11 (1H, m).

MS: 467 (M$^+$+1).

Example 222

2-{[4-(2-{[6-(2,4-dichlorophenyl)pyridazin-3-yl]amino}ethyl)-1,3-thiazol-2-yl]thio}-2-methylpropionic acid

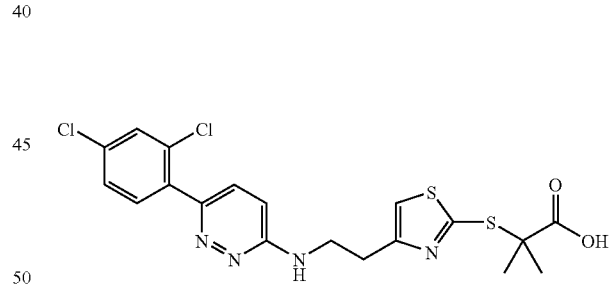

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 2,4-dichlorophenylboric acid as starting materials and by operations similar to those of Example 213-2 and Example 213-3.

$^1$H-NMR (CDCl$_3$, 300 MHz) δ: 1.69 (6H, s), 3.08 (2H, t, J=5.4 Hz), 3.52-3.57 (2H, m), 6.90-6.93 (1H, m), 7.05 (1H, s), 7.33-7.37 (1H, m), 7.48 (1H, d, J=1.8 Hz), 7.61-7.72 (2H, m).

MS: 469 (M$^+$+1).

Example 223

2-[(4-{2-[[6-(2,4-dichlorophenyl)pyridazin-3-yl](methyl)amino]ethyl}-1,3-thiazol-2-yl)thio]-2-methylpropionic acid

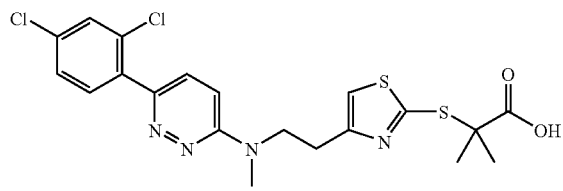

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 2,4-dichlorophenylboric acid as starting materials and by operations similar to those of Example 213-2 and Example 214.

$^1$H-NMR (CDCl$_3$, 300 MHz) δ: 1.64 (6H, s), 3.12 (3H, s), 3.18 (2H, t, J=6.9 Hz), 4.11 (2H, t, J=6.9 Hz), 6.82 (1H, d, J=9.6 Hz), 7.03 (1H, s), 7.36 (1H, dd, J=2.1, 8.4 Hz), 7.48 (1H, d, J=2.1 Hz), 7.63 (1H, d, J=9.6 Hz), 7.70 (1H, d, J=8.4 Hz).

MS: 483 (M$^+$+1).

Example 224

2-({4-[2-({6-[2-fluoro-4-(trifluoromethyl)phenyl]pyridazin-3-yl}amino)ethyl]-1,3-thiazol-2-yl}thio)-2-methylpropionic acid

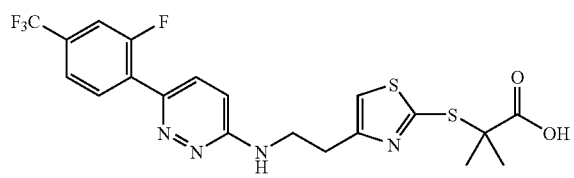

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 2-fluoro-4-(trifluoromethyl)phenylboric acid synthesized in the same manner as in Reference Example 3 from 4-bromo-3-fluorobenzotrifluoride as starting materials, and by operations similar to those of Example 213-2 and Example 213-3.

$^1$H-NMR (CDCl$_3$, 300 MHz) δ: 1.70 (6H, s), 3.09 (2H, t, J=5.0 Hz), 3.55-3.57 (2H, m), 6.93 (1H, d, J=9.8 Hz), 7.05 (1H, s), 7.42 (1H, d, J=11.4 Hz), 7.51-7.57 (2H, m), 7.82 (1H, d, J=9.8 Hz), 8.21 (1H, t, J=7.8 Hz).

MS: 487 (M$^+$+1).

Example 225

2-({4-[2-({6-[2-chloro-4-(trifluoromethyl)phenyl]pyridazin-3-yl}amino)ethyl]-1,3-thiazol-2-yl}thio)-2-methylpropionic acid

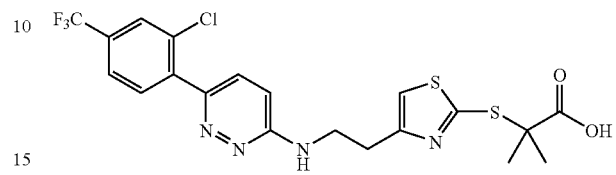

The title compound was obtained using 2-[(4-{2-[(6-chloropyridazin-3-yl)amino]ethyl}-1,3-thiazol-2-yl)thio]-2-methylpropionic acid tert-butyl ester synthesized in Example 213-1 and 2-chloro-4-(trifluoromethyl)phenylboric acid synthesized in the same manner as in Reference Example 3 from 3-chloro-4-iodobenzotrifluoride as starting materials, and by operations similar to those of Example 213-2 and Example 213-3.

$^1$H-NMR (CDCl$_3$, 300 MHz) δ: 1.69 (6H, s), 3.10 (2H, t, J=5.2 Hz), 3.54-3.59 (2H, m), 6.93 (1H, d, J=9.6 Hz), 7.06 (1H, s), 7.61-7.64 (2H, m), 7.72-7.76 (2H, m), 7.84 (1H, d, J=8.2 Hz).

MS: 503 (M$^+$+1).

Example 226

2-{[4-(2-{[5-(4-chlorophenyl)pyrazin-2-yl]amino}ethyl)-1,3-thiazol-2-yl]thio}-2-methylpropionic acid

Example 226-1

2-[(4-{2-[(5-bromopyrazin-2-yl)amino]ethyl}-1,3-thiazol-2-yl)thio]-2-methylpropionic acid tert-butyl ester

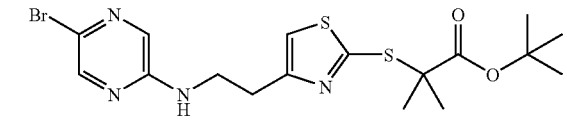

2-{[4-(2-Aminoethyl)-1,3-thiazol-2-yl]thio}-2-methylpropionic acid tert-butyl ester (12.1 g) synthesized in Example 7 and 2,5-bromopyrazine (9.5 g) were dissolved in N-methyl-2-pyrrolidone (10 mL), N,N-diisopropylethylamine (5.16 g) was added, and the mixture was stirred at 80° C. for 4 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1 to 2:1) to give the title compound (11.2 g) as a yellow oil.

$^1$H-NMR (CDCl$_3$, 300 MHz) δ: 1.42 (9H, s), 1.60 (6H, s), 3.00 (2H, t, J=6.2 Hz), 3.67-3.74 (2H, m), 5.77-5.80 (1H, m), 6.93 (1H, s), 7.89 (1H, s), 8.03 (1H, s).

Example 226-2

2-{[4-(2-{[5-(4-chlorophenyl)pyrazin-2-yl]amino}ethyl)-1,3-thiazol-2-yl]thio}-2-methylpropionic acid tert-butyl ester

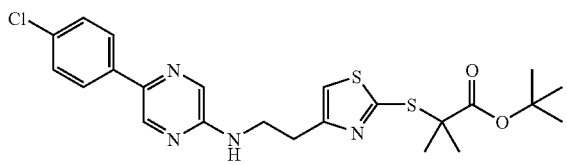

Under nitrogen atmosphere, 2-[(4-{2-[(5-bromopyrazin-2-yl)amino]ethyl}-1,3-thiazol-2-yl)thio]-2-methylpropionic acid tert-butyl ester (10.5 g) synthesized in Example 226-1 and 4-chlorophenylboric acid (5.36 g) were dissolved in dioxane (80 mL) and aqueous sodium carbonate solution (2 mol/L, 40 mL), tetrakis(triphenylphosphine)palladium (1.32 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (10.2 g) as a brown oil.

$^1$H-NMR (CDCl$_3$, 300 MHz) δ: 1.43 (9H, s), 1.62 (6H, s), 3.05 (2H, t, J=6.0 Hz), 3.76-3.82 (2H, m), 5.73-5.77 (1H, m), 6.96 (1H, s), 7.38 (2H, d, J=8.7 Hz), 7.79 (2H, d, J=8.7 Hz), 8.14 (1H, d, J=1.5 Hz), 8.40 (1H, d, J=1.5 Hz).

Example 226-3

2-{[4-(2-{[5-(4-chlorophenyl)pyrazin-2-yl]amino}ethyl)-1,3-thiazol-2-yl]thio}-2-methylpropionic acid

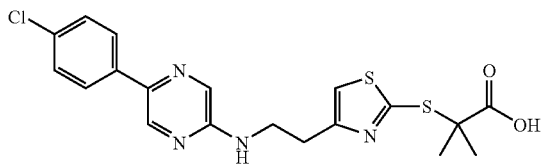

2-{[4-(2-{[5-(4-Chlorophenyl)pyrazin-2-yl]amino}ethyl)-1,3-thiazol-2-yl]thio}-2-methylpropionic acid tert-butyl ester (10 g) obtained in Example 226-2 was dissolved in dichloromethane (80 mL), trifluoroacetic acid (30 mL) was added, and the mixture was stirred at room temperature for 12 hr. The reaction mixture was concentrated under reduced pressure, ethyl acetate was added, and the mixture was washed (neutralized) with

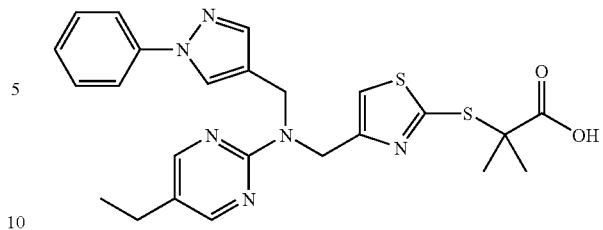

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 4-(chloromethyl)-1-phenyl-1H-pyrazole as starting materials and by an operation similar to that of Example 327.

$^1$H-NMR (CDCl$_3$, 300 MHz) δ: 1.29 (3H, t, J=7.5 Hz), 1.57 (6H, s), 2.64 (2H, q, J=7.5 Hz), 5.06 (2H, s), 5.17 (2H, s), 7.28-7.33 (1H, m), 7.42-7.48 (3H, m), 7.65-7.68 (3H, m), 8.24 (1H, s), 8.50 (2H, s).

MS: 495 (M$^+$+1).

Example 425

2-({4-[((5-ethylpyrimidin-2-yl){[1-(4-fluorophenyl)-1H-pyrazol-4-yl]methyl}amino)methyl]-1,3-thiazol-2-yl}thio)-2-methylpropionic acid hydrochloride

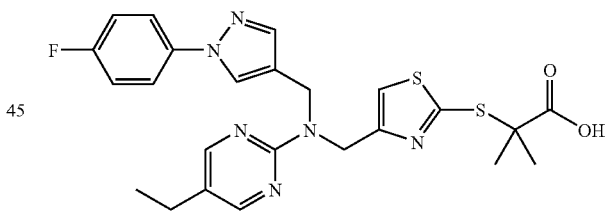

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 4-(chloromethyl)-1-(4-fluorophenyl)-1H-pyrazole synthesized in the same manner as in Reference Examples 16 to 18 as starting materials and by an operation similar to that of Example 327.

$^1$H-NMR (CDCl$_3$, 300 MHz) δ: 1.28 (3H, t, J=7.5 Hz), 1.57 (6H, s), 2.63 (2H, q, J=7.5 Hz), 5.03 (2H, s), 5.14 (2H, s), 7.09-7.16 (2H, m), 7.41 (1H, brs), 7.59-7.64 (3H, m), 8.13 (1H, brs), 8.47 (2H, s).

MS: 513 (M$^+$+1).

Example 426

2-{[4-({(5-ethylpyrimidin-2-yl)[(2-phenyl-1,3-oxazol-4-yl)methyl]amino}methyl)-1,3-thiazol-2-yl]thio}-2-methylpropionic acid hydrochloride

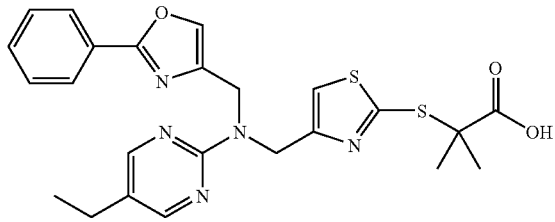

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 4-(chloromethyl)-2-phenyl-1,3-oxazole synthesized in Reference Example 26 as starting materials and by an operation similar to that of Example 327.

$^1$H-NMR (CDCl$_3$, 300 MHz) δ: 1.28 (3H, t, J=7.5 Hz), 1.58 (6H, s), 2.64 (2H, q, J=7.5 Hz), 5.19 (2H, s), 5.39 (2H, s), 7.47-7.53 (3H, m), 7.59 (1H, s), 8.08-8.12 (2H, m), 8.16 (1H, s), 8.49 (2H, s).

MS: 496 (M$^+$+1).

Example 427

2-({4-[((5-ethylpyrimidin-2-yl){[2-(4-fluorophenyl)-1,3-oxazol-4-yl]methyl}amino)methyl]-1,3-thiazol-2-yl}thio)-2-methylpropionic acid-hydrochloride

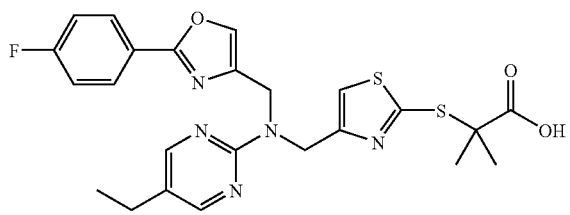

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 4-(chloromethyl)-2-(4-fluorophenyl)-1,3-oxazole synthesized in Reference Example 28 as starting materials and by an operation similar to that of Example 327.

$^1$H-NMR (CDCl$_3$, 300 MHz) δ: 1.28 (3H, t, J=7.5 Hz), 1.58 (6H, s), 2.64 (2H, q, J=7.5 Hz), 5.13 (2H, s), 5.37 (2H, s), 7.13-7.19 (2H, m), 7.52 (1H, s), 8.03-8.10 (3H, m), 8.49 (2H, s).

MS: 514 (M$^+$+1).

Example 428

2-[(4-{[[(6-chloroquinolin-2-yl)methyl](5-ethylpyrimidin-2-yl)amino]methyl}-1,3-thiazol-2-yl)thio]-2-methylpropionic acid hydrochloride

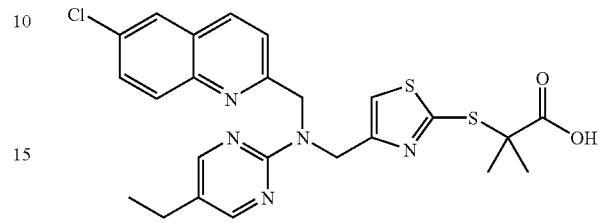

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 6-chloro-2-(chloromethyl)quinoline synthesized in Reference Example 35 as starting materials and by an operation similar to that of Example 327.

$^1$H-NMR (CDCl$_3$, 300 MHz) δ: 1.20 (3H, t, J=7.5 Hz), 1.59 (6H, s), 2.53 (2H, q, J=7.5 Hz), 5.30 (2H, s), 5.90 (2H, s), 7.73-7.78 (2H, m), 7.95 (1H, dd, J=2.1, 9.0 Hz), 8.02 (1H, d, J=2.1 Hz), 8.29 (2H, s), 8.55 (1H, d, J=8.7 Hz), 8.94 (1H, d, J=9.0 Hz).

MS: 514 (M$^+$+1).

Example 429

2-[(4-{[(5-ethylpyrimidin-2-yl)(2-phenoxyethyl)amino]methyl}-1,3-thiazol-2-yl)thio]-2-methylpropionic acid hydrochloride

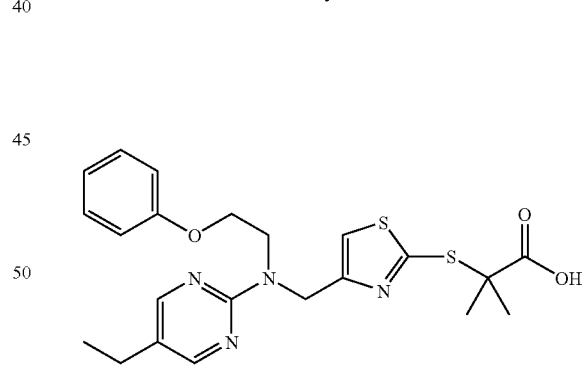

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and (2-bromoethoxy)benzene as starting materials and by an operation similar to that of Example 327.

$^1$H-NMR (DMSO-d$_6$, 300 MHz) δ: 1.13 (3H, t, J=7.5 Hz), 1.49 (6H, s), 2.45 (2H, q, J=7.5 Hz), 4.00 (2H, t, J=6.0 Hz), 4.17 (2H, t, J=6.0 Hz), 4.99 (2H, s), 6.89-6.93 (3H, m), 7.24-7.29 (2H, m), 7.47 (1H, s), 8.31 (2H, s).

MS: 459 (M$^+$+1).

Example 430

2-methyl-2-[(4-{2-[[(1-phenyl-1H-pyrazol-4-yl)methyl](5-propylpyrimidin-2-yl)amino]ethyl}-1,3-thiazol-2-yl)thio]propionic acid

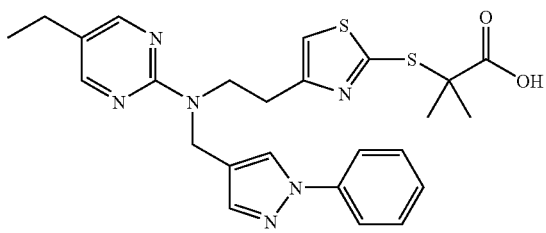

The title compound was obtained by an operation similar to that of Example 265-1 and using 2-{[4-(2-aminoethyl)-1,3-thiazol-2-yl]thio}-2-methylpropionic acid tert-butyl ester synthesized in Example 7 and 2-chloro-5-propylpyrimidine as starting materials, followed by an operation similar to that of Example 326.

$^1$H-NMR (CDCl$_3$, 300 MHz) δ: 0.96 (3H, t, J=7.5 Hz), 1.56-1.64 (8H, m), 2.43 (2H, t, J=7.2 Hz), 3.09 (2H, t, J=6.9 Hz), 3.94 (2H, t, J=6.9 Hz), 4.70 (2H, s), 6.96 (1H, s), 7.22-7.27 (1H, m), 7.39-7.45 (2H, m), 7.65-7.69 (3H, m), 7.96 (1H, s), 8.21 (2H, s).

MS: 523 (M$^+$+1).

Example 431

2-{[4-(2-{(5-isopropylpyrimidin-2-yl)[(1-phenyl-1H-pyrazol-4-yl)methyl]amino}ethyl)-1,3-thiazol-2-yl]thio}-2-methylpropionic acid

Reference Example 49

5-isopropyl-2-(methylsulfonyl)pyrimidine

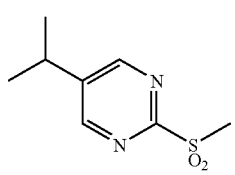

The title compound was obtained using 3-(dimethylamino)-2-isopropylacrylaldehyde as a starting material and by operations similar to those of Reference Examples 7 to 9.

$^1$H-NMR (CDCl$_3$, 300 MHz) δ: 1.38 (6H, d, J=6.9 Hz), 3.03-3.13 (1H, m), 3.36 (3H, s), 8.79 (2H, s).

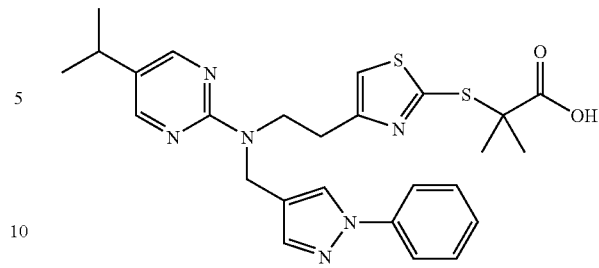

The title compound was obtained by an operation similar to that of Example 265-1 and using 2-{[4-(2-aminoethyl)-1,3-thiazol-2-yl]thio}-2-methylpropionic acid tert-butyl ester synthesized in Example 7 and 5-isopropyl-2-(methylsulfonyl)pyrimidine synthesized in Reference Example 49 as starting materials, followed by an operation similar to that of Example 326.

$^1$H-NMR (CDCl$_3$, 300 MHz) δ: 1.26 (6H, d, J=7.2 Hz), 1.62 (6H, s), 2.75-2.85 (1H, m), 3.10 (2H, t, J=6.9 Hz), 3.93 (2H, t, J=6.9 Hz), 4.71 (2H, s), 6.95 (1H, s), 7.22-7.26 (1H, m), 7.39-7.45 (2H, m), 7.66-7.69 (3H, m), 7.95 (1H, s), 8.25 (2H, s).

MS: 523 (M$^+$+1).

Example 432

2-{[4-(2-{(5-isobutylpyrimidin-2-yl)[(1-phenyl-1H-pyrazol-4-yl)methyl]amino}ethyl)-1,3-thiazol-2-yl]thio}-2-methylpropionic acid

Reference Example 50

5-isobutyl-2-(methylsulfonyl)pyrimidine

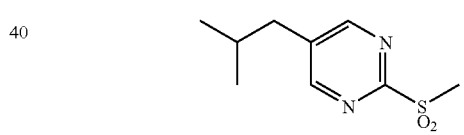

The title compound was obtained using 3-(dimethylamino)-2-isobutylacrylaldehyde as a starting material and by operations similar to those of Reference Examples 7 to 9.

$^1$H-NMR (CDCl$_3$, 300 MHz) δ: 0.97 (6H, d, J=6.3 Hz), 1.89-1.99 (1H, m), 2.60 (2H, d, J=6.9 Hz), 3.36 (3H, s), 8.71 (2H, s).

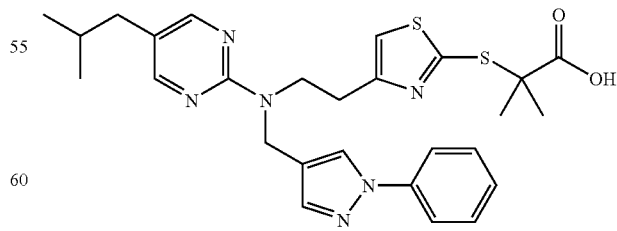

The title compound was obtained by an operation similar to that of Example 265-1 and using 2-{[4-(2-aminoethyl)-1,3-thiazol-2-yl]thio}-2-methylpropionic acid tert-butyl ester synthesized in Example 7 and 5-isobutyl-2-(methylsulfonyl)

pyrimidine synthesized in Reference Example 50 as starting materials, followed by an operation similar to that of Example 326.

¹H-NMR (CDCl₃, 300 MHz) δ: 0.92 (6H, d, J=6.6 Hz), 1.63 (6H, s), 1.73-1.83 (1H, m), 2.31 (2H, d, J=6.9 Hz), 3.09 (2H, t, J=6.9 Hz), 3.92 (2H, t, J=6.9 Hz), 4.71 (2H, s), 6.95 (1H, s), 7.22-7.27 (1H, m), 7.38-7.45 (2H, m), 7.64-7.69 (3H, m), 7.96 (1H, s), 8.17 (2H, s).

MS: 537 (M⁺+1).

Example 433

2-{[4-(2-{(4,6-dimethylpyrimidin-2-yl)[(1-phenyl-1H-pyrazol-4-yl)methyl]amino}ethyl)-1,3-thiazol-2-yl]thio}-2-methylpropionic acid

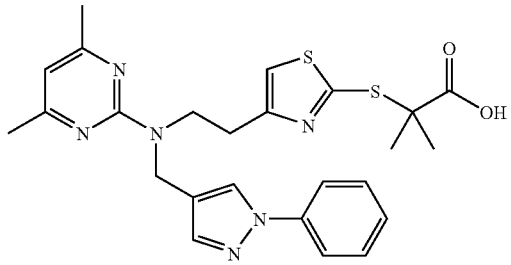

The title compound was obtained by an operation similar to that of Example 265-1 and using 2-{[4-(2-aminoethyl)-1,3-thiazol-2-yl]thio}-2-methylpropionic acid tert-butyl ester synthesized in Example 7 and 2-chloro-4,6-dimethylpyrimidine as starting materials, followed by an operation similar to that of Example 326.

¹H-NMR (CDCl₃, 300 MHz) δ: 1.62 (6H, s), 2.31 (6H, s), 3.10 (2H, t, J=7.0 Hz), 3.94 (2H, t, J=7.0 Hz), 4.71 (2H, s), 6.31 (1H, s), 6.95 (1H, s), 7.22-7.26 (1H, m), 7.43 (2H, t, J=7.8 Hz), 7.65-7.68 (3H, m), 7.95 (1H, s).

MS: 509 (M⁺+1).

Example 434

2-{[4-(2-{(4,6-dimethoxypyrimidin-2-yl)[(1-phenyl-1H-pyrazol-4-yl)methyl]amino}ethyl)-1,3-thiazol-2-yl]thio}-2-methylpropionic acid

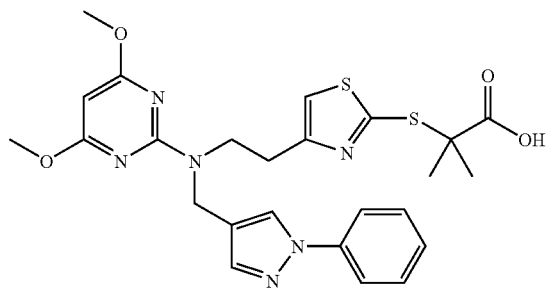

The title compound was obtained by an operation similar to that of Example 265-1 and using 2-{[4-(2-aminoethyl)-1,3-thiazol-2-yl]thio}-2-methylpropionic acid tert-butyl ester synthesized in Example 7 and 2-chloro-4,6-dimethoxypyrimidine as starting materials, followed by an operation similar to that of Example 326.

¹H-NMR (CDCl₃, 300 MHz) δ: 1.61 (6H, s), 3.11 (2H, t, J=6.9 Hz), 3.89-3.94 (8H, m), 4.70 (2H, s), 5.44 (1H, s), 6.93 (1H, s), 7.23-7.28 (1H, m), 7.40-7.46 (2H, m), 7.66-7.69 (3H, m), 7.96 (1H, s).

MS: 541 (M⁺+1).

Example 435

2-{[4-(2-{(5-bromopyrimidin-2-yl)[(1-phenyl-1H-pyrazol-4-yl)methyl]amino}ethyl)-1,3-thiazol-2-yl]thio}-2-methylpropionic acid hydrochloride

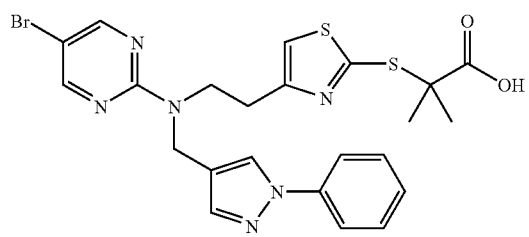

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(chloromethyl)-1-phenyl-1H-pyrazole synthesized in Reference Example 18 as starting materials and by an operation similar to that of Example 327.

¹H-NMR (DMSO-d₆, 300 MHz) δ: 1.50 (6H, s), 3.04 (2H, t, J=7.2 Hz), 3.89 (2H, t, J=7.2 Hz), 4.60 (2H, s), 7.28-7.31 (1H, m), 7.44-7.50 (3H, m), 7.68 (1H, s), 7.78 (2H, d, J=8.1 Hz), 8.40 (1H, s), 8.49 (2H, s).

MS: 561 (M⁺+1).

Example 436

2-[(4-{2-[(5-bromopyrimidin-2-yl)(2-phenoxyethyl)amino]ethyl}-1,3-thiazol-2-yl)thio]-2-methylpropionic acid

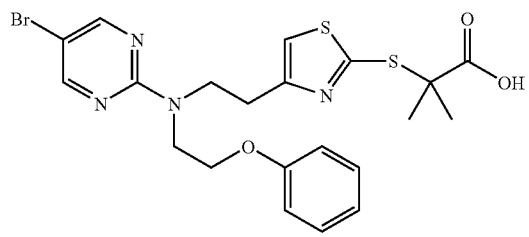

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and (2-bromoethoxy)benzene as starting materials and by an operation similar to that of Example 326.

¹H-NMR (CDCl₃, 300 MHz) δ: 1.66 (6H, s), 3.15 (2H, t, J=7.2 Hz), 3.88 (2H, t, J=5.4 Hz), 4.02 (2H, t, J=7.2 Hz), 4.15 (2H, t, J=5.4 Hz), 6.87-6.96 (4H, m), 7.24-7.29 (2H, m), 8.29 (2H, s).

MS: 525 (M⁺+1).

Example 437

2-[(4-{2-[(4-[(ethylamino)carbonyl]benzyl)(5-eth-ylpyrimidin-2-yl)amino]ethyl}-1,3-thiazol-2-yl)thio]-2-methylpropionic acid

Example 437-1

4-{[(2-{2-[(2-tert-butyl-1,1-dimethyl-2-oxoethyl)thio]-1,3-thiazol-4-yl}ethyl)(5-ethylpyrimidin-2-yl)amino]methyl}benzoic acid methyl ester

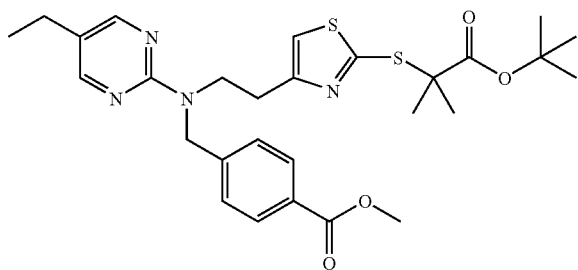

2-[(4-{2-[(5-Ethylpyrimidin-2-yl)amino]ethyl}-1,3-thiazol-2-yl)thio]-2-methylpropionic acid tert-butyl ester (3.0 g) synthesized in Example 265-1 and 4-(bromomethyl)benzoic acid methyl ester (2.0 g) were dissolved in N,N-dimethylformamide (37 mL), potassium tert-butoxide (0.91 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (2.2 g) as a colorless oil.

$^1$H-NMR (CDCl$_3$, 300 MHz) δ: 1.21 (3H, t, J=7.5 Hz), 1.42 (9H, s), 1.56 (6H, s), 2.48 (2H, q, J=7.5 Hz), 3.10 (2H, t, J=7.2 Hz), 3.89-3.96 (5H, m), 4.80 (2H, s), 6.99 (1H, s), 7.25-7.27 (2H, m), 7.92-7.95 (2H, m), 8.19 (2H, s).

Example 437-2

4-{[(2-{2-[(2-tert-butyl-1,1-dimethyl-2-oxoethyl)thio]-1,3-thiazol-4-yl}ethyl)(5-ethylpyrimidin-2-yl)amino]methyl}benzoic acid

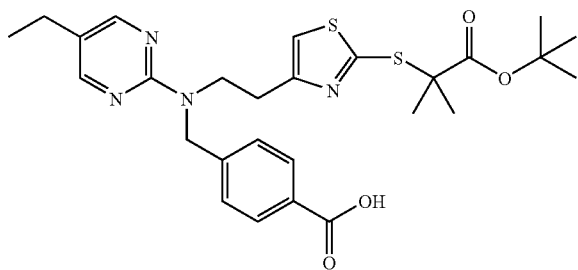

4-{[(2-{2-[(2-tert-Butyl-1,1-dimethyl-2-oxoethyl)thio]-1,3-thiazol-4-yl}ethyl)(5-ethylpyrimidin-2-yl)amino]methyl}benzoic acid methyl ester (2.2 g) synthesized in Example 437-1 was dissolved in methanol (50 mL) and tetrahydrofuran (50 mL), 1N aqueous sodium hydroxide solution (16 ml) was added, and the mixture was stirred at 60° C. for 4 hr. Aqueous 10% citric acid solution was added, and the mixture was extracted with chloroform. The insoluble material was filtered off, and the filtrate was washed with water and dried over anhydrous sodium sulfate. The solvent was evaporated under reduced pressure to give the title compound (2.0 g) as an oil.

$^1$H-NMR (CDCl$_3$, 300 MHz) δ: 1.21 (3H, t, J=7.5 Hz), 1.42 (9H, s), 1.56 (6H, s), 2.49 (2H, q, J=7.5 Hz), 3.12 (2H, t, J=7.2 Hz), 3.95 (2H, t, J=7.2 Hz), 4.82 (2H, s), 7.01 (1H, s), 7.26-7.29 (2H, m), 7.96-7.99 (2H, m), 8.21 (2H, s).

Example 437-3

2-[(4-{2-[{4-[(ethylamino)carbonyl]benzyl}(5-eth-ylpyrimidin-2-yl)amino]ethyl}-1,3-thiazol-2-yl)thio]-2-methylpropionic acid tert-butyl ester

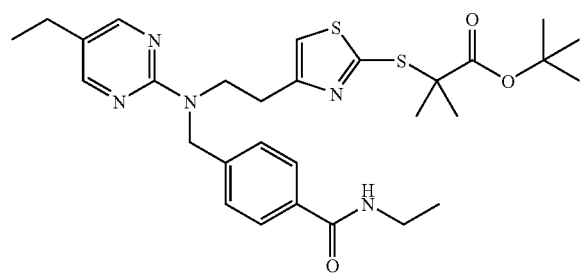

4-{[(2-{2-[(2-tert-Butoxy-1,1-dimethyl-2-oxoethyl)thio]-1,3-thiazol-4-yl}ethyl)(5-ethylpyrimidin-2-yl)amino]methyl}benzoic acid (261 mg) synthesized in Example 437-2 and ethylamine hydrochloride (47 mg) were dissolved in N,N-dimethylformamide (2.5 mL), triethylamine (80 μL), N-(3-dimethylaminopropyl)-N'-ethylcarbodiimide (EDC) hydrochloride (110 mg) and 1-hydroxybenztriazole (HOBt) monohydrate (86 mg) were successively added thereto, and the mixture was stirred at room temperature for 6 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=1:1) to give the title compound (268 mg) as a white solid.

$^1$H-NMR (CDCl$_3$, 300 MHz) δ: 1.19-1.26 (6H, m), 1.42 (9H, s), 1.56 (6H, s), 2.48 (2H, q, J=7.5 Hz), 3.09 (2H, t, J=7.2

Hz), 3.46-3.53 (2H, m), 3.93 (2H, t, J=7.2 Hz), 4.79 (2H, s), 6.05 (1H, brs), 6.99 (1H, s), 7.24-7.26 (2H, m), 7.65-7.67 (2H, m), 8.19 (2H, s).

Example 437-4

2-[(4-{2-[{4-[(ethylamino)carbonyl]benzyl}(5-ethylpyrimidin-2-yl)amino]ethyl}-1,3-thiazol-2-yl)thio]-2-methylpropionic acid

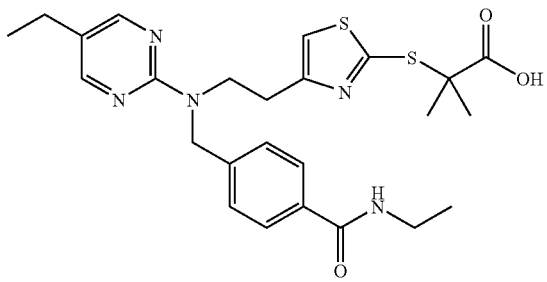

2-[(4-{2-[{4-[(Ethylamino)carbonyl]benzyl}(5-ethylpyrimidin-2-yl)amino]ethyl}-1,3-thiazol-2-yl)thio]-2-methylpropionic acid tert-butyl ester (268 mg) synthesized in Example 437-3 was dissolved in dichloromethane (2.0 mL), trifluoroacetic acid (2.0 mL) was added, and the mixture was stirred at room temperature for 20 hr. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1) to give the title compound (159 mg) as a white amorphous solid.

$^{1}$H-NMR (CDCl$_{3}$, 300 MHz) δ: 1.19-1.27 (6H, m), 1.61 (6H, s), 2.49 (2H, q, J=7.5 Hz), 3.01 (2H, t, J=7.2 Hz), 3.44-3.53 (2H, m), 3.88 (2H, t, J=7.2 Hz), 4.87 (2H, s), 6.17 (1H, brs), 6.93 (1H, s), 7.27-7.30 (2H, m), 7.66-7.68 (2H, m), 8.21 (2H, s).

MS: 514 (M$^{+}$+1).

Example 438

2-{[4-(2-{(5-ethylpyrimidin-2-yl)[4-(pyrrolidin-1-ylcarbonyl)benzyl]amino}ethyl)-1,3-thiazol-2-yl]thio}-2-methylpropionic acid

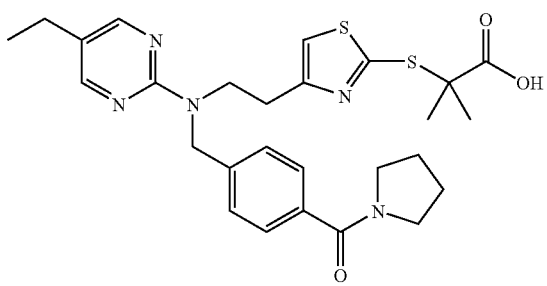

The title compound was obtained using 4-{[(2-{2-[(2-tert-butoxy-1,1-dimethyl-2-oxoethyl)thio]-1,3-thiazol-4-yl}ethyl)(5-ethylpyrimidin-2-yl)amino]methyl}benzoic acid synthesized in Example 437-2 and pyrrolidine as starting materials and by operations similar to those of Example 437-3 and Example 437-4.

$^{1}$H-NMR (CDCl$_{3}$, 300 MHz) δ: 1.22 (3H, t, J=7.5 Hz), 1.62 (6H, s), 1.84-1.98 (4H, m), 2.49 (2H, q, J=7.5 Hz), 3.01 (2H, t, J=7.2 Hz), 3.42 (2H, t, J=6.6 Hz), 3.64 (2H, t, J=6.6 Hz), 3.90 (2H, t, J=7.2 Hz), 4.86 (2H, s), 6.93 (1H, s), 7.24-7.26 (2H, m), 7.44-7.46 (2H, m), 8.21 (2H, s).

MS: 540 (M$^{+}$+1).

Example 439

2-{[4-(2-{(5-ethylpyrimidin-2-yl)[4-(propionylamino)benzyl]amino}ethyl)-1,3-thiazol-2-yl]thio}-2-methylpropionic acid hydrochloride Example 439-1

2-[(4-{2-[{4-[(tert-butoxycarbonyl)amino]benzyl}(5-ethylpyrimidin-2-yl)amino]ethyl}-1,3-thiazol-2-yl)thio]-2-methylpropionic acid tert-butyl ester

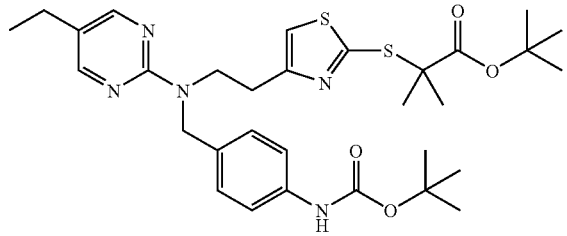

4-{[(2-{2-[(2-tert-Butyl-1,1-dimethyl-2-oxoethyl)thio]-1,3-thiazol-4-yl}ethyl)(5-ethylpyrimidin-2-yl)amino]methyl}benzoic acid (2.2 g) synthesized in Example 437-2 was dissolved in tert-butanol (20 mL), triethylamine (0.85 mL) and diphenylphosphinoazide (1.31 g) were successively added thereto, and the mixture was heated under reflux for 2 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1 to 3:1) to give the title compound (1.4 g) as a colorless oil.

$^{1}$H-NMR (CDCl$_{3}$, 300 MHz) δ: 1.20 (3H, t, J=7.5 Hz), 1.42 (9H, s), 1.50 (9H, s), 1.56 (6H, s), 2.47 (2H, q, J=7.5 Hz), 3.07

(2H, t, J=7.2 Hz), 3.89 (2H, t, J=7.2 Hz), 4.71 (2H, s), 6.39 (1H, brs), 6.96 (1H, s), 7.13-7.16 (2H, m), 7.23-7.26 (2H, m), 8.18 (2H, s).

Example 439-2

2-[(4-{2-[(4-aminobenzyl)(5-ethylpyrimidin-2-yl)amino]ethyl}-1,3-thiazol-2-yl)thio]-2-methylpropionic acid tert-butyl ester

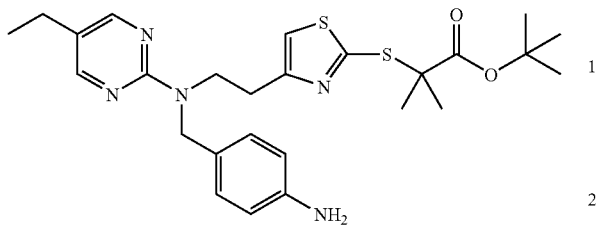

2-[(4-{2-[{4-[(tert-Butoxycarbonyl)amino]benzyl}(5-ethylpyrimidin-2-yl)amino]ethyl}-1,3-thiazol-2-yl)thio]-2-methylpropionic acid tert-butyl ester (1.2 g) synthesized in Example 439-1 was dissolved in dichloromethane (20 mL), p-toluenesulfonic acid monohydrate (3.64 g) was added thereto by small portions at room temperature. After 2.5 hr, the mixture was diluted with dichloromethane, washed successively with saturated aqueous sodium hydrogen carbonate solution and saturated brine, and dried over anhydrous sodium sulfate. The solvent was evaporated under reduced pressure, and the residue was purified by silica gel chromatography (elution solvent; hexane:ethyl acetate=3:1 to 1:1) to give the title compound (0.78 g) as a colorless oil.

$^1$H-NMR (CDCl$_3$, 300 MHz) δ: 1.20 (3H, t, J=7.5 Hz), 1.43 (9H, s), 1.57 (6H, s), 2.47 (2H, q, J=7.5 Hz), 3.06 (2H, t, J=7.5 Hz), 3.87 (2H, t, J=7.5 Hz), 4.66 (2H, s), 6.58-6.61 (2H, m), 6.97 (1H, s), 7.02-7.05 (2H, m), 8.18 (2H, s).

Example 439-3

2-{[4-(2-{(5-ethylpyrimidin-2-yl)[4-(propionylamino)benzyl]amino}ethyl)-1,3-thiazol-2-yl]thio}-2-methylpropionic acid tert-butyl ester

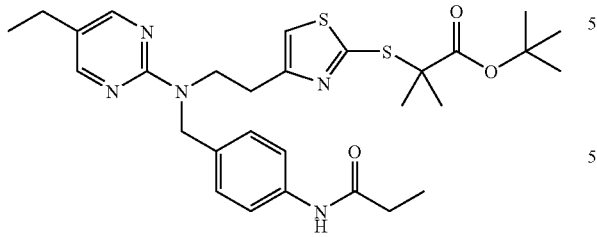

2-[(4-{2-[(4-Aminobenzyl)(5-ethylpyrimidin-2-yl)amino]ethyl}-1,3-thiazol-2-yl)thio]-2-methylpropionic acid tert-butyl ester (120 mg) synthesized in Example 439-2 was dissolved in tetrahydrofuran (2.5 mL), triethylamine (40 mL) and propionyl chloride (22 μL) were added thereto, and the mixture was stirred at room temperature for 30 min. The reaction solution was concentrated under reduced pressure, the residue was directly purified by silica gel chromatography (elution solvent; hexane:ethyl acetate=1:1) to give the title compound (100 mg) as a colorless oil.

$^1$H-NMR (CDCl$_3$, 300 MHz) δ: 1.18-1.26 (6H, m), 1.43 (9H, s), 1.56 (6H, s), 2.37 (2H, q, J=7.5 Hz), 2.48 (2H, q, J=7.5 Hz), 3.08 (2H, t, J=7.5 Hz), 3.89 (2H, t, J=7.5 Hz), 4.72 (2H, s), 6.98 (1H, s), 7.06 (1H, brs), 7.16-7.19 (2H, m), 7.40-7.42 (2H, m), 8.18 (2H, s).

Example 439-4

2-{[4-(2-{(5-ethylpyrimidin-2-yl)[4-(propionylamino)benzyl]amino}ethyl)-1,3-thiazol-2-yl]thio}-2-methylpropionic acid hydrochloride

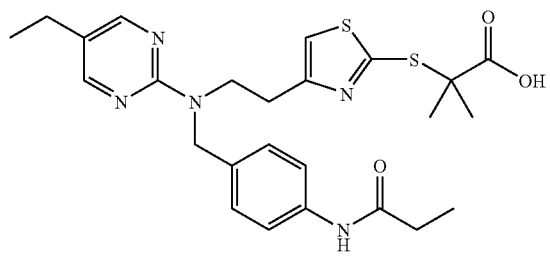

2-{[4-(2-{(5-Ethylpyrimidin-2-yl)[4-(propionylamino)benzyl]amino}ethyl)-1,3-thiazol-2-yl]thio}-2-methylpropionic acid tert-butyl ester (100 mg) synthesized in Example 439-3 was dissolved in formic acid (2.5 mL), 4 mol/L hydrochloric acid-ethyl acetate (0.5 mL) was added thereto, and the mixture was stirred at room temperature overnight. The reaction solution was evaporated under reduced pressure, and the residue was dried by heating at 60° C. to give the title compound (98 mg) as a white amorphous solid.

$^1$H-NMR (CDCl$_3$, 300 MHz) δ: 1.21 (3H, t, J=7.5 Hz), 1.30 (3H, t, J=7.5 Hz), 1.65 (6H, s), 2.46 (2H, q, J=7.5 Hz), 2.65 (2H, q, J=7.5 Hz), 3.28 (2H, brs), 4.03 (2H, brs), 5.06 (2H, brs), 7.23-7.26 (2H, m), 7.54-7.57 (2H, m), 8.04 (1H, s), 8.41 (2H, brs).

MS: 514 (M$^+$+1).

Example 440

2-[(4-{2-[{4-[(cyclopentylcarbonyl)amino]benzyl}(5-ethylpyrimidin-2-yl)amino]ethyl}-1,3-thiazol-2-yl)thio]-2-methylpropionic acid hydrochloride

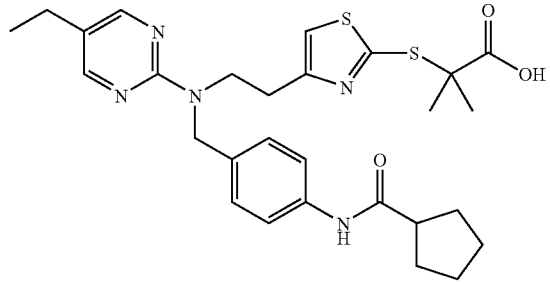

The title compound was obtained using 2-[(4-{2-[(4-aminobenzyl)(5-ethylpyrimidin-2-yl)amino]ethyl}-1,3-thiazol-2-yl)thio]-2-methylpropionic acid tert-butyl ester synthesized in Example 439-2 and cyclopentanecarbonyl chloride as starting materials and by operations similar to those of Example 439-3 and Example 439-4.

$^1$H-NMR (CDCl$_3$, 300 MHz) δ: 1.29 (3H, t, J=7.5 Hz), 1.63 (6H, s), 1.76-1.92 (8H, m), 2.64 (2H, q, J=7.5 Hz), 2.75-2.81 (1H, m), 3.21 (2H, brs), 4.05 (2H, brs), 5.03 (2H, s), 7.21-7.26 (2H, m), 7.54-7.57 (2H, m), 7.95 (2H, brs), 8.48 (2H, brs).

MS: 554 (M$^+$+1).

Example 441

2-{[4-(2-{(5-ethylpyrimidin-2-yl)[4-(propylamino) benzyl]amino}ethyl)-1,3-thiazol-2-yl]thio}-2-methylpropionic acid hydrochloride

Example 441-1

2-{[4-(2-{(5-ethylpyrimidin-2-yl)[4-(propylamino) benzyl]amino}ethyl)-1,3-thiazol-2-yl]thio}-2-methylpropionic acid tert-butyl ester

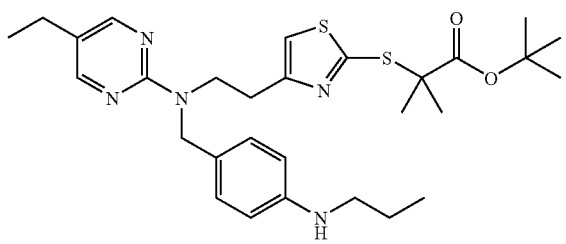

2-[(4-{2-[(4-Aminobenzyl)(5-ethylpyrimidin-2-yl) amino]ethyl}-1,3-thiazol-2-yl)thio]-2-methylpropionic acid tert-butyl ester (175 mg) synthesized in Example 439-2 was dissolved in dichloroethane (2.0 mL), propionylaldehyde (24 mg), acetic acid (20 μL) and triacetoxysodium tetrahydroborate (100 mg) were successively added thereto, and the mixture was stirred at room temperature for 2 hr. Saturated aqueous sodium hydrogen carbonate solution was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1) to give the title compound (68 mg) as a colorless oil.

$^1$H-NMR (CDCl$_3$, 300 MHz) δ: 0.98 (3H, t, J=7.5 Hz), 1.20 (3H, t, J=7.5 Hz), 1.43 (9H, s), 1.57-1.65 (8H, s), 2.47 (2H, q, J=7.5 Hz), 3.07 (2H, t, J=7.4 Hz), 3.87 (2H, t, J=7.4 Hz), 4.66 (2H, s), 6.50-6.54 (2H, m), 6.97 (1H, s), 7.04-7.07 (2H, m), 8.18 (2H, s).

Example 441-2

2-{[4-(2-{(5-ethylpyrimidin-2-yl)[4-(propylamino) benzyl]amino}ethyl)-1,3-thiazol-2-yl]thio}-2-methylpropionic acid hydrochloride

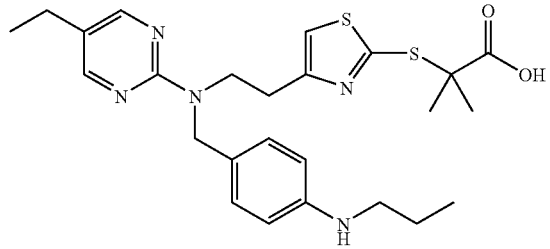

2-{[4-(2-{(5-Ethylpyrimidin-2-yl)[4-(propylamino)benzyl]amino}ethyl)-1,3-thiazol-2-yl]thio}-2-methylpropionic acid tert-butyl ester (68 mg) synthesized in Example 441-1 was dissolved in formic acid (2.5 mL), 4 mol/L hydrochloric acid-ethyl acetate (0.5 mL) was added thereto, and the mixture was stirred at room temperature overnight. The reaction solution was evaporated under reduced pressure, and the residue was dried by heating at 60° C. to give the title compound (77 mg) as a white amorphous solid.

$^1$H-NMR (CDCl$_3$, 300 MHz) δ: 0.98 (3H, t, J=7.2 Hz), 1.30 (3H, t, J=7.5 Hz), 1.69 (6H, s), 1.84-1.92 (2H, m), 2.67 (2H, q, J=7.5 Hz), 3.21-3.31 (6H, m), 5.10 (2H, brs), 7.30-7.32 (2H, m), 7.59-7.62 (2H, m), 8.07 (1H, s), 8.59 (2H, brs).

MS: 500 (M$^+$+1).

Example 442

2-[(4-{2-[heptyl(5-morpholin-4-ylpyrimidin-2-yl) amino]ethyl}-1,3-thiazol-2-yl)thio]-2-methylpropionic acid

Example 442-1

2-[(4-{2-[(5-bromopyrimidin-2-yl)(heptyl)amino] ethyl}-1,3-thiazol-2-yl)thio]-2-methylpropionic acid tert-butyl ester

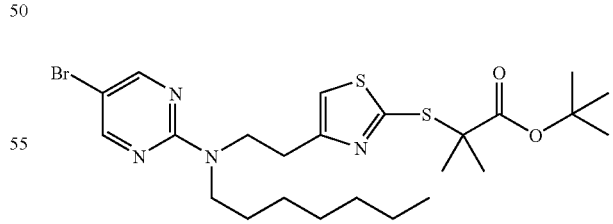

2-[(4-{2-[(5-Bromopyrimidin-2-yl)amino]ethyl}-1,3-thiazol-2-yl)thio]-2-methylpropionic acid tert-butyl ester (3.27 g) synthesized in Example 162-1 and heptyl iodide (1.77 g) were dissolved in N,N-dimethylformamide (36 mL), potassium tert-butoxide (0.80 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (2.80 g) as a colorless oil.

¹H-NMR (CDCl₃, 300 MHz) δ: 0.88 (3H, t, J=6.8 Hz), 1.24-1.29 (8H, m), 1.45 (9H, s), 1.53 (2H, brs), 1.58 (6H, s), 3.06 (2H, t, J=7.3 Hz), 3.40 (2H, t, J=7.3 Hz), 3.84 (2H, t, J=7.3 Hz), 7.01 (1H, s), 8.27 (2H, s).

Example 442-2

2-[(4-{2-[heptyl(5-morpholin-4-ylpyrimidin-2-yl)amino]ethyl}-1,3-thiazol-2-yl)thio]-2-methylpropionic acid tert-butyl ester

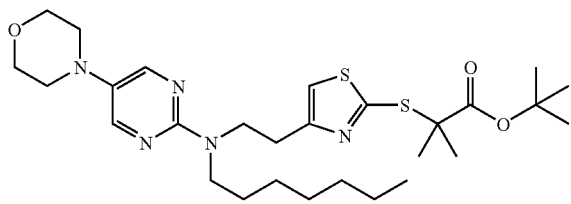

Tris(dibenzylideneacetone)dipalladium (45 mg), 2-(di-tert-butylphosphino)biphenyl (29 mg) and sodium tert-butoxide (104 mg) were added to a 20 mL screw cap test tube substituted with nitrogen, and a solution of 2-[(4-{2-[(5-bromopyrimidin-2-yl)(heptyl)amino]ethyl}-1,3-thiazol-2-yl)thio]-2-methylpropionic acid tert-butyl ester (550 mg) synthesized in Example 442-1 and morpholine (129 mg) in toluene (2.0 mL) was added thereto. The test tube was capped, and stirred at 110° C. for 8 hr. After cooling to room temperature, the solution was directly packed and purified by silica gel chromatography (elution solvent; hexane:ethyl acetate=3:1 to 2:1) to give the title compound (300 mg) as a colorless oil.

¹H-NMR (CDCl₃, 300 MHz) δ: 0.87 (3H, t, J=6.6 Hz), 1.24-1.28 (8H, m), 1.45 (9H, s), 1.51-1.53 (2H, m), 1.60 (6H, s), 2.97-3.00 (4H, m), 3.07 (2H, t, J=7.5 Hz), 3.42 (2H, t, J=7.5 Hz), 3.83-3.87 (6H, m), 7.01 (1H, s), 8.09 (2H, s).

Example 442-3

2-[(4-{2-[heptyl(5-morpholin-4-ylpyrimidin-2-yl)amino]ethyl}-1,3-thiazol-2-yl)thio]-2-methylpropionic acid

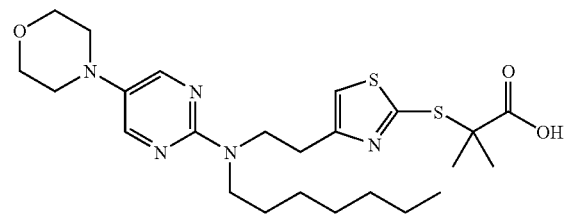

2-[(4-{2-[Heptyl(5-morpholin-4-ylpyrimidin-2-yl)amino]ethyl}-1,3-thiazol-2-yl)thio]-2-methylpropionic acid tert-butyl ester (710 mg) obtained in Example 442-2 was dissolved in dichloromethane (4 mL), trifluoroacetic acid (4 mL) was added, and the mixture was stirred at room temperature for 20 hr. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (300 mg) as a white solid.

¹H-NMR (CDCl₃, 300 MHz) δ: 0.87 (3H, t, J=6.6 Hz), 1.28 (8H, brs), 1.53 (2H, brs), 1.65 (6H, s), 2.98-3.01 (4H, m), 3.09 (2H, t, J=7.2 Hz), 3.45 (2H, t, J=7.2 Hz), 3.83-3.87 (6H, m), 6.95 (1H, s), 8.09 (2H, s).

MS: 508 (M⁺+1).

Example 443

2-{[4-(2-{heptyl[5-(4-methylpiperazin-1-yl)pyrimidin-2-yl]amino}ethyl)-1,3-thiazol-2-yl]thio}-2-methylpropionic acid trifluoroacetate

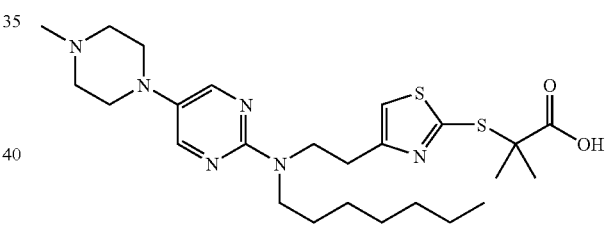

A compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and 1-methylpiperazine as starting materials and by an operation similar to that of Example 442-2 was treated with dichloromethane and trifluoroacetic acid. The reaction solution was concentrated under reduced pressure, and the residue was purified by high performance liquid chromatography (elution solvent; 0.05% trifluoroacetic acid-water:0.05% trifluoroacetic acid-acetonitrile=65:35 to 15:85) to give the title compound.

¹H-NMR (CDCl₃, 300 MHz) δ: 0.88 (3H, t, J=6.9 Hz), 1.27-1.37 (8H, m), 1.55 (2H, brs), 1.63 (6H, s), 2.18 (4H, m), 2.88 (3H, s), 3.10 (2H, t, J=6.9 Hz), 3.36 (4H, brs), 3.45-3.50 (2H, m), 3.89 (2H, t, J=6.9 Hz), 6.98 (1H, s), 8.17 (2H, s).

MS: 521 (M⁺+1).

Example 444

2-[(4-{2-[heptyl(5-pyrrolidin-1-ylpyrimidin-2-yl)amino]ethyl}-1,3-thiazol-2-yl)thio]-2-methylpropionic acid trifluoroacetate

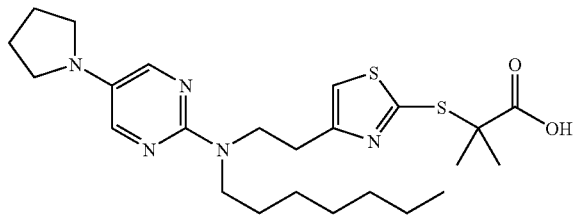

The compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and pyrrolidine as starting materials and by an operation similar to that of Example 442-2 was treated with dichloromethane and trifluoroacetic acid. The reaction solution was concentrated under reduced pressure, and the residue was purified by silica gel chromatography (elution solvent; chloroform:methanol=10:1) to give the title compound.

$^1$H-NMR (CDCl$_3$, 300 MHz) δ: 0.85-0.87 (3H, m), 1.27 (8H, brs), 1.52 (2H, brs), 1.65 (6H, s), 1.99-2.01 (4H, m), 3.09 (2H, t, J=6.9 Hz), 3.19-3.21 (4H, m), 3.42 (2H, t, J=7.5 Hz), 3.84 (2H, t, J=6.9 Hz), 6.95 (1H, s), 7.87 (2H, s).

MS: 492 (M$^+$+1).

Example 445

2-methyl-2-{[4-(2-{(5-morpholin-4-ylpyrimidin-2-yl)[(1-phenyl-1H-pyrazol-4-yl)methyl]amino}ethyl)-1,3-thiazol-2-yl]thio}propionic acid hydrochloride

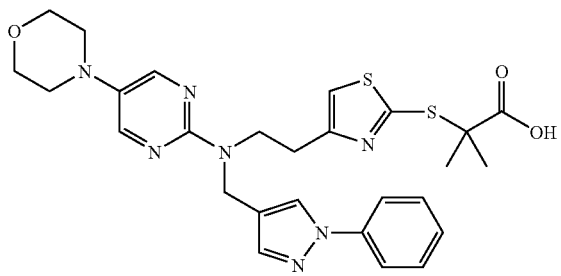

A compound obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(chloromethyl)-1-phenyl-1H-pyrazole synthesized in Reference Example 18 as starting materials and by an operation similar to that of Example 442 was dissolved in diethyl ether, and reacted with 4 mol/L hydrochloric acid-ethyl acetate to give the title compound.

$^1$H-NMR (DMSO-d$_6$, 300 MHz) δ: 1.50 (6H, s), 3.04 (2H, t, J=7.2 Hz), 3.14 (4H, brs), 3.79 (4H, brs), 3.90 (2H, t, J=7.2 Hz), 4.63 (2H, s), 7.25-7.30 (1H, m), 7.44-7.49 (3H, m), 7.66 (1H, s), 7.77-7.79 (2H, m), 8.40 (3H, brs).

MS: 566 (M$^+$+1).

Example 446

2-[(4-{2-[heptyl(3-methyl-1H-pyrazol-5-yl)amino]ethyl}-1,3-thiazol-2-yl)thio]-2-methylpropionic acid trifluoroacetate

Example 446-1

2-[(4-{2-[heptyl(3-methyl-1H-pyrazol-5-yl)amino]ethyl}-1,3-thiazol-2-yl)thio]-2-methylpropionic acid tert-butyl ester

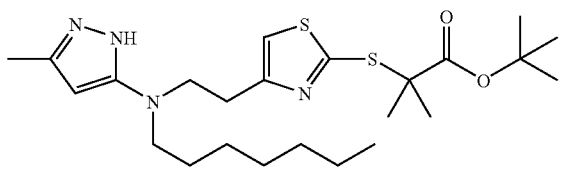

2-({4-[2-(Heptylamino)ethyl]-1,3-thiazol-2-yl}thio)-2-methylpropionic acid tert-butyl ester (3.41 g) synthesized in Example 303-2 was dissolved in N,N-dimethylformamide (43 mL), and diketene (0.75 g) was added dropwise under ice-cooling. After warming to room temperature, the mixture was stirred for one hour. The mixture was diluted with ethyl acetate. The organic layer was washed with saturated brine and dried over anhydrous sodium sulfate. The solvent was evaporated under reduced pressure to give 2-[(4-{2-[acetoacetyl(heptyl)amino]ethyl}-1,3-thiazol-2-yl)thio]-2-methylpropionic acid tert-butyl ester (3.4 g) as a colorless oil. The present compound was used in the next step without particular purification. The present compound (1.0 g) was dissolved in ethanol (10 mL), hydrazine monohydrate (0.103 g) was added thereto at room temperature, and the mixture was stirred overnight. The solvent was evaporated under reduced pressure, the residue was dissolved in tetrahydrofuran (10 mL), diphosphorus pentasulfide (0.459 g) and sodium carbonate (0.437 g) were added thereto, and the mixture was heated under reflux for 2 hr. The solvent was evaporated, and the residue was directly purified by silica gel chromatography (elution solvent; hexane:ethyl acetate=1:1 to 1:2) to give the title compound (0.54 g) as a colorless oil.

$^1$H-NMR (CDCl$_3$, 300 MHz) δ: 0.87 (3H, t, J=6.6 Hz), 1.26-1.32 (8H, m), 1.44 (9H, s), 1.52 (2H, brs), 1.58 (6H, s), 2.22 (3H, s), 3.02 (2H, t, J=7.5 Hz), 3.13 (2H, t, J=7.5 Hz), 3.55 (2H, t, J=7.5 Hz), 5.35 (1H, s), 7.05 (1H, s).

Example 446-2

2-[(4-{2-[heptyl(3-methyl-1H-pyrazol-5-yl)amino]ethyl}-1,3-thiazol-2-yl)thio]-2-methylpropionic acid trifluoroacetate

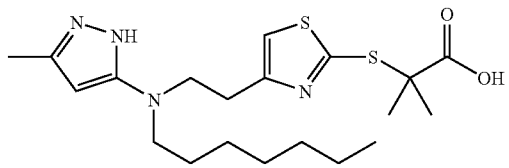

2-[(4-{2-[Heptyl(3-methyl-1H-pyrazol-5-yl)amino]ethyl}-1,3-thiazol-2-yl)thio]-2-methylpropionic acid tert-butyl ester (540 mg) synthesized in Example 446-1 was dissolved in dioxane (1.0 mL), hydrochloric acid-dioxane (4 mol/L, 4.0 mL) was added, and the mixture was stirred at room temperature for 12 hr. The reaction mixture was concentrated under reduced pressure, and the residue was purified by high performance liquid chromatography (elution solvent; 0.05% trifluoroacetic acid-water:0.05% trifluoroacetic acid-acetonitrile=85:15 to 40:60) to give the title compound (229 mg) as a white solid.

$^1$H-NMR (CDCl$_3$, 300 MHz) δ: 0.87-0.91 (3H, m), 1.29-1.31 (8H, m), 1.62 (8H, brs), 2.34 (3H, s), 2.99 (2H, t, J=7.7 Hz), 3.23 (2H, t, J=7.5 Hz), 3.56 (2H, t, J=7.7 Hz), 5.37 (1H, s), 7.06 (1H, s).

MS: 425 (M$^+$+1).

Example 447

2-[(4-{2-[(1,3-dimethyl-1H-pyrazol-5-yl)(heptyl)amino]ethyl}-1,3-thiazol-2-yl)thio]-2-methylpropionic acid

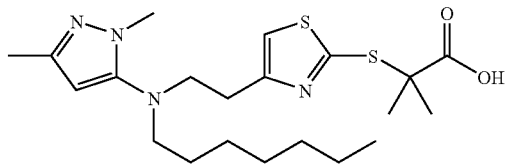

A compound obtained using 2-[(4-{2-[acetoacetyl(heptyl)amino]ethyl}-1,3-thiazol-2-yl)thio]-2-methylpropionic acid tert-butyl ester synthesized in Example 446-1 and methylhydrazine, and by an operation similar to that of Example 446 was purified by silica gel chromatography (elution solvent; chloroform:methanol=10:1) to give the title compound.

$^1$H-NMR (CDCl$_3$, 300 MHz) δ: 0.87 (3H, t, J=6.8 Hz), 1.22-1.27 (8H, m), 1.36-1.41 (2H, m), 1.64 (6H, s), 2.21 (3H, s), 2.81-2.88 (4H, m), 3.27 (2H, t, J=6.9 Hz), 3.51 (3H, s), 5.69 (1H, s), 6.84 (1H, s).

MS: 439 (M$^+$+1).

Example 448

2-[(4-{2-[[1-(4-fluorophenyl)-3-methyl-1H-pyrazol-5-yl](heptyl)amino]ethyl}-1,3-thiazol-2-yl)thio]-2-methylpropionic acid

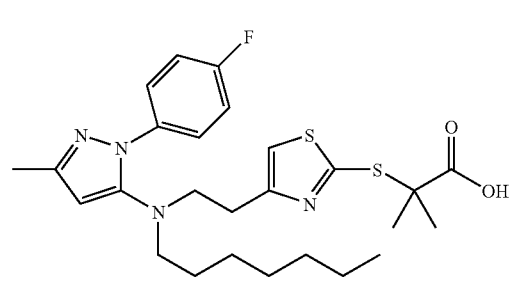

A compound obtained using 2-[(4-{2-[acetoacetyl(heptyl)amino]ethyl}-1,3-thiazol-2-yl)thio]-2-methylpropionic acid tert-butyl ester synthesized in Example 446-1, and (4-fluorophenyl)hydrazine hydrochloride and sodium acetate for neutralization, and by an operation similar to that of Example 446 was purified by silica gel chromatography (elution solvent; chloroform:methanol=10:1) to give the title compound.

$^1$H-NMR (CDCl$_3$, 300 MHz) δ: 0.86 (3H, t, J=7.2 Hz), 1.12-1.26 (8H, m), 1.37-1.41 (2H, m), 1.61 (6H, s), 2.27 (3H, s), 2.77 (2H, t, J=7.8 Hz), 2.91 (2H, t, J=7.2 Hz), 3.25 (2H, t, J=7.2 Hz), 5.77 (1H, s), 6.80 (1H, s), 7.00-7.06 (2H, m), 7.46-7.50 (2H, m).

MS: 519 (M$^+$+1).

Example 449

2-[(4-{2-[(3-ethyl-1H-pyrazol-5-yl)(heptyl)amino]ethyl}-1,3-thiazol-2-yl)thio]-2-methylpropionic acid trifluoroacetate

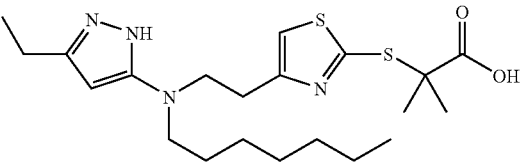

2-({4-[2-(Heptylamino)ethyl]-1,3-thiazol-2-yl}thio)-2-methylpropionic acid tert-butyl ester (3.0 g) synthesized in Example 303-2 and 3-keto-n-valeric acid methyl ester (1.46 g) were dissolved in xylene (10 mL), and the mixture was stirred at 135° C. for 8 hr. After cooling to room temperature, the solution was directly packed and purified by silica gel chromatography (elution solvent; hexane:ethyl acetate=1:1) to give 2-[(4-{2-[heptyl(3-oxopentanoyl)amino]ethyl}-1,3-thiazol-2-yl)thio]-2-methylpropionic acid tert-butyl ester (1.6 g) as a colorless oil. The present compound was used in the next step without particular purification. The title compound was obtained by an operation similar to that of Example 446 for the steps after cyclization reaction using hydrazine monohydrate.

$^1$H-NMR (CDCl$_3$, 300 MHz) δ: 0.89 (3H, t, J=6.6 Hz), 1.27-1.32 (11H, m), 1.56-1.65 (8H, m), 2.69 (2H, q, J=7.5

Hz), 3.00 (2H, t, J=7.5 Hz), 3.24 (2H, t, J=7.5 Hz), 3.57 (2H, t, J=7.5 Hz), 5.38 (1H, s), 7.06 (1H, s).

MS: 439 (M⁺+1).

Example 450

2-[(4-{2-[heptyl(3-propyl-1H-pyrazol-5-yl)amino]ethyl}-1,3-thiazol-2-yl)thio]-2-methylpropionic acid trifluoroacetate

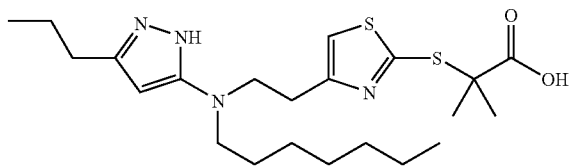

The title compound was obtained using 2-({4-[2-(heptylamino)ethyl]-1,3-thiazol-2-yl}thio)-2-methylpropionic acid tert-butyl ester synthesized in Example 303-2 and 3-keto-n-hexanoic acid methyl ester as starting materials and by an operation similar to that of Example 449.

$^1$H-NMR (CDCl$_3$, 300 MHz) δ: 0.87-0.91 (3H, m), 0.99 (3H, t, J=7.2 Hz), 1.29 (8H, brs), 1.62 (8H, brs), 1.66-1.74 (2H, m), 2.62 (2H, t, J=7.5 Hz), 3.00 (2H, t, J=7.5 Hz), 3.23 (2H, t, J=7.5 Hz), 3.57 (2H, t, J=7.5 Hz), 5.36 (1H, s), 7.06 (1H, s).

MS: 453 (M⁺+1).

Example 451

2-methyl-2-{[4-(2-{(3-methyl-1H-pyrazol-5-yl)[(1-phenyl-1H-pyrazol-4-yl)methyl]amino}ethyl)-1,3-thiazol-2-yl]thio}propionic acid hydrochloride

Example 451-1

2-methyl-2-{[4-(2-{[(1-phenyl-1H-pyrazol-4-yl)carbonyl]amino}ethyl)-1,3-thiazol-2-yl]thio}propionic acid tert-butyl ester

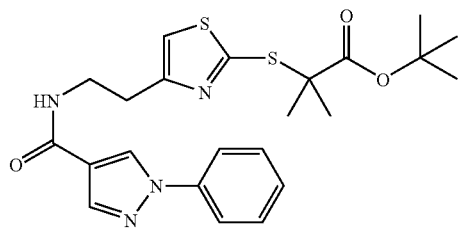

1-Phenyl-1H-pyrazole-4-carboxylic acid ethyl ester (4.1 g) synthesized in Reference Example 16 was dissolved in methanol (40 mL) and tetrahydrofuran (40 mL), aqueous sodium hydroxide solution (1 mol/L, 40 mL) was added, and the mixture was stirred at 60° C. for one hour. The reaction mixture was concentrated under reduced pressure, aqueous hydrochloric acid solution (1 mol/L, 50 mL) was added, and the precipitated solid was filtrated. The solid was dissolved in ethyl acetate, and dried over anhydrous sodium sulfate. The solvent was evaporated under reduced pressure to give 1-phenyl-1H-pyrazole-4-carboxylic acid (2.5 g) as a white solid.

This carboxylic acid (8.72 g) and 2-{[4-(2-aminoethyl)-1,3-thiazol-2-yl]thio}-2-methylpropionic acid tert-butyl ester (14 g) synthesized in Example 7 were dissolved in N,N-dimethylformamide (225 mL), N-(3-dimethylaminopropyl)-N'-ethylcarbodiimide (EDC) hydrochloride (10.65 g) and 1-hydroxybenztriazole (HOBt) monohydrate (10.62 g) were successively added thereto, and the mixture was stirred at room temperature for 6 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=1:1) to give the title compound (16.2 g) as a white solid.

$^1$H-NMR (CDCl$_3$, 300 MHz) δ: 1.45 (9H, s), 1.57 (6H, s), 3.05 (2H, t, J=6.0 Hz), 3.80-3.86 (2H, m), 7.02 (1H, s), 7.05 (1H, brs), 7.29-7.35 (1H, m), 7.43-7.48 (2H, m), 7.69-7.72 (2H, m), 8.12 (1H, s), 8.49 (1H, s).

Example 451-2

2-methyl-2-{[4-(2-{[(1-phenyl-1H-pyrazol-4-yl)methyl]amino}ethyl)-1,3-thiazol-2-yl]thio}propionic acid tert-butyl ester

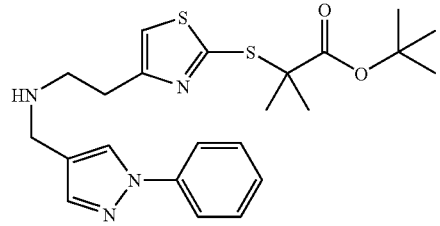

2-Methyl-2-{[4-(2-{[(1-phenyl-1H-pyrazol-4-yl)carbonyl]amino}ethyl)-1,3-thiazol-2-yl]thio}propionic acid tert-butyl ester (16.2 g) obtained in Example 451-1 was dissolved in tetrahydrofuran (20 mL), 1 mol/L-borane/tetrahydrofuran complex (160 mL) was added under ice-cooling, and the mixture was stirred at room temperature for 12 hr. The reaction mixture was ice-cooled, and methanol (200 mL) was added dropwise. After warming to room temperature, the mixture was stirred for 1 hr. The reaction mixture was concentrated under reduced pressure, piperidine (60 mL) was added, and the mixture was stirred at 60° C. for 4 hr. The reaction mixture was concentrated under reduced pressure, and the residue was purified by silica gel chromatography (elution solvent; dichloromethane:methanol=20:1 to 10:1) to give the title compound (9.5 g) as a slightly yellow oil.

¹H-NMR (CDCl₃, 300 MHz) δ: 1.42 (9H, s), 1.57 (6H, s), 2.98-3.06 (4H, m), 3.79 (2H, s), 7.02 (1H, s), 7.24-7.29 (1H, m), 7.41-7.46 (2H, m), 7.64-7.68 (3H, m), 7.89 (1H, s).

Example 451-3

2-methyl-2-{[4-(2-{(3-methyl-1H-pyrazol-5-yl)[(1-phenyl-1H-pyrazol-4-yl)methyl]amino}ethyl)-1,3-thiazol-2-yl]thio}propionic acid hydrochloride

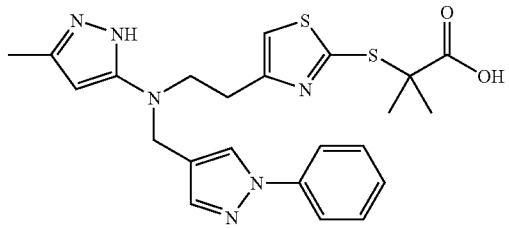

A compound obtained using 2-methyl-2-{[4-(2-{[(1-phenyl-1H-pyrazol-4-yl)methyl]amino}ethyl)-1,3-thiazol-2-yl]thio}propionic acid tert-butyl ester synthesized in Example 451-2, and by an operation similar to that of Example 446 was dissolved in diethyl ether, and reacted with 4 mol/L hydrochloric acid-ethyl acetate to give the title compound.

¹H-NMR (DMSO-d₆, 300 MHz) δ: 1.50 (6H, s), 2.24 (3H, s), 3.04 (2H, t, J=6.9 Hz), 3.67 (2H, t, J=6.9 Hz), 4.40 (2H, s), 5.85 (1H, s), 7.28-7.33 (1H, m), 7.49 (2H, t, J=7.8 Hz), 7.58 (1H, s), 7.75-7.81 (3H, m), 8.54 (1H, s).

MS: 483 (M⁺+1).

Example 452

2-[(4-{2-[(biphenyl-4-ylmethyl)(3-methyl-1H-pyrazol-5-yl)amino]ethyl}-1,3-thiazol-2-yl)thio]-2-methylpropionic acid

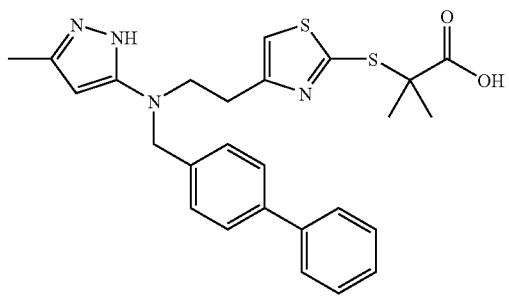

The compound obtained using 2-{[4-(2-aminoethyl)-1,3-thiazol-2-yl]thio}-2-methylpropionic acid tert-butyl ester and 4-phenylbenzoic acid synthesized in Example 7 as starting materials and by operations similar to those of Example 451-1, Example 451-2 and Example 446-1 was treated with dichloromethane and trifluoroacetic acid. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound.

¹H-NMR (CDCl₃, 300 MHz) δ: 1.63 (6H, s), 2.21 (3H, s), 3.00 (2H, t, J=7.2 Hz), 3.59 (2H, t, J=7.2 Hz), 4.41 (2H, s), 5.33 (1H, s), 6.93 (1H, s), 7.27-7.58 (9H, m).

MS: 493 (M⁺+1).

Example 453

2-methyl-2-{[4-(2-{(3-methyl-1H-pyrazol-5-yl)[(6-phenylpyridin-3-yl)methyl]amino}ethyl)-1,3-thiazol-2-yl]thio}propionic acid hydrochloride

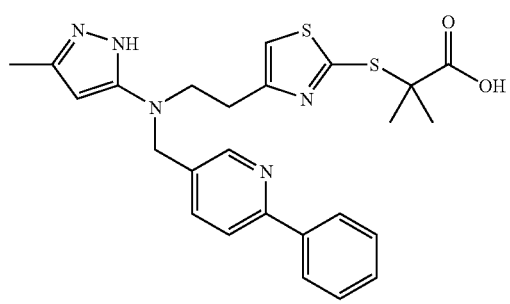

The title compound was obtained using 2-{[4-(2-aminoethyl)-1,3-thiazol-2-yl]thio}-2-methylpropionic acid tert-butyl ester synthesized in Example 7 and 6-phenylnicotinic acid ethyl ester synthesized in Reference Example 21, and by an operation similar to that of Example 451.

¹H-NMR (DMSO-d₆, 300 MHz) δ: 1.50 (6H, s), 2.24 (3H, s), 3.04 (2H, t, J=6.9 Hz), 3.74 (2H, t, J=6.9 Hz), 4.64 (2H, s), 5.84 (1H, s), 7.50-7.57 (4H, m), 7.91-7.94 (1H, m), 8.05-8.09 (3H, m), 8.63 (1H, d, J=1.8 Hz).

MS: 494 (M⁺+1).

Example 454

2-{[4-(2-{(3-ethyl-1H-pyrazol-5-yl)[(1-phenyl-1H-pyrazol-4-yl)methyl]amino}ethyl)-1,3-thiazol-2-yl]thio}-2-methylpropionic acid hydrochloride

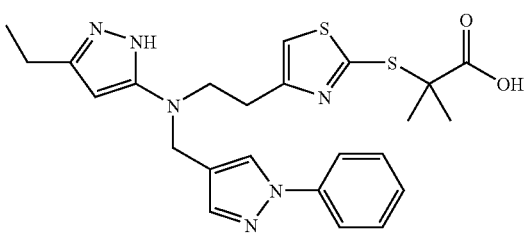

A compound obtained using 2-methyl-2-{[4-(2-{[(1-phenyl-1H-pyrazol-4-yl)methyl]amino}ethyl)-1,3-thiazol-2-yl]thio}propionic acid tert-butyl ester synthesized in Example 451-2 and 3-keto-n-hexanoic acid methyl ester, and by an operation similar to that of Example 449 was dissolved in diethyl ether, and reacted with 4 mol/L hydrochloric acid-ethyl acetate to give the title compound.

$^1$H-NMR (DMSO-d$_6$, 300 MHz) δ: 1.20 (3H, t, J=7.5 Hz), 1.50 (6H, s), 2.59 (2H, q, J=7.5 Hz), 3.04 (2H, t, J=6.9 Hz), 3.68 (2H, t, J=6.9 Hz), 4.42 (2H, s), 5.88 (1H, s), 7.28-7.33 (1H, m), 7.49 (2H, t, J=7.8 Hz), 7.58 (1H, s), 7.76-7.81 (3H, m), 8.55 (1H, s).
MS: 497 (M$^+$+1).

Example 455

2-methyl-2-({4-[({[4'-(trifluoromethyl)biphenyl-4-yl]carbonyl}amino)ethyl]-1,3-thiazol-2-yl}thio)propionic acid

Example 455-1

2-[(4-{[(4-bromobenzoyl)amino]methyl}-1,3-thiazol-2-yl)thio]-2-methylpropionic acid tert-butyl ester

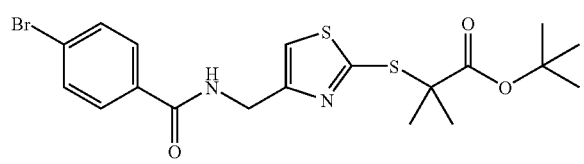

2-{[4-(Aminomethyl)-1,3-thiazol-2-yl]thio}-2-methylpropionic acid tert-butyl ester (3.0 g) synthesized in Example 13 and 4-bromobenzoic acid (2.51 g) was dissolved in dichloromethane (50 mL), N-(3-dimethylaminopropyl)-N'-ethylcarbodiimide (EDC) hydrochloride (2.99 g) and hydroxybenzotriazole (HOBT) monohydrate (2.39 g) were successively added thereto, and the mixture was stirred at room temperature for 12 hr. Water was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (3.5 g) as a white solid.
$^1$H-NMR (CDCl$_3$, 300 MHz) δ: 1.38 (9H, s), 1.59 (6H, s), 4.67 (2H, d, J=5.4 Hz), 6.90-6.94 (1H, m), 7.22 (1H, s), 7.58 (2H, d, J=8.6 Hz), 7.74 (2H, d, J=8.6 Hz).

Example 455-2

2-methyl-2-({4-[({[4'-(trifluoromethyl)biphenyl-4-yl]carbonyl}amino)methyl]-1,3-thiazol-2-yl}thio)propionic acid tert-butyl ester

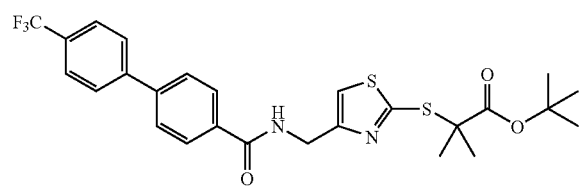

Under nitrogen atmosphere, 2-[(4-{[(4-bromobenzoyl)amino]methyl}-1,3-thiazol-2-yl)thio]-2-methylpropionic acid tert-butyl ester (600 mg) synthesized in Example 455-1 and 4-trifluoromethylphenylboric acid (363 mg) were dissolved in dioxane (8 mL) and 2 M aqueous sodium carbonate solution (4 mL), tetrakis(triphenylphosphine)palladium (73 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1 to 1:1) to give the title compound (590 mg) as a white solid.
$^1$H-NMR (CDCl$_3$, 300 MHz) δ: 1.43 (9H, s), 1.64 (6H, s), 4.76 (2H, d, J=5.3 Hz), 6.98-7.02 (1H, m), 7.29 (1H, s), 7.69-7.81 (6H, m), 8.00 (2H, d, J=8.2 Hz).

Example 455-3

2-methyl-2-({4-[({[4'-(trifluoromethyl)biphenyl-4-yl]carbonyl}amino)ethyl]-1,3-thiazol-2-yl}thio)propionic acid

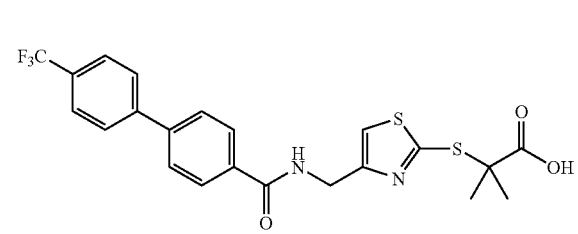

2-Methyl-2-({4-[({[4'-(trifluoromethyl)biphenyl-4-yl]carbonyl}amino)methyl]-1,3-thiazol-2-yl}thio)propionic acid tert-butyl ester (580 mg) obtained in Example 455-2 was dissolved in dichloromethane (10 mL), trifluoroacetic acid (4 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (330 mg) as a white solid.
$^1$H-NMR (CDCl$_3$, 300 MHz) δ: 1.65 (6H, s), 4.66 (2H, d, J=5.6 Hz), 7.37 (1H, s), 7.49-7.54 (3H, m), 6.64-7.72 (4H, m), 7.78 (2H, d, J=8.3 Hz).
MS: 481 (M$^+$+1).

Example 456

2-{[4-({[(4'-fluorobiphenyl-4-yl)carbonyl]amino}methyl)-1,3-thiazol-2-yl]thio}-2-methylpropionic acid

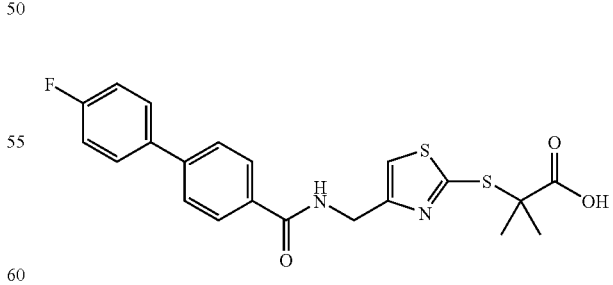

The title compound was obtained using 2-[(4-{[(4-bromobenzoyl)amino]methyl}-1,3-thiazol-2-yl)thio]-2-methylpropionic acid tert-butyl ester synthesized in Example 455-1 and 4-fluorophenylboric acid as starting materials and by operations similar to those of Example 455-2 and Example 455-3.

¹H-NMR (CDCl₃, 300 MHz) δ: 1.66 (6H, s), 4.68 (2H, d, J=5.4 Hz), 7.13-7.29 (3H, m), 7.35 (1H, s), 7.52-7.58 (4H, m), 7.82 (2H, d, J=8.2 Hz).
MS: 431 (M⁺+1).

Example 457

2-{[4-({[(4'-chlorobiphenyl-4-yl)carbonyl]amino}methyl)-1,3-thiazol-2-yl]thio}-2-methylpropionic acid

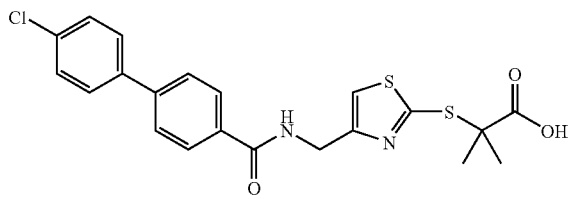

The title compound was obtained using 2-[(4-{[(4-bromobenzoyl)amino]methyl}-1,3-thiazol-2-yl)thio]-2-methylpropionic acid tert-butyl ester synthesized in Example 455-1 and 4-chlorophenylboric acid as starting materials and by operations similar to those of Example 455-2 and Example 455-3.

¹H-NMR (CDCl₃, 300 MHz) δ: 1.63 (6H, s), 4.61 (2H, d, J=5.5 Hz), 7.35 (1H, s), 7.39-7.53 (7H, m), 7.76 (2H, d, J=8.2 Hz).
MS: 447 (M⁺+1).

Example 458

2-methyl-2-{[4-(2-oxo-2-{[4'-(trifluoromethyl)biphenyl-4-yl]amino}ethyl)-1,3-thiazol-2-yl]thio}propionic acid

Example 458-1

2-[(4-{2-[(4-bromophenyl)amino]-2-oxoethyl}-1,3-thiazol-2-yl)thio]-2-methylpropionic acid tert-butyl ester

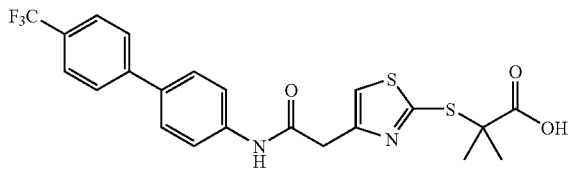

{2-[(2-tert-Butoxy-1,1-dimethyl-2-oxoethyl)thio]-1,3-thiazol-4-yl}acetic acid (3.0 g) synthesized in Example 3 and 4-bromoaniline (1.63 g) were dissolved in dichloromethane (50 mL), N-(3-dimethylaminopropyl)-N'-ethylcarbodiimide (EDC) hydrochloride (2.72 g) and 4-dimethylaminopyridine (DMAP) (1.73 g) were successively added thereto, and the mixture was stirred at room temperature for 12 hr. Water was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (4.5 g) as a colorless oil.

¹H-NMR (CDCl₃, 300 MHz) δ: 1.42 (9H, s), 1.61 (6H, s), 3.81 (2H, s), 7.15 (1H, s), 7.41 (2H, d, J=8.8 Hz), 7.57 (2H, d, J=8.8 Hz), 8.75 (1H, brs).

Example 458-2

2-methyl-2-{[4-(2-oxo-2-{[4'-(trifluoromethyl)biphenyl-4-yl]amino}ethyl)-1,3-thiazol-2-yl]thio}propionic acid tert-butyl ester

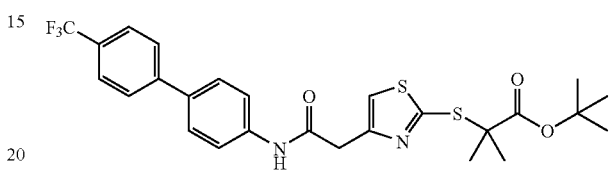

Under nitrogen atmosphere, 2-[(4-{2-[(4-bromophenyl)amino]-2-oxoethyl}-1,3-thiazol-2-yl)thio]-2-methylpropionic acid tert-butyl ester (600 mg) synthesized in Example 458-1 and 4-trifluoromethylphenylboric acid (363 mg) were dissolved in dioxane (8 mL) and 2M aqueous sodium carbonate solution (4 mL), tetrakis(triphenylphosphine)palladium (73 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (550 mg) as a colorless oil.

¹H-NMR (CDCl₃, 300 MHz) δ: 1.47 (9H, s), 1.67 (6H, s), 3.89 (2H, s), 7.22 (1H, s), 7.59 (2H, d, J=8.8 Hz), 7.70 (4H, s), 7.79 (2H, d, J=8.8 Hz), 8.86 (1H, brs).

Example 458-3

2-methyl-2-{[4-(2-oxo-2-{[4'-(trifluoromethyl)biphenyl-4-yl]amino}ethyl)-1,3-thiazol-2-yl]thio}propionic acid

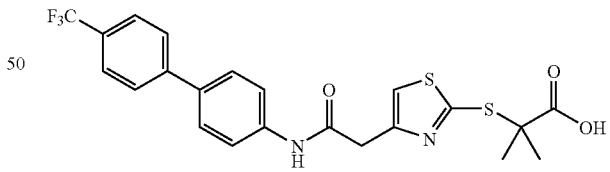

2-Methyl-2-{[4-(2-oxo-2-{[4'-(trifluoromethyl)biphenyl-4-yl]amino}ethyl)-1,3-thiazol-2-yl]thio}propionic acid tert-butyl ester (540 mg) obtained in Example 458-2 was dissolved in dichloromethane (10 mL), trifluoroacetic acid (4 mL) was added, and the mixture was stirred at room temperature for 12 hr. The reaction mixture was concentrated under reduced pressure, and the residue was purified by silica gel chromatography (elution solvent; hexane:ethyl acetate=1:1 to 0:1) to give the title compound (290 mg) as a white solid.

¹H-NMR (CDCl₃, 300 MHz) δ: 1.66 (6H, s), 3.84 (2H, s), 7.30-7.66 (9H, m), 8.70 (1H, brs).
MS: 481 (M⁺+1).

Example 459

2-[(4-{2-[(4'-fluorobiphenyl-4-yl)amino]-2-oxoethyl}-1,3-thiazol-2-yl)thio]-2-methylpropionic acid

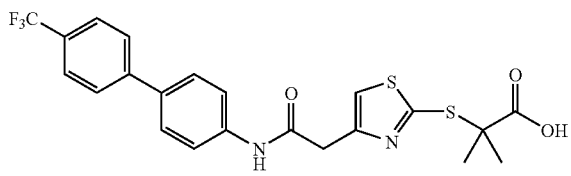

The title compound was obtained using 2-[(4-{2-[(4-bromophenyl)amino]-2-oxoethyl}-1,3-thiazol-2-yl)thio]-2-methylpropionic acid tert-butyl ester synthesized in Example 458-1 and 4-fluorophenylboric acid as starting materials and by operations similar to those of Example 458-2 and Example 458-3.

$^1$H-NMR (CDCl$_3$, 300 MHz) δ: 1.66 (6H, s), 3.84 (2H, s), 7.05-7.11 (2H, m), 7.23-7.54 (7H, m), 8.47 (1H, brs).

MS: 431 (M$^+$+1).

Example 460

2-[(4-{2-[(4'-chlorobiphenyl-4-yl)amino]-2-oxoethyl}-1,3-thiazol-2-yl)thio]-2-methylpropionic acid

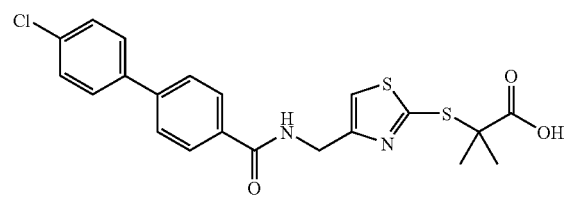

The title compound was obtained using 2-[(4-{[(4-bromobenzoyl)amino]methyl}-1,3-thiazol-2-yl)thio]-2-methylpropionic acid tert-butyl ester synthesized in Example 458-1 and 4-chlorophenylboric acid as starting materials and by operations similar to those of Example 458-2 and Example 458-3.

$^1$H-NMR (CDCl$_3$, 300 MHz) δ: 1.66 (6H, s), 3.84 (2H, s), 7.31-7.55 (9H, m), 8.46 (1H, brs).

MS: 447 (M$^+$+1).

Example 461

2-[(4-{2-[heptyl(3-nitropyridin-2-yl)amino]ethyl}-1,3-thiazol-2-yl)thio]-2-methylpropionic acid

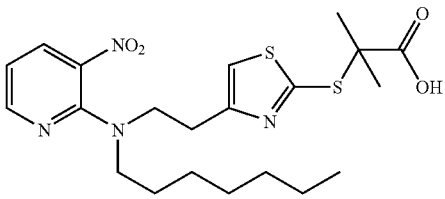

Example 461-1

2-({4-[2-(9H-fluorene-9-ylmethoxy)-2-oxoethyl]-1,3-thiazol-2-yl}thio)-2-methylpropionic acid tert-butyl ester

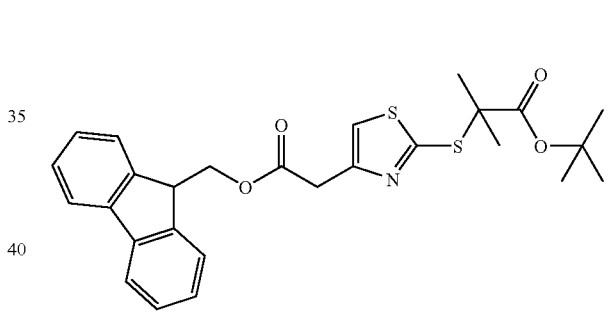

To a solution of {2-[(2-tert-butoxy-1,1-dimethyl-2-oxoethyl)thio]-1,3-thiazol-4-yl}acetic acid (160 g) obtained in Example 3 in dichloromethane (500 mL) were added 9H-fluorene-9-ylmethanol (98 g) and 4-dimethylaminopyridine (3.1 g), diisopropylcarbodiimide (78 ml) was added dropwise under ice-cooling, and the mixture was stirred at 0° C. for 1 hr and further stirred at room temperature for 2 hr. The precipitate was removed from the reaction mixture by filtration, and the filtrate was concentrated under reduced pressure and purified by silica gel chromatography (elution solvent; hexane:ethyl acetate=4:1) to give the title compound (260 g) as a yellow oil.

$^1$H-NMR (CDCl$_3$, 300 MHz) δ: 1.43 (9H, s), 1.55 (6H, s), 3.91 (2H, s), 4.20 (1H, t, J=6.9 Hz), 4.44 (2H, d, J=6.9 Hz), 7.15 (1H, s), 7.30 (2H, dt, J=7.5, 1.2 Hz), 7.39 (2H, t, J=7.5 Hz), 7.51 (2H, d, J=7.5 Hz), 7.76 (2H, d, J=7.5 Hz).

MS: 496 (M$^+$+1).

Example 461-2

2-({4-[2-(9H-fluorene-9-ylmethoxy)-2-oxoethyl]-1,3-thiazol-2-yl}thio)-2-methylpropionic acid

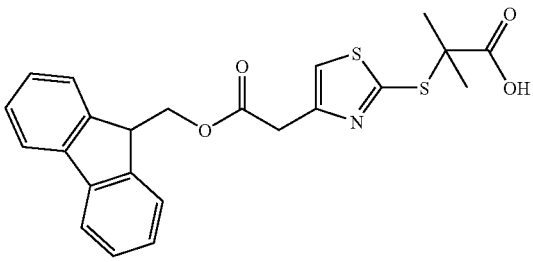

To a solution of 2-({4-[2-(9H-fluorene-9-ylmethoxy)-2-oxoethyl]-1,3-thiazol-2-yl}thio)-2-methylpropionic acid tert-butyl ester (260 g) obtained in Example 461-1 in dichloromethane (400 mL) was added trifluoroacetic acid (100 mL), and the mixture was stirred at room temperature overnight and heated at 45° C. with stirring for 8 hr. The reaction mixture was concentrated, ethyl acetate was added, and the organic layer was washed with saturated brine and dried over sodium sulfate. The solvent was evaporated under reduced pressure. The obtained residue was purified by silica gel chromatography (elution solvent; hexane:ethyl acetate=1:1) to give the title compound (250 g) as a yellow oil.

$^1$H-NMR (CDCl$_3$, 300 MHz) δ: 1.63 (6H, s), 3.52 (1H, bs), 3.89 (2H, s), 4.22 (1H, t, J=6.9 Hz), 4.50 (2H, d, J=6.9 Hz), 7.08 (1H, s), 7.31 (2H, dt, J=7.5, 1.2 Hz), 7.41 (2H, t, J=7.5 Hz), 7.52 (2H, d, J=7.5 Hz), 7.76 (2H, d, J=7.5 Hz).

MS: 440 (M$^+$+1).

Example 461-3

2-({4-[2-(9H-fluorene-9-ylmethoxy)-2-oxoethyl]-1,3-thiazol-2-yl}thio)-2-methylpropionic acid resin

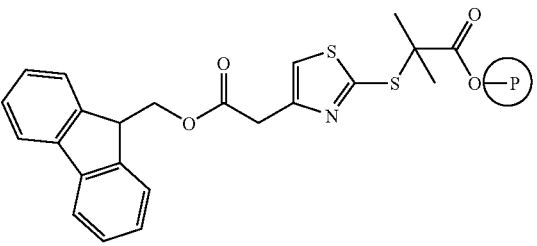

To a suspension of Wang resin (100 g) in dimethylformamide (500 mL) were added pyridine (42 ml) and 2-({4-[2-(9H-fluorene-9-ylmethoxy)-2-oxoethyl]-1,3-thiazol-2-yl}thio)-2-methylpropionic acid (130 g) obtained in Example 461-2, 2,6-dichlorobenzoylchloride (42 ml) was added dropwise under ice-cooling, and the mixture was stirred at room temperature overnight. The resin was collected by filtration from the mixture, washed three times each with methanol and dimethylformamide, then twice each with tetrahydrofuran and methanol, and finally once with tetrahydrofuran, and air dried to give the title pale-yellow resin (150 g).

IR (KBr) cm$^{-1}$: 3060, 3024, 2926, 1730.

Example 461-4

2-{[4-(carboxymethyl)-1,3-thiazol-2-yl]thio}-2-methylpropionic acid resin

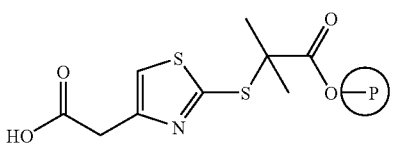

To a suspension of 2-({4-[2-(9H-fluorene-9-ylmethoxy)-2-oxoethyl]-1,3-thiazol-2-yl}thio)-2-methylpropionic acid resin (150 g) obtained in Example 461-3 in dimethylformamide (500 mL) was added piperidine (100 mL), and the mixture was stirred at room temperature overnight. The resin was collected by filtration from the mixture, washed once each with dimethylformamide, methanol and water, then three times each with dimethylformamide and methanol, and finally twice with dichloromethane, and vacuum dried to give the title pale-yellow resin (130 g).

IR (KBr) cm$^{-1}$: 3058, 3025, 2922, 1728, 1677.

Example 461-5

2-({4-[2-(heptylamino)-2-oxoethyl]-1,3-thiazol-2-yl}thio)-2-methylpropionic acid resin

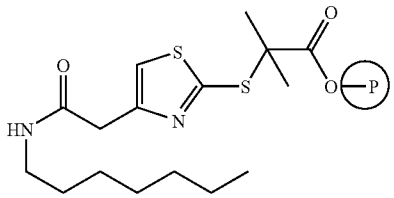

To a suspension of 2-{[4-(carboxymethyl)-1,3-thiazol-2-yl]thio}-2-methylpropionic acid resin (5.0 g) synthesized in Example 461-4 in dimethylformamide (20 mL) were added pyridine (1.2 ml) and 4 mol/L-hydrochloric acid-dioxane solution (2.3 ml) and the mixture was gently stirred at room temperature for 30 min. The resin was collected by filtration, and washed three times with dimethylformamide. To the resin were added dimethylformamide (20 mL), pyridine (0.75 ml) and 2-chloro-1,3-dimethylimidazolinium chloride (1.6 g), and the mixture was stirred at room temperature for 30 min. To the reaction mixture was added heptylamine (1.4 ml), and the mixture was stirred at room temperature overnight. The resin was collected by filtration from the mixture, successively washed three times with dimethylformamide, once with water and methanol, three times with tetrahydrofuran, once with methanol, and finally three times with dichloromethane, and vacuum dried to give the title pale-yellow resin (5.2 g).

A part of the resin was cleaved with trifluoroacetic acid and the structure was confirmed.

MS: 359 (M$^+$+1).

Example 461-6

2-({4-[2-(heptylamino)ethyl]-1,3-thiazol-2-yl}thio)-2-methylpropionic acid resin

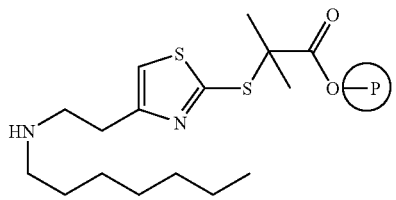

To a suspension of 2-({4-[2-(heptylamino)-2-oxoethyl]-1,3-thiazol-2-yl}thio)-2-methylpropionic acid resin (5.2 g) synthesized in Example 461-5 in tetrahydrofuran (20 mL) was added 1 mol/L borane-tetrahydrofuran complex (18 ml), and the mixture was stirred at room temperature for 30 min, and at 50° C. for 16.5 hr. The resin was collected by filtration from the mixture, washed three times each with tetrahydrofuran and methanol, and vacuum dried to give the title pale-yellow resin (4.0 g).

A part of the resin was cleaved with trifluoroacetic acid and the structure was confirmed.

MS: 345 (M$^+$+1).

Example 461-7

2-[(4-{2-[heptyl(3-nitropyridin-2-yl)amino]ethyl}-1,3-thiazol-2-yl)thio]-2-methylpropionic acid To a suspension of 2-({4-[2-(heptylamino)ethyl]-1,3-thiazol-2-yl}thio)-2-methylpropionic acid resin (0.15 g) synthesized in Example 461-6 in acetonitrile (1.5 ml) were added triethylamine (0.16 ml) and 2-chloro-3-nitropyridine (0.089 g), and the mixture was stirred at room temperature overnight. The resin was collected by filtration from the mixture, washed three times with dimethylformamide, tetrahydrofuran and methanol, and vacuum dried. Trifluoroacetic acid (2.0 mL) was added to the obtained resin, and the mixture was left standing at room temperature for 2 hr. Then the resin was removed by filtration from the reaction mixture, and the filtrate was concentrated by blowing a nitrogen gas, vacuum dried, and purified by preparative HPLC to give the title compound (1.5 mg) as a pale-brown oil.

MS: 467 (M$^+$+1).

The following compounds were obtained by an operation similar to that of Example 461.

TABLE 1

| NO. | Ar | R | MS (M$^+$ + 1) | yield (mg) |
|---|---|---|---|---|
| 462 | 5-O$_2$N-6-Me-pyridin-2-yl | *-(CH$_2$)$_5$-CH$_3$ | 453 | 21 |
| 463 | 5-O$_2$N-6-Me-pyridin-2-yl | *-(CH$_2$)$_8$-CH$_3$ | 495 | 22 |
| 464 | 5-O$_2$N-6-Me-pyridin-2-yl | *-(CH$_2$)$_{10}$-CH$_3$ | 523 | 16 |
| 465 | 5-O$_2$N-6-Me-pyridin-2-yl | *-(CH$_2$)$_6$-CH(CH$_3$)$_2$ | 495 | 25 |

TABLE 1-continued

Structure: Ar-N(R)-CH₂CH₂-[thiazole]-S-C(CH₃)₂-C(=O)-OH

| NO. | Ar | R | MS (M⁺ + 1) | yield (mg) |
|---|---|---|---|---|
| 466 | 5-O₂N-6-methyl-pyridin-2-yl | *-CH₂CH₂-(4-propylphenyl) | 515 | 22 |
| 467 | 5-O₂N-6-methyl-pyridin-2-yl | *-(CH₂)₃-(4-ethylphenyl) | 515 | 23 |
| 468 | 5-O₂N-6-methyl-pyridin-2-yl | *-CH₂-(4-ethylphenyl, with extra CH₃) | 515 | 11 |
| 469 | 5-O₂N-6-methyl-pyridin-2-yl | *-CH₂-(4-propylphenyl) | 515 | 11 |
| 470 | 5-O₂N-6-methyl-pyridin-2-yl | *-CH₂-(4-butylphenyl) | 515 | 29 |

TABLE 2

| NO. | Ar | R | MS (M⁺ + 1) | yield (mg) |
|---|---|---|---|---|
| 471 | 5-O₂N-6-methyl-pyridin-2-yl | *-CH₂-phenyl | 459 | 4.0 |
| 472 | 5-O₂N-6-methyl-pyridin-2-yl | *-(CH₂)₂-phenyl | 473 | 7.2 |
| 473 | 5-O₂N-6-methyl-pyridin-2-yl | *-(CH₂)₃-phenyl | 487 | 13 |
| 474 | 5-O₂N-6-methyl-pyridin-2-yl | *-(CH₂)₄-phenyl | 501 | 13 |
| 475 | 5-O₂N-6-methyl-pyridin-2-yl | *-(CH₂)₅-phenyl | 515 | 12 |

TABLE 2-continued

| NO. | Ar | R | MS (M⁺ + 1) | yield (mg) |
|---|---|---|---|---|
| 476 | O₂N-pyridinyl-methyl | biphenyl-CH₂- | 535 | 8.9 |
| 477 | O₂N-pyridinyl-methyl | 4-(1,2,3-thiadiazol-4-yl)phenyl-CH₂- | 543 | 2.0 |
| 478 | O₂N-pyridinyl-methyl | furan-2-yl-CH₂- | 449 | 20 |
| 479 | O₂N-pyridinyl-methyl | naphthalen-2-yl-CH₂- | 509 | 14 |
| 480 | O₂N-pyridinyl-methyl | -CH₂-CH(Ph)₂ | 549 | 22 |
| 481 | 3,5-dinitropyridin-2-yl | -CH₂-(CH₂)₆-CH₃ | 512 | 3.9 |
| 482 | 6-methoxy-3-nitropyridin-2-yl | -CH₂-(CH₂)₆-CH₃ | 497 | 2.4 | saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (6.6 g) as a pale-yellow solid.

¹H-NMR (CDCl₃, 300 MHz) δ: 1.69 (6H, s), 3.09 (2H, t, J=6.0 Hz), 3.57-3.61 (2H, m), 6.84-6.87 (1H, m), 7.04 (1H, s), 7.40 (2H, d, J=8.6 Hz), 7.77 (2H, d, J=8.6 Hz), 8.10 (1H, s), 8.31 (1H, s).

MS: 435 (M⁺+1).

Example 227

2-[(4-{2-[[5-(4-chlorophenyl)pyrazin-2-yl](methyl)amino]ethyl}-1,3-thiazol-2-yl)thio]-2-methylpropionic acid

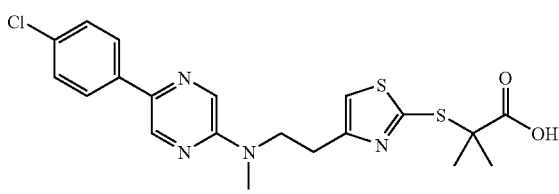

The title compound was obtained using 2-[(4-{2-[[5-(4-chlorophenyl)pyrazin-2-yl](methyl)amino]ethyl}-1,3-thiazol-2-yl)thio]-2-methylpropionic acid tert-butyl ester synthesized in Example 226-2 as a starting material and by an operation similar to that of Example 163.

¹H-NMR (CDCl₃, 300 MHz) δ: 1.67 (6H, s), 3.09 (2H, t, J=6.8 Hz), 3.12 (3H, s), 3.94 (2H, t, J=6.8 Hz), 6.96 (1H, s), 7.40 (2H, d, J=8.6 Hz), 7.77 (2H, d, J=8.6 Hz), 8.08 (1H, s), 8.45 (1H, s).

MS: 449 (M⁺+1).

Example 228

2-methyl-2-({4-[2-({5-[4-(trifluoromethyl)phenyl] pyrazin-2-yl}amino)ethyl]-1,3-thiazol-2-yl}thio) propionic acid

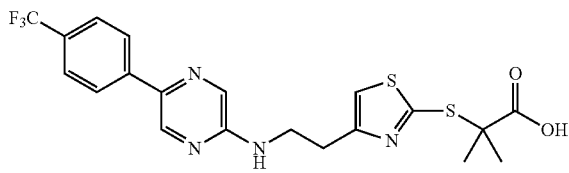

The title compound was obtained using 2-[(4-{2-[(5-bromopyrazin-2-yl)amino]ethyl}-1,3-thiazol-2-yl)thio]-2-methylpropionic acid tert-butyl ester synthesized in Example 226-1 and [4-(trifluoromethyl)phenyl]boric acid as starting materials and by operations similar to those of Example 226-2 and Example 226-3.

¹H-NMR (CDCl₃, 300 MHz) δ: 1.72 (6H, s), 3.09-3.15 (2H, m), 3.60-3.66 (2H, m), 6.94-6.96 (1H, m), 7.07 (1H, s), 7.70 (2H, d, J=8.2 Hz), 7.98 (2H, d, J=8.2 Hz), 8.16 (1H, s), 8.41 (1H, s).

MS: 469 (M⁺+1).

Example 229

2-methyl-2-({4-[2-(methyl{5-[4-(trifluoromethyl) phenyl]pyrazin-2-yl}amino)ethyl]-1,3-thiazol-2-yl}thio)propionic acid

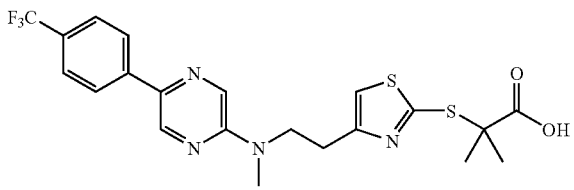

The title compound was obtained using 2-methyl-2-({4-[2-({5-[4-(trifluoromethyl)phenyl]pyrazin-2-yl}amino) ethyl]-1,3-thiazol-2-yl}thio)propionic acid tert-butyl ester, which is an intermediate synthesize in Example 228, as a starting material and by an operation similar to that of Example 163.

¹H-NMR (CDCl₃, 300 MHz) δ: 1.67 (6H, s), 3.11 (2H, t, J=6.8 Hz), 3.15 (3H, s), 3.96 (2H, t, J=6.8 Hz), 6.97 (1H, s), 7.69 (2H, d, J=8.2 Hz), 7.95 (2H, d, J=8.2 Hz), 8.12 (1H, s), 8.52 (1H, s).

MS: 483 (M⁺+1).

Example 230

2-methyl-2-({4-[2-({5-[4-(trifluoromethoxy)phenyl] pyrazin-2-yl}amino)ethyl]-1,3-thiazol-2-yl}thio) propionic acid

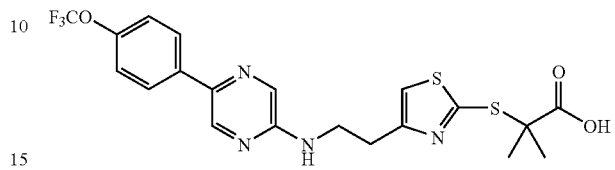

The title compound was obtained using 2-[(4-{2-[(5-bromopyrazin-2-yl)amino]ethyl}-1,3-thiazol-2-yl)thio]-2-methylpropionic acid tert-butyl ester synthesized in Example 226-1 and [4-(trifluoromethoxy)phenyl]boric acid as starting materials and by operations similar to those of Example 226-2 and Example 226-3.

¹H-NMR (CDCl₃, 300 MHz) δ: 1.69 (6H, s), 3.10 (2H, t, J=6.0 Hz), 3.57-3.62 (2H, m), 6.85-6.87 (1H, m), 7.04 (1H, s), 7.27 (2H, d, J=8.9 Hz), 7.86 (2H, d, J=8.9 Hz), 8.11 (1H, s), 8.32 (1H, s).

MS: 485 (M⁺+1).

Example 231

2-methyl-2-({4-[2-(methyl{5-[4-(trifluoromethoxy) phenyl]pyrazin-2-yl}amino)ethyl]-1,3-thiazol-2-yl}thio)propionic acid

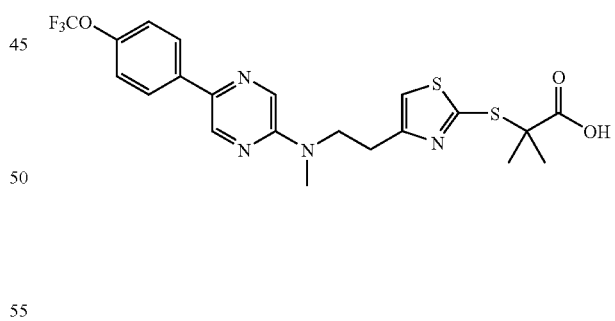

The title compound was obtained using 2-methyl-2-({4-[2-({5-[4-(trifluoromethoxy)phenyl]pyrazin-2-yl}amino) ethyl]-1,3-thiazol-2-yl}thio)propionic acid tert-butyl ester, which is an intermediate synthesize in Example 230, as a starting material and by an operation similar to that of Example 163.

¹H-NMR (CDCl₃, 300 MHz) δ: 1.70 (6H, s), 3.12 (2H, t, J=6.8 Hz), 3.16 (3H, s), 3.97 (2H, t, J=6.8 Hz), 6.99 (1H, s), 7.30 (2H, d, J=8.7 Hz), 7.88 (2H, d, J=8.7 Hz), 8.12 (1H, s), 8.48 (1H, s).

MS: 499 (M⁺+1).

Example 232

2-({4-[2-({5-[2-fluoro-4-(trifluoromethyl)phenyl]pyrazin-2-yl}amino)ethyl]-1,3-thiazol-2-yl}thio)-2-methylpropionic acid

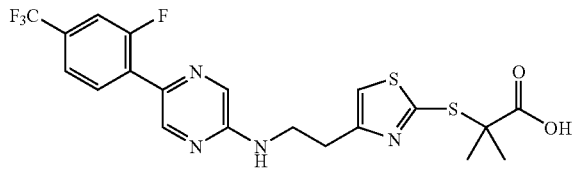

The title compound was obtained using 2-[(4-{2-[(5-bromopyrazin-2-yl)amino]ethyl}-1,3-thiazol-2-yl)thio]-2-methylpropionic acid tert-butyl ester synthesized in Example 226-1 and 2-fluoro-4-(trifluoromethyl)phenylboric acid synthesized in the same manner as in Reference Example 3 from 4-bromo-3-fluorobenzotrifluoride as starting materials, and by operations similar to those of Example 226-2 and Example 226-3.

$^1$H-NMR (CDCl$_3$, 300 MHz) δ: 1.69 (6H, s), 3.07-3.12 (2H, m), 3.60-3.65 (2H, m), 6.97-7.01 (1H, m), 7.04 (1H, s), 7.39-7.50 (2H, m), 8.09 (1H, t, J=8.1 Hz), 8.15 (1H, s), 8.50 (1H, s).

MS: 487 (M$^+$+1).

Example 233

2-{[4-(2-{[6-(4-chlorophenyl)-4-methylpyridazin-3-yl]amino}ethyl)-1,3-thiazol-2-yl]thio}-2-methylpropionic acid

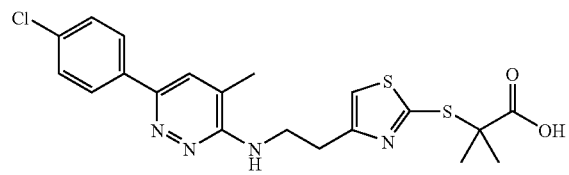

The title compound was obtained using 2-{[4-(2-aminoethyl)-1,3-thiazol-2-yl]thio}-2-methylpropionic acid tert-butyl ester synthesized in Example 7 and 3-chloro-6-(4-chlorophenyl)-4-methylpyridazine synthesized in reference to non-patent reference [J. Med. Chem. 32, 528 (1989)] as starting materials and by operations similar to those of Example 162-1 and Example 162-3.

$^1$H-NMR (CDCl$_3$, 300 MHz) δ: 1.63 (6H, s), 2.18 (3H, s), 3.22 (2H, t, J=6.3 Hz), 3.98-4.04 (2H, m), 5.00-5.05 (1H, m), 7.03 (1H, s), 7.37-7.42 (3H, m), 7.88 (2H, d, J=8.6 Hz).

MS: 449 (M$^+$+1).

Example 234

2-[(4-{2-[[6-(4-chlorophenyl)-4-methylpyridazin-3-yl](methyl)amino]ethyl}-1,3-thiazol-2-yl)thio]-2-methylpropionic acid

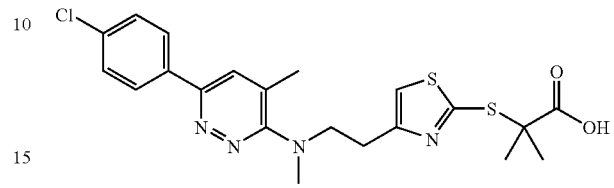

The title compound was obtained using 2-{[4-(2-aminoethyl)-1,3-thiazol-2-yl]thio}-2-methylpropionic acid tert-butyl ester synthesized in Example 7 and 3-chloro-6-(4-chlorophenyl)-4-methylpyridazine synthesized in reference to non-patent reference [J. Med. Chem. 32, 528 (1989)] as starting materials and by operations similar to those of Example 162-1 and Example 163.

$^1$H-NMR (CDCl$_3$, 300 MHz) δ: 1.60 (6H, s), 2.35 (3H, s), 3.11-3.17 (5H, m), 3.84 (2H, t, J=6.9 Hz), 6.97 (1H, s), 7.46 (2H, d, J=8.6 Hz), 7.51 (1H, s), 7.92 (2H, d, J=8.6 Hz).

MS: 463 (M$^+$).

Example 235

2-methyl-2-({4-[2-({4-methyl-6-[4-(trifluoromethyl)phenyl]pyridazin-3-yl}amino)ethyl]-1,3-thiazol-2-yl}thio)propionic acid

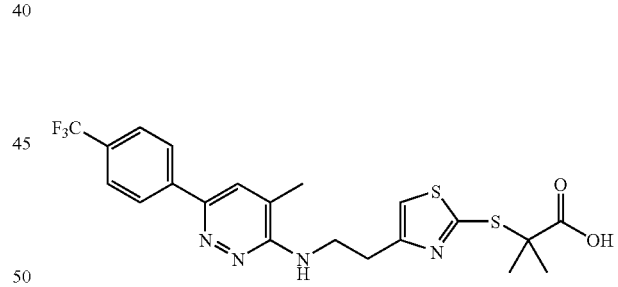

The title compound was obtained using 2-{[4-(2-aminoethyl)-1,3-thiazol-2-yl]thio}-2-methylpropionic acid tert-butyl ester synthesized in Example 7 and 3-chloro-4-methyl-6-[4-(trifluoromethyl)phenyl]pyridazine synthesized in reference to non-patent reference [J. Med. Chem. 32, 528 (1989)] as starting materials and by operations similar to those of Example 162-1 and Example 162-3.

$^1$H-NMR (CDCl$_3$, 300 MHz) δ: 1.60 (6H, s), 2.43 (3H, s), 3.14-3.20 (2H, m), 4.05-4.11 (2H, m), 7.13 (1H, s), 7.63-7.69 (3H, m), 7.88 (2H, d, J=7.9 Hz).

MS: 483 (M$^+$+1).

Example 236

2-methyl-2-({4-[2-(methyl{4-methyl-6-[4-(trifluoromethyl)phenyl]pyridazin-3-yl}amino)ethyl]-1,3-thiazol-2-yl}thio)propionic acid

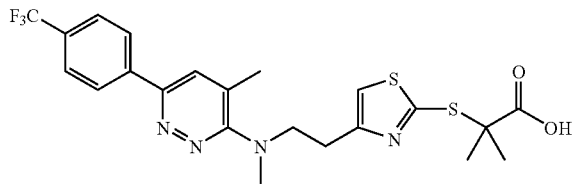

The title compound was obtained using 2-{[4-(2-aminoethyl)-1,3-thiazol-2-yl]thio}-2-methylpropionic acid tert-butyl ester synthesized in Example 7 and 3-chloro-4-methyl-6-[4-(trifluoromethyl)phenyl]pyridazine synthesized in reference to non-patent reference [J. Med. Chem. 32, 528 (1989)] as starting materials and by operations similar to those of Example 162-1 and Example 163.

$^1$H-NMR (CDCl$_3$, 300 MHz) δ: 1.59 (6H, s), 2.39 (3H, s), 3.12-3.19 (5H, m), 3.88 (2H, t, J=6.9 Hz), 7.00 (1H, s), 7.58 (1H, s), 7.74 (2H, d, J=8.2 Hz), 8.08 (2H, d, J=8.2 Hz).

MS: 497 (M$^+$+1).

Example 237

2-methyl-2-({4-[2-({4-methyl-6-[4-(trifluoromethoxy)phenyl]pyridazin-3-yl}amino)ethyl]-1,3-thiazol-2-yl}thio)propionic acid

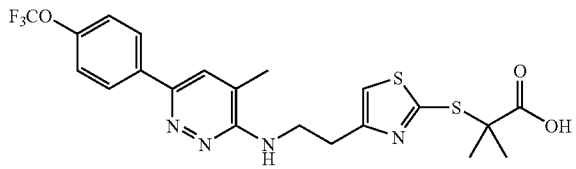

The title compound was obtained using 2-{[4-(2-aminoethyl)-1,3-thiazol-2-yl]thio}-2-methylpropionic acid tert-butyl ester synthesized in Example 7 and 3-chloro-4-methyl-6-[4-(trifluoromethoxy)phenyl]pyridazine synthesized in reference to non-patent reference [J. Med. Chem. 32, 528 (1989)] as starting materials and by operations similar to those of Example 162-1 and Example 162-3.

$^1$H-NMR (CDCl$_3$, 300 MHz) δ: 1.58 (6H, s), 2.41 (3H, s), 3.12-3.18 (2H, m), 4.03-4.09 (2H, m), 7.10 (1H, s), 7.24 (2H, d, J=8.8 Hz), 7.56 (1H, s), 7.82 (2H, d, J=8.8 Hz).

MS: 499 (M$^+$+1).

Example 238

2-{[4-(2-{[3-cyano-5-(4-fluorophenyl)pyridin-2-yl]amino}ethyl)-1,3-thiazol-2-yl]thio}-2-methylpropionic acid

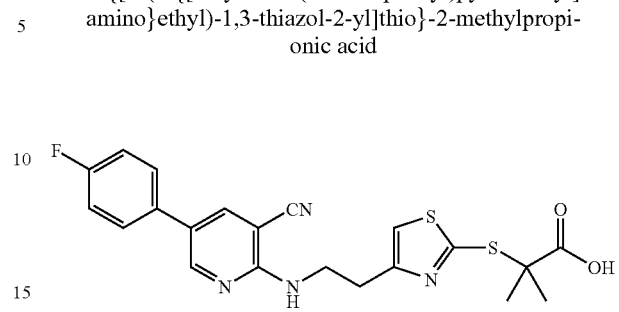

The title compound was obtained by an operation similar to that of Example 162-1 and using 2-{[4-(2-aminoethyl)-1,3-thiazol-2-yl]thio}-2-methylpropionic acid tert-butyl ester synthesized in Example 7 and 5-bromo-2-chloronicotinonitrile synthesized in reference to patent reference [WO0224694] and the like as starting materials, followed by operations similar to those of Example 162-2 and Example 162-3 and using 4-fluorophenylboric acid.

$^1$H-NMR (DMSO-d$_6$, 300 MHz) δ: 1.51 (6H, s), 3.04 (2H, t, J=7.2 Hz), 3.71-3.78 (2H, m), 7.24-7.37 (3H, m), 7.51 (1H, s), 7.67-7.72 (2H, m), 8.25 (1H, d, J=2.7 Hz), 8.63 (1H, d, J=2.7 Hz).

MS: 443 (M$^+$+1).

Example 239

2-{[4-(2-{[5-(4-chlorophenyl)-3-cyanopyridin-2-yl]amino}ethyl)-1,3-thiazol-2-yl]thio}-2-methylpropionic acid

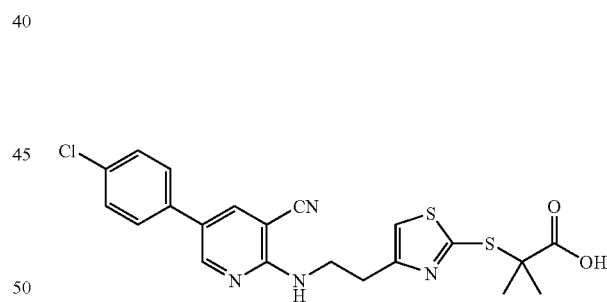

The title compound was obtained by an operation similar to that of Example 162-1 and using 2-{[4-(2-aminoethyl)-1,3-thiazol-2-yl]thio}-2-methylpropionic acid tert-butyl ester synthesized in Example 7 and 5-bromo-2-chloronicotinonitrile synthesized in reference to patent reference [WO0224694] and the like as starting materials, followed by operations similar to those of Example 162-2 and Example 162-3 and using 4-chlorophenylboric acid.

$^1$H-NMR (DMSO-d$_6$, 300 MHz) δ: 1.51 (6H, s), 3.03 (2H, t, J=7.2 Hz), 3.72-3.78 (2H, m), 7.39-7.51 (4H, m), 7.68-7.71 (2H, m), 8.29 (1H, d, J=2.4 Hz), 8.66 (1H, d, J=2.4 Hz).

MS: 459 (M$^+$+1).

Example 240

2-({4-[2-({3-cyano-5-[4-(trifluoromethyl)phenyl]pyridin-2-yl}amino)ethyl]-1,3-thiazol-2-yl}thio)-2-methylpropionic acid

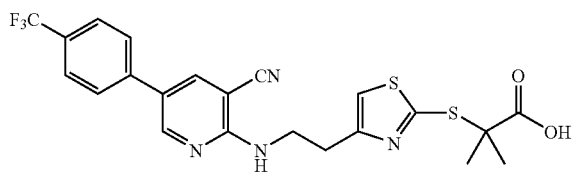

The title compound was obtained by an operation similar to that of Example 162-1 and using 2-{[4-(2-aminoethyl)-1,3-thiazol-2-yl]thio}-2-methylpropionic acid tert-butyl ester synthesized in Example 7 and 5-bromo-2-chloronicotinonitrile synthesized in reference to patent reference [WO0224694] and the like as starting materials, followed by operations similar to those of Example 162-2 and Example 162-3 and using 4-(trifluoromethyl)phenylboric acid.

$^1$H-NMR (CDCl$_3$, 300 MHz) δ: 1.67 (6H, s), 3.14 (2H, t, J=6.3 Hz), 3.95-4.01 (2H, m), 6.03 (1H, brs), 7.02 (1H, s), 7.57 (2H, d, J=8.4 Hz), 7.70 (2H, d, J=8.4 Hz), 7.90 (1H, d, J=2.7 Hz), 8.54 (1H, d, J=2.7 Hz).

MS: 493 (M$^+$+1).

Example 241

2-({4-[2-({3-cyano-5-[4-(trifluoromethoxy)phenyl]pyridin-2-yl}amino)ethyl]-1,3-thiazol-2-yl}thio)-2-methylpropionic acid

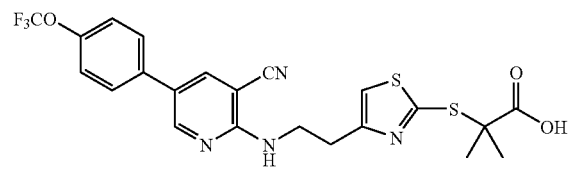

The title compound was obtained by an operation similar to that of Example 162-1 and using 2-{[4-(2-aminoethyl)-1,3-thiazol-2-yl]thio}-2-methylpropionic acid tert-butyl ester synthesized in Example 7 and 5-bromo-2-chloronicotinonitrile synthesized in reference to patent reference [WO0224694] and the like as starting materials, followed by operations similar to those of Example 162-2 and Example 162-3 and using 4-(trifluoromethoxy)phenylboric acid.

$^1$H-NMR (CDCl$_3$, 300 MHz) δ: 1.67 (6H, s), 3.13 (2H, t, J=6.3 Hz), 3.94-4.00 (2H, m), 5.98 (1H, brs), 7.01 (1H, s), 7.28-7.31 (2H, m), 7.46-7.49 (2H, m), 7.85 (1H, d, J=2.4 Hz), 8.49 (1H, d, J=2.4 Hz).

MS: 509 (M$^+$+1).

Example 242

2-{[4-(2-{[5-(4-chlorophenyl)pyridin-2-yl]amino}ethyl)-1,3-thiazol-2-yl]thio}-2-methylpropionic acid hydrochloride

Example 242-1

2-[(4-{2-[(5-bromopyridin-2-yl)amino]-2-oxoethyl}-1,3-thiazol-2-yl)thio]-2-methylpropionic acid tert-butyl ester

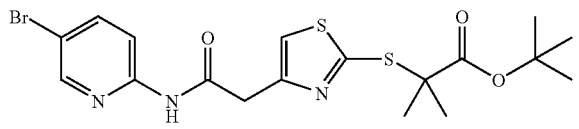

{2-[(2-tert-Butoxy-1,1-dimethyl-2-oxoethyl)thio]-1,3-thiazol-4-yl}acetic acid (16 g) obtained in Example 3 and 2-amino-5-bromopyridine (8.7 g) were dissolved in dichloromethane (100 mL), N-(3-dimethylaminopropyl)-N'-ethylcarbodiimide (EDC) hydrochloride (14.5 g) and 4-dimethylaminopyridine (DMAP) (9.2 g) was successively added, and the mixture was stirred at room temperature for 6 hr. The reaction mixture was concentrated under reduced pressure, and the residue was purified by silica gel chromatography (elution solvent; hexane:ethyl acetate=2:1) to give the title compound (22 g) as a white solid.

$^1$H-NMR (CDCl$_3$, 300 MHz) δ: 1.41 (9H, s), 1.56 (6H, s), 3.87 (2H, s), 7.24 (1H, s), 7.74-7.77 (1H, m), 8.11 (1H, d, J=9.0 Hz), 8.30 (1H, d, J=2.1 Hz), 9.07 (1H, brs).

Example 242-2

2-[(4-{2-[(5-bromopyridin-2-yl)amino]ethyl}-1,3-thiazol-2-yl)thio]-2-methylpropionic acid tert-butyl ester

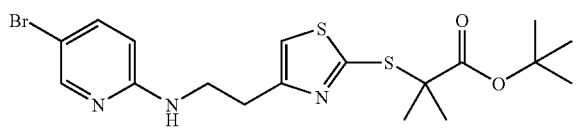

2-[(4-{2-[(5-Bromopyridin-2-yl)amino]-2-oxoethyl}-1,3-thiazol-2-yl)thio]-2-methylpropionic acid tert-butyl ester (12.5 g) obtained in Example 242-1 was dissolved in tetrahydrofuran (20 mL), 1 mol/L-borane/tetrahydrofuran complex (100 mL) was added under ice-cooling, and the mixture was stirred at room temperature for 12 hr. The reaction mixture was ice-cooled, and methanol (100 mL) was added dropwise. After warming to room temperature, the mixture was stirred for 1 hr. The reaction mixture was concentrated under reduced pressure, 2-aminoethanol (40 mL) was added, and the mixture was stirred at 70° C. for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane: ethyl acetate=10:1) to give the title compound (5.7 g) as a colorless oil.

$^1$H-NMR (CDCl$_3$, 300 MHz) δ: 1.43 (9H, s), 1.60 (6H, s), 3.02 (2H, t, J=6.3 Hz), 3.64-3.70 (2H, m), 5.20 (1H, brs), 6.45 (1H, d, J=8.7 Hz), 6.97 (1H, s), 7.40-7.44 (1H, m), 8.09 (1H, d, J=2.1 Hz).

MS: 460 (M$^+$+1).

Example 242-3

2-{[4-(2-{[5-(4-chlorophenyl)pyridin-2-yl]amino}-2-oxoethyl)-1,3-thiazol-2-yl]thio}-2-methylpropionic acid tert-butyl ester

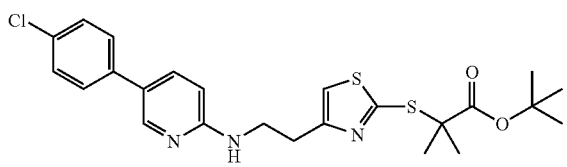

2-[(4-{2-[(5-Bromopyridin-2-yl)amino]ethyl}-1,3-thiazol-2-yl)thio]-2-methylpropionic acid tert-butyl ester (700 mg) obtained in Example 242-2 and 4-chlorophenylboric acid (358 mg) were dissolved in dioxane (8 mL) and 2 mol/L sodium carbonate (4 mL), tetrakis(triphenylphosphine)palladium (88 mg) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:2 to 2:1) to give the title compound (450 mg) as a colorless oil.

$^1$H-NMR (CDCl$_3$, 300 MHz) δ: 1.44 (9H, s), 1.61 (6H, s), 3.07 (2H, t, J=6.3 Hz), 3.72-3.78 (2H, m), 5.20 (1H, brs), 6.57 (1H, d, J=8.4 Hz), 7.00 (1H, s), 7.35-7.43 (4H, m), 7.56-7.60 (1H, m), 8.30 (1H, d, J=2.4 Hz).

MS: 490 (M$^+$+1).

Example 242-4

2-{[4-(2-{[5-(4-chlorophenyl)pyridin-2-yl]amino}ethyl)-1,3-thiazol-2-yl]thio}-2-methylpropionic acid hydrochloride

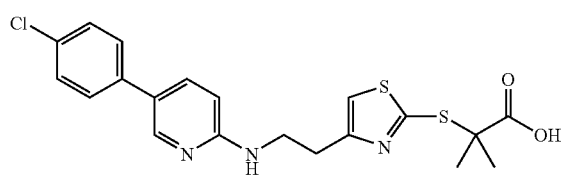

2-{[4-(2-{[5-(4-Chlorophenyl)pyridin-2-yl]amino}-2-oxoethyl)-1,3-thiazol-2-yl]thio}-2-methylpropionic acid tert-butyl ester (145 mg) obtained in Example 242-3 was dissolved in dichloromethane (2 mL), trifluoroacetic acid (2 mL) was added, and the mixture was stirred at room temperature for 20 hr. The reaction mixture was concentrated under reduced pressure, and the residue was purified by silica gel chromatography (elution solvent; chloroform:methanol=20:1). The obtained compound was dissolved in diethyl ether (4 mL), 4 mol/L hydrochloric acid-ethyl acetate (0.5 mL) was added, and the mixture was stirred at room temperature for 1 hr. The precipitated solid was collected by filtration to give the title compound (69 mg) as a white solid.

$^1$H-NMR (DMSO-d$_6$, 300 MHz) δ: 1.50 (6H, s), 3.09 (2H, t, J=6.9 Hz), 3.69-3.77 (2H, m), 7.18 (1H, d, J=9.6 Hz), 7.55-7.58 (2H, m), 7.63 (1H, s), 7.70-7.74 (2H, m), 8.20-8.28 (2H, m).

MS: 434 (M$^+$+1).

Example 243

2-methyl-2-({4-[2-({5-[4-(trifluoromethyl)phenyl]pyridin-2-yl}amino)ethyl]-1,3-thiazol-2-yl}thio)propionic acid hydrochloride

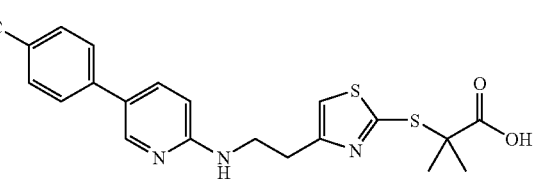

The title compound was obtained using 2-[(4-{2-[(5-bromopyridin-2-yl)amino]ethyl}-1,3-thiazol-2-yl)thio]-2-methylpropionic acid tert-butyl ester synthesized in Example 242-2 and 4-(trifluoromethyl)phenylboric acid as starting materials and by operations similar to those of Example 242-3 and Example 242-4.

$^1$H-NMR (DMSO-d$_6$, 300 MHz) δ: 1.50 (6H, s), 3.10 (2H, t, J=6.9 Hz), 3.79-3.81 (2H, m), 7.21 (1H, d, J=9.3 Hz), 7.64 (1H, s), 7.85 (2H, d, J=8.4 Hz), 7.92 (2H, d, J=8.4 Hz), 8.30-8.33 (2H, m).

MS: 468 (M$^+$+1).

Example 244

2-methyl-2-({4-[2-({5-[4-(trifluoromethoxy)phenyl]pyridin-2-yl}amino)ethyl]-1,3-thiazol-2-yl}thio)propionic acid hydrochloride

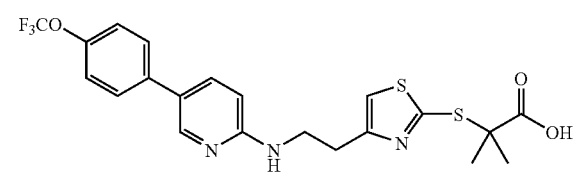

The title compound was obtained using 2-[(4-{2-[(5-bromopyridin-2-yl)amino]ethyl}-1,3-thiazol-2-yl)thio]-2-methylpropionic acid tert-butyl ester synthesized in Example 242-2 and 4-(trifluoromethoxy)phenylboric acid as starting materials and by operations similar to those of Example 242-3 and Example 242-4.

$^1$H-NMR (DMSO-d$_6$, 300 MHz) δ: 1.50 (6H, s), 3.09 (2H, t, J=6.9 Hz), 3.77-3.90 (2H, m), 7.18 (1H, d, J=9.6 Hz), 7.48-7.51 (2H, m), 7.63 (1H, s), 7.79-7.82 (2H, m), 8.21-8.28 (2H, m).

MS: 484 (M$^+$+1).

Example 245

2-methyl-2-({4-[2-(methyl{5-[4-(trifluoromethyl)phenyl]pyridin-2-yl}amino)ethyl]-1,3-thiazol-2-yl}thio)propionic acid hydrochloride

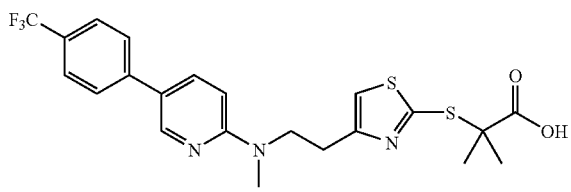

The title compound was obtained using 2-[(4-{2-[(5-bromopyridin-2-yl)amino]ethyl}-1,3-thiazol-2-yl)thio)-2-methylpropionic acid tert-butyl ester synthesized in Example 242-2 and 4-(trifluoromethyl)phenylboric acid as starting materials and by operations similar to those of Example 242-3, Example 163-1 and Example 164-2.

$^1$H-NMR (DMSO-d$_6$, 300 MHz) δ: 1.50 (6H, s), 3.08 (2H, t, J=6.6 Hz), 3.15 (3H, s), 4.01 (2H, t, J=6.6 Hz), 7.18 (1H, brd, J=9.6 Hz), 7.58 (1H, s), 7.84 (2H, d, J=8.4 Hz), 7.92 (2H, d, J=8.4 Hz), 8.26 (1H, brd, J=9.6 Hz), 8.33 (1H, d, J=2.1 Hz).

MS: 482 (M$^+$+1).

Example 246

2-{[4-(2-{[3-(4-chlorophenyl)-1H-pyrazol-5-yl]amino}ethyl)-1,3-thiazol-2-yl]thio}-2-methylpropionic acid

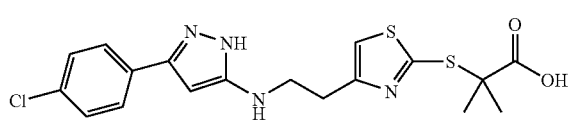

The compound obtained using {2-[(2-tert-butoxy-1,1-dimethyl-2-oxoethyl)thio]-1,3-thiazol-4-yl}acetic acid synthesized in Example 3 and 3-(4-chlorophenyl)-1H-pyrazole-5-amine as starting materials and by operations similar to those of Example 242-1 and Example 242-2 was treated with dichloromethane and trifluoroacetic acid, and the mixture was stirred at room temperature for 12 hr. The reaction mixture was concentrated under reduced pressure, ethyl acetate was added, and the mixture was washed with saturated aqueous sodium hydrogen carbonate solution (The objective compound was extracted in the saturated aqueous sodium hydrogen carbonate solution layer). Aqueous 10% citric acid solution was added to the aqueous layer, and the mixture was extracted with ethyl acetate. The organic layer was washed with water and dried over anhydrous sodium sulfate. The solvent was evaporated under reduced pressure to give the title compound.

$^1$H-NMR (CDCl$_3$, 300 MHz) δ: 1.74 (6H, s), 2.85 (2H, t, J=5.8 Hz), 3.05 (2H, t, J=5.8 Hz), 5.52 (1H, s), 6.87 (1H, s), 7.12-7.15 (2H, m), 7.42-7.46 (2H, m).

MS: 423 (M$^+$+1).

Example 247

2-{[4-(2-{[3-(4-chlorophenyl)-1-methyl-1H-pyrazol-5-yl]amino}ethyl)-1,3-thiazol-2-yl]thio}-2-methyl-propionic acid

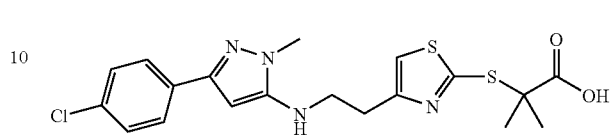

The compound obtained using {2-[(2-tert-butoxy-1,1-dimethyl-2-oxoethyl)thio]-1,3-thiazol-4-yl}acetic acid synthesized in Example 3 and 3-(4-chlorophenyl)-1-methyl-1H-pyrazole-5-amine as starting materials and by operations similar to those of Example 242-1 and Example 242-2 was treated with dichloromethane and trifluoroacetic acid, and the mixture was stirred at room temperature for 12 hr. The reaction mixture was concentrated under reduced pressure, and the residue was purified by silica gel chromatography (elution solvent; chloroform:methanol=20:1) to give the title compound.

$^1$H-NMR (CDCl$_3$, 300 MHz) δ: 1.66 (6H, s), 3.04 (2H, t, J=6.3 Hz), 3.37 (2H, t, J=6.3 Hz), 3.64 (3H, s), 5.66 (1H, s), 7.00 (1H, s), 7.26-7.30 (2H, m), 7.60-7.65 (2H, m).

MS: 437 (M$^+$+1).

Example 248

2-[(4-{2-[(5-chloro-1,3-benzoxazol-2-yl)amino]ethyl}-1,3-thiazol-2-yl)thio]-2-methylpropionic acid

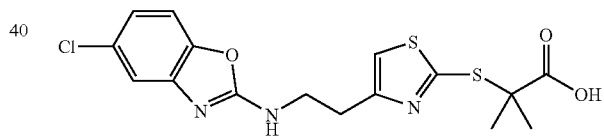

The compound obtained using {2-[(2-tert-butoxy-1,1-dimethyl-2-oxoethyl)thio]-1,3-thiazol-4-yl}acetic acid synthesized in Example 3 and 5-chloro-1,3-benzoxazol-2-amine as starting materials and by operations similar to those of Example 242-1 and Example 242-2 was treated with dichloromethane and trifluoroacetic acid, and the mixture was stirred at room temperature for 12 hr. The reaction mixture was concentrated under reduced pressure, and the residue was purified by silica gel chromatography (elution solvent; chloroform:methanol=20:1). Ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure to give the title compound.

$^1$H-NMR (CDCl$_3$, 300 MHz) δ: 1.67 (6H, s), 3.04 (2H, t, J=5.7 Hz), 3.70 (2H, brs), 6.98-7.02 (1H, m), 7.08 (1H, s), 7.17 (1H, d, J=8.7 Hz), 7.29-7.30 (2H, m)

MS: 398 (M$^+$+1). .

Example 249

2-methyl-2-({4-[2-({6-[4-(trifluoromethyl)phenyl]pyridin-2-yl}amino)ethyl]-1,3-thiazol-2-yl}thio)propionic acid

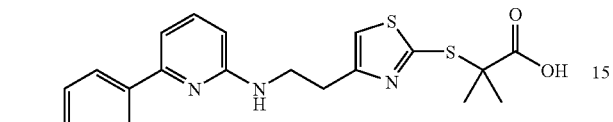

The title compound was obtained by an operation similar to that of Example 242-1 and using {2-[(2-tert-butoxy-1,1-dimethyl-2-oxoethyl)thio]-1,3-thiazol-4-yl}acetic acid synthesized in Example 3 and 6-bromopyridin-2-amine as starting materials, followed by operations similar to those of Example 242-3, Example 242-2 and Example 242-4 and using by 4-(trifluoromethyl)phenylboric acid.

$^1$H-NMR (DMSO-$d_6$, 300 MHz) δ: 1.52 (6H, s), 3.06 (2H, t, J=6.9 Hz), 3.73 (2H, t, J=6.9 Hz), 6.83 (1H, brs), 7.23 (1H, d, J=7.5 Hz), 7.56 (1H, s), 7.76 (1H, s), 7.88 (2H, d, J=8.1 Hz), 8.19 (2H, d, J=8.1 Hz).

MS: 468 (M$^+$+1).

Example 250

2-{[4-(2-{[4-(4-fluorophenyl)pyrimidin-2-yl]amino}ethyl)-1,3-thiazol-2-yl]thio}-2-methylpropionic acid hydrochloride

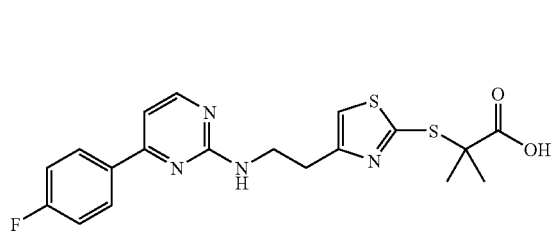

The title compound was obtained using 2-{[4-(2-aminoethyl)-1,3-thiazol-2-yl]thio}-2-methylpropionic acid tert-butyl ester synthesized in Example 7 and 4-(4-fluorophenyl)-2-(methylsulfonyl)pyrimidine synthesized in reference to patent reference [WO2004000762 A2] and the like as starting materials and by operations similar to those of Example 162-1 and Example 164-2.

$^1$H-NMR (DMSO-$d_6$, 300 MHz) δ: 1.50 (6H, s), 3.07 (2H, t, J=6.9 Hz), 3.81 (2H, brs), 7.39-7.45 (3H, m), 7.57 (1H, s), 8.30 (2H, brs), 8.46 (1H, d, J=6.0 Hz).

Example 251

MS: 419 (M$^+$+1).

2-methyl-2-({4-[2-({4-[4-(trifluoromethyl)phenyl]pyrimidin-2-yl}amino)ethyl]-1,3-thiazol-2-yl}thio)propionic acid hydrochloride

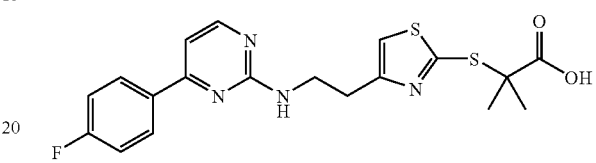

The title compound was obtained using 2-{[4-(2-aminoethyl)-1,3-thiazol-2-yl]thio}-2-methylpropionic acid tert-butyl ester synthesized in Example 7 and 2-(methylsulfonyl)-4-[4-(trifluoromethyl)phenyl]pyrimidine synthesized in reference to patent reference [WO2004000762 A2] and the like as starting materials and by operations similar to those of Example 162-1 and Example 164-2.

$^1$H-NMR (DMSO-$d_6$, 300 MHz) δ: 1.50 (6H, s), 3.04 (2H, t, J=7.2 Hz), 3.64-3.80 (2H, m), 7.32-7.34 (1H, m), 7.53 (1H, s), 7.89-7.91 (2H, m), 8.36 (2H, brs), 8.46 (1H, d, J=5.4 Hz).

MS: 469 (M$^+$+1).

Example 252

2-methyl-2-({4-[2-({4-[4-(trifluoromethoxy)phenyl]pyrimidin-2-yl}amino)ethyl]-1,3-thiazol-2-yl}thio)propionic acid hydrochloride

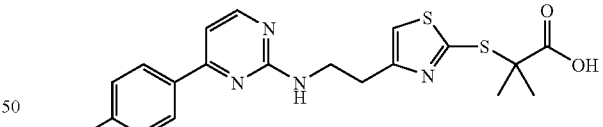

The title compound was obtained using 2-{[4-(2-aminoethyl)-1,3-thiazol-2-yl]thio}-2-methylpropionic acid tert-butyl ester synthesized in Example 7 and 2-(methylsulfonyl)-4-[4-(trifluoromethoxy)phenyl]pyrimidine synthesized in reference to patent reference [WO2004000762 A2] and the like as starting materials and by operations similar to those of Example 162-1 and Example 164-2.

$^1$H-NMR (DMSO-$d_6$, 300 MHz) δ: 1.50 (6H, s), 3.05 (2H, t, J=7.2 Hz), 3.85-3.90 (2H, m), 7.36 (1H, brs), 7.53-7.55 (3H, m), 8.30 (2H, brs), 8.44 (1H, d, J=6.0 Hz).

MS: 485 (M$^+$+1).

Example 253

2-methyl-2-({4-[2-({3-methyl-1-[4-(trifluoromethoxy)phenyl]-1H-pyrazol-5-yl}amino)ethyl]-1,3-thiazol-2-yl}thio)propionic acid hydrochloride

Example 253-1

2-methyl-2-({4-[2-({3-methyl-1-[4-(trifluoromethoxy)phenyl]-1H-pyrazol-5-yl}amino)ethyl]-1,3-thiazol-2-yl}thio)propionic acid tert-butyl ester

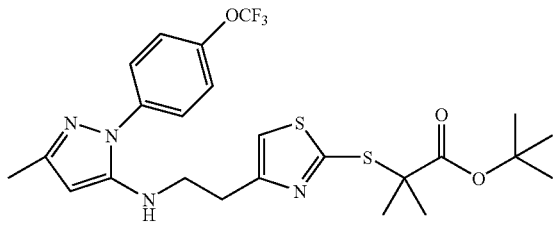

2-{[4-(2-Aminoethyl)-1,3-thiazol-2-yl]thio}-2-methylpropionic acid tert-butyl ester (3.0 g) synthesized in Example 7 was dissolved in N,N-dimethylformamide (50 mL), and diketene (0.88 g) was added dropwise under ice-cooling. After raising to room temperature, the mixture was stirred for one hour. The mixture was diluted with ethyl acetate, and the organic layer was washed with saturated brine and dried over anhydrous sodium sulfate. The solvent was evaporated under reduced pressure to give 2-({4-[2-(acetoacetylamino)ethyl]-1,3-thiazol-2-yl}thio)-2-methylpropionic acid tert-butyl ester (3.4 g) as a colorless oil. This compound was used in the next step without particular purification. [4-(Trifluoromethoxy)phenyl]hydrazine hydrochloride (390 mg) was dissolved in ethanol (8 mL), pulverized sodium hydroxide (65 mg) was added at room temperature. The insoluble material was filtered through celite, and the solvent was evaporated under reduced pressure. The residue was dissolved again in ethanol (8 mL), 2-({4-[2-(acetoacetylamino)ethyl]-1,3-thiazol-2-yl}thio)-2-methylpropionic acid tert-butyl ester (600 mg) obtained earlier was added at room temperature, and the mixture was stirred for 30 min. The solvent was evaporated under reduced pressure, water was added, and the mixture was extracted with ethyl acetate. The organic layer was washed with saturated brine and dried over anhydrous sodium sulfate. The solvent was evaporated under reduced pressure, and the residue was dissolved in tetrahydrofuran (8 mL), diphosphorus pentasulfide (345 mg) and sodium carbonate (329 mg) were added, and the mixture was heated under reflux for 2 hr. The solvent was evaporated, and the residue was purified by silica gel chromatography (elution solvent; hexane:ethyl acetate=4:1) to give the title compound (690 mg) as a colorless oil.

$^1$H-NMR (CDCl$_3$, 300 MHz) δ: 1.40 (9H, s) 1.49 (6H, s), 2.24 (3H, s), 3.05 (2H, t, J=6.3 Hz), 3.41-3.47 (2H, m), 4.45-4.49 (1H, m), 5.40 (1H, s), 7.01 (1H, s), 7.28-7.31 (2H, m), 7.53-7.59 (2H, m).

Example 253-2

2-methyl-2-({4-[2-({3-methyl-1-[4-(trifluoromethoxy)phenyl]-1H-pyrazol-5-yl}amino)ethyl]-1,3-thiazol-2-yl}thio)propionic acid hydrochloride

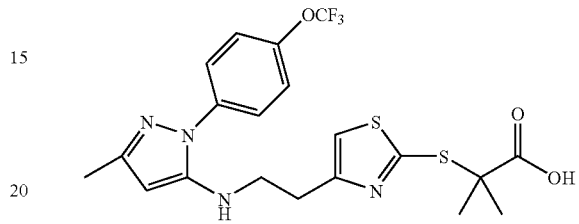

2-Methyl-2-({4-[2-({3-methyl-1-[4-(trifluoromethoxy)phenyl]-1H-pyrazol-5-yl}amino)ethyl]-1,3-thiazol-2-yl}thio)propionic acid tert-butyl ester (690 mg) synthesized in Example 253-1 was dissolved in dichloromethane (4 mL), trifluoroacetic acid (4 mL) was added, and the mixture was stirred at room temperature for 20 hr. The reaction mixture was concentrated under reduced pressure, and the residue was purified by silica gel chromatography (elution solvent; hexane:ethyl acetate=2:1 to 1:1). The obtained compound was dissolved in diethyl ether (4 mL), 4 mol/L hydrochloric acid-ethyl acetate (0.5 mL) was added, and the mixture was stirred at room temperature for 1 hr. The precipitated solid was collected by filtration to give the title compound (461 mg) as a white solid.

$^1$H-NMR (DMSO-d$_6$, 300 MHz) δ: 1.49 (6H, s), 2.20 (3H, s), 2.97 (2H, t, J=6.9 Hz), 3.37 (2H, t, J=6.9 Hz), 5.70 (1H, s), 7.52-7.56 (3H, m), 7.67-7.71 (2H, m).

MS: 487 (M$^+$+1).

Example 254

2-methyl-2-[(4-{2-[(3-methyl-1-phenyl-1H-pyrazol-5-yl)amino]ethyl}-1,3-thiazol-2-yl)thio]propionic acid hydrochloride

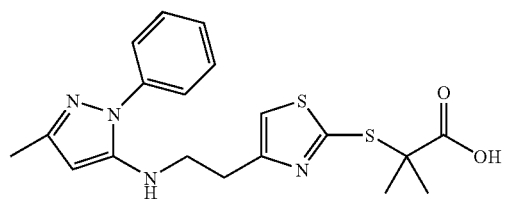

The title compound was obtained using 2-{[4-(2-aminoethyl)-1,3-thiazol-2-yl]thio}-2-methylpropionic acid tert-butyl ester synthesized in Example 7 and phenylhydrazine as starting materials and by an operation similar to that of Example 253.

$^1$H-NMR (DMSO-d$_6$, 300 MHz) δ: 1.50 (6H, s), 2.25 (3H, s), 2.96 (2H, t, J=6.9 Hz), 3.39-3.43 (2H, m), 5.80 (1H, s), 7.52-7.63 (6H, m).

MS: 403 (M$^+$+1).

Example 255

2-methyl-2-({4-[2-({3-methyl-1-[4-(trifluoromethyl)phenyl]-1H-pyrazol-5-yl}amino)ethyl]-1,3-thiazol-2-yl}thio)propionic acid hydrochloride

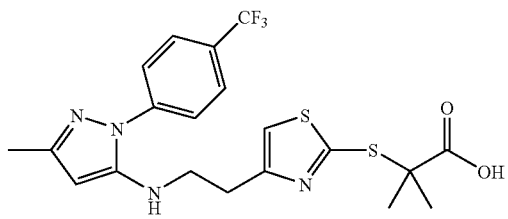

The title compound was obtained using 2-{[4-(2-aminoethyl)-1,3-thiazol-2-yl]thio}-2-methylpropionic acid tert-butyl ester synthesized in Example 7 and [4-(trifluoromethyl)phenyl]hydrazine as starting materials and by an operation similar to that of Example 253.

$^1$H-NMR (DMSO-d$_6$, 300 MHz) δ: 1.49 (6H, s), 2.17 (3H, s), 2.99 (2H, t, J=6.9 Hz), 3.34 (2H, t, J=6.9 Hz), 5.61 (1H, s), 7.53 (1H, s), 7.78-7.87 (4H, m).

MS: 471 (M$^+$+1).

Example 256

2-[(4-{2-[(4'-fluorobiphenyl-4-yl)amino]ethyl}-1,3-thiazol-2-yl)thio]-2-methylpropionic acid hydrochloride

Reference Example 4

N-(4-bromophenyl)-2-nitrobenzenesulfoneamide

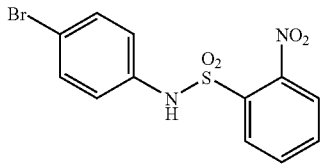

4-Bromoaniline (15.1 g) was dissolved in dichloromethane (300 mL), pyridine (7.73 g) and 2-nitrobenzenesulfonyl chloride (20.7 g) were added at room temperature, and the mixture was stirred for one hour. Water was added, and the organic layer was separated and dried over anhydrous magnesium sulfate. The solvent was evaporated under reduced pressure, and the residue was washed by suspending in ether. The obtained solid was vacuum dried to give the title compound (21.9 g) as a pale-yellow solid.

$^1$H-NMR (CDCl$_3$, 300 MHz) δ: 7.08-7.10 (2H, m), 7.38-7.41 (2H, m), 7.61-7.63 (1H, m), 7.69-7.71 (1H, m), 7.82-7.87 (2H, m).

Example 256-1

2-{[4-(2-{(4-bromophenyl)[(2-nitrophenyl)sulfonyl]amino}ethyl)-1,3-thiazol-2-yl]thio}-2-methylpropionic acid tert-butyl ester

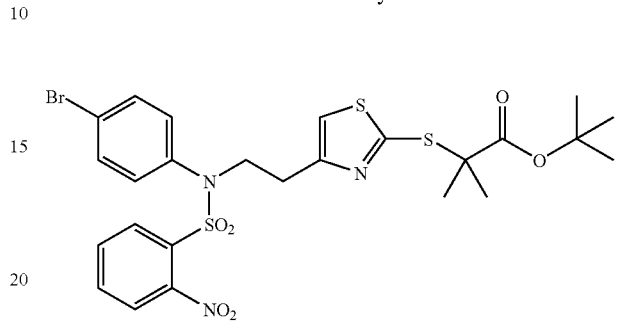

2-{[4-(2-Hydroxyethyl)-1,3-thiazol-2-yl]thio}-2-methylpropionic acid tert-butyl ester (5.0 g) synthesized in Example 4 and N-(4-bromophenyl)-2-nitrobenzenesulfoneamide (5.9 g) synthesized in Reference Example 4 were dissolved in dichloromethane (80 mL), triphenylphosphine (6.5 g) and diethyl diazodicarboxylate (40% toluene solution, 10.8 g) were added under ice-cooling, and the mixture was stirred at room temperature for 8 hr. The reaction mixture was concentrated under reduced pressure, and the residue was purified by silica gel chromatography (elution solvent; hexane:ethyl acetate=3:1 to 2:1) to give the title compound (8.4 g) as a colorless oil.

$^1$H-NMR (CDCl$_3$, 300 MHz) δ: 1.41 (9H, s), 1.51 (6H, s), 2.99 (2H, t, J=7.2 Hz), 4.09-4.16 (2H, m), 7.02-7.05 (2H, m), 7.11 (1H, s), 7.41-7.44 (2H, m), 7.51-7.69 (4H, m).

Example 256-2

2-{[4-(2-{(4'-fluorobiphenyl-4-yl)[(2-nitrophenyl)sulfonyl]amino}ethyl)-1,3-thiazol-2-yl]thio}-2-methylpropionic acid tert-butyl ester

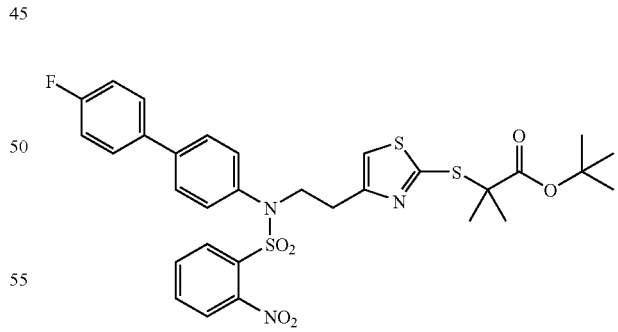

2-{[4-(2-{(4-Bromophenyl)[(2-nitrophenyl)sulfonyl]amino}ethyl)-1,3-thiazol-2-yl]thio}-2-methylpropionic acid tert-butyl ester (1.2 g) synthesized in Example 256-1 and 4-fluorophenylboric acid (0.31 g) were dissolved in dioxane (10 mL) and 2 mol/L sodium carbonate (5 mL), tetrakis(triphenylphosphine)palladium (0.11 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1 to 2:1) to give the title compound (1.1 g) as a colorless oil.

¹H-NMR (CDCl₃, 300 MHz) δ: 1.40 (9H, s), 1.51 (6H, s) 3.04 (2H, t, J=7.2 Hz), 4.15-4.20 (2H, m), 7.13-7.23 (5H, m), 7.45-7.63 (8H, m).

Example 256-3

2-[(4-{2-[(4'-fluorobiphenyl-4-yl)amino]ethyl}-1,3-thiazol-2-yl)thio]-2-methylpropionic acid tert-butyl ester

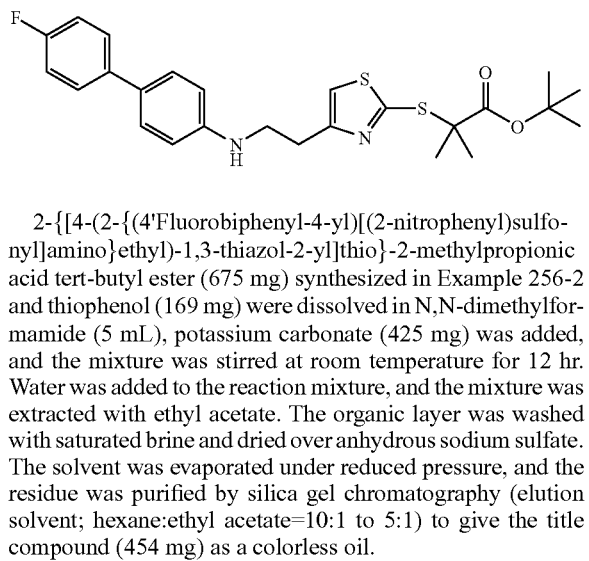

2-{[4-(2-{(4'Fluorobiphenyl-4-yl)[(2-nitrophenyl)sulfonyl]amino}ethyl)-1,3-thiazol-2-yl]thio}-2-methylpropionic acid tert-butyl ester (675 mg) synthesized in Example 256-2 and thiophenol (169 mg) were dissolved in N,N-dimethylformamide (5 mL), potassium carbonate (425 mg) was added, and the mixture was stirred at room temperature for 12 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (454 mg) as a colorless oil.

¹H-NMR (CDCl₃, 300 MHz) δ: 1.44 (9H, s), 1.61 (6H, s), 3.07 (2H, t, J=6.3 Hz), 3.53 (2H, t, J=6.3 Hz), 6.70-6.73 (2H, m), 7.01-7.09 (3H, m), 7.34-7.38 (2H, m), 7.44-7.49 (2H, m).

Example 256-4

2-[(4-{2-[(4'-fluorobiphenyl-4-yl)amino]ethyl}-1,3-thiazol-2-yl)thio]-2-methylpropionic acid hydrochloride

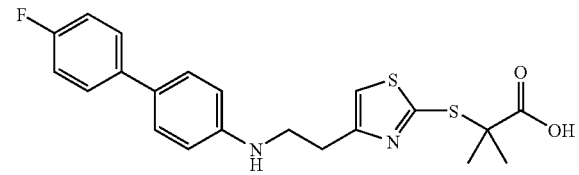

2-[(4-{2-[(4'Fluorobiphenyl-4-yl)amino]ethyl}-1,3-thiazol-2-yl)thio]-2-methylpropionic acid tert-butyl ester (300 mg) obtained in Example 256-3 was dissolved in dichloromethane (4 mL), trifluoroacetic acid (4 mL) was added, and the mixture was stirred at room temperature for 20 hr. The reaction mixture was concentrated under reduced pressure, and the residue was purified by silica gel chromatography (elution solvent; hexane:ethyl acetate=2:1 to 1:1). The obtained compound was dissolved in diethyl ether (4 mL), 4 mol/L hydrochloric acid-ethyl acetate (0.5 mL) was added, and the mixture was stirred at room temperature for 1 hr. The precipitated solid was collected by filtration to give the title compound (199 mg) as a white solid.

¹H-NMR (DMSO-d₆, 300 MHz) δ: 1.53 (6H, s), 3.07 (2H, t, J=7.3 Hz), 3.50 (2H, t, J=7.3 Hz), 7.09 (2H, brs), 7.22-7.28 (2H, m), 7.56-7.67 (5H, m).

MS: 417 (M⁺+1).

Example 257

2-[(4-{2-[(4'-fluorobiphenyl-4-yl)(methyl)amino]ethyl}-1,3-thiazol-2-yl)thio]-2-methylpropionic acid

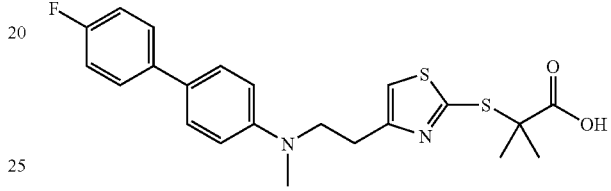

The title compound was obtained using 2-[(4-{2-[(4'-fluorobiphenyl-4-yl)amino]ethyl}-1,3-thiazol-2-yl)thio]-2-methylpropionic acid tert-butyl ester synthesized in Example 256-3 as a starting material and by an operation similar to that of Example 163.

¹H-NMR (CDCl₃, 300 MHz) δ: 1.64 (6H, s), 2.95 (3H, s), 3.06 (2H, t, J=7.2 Hz), 3.74 (2H, t, J=7.2 Hz), 6.74-6.77 (2H, m), 6.96 (1H, s), 7.05-7.11 (2H, m), 7.42-7.51 (4H, m).

MS: 431 (M⁺+1).

Example 258

2-methyl-2-{[4-(2-{[4'-(trifluoromethoxy)biphenyl-4-yl]amino}ethyl)-1,3-thiazol-2-yl]thio}propionic acid hydrochloride

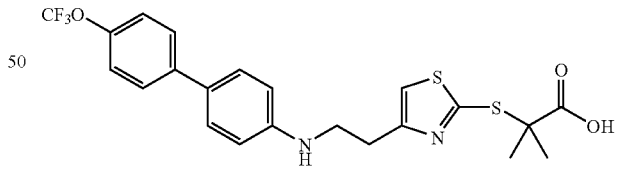

The title compound was obtained using 2-{[4-(2-{(4-bromophenyl)[(2-nitrophenyl)sulfonyl]amino}ethyl)-1,3-thiazol-2-yl]thio}-2-methylpropionic acid tert-butyl ester synthesized in Example 256-1 and 4-(trifluoromethoxy)phenylboric acid as starting materials and by operations similar to those of Example 256-2, Example 256-3 and Example 256-4.

¹H-NMR (DMSO-d₆, 300 MHz) δ: 1.53 (6H, s), 3.02 (2H, t, J=7.2 Hz), 3.45 (2H, t, J=7.2 Hz), 6.89-6.91 (2H, m), 7.37-7.39 (2H, m), 7.51-7.54 (3H, m), 7.68-7.71 (2H, m).

MS: 483 (M⁺+1).

Example 259

2-{[4-(2-{[6-(4-fluorophenyl)pyridin-3-yl]amino}ethyl)-1,3-thiazol-2-yl]thio}-2-methylpropionic acid

Reference Example 5

N-(6-chloropyridin-3-yl)-2-nitrobenzenesulfoneamide

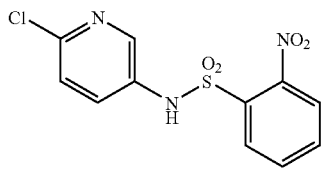

6-Chloropyridine-3-amine (3.0 g) was dissolved in dichloromethane (80 mL), pyridine (2.0 g) and 2-nitrobenzenesulfonyl chloride (5.4 g) was added at room temperature, and the mixture was stirred overnight. The precipitated solid was collected by filtration to give the title compound (5.6 g) as a purple solid.

$^1$H-NMR (DMSO-$d_6$, 300 MHz) δ: 7.48 (1H, d, J=8.7 Hz), 7.56-7.60 (1H, m), 7.85-7.90 (2H, m), 8.00-8.03 (2H, m), 8.16 (1H, d, J=2.7 Hz).

Example 259-1

2-{[4-(2-{[6-(4-fluorophenyl)pyridin-3-yl]amino}ethyl)-1,3-thiazol-2-yl]thio}-2-methylpropionic acid tert-butyl ester

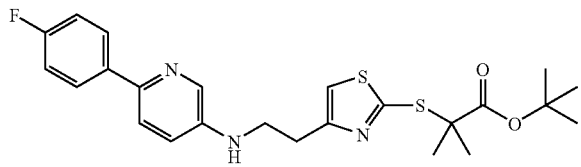

2-{[4-(2-Hydroxyethyl)-1,3-thiazol-2-yl]thio}-2-methylpropionic acid tert-butyl ester (5.0 g) synthesized in Example 4 and N-(6-chloropyridin-3-yl)-2-nitrobenzenesulfoneamide (5.2 g) synthesized in Reference Example 5 were dissolved in dichloromethane (70 mL) and tetrahydrofuran (70 mL), triphenylphosphine (6.5 g) and diethyl diazodicarboxylate (40% toluene solution, 10.7 g) were added under ice-cooling, and the mixture was stirred at room temperature for 8 hr. The reaction mixture was concentrated under reduced pressure, and the residue was purified by silica gel chromatography (elution solvent; hexane:ethyl acetate=2:1 to 1:1) to give the title compound 2-{[4-(2-{(6-chloropyridin-3-yl)[(2-nitrophenyl)sulfonyl]amino}ethyl)-1,3-thiazol-2-yl]thio}-2-methylpropionic acid tert-butyl ester containing impurity (7.8 g). This compound (2.0 g) and 4-fluorophenylboric acid (0.47 g) were dissolved in dioxane (16 mL) and 2 mol/L sodium carbonate (8 mL), tetrakis(triphenylphosphine)palladium (0.19 g) was added, and the mixture was refluxed for 4 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=3:1 to 3:2) to give 2-{[4-(2-{[6-(4-fluorophenyl)pyridin-3-yl][(2-nitrophenyl)sulfonyl]amino}ethyl)-1,3-thiazol-2-yl]thio}-2-methylpropionic acid tert-butyl ester containing impurity (1.9 g). This compound (1.9 g) and thiophenol (0.49 g) were dissolved in N,N-dimethylformamide (15 mL), potassium carbonate (1.2 g) was added, and the mixture was stirred at room temperature for 12 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (0.7 g) as a colorless oil.

$^1$H-NMR (CDCl$_3$, 300 MHz) δ: 1.44 (9H, s), 1.61 (6H, s), 3.07 (2H, t, J=6.2 Hz), 3.51-3.57 (2H, m), 4.56 (1H, brs), 7.00-7.12 (4H, m), 7.49 (1H, d, J=8.7 Hz), 7.83-7.88 (2H, m), 8.14 (1H, d, J=2.8 Hz).

Example 259-2

2-{[4-(2-{[6-(4-fluorophenyl)pyridin-3-yl]amino}ethyl)-1,3-thiazol-2-yl]thio}-2-methylpropionic acid

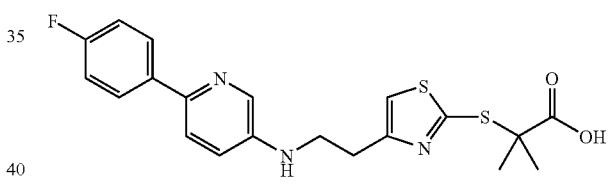

2-{[4-(2-{[6-(4-Fluorophenyl)pyridin-3-yl]amino}ethyl)-1,3-thiazol-2-yl]thio}-2-methylpropionic acid tert-butyl ester (270 mg) synthesized in Example 259-1 was dissolved in dichloromethane (4 mL), trifluoroacetic acid (4 mL) was added, and the mixture was stirred at room temperature for 12 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=2:1 to 1:1) to give the title compound (183 mg) as a white solid.

$^1$H-NMR (CDCl$_3$, 300 MHz) δ: 1.68 (6H, s), 3.04 (2H, t, J=6.3 Hz), 3.53 (2H, t, J=6.3 Hz), 6.95-6.99 (2H, m), 7.06-7.11 (2H, m), 7.42 (1H, d, J=8.7 Hz), 7.75-7.80 (2H, m), 8.22 (1H, d, J=3.0 Hz).

MS: 418 (M$^+$+1).

Example 260

2-{4-(2-{[6-(4-chlorophenyl)pyridin-3-yl]amino}ethyl)-1,3-thiazol-2-yl]thio}-2-methylpropionic acid

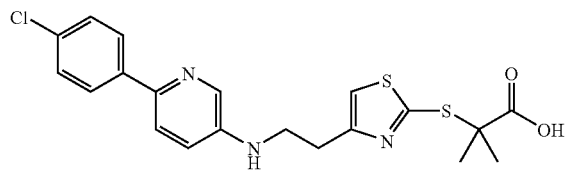

The title compound was obtained using 2-{[4-(2-{(6-chloropyridin-3-yl)[(2-nitrophenyl)sulfonyl]amino}ethyl)-1,3-thiazol-2-yl]thio}-2-methylpropionic acid tert-butyl ester synthesized during the operation of Example 259-1 and 4-chlorophenylboric acid as starting materials and by an operation similar to that of Example 259.

$^1$H-NMR (CDCl$_3$, 300 MHz) δ: 1.68 (6H, s), 3.06 (2H, t, J=6.3 Hz), 3.57 (2H, t, J=6.3 Hz), 6.95-6.99 (2H, m), 7.36-7.38 (2H, m), 7.47 (1H, d, J=8.7 Hz), 7.76-7.78 (2H, m), 8.19 (1H, d, J=3.0 Hz).

MS: 434 (M$^+$+1).

Example 261

2-methyl-2-({4-[2-({6-[4-(trifluoromethyl)phenyl]pyridin-3-yl}amino)ethyl]-1,3-thiazol-2-yl}thio)propionic acid

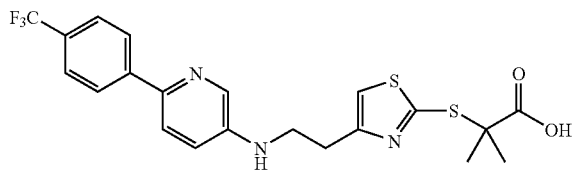

The title compound was obtained using 2-{[4-(2-{(6-chloropyridin-3-yl)[(2-nitrophenyl)sulfonyl]amino}ethyl)-1,3-thiazol-2-yl]thio}-2-methylpropionic acid tert-butyl ester synthesized during the operation of Example 259-1 and 4-(trifluoromethyl)phenylboric acid as starting materials and by an operation similar to that of Example 259.

$^1$H-NMR (CDCl$_3$, 300 MHz) δ: 1.68 (6H, s), 3.07 (2H, t, J=6.3 Hz), 3.56 (2H, t, J=6.3 Hz), 6.96-6.99 (2H, m), 7.54 (1H, d, J=8.7 Hz), 7.65 (2H, d, J=8.4 Hz), 7.94 (2H, d, J=8.4 Hz), 8.22 (1H, d, J=3.0 Hz).

MS: 468 (M$^+$+1).

Example 262

2-methyl-2-({4-[2-({6-[4-(trifluoromethoxy)phenyl]pyridin-3-yl}amino)ethyl]-1,3-thiazol-2-yl}thio)propionic acid

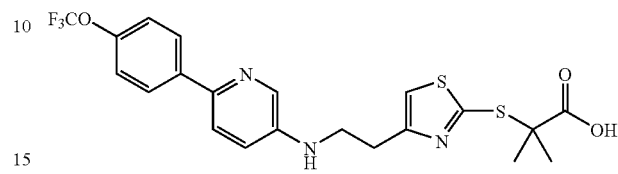

The title compound was obtained using 2-{[4-(2-{(6-chloropyridin-3-yl)[(2-nitrophenyl)sulfonyl]amino}ethyl)-1,3-thiazol-2-yl]thio}-2-methylpropionic acid tert-butyl ester synthesized during the operation of Example 259-1 and 4-(trifluoromethoxy)phenylboric acid as starting materials and by an operation similar to that of Example 259.

$^1$H-NMR (CDCl$_3$, 300 MHz) δ: 1.68 (6H, s), 3.05 (2H, t, J=6.3 Hz), 3.54 (2H, t, J=6.3 Hz), 6.95-6.99 (2H, m), 7.22-7.26 (2H, m), 7.46 (1H, d, J=8.6 Hz), 7.82-7.85 (2H, m), 8.21 (1H, d, J=2.9 Hz).

MS: 484 (M$^+$+1).

Example 263

2-[(4-{2-[[6-(4-fluorophenyl)pyridin-3-yl](methyl)amino]ethyl}-1,3-thiazol-2-yl)thio]-2-methylpropionic acid

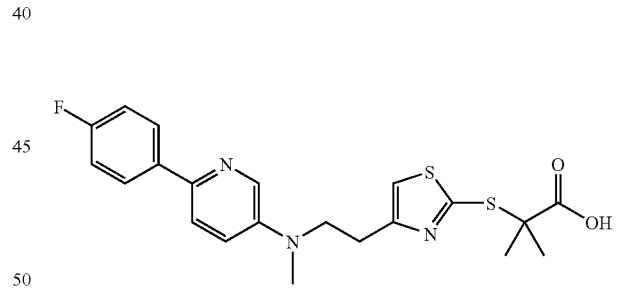

The title compound was obtained using 2-{[4-(2-{[6-(4-fluorophenyl)pyridin-3-yl]amino}ethyl)-1,3-thiazol-2-yl]thio}-2-methylpropionic acid tert-butyl ester synthesized during the operation of Example 259-1 as a starting material and by an operation similar to that of Example 163.

$^1$H-NMR (CDCl$_3$, 300 MHz) δ: 1.72 (6H, s), 3.02-3.05 (5H, m), 3.80 (2H, t, J=6.4 Hz), 6.91 (1H, s), 7.02-7.14 (3H, m), 7.49 (1H, d, J=8.9 Hz), 7.77-7.82 (2H, m), 8.27 (1H, d, J=3.0 Hz).

MS: 432 (M$^+$+1).

Example 264

2-[(4-{2-[[6-(4-chlorophenyl)pyridin-3-yl](methyl)amino]ethyl}-1,3-thiazol-2-yl)thio]-2-methylpropionic acid

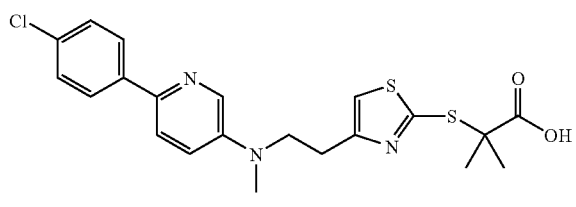

The title compound was obtained using 2-{[4-(2-{[6-(4-chlorophenyl)pyridin-3-yl]amino}ethyl)-1,3-thiazol-2-yl]thio}-2-methylpropionic acid tert-butyl ester synthesized during the operation of Example 260 as a starting material and by an operation similar to that of Example 163.

$^1$H-NMR (CDCl$_3$, 300 MHz) δ: 1.72 (6H, s), 3.02-3.05 (5H, m), 3.80 (2H, t, J=6.3 Hz), 6.91 (1H, s), 7.03 (1H, dd, J=3.0, 8.7 Hz), 7.37-7.41 (2H, m), 7.52 (1H, d, J=8.7 Hz), 7.75-7.77 (2H, m), 8.28 (1H, d, J=3.0 Hz).

MS: 448 (M$^+$+1).

Example 265

2-[(4-{2-[(5-ethylpyrimidin-2-yl)(heptyl)amino]ethyl}-1,3-thiazol-2-yl)thio]-2-methylpropionic acid

Example 265-1

2-[(4-{2-[(5-ethylpyrimidin-2-yl)amino]ethyl}-1,3-thiazol-2-yl)thio]-2-methylpropionic acid tert-butyl ester

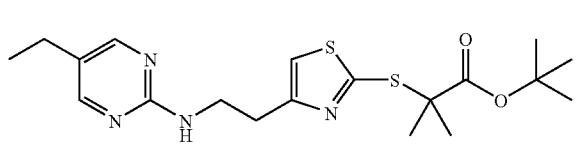

N,N-Diisopropylethylamine (13.1 g) was added to 2-{[4-(2-Aminoethyl)-1,3-thiazol-2-yl]thio}-2-methylpropionic acid tert-butyl ester (27.9 g) synthesized in Example 7 and 2-chloro-5-ethylpyrimidine (13.2 g), and the mixture was stirred at 130° C. for 20 hr. The reaction mixture was directly purified by silica gel chromatography (elution solvent; hexane:ethyl acetate=2:1 to 1:1) to give the title compound (23.5 g) as a slightly yellow solid.

$^1$H-NMR (CDCl$_3$, 300 MHz) δ: 1.19 (3H, t, J=7.8 Hz), 1.44 (9H, s), 1.59 (6H, s), 2.46 (2H, q, J=7.8 Hz), 3.06 (2H, t, J=6.6 Hz), 3.74-3.81 (2H, m), 5.26-5.30 (1H, m), 7.02 (1H, s), 8.13 (2H, s).

Example 265-2

2-[(4-{2-[(5-ethylpyrimidin-2-yl)(heptyl)amino]ethyl}-1,3-thiazol-2-yl)thio]-2-methylpropionic acid tert-butyl ester

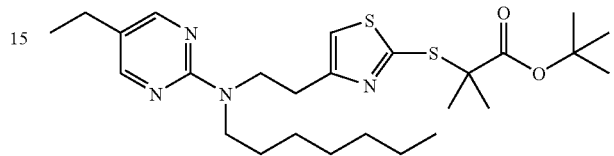

2-[(4-{2-[(5-Ethylpyrimidin-2-yl)amino]ethyl}-1,3-thiazol-2-yl)thio]-2-methylpropionic acid tert-butyl ester (8.90 g) synthesized in Example 265-1 and heptyl iodide (5.92 g) were dissolved in N,N-dimethylformamide (100 mL), potassium tert-butoxide (2.94 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=7:1) to give the title compound (6.20 g) as a colorless oil.

$^1$H-NMR (CDCl$_3$, 300 MHz) δ: 0.87 (3H, t, J=6.9 Hz), 1.16-1.35 (11H, m), 1.45 (9H, s), 1.48-1.57 (2H, m), 1.58 (6H, s), 2.45 (2H, q, J=7.5 Hz), 3.08 (2H, t, J=7.5 Hz), 3.43 (2H, t, J=7.5 Hz), 3.87 (2H, t, J=7.5 Hz), 7.02 (1H, s), 8.12 (2H, s).

Example 265-3

2-[(4-{2-[(5-ethylpyrimidin-2-yl)(heptyl)amino]ethyl}-1,3-thiazol-2-yl)thio]-2-methylpropionic acid

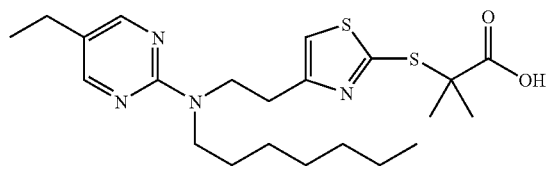

2-[(4-{2-[(5-Ethylpyrimidin-2-yl)(heptyl)amino]ethyl}-1,3-thiazol-2-yl)thio]-2-methylpropionic acid tert-butyl ester (6.20 g) obtained in Example 265-2 was dissolved in dichloromethane (60 mL), trifluoroacetic acid (12 mL) was added, and the mixture was stirred at room temperature for 20 hr. The reaction mixture was concentrated under reduced pressure, ethyl acetate was added, and the mixture was washed with saturated aqueous sodium hydrogen carbonate solution (the objective compound was extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (4.50 g) as a colorless oil.

$^1$H-NMR (CDCl$_3$, 300 MHz) δ: 0.87 (3H, t, J=6.9 Hz), 1.16-1.34 (11H, m), 1.51-1.57 (2H, m), 1.66 (6H, s), 2.45 (2H, q, J=7.5 Hz), 3.10 (2H, t, J=7.2 Hz), 3.46 (2H, t, J=7.2 Hz), 3.82 (2H, t, J=7.2 Hz), 6.96 (1H, s), 8.16 (2H, s).

MS: 451 (M$^+$+1).

Example 266

2-[(4-{2-[heptyl(pyrimidin-2-yl)amino]ethyl}-1,3-thiazol-2-yl)thio]-2-methylpropionic acid

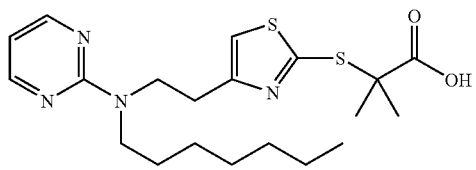

The title compound was obtained using 2-{[4-(2-aminoethyl)-1,3-thiazol-2-yl]thio}-2-methylpropionic acid tert-butyl ester synthesized in Example 7 and 2-chloropyrimidine as starting materials and by an operation similar to that of Example 265.

$^1$H-NMR (CDCl$_3$, 300 MHz) δ: 0.87 (3H, t, J=7.0 Hz), 1.22-1.32 (8H, m), 1.52-1.57 (2H, m), 1.66 (6H, s), 3.11 (2H, t, J=7.4 Hz), 3.47 (2H, t, J=7.6 Hz), 3.89 (2H, t, J=7.4 Hz), 6.46 (1H, s), 6.96 (1H, s), 8.29 (2H, d, J=4.8 Hz).

MS: 423 (M$^+$+1).

Example 267

2-[(4-{2-[heptyl(5-propylpyrimidin-2-yl)amino]ethyl}-1,3-thiazol-2-yl)thio]-2-methylpropionic acid

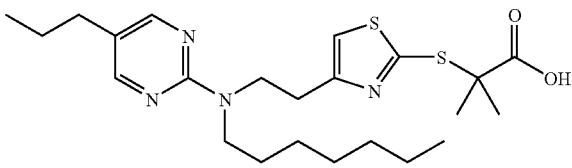

The title compound was obtained using 2-{[4-(2-aminoethyl)-1,3-thiazol-2-yl]thio}-2-methylpropionic acid tert-butyl ester synthesized in Example 7 and 2-chloro-5-propylpyrimidine as starting materials and by an operation similar to that of Example 265.

$^1$H-NMR (CDCl$_3$, 300 MHz) δ: 0.87 (3H, t, J=6.9 Hz), 1.20-1.32 (11H, m), 1.48-1.60 (4H, m), 1.66 (6H, s), 2.38 (2H, t, J=7.2 Hz), 3.10 (2H, t, J=7.2 Hz), 3.46 (2H, t, J=7.5 Hz), 3.82 (2H, t, J=7.2 Hz), 6.96 (1H, s), 8.13 (2H, s).

MS: 465 (M$^+$+1).

Example 268

2-{[4-(2-{heptyl[4-(trifluoromethyl)pyrimidin-2-yl]amino}ethyl)-1,3-thiazol-2-yl]thio}-2-methylpropionic acid

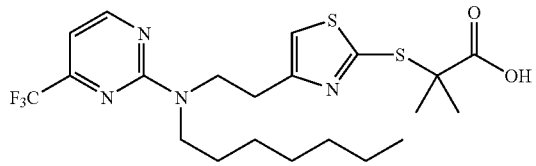

The title compound was obtained using 2-{[4-(2-aminoethyl)-1,3-thiazol-2-yl]thio}-2-methylpropionic acid tert-butyl ester synthesized in Example 7 and 2-chloro-4-(trifluoromethyl)pyrimidine as starting materials and by an operation similar to that of Example 265.

$^1$H-NMR (CDCl$_3$, 300 MHz) δ: 0.88 (3H, t, J=6.9 Hz), 1.23-1.37 (8H, m), 1.52-1.60 (2H, m), 1.65 (6H, s), 3.12 (2H, t, J=7.5 Hz), 3.53 (2H, t, J=7.2 Hz), 3.90 (2H, t, J=7.5 Hz), 6.74 (1H, d, J=5.1 Hz), 6.99 (1H, s), 8.48 (1H, d, J=5.1 Hz).

MS: 491 (M$^+$+1).

Example 269

2-[(4-{2-[(5-bromopyrimidin-2-yl)(heptyl)amino]ethyl}-1,3-thiazol-2-yl)thio]-2-methylpropionic acid

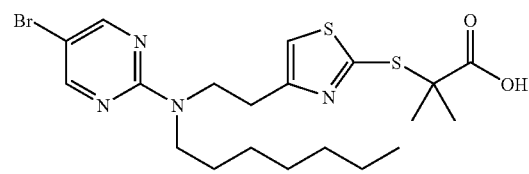

The title compound was obtained using 2-{[4-(2-aminoethyl)-1,3-thiazol-2-yl]thio}-2-methylpropionic acid tert-butyl ester synthesized in Example 7 and 5-bromo-2-chloropyrimidine as starting materials and by an operation similar to that of Example 265.

$^1$H-NMR (CDCl$_3$, 300 MHz) δ: 0.88 (3H, t, J=6.9 Hz), 1.20-1.37 (8H, m), 1.46-1.58 (2H, m), 1.66 (6H, s), 3.08 (2H, t, J=7.5 Hz), 3.44 (2H, t, J=7.5 Hz), 3.85 (2H, t, J=7.5 Hz), 6.96 (1H, s), 8.27 (2H, s).

MS: 503 (M$^+$+1).

Example 270

2-[(4-{2-[(6-chloropyrimidin-4-yl)(heptyl)amino]ethyl}-1,3-thiazol-2-yl)thio]-2-methylpropionic acid

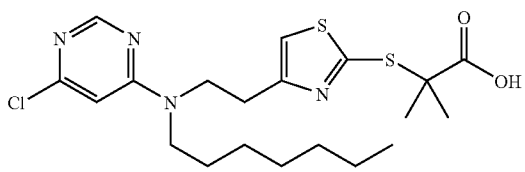

The title compound was obtained using 2-{[4-(2-aminoethyl)-1,3-thiazol-2-yl]thio}-2-methylpropionic acid tert-butyl ester synthesized in Example 7 and 4,6-dichloropyrimidine as starting materials and by an operation similar to that of Example 265.

$^1$H-NMR (CDCl$_3$, 300 MHz) δ: 0.89 (3H, t, J=6.9 Hz), 1.20-1.37 (8H, m), 1.47-1.60 (2H, m), 1.66 (6H, s), 3.07 (2H, t, J=7.2 Hz), 3.25-3.33 (2H, m), 3.81-3.89 (2H, m), 6.36 (1H, s), 7.01 (1H, s), 8.35 (2H, s).

MS: 457 (M$^+$+1).

Example 271

2-[(4-{2-[(6-chloropyridazin-3-yl)(heptyl)amino]ethyl}-1,3-thiazol-2-yl)thio]-2-methylpropionic acid

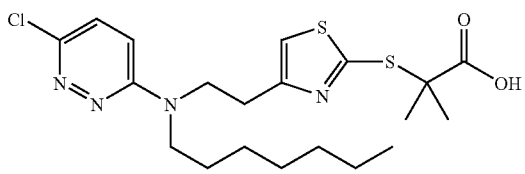

The title compound was obtained using 2-{[4-(2-aminoethyl)-1,3-thiazol-2-yl]thio}-2-methylpropionic acid tert-butyl ester synthesized in Example 7 and 3,6-dichloropyridazine as starting materials and by an operation similar to that of Example 265.

$^1$H-NMR (CDCl$_3$, 300 MHz) δ: 0.88 (3H, t, J=6.9 Hz), 1.20-1.36 (8H, m), 1.44-1.58 (2H, m), 1.64 (6H, s), 3.13 (2H, t, J=6.9 Hz), 3.34 (2H, t, J=7.5 Hz), 3.94 (2H, t, J=6.9 Hz), 6.75 (1H, d, J=9.3 Hz), 7.01 (1H, s), 7.18 (1H, d, J=9.3 Hz).

MS: 457 (M$^+$+1).

Example 272

2-[(4-{2-[heptyl(4-morpholin-4-ylpyrimidin-2-yl)amino]ethyl}-1,3-thiazol-2-yl)thio]-2-methylpropionic acid

Reference Example 6

4-(2-chloropyrimidin-4-yl)morpholine and 4-(4-chloropyrimidin-2-yl)morpholine

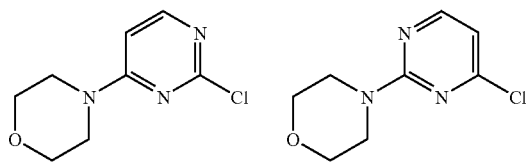

2,4-Dichloropyrimidine (5.0 g) and triethylamine (4.07 g) were dissolved in tetrahydrofuran (50 mL), morpholine (2.92 g) was added dropwise, and the mixture was stirred at room temperature for 1 hr. The reaction mixture was concentrated under reduced pressure, and the residue was purified by silica gel chromatography (elution solvent; hexane:ethyl acetate=1:1 to 1:3) to give, as a white solid, the 4-(2-chloropyrimidin-4-yl)morpholine (5.2 g) as a high polar compound and 4-(4-chloropyrimidin-2-yl)morpholine (1.4 g) as a low polar compound.

4-(2-chloropyrimidin-4-yl)morpholine $^1$H-NMR (CDCl$_3$, 300 MHz) δ: 3.60-3.69 (4H, m), 3.75-3.81 (4H, m), 6.38 (1H, d, J=6.3 Hz), 8.07 (1H, d, J=6.3 Hz).

4-(4-chloropyrimidin-2-yl)morpholine $^1$H-NMR (CDCl$_3$, 300 MHz) δ: 3.73-3.77 (4H, m), 3.78-3.83 (4H, m), 6.38 (1H, d, J=5.2 Hz), 8.07 (1H, d, J=5.2 Hz).

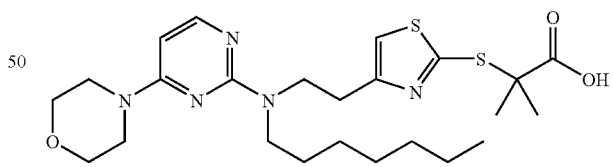

The title compound was obtained using 2-{[4-(2-aminoethyl)-1,3-thiazol-2-yl]thio}-2-methylpropionic acid tert-butyl ester synthesized in Example 7 and 4-(2-chloropyrimidin-4-yl)morpholine synthesized in Reference Example 6 as starting materials and by an operation similar to that of Example 265.

$^1$H-NMR (DMSO-d$_6$, 300 MHz) δ: 0.86 (3H, t, J=6.6 Hz), 1.15-1.36 (8H, m), 1.43-1.56 (8H, m), 3.00-3.06 (2H, m), 3.35-3.40 (2H, m), 3.68-4.06 (10H, m), 6.54 (1H, d, J=7.4 Hz), 7.55 (1H, s), 7.86 (1H, d, J=7.4 Hz).

MS: 508 (M$^+$+1).

Example 273

2-[(4-{2-[heptyl(2-morpholin-4-ylpyrimidin-4-yl)amino]ethyl}-1,3-thiazol-2-yl)thio]-2-methylpropionic acid

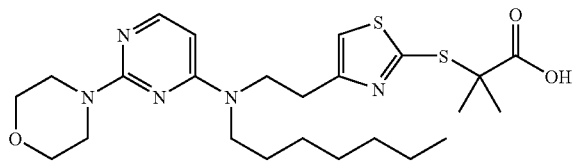

The title compound was obtained using 2-{[4-(2-aminoethyl)-1,3-thiazol-2-yl]thio}-2-methylpropionic acid tert-butyl ester synthesized in Example 7 and 4-(4-chloropyrimidin-2-yl)morpholine synthesized in Reference Example 6 as starting materials and by an operation similar to that of Example 265.

$^1$H-NMR (DMSO-d$_6$, 300 MHz) δ: 0.83 (3H, t, J=6.6 Hz), 1.15-1.26 (8H, m), 1.41-1.54 (8H, m), 2.96-3.03 (2H, m), 3.36-4.00 (12H, m), 6.31-6.41 (1H, m), 7.50 (1H, s), 7.77-7.81 (1H, m).
MS: 508 (M$^+$+1).

Example 274

2-[(4-{2-[heptyl(5-methylpyrimidin-2-yl)amino]ethyl}-1,3-thiazol-2-yl)thio]-2-methylpropionic acid

Reference Example 7

5-methylpyrimidine-2(1H)-thione

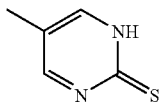

3-(Dimethylamino)-2-methylacrylaldehyde (10.0 g) and thiourea (13.5 g) was dissolved in ethanol (200 mL), sodium ethoxide (12.0 g) was added, and the mixture was refluxed for 8 hr. After cooling, the reaction mixture was concentrated under reduced pressure. The obtained residue was dissolved in water, and 1 mol/L hydrochloric acid was added. The precipitated solid was collected by filtration, and dried under reduced pressure to give the title compound (7.2 g) as a yellow solid.

$^1$H-NMR (DMSO-d$_6$, 300 MHz) δ: 2.07 (3H, s), 8.17 (2H, s), 13.7 (1H, brs).

Reference Example 8

5-methyl-2-(methylthio)pyrimidine

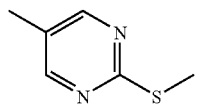

5-Methylpyrimidine-2(1H)-thione (7.2 g) obtained in Reference Example 7 was dissolved in methanol (60 mL) and aqueous sodium hydroxide solution (1 mol/L, 60 mL), methyl iodide (8.1 g) was added, the mixture was stirred at room temperature for 1 hr. The reaction mixture was concentrated under reduced pressure, water was added, and the mixture was extracted with diethyl ether. The organic layer was washed with saturated brine and dried over anhydrous sodium sulfate, and the solvent was evaporated under reduced pressure to give the title compound (6.6 g) as a slightly yellow oil.

$^1$H-NMR (CDCl$_3$, 300 MHz) δ: 2.24 (3H, s), 2.56 (3H, s), 8.37 (2H, s).

Reference Example 9

5-methyl-2-(methylsulfonyl)pyrimidine

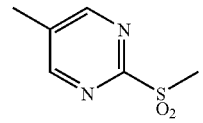

5-Methyl-2-(methylthio)pyrimidine (6.0 g) obtained in Reference Example 8 was dissolved in dichloromethane (100 mL), m-chloroperbenzoic acid (30 g) was added after ice-cooling, and the mixture was stirred at 0° C. for 3 hr. Aqueous 10% sodium sulfite solution was added to the reaction mixture, and the mixture was extracted with dichloromethane. The organic layer was washed with saturated aqueous sodium hydrogen carbonate solution and saturated brine, and dried over anhydrous sodium sulfate. The solvent was evaporated under reduced pressure to give the title compound (7.3 g) as a white solid.

$^1$H-NMR (CDCl$_3$, 300 MHz) δ: 2.47 (3H, s), 3.35 (3H, s), 8.76 (2H, s).

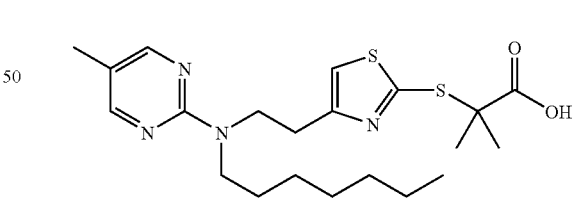

The title compound was obtained using 2-{[4-(2-aminoethyl)-1,3-thiazol-2-yl]thio}-2-methylpropionic acid tert-butyl ester synthesized in Example 7 and 5-methyl-2-(methylsulfonyl)pyrimidine synthesized in Reference Example 9 as starting materials and by an operation similar to that of Example 265.

¹H-NMR (CDCl₃, 300 MHz) δ: 0.87 (3H, t, J=7.2 Hz), 1.18-1.32 (8H, m), 1.45-1.58 (2H, m), 1.66 (6H, s), 2.11 (3H, s), 3.10 (2H, t, J=6.9 Hz), 3.45 (2H, t, J=7.2 Hz), 3.87 (2H, t, J=6.9 Hz), 6.95 (1H, s), 8.14 (2H, s).

MS: 437 (M⁺+1).

Example 275

2-[(4-{2-[(4-ethoxypyrimidin-2-yl)(heptyl)amino]ethyl}-1,3-thiazol-2-yl)thio]-2-methylpropionic acid Reference Example 10

4-ethoxy-2-(methylthio)pyrimidine

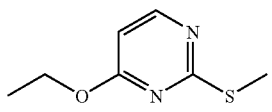

4-Chloro-2-(methylthio)pyrimidine (3.0 g) was dissolved in ethanol (30 mL), sodium ethoxide (2.54 g) was added, and the mixture was stirred at 60° C. for 10 hr. The reaction mixture was cooled, and the solvent was concentrated under reduced pressure. Water was added, and the mixture was extracted with diethyl ether. The organic layer was washed with saturated brine and dried over anhydrous sodium sulfate. The solvent was evaporated under reduced pressure to give the title compound (3.0 g) as a slightly yellow oil.

¹H-NMR (CDCl₃, 300 MHz) δ: 1.39 (3H, t, J=7.5 Hz), 2.54 (3H, s), 4.42 (2H, q, J=7.5 Hz), 6.36 (1H, d, J=6.0 Hz), 8.20 (1H, d, J=6.0 Hz).

Reference Example 11

5-ethoxy-2-(methylsulfonyl)pyrimidine

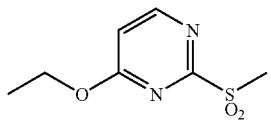

4-Ethoxy-2-(methylthio)pyrimidine (3.0 g) obtained in Reference Example 10 was dissolved in dichloromethane (100 mL), m-chloroperbenzoic acid (12.2 g) was added after ice-cooling, and the mixture was stirred at 0° C. for 5 hr. Aqueous 10% sodium sulfite solution was added to the reaction mixture, and the mixture was extracted with dichloromethane. The organic layer was washed with saturated aqueous sodium hydrogen carbonate solution and saturated brine, and dried over anhydrous sodium sulfate. The solvent was evaporated under reduced pressure to give the title compound (3.2 g) as a white solid.

¹H-NMR (CDCl₃, 300 MHz) δ: 1.44 (3H, t, J=7.1 Hz), 3.34 (3H, s), 4.55 (2H, q, J=7.1 Hz), 6.89 (1H, d, J=5.9 Hz), 8.54 (1H, d, J=5.9 Hz).

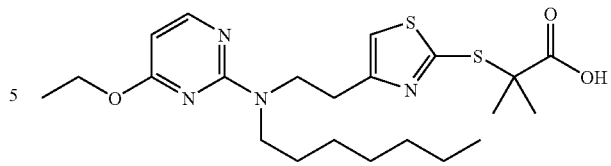

The title compound was obtained using 2-{[4-(2-aminoethyl)-1,3-thiazol-2-yl]thio}-2-methylpropionic acid tert-butyl ester synthesized in Example 7 and 4-ethoxy-2-(methylsulfonyl)pyrimidine synthesized in Reference Example 11 as starting materials and by an operation similar to that of Example 265.

¹H-NMR (CDCl₃, 300 MHz) δ: 0.87 (3H, t, J=6.6 Hz), 1.16-1.35 (8H, m), 1.40 (3H, t, J=7.2 Hz), 1.61 (6H, s), 3.12-3.17 (2H, m), 3.53 (2H, t, J=7.5 Hz), 3.94-3.99 (2H, m), 4.40 (2H, q, J=7.2 Hz), 6.10 (1H, d, J=6.0 Hz), 7.00 (1H, s), 8.16 (1H, d, J=6.0 Hz).

MS: 467 (M⁺+1).

Example 276

2-{[4-(2-{heptyl[4-(2,2,2-trifluoroethoxy)pyrimidin-2-yl]amino}ethyl)-1,3-thiazol-2-yl]thio}-2-methylpropionic acid Reference Example 12

2-(methylthio)-4-(2,2,2-trifluoroethoxy)pyrimidine

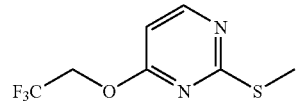

2,2,2-Trifluoroethanol (3.74 g) was dissolved in N,N-dimethylformamide (50 mL), sodium hydride (about 60% in oil) (1.37 g) was added under ice-cooling, and the mixture was stirred at room temperature for 20 min. After ice-cooling again, 4-chloro-2-(methylthio)pyrimidine (5.0 g) was added, and the mixture was stirred at 0° C. for 1 hr. Saturated aqueous ammonia chloride solution was added to the reaction mixture, and the mixture was extracted with ethyl acetate. The organic layer was washed with saturated brine and dried over anhydrous sodium sulfate. The solvent was evaporated under reduced pressure to give the title compound (5.1 g) as a slightly yellow oil.

¹H-NMR (CDCl₃, 300 MHz) δ: 2.55 (3H, s), 4.79 (2H, q, J=8.3 Hz), 6.53 (1H, d, J=5.8 Hz), 8.33 (1H, d, J=5.8 Hz).

Reference Example 13

2-(methylsulfonyl)-4-(2,2,2-trifluoroethoxy)pyrimidine

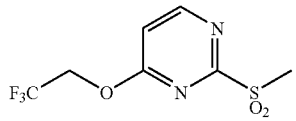

2-(Methylthio)-4-(2,2,2-trifluoroethoxy)pyrimidine (5.1 g) obtained in Reference Example 12 was dissolved in dichloromethane (100 mL), m-chloroperbenzoic acid (21.0 g) was added after ice-cooling, and the mixture was stirred at 0° C. for 5 hr. Aqueous 10% sodium sulfite solution was added to the reaction mixture, and the mixture was extracted with dichloromethane. The organic layer was washed with saturated aqueous sodium hydrogen carbonate solution and saturated brine, and dried over anhydrous sodium sulfate. The solvent was evaporated under reduced pressure to give the title compound (4.8 g) as a colorless oil.

¹H-NMR (CDCl₃, 300 MHz) δ: 3.36 (3H, s), 4.92 (2H, q, J=8.2 Hz), 7.10 (1H, d, J=5.6 Hz), 8.69 (1H, d, J=5.6 Hz).

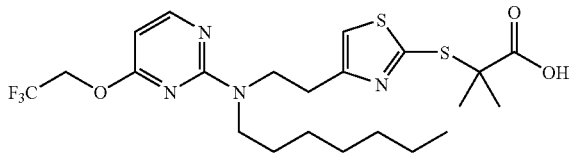

The title compound was obtained using 2-{[4-(2-aminoethyl)-1,3-thiazol-2-yl]thio}-2-methylpropionic acid tert-butyl ester synthesized in Example 7 and 2-(methylsulfonyl)-4-(2,2,2-trifluoroethoxy)pyrimidine synthesized in Reference Example 13 as starting materials and by an operation similar to that of Example 265.

¹H-NMR (CDCl₃, 300 MHz) δ: 0.88 (3H, t, J=6.9 Hz), 1.19-1.34 (8H, m), 1.50-1.59 (2H, m), 1.65 (6H, s), 3.10 (2H, t, J=6.9 Hz), 3.45 (2H, t, J=7.4 Hz), 3.87 (2H, t, J=6.9 Hz), 4.72 (2H, q, J=8.5 Hz), 6.07 (1H, d, J=5.5 Hz), 6.97 (1H, s), 8.12 (1H, d, J=5.5 Hz).

MS: 521 (M⁺+1).

Example 277

2-[(4-{2-[(3,4-dicyanophenyl)(heptyl)amino]ethyl}-1,3-thiazol-2-yl)thio]-2-methylpropionic acid

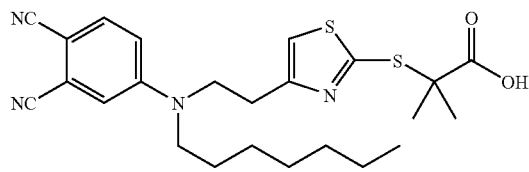

The compound obtained using 2-{[4-(2-aminoethyl)-1,3-thiazol-2-yl]thio}-2-methylpropionic acid tert-butyl ester synthesized in Example 7 and 4-fluorophthalonitrile as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile) to give the title compound.

¹H-NMR (CDCl₃, 270 MHz) δ: 0.86 (3H, t, J=7.0 Hz), 1.15-1.49 (10H, m), 1.53 (6H, s), 2.96 (2H, t, J=7.0 Hz), 3.73 (2H, t, J=7.0 Hz), 7.00 (1H, dd, J=2.2, 8.9 Hz), 7.27 (1H, d, J=2.2 Hz), 7.49 (1H, s), 7.73 (1H, d, J=8.9 Hz).

MS: 471 (M⁺+1).

Example 278

2-[(4-{2-[(3-chloro-4-cyanophenyl)(heptyl)amino]ethyl}-1,3-thiazol-2-yl)thio]-2-methylpropionic acid

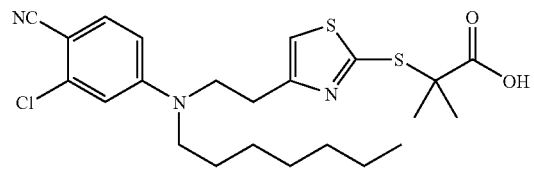

The compound obtained using 2-{[4-(2-aminoethyl)-1,3-thiazol-2-yl]thio}-2-methylpropionic acid tert-butyl ester synthesized in Example 7 and 2-chloro-4-fluorobenzonitrile as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

¹H-NMR (CDCl₃, 270 MHz) δ: 0.89 (3H, t, J=7.0 Hz), 1.18-1.60 (10H, m), 1.65 (6H, s), 3.03 (2H, t, J=7.6 Hz), 3.23 (2H, t, J=7.6 Hz), 3.69 (2H, t, J=7.0 Hz), 6.51 (1H, dd, J=2.4, 8.9 Hz), 6.60 (1H, d, J=2.4 Hz), 7.99 (1H, s), 7.42 (1H, d, J=8.9 Hz).

MS: 480 (M⁺+1).

Example 279

2-[(4-{2-[(2-chloro-4-cyanophenyl)(heptyl)amino]ethyl}-1,3-thiazol-2-yl)thio]-2-methylpropionic acid

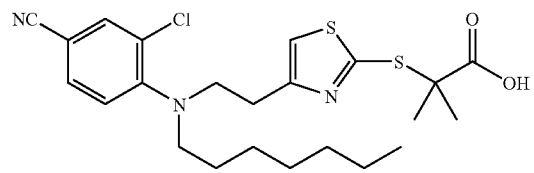

The compound obtained using 2-{[4-(2-aminoethyl)-1,3-thiazol-2-yl]thio}-2-methylpropionic acid tert-butyl ester synthesized in Example 7 and 3-chloro-4-fluorobenzonitrile as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (CDCl$_3$, 270 MHz) δ: 0.86 (3H, t, J=7.0 Hz), 1.10-1.53 (10H, m), 1.61 (6H, s), 2.97 (2H, t, J=7.6 Hz), 3.19 (2H, t, J=7.6 Hz), 3.59 (2H, t, J=7.0 Hz) 6.90 (1H, s), 7.05 (1H, d, J=8.4 Hz), 7.45 (1H, dd, J=2.2, 8.4 Hz), 7.59 (1H, d, J=2.2 Hz).

MS: 480 (M$^+$+1).

Example 280

2-[(4-{2-[[3-chloro-5-(trifluoromethyl)pyridin-2-yl](heptyl)amino]ethyl}-1,3-thiazol-2-yl)thio]-2-methylpropionic acid

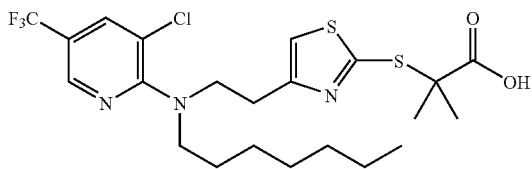

The compound obtained using 2-{[4-(2-aminoethyl)-1,3-thiazol-2-yl]thio}-2-methylpropionic acid tert-butyl ester synthesized in Example 7 and 2,3-dichloro-5-(trifluoromethyl)pyridine as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (CDCl$_3$, 300 MHz) δ: 0.87 (3H, t, J=7.0 Hz), 1.14-1.38 (8H, m), 1.45-1.72 (8H, m), 3.09 (2H, t, J=7.0 Hz), 3.47 (2H, t, J=7.0 Hz), 3.85 (2H, t, J=7.0 Hz) 6.92 (1H, s), 7.69 (1H, d, J=2.2 Hz), 8.33 (1H, d, J=2.2 Hz).

MS: 524 (M$^+$+1).

Example 281

2-[(4-{2-[(5-carbamoyl-3-chloropyridin-2-yl)(heptyl)amino]ethyl}-1,3-thiazol-2-yl)thio]-2-methylpropionic acid hydrochloride Example 281-1

2-[(4-{2-[(3-chloro-5-methoxycarbonylpyridin-2-yl)(heptyl)amino]ethyl}-1,3-thiazol-2-yl)thio]-2-methylpropionic acid tert-butyl ester

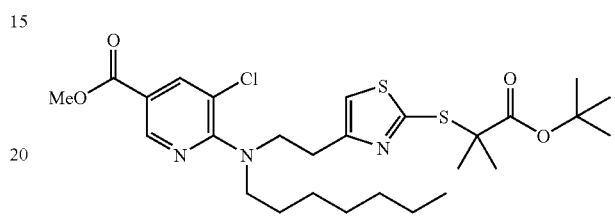

2-[(4-{2-[(3-Chloro-5-methoxycarbonylpyridin-2-yl)amino]ethyl}-1,3-thiazol-2-yl)thio]-2-methylpropionic acid tert-butyl ester (5.14 g) was obtained using 2-{[4-(2-aminoethyl)-1,3-thiazol-2-yl]thio}-2-methylpropionic acid tert-butyl ester (5 g) synthesized in Example 7 and 2,3-dichloro-5-(methoxycarbonyl)pyridine (3.41 g) as starting materials and by an operation similar to that of Example 265-1. The obtained compound (5.14 g) and heptyl iodide (1.86 mL) were dissolved in N,N-dimethylformamide (40 mL), potassium tert-butoxide (1.34 g) was added thereto, and the mixture was stirred at room temperature for 12 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=9:1) to give the title compound (2.59 g) as a yellow oil.

$^1$H-NMR (CDCl$_3$, 270 MHz) δ: 0.87 (3H, t, J=7.0 Hz), 1.14-1.38 (8H, m), 1.50-1.72 (14H, m), 3.09 (2H, t, J=7.0 Hz), 3.51 (2H, t, J=7.0 Hz), 3.85-3.97 (4H, m), 6.97 (1H, s), 8.04 (1H, d, J=1.9 Hz), 8.67 (1H, d, J=1.9 Hz).

MS: 570 (M$^+$+1).

Example 281-2

2-[(4-{2-[(5-carbamoyl-3-chloropyridin-2-yl)(heptyl)amino]ethyl}-1,3-thiazol-2-yl}thio}-2-methylpropionic acid tert-butyl ester

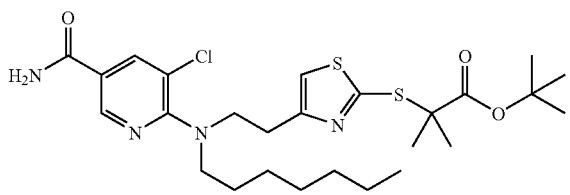

2-[(4-{2-[[3-Chloro-5-(methoxycarbonyl)pyridin-2-yl](heptyl)amino]ethyl}-1,3-thiazol-2-yl)thio]-2-methylpropionic acid tert-butyl ester (2.50 g) obtained in Example 281-1 was dissolved in ethanol (25 mL), 1N aqueous sodium hydroxide solution (5 mL) was added, and the mixture was left standing for 12 hr. The reaction mixture was concentrated, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; chloroform:methanol=50:1) to give 2-[(4-{2-[(5-carboxy-3-chloropyridin-2-yl)(heptyl)amino]ethyl}-1,3-thiazol-2-yl)thio]-2-methylpropionic acid tert-butyl ester (2.5 g) as a colorless oil. Without purification, the present compound was dissolved in dichloromethane (20 mL), WSCD (0.72 g) and ammonia/methanol solution (7M, 1 mL) was added, and the mixture was stirred at room temperature for 12 hr. The solvent was evaporated under reduced pressure, and the residue was purified by silica gel chromatography (elution solvent; hexane:ethyl acetate=3:2) to give the title compound (0.86 g) as a colorless oil.

$^1$H-NMR (CDCl$_3$, 270 MHz) δ: 0.90 (3H, t, J=7.0 Hz), 1.15-1.37 (8H, m), 1.40 (9H, s), 1.51-1.70 (8H, m), 3.07 (2H, t, J=7.6 Hz), 3.49 (2H, t, J=7.6 Hz), 3.89 (2H, t, J=7.6 Hz), 5.77 (2H, brs), 6.95 (1H, s), 7.97 (1H, d, J=2.2 Hz), 8.47 (1H, d, J=2.2 Hz).

Example 281-3

2-[(4-{2-[(5-carbamoyl-3-chloropyridin-2-yl)(heptyl)amino]ethyl}-1,3-thiazol-2-yl)thio]-2-methylpropionic acid hydrochloride

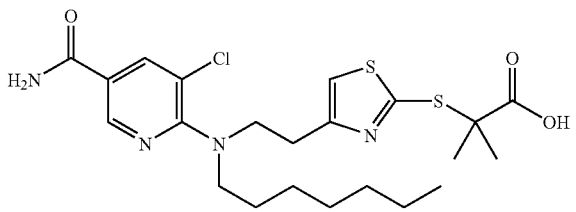

2-[(4-{2-[(5-Carbamoyl-3-chloropyridin-2-yl)(heptyl)amino]ethyl}-1,3-thiazol-2-yl)thio]-2-methylpropionic acid tert-butyl ester (300 mg) obtained in Example 281-2 was dissolved in trifluoroacetic acid (5 mL), and the mixture was stirred at room temperature for 12 hr. The reaction mixture was concentrated under reduced pressure, dissolved in ether, and 4N hydrochloric acid/ethyl acetate was added. The precipitated crystals were collected by filtration to give the title compound (243 mg) as white crystals.

$^1$H-NMR (DMSO-d$_6$, 270 MHz) δ: 0.84 (3H, t, J=7.0 Hz), 1.12-1.30 (8H, m), 1.40-1.55 (8H, m), 1.40-1.55 (8H, m), 2.99 (2H, t, J=6.7 Hz), 3.76 (2H, t, J=6.7 Hz), 7.35 (1H, brs), 7.43 (1H, brs), 8.08 (1H, d, J=1.9 Hz), 8.59 (1H, d, J=1.9 Hz).

MS: 499 (M$^+$+1).

Example 282

2-[(4-{2-[(3-chloro-5-cyanopyridin-2-yl)(heptyl)amino]ethyl}-1,3-thiazol-2-yl)thio]-2-methylpropionic acid hydrochloride Example 282-1

2-[(4-{2-[(3-chloro-5-cyanopyridin-2-yl)(heptyl)amino]ethyl}-1,3-thiazol-2-yl)thio]-2-methylpropionic acid tert-butyl ester

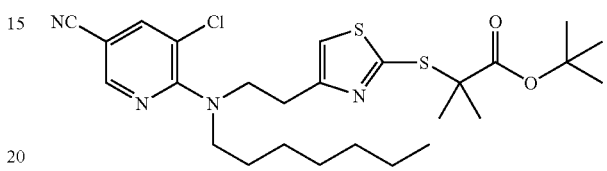

2-[(4-{2-[(5-Carbamoyl-3-chloropyridin-2-yl)(heptyl)amino)ethyl}-1,3-thiazol-2-yl)thio]-2-methylpropionic acid tert-butyl ester (0.85 g) synthesized in Example 281-2 was dissolved in dichloromethane (10 mL), triethylamine (0.26 mL), trifluoroacetic acid anhydride (0.24 mL) was added, and the mixture was stirred at room temperature for 3 hr. The reaction mixture was washed with water, and dried over anhydrous sodium sulfate. The solvent was evaporated under reduced pressure, and the residue was purified by silica gel chromatography (elution solvent; hexane:ethyl acetate=9:1) to give the title compound (0.37 g).

$^1$H-NMR (CDCl$_3$, 270 MHz) δ: 0.88 (3H, t, J=7.0 Hz), 1.12-1.85 (28H, m), 3.09 (2H, t, J=8.6 Hz), 3.53 (2H, t, J=8.6 Hz), 3.93 (2H, t, J=8.6 Hz), 6.97 (1H, s), 7.65 (1H, d, J=1.9 Hz), 8.30 (1H, d, J=2.2 Hz).

Example 282-2

2-[(4-{2-[(3-chloro-5-cyanopyridin-2-yl)(heptyl)amino]ethyl}-1,3-thiazol-2-yl)thio]-2-methylpropionic acid hydrochloride

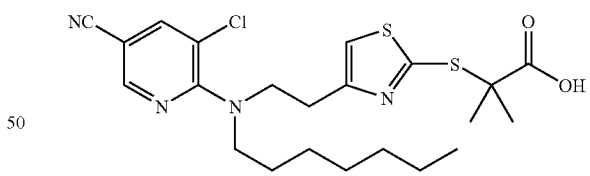

2-[(4-{2-[(3-Chloro-5-cyanopyridin-2-yl)(heptyl)amino]ethyl}-1,3-thiazol-2-yl)thio]-2-methylpropionic acid tert-butyl ester (0.37 g) obtained in Example 282-1 was dissolved in dichloromethane (10 mL), trifluoroacetic acid (2 mL) was added, and the mixture was stirred at room temperature for 12 hr. The reaction mixture was concentrated under reduced pressure, dissolved in ether, and 4N hydrochloric acid/ethyl acetate was added. The precipitated crystals were collected by filtration to give the title compound (280 mg) as white crystals.

$^1$H-NMR (DMSO-d$_6$, 270 MHz) δ: 0.83 (3H, t, J=7.6 Hz), 1.11-1.34 (8H, m), 1.42-1.61 (8H, m), 3.01 (2H, t, J=6.7 Hz), 3.87 (2H, t, J=6.7 Hz), 7.43 (1H, s), 8.11 (1H, d, J=2.2 Hz), 8.47 (1H, d, J=2.2 Hz).

Example 283

2-[(4-{2-[(5-chloro-3-cyanopyridin-2-yl)(heptyl)amino]ethyl}-1,3-thiazol-2-yl)thio]-2-methylpropionic acid hydrochloride

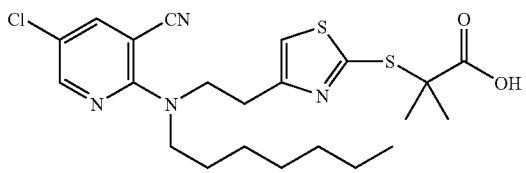

A compound obtained by using, as starting materials, 2-{[4-(2-aminoethyl)-1,3-thiazol-2-yl]thio}-2-methylpropionic acid tert-butyl ester synthesized in Example 7 and 2,5-dichloronicotinonitrile synthesized in reference to non-patent reference [Liebigs Ann. Chem., 487, 127 (1931)] and the like, and by operations similar to those of Example 265-1 and Example 265-2, was dissolved in dioxane, an excess amount of 4 mol/L hydrochloric acid-dioxane was added, and the mixture was stirred at room temperature for 12 hr. The reaction mixture was concentrated under reduced pressure, and the residue was purified by silica gel chromatography (elution solvent; chloroform:methanol=10:1) to give the title compound as a colorless oil.

$^1$H-NMR (CDCl$_3$, 300 MHz) δ: 0.88 (3H, t, J=6.9 Hz), 1.28-1.30 (8H, m), 1.65 (8H, brs), 3.13 (2H, t, J=7.8 Hz), 3.59 (2H, t, J=7.8 Hz), 3.90-3.95 (2H, m), 7.04 (1H, s), 7.67 (1H, d, J=2.7 Hz), 8.24 (1H, d, J=2.7 Hz).

MS: 481 (M$^+$+1).

Example 284

2-[(4-{2-[(5-bromo-3-cyanopyridin-2-yl)(heptyl)amino]ethyl}-1,3-thiazol-2-yl)thio]-2-methylpropionic acid hydrochloride

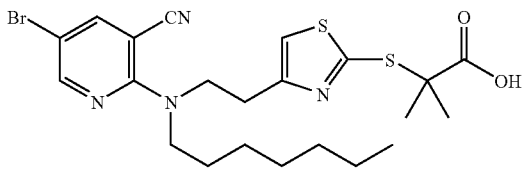

A compound obtained by using, as starting materials, 2-{[4-(2-aminoethyl)-1,3-thiazol-2-yl]thio}-2-methylpropionic acid tert-butyl ester synthesized in Example 7 and 5-bromo-2-chloronicotinonitrile synthesized in reference to patent reference [WO0224694] and the like, and by operations similar to those of Example 265-1 and Example 265-2, was dissolved in dioxane, an excess amount of 4 mol/L hydrochloric acid-dioxane was added, and the mixture was stirred at room temperature for 12 hr. The reaction mixture was concentrated under reduced pressure, azeotroped with diethyl ether, and the precipitated solid was collected by filtration to give the title compound as a white solid.

$^1$H-NMR (DMSO-d$_6$, 300 MHz) δ: 0.85 (3H, t, J=6.9 Hz), 1.24 (8H, brs), 1.50 (8H, brs), 3.03 (2H, t, J=6.9 Hz), 3.49 (2H, t, J=7.8 Hz), 3.91 (2H, t, J=6.9 Hz), 7.47 (1H, s), 8.22 (1H, d, J=2.4 Hz), 8.41 (1H, d, J=2.4 Hz).

MS: 527 (M$^+$+1).

Example 285

2-[(4-{2-[heptyl(pyrazin-2-yl)amino]ethyl}-1,3-thiazol-2-yl)thio]-2-methylpropionic acid

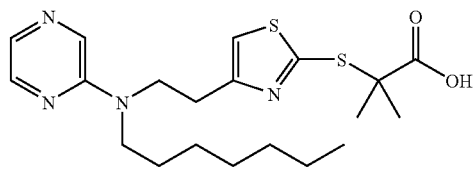

A compound obtained by using, as starting materials, 2-{[4-(2-aminoethyl)-1,3-thiazol-2-yl]thio}-2-methylpropionic acid tert-butyl ester synthesized in Example 7 and 2-chloropyrazine and by operations similar to those of Example 265-1 and Example 265-2 was dissolved in dioxane, an excess amount of 4 mol/L hydrochloric acid-dioxane was added, and the mixture was stirred at room temperature for 12 hr. The reaction mixture was concentrated under reduced pressure, and the residue was purified by silica gel chromatography (elution solvent; ethyl acetate) to give the title compound as a colorless oil.

$^1$H-NMR (CDCl$_3$, 300 MHz) δ: 0.88 (3H, t, J=6.9 Hz), 1.26-1.31 (8H, m), 1.58-1.60 (2H, m), 1.67 (6H, s), 3.05 (2H, t, J=7.2 Hz), 3.41-3.47 (2H, m), 3.81 (2H, t, J=7.2 Hz), 6.93 (1H, s), 7.71 (1H, d, J=2.7 Hz), 8.03 (1H, brs), 8.08 (1H, s).

MS: 423 (M$^+$+1).

Example 286

2-[(4-{2-[(4-chlorophenyl)(heptyl)amino]ethyl}-1,3-thiazol-2-yl)thio]-2-methylpropionic acid

Reference Example 14

N-(4-chlorophenyl)-2-nitrobenzenesulfoneamide

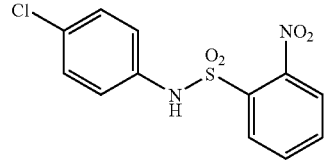

4-Chloroaniline (2.0 g) was dissolved in dichloromethane (70 mL), pyridine (1.39 mL) and 2-nitrobenzenesulfonyl chloride (3.65 g) were added at room temperature, and the mixture was stirred for one hr. Water was added, and the organic layer was separated, washed with water and dried over anhydrous magnesium sulfate. The solvent was evaporated under reduced pressure, and the residue was washed by suspending in ether. The obtained solid was vacuum dried to give the title compound (5.4 g) as a pale-yellow solid.

¹H-NMR (CDCl₃, 300 MHz) δ: 7.13-7.16 (2H, m), 7.23-7.27 (3H, m), 7.58-7.62 (1H, m), 7.70-7.74 (1H, m), 7.81-7.88 (2H, m).

Example 286-1

2-{[4-(2-{(4-chlorophenyl)[(2-nitrophenyl)sulfonyl]amino}ethyl)-1,3-thiazol-2-yl]thio}-2-methylpropionic acid tert-butyl ester

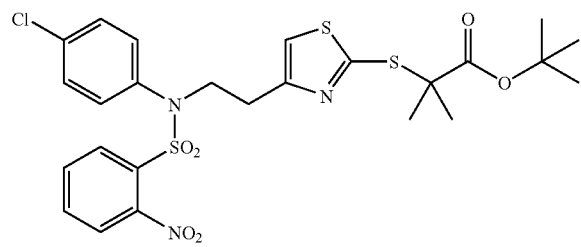

2-{[4-(2-Hydroxyethyl)-1,3-thiazol-2-yl]thio}-2-methylpropionic acid tert-butyl ester (788 mg) synthesized in Example 4 and N-(4-chlorophenyl)-2-nitrobenzenesulfoneamide (812 mg) synthesized in Reference Example 14 were dissolved in dichloromethane (13 mL), triphenylphosphine (1.0 g) and diethyl diazodicarboxylate (40% toluene solution) (1.7 g) were added under ice-cooling, and the mixture was stirred at room temperature for 8 hr. The reaction mixture was concentrated under reduced pressure, and the residue was purified by silica gel chromatography (elution solvent; hexane:ethyl acetate=2:1) to give the title compound (1.2 g) as a colorless oil.

¹H-NMR (CDCl₃, 300 MHz) δ: 1.41 (9H, s), 1.51 (6H, s), 2.99 (2H, t, J=7.2 Hz), 4.13 (2H, t, J=7.2 Hz), 7.08-7.16 (3H, m), 7.23-7.28 (2H, m), 7.50-7.52 (2H, m), 7.62-7.67 (2H, m).

Example 286-2

2-[(4-{2-[(4-chlorophenyl)amino]ethyl}-1,3-thiazol-2-yl)thio]-2-methylpropionic acid tert-butyl ester

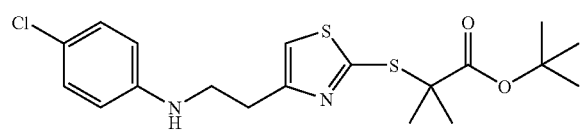

2-{[4-(2-{(4-Chlorophenyl)[(2-nitrophenyl)sulfonyl]amino}ethyl)-1,3-thiazol-2-yl]thio}-2-methylpropionic acid tert-butyl ester (1.2 g) synthesized in Example 286-1 and thiophenol (0.26 mL) were dissolved in N,N-dimethylformamide (12 mL), potassium carbonate (0.88 g) was added, and the mixture was stirred at room temperature for 12 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 3:1) to give the title compound (0.52 g) as a colorless oil.

¹H-NMR (CDCl₃, 300 MHz) δ: 1.43 (9H, s), 1.60 (6H, s), 3.03 (2H, t, J=6.3 Hz), 3.45 (2H, t, J=6.3 Hz), 6.56-6.59 (2H, m), 6.98 (1H, s), 7.08-7.12 (2H, m).

Example 286-3

2-[(4-{2-[(4-chlorophenyl)(heptyl)amino]ethyl}-1,3-thiazol-2-yl)thio]-2-methylpropionic acid tert-butyl ester

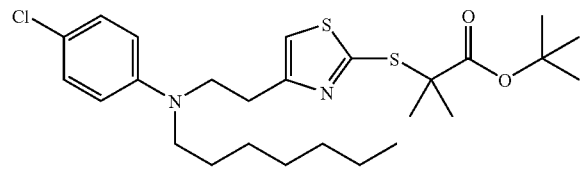

2-[(4-{2-[(4-Chlorophenyl)amino]ethyl}-1,3-thiazol-2-yl)thio]-2-methylpropionic acid tert-butyl ester (1.03 g) synthesized in Example 286-2 and heptylaldehyde (0.34 g) were dissolved in dichloroethane (15 mL), acetic acid (171 μL) and hydrogenated tri(acetoxy)boric acid (0.79 g) were successively added thereto, and the mixture was stirred at room temperature for 2.5 hr. Saturated aqueous sodium hydrogen carbonate was added, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1) to give the title compound (1.07 g) as a colorless oil.

¹H-NMR (CDCl₃, 300 MHz) δ: 0.86-0.90 (3H, m), 1.24-1.27 (8H, m), 1.45 (9H, s), 1.48-1.53 (2H, m), 1.60 (6H, s), 2.97 (2H, t, J=7.5 Hz), 3.17 (2H, t, J=7.5 Hz), 3.62 (2H, t, J=7.5 Hz), 6.58-6.61 (2H, m), 6.97 (1H, s), 7.13-7.16 (2H, m).

Example 286-4

2-[(4-{2-[(4-chlorophenyl)(heptyl)amino]ethyl}-1,3-thiazol-2-yl)thio]-2-methylpropionic acid

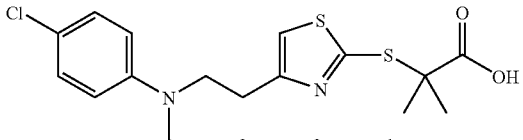

2-[(4-{2-[(4-Chlorophenyl)(heptyl)amino]ethyl}-1,3-thiazol-2-yl)thio]-2-methylpropionic acid tert-butyl ester (1.1 g) obtained in Example 286-3 was dissolved in dichloromethane (20 mL), trifluoroacetic acid (4.0 mL) was added, and the mixture was stirred at room temperature for 20 hr. The reaction mixture was concentrated under reduced pressure, and the residue was purified by silica gel chromatography (elution solvent; hexane:ethyl acetate=3:1 to 1:1) to give the title compound (0.99 g) as a colorless oil.

¹H-NMR (CDCl₃, 300 MHz) δ: 0.84 (3H, t, J=6.7 Hz), 1.21-1.29 (8H, m), 1.45 (2H, brs), 1.63 (6H, s), 2.94 (2H, t, J=7.4 Hz), 3.45 (2H, t, J=8.1 Hz), 3.88 (2H, t, J=7.4 Hz), 6.96 (1H, s), 7.38-7.48 (4H, m).

MS: 455 (M⁺+1).

Example 287

2-[(4-{2-[(2-chlorophenyl)(heptyl)amino]ethyl}-1,3-thiazol-2-yl)thio]-2-methylpropionic acid

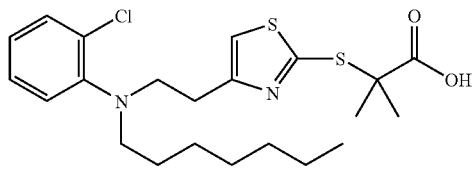

The title compound was obtained using 2-{[4-(2-hydroxyethyl)-1,3-thiazol-2-yl]thio}-2-methylpropionic acid tert-butyl ester synthesized in Example 4 and 2-chloroaniline as starting materials and by an operation similar to that of Example 286.
$^1$H-NMR (CDCl$_3$, 300 MHz) δ: 0.83 (3H, t, J=6.6 Hz), 1.19-1.32 (8H, m), 1.41-1.45 (2H, m), 1.64 (6H, s), 2.96 (2H, t, J=6.9 Hz), 3.83 (2H, t, J=8.1 Hz), 4.23 (2H, t, J=6.9 Hz), 7.07 (1H, s), 7.51-7.59 (3H, m), 7.70-7.73 (1H, m).
MS: 455 (M$^+$+1).

Example 288

2-[(4-{2-[heptyl(4-methoxyphenyl)amino]ethyl}-1,3-thiazol-2-yl)thio]-2-methylpropionic acid

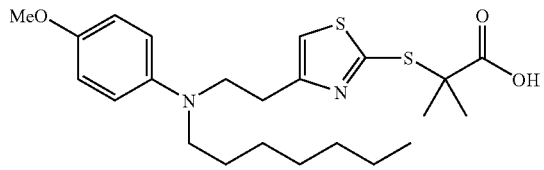

The title compound was obtained using 2-{[4-(2-hydroxyethyl)-1,3-thiazol-2-yl]thio}-2-methylpropionic acid tert-butyl ester synthesized in Example 4 and 4-methoxyaniline (p-anisidine) as starting materials and by an operation similar to that of Example 286.
$^1$H-NMR (CDCl$_3$, 300 MHz) δ: 0.83 (3H, t, J=6.8 Hz), 1.19-1.29 (8H, m), 1.43-1.45 (2H, m), 1.62 (6H, s), 2.92 (2H, t, J=6.9 Hz), 3.43 (2H, brs), 3.85-3.91 (5H, m), 6.94-7.01 (3H, m), 7.42-7.46 (2H, m).
MS: 451 (M$^+$+1).

Example 289

2-[(4-{2-[(4-cyanophenyl)(heptyl)amino]ethyl}-1,3-thiazol-2-yl)thio]-2-methylpropionic acid

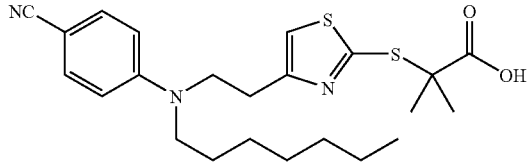

The title compound was obtained using 2-{[4-(2-hydroxyethyl)-1,3-thiazol-2-yl]thio}-2-methylpropionic acid tert-butyl ester synthesized in Example 4 and 4-aminobenzonitrile as starting materials, and by operations similar to those of Reference Example 14, Example 286-1, Example 286-2, Example 265-2 and Example 265-3.
$^1$H-NMR (CDCl$_3$, 300 MHz) δ: 0.88 (3H, t, J=6.6 Hz), 1.23-1.31 (8H, m), 1.51-1.58 (2H, m), 1.65 (6H, s), 3.03 (2H, t, J=7.3 Hz), 3.25 (2H, t, J=7.5 Hz), 3.70 (2H, t, J=7.5 Hz), 6.59-6.63 (2H, m), 6.98 (1H, s), 7.42-7.46 (2H, m).
MS: 446 (M$^+$+1).

Example 290

2-[(4-{2-[(3-cyanophenyl)(heptyl)amino]ethyl}-1,3-thiazol-2-yl)thio]-2-methylpropionic acid

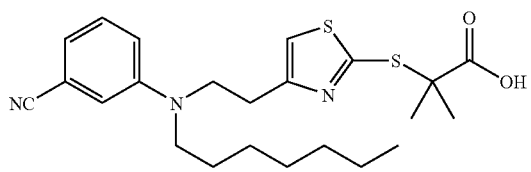

The title compound was obtained using 2-{[4-(2-hydroxyethyl)-1,3-thiazol-2-yl]thio}-2-methylpropionic acid tert-butyl ester synthesized in Example 4 and 3-aminobenzonitrile as starting materials and by operations similar to those of Reference Example 14, Example 286-1, Example 286-2, Example 265-2 and Example 265-3.
$^1$H-NMR (CDCl$_3$, 300 MHz) δ: 0.89 (3H, t, J=6.6 Hz), 1.29 (8H, brs), 1.47-1.54 (2H, m), 1.65 (6H, s), 3.02 (2H, t, J=7.2 Hz), 3.21 (2H, t, J=7.4 Hz), 3.67 (2H, t, J=7.4 Hz), 6.82-6.93 (3H, m), 6.97 (1H, s), 7.24-7.29 (1H, m).
MS: 446 (M$^+$+1).

Example 291

2-[(4-{2-[(2-cyanophenyl)(heptyl)amino]ethyl}-1,3-thiazol-2-yl)thio]-2-methylpropionic acid

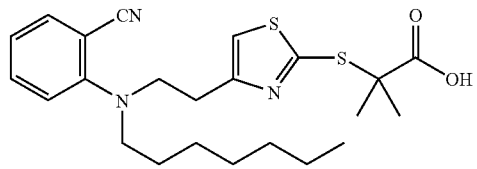

The title compound was obtained using 2-{[4-(2-hydroxyethyl)-1,3-thiazol-2-yl]thio}-2-methylpropionic acid tert-butyl ester synthesized in Example 4 and 2-aminobenzonitrile as starting materials and by operations similar to those of Reference Example 14, Example 286-1, Example 286-2, Example 265-2 and Example 265-3.
$^1$H-NMR (CDCl$_3$, 300 MHz) δ: 0.86 (3H, t, J=6.6 Hz), 1.26 (8H, brs), 1.50-1.52 (2H, m), 1.62 (6H, s), 3.06 (2H, t, J=7.3 Hz), 3.29 (2H, t, J=7.6 Hz), 3.68 (2H, t, J=7.6 Hz), 6.91 (1H, t, J=7.5 Hz), 6.98-7.03 (2H, m), 7.41-7.53 (2H, m).
MS: 446 (M$^+$+1).

Example 292

2-[(4-{2-[heptyl(pyridin-4-yl)amino]ethyl}-1,3-thiazol-2-yl)thio]-2-methylpropionic acid hydrochloride

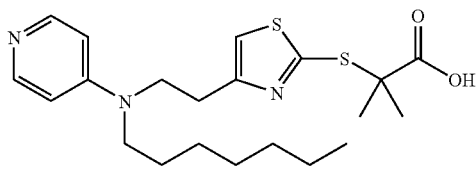

A compound obtained using 2-{[4-(2-hydroxyethyl)-1,3-thiazol-2-yl]thio}-2-methylpropionic acid tert-butyl ester synthesized in Example 4 and 4-aminopyridine as starting materials and by operations similar to those of Reference Example 14, Example 286-1, Example 286-2 and Example 265-2 was dissolved in dioxane, an excess amount of 4 mol/L hydrochloric acid-dioxane was added, and the mixture was stirred at room temperature for 12 hr. The reaction mixture was concentrated under reduced pressure, and the residue was purified by silica gel chromatography (elution solvent; chloroform:methanol=10:1) to give the title compound as an amorphous solid.

$^1$H-NMR (CDCl$_3$, 300 MHz) δ: 0.89 (3H, t, J=6.6 Hz), 1.24-1.32 (8H, m), 1.59 (2H, brs), 1.70 (6H, s), 2.98 (2H, t, J=6.9 Hz), 3.33-3.39 (2H, m), 3.77 (2H, t, J=6.9 Hz), 6.62 (2H, d, J=7.2 Hz), 6.91 (1H, s), 8.23 (2H, d, J=7.2 Hz).

MS: 422 (M$^+$+1).

Example 293

2-[(4-{2-[(5-bromopyridin-2-yl)(heptyl)amino]ethyl}-1,3-thiazol-2-yl)thio]-2-methylpropionic acid hydrochloride

Example 293-1

2-[(4-{2-[(5-bromopyridin-2-yl)(heptyl)amino]ethyl}-1,3-thiazol-2-yl)thio]-2-methylpropionic acid tert-butyl ester

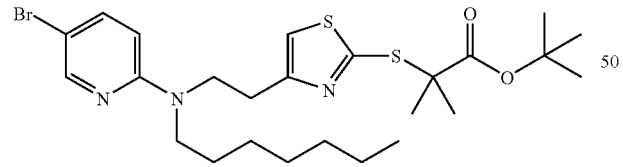

2-[(4-{2-[(5-Bromopyridin-2-yl)amino]ethyl}-1,3-thiazol-2-yl)thio]-2-methylpropionic acid tert-butyl ester (4.78 g) synthesized in Example 242 from 2-amino-5-bromopyridine and {2-[(2-tert-butoxy-1,1-dimethyl-2-oxoethyl)thio]-1,3-thiazol-4-yl}acetic acid obtained in Example 3, and heptyl iodide (3.54 g) were dissolved in N,N-dimethylformamide (50 mL), potassium tert-butoxide (1.75 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:1) to give the title compound (1.72 g) as a colorless oil.

$^1$H-NMR (CDCl$_3$, 300 MHz) δ: 0.86-0.91 (3H, m), 1.27 (8H, brs), 1.45 (9H, s), 1.53-1.56 (2H, m), 1.59 (6H, s), 3.02 (2H, t, J=7.3 Hz), 3.28 (2H, t, J=7.5 Hz), 3.75-3.80 (2H, m), 6.38 (1H, d, J=9.4 Hz), 6.99 (1H, s), 7.43-7.47 (1H, m), 8.14 (1H, d, J=2.2 Hz).

Example 293-2

2-[(4-{2-[(5-bromopyridin-2-yl)(heptyl)amino]ethyl}-1,3-thiazol-2-yl)thio]-2-methylpropionic acid hydrochloride

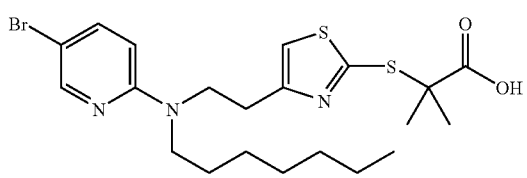

2-[(4-{2-[(5-Bromopyridin-2-yl)(heptyl)amino]ethyl}-1,3-thiazol-2-yl)thio]-2-methylpropionic acid tert-butyl ester (1.72 g) synthesized in Example 293-1 was dissolved in dioxane (5 mL), 4 mol/L hydrochloric acid-dioxane (25 mL) was added, and the mixture was stirred at room temperature for 12 hr. The reaction mixture was concentrated under reduced pressure, azeotroped with diethyl ether, and the precipitated solid was collected by filtration to give the title compound (1.0 g) as a white solid.

$^1$H-NMR (DMSO-d$_6$, 300 MHz) δ: 0.85 (3H, t, J=7.2 Hz), 1.24 (8H, brs), 1.46-1.55 (8H, m), 2.98 (2H, t, J=6.6 Hz), 3.35 (2H, t, J=7.2 Hz), 3.80 (2H, t, J=6.6 Hz), 6.80 (1H, d, J=9.3 Hz), 7.51 (1H, s), 7.76-7.80 (1H, m), 8.11 (1H, brs).

MS: 502 (M$^+$+1).

Example 294

2-[(4-{2-[heptyl(pyridin-2-yl)amino]ethyl}-1,3-thiazol-2-yl)thio]-2-methylpropionic acid

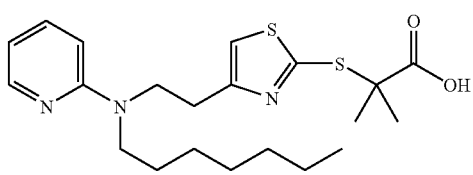

A compound obtained using {2-[(2-tert-butoxy-1,1-dimethyl-2-oxoethyl)thio]-1,3-thiazol-4-yl}acetic acid synthesized in Example 3 and 2-aminopyridine as starting materials and by an operation similar to that of Example 293-1 was treated with dichloromethane and trifluoroacetic acid and the mixture was stirred at room temperature for 12 hr. The reaction solution was concentrated under reduced pressure, and the residue was purified by high performance liquid chromatography (elution solvent; 0.05% trifluoroacetic acid-water: 0.05% trifluoroacetic acid-acetonitrile=85:15 to 40:60) to give the title compound as a white solid.

¹H-NMR (CDCl₃, 300 MHz) δ: 0.88 (3H, t, J=6.6 Hz), 1.28-1.37 (8H, m), 1.62-1.64 (8H, m), 3.14 (2H, t, J=6.9 Hz), 3.48-3.53 (2H, m), 3.96 (2H, t, J=6.9 Hz), 6.79-6.82 (2H, m), 7.19 (1H, s), 7.77-7.82 (1H, m), 8.12-8.14 (1H, m).

MS: 422 (M⁺+1).

Example 295

2-[(4-{2-[(5-chloropyridin-2-yl)(heptyl)amino]ethyl}-1,3-thiazol-2-yl)thio]-2-methylpropionic acid trifluoroacetate

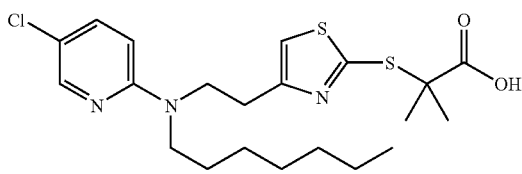

A compound obtained using {2-[(2-tert-butoxy-1,1-dimethyl-2-oxoethyl)thio]-1,3-thiazol-4-yl}acetic acid synthesized in Example 3 and 2-amino-5-chloropyridine as starting materials and by an operation similar to that of Example 293-1 was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile=50:50 to 5:95) to give the title compound as a white solid.

¹H-NMR (CDCl₃, 300 MHz) δ: 0.88 (3H, t, J=6.6 Hz), 1.24-1.28 (8H, m), 1.49-1.53 (2H, m), 1.64 (6H, s), 3.06 (2H, t, J=7.2 Hz), 3.28 (2H, t, J=7.5 Hz), 3.81 (2H, t, J=7.5 Hz), 6.39 (1H, d, J=9.0 Hz), 6.96 (1H, s), 7.34-7.38 (1H, m), 8.05 (1H, d, J=2.7 Hz).

MS: 456 (M⁺+1).

Example 296

2-[(4-{2-[heptyl(pyridin-3-yl)amino]ethyl}-1,3-thiazol-2-yl)thio]-2-methylpropionic acid trifluoroacetate

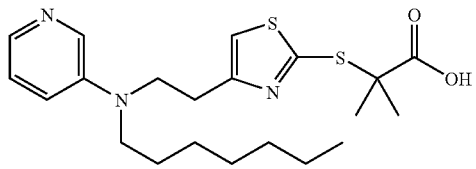

A compound obtained using {2-[(2-tert-butoxy-1,1-dimethyl-2-oxoethyl)thio]-1,3-thiazol-4-yl}acetic acid synthesized in Example 3 and 3-aminopyridine as starting materials and by an operation similar to that of Example 293-1 was treated with dichloromethane and trifluoroacetic acid, and the mixture was stirred at room temperature for 12 hr. The reaction solution was concentrated under reduced pressure, azeotroped with diethyl ether, and the precipitated solid was collected by filtration to give the title compound.

¹H-NMR (DMSO-d₆, 300 MHz) δ: 0.86 (3H, t, J=6.6 Hz), 1.26 (8H, brs), 1.46 (2H, brs), 1.52 (6H, s), 2.97 (2H, t, J=6.6 Hz), 3.25-3.28 (2H, m), 3.73 (2H, t, J=6.6 Hz), 7.51 (1H, s), 7.62 (2H, brs), 7.98-8.00 (1H, m), 8.13 (1H, brs).

MS: 422 (M⁺+1).

Example 297

2-[(4-{2-[heptyl(5-nitro-1,3-thiazol-2-yl)amino]ethyl}-1,3-thiazol-2-yl)thio]-2-methylpropionic acid

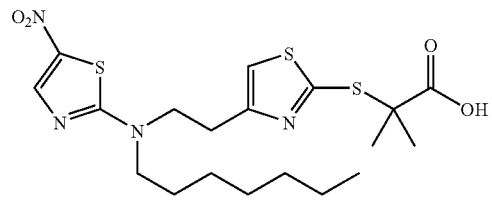

The title compound was obtained using 2-{[4-(2-aminoethyl)-1,3-thiazol-2-yl]thio}-2-methylpropionic acid tert-butyl ester synthesized in Example 7 and 2-bromo-5-nitro-1,3-thiazole as starting materials and by an operation similar to that of Example 265.

¹H-NMR (CDCl₃, 300 MHz) δ: 0.89 (3H, t, J=6.9 Hz), 1.20-1.36 (8H, m), 1.58-1.66 (8H, m), 3.17 (2H, t, J=6.9 Hz), 3.35 (2H, t, J=7.5 Hz), 3.90 (2H, t, J=6.9 Hz), 7.05 (1H, s), 8.12 (1H, s).

MS: 473 (M⁺+1).

Example 298

2-[(4-{[(5-ethylpyrimidin-2-yl)(heptyl)amino]methyl}-1,3-thiazol-2-yl)thio]-2-methylpropionic acid

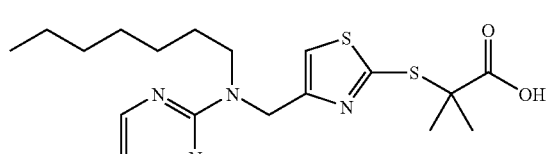

The title compound was obtained using 2-{([4-(aminomethyl)-1,3-thiazol-2-yl]thio}-2-methylpropionic acid tert-butyl ester synthesized in Example 13 and 2-chloro-5-ethylpyrimidine as starting materials and by an operation similar to that of Example 265.

¹H-NMR (CDCl₃, 300 MHz) δ: 0.87 (3H, t, J=6.9 Hz), 1.16-1.38 (11H, m), 1.52-1.63 (8H, m), 2.46 (2H, q, J=7.5 Hz), 3.63 (2H, t, J=7.5 Hz), 4.91 (2H, s), 7.08 (1H, s), 8.18 (2H, s).

MS: 437 (M⁺+1).

Example 299

2-[(5-{[(5-ethylpyrimidin-2-yl)(heptyl)amino]methyl}-4-methyl-1,3-thiazol-2-yl)thio]-2-methylpropionic acid

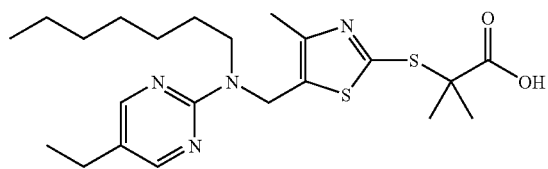

The title compound was obtained using 2-{[5-(2-aminoethyl)-4-methyl-1,3-thiazol-2-yl]thio}-2-methylpropionic acid tert-butyl ester synthesized in Example 30 and 2-chloro-5-ethylpyrimidine as starting materials and by an operation similar to that of Example 265

$^1$H-NMR (CDCl$_3$, 300 MHz) δ: 0.88 (3H, t, J=7.2 Hz), 1.18-1.36 (11H, m), 1.54-1.65 (8H, m), 2.04-2.52 (5H, m), 3.57 (2H, t, J=7.4 Hz), 4.79 (2H, s), 8.20 (2H, s).

MS: 451 (M$^+$+1).

Example 300

2-[(4-{3-[(5-ethylpyridin-2-yl)(heptyl)amino]propyl}-1,3-thiazol-2-yl)thio]-2-methylpropionic acid hydrochloride

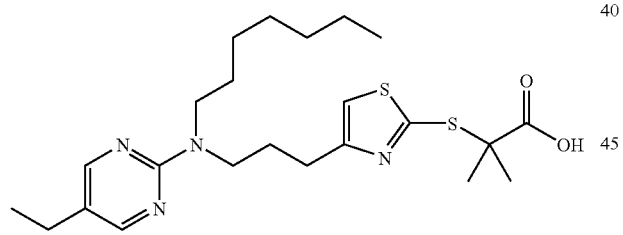

A compound obtained using 2-{[4-(3-aminopropyl)-1,3-thiazol-2-yl]thio}-2-methylpropionic acid tert-butyl ester synthesized in Example 33 and 2-chloro-5-ethylpyrimidine as starting materials and by operations similar to those of Example 265-1 and Example 265-2 was treated with formic acid and 4 mol/L hydrochloric acid-ethyl acetate, and the mixture was stirred at room temperature for 12 hr. The reaction mixture was concentrated under reduced pressure to give the title compound.

$^1$H-NMR (DMSO-d$_6$, 270 MHz) δ: 0.83 (3H, t, J=7.3H), 1.11 (3H, t, J=7.6 Hz), 1.14-1.35 (8H, m), 1.41-1.60 (8H, m), 1.80-1.99 (2H, m), 2.35-2.50 (2H, m), 2.71 (2H, t, J=7.0 Hz), 7.46 (1H, s), 8.25 (2H, s).

MS: 465 (M$^+$+1).

Example 301

2-[(4-{3-[(3-cyanopyridin-2-yl)(heptyl)amino]propyl}-1,3-thiazol-2-yl)thio]-2-methylpropionic acid trifluoroacetate

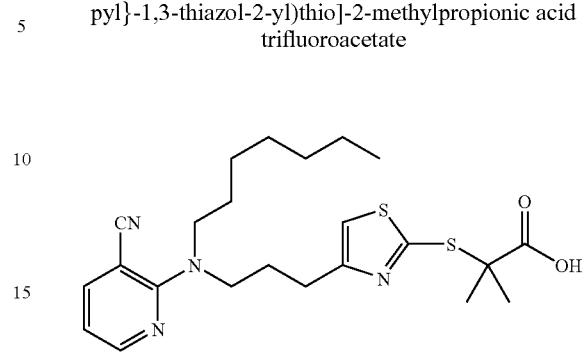

A compound obtained using 2-{[4-(3-aminopropyl)-1,3-thiazol-2-yl]thio}-2-methylpropionic acid tert-butyl ester synthesized in Example 33 and 2-chloronicotinonitrile as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (CDCl$_3$, 270 MHz) δ: 0.77-0.98 (3H, m), 1.17-1.44 (8H, m), 1.50-1.79 (8H, m), 2.03-2.21 (2H, m), 2.88 (2H, t, J=7.0 Hz). 6.81 ((1H, dd, J=5.9, 3.8 Hz), 6.83 (1H, brs), 7.09 (1H, s), 7.99 (1H, dd, J=5.9 Hz), 8.44 (1H, dd, J=3.8 Hz).

MS: 461 (M$^+$+1).

Example 302

2-[(4-{3-[(5-cyanopyridin-2-yl)(heptyl)amino]propyl}-1,3-thiazol-2-yl)thio]-2-methylpropionic acid trifluoroacetate

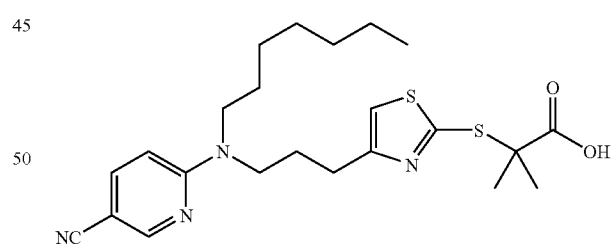

A compound obtained using 2-{[4-(3-aminopropyl)-1,3-thiazol-2-yl]thio}-2-methylpropionic acid tert-butyl ester synthesized in Example 33 and 6-chloronicotinonitrile as starting materials and by operations similar to those of Example 265-1 and Example 265-2 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (CDCl$_3$, 270 MHz) δ: 0.89 (3H, t, J=7.0 Hz), 1.18-1.42 (8H, m), 1.55-1.75 (8H, m), 2.00-2.17 (2H, m), 2.87 (2H, t, J=7.0 Hz). 3.44-3.60 (2H, m), 6.79 (1H, d, J=9.7 Hz), 7.14 (1H, s), 7.75 (1H, dd, J=9.7, 2.2 Hz), 8.54 (1H, d, J=2.2 Hz).
MS: 461 (M$^+$+1).

Example 303

2-[(4-{2-[heptyl(4-nitrophenyl)amino]ethyl}-1,3-thiazol-2-yl)thio]-2-methylpropionic acid

Example 303-1

2-({4-[2-(heptylamino)-2-oxoethyl]-1,3-thiazol-2-yl}thio)-2-methylpropionic acid tert-butyl ester

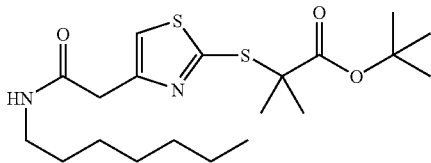

{2-[(2-tert-Butoxy-1,1-dimethyl-2-oxoethyl)thio]-1,3-thiazol-4-yl}acetic acid (25.0 g) synthesized in Example 3 and heptylamine (10.0 g) were dissolved in dichloromethane (250 mL), N-(3-dimethylaminopropyl)-N'-ethylcarbodiimide (EDC) hydrochloride (18.0 g) and hydroxybenzotriazole (HOBT) monohydrate (16.6 g) were successively added thereto, and the mixture was stirred at room temperature for 5 hr. Water was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (30.0 g) as a slightly yellow oil.
$^1$H-NMR (CDCl$_3$, 300 MHz) δ: 0.87 (3H, t, J=6.9 Hz), 1.23-1.35 (8H, m), 1.44 (9H, s), 1.45-1.55 (2H, m), 1.58 (6H, s), 3.25 (2H, q, J=6.9 Hz), 3.67 (2H, s), 6.82 (1H, brs), 7.10 (1H, s).

Example 303-2

2-({4-[2-(heptylamino)ethyl]-1,3-thiazol-2-yl}thio)-2-methylpropionic acid tert-butyl ester

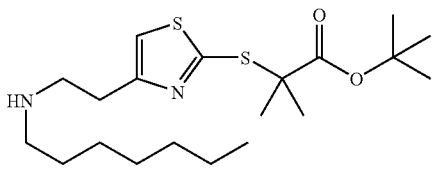

2-({4-[2-(Heptylamino)-2-oxoethyl]-1,3-thiazol-2-yl}thio)-2-methylpropionic acid tert-butyl ester (12.0 g) obtained in Example 303-1 was dissolved in tetrahydrofuran (120 mL), 1 M-borane/tetrahydrofuran complex (100 mL) was added under ice-cooling, and the mixture was stirred at room temperature for 12 hr. The reaction mixture was ice-cooled, and methanol (400 mL) was added dropwise. After warming to room temperature, the mixture was stirred for 1 hr. The reaction mixture was concentrated under reduced pressure, piperidine (120 mL) was added, and the mixture was stirred at 50° C. for 3 hr. The reaction mixture was concentrated under reduced pressure, and the residue was purified by silica gel chromatography (elution solvent; dichloromethane:methanol=20:1 to 10:1) to give the title compound (5.5 g) as a slightly yellow oil.
$^1$H-NMR (CDCl$_3$, 300 MHz) δ: 0.88 (3H, t, J=7.1 Hz), 1.20-1.35 (8H, m), 1.42-1.50 (11H, m), 1.58 (6H, s), 2.62 (2H, t, J=7.1 Hz), 2.95-2.97 (4H, m), 7.02 (1H, s).

Example 303-3

2-[(4-{2-[heptyl(4-nitrophenyl)amino]ethyl}-1,3-thiazol-2-yl)thio]-2-methylpropionic acid tert-butyl ester

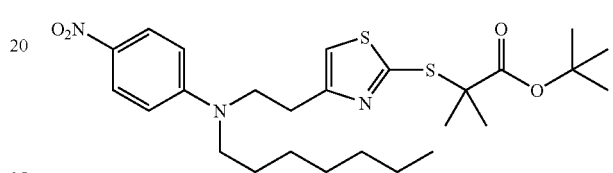

2-({4-[2-(Heptylamino)ethyl]-1,3-thiazol-2-yl}thio)-2-methylpropionic acid tert-butyl ester (0.40 g) synthesized in Example 303-2 and 1-fluoro-4-nitrobenzene (0.14 g) were dissolved in N,N-dimethylformamide (10 mL), N,N-diisopropylethylamine (0.52 mL) was added thereto, and the mixture was stirred at 80° C. for 4 hr. Water was added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel chromatography (elution solvent; hexane:ethyl acetate=7:3) to give the title compound (0.20 g) as a yellow oil.
$^1$H-NMR (CDCl$_3$, 270 MHz) δ: 0.89 (3H, t, J=7.0 Hz), 1.19-1.47 (8H, m), 1.41 (9H, s), 1.49-1.68 (8H, m), 3.03 (2H, t, J=7.3 Hz), 3.29 (2H, t, J=7.3 Hz), 3.77 (2H, t, J=7.0 Hz), 6.62 (2H, d, J=9.2 Hz), 6.99 (1H, s), 8.11 (2H, d, J=9.2 Hz).

Example 303-4

2-[(4-{2-[heptyl(4-nitrophenyl)amino]ethyl}-1,3-thiazol-2-yl)thio]-2-methylpropionic acid

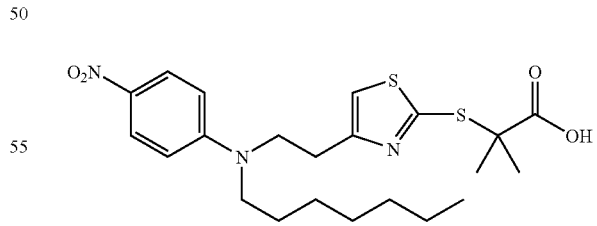

2-[(4-{2-[Heptyl(4-nitrophenyl)amino]ethyl}-1,3-thiazol-2-yl)thio]-2-methylpropionic acid tert-butyl ester (200 mg) obtained in Example 303-3 was dissolved in dichloromethane (5 mL), trifluoroacetic acid (5 mL) was added, and the mixture was stirred at room temperature for 12 hr. The reaction mixture was concentrated under reduced pressure, and hexane was added to the residue to give the title compound (108 mg) as a pale-yellow solid.

¹H-NMR (CDCl₃, 270 MHz) δ: 0.83-0.97 (3H, m), 1.20-1.43 (8H, m), 1.50-1.75 (8H, m), 3.09 (2H, t, J=7.0 Hz), 3.33 (2H, t, J=7.5 Hz), 3.78 (2H, t, J=7.5 Hz), 6.59 (2H, d, J=7.0 Hz), 7.00 (1H, s), 8.13 (2H, d, J=7.0 Hz).

MS: 466 (M⁺+1).

Example 304

2-[(4-{2-[1,3-benzothiazol-2-yl(heptyl)amino]ethyl}-1,3-thiazol-2-yl)thio]-2-methylpropionic acid

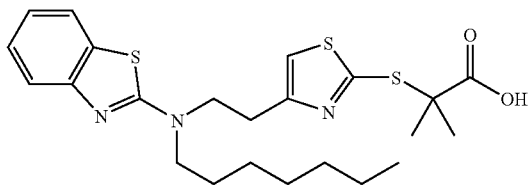

The title compound was obtained using 2-({4-[2-(heptylamino)ethyl]-1,3-thiazol-2-yl}thio)-2-methylpropionic acid tert-butyl ester synthesized in Example 303-2 and 2-chloro-1,3-benzothiazole as starting materials and by operations similar to those of Example 303-3 and Example 303-4.

¹H-NMR (CDCl₃, 270 MHz) δ: 0.88 (3H, t, J=7.0 Hz), 1.15-1.39 (8H, m), 1.53-1.75 (8H, m), 3.22 (2H, t, J=7.0 Hz), 3.36 (2H, t, J=7.5 Hz), 3.92 (2H, t, J=7.5 Hz), 6.98-7.09 (2H, m), 7.20-7.34 (1H, m), 7.50-7.62 (2H, m).

MS: 478 (M⁺+1).

Example 305

2-[(4-{2-[(5-cyanopyridin-2-yl)(heptyl)amino]ethyl}-1,3-thiazol-2-yl)thio]-2-methylpropionic acid trifluoroacetate

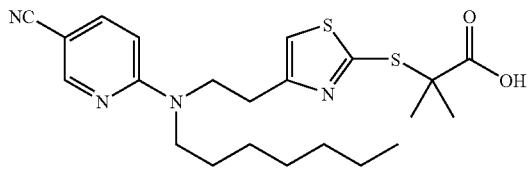

A compound obtained using 2-({4-[2-(heptylamino)ethyl]-1,3-thiazol-2-yl}thio)-2-methylpropionic acid tert-butyl ester synthesized in Example 303-2 and 6-chloronicotinonitrile as starting materials and by an operation similar to that of Example 303-3 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

¹H-NMR (DMSO-d₆, 270 MHz) δ: ¹H-NMR (CDCl₃, 270 MHz) δ: 0.85 (3H, t, J=7.0 Hz), 1.13-1.35 (8H, m), 1.40-1.61 (8H, m), 2.98 (2H, t, J=7.0 Hz), 3.37 (2H, t, J=7.3 Hz), 3.81 (2H, t, J=7.0 Hz), 6.67 (1H, d, J=9.2 Hz), 7.48 (1H, s), 7.78 (1H, dd, J=9.2, 2.2 Hz), 8.46 (1H, d, J=2.2 Hz).

MS: 447 (M⁺+1).

Example 306

2-[(4-{2-[heptyl([1,3]oxazolo[4,5-b]pyridin-2-yl)amino]ethyl}-1,3-thiazol-2-yl)thio]-2-methylpropionic acid trifluoroacetate

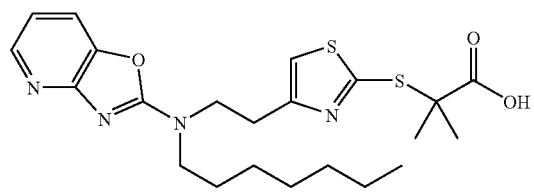

A compound obtained using 2-({4-[2-(heptylamino)ethyl]-1,3-thiazol-2-yl}thio)-2-methylpropionic acid tert-butyl ester synthesized in Example 303-2 and 2-chloro[1,3]oxazolo[4,5-b]pyridine as starting materials and by an operation similar to that of Example 303-3 was treated with dichloromethane and trifluoroacetic acid, and the mixture was stirred at room temperature for 12 hr. The reaction solution was concentrated under reduced pressure to give the title compound.

¹H-NMR (CDCl₃, 270 MHz) δ: 0.78-0.96 (3H, m), 1.16-1.42 (8H, m), 1.53-1.78 (8H, m), 3.12-3.28 (2H, m), 3.50-3.67 (2H, m), 3.90-4.07 (2H, m), 7.08-7.25 (2H, m), 7.83 (1H, d, J=7.3 Hz), 7.90-8.32 (2H, m)

MS: 478 (M⁺+1).

Example 307

2-[(4-{2-[1,3-benzoxazol-2-yl(heptyl)amino]ethyl}-1,3-thiazol-2-yl)thio]-2-methylpropionic acid hydrochloride

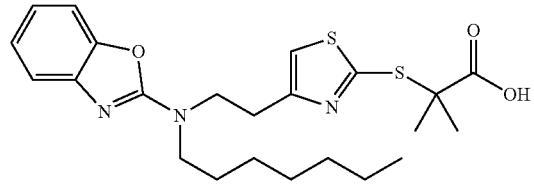

A compound obtained using 2-({4-[2-(heptylamino)ethyl]-1,3-thiazol-2-yl}thio)-2-methylpropionic acid tert-butyl ester synthesized in Example 303-2 and 2-chloro-1,3-benzooxazole as starting materials and by operations similar to those of Example 303-3 and 303-4 was dissolved in diethyl ether, and reacted with 4 mol/L hydrochloric acid-ethyl acetate to give the title compound.

¹H-NMR (DMSO-d₆, 270 MHz) δ: 0.88 (3H, t, J=6.5 Hz), 1.13-1.35 (8H, m), 1.40-1.61 (8H, m), 2.98 (2H, t, J=7.0 Hz), 3.37 (2H, t, J=7.3 Hz), 3.81 (2H, t, J=7.0 Hz), 6.67 (1H, d, J=9.2 Hz), 7.48 (1H, s), 7.78 (1H, dd, J=9.2, 2.2 Hz), 8.46 (1H, d, J=2.2 Hz).

MS: 462 (M⁺+1).

Example 308

2-[(4-{2-[(6-chloro-1,3-benzothiazol-2-yl)(heptyl)amino]ethyl}-1,3-thiazol-2-yl)thio]-2-methylpropionic acid hydrochloride

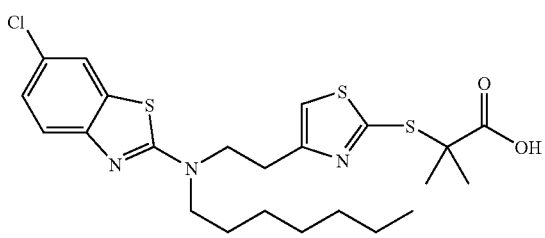

A compound obtained using 2-({4-[2-(heptylamino)ethyl]-1,3-thiazol-2-yl}thio)-2-methylpropionic acid tert-butyl ester synthesized in Example 303-2 and 2,6-dichloro-1,3-benzothiazole as starting materials and by an operation similar to that of Example 303-3 was treated with formic acid and 4 mol/L hydrochloric acid-ethyl acetate, and the mixture was stirred at room temperature for 12 hr. The reaction mixture was concentrated under reduced pressure to give the title compound.

$^1$H-NMR (DMSO-$d_6$, 270 MHz) δ: 0.86 (3H, t, J=6.5 Hz), 1.17-1.39 (8H, m), 1.45-1.65 (8H, m), 3.11 (2H, t, J=6.8 Hz), 3.37 (2H, t, J=6.8 Hz), 6.67 (1H, d, J=9.2 Hz), 7.28 (1H, dd, J=8.9, 2.2 Hz), 7.42 (1H, d, J=8.9 Hz) 7.55 (1H, s), 7.88 (1H, d, J=2.2 Hz).

MS: 462 (M$^+$+1).

Example 309

2-[(4-{2-[(3-cyanopyridin-2-yl)(heptyl)amino]ethyl}-1,3-thiazol-2-yl)thio]-2-methylpropionic acid hydrochloride

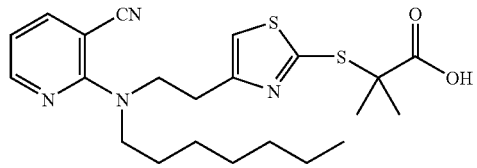

A compound obtained using 2-({4-[2-(heptylamino)ethyl]-1,3-thiazol-2-yl}thio)-2-methylpropionic acid tert-butyl ester synthesized in Example 303-2 and 2-chloronicotinonitrile as starting materials and by operations similar to those of Example 303-3 and 303-4 was dissolved in diethyl ether, and reacted with 4 mol/L hydrochloric acid-ethyl acetate to give the title compound.

$^1$H-NMR (DMSO-$d_6$, 270 MHz) δ: 0.85 (3H, t, J=7.0 Hz), 1.13-1.36 (8H, m), 1.42-1.62 (8H, m), 3.04 (2H, t, J=6.7 Hz), 3.52 (2H, t, J=6.7 Hz), 6.74 (1H, dd, J=7.6, 4.6 Hz), 7.47 (1H, s), 7.95 (1H, dd, J=7.6, 2.2 Hz) 8.35 (1H, dd, J=4.6, 2.2 Hz).

MS: 447 (M$^+$+1).

Example 310

2-[(4-{2-[(4-cyanopyridin-2-yl)(heptyl)amino]ethyl}-1,3-thiazol-2-yl)thio]-2-methylpropionic acid hydrochloride

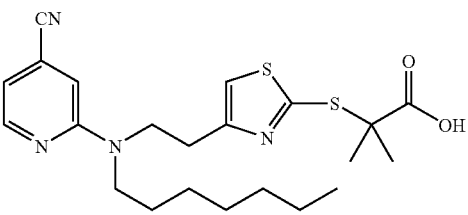

A compound obtained using 2-({4-[2-(heptylamino)ethyl]-1,3-thiazol-2-yl}thio)-2-methylpropionic acid tert-butyl ester synthesized in Example 303-2 and 2-chloroisonicotinonitrile as starting materials and by operations similar to those of Example 303-3 and Example 303-4 was dissolved in diethyl ether, and reacted with 4 mol/L hydrochloric acid-ethyl acetate to give the title compound.

$^1$H-NMR (DMSO-$d_6$, 270 MHz) δ: 0.85 (3H, t, J=7.0 Hz), 1.10-1.60 (16H, m), 2.98 (2H, t, J=6.7 Hz), 3.35 (2H, t, J=6.7 Hz), 6.89 (1H, d, J=5.4 Hz), 7.16 (1H, s), 7.50 (1H, s), 8.22 (1H, d, J=5.4 Hz).

MS: 447 (M$^+$+1).

Example 311

2-[(3-{2-[1,3-benzoxazol-2-yl(heptyl)amino]propyl}-1,3-thiazol-2-yl)thio]-2-methylpropionic acid

Example 311-1

2-({4-[3-(heptylamino)propyl]-1,3-thiazol-2-yl}thio)-2-methylpropionic acid tert-butyl ester

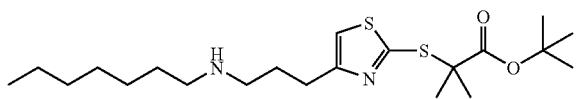

2-{[4-(3-Aminopropyl)-1,3-thiazol-2-yl]thio}-2-methylpropionic acid tert-butyl ester (3.16 g) synthesized in Example 33 and triethylamine (1.68 mL) were dissolved in dichloromethane (50 mL), heptanoyl chloride (1.62 mL) was added under ice-cooling, and the mixture was stirred at room temperature for 1 hr. Water was added to the reaction mixture, and the organic layer was washed with saturated brine and dried over anhydrous sodium sulfate. The solvent was evaporated under reduced pressure and the residue was dissolved in tetrahydrofuran (10 mL), 1 M-borane/tetrahydrofuran complex (26.6 mL) was added under ice-cooling, and the mixture was stirred at room temperature for 12 hr. The reaction mixture was ice-cooled, and methanol (30 mL) was added dropwise. After warming to room temperature, the mixture was stirred for 1 hr. The reaction mixture was concentrated under reduced pressure, piperidine (30 mL) was added, and the mixture was stirred at 60° C. for 3 hr. The reaction mixture was concentrated under reduced pressure, and the residue was purified by silica gel chromatography (elution solvent; chloroform:methanol=50:1) to give the title compound (2.86 g) as a colorless oil.

Example 311-2

2-[(3-{2-[1,3-benzoxazol-2-yl(heptyl)amino]propyl}-1,3-thiazol-2-yl)thio]-2-methylpropionic acid

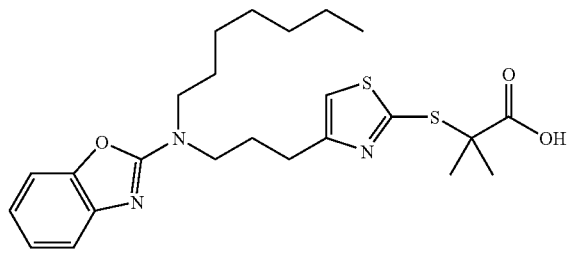

A compound obtained using 2-({4-[3-(heptylamino)propyl]-1,3-thiazol-2-yl}thio)-2-methylpropionic acid tert-butyl ester synthesized in Example 311-1 and 2-chloro-1,3-benzooxazole as starting materials and by an operation similar to that of Example 303-3 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (CDCl$_3$, 270 MHz) δ: 0.89 (3H, t, J=7.0 Hz), 1.18-1.43 (8H, m), 1.52-1.78 (8H, m), 2.09-2.25 (2H, m), 2.86 (2H, t, J=7.6 Hz), 3.58 (2H, t, J=7.6 Hz), 3.67 (2H, t, J=7.6 Hz), 6.47 (1H, brs), 7.02 (1H, s), 7.01-7.54 (4H, m).

MS: 476 (M$^+$+1).

Example 312

2-[(4-{2-[[(5-chloro-1H-indol-2-yl)carbonyl](heptyl)amino]ethyl}-1,3-thiazol-2-yl)thio]-2-methylpropionic acid

Example 312-1

2-[(4-{2-[[(5-chloro-1H-indol-2-yl)carbonyl](heptyl)amino]ethyl}-1,3-thiazol-2-yl)thio]-2-methylpropionic acid tert-butyl ester

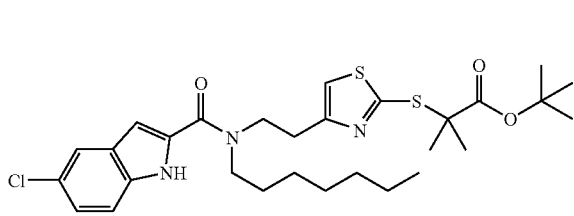

2-({4-[2-(Heptylamino)ethyl]-1,3-thiazol-2-yl}thio)-2-methylpropionic acid tert-butyl ester (400 mg) obtained in Example 303-2 and 5-chloro-1H-indole-2-carboxylic acid (196 mg) were dissolved in N,N-dimethylformamide (5 mL), N-(3-dimethylaminopropyl)-N'-ethylcarbodiimide (EDC) hydrochloride (211 mg) and hydroxybenzotriazole (HOBT) (168 mg) were successively added thereto, and the mixture was stirred at room temperature for 14 hr. Water was added to the reaction mixture, and the mixture was extracted with ethyl acetate. The organic layer was washed with saturated brine, and dried over anhydrous magnesium sulfate. The solvent was evaporated under reduced pressure, and ether was added to the residue to give the title compound as a white powder.

Example 312-2

2-[(4-{2-[[(5-chloro-1H-indol-2-yl)carbonyl](heptyl)amino]ethyl}-1,3-thiazol-2-yl)thio]-2-methylpropionic acid

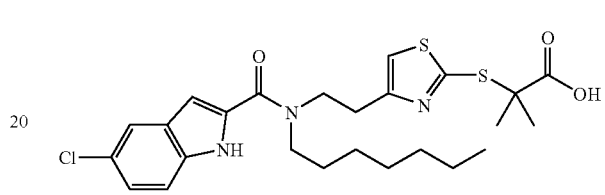

2-[(4-{2-[[(5-Chloro-1H-indol-2-yl)carbonyl](heptyl)amino]ethyl}-1,3-thiazol-2-yl)thio]-2-methylpropionic acid tert-butyl ester (270 mg) obtained in Example 312-1 was dissolved in formic acid (5 mL), 4N hydrochloric acid/ethyl acetate solution (5 mL) was added, and the mixture was stirred at room temperature for 3 hr. The reaction mixture was concentrated under reduced pressure, and ether was added to the residue to give the title compound (192 mg) as a white solid.

$^1$H-NMR (DMSO-d$_6$, 270 MHz) δ: 0.72-0.95 (3H, m), 1.10-1.66 (16H, m), 2.99-4.00 (6H, m), 6.65-6.96 (1H, m), 7.18 (1H, dd, J=8.9, 2.2 Hz), 7.43 (1H, d, J=8.9 Hz), 7.55 (1H, s), 7.67 (1H, d, J=2.2 Hz), 11.75 (1H, s).

MS: 522 (M$^+$+1).

Example 313

2-[(4-{2-[(4-chlorobenzoyl)(heptyl)amino]ethyl}-1,3-thiazol-2-yl)thio]-2-methylpropionic acid

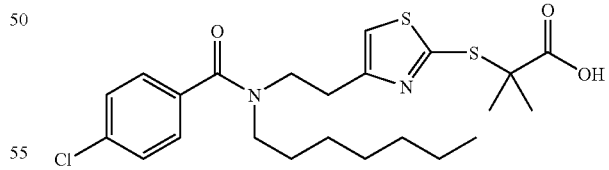

The title compound was obtained using 2-({4-[2-(heptylamino)ethyl]-1,3-thiazol-2-yl}thio)-2-methylpropionic acid tert-butyl ester synthesized in Example 303-2 and 4-chlorobenzoic acid as starting materials and by an operation similar to that of Example 312.

$^1$H-NMR (CDCl$_3$, 300 MHz) δ: 0.86-0.88 (3H, m), 1.14-1.64 (16H, m), 2.90-3.80 (6H, m), 6.87-7.12 (1H, m), 7.26-7.38 (4H, m).

MS: 483 (M$^+$+1).

Example 314

2-[(4-{2-[[(2E)-3-(4-chlorophenyl)prope-2-noyl](heptyl)amino]ethyl}-1,3-thiazol-2-yl)thio]-2-methylpropionic acid

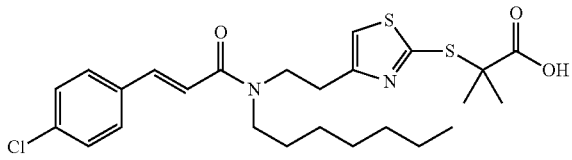

The title compound was obtained using 2-({4-[2-(heptylamino)ethyl]-1,3-thiazol-2-yl}thio)-2-methylpropionic acid tert-butyl ester synthesized in Example 303-2 and (2E)-3-(4-chlorophenyl)acrylic acid as starting materials and by an operation similar to that of Example 312.

$^1$H-NMR (DMSO-$d_6$, 270 MHz) δ: 0.72-0.92 (3H, m), 1.11-1.60 (16H, m), 2.90-3.06 (2H, m), 3.20-3.87 (4H, m), 6.98-7.38 (1H, m), 7.42-7.53 (4H, m), 7.66-7.80 (4H, m), 12.91 (1H, s).
MS: 509 (M$^+$+1).

Example 315

2-[(4-{2-[heptyl(quinolin-3-ylcarbonyl)amino]ethyl}-1,3-thiazol-2-yl)thio]-2-methylpropionic acid

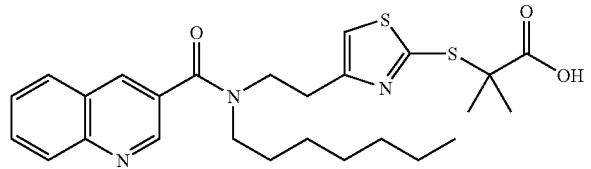

The title compound was obtained using 2-({4-[2-(heptylamino)ethyl]-1,3-thiazol-2-yl}thio)-2-methylpropionic acid tert-butyl ester synthesized in Example 303-2 and quinoline-3-carboxylic acid as starting materials and by an operation similar to that of Example 312.

$^1$H-NMR (DMSO-$d_6$, 270 MHz) δ: 0.60-1.12 (7H, m), 1.11-1.70 (14H, m), 2.90-3.52 (4H, m), 3.57-3.85 (2H, m), 6.39-7.62 (1H, m), 7.75-8.34 (5H, m), 9.47 (1H, s).
MS: 500 (M$^+$+1).

Example 316

2-[(4-{2-[heptyl(quinoxalin-2-ylcarbonyl)amino]ethyl}-1,3-thiazol-2-yl)thio]-2-methylpropionic acid

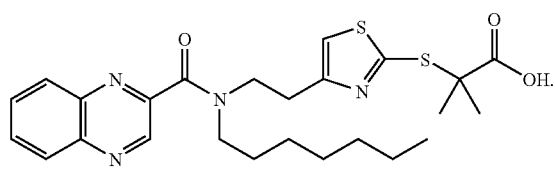

A compound obtained using 2-({4-[2-(heptylamino)ethyl]-1,3-thiazol-2-yl}thio)-2-methylpropionic acid tert-butyl ester synthesized in Example 303-2 and quinoxaline-2-carboxylic acid as starting materials and by an operation similar to that of Example 312-1 was treated with dichloromethane and trifluoroacetic acid, and the mixture was stirred at room temperature for 12 hr. The reaction solution was concentrated under reduced pressure, and the residue was purified by silica gel chromatography (elution solvent; chloroform:methanol=50:1) to give the title compound.

$^1$H-NMR (DMSO-$d_6$, 270 MHz) δ: 0.63-1.14 (13H, m), 1.21-1.42 (8H, m), 3.00-3.85 (6H, m), 7.38-7.72 (3H, m), 7.78-7.90 (1H, m), 7.96-8.10 (2H, m), 8.41-8.52 (1H, m).
MS: 500 (M$^+$+1).

Example 317

2-{[4-(2-{heptyl[(2-phenyl-1,3-thiazol-4-yl)carbonyl]amino}ethyl)-1,3-thiazol-2-yl]thio}-2-methylpropionic acid

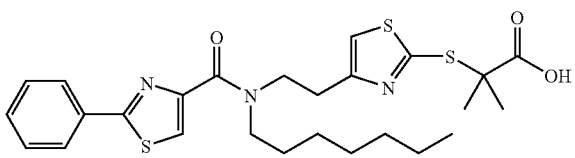

The title compound was obtained using 2-({4-[2-(heptylamino)ethyl]-1,3-thiazol-2-yl}thio)-2-methylpropionic acid tert-butyl ester synthesized in Example 303-2 and 2-phenyl-1,3-thiazole-4-carboxylic acid as starting materials and by an operation similar to that of Example 312.

$^1$H-NMR (CDCl$_3$, 300 MHz) δ: 0.82-0.89 (3H, m), 1.24-1.35 (8H, m), 1.58-1.67 (8H, m), 3.24-3.26 (2H, m), 3.47-3.70 (2H, m), 3.87-4.16 (2H, m), 6.90-7.15 (1H, m), 7.45-7.47 (3H, m), 7.88-7.99 (3H, m).
MS: 532 (M$^+$+1).

Example 318

2-[(4-{2-[(biphenyl-2-ylcarbonyl)(heptyl)amino]ethyl}-1,3-thiazol-2-yl)thio]-2-methylpropionic acid

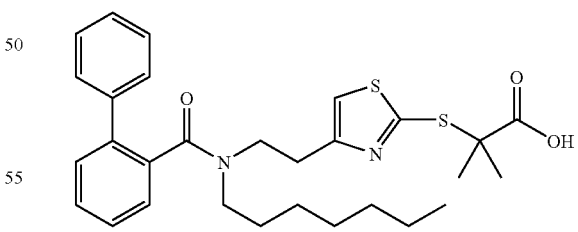

A compound obtained using 2-({4-[2-(heptylamino)ethyl]-1,3-thiazol-2-yl}thio)-2-methylpropionic acid tert-butyl ester synthesized in Example 303-2 and biphenyl-2-carboxylic acid as starting materials and by an operation similar to that of Example 312-1 was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile) to give the title compound.

¹H-NMR (CDCl₃, 270 MHz) δ: 0.70-1.37 (13H, m), 1.62 (6H, m), 2.33-3.96 (5H, m), 3.13-4.02 (3H, m), 6.65-6.77 (1H, m), 7.03-7.52 (9H, m).

MS: 525 (M⁺+1).

Example 319

2-[(4-{2-[3-(2,4-difluorophenyl)-1-heptylureido]ethyl}-1,3-thiazol-2-yl)thio]-2-methylpropionic acid

Example 319-1

2-[(4-{2-[3-(2,4-difluorophenyl)-1-heptylureido]ethyl}-1,3-thiazol-2-yl)thio]-2-methylpropionic acid tert-butyl ester

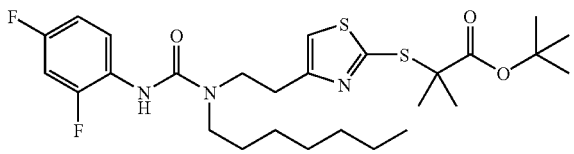

To 2-({4-[2-(heptylamino)ethyl]-1,3-thiazol-2-yl}thio)-2-methylpropionic acid tert-butyl ester (1.2 g) synthesized in Example 303-2 were added 2,4-difluoroisocyanate (0.40 mL) and pyridine (0.25 mL), and the mixture was stirred at room temperature overnight. The reaction mixture was poured into water, and the mixture was extracted with ethyl acetate, washed with saturated brine, and dried over sodium sulfate. The solvent was evaporated under reduced pressure and the obtained residue was purified by silica gel chromatography (elution solvent hexane-ethyl acetate=4:1) to give the title compound (0.77 g) as a pale-brown oil.

¹H-NMR (CDCl₃, 300 MHz) δ: 0.88 (2H, t, J=6.6 Hz), 1.24-1.30 (8H, m), 1.43 (9H, s), 1.56 (3H, s), 1.57 (3H, s), 1.55-1.58 (2H, m), 3.08 (2H, t, J=7.2 Hz), 3.22 (2H, t, J=7.2 Hz), 3.70 (2H, t, J=7.5 Hz), 6.62 (1H, brs), 6.81-6.87 (2H, m), 7.09 (1H, s), 7.95-8.00 (1H, m).

MS: 556 (M⁺+1).

Example 319-2

2-[(4-{2-[3-(2,4-difluorophenyl)-1-heptylureido]ethyl}-1,3-thiazol-2-yl)thio]-2-methylpropionic acid

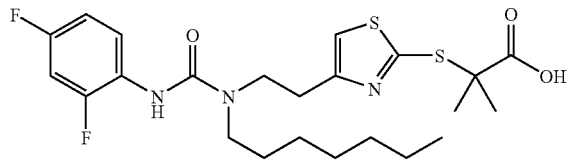

To 2-[(4-{2-[3-(2,4-difluorophenyl)-1-heptylureido]ethyl}-1,3-thiazol-2-yl)thio]-2-methylpropionic acid tert-butyl ester (0.67 g) obtained in Example 319-1 was added formic acid (10 mL), and the mixture was stirred at room temperature overnight, stirred at 50° C. for 3 hr and further stirred at 70° C. for 4 hr. The reaction mixture was poured into water, and the mixture was extracted with ethyl acetate, washed with saturated brine, and dried over sodium sulfate. The solvent was evaporated under reduced pressure and the obtained residue was purified by silica gel chromatography (elution solvent hexane-ethyl acetate=1:1) to give the title compound (0.55 g) as a pale-brown oil.

¹H-NMR (CDCl₃, 300 MHz) δ: 0.89 (2H, t, J=7.2 Hz), 1.24-1.32 (8H, m), 1.57-1.64 (2H, m), 1.64 (6H, s), 3.09 (2H, t, J=7.2 Hz), 3.24 (2H, t, J=7.2 Hz), 3.70 (2H, t, J=7.2 Hz), 6.45 (1H, d, J=3.0 Hz), 6.80-6.88 (2H, m), 7.07 (1H, s), 7.94-8.01 (1H, m).

MS: 500 (M⁺+1).

Example 320

2-({4-[2-(3-cyclohexyl-1-heptylureido)ethyl]-1,3-thiazol-2-yl}thio)-2-methylpropionic acid dicyclohexylamine salt

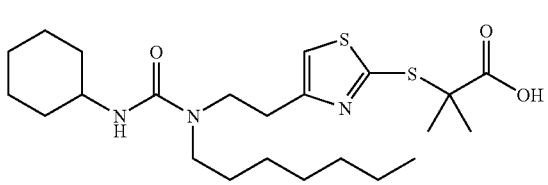

The title compound was obtained using 2-({4-[2-(heptylamino)ethyl]-1,3-thiazol-2-yl}thio)-2-methylpropionic acid tert-butyl ester synthesized in Example 303-2 and cyclohexyl isocyanate as starting materials and by an operation similar to that of Example 319, followed by reaction with dicyclohexylamine.

¹H-NMR (DMSO-d₆, 270 MHz) δ: 0.85 (3H, t, J=6.8 Hz), 0.96-2.04 (46H, m), 2.77-3.72 (9H, m), 7.26 (1H, s)

MS: 470 (M⁺+1).

Example 321

2-({4-[3-(3-cyclohexyl-1-heptylureido)propyl]-1,3-thiazol-2-yl}thio)-2-methylpropionic acid dicyclohexylamine salt

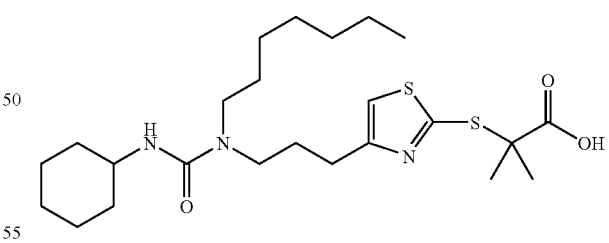

The title compound was obtained using 2-({4-[3-(heptylamino)propyl]-1,3-thiazol-2-yl}thio)-2-methylpropionic acid tert-butyl ester synthesized in Example 311-1 and cyclohexylisocyanate as starting materials and by an operation similar to that of Example 319, followed by reaction with dicyclohexylamine.

¹H-NMR (CDCl₃, 270 MHz) δ: 0.88 (3H, t, J=6.7 Hz), 1.02-2.12 (36H, m), 2.77 (2H, t, J=7.0 Hz), 2.88-3.06 (2H, m), 3.14 (2H, t, J=7.6 Hz), 3.27 (2H, t, J=7.6 Hz), 3.54-3.72 (1H, m), 4.40 (1H, d, J=7.6 Hz), 6.96 (1H, s)

MS: 484 (M⁺+1).

Example 322

2-[4-(2-{[3-cyclohexyl-1-(4-cyclohexylbutyl)ureido]ethyl}-1,3-thiazol-2-yl)thio]-2-methylpropionic acid dicyclohexylamine salt

Example 322-1

2-({4-[2-(4-cyclohexylbutylamino)ethyl]-1,3-thiazol-2-yl}thio)-2-methylpropionic acid tert-butyl ester

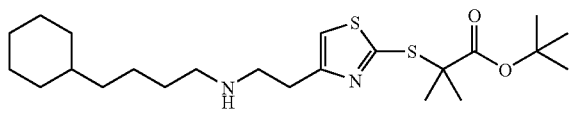

2-{[4-(2-Aminoethyl)-1,3-thiazol-2-yl]thio}-2-methylpropionic acid tert-butyl ester (1.51 g) synthesized in Example 7 and 4-cyclohexylbutanoic acid (0.85 g) were dissolved in N,N-dimethylformamide (10 mL), N-(3-dimethylaminopropyl)-N'-ethylcarbodiimide (EDC) hydrochloride (1.05 g) and hydroxybenzotriazole (HOBT) monohydrate (0.85 g) were successively added thereto, and the mixture was stirred at room temperature for 5 hr. Water was added to the reaction mixture, and the mixture was extracted with ethyl acetate. The organic layer was washed with saturated aqueous sodium hydrogen carbonate solution and saturated brine, and dried over anhydrous sodium sulfate. The solvent was evaporated under reduced pressure, and the residue was purified by silica gel chromatography (elution solvent; hexane:ethyl acetate=2:1) and the reaction mixture was directly purified by silica gel chromatography (elution solvent; hexane:ethyl acetate=1:1) to give 2-({4-[2-(4-cyclohexylbutanoylamino)ethyl]-1,3-thiazol-2-yl}thio)-2-methylpropionic acid tert-butyl ester (2.2 g) as a colorless oil. The obtained compound (2.2 g) was dissolved in tetrahydrofuran (10 mL), 1 M-borane/tetrahydrofuran complex (19.5 mL) was added under ice-cooling, and the mixture was stirred at room temperature for 12 hr. The reaction mixture was ice-cooled, and methanol (30 mL) was added dropwise. After warming to room temperature, the mixture was stirred for 1 hr. The reaction mixture was concentrated under reduced pressure, piperidine (30 mL) was added, and the mixture was stirred at 50° C. for 3 hr. The reaction mixture was concentrated under reduced pressure, and the residue was purified by silica gel chromatography (elution solvent; chloroform:methanol=50:1) to give the title compound (1.2 g) as a colorless oil.

Example 322-2

2-[4-(2-{[3-cyclohexyl-1-(4-cyclohexylbutyl)ureido]ethyl}-1,3-thiazol-2-yl)thio]-2-methylpropionic acid dicyclohexylamine salt

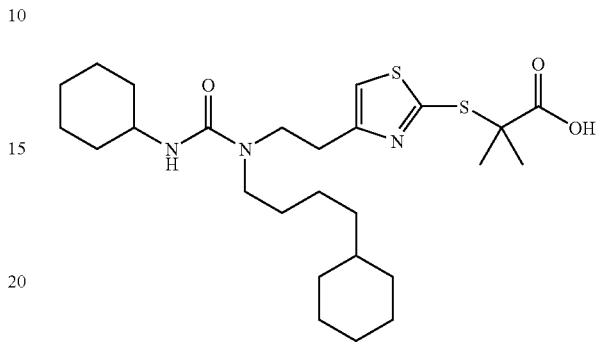

A compound obtained using 2-({4-[2-(4-cyclohexylbutylamino)ethyl]-1,3-thiazol-2-yl}thio)-2-methylpropionic acid tert-butyl ester obtained in Example 322-1 and cyclohexylisocyanate as starting materials and by an operation similar to that of Example 319-1 was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile) to give the title compound.

$^1$H-NMR (DMSO-$d_6$, 270 MHz) δ: 0.75-1.99 (33H, m), 2.94-3.18 (4H, m), 3.50-3.70 (3H, m), 4.24 (1H, m), 7.04 (1H, s)

MS: 510 (M$^+$+1).

Example 323

2-[4-(2-{[1-heptyl-3-(3-pyridyl)ureido]ethyl}-1,3-thiazol-2-yl)thio]-2-methylpropionic acid

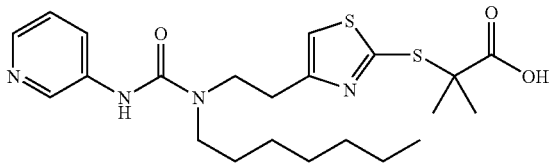

Nicotinic acid (148 mg) was dissolved in toluene (8 mL), triethylamine (0.2 mL) and diphenylphosphoric acid azide (0.28 mL) were added and the mixture was refluxed for 1 hr to give 3-pyridylisocyanate. The reaction mixture was cooled to room temperature, 2-({4-[2-(heptylamino)ethyl]-1,3-thiazol-2-yl}thio)-2-methylpropionic acid tert-butyl ester (400 mg) synthesized in Example 303-2 was added and the mixture was stirred for 1 hr. The reaction mixture was diluted with ethyl acetate, and washed with water. The organic layer was washed with saturated brine, and dried over anhydrous magnesium sulfate. The solvent was evaporated under reduced pressure, and the residue was purified by silica gel chromatography (elution solvent; ethyl acetate:hexane=1:9) to give 2-[4-(2-{[1-heptyl-3-(3-pyridyl)ureido]ethyl}-1,3-thiazol-2-yl)thio]-2-methylpropionic acid tert-butyl ester (0.43 g) as a colorless oil.

The obtained compound (0.43 g) was dissolved in dichloromethane (5 mL), trifluoroacetic acid (2 mL) was added and the mixture was stirred at room temperature for 20 hr. The reaction mixture was concentrated, and the residue was purified by silica gel chromatography (elution solvent; hexane: ethyl acetate=1:1 to 0:1) to give the title compound (380 mg) as a colorless oil.

$^1$H-NMR (CDCl$_3$, 400 MHz) δ: 0.88 (3H, t, J=6.9 Hz), 1.18-1.35 (8H, m), 1.52-1.68 (8H, m), 3.11 (2H, t, J=6.8 Hz), 3.34 (2H, t, J=6.8 Hz), 3.76 (2H, t, J=6.8 Hz), 7.18 (1H, s), 7.76 (1H, dd, J=5.6, 8.8 Hz), 8.32 (1H, d, J=5.6 Hz), 8.76 (1H, brs), 8.86 (1H, d, J=8.8 Hz), 9.22 (1H, s).

MS: 465 (M$^+$+1).

Example 324

2-[4-(2-{[1-heptyl-3-(4-pyridyl)ureido]ethyl}-1,3-thiazol-2-yl)thio]-2-methylpropionic acid

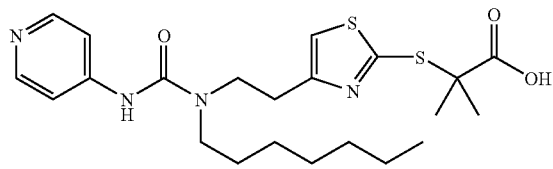

A compound obtained using isonicotinic acid and 2-({4-[2-(heptylamino)ethyl]-1,3-thiazol-2-yl}thio)-2-methylpropionic acid tert-butyl ester synthesized in Example 303-2 as starting materials and by an operation similar to that of Example 323 was purified by high performance liquid chromatography (elution solvent; 0.05% trifluoroacetic acid-water:0.05% trifluoroacetic acid-acetonitrile) to give the title compound.

$^1$H-NMR (CDCl$_3$, 400 MHz) δ: 0.88 (3H, t, J=6.9 Hz), 1.19-1.37 (8H, m), 1.50-1.65 (8H, m), 3.10 (2H, t, J=6.4 Hz), 3.33 (2H, t, J=6.8 Hz), 3.82 (2H, t, J=6.8 Hz), 7.15 (1H, s), 8.09 (1H, d, J=6.8 Hz), 8.33 (1H, d, J=8.8 Hz), 9.93 (1H, s).

MS: 465 (M$^+$+1).

Example 325

2-[4-(2-{[1-heptyl-3-(5-methylthiophene-2-yl)ureido]ethyl}-1,3-thiazol-2-yl)thio]-2-methylpropionic acid

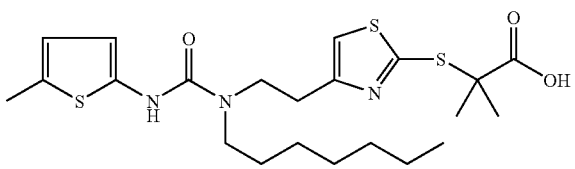

A compound obtained using 5-methylthiophenecarboxylic acid and 2-({4-[2-(heptylamino)ethyl]-1,3-thiazol-2-yl}thio)-2-methylpropionic acid tert-butyl ester synthesized in Example 303-2 as starting materials and by an operation similar to that of Example 323, was purified by high performance liquid chromatography (elution solvent; 0.05% trifluoroacetic acid-water:0.05% trifluoroacetic acid-acetonitrile) to give the title compound.

$^1$H-NMR (CDCl$_3$, 400 MHz) δ: 0.80-0.91 (3H, m), 1.10-1.35 (8H, m), 1.50-1.70 (8H, m), 2.37 (3H, s), 3.06 (2H, t, J=6.8 Hz), 3.22 (2H, t, J=7.6 Hz), 3.67 (2H, t, J=6.8 Hz), 6.36 (1H, d, J=3.6 Hz), 6.43 (1H, d, J=3.6 Hz), 7.01 (1H, s), 7.06 (1H, s).

MS: 484 (M$^+$+1).

Example 326

2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid Reference Example 15

3-amino-1-phenyl-1H-pyrazole-4-carboxylic acid ethyl ester

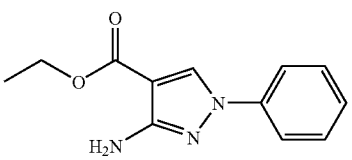

2-(Ethoxymethylene)-2-cyanoacetic acid ethyl ester (78.2 g) and phenylhydrazine (50.0 g) were dissolved in ethanol (500 mL), and the mixture was refluxed for 3 hr. After cooling, the reaction mixture was concentrated under reduced pressure. Hexane (500 mL) was added, to the residue, and the residue was washed by suspending and filtered. The obtained solid was vacuum dried to give the title compound (86.0 g) as a white solid.

$^1$H-NMR (CDCl$_3$, 300 MHz) δ: 1.36 (3H, t, J=7.5 Hz), 4.31 (2H, q, J=7.5 Hz), 5.31 (2H, brs), 7.38-7.54 (5H, m), 7.79 (1H, s).

Reference Example 16

1-phenyl-1H-pyrazole-4-carboxylic acid ethyl ester

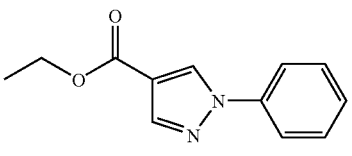

3-Amino-1-phenyl-1H-pyrazole-4-carboxylic acid ethyl ester (64.8 g) synthesized in Reference Example 15 was dissolved in tetrahydrofuran (500 mL), isoamyl nitrite (98.5 g) was added, and the mixture was stirred at 65° C. for 3 hr. After cooling, the reaction mixture was concentrated under reduced pressure. Hexane (500 mL) was added to the residue, and the residue was washed by suspending and filtered. The obtained solid was vacuum dried to give the title compound (43.0 g) as a white solid.

$^1$H-NMR (CDCl$_3$, 300 MHz) δ: 1.38 (3H, t, J=7.5 Hz), 4.35 (2H, q, J=7.5 Hz), 7.36 (1H, t, J=7.7 Hz), 7.49 (2H, t, J=7.7 Hz), 7.71 (2H, d, J=7.7 Hz), 8.11 (1H, s), 8.41 (1H, s).

Reference Example 17

(1-phenyl-1H-pyrazol-4-yl)methanol

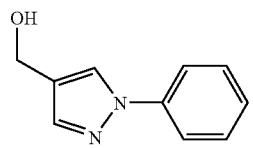

Lithium aluminum hydride (3.51 g) was suspended in tetrahydrofuran (200 mL), 1-phenyl-1H-pyrazole-4-carboxylic acid ethyl ester (20 g) synthesized in Reference Example 16 was added under ice-cooling, and the mixture was stirred at room temperature for 1.5 hr. The reaction mixture was ice-cooled, water (7 mL) and aqueous sodium hydroxide solution (1 mol/L, 3.5 mL) were successively added dropwise. After warming to room temperature, the mixture was stirred for 30 min. Anhydrous sodium sulfate was added to the reaction mixture, the mixture was filtered through celite, and the filtrate was concentrated under reduced pressure. Diethyl ether (30 mL) and hexane (30 mL) were added to the residue, and the residue was washed by suspending and filtered. The obtained solid was vacuum dried to give the title compound (14.8 g) as a white solid.

$^1$H-NMR (CDCl$_3$, 300 MHz) δ: 1.61 (1H, t, J=4.8 Hz), 4.68 (2H, d, J=4.8 Hz), 7.29 (1H, t, J=7.7 Hz), 7.45 (2H, t, J=7.7 Hz), 7.67 (2H, d, J=7.7 Hz), 7.72 (1H, s), 7.93 (1H, s).

Reference Example 18

4-(chloromethyl)-1-phenyl-1H-pyrazole

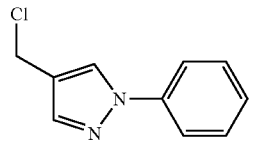

(1-Phenyl-1H-pyrazol-4-yl)methanol (6.3 g) synthesized in Reference Example 17 was dissolved in dichloromethane (100 mL) and, after ice-cooling, thionyl chloride (5.59 g) was added thereto, and the mixture was stirred at 0° C. for 2 hr. Saturated aqueous sodium hydrogen carbonate solution was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (7.4 g) as a white solid.

$^1$H-NMR (CDCl$_3$, 300 MHz) δ: 4.62 (2H, s), 7.30 (1H, t, J=8.4 Hz), 7.46 (2H, t, J=8.4 Hz), 7.66 (2H, d, J=8.4 Hz), 7.74 (1H, s), 7.96 (1H, s).

In the following, 4-(chloromethyl)-1-(4-methylphenyl)-1H-pyrazole, 4-(chloromethyl)-1-(3-methylphenyl)-1H-pyrazole, 4-(chloromethyl)-1-(2-methylphenyl)-1H-pyrazole, 4-(chloromethyl)-1-(4-chlorophenyl)-1H-pyrazole and 4-(chloromethyl)-1-(4-fluorophenyl)-1H-pyrazole were obtained using various substituted phenylhydrazines, 4-(chloromethyl)-1-cyclohexyl-1H-pyrazole was obtained using cyclohexylhydrazine, and 4-(chloromethyl)-1-(2-pyridyl)-1H-pyrazole was obtained using pyridylhydrazine, in the same manner as above.

Example 326-1

2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid tert-butyl ester

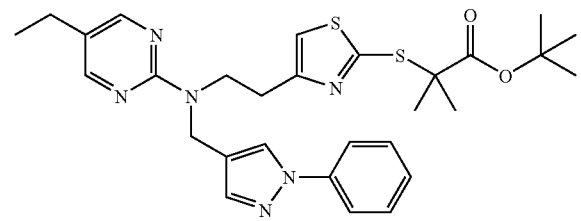

2-[(4-{2-[(5-Ethylpyrimidin-2-yl)amino]ethyl}-1,3-thiazol-2-yl)thio]-2-methylpropionic acid tert-butyl ester (7.0 g) synthesized in Example 265-1 and 4-(chloromethyl)-1-phenyl-1H-pyrazole (3.47 g) synthesized in Reference Example 18 were dissolved in N,N-dimethylformamide (80 mL), potassium tert-butoxide (2.32 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1 to 3:1) to give the title compound (7.30 g) as a colorless oil.

$^1$H-NMR (CDCl$_3$, 300 MHz) δ: 1.22 (3H, t, J=7.5 Hz), 1.44 (9H, s), 1.58 (6H, s), 2.49 (2H, q, J=7.5 Hz), 3.11 (2H, t, J=7.5 Hz), 3.95 (2H, t, J=7.5 Hz), 4.61 (2H, s), 7.00 (1H, s), 7.24 (1H, t, J=7.6 Hz), 7.41 (2H, t, J=7.6 Hz), 7.63-7.66 (3H, m), 7.90 (1H, s), 8.22 (2H, s).

Example 326-2

2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid

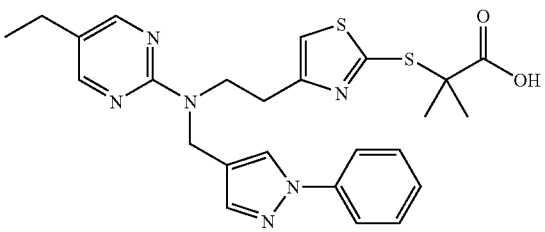

2-{[4-(2-{(5-Ethylpyrimidin-2-yl)[(1-phenyl-1H-pyrazol-4-yl)methyl]amino}ethyl)-1,3-thiazol-2-yl]thio}-2-methylpropionic acid tert-butyl ester (7.3 g) obtained in Example 326-1 was dissolved in dichloromethane (80 mL), trifluoroacetic acid (20 mL) was added, and the mixture was stirred at room temperature for 20 hr. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (5.0 g) as a white solid.

$^1$H-NMR (CDCl$_3$, 300 MHz) δ: 1.22 (3H, t, J=7.5 Hz), 1.62 (6H, s), 2.49 (2H, q, J=7.5 Hz), 3.09 (2H, t, J=7.1 Hz), 3.93 (2H, t, J=7.1 Hz), 4.70 (2H, s), 6.94 (1H, s), 7.21-7.26 (1H, m), 7.39-7.45 (2H, m), 7.64-7.68 (3H, m), 7.95 (1H, s), 8.22 (2H, s).

MS: 509 (M$^+$+1).

Example 327

2-{[4-(2-{(5-ethylpyrimidin-2-yl)[(6-phenylpyridin-3-yl)methyl]amino}ethyl)-1,3-thiazol-2-yl]thio}-2-methylpropionic acid hydrochloride Reference Example 19

6-phenylnicotinic acid ethyl ester

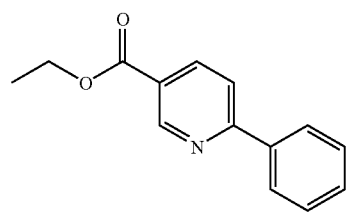

Under nitrogen atmosphere, 6-chloronicotinic acid ethyl ester (24.0 g) and phenylboric acid (23.6 g) were dissolved in dioxane (200 mL) and aqueous sodium carbonate solution (2M, 100 mL), tetrakis(triphenylphosphine)palladium (7.0 g) was added, and the mixture was refluxed for 8 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=7:1 to 5:1) to give the title compound (25.5 g) as a white solid.

$^1$H-NMR (CDCl$_3$, 300 MHz) δ: 1.43 (3H, t, J=7.0 Hz), 4.43 (2H, q, J=7.0 Hz), 7.45-7.53 (3H, m), 7.81 (1H, d, J=8.3 Hz), 8.04-8.07 (2H, m), 8.34 (1H, dd, J=2.2, 8.3 Hz), 9.29 (1H, s).

Reference Example 20

(6-phenylpyridin-3-yl)methanol

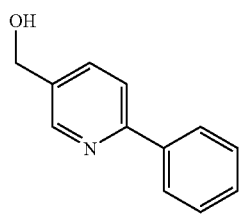

Lithium aluminum hydride (3.50 g) was suspended in tetrahydrofuran (200 mL), 6-phenylnicotinic acid ethyl ester (21.0 g) synthesized in Reference Example 19 was added under ice-cooling, and the mixture was stirred at room temperature for 12 hr. The reaction mixture was ice-cooled, water (5 mL) and aqueous sodium hydroxide solution (1 mol/L, 10 mL) were successively added dropwise. After warming to room temperature, the mixture was stirred for 1 hr. Anhydrous sodium sulfate was added to the reaction mixture, the mixture was filtered through celite, and the filtrate was concentrated under reduced pressure. The residue was purified by silica gel chromatography (elution solvent; hexane:ethyl acetate=1:1 to 1:3) to give the title compound (17.0 g) as a colorless oil.

$^1$H-NMR (CDCl$_3$, 300 MHz) δ: 2.21 (1H, brs), 4.75 (2H, s), 7.41-7.48 (3H, m), 7.70-7.79 (2H, m), 7.95-7.99 (2H, m), 8.64 (1H, s).

Reference Example 21

5-(chloromethyl)-2-phenylpyridine

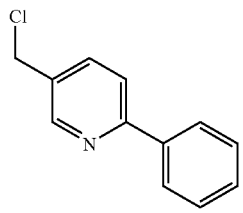

(6-Phenylpyridin-3-yl)methanol (15.0 g) synthesized in Reference Example 20 was dissolved in dichloromethane (150 mL) and, after ice-cooling, thionyl chloride (12.5 g) was added to, and the mixture was stirred at 0° C. for 2 hr. Saturated aqueous sodium hydrogen carbonate solution was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (13.5 g) as a white solid.

¹H-NMR (CDCl₃, 300 MHz) δ: 4.64 (2H, s), 7.42-7.51 (3H, m), 7.72-7.80 (2H, m), 7.97-8.01 (2H, m), 8.69 (1H, s).

Example 327-1

2-{[4-(2-{(5-ethylpyrimidin-2-yl)[(6-phenylpyridin-3-yl)methyl]amino}ethyl)-1,3-thiazol-2-yl]thio}-2-methylpropionic acid tert-butyl ester

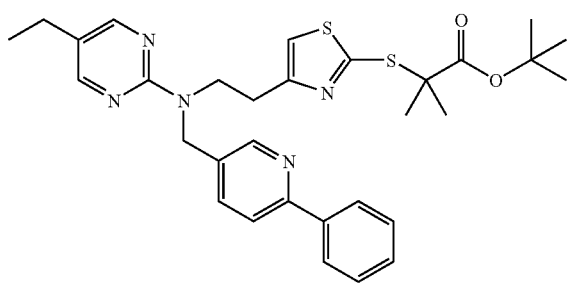

2-[(4-{2-[(5-Ethylpyrimidin-2-yl)amino]ethyl}-1,3-thiazol-2-yl)thio]-2-methylpropionic acid tert-butyl ester (600 mg) synthesized in Example 265-1 and 5-(chloromethyl)-2-phenylpyridine (360 mg) synthesized in Reference Example 21 were dissolved in N,N-dimethylformamide (10 mL), potassium tert-butoxide (200 mg) was added thereto, and the mixture was stirred at room temperature for 3 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=5:2 to 2:1) to give the title compound (740 mg) as a colorless oil.
¹H-NMR (CDCl₃, 300 MHz) δ: 1.21 (3H, t, J=7.6 Hz), 1.42 (9H, s), 1.57 (6H, s), 2.49 (2H, q, J=7.5 Hz), 3.13 (2H, t, J=6.9 Hz), 3.98 (2H, t, J=6.9 Hz), 4.78 (2H, s), 7.00 (1H, s), 7.38-7.48 (3H, m), 7.60-7.63 (2H, m), 7.93-7.97 (2H, m), 8.20 (2H, s), 8.58 (1H, s).

Example 327-2

2-{[4-(2-{(5-ethylpyrimidin-2-yl)[(6-phenylpyridin-3-yl)methyl]amino}ethyl)-1,3-thiazol-2-yl]thio}-2-methylpropionic acid hydrochloride

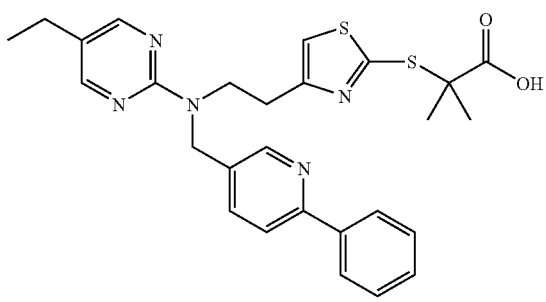

2-{[4-(2-{(5-Ethylpyrimidin-2-yl)[(6-phenylpyridin-3-yl)methyl]amino}ethyl)-1,3-thiazol-2-yl]thio}-2-methylpropionic acid tert-butyl ester (740 mg) obtained in Example 327-1 was dissolved in dichloromethane (10 mL), trifluoroacetic acid (4 mL) was added, and the mixture was stirred at room temperature for 20 hr. The reaction mixture was concentrated under reduced pressure, and the residue was purified by silica gel chromatography (elution solvent; hexane:ethyl acetate=1:1 to 0:1). The obtained compound was dissolved in diethyl ether (10 mL), 4 mol/L hydrochloric acid-ethyl acetate (2 mL) was added, and the mixture was stirred at room temperature for 1 hr. The precipitated solid was collected by filtration to give the title compound (220 mg) as a white solid.
¹H-NMR (DMSO-d₆, 300 MHz) δ: 1.16 (3H, t, J=7.2 Hz), 1.50 (6H, s), 2.48 (2H, q, J=7.2 Hz), 3.08 (2H, t, J=7.2 Hz), 4.03 (2H, t, J=7.2 Hz), 4.92 (2H, s), 7.49 (1H, s), 7.57-7.61 (3H, m), 8.08-8.11 (2H, m), 8.19 (2H, s), 8.34 (2H, s), 8.66 (1H, s).
MS: 520 (M⁺+1).

Example 328

2-[(4-{2-[(5-ethylpyrimidin-2-yl)(pentyl)amino]ethyl}-1,3-thiazol-2-yl)thio]-2-methylpropionic acid hydrogen bromide

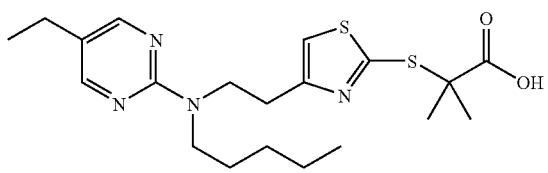

A compound obtained using 2-[(4-{2-[(5-Ethylpyrimidin-2-yl)amino]ethyl}-1,3-thiazol-2-yl)thio]-2-methylpropionic acid tert-butyl ester synthesized in Example 265-1 and 1-iodopentane as starting materials, and by an operation similar to that of Example 326 was dissolved in diethyl ether, and reacted with 30% hydrobromic acid-acetic acid to give the title compound.
¹H-NMR (DMSO-d₆, 400 MHz) δ: 0.86 (3H, t, J=6.9 Hz), 1.16 (3H, t, J=7.5 Hz), 1.20-1.30 (4H, m), 1.43-1.58 (8H, m), 2.47-2.53 (2H, m), 3.03 (2H, t, J=7.0 Hz), 3.44 (2H, t, J=7.6 Hz), 3.89 (2H, t, J=7.0 Hz), 7.50 (1H, s), 8.39 (2H, s).
MS: 423 (M⁺+1).

Example 329

2-[(4-{2-[(5-ethylpyrimidin-2-yl)(hexyl)amino]ethyl}-1,3-thiazol-2-yl)thio]-2-methylpropionic acid hydrogen bromide

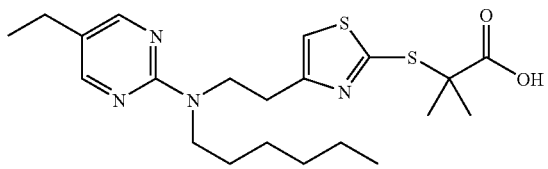

A compound obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-iodohexane as starting materials and by an operation similar to

Example 330

2-[(4-{2-[(5-ethylpyrimidin-2-yl)(octyl)amino]ethyl}-1,3-thiazol-2-yl)thio]-2-methylpropionic acid hydrogen bromide

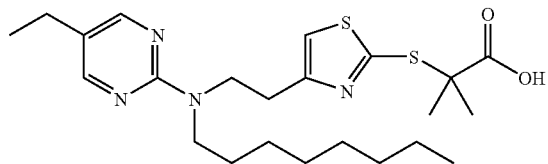

A compound obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-iodooctane as starting materials and by an operation similar to that of Example 326 was dissolved in diethyl ether, and reacted with 30% hydrobromic acid-acetic acid to give the title compound.

$^1$H-NMR (DMSO-d$_6$, 400 MHz) δ: 0.87 (3H, t, J=7.2 Hz), 1.17-1.45 (10H, m), 1.62-1.81 (8H, m), 2.65 (2H, t, J=7.2 Hz), 3.54-3.65 (2H, m), 4.05-4.25 (4H, m), 8.29 (1H, s), 8.67 (1H, s), 9.05 (1H, s).

MS: 465 (M$^+$+1).

Example 331

2-[(4-{2-[(5-ethylpyrimidin-2-yl)(nonyl)amino]ethyl}-1,3-thiazol-2-yl)thio]-2-methylpropionic acid hydrogen bromide

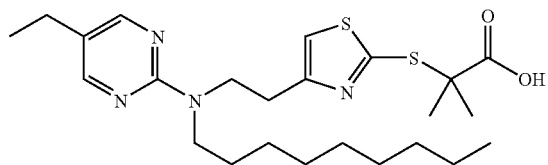

A compound obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-iodononane as starting materials and by an operation similar to that of Example 326 was dissolved in diethyl ether, and reacted with 30% hydrobromic acid-acetic acid to give the title compound.

$^1$H-NMR (DMSO-d$_6$, 400 MHz) δ: 0.87 (3H, t, J=7.2 Hz), 1.19-1.44 (12H, m), 1.60-1.81 (8H, m), 2.65 (2H, t, J=7.2 Hz), 3.55-3.68 (2H, m), 4.03-4.25 (4H, m), 8.29 (1H, s), 8.67 (1H, s), 8.98 (1H, s).

MS: 479 (M$^+$+1).

that of Example 326 was dissolved in diethyl ether, and reacted with 30% hydrobromic acid-acetic acid to give the title compound.

$^1$H-NMR (DMSO-d$_6$, 400 MHz) δ: 0.856 (3H, t, J=7.0 Hz), 1.16 (3H, t, J=7.7 Hz), 1.20-1.30 (6H, m), 1.42-1.54 (8H, m), 2.44-2.53 (2H, m), 3.03 (2H, t, J=6.8 Hz), 3.40-3.47 (2H, m), 3.90 (2H, t, J=6.8 Hz), 7.50 (1H, s), 8.40 (2H, s).

MS: 437 (M$^+$+1).

Example 332

2-[(4-{2-[(5-ethylpyrimidin-2-yl)(4-methylpentyl)amino]ethyl}-1,3-thiazol-2-yl)thio]-2-methylpropionic acid hydrogen bromide

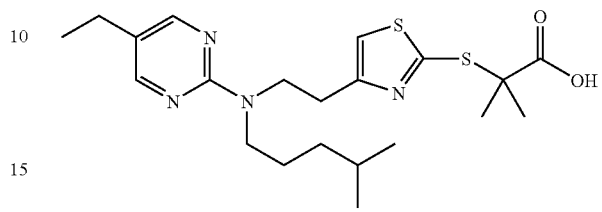

A compound obtained using 1-iodo-4-methylpentane, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-methylpentanol as starting materials and in reference to non-patent reference [Tetrahedron, 38, 11461 (1998)], and by an operation similar to that of Example 326, was dissolved in diethyl ether, and reacted with 30% hydrobromic acid-acetic acid to give the title compound.

$^1$H-NMR (DMSO-d$_6$, 400 MHz) δ: 0.87 (3H, t, J=7.0 Hz), 1.10-1.18 (5H, m), 1.48-1.55 (9H, m), 2.47-2.55 (9H, m), 3.03 (2H, t, J=7.0 Hz), 3.41 (2H, t, J=7.0 Hz), 3.90 (2H, t, J=7.0 Hz), 7.52 (1H, s), 8.41 (1H, s).

MS: 437 (M$^+$+1).

Example 333

2-[(4-{2-[(5-ethylpyrimidin-2-yl)(5-methylhexyl)amino]ethyl}-1,3-thiazol-2-yl)thio]-2-methylpropionic acid hydrogen bromide

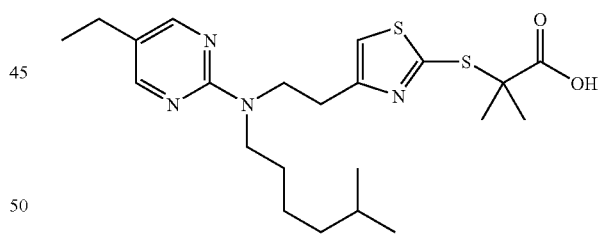

A compound obtained using 1-iodo-5-methylhexane, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 5-methylhexanol as starting materials and in reference to non-patent reference [Tetrahedron, 38, 11461 (1998)], and by an operation similar to that of Example 326, was dissolved in diethyl ether, and reacted with 30% hydrobromic acid-acetic acid to give the title compound.

$^1$H-NMR (DMSO-d$_6$, 400 MHz) δ: 0.84 (3H, t, J=7.0 Hz), 1.10-1.29 (7H, m), 1.46-1.51 (9H, m), 2.48-2.55 (2H, m), 3.03 (2H, t, J=7.0 Hz), 3.44 (2H, t, J=7.0 Hz), 3.91 (2H, t, J=7.0 Hz), 7.53 (1H, s), 8.44 (1H, s).

MS: 451 (M$^+$+1).

Example 334

2-[(4-{2-[(5-ethylpyrimidin-2-yl)(6-methylheptyl)amino]ethyl}-1,3-thiazol-2-yl)thio]-2-methylpropionic acid hydrogen bromide

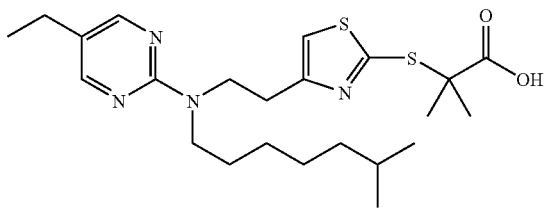

A compound obtained using 6-methyl-1-iodoheptane, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 6-methylheptanol as starting materials and in reference to non-patent reference [Tetrahedron, 38, 11461 (1998)], and by an operation similar to that of Example 326, was dissolved in diethyl ether, and reacted with 30% hydrobromic acid-acetic acid to give the title compound.

$^1$H-NMR (DMSO-$d_6$, 400 MHz) δ: 0.82-0.95 (8H, m), 0.97-1.60 (16H, m), 2.50-2.54 (2H, m), 3.03 (2H, t, J=7.0 Hz), 3.37-3.46 (2H, m), 3.85-3.91 (2H, m), 7.52 (1H, s), 8.40 (1H, s), 8.47 (1H, s).

MS: 465 (M$^+$+1).

Example 335

2-({4-[2-((5-ethylpyrimidin-2-yl){1-(4-fluorophenyl)-1H-pyrazol-4-yl]methyl}amino)ethyl]-1,3-thiazol-2-yl}thio)-2-methylpropionic acid hydrochloride

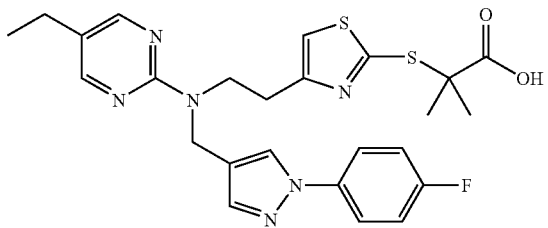

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(4-fluorophenyl)-1H-pyrazole synthesized in the same manner as in Reference Examples 16 to 18 as starting materials and by an operation similar to that of Example 327.

$^1$H-NMR (DMSO-$d_6$, 400 MHz) δ: 1.16 (3H, t, J=7.7 Hz), 1.50 (6H, s), 2.47 (2H, q, J=7.7 Hz), 3.05 (2H, t, J=7.1 Hz), 3.92 (2H, t, J=7.1 Hz), 4.64 (2H, s), 7.28-7.34 (2H, m), 7.50 (1H, s), 7.67 (1H, s), 7.79-7.83 (2H, m), 8.35 (2H, s), 8.39 (1H, s).

MS: 527 (M$^+$+1).

Example 336

2-[(4-{2-[{[1-(4-chlorophenyl)-1H-pyrazol-4-yl]methyl}(5-ethylpyrimidin-2-yl)amino]ethyl}-1,3-thiazol-2-yl)thio]-2-methylpropionic acid hydrochloride

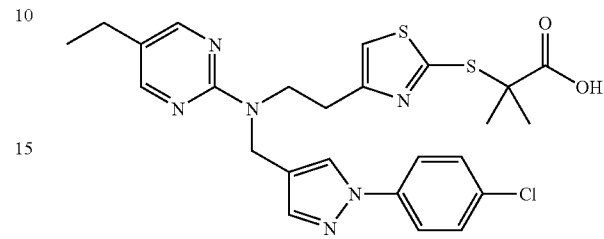

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(4-chlorophenyl)-1H-pyrazole synthesized in the same manner as in Reference Examples 16 to 18 as starting materials and by an operation similar to that of Example 327.

$^1$H-NMR (DMSO-$d_6$, 400 MHz) δ: 1.15 (3H, t, J=7.6 Hz), 1.50 (6H, s), 2.45 (2H, q, J=7.6 Hz), 3.03 (2H, t, J=7.0 Hz), 3.90 (2H, t, J=7.0 Hz), 4.62 (2H, s), 7.48 (1H, s), 7.53 (2H, d, J=7.0 Hz), 7.68 (1H, s), 7.82 (2H, d, J=7.0 Hz), 8.31 (2H, s), 8.41 (1H, s).

MS: 534 (M$^+$+1).

Example 337

2-({4-[2-((5-ethylpyrimidin-2-yl){1-(4-methylphenyl)-1H-pyrazol-4-yl]methyl}amino)ethyl]-1,3-thiazol-2-yl}thio)-2-methylpropionic acid hydrochloride

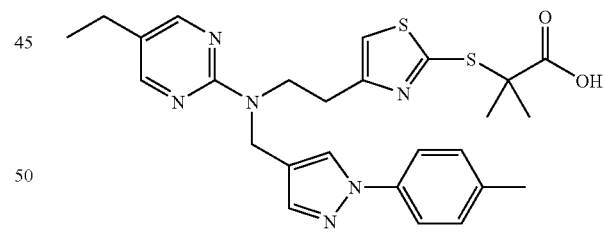

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(4-methylphenyl)-1H-pyrazole synthesized in the same manner as in Reference Examples 16 to 18 as starting materials and by an operation similar to that of Example 327.

$^1$H-NMR (DMSO-$d_6$, 400 MHz) δ: 1.15 (3H, t, J=7.5 Hz), 1.50 (6H, s), 2.32 (3H, s), 2.46 (2H, q, J=7.5 Hz), 3.03 (2H, t, J=7.0 Hz), 3.90 (2H, t, J=7.0 Hz), 4.62 (2H, s), 7.26 (2H, d, J=8.4 Hz), 7.49 (1H, s), 7.63 (1H, s), 7.65 (2H, d, J=8.4 Hz), 8.32 (2H, s).

MS: 523 (M$^+$+1).

Example 338

2-({4-[2-((5-ethylpyrimidin-2-yl){[1-(3-methylphenyl)-1H-pyrazol-4-yl]methyl}amino)ethyl]-1,3-thiazol-2-yl}thio)-2-methylpropionic acid hydrochloride

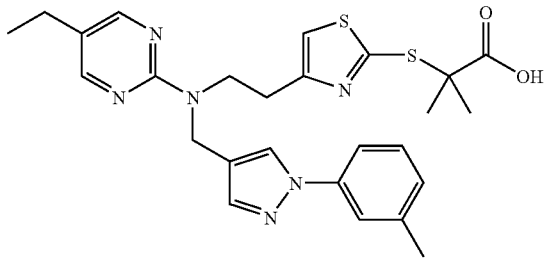

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(3-methylphenyl)-1H-pyrazole synthesized in the same manner as in Reference Examples 16 to 18 as starting materials and by an operation similar to that of Example 327.

$^1$H-NMR (DMSO-$d_6$, 400 MHz) δ: 1.15 (3H, t, J=7.5 Hz), 1.50 (6H, s), 2.36 (3H, s), 2.47 (2H, q, J=7.5 Hz), 3.04 (2H, t, J=7.1 Hz), 3.92 (2H, t, J=7.1 Hz), 4.63 (2H, s), 7.08-7.10 (1H, m), 7.34 (1H, t, J=7.8 Hz), 7.50 (1H, s), 7.56-7.65 (3H, m), 8.34 (2H, s), 8.38 (1H, s).

MS: 523 (M$^+$+1).

Example 339

2-({4-[2-((5-ethylpyrimidin-2-yl){[1-(2-methylphenyl)-1H-pyrazol-4-yl]methyl}amino)ethyl]-1,3-thiazol-2-yl}thio)-2-methylpropionic acid hydrochloride

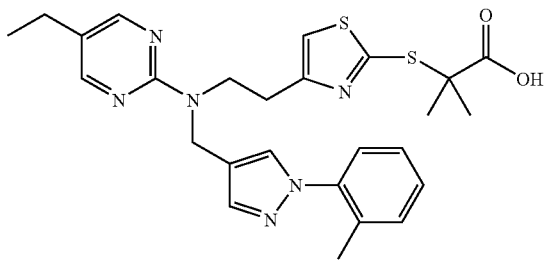

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(2-methylphenyl)-1H-pyrazole synthesized in the same manner as in Reference Examples 16 to 18 as starting materials and by an operation similar to that of Example 327.

$^1$H-NMR (DMSO-$d_6$, 400 MHz) δ: 1.16 (3H, t, J=7.9 Hz), 1.50 (6H, s), 2.17 (3H, s), 2.46-2.51 (2H, m), 3.04 (2H, t, J=7.0 Hz), 3.93 (2H, t, J=7.0 Hz), 4.69 (2H, s), 7.30-7.38 (4H, m), 7.51 (1H, s), 7.67 (1H, s), 8.00 (1H, s), 8.39 (2H, s).

MS: 523 (M$^+$+1).

Example 340

2-{[4-(2-{(5-ethylpyrimidin-2-yl)[(1-pyridin-2-yl-1H-pyrazol-4-yl)methyl]amino}ethyl)-1,3-thiazol-2-yl]thio}-2-methylpropionic acid hydrochloride

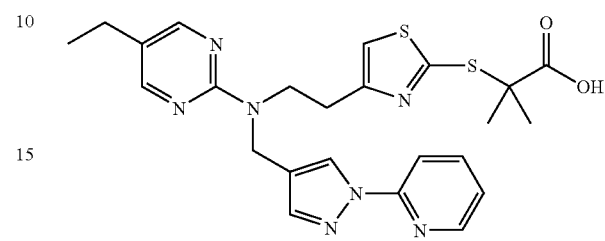

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 2-[4-(chloromethyl)-1H-pyrazol-1-yl]pyridine synthesized in the same manner as in Reference Examples 16 to 18 as starting materials and by an operation similar to that of Example 327.

$^1$H-NMR (DMSO-$d_6$, 400 MHz) δ: 1.16 (3H, t, J=7.7 Hz), 1.50 (6H, s), 2.46-2.51 (2H, m), 3.05 (2H, t, J=7.0 Hz), 3.94 (2H, t, J=7.0 Hz), 4.68 (2H, s), 7.33 (2H, dd, J=4.7, 7.0 Hz), 7.51 (1H, s), 7.77 (1H, s), 8.37-8.54 (4H, m).

MS: 510 (M$^+$+1).

Example 341

2-[(4-{2-[[(1-cyclohexyl-1H-pyrazol-4-yl)methyl](5-ethylpyrimidin-2-yl)amino]ethyl}-1,3-thiazol-2-yl)thio]-2-methylpropionic acid hydrochloride

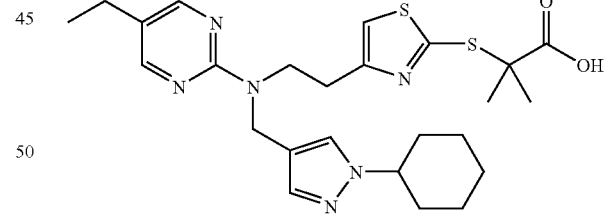

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-cyclohexyl-1H-pyrazole synthesized in the same manner as in Reference Examples 16 to 18 as starting materials and by an operation similar to that of Example 327.

$^1$H-NMR (DMSO-$d_6$, 400 MHz) δ: 1.08-1.41 (6H, m), 1.50 (6H, s), 1.58-2.00 (7H, m), 2.47-2.54 (2H, m), 2.99 (2H, t, J=6.5 Hz), 3.86 (2H, t, J=6.5 Hz), 4.05 (1H, s), 4.57 (2H, s), 7.39 (1H, s), 7.49 (1H, s), 7.72 (2H, s).

MS: 515 (M$^+$+1).

Example 342

2-({4-[2-((5-ethylpyrimidin-2-yl){[1-(2-thienyl)-1H-pyrazol-4-yl]methyl}amino)ethyl]-1,3-thiazol-2-yl}thio)-2-methylpropionic acid hydrochloride

Reference Example 22

4-(chloromethyl)-1-(2-thienyl)-1H-pyrazole

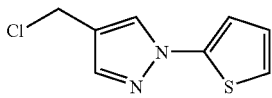

1H-Pyrazole-4-carboxylic acid ethyl ester (7.0 g) and 2-iodothiophene (10.5 g) were dissolved in DMSO (50 mL), potassium carbonate (6.91 g) and copper powder (31.7 mg) were added, and the mixture was stirred at 150° C. for 6 hr. The reaction mixture was cooled to 80° C., bromoethane (2 mL) was added, and the mixture was stirred for 2 hr and cooled to room temperature. The reaction mixture was diluted with ethyl acetate. The organic layer was washed with water, dried over magnesium sulfate, and concentrated under reduced pressure. The residue was purified by silica gel chromatography (elution solvent; hexane:ethyl acetate=9:1) to give 1-(2-thienyl)-1H-pyrazole-4-carboxylic acid ethyl ester (2.23 g) as a white solid. The obtained compound was subjected to reactions in the same manner as in Reference Examples 17 to 18 to give the title compound.

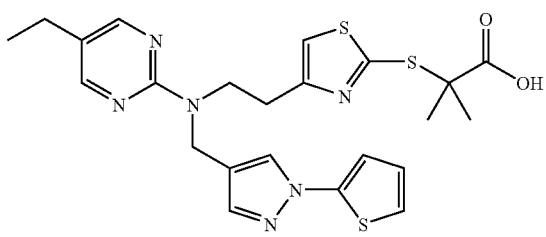

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(2-thienyl)-1H-pyrazole synthesized in Reference Example 22 as starting materials and by an operation similar to that of Example 327.

$^1$H-NMR (DMSO-d$_6$, 400 MHz) δ: 1.16 (3H, t, J=7.4 Hz), 1.51 (6H, s) 2.49 (2H, q, J=7.4 Hz), 3.06 (2H, t, J=7.0 Hz), 3.94 (2H, t, J=7.0 Hz), 4.64 (2H, s), 6.96-7.00 (1H, m), 7.23-7.26 (1H, m), 7.52 (1H, s), 7.64 (1H, s), 8.33 (1H, s), 8.39 (2H, s).

MS: 515 (M$^+$+1).

Example 343

2-{[4-(2-{(5-ethylpyrimidin-2-yl)[(1-isobutyl-1H-pyrazol-4-yl)methyl]amino}ethyl)-1,3-thiazol-2-yl]thio}-2-methylpropionic acid hydrochloride

Reference Example 23

4-(chloromethyl)-1-(2-methylpropyl)-1H-pyrazole

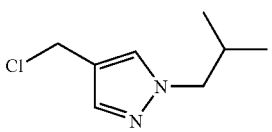

1H-Pyrazole-4-carboxylic acid ethyl ester (5.0 g) was dissolved in DMF (50 mL), 60% sodium hydride (1.57 g) was added, and the mixture was stirred at 0° C. for 30 min. Then, isobutyl iodide (4.7 mL) was added, and the mixture was stirred for 14 hr. Water was added to the reaction mixture, and the mixture was extracted with ethyl acetate. The organic layer was washed with water, dried over magnesium sulfate, and concentrated under reduced pressure. The residue was purified by silica gel chromatography (elution solvent; hexane:ethyl acetate=8:2) to give 1-(2-methylpropyl)-1H-pyrazole-4-carboxylic acid ethyl ester (6.0 g) as an oil. The obtained compound was subjected to reactions in the same manner as in Reference Examples 17 to 18 to give the title compound.

In the same manner as above, 4-(chloromethyl)-1-(2-methylpropyl)-1H-pyrazole was obtained using 1H-pyrazole-4-carboxylic acid ethyl ester and butyl iodide, and 4-(chloromethyl)-1-(phenylmethyl)-1H-pyrazole was obtained using 1H-pyrazole-4-carboxylic acid ethyl ester and benzylbromide.

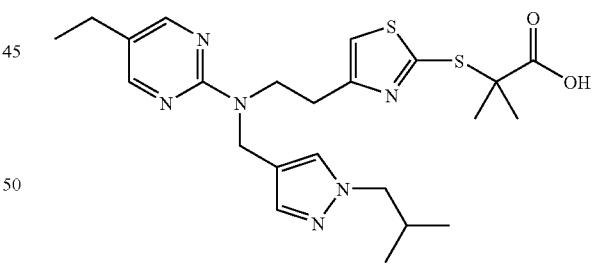

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-isobutyl-1H-pyrazole synthesized in Reference Example 23 as starting materials and by an operation similar to that of Example 327.

$^1$H-NMR (DMSO-d$_6$, 400 MHz) δ: 0.78 (6H, d, J=6.6 Hz), 1.16 (3H, t, J=7.4 Hz), 1.51 (6H, s), 2.00-2.08 (1H, m), 2.46-2.55 (2H, m), 3.00 (2H, t, J=7.4 Hz), 3.83-3.89 (4H, m), 4.60 (2H, s), 7.43 (1H, s), 7.50 (1H, s), 7.69 (1H, s), 8.39 (2H, s).

MS: 489 (M$^+$+1).

Example 344

2-[(4-{2-[[(1-butyl-1H-pyrazol-4-yl)methyl](5-ethylpyrimidin-2-yl)amino]ethyl}-1,3-thiazol-2-yl)thio]-2-methylpropionic acid hydrochloride

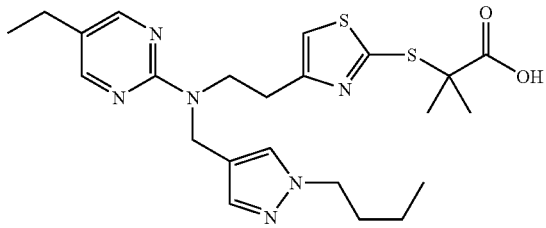

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 256-1 and 1-butyl-4-(chloromethyl)-1H-pyrazole synthesized in the same manner as in Reference Example 23 as starting materials and by an operation similar to that of Example 327.

$^1$H-NMR (DMSO-$d_6$, 400 MHz) δ: 0.84 (3H, t, J=7.0 Hz), 1.13-2.26 (5H, m), 1.34 (6H, s), 1.64-1.72 (2H, m), 2.47-2.68 (2H, m), 2.99 (2H, m), 2.85 (2H, m) 4.02 (2H, t, J=7.0 Hz), 4.57 (2H, s), 7.39 (1H, s), 7.48 (1H, s), 7.68 (1H, s), 8.36 (2H, s).

MS: 515 ($M^+$+1).

Example 345

2-[(4-{2-[[(1-benzyl-1H-pyrazol-4-yl)methyl](5-ethylpyrimidin-2-yl)amino]ethyl}-1,3-thiazol-2-yl)thio]-2-methylpropionic acid hydrochloride

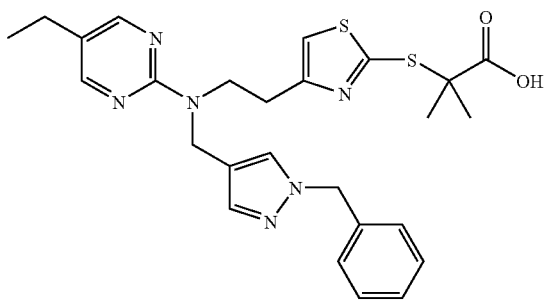

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-benzyl-4-(chloromethyl)-1H-pyrazole synthesized in the same manner as in Reference Example 23 as starting materials and by an operation similar to that of Example 327.

$^1$H-NMR (DMSO-$d_6$, 400 MHz) δ: 1.15 (3H, t, J=7.8 Hz), 1.56 (6H, s), 2.50 (2H, t, J=7.8 Hz), 2.90-3.03 (2H, m), 3.80-3.88 (2H, m), 4.56 (2H, s), 5.26 (2H, s), 7.16-7.45 (7H, m), 7.77 (1H, s), 8.34 (2H, s).

MS: 523 ($M^+$+1).

Example 346

2-{[4-(2-{(5-ethylpyrimidin-2-yl)[(2E)-3-phenylprop-2-en-1-yl]amino}ethyl)-1,3-thiazol-2-yl]thio}-2-methylpropionic acid

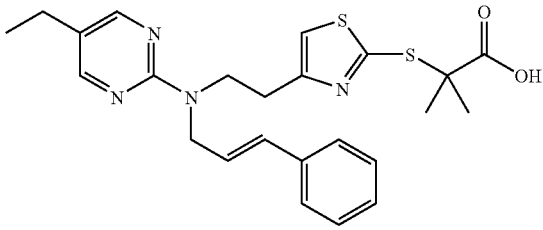

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and cinnamyl bromide as starting materials and by an operation similar to that of Example 326.

$^1$H-NMR (CDCl$_3$, 400 MHz) δ: 1.21 (3H, t, J=7.9 Hz), 1.63 (6H, s), 2.48 (2H, t, J=7.9 Hz), 3.13 (2H, t, J=7.0 Hz), 3.93 (2H, t, J=7.0 Hz), 4.33 (2H, d, J=4.7 Hz), 6.17-6.25 (1H, m), 6.50 (1H, d, J=16.4 Hz), 6.96 (1H, s), 7.18-7.37 (6H, m), 8.20 (2H, s).

MS: 469 ($M^+$+1).

Example 347

2-{[4-(2-{(5-ethylpyrimidin-2-yl)[(2E)-3-(4-fluorophenyl)prop-2-en-1-yl]amino}ethyl)-1,3-thiazol-2-yl]thio}-2-methylpropionic acid

Reference Example 24

(2E)-3-(4-fluorophenyl)prop-2-en-1-ol

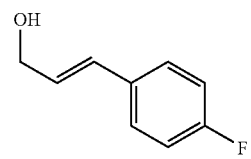

4-Fluorocinnamic acid (10 g) was dissolved in tetrahydrofuran (120 mL), triethylamine (10.12 mL) and ethyl chloroformate (6.92 mL) were added dropwise under ice-cooling, and the mixture was stirred for 1 hr. An aqueous solution (60 mL) of sodium tetrahydroborate (6.87 g) was added dropwise to the reaction solution, and the mixture was stirred at room temperature overnight. Aqueous hydrochloric acid solution (1 mol/L, 200 mL) was added, and the mixture was extracted with ethyl acetate. The organic layer was washed successively with saturated aqueous sodium hydrogen carbonate solution and water, and dried over anhydrous sodium sulfate. The solvent was evaporated under reduced pressure, and the residue was purified by silica gel chromatography (elution solvent; hexane:ethyl acetate=5:1 to 1:1) to give the title compound (9.36 g) as a white solid.

¹H-NMR (CDCl₃, 300 MHz) δ: 4.31-4.33 (2H, m), 6.24-6.33 (1H, m), 6.59 (1H, d, J=15.9 Hz), 6.98-7.04 (2H, m), 7.33-7.38 (2H, m).

Reference Example 25

1-[(1E)-3-chloroprop-1-en-1-yl]-4-fluorobenzene

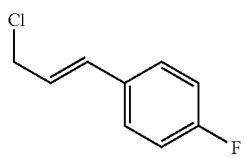

(2E)-3-(4-Fluorophenyl)prop-2-en-1-ol (1.36 g) synthesized in Reference Example 24 was dissolved in dichloromethane (45 mL), pyridine (0.78 g) and thionyl chloride (0.72 mL) were added under ice-cooling, and the mixture was stirred for 30 min. The mixture was diluted with dichloromethane. The organic layer was washed successively with water and saturated brine, and dried over anhydrous sodium sulfate. The solvent was evaporated under reduced pressure, and the residue was purified by silica gel chromatography (elution solvent; hexane) to give the title compound (1.1 g) as a colorless oil.

¹H-NMR (CDCl₃, 300 MHz) δ: 4.23 (2H, d, J=6.3 Hz), 6.19-6.29 (1H, m), 6.62 (1H, d, J=15.6 Hz), 6.99-7.05 (2H, m), 7.33-7.38 (2H, m).

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-[(1E)-3-chloroprop-1-en-1-yl]-4-fluorobenzene synthesized in Reference Example 25 as starting materials and by an operation similar to that of Example 326.

¹H-NMR (CDCl₃, 300 MHz) δ: 1.26 (3H, t, J=7.6 Hz), 1.61 (6H, s), 2.57 (2H, q, J=7.6 Hz), 3.15 (2H, t, J=7.0 Hz), 4.02 (2H, t, J=7.0 Hz), 4.40 (2H, d, J=6.1 Hz), 6.04-6.14 (1H, m), 6.57 (1H, d, J=15.8 Hz), 6.96-7.01 (2H, m), 7.07 (1H, s), 7.26-7.36 (2H, m), 8.39 (2H, s).

MS: 487 (M⁺+1).

Example 348

2-[(4-{2-[[(2E)-3-(4-chlorophenyl)prop-2-en-1-yl](5-ethylpyrimidin-2-yl)amino]ethyl}-1,3-thiazol-2-yl)thio]-2-methylpropionic acid

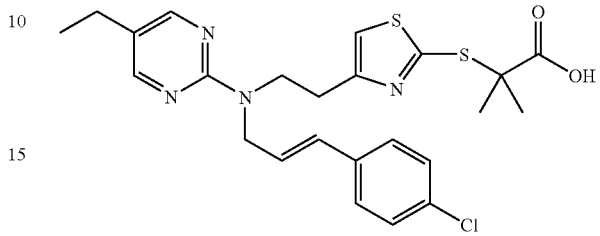

The title compound was obtained using 2-[(4-{2-[(5-Ethylpyrimidin-2-yl)amino]ethyl}-1,3-thiazol-2-yl)thio]-2-methylpropionic acid tert-butyl ester synthesized in Example 265-1 and 1-chloro-4-[(1E)-3-chloroprop-1-en-1-yl]benzene synthesized using 4-chlorocinnamic acid as starting materials and by operations similar to those of Reference Example 24 and Reference Example 24 to 25, and by an operation similar to that of Example 326.

¹H-NMR (CDCl₃, 300 MHz) δ: 1.21 (3H, t, J=7.5 Hz), 1.63 (6H, s), 2.48 (2H, q, J=7.5 Hz), 3.13 (2H, t, J=7.2 Hz), 3.92 (2H, t, J=7.2 Hz), 4.32 (2H, d, J=6.0 Hz), 6.13-6.22 (1H, m), 6.46 (1H, d, J=15.9 Hz), 6.96 (1H, s), 7.22-7.29 (4H, m), 8.20 (2H, s).

MS: 503 (M⁺+1).

Example 349

2-{[4-(2-{(5-ethylpyrimidin-2-yl)[4-(trifluoromethyl)benzyl]amino}ethyl)-1,3-thiazol-2-yl]thio}-2-methylpropionic acid

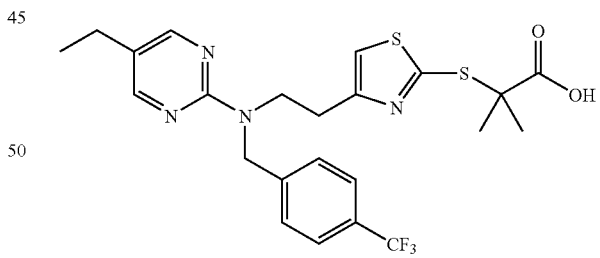

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(bromomethyl)-4-(trifluoromethyl)benzene as starting materials and by an operation similar to that of Example 326.

¹H-NMR (CDCl₃, 300 MHz) δ: 1.21 (3H, t, J=7.6 Hz), 1.62 (6H, s), 2.49 (2H, q, J=7.6 Hz), 3.09 (2H, t, J=6.9 Hz), 3.92 (2H, t, J=6.9 Hz), 4.86 (2H, s), 6.93 (1H, s), 7.33 (2H, d, J=8.1 Hz), 7.53 (2H, d, J=8.1 Hz), 8.20 (2H, s)

MS: 511 (M⁺+1). .

Example 350

2-{[4-(2-{(5-ethylpyrimidin-2-yl)[4-(trifluoromethoxy)benzyl]amino}ethyl)-1,3-thiazol-2-yl]thio}-2-methylpropionic acid

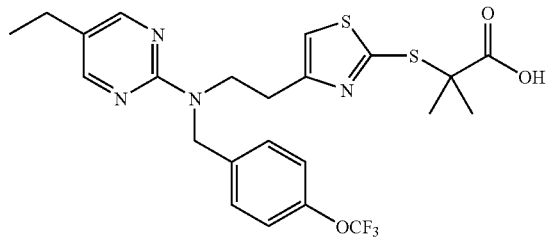

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(bromomethyl)-4-(trifluoromethoxy)benzene as starting materials and by an operation similar to that of Example 326.

$^1$H-NMR (CDCl$_3$, 300 MHz) δ: 1.22 (3H, t, J=7.5 Hz), 1.62 (6H, s), 2.50 (2H, q, J=7.5 Hz), 3.08 (2H, t, J=6.9 Hz), 3.91 (2H, t, J=6.9 Hz), 4.82 (2H, s), 6.95 (1H, s), 7.13 (2H, d, J=8.4 Hz), 7.25 (2H, d, J=8.4 Hz), 8.23 (2H, s).

MS: 527 (M$^+$+1).

Example 351

2-[(4-{2-[(5-ethylpyrimidin-2-yl)(4-phenoxybutyl)amino]ethyl}-1,3-thiazol-2-yl)thio]-2-methylpropionic acid

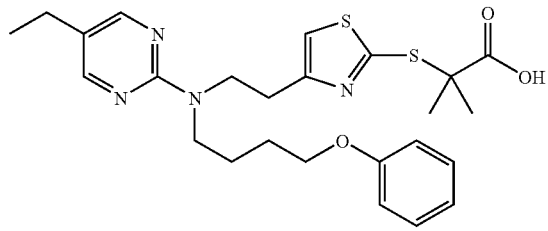

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and (4-bromobutoxy)benzene as starting materials and by an operation similar to that of Example 326.

$^1$H-NMR (CDCl$_3$, 300 MHz) δ: 1.20 (3H, t, J=7.8 Hz), 1.65 (6H, s), 1.68-1.83 (4H, m), 2.46 (2H, q, J=7.8 Hz), 3.11 (2H, t, J=6.9 Hz), 3.56 (2H, t, J=6.9 Hz), 3.91 (2H, t, J=6.9 Hz), 3.98 (2H, t, J=6.0 Hz), 6.80-6.96 (4H, m), 7.24-7.30 (2H, m), 8.17 (2H, s).

MS: 515 (M$^+$+1).

Example 352

2-[(4-{2-[(biphenyl-4-ylmethyl)(5-ethylpyrimidin-2-yl)amino]ethyl}-1,3-thiazol-2-yl)thio]-2-methylpropionic acid hydrochloride

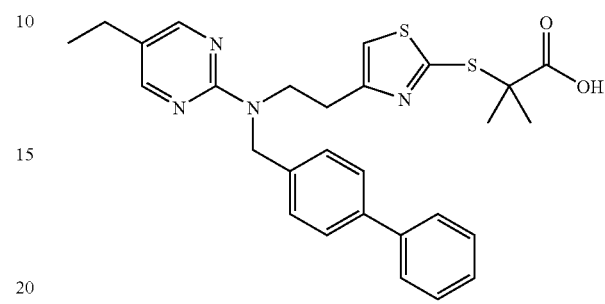

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(bromomethyl)biphenyl as starting materials and by an operation similar to that of Example 327.

$^1$H-NMR (CDCl$_3$, 300 MHz) δ: 1.31 (3H, t, J=7.5 Hz), 1.66 (6H, s), 2.66 (2H, q, J=7.5 Hz), 3.49-3.58 (2H, m), 4.11-4.18 (2H, m), 5.31 (2H, s), 7.30-7.56 (10H, m), 8.47 (2H, brs).

MS: 519 (M$^+$+1).

Example 353

2-{[4-(2-{(5-ethylpyrimidin-2-yl)[4-(1H-pyrazol-1-yl)benzyl]amino}ethyl)-1,3-thiazol-2-yl]thio}-2-methylpropionic acid hydrochloride

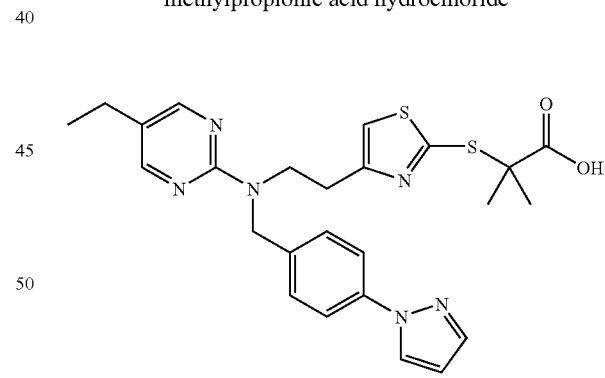

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-[4-(bromomethyl)phenyl]-1H-pyrazole as starting materials and by an operation similar to that of Example 327.

$^1$H-NMR (CDCl$_3$, 300 MHz) δ: 1.29 (3H, t, J=7.5 Hz), 1.61 (6H, s), 2.62 (2H, q, J=7.5 Hz), 3.13 (2H, t, J=6.9 Hz), 4.13 (2H, t, J=6.9 Hz), 5.05 (2H, s), 6.47 (1H, s), 7.39-7.42 (3H, m), 7.66-7.72 (3H, m), 7.92 (1H, d, J=2.4 Hz), 8.46 (2H, s).

MS: 509 (M$^+$+1).

Example 354

2-{[4-(2-{(5-ethylpyrimidin-2-yl)[4-(1H-1,2,4-triazol-1-yl)benzyl]amino}ethyl)-1,3-thiazol-2-yl]thio}-2-methylpropionic acid hydrochloride

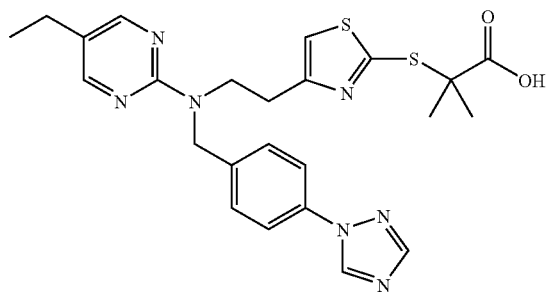

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-[4-(bromomethyl)phenyl]-1H-1,2,4-triazole as starting materials and by an operation similar to that of Example 327.

$^1$H-NMR (CDCl$_3$, 300 MHz) δ: 1.30 (3H, t, J=7.5 Hz), 1.63 (6H, s), 2.65 (2H, q, J=7.5 Hz), 3.30 (2H, t, J=7.2 Hz), 4.20 (2H, t, J=7.2 Hz), 5.18 (2H, s), 7.52 (2H, d, J=8.4 Hz), 7.68-7.72 (3H, m), 8.17 (1H, s), 8.50 (2H, s), 8.95 (1H, s).

MS: 510 (M$^+$+1).

Example 355

2-[(4-{2-[(5-ethylpyrimidin-2-yl)(2-naphthylmethyl)amino]ethyl}-1,3-thiazol-2-yl)thio]-2-methylpropionic acid hydrochloride

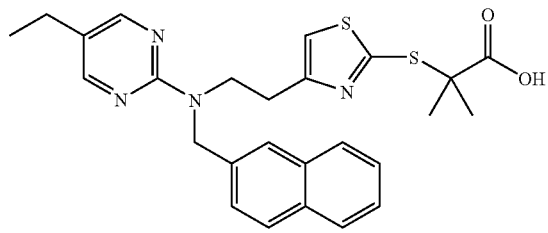

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 2-(bromomethyl)naphthalene as starting materials and by an operation similar to that of Example 327.

$^1$H-NMR (DMSO-d$_6$, 300 MHz) δ: 1.13 (3H, t, J=7.5 Hz), 1.46 (6H, s), 2.44 (2H, q, J=7.5 Hz), 3.02 (2H, t, J=6.9 Hz), 3.90 (2H, t, J=6.9 Hz), 4.90 (2H, s), 7.33-7.45 (4H, m), 7.66 (1H, s), 7.79-7.86 (3H, m), 8.30 (2H, s).

MS: 493 (M$^+$+1).

Example 356

2-[(4-{2-[(5-ethylpyrimidin-2-yl)(1-naphthylmethyl)amino]ethyl}-1,3-thiazol-2-yl)thio]-2-methylpropionic acid hydrochloride

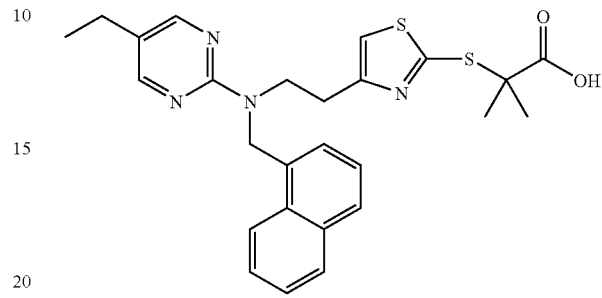

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(chloromethyl)naphthalene as starting materials and by an operation similar to that of Example 327.

$^1$H-NMR (DMSO-d$_6$, 300 MHz) δ: 1.16 (3H, t, J=7.5 Hz), 1.46 (6H, s), 2.47 (2H, q, J=7.5 Hz), 3.04 (2H, t, J=7.2 Hz), 3.91 (2H, t, J=7.2 Hz), 5.25 (2H, s), 7.22 (1H, d, J=7.2 Hz), 7.39-7.46 (2H, m), 7.52-7.56 (2H, m), 7.83 (1H, d, J=8.4 Hz), 7.94-7.97 (1H, m), 8.03-8.06 (1H, m), 8.33 (2H, s).

MS: 493 (M$^+$+1).

Example 357

2-{[4-(2-{(5-ethylpyrimidin-2-yl)[(2-phenyl-1,3-oxazol-4-yl)methyl]amino}ethyl)-1,3-thiazol-2-yl]thio}-2-methylpropionic acid hydrochloride

Reference Example 26

4-(chloromethyl)-2-phenyl-1,3-oxazole

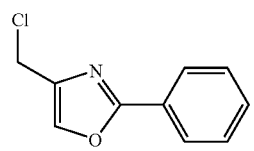

Benzamide (10.0 g) and 1,3-dichloroacetone (10.5 g) were dissolved in ethanol (100 mL), and the mixture was refluxed for 8 hr. After cooling, the reaction mixture was concentrated under reduced pressure, and the residue was purified by silica gel chromatography (elution solvent; hexane:ethyl acetate=7:1) to give the title compound (4.6 g) as a white solid.

$^1$H-NMR (CDCl$_3$, 300 MHz) δ: 4.58 (2H, s), 7.45-7.47 (3H, m), 7.71 (1H, s), 8.01-8.06 (2H, m).

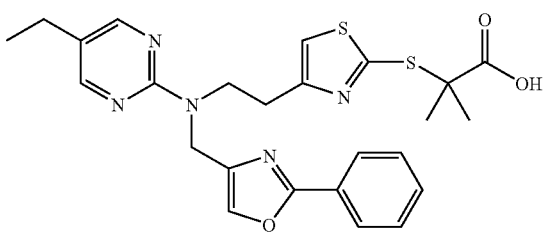

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-2-phenyl-1,3-oxazole synthesized in Reference Example 26 as starting materials, and by an operation similar to that of Example 327.

$^1$H-NMR (CDCl$_3$, 300 MHz) δ: 1.27 (3H, t, J=7.6 Hz), 1.68 (6H, s), 2.62 (2H, q, J=7.5 Hz), 3.27 (2H, t, J=6.3 Hz), 4.43 (2H, t, J=6.3 Hz), 4.89 (2H, s), 7.17 (1H, s), 7.43-7.47 (3H, m), 7.99-8.04 (2H, m), 8.16 (1H, brs), 8.48 (2H, s).

MS: 510 (M$^+$+1).

Example 358

2-({4-[2-((5-ethylpyrimidin-2-yl){[2-(4-methylphenyl)-1,3-oxazol-4-yl]methyl}amino)ethyl]-1,3-thiazol-2-yl}thio)-2-methylpropionic acid hydrochloride Reference Example 27

4-(chloromethyl)-2-(4-methylphenyl)-1,3-oxazole

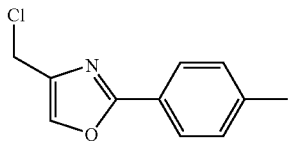

4-Methylbenzamide (10.0 g) and 1,3-dichloroacetone (9.4 g) were dissolved in ethanol (100 mL), and the mixture was refluxed for 8 hr. After cooling, the reaction mixture was concentrated under reduced pressure, and the residue was purified by silica gel chromatography (elution solvent; hexane:ethyl acetate=10:1 to 7:1) to give the title compound (7.8 g) as a white solid.

$^1$H-NMR (CDCl$_3$, 300 MHz) δ: 2.40 (3H, s), 4.57 (2H, s), 7.26 (2H, d, J=8.1 Hz), 7.67 (1H, s), 7.92 (2H, d, J=8.1 Hz).

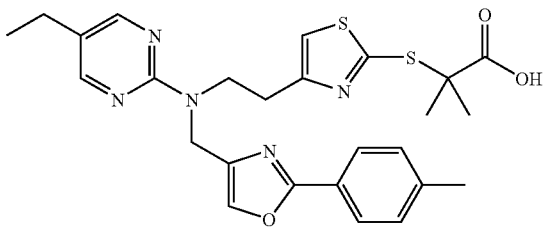

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-2-(4-methylphenyl)-1,3-oxazole synthesized in Reference Example 27 as starting materials and by an operation similar to that of Example 327.

$^1$H-NMR (DMSO-d$_6$, 300 MHz) δ: 1.15 (3H, t, J=7.5 Hz), 1.50 (6H, s), 2.36 (3H, s), 2.47 (2H, q, J=7.5 Hz), 3.08 (2H, t, J=7.2 Hz), 3.99 (2H, t, J=7.2 Hz), 4.71 (2H, s), 7.32 (2H, d, J=8.1 Hz), 7.50 (1H, s), 7.82 (2H, d, J=8.1 Hz), 7.97 (1H, s), 8.33 (2H, s),

MS: 524 (M$^+$+1).

Example 359

2-({4-[2-((5-ethylpyrimidin-2-yl){[2-(4-fluorophenyl)-1,3-oxazol-4-yl]methyl}amino)ethyl]-1,3-thiazol-2-yl}thio)-2-methylpropionic acid hydrochloride Reference Example 28

4-(chloromethyl)-2-(4-fluorophenyl)-1,3-oxazole

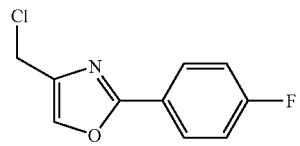

4-Fluorobenzamide (10.0 g) and 1,3-dichloroacetone (9.5 g) were dissolved in ethanol (100 mL), and the mixture was refluxed for 8 hr. After cooling, the reaction mixture was concentrated under reduced pressure, and the residue was purified by silica gel chromatography (elution solvent; hexane:ethyl acetate=10:1 to 7:1) to give the title compound (4.3 g) as a white solid.

$^1$H-NMR (CDCl$_3$, 300 MHz) δ: 4.56 (2H, s), 7.11-7.17 (2H, m), 7.69 (1H, s), 8.00-8.05 (2H, m).

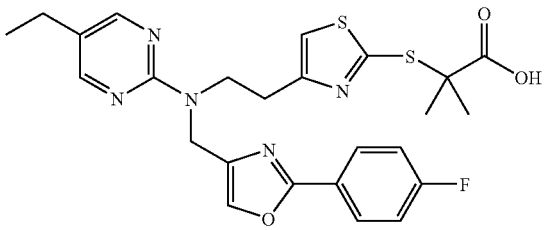

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-2-(4-fluorophenyl)-1,3-oxazole synthesized in Reference Example 18 as starting materials and by an operation similar to that of Example 327.

$^1$H-NMR (DMSO-d$_6$, 300 MHz) δ: 1.16 (3H, t, J=7.5 Hz), 1.51 (6H, s), 2.49 (2H, q, J=7.5 Hz), 3.11 (2H, t, J=7.2 Hz), 4.03 (2H, t, J=7.2 Hz), 4.75 (2H, s), 7.33-7.39 (2H, m), 7.53 (1H, s), 7.96-8.01 (2H, m), 8.07 (1H, s), 8.39 (2H, s).

MS: 528 (M$^+$+1).

Example 360

2-{[4-(2-{(5-ethylpyrimidin-2-yl)[(2-phenyl-1,3-thiazol-4-yl)methyl]amino}ethyl)-1,3-thiazol-2-yl]thio}-2-methylpropionic acid hydrochloride Reference Example 29

4-(chloromethyl)-2-phenyl-1,3-thiazole

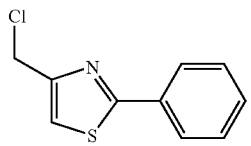

Thiobenzamide (10.0 g) and 1,3-dichloroacetone (9.25 g) were dissolved in acetone (200 mL), and the mixture was stirred at room temperature for 8 hr. The reaction mixture was concentrated under reduced pressure, methanol (200 mL) was added, and the mixture was refluxed for 1.5 hr. After cooling, the reaction mixture was concentrated under reduced pressure, and the residue was purified by silica gel chromatography (elution solvent; hexane:ethyl acetate=7:1) to give the title compound (5.1 g) as a brown oil.

$^1$H-NMR (CDCl$_3$, 300 MHz) δ: 4.75 (2H, s), 7.31 (1H, s), 7.41-7.46 (3H, m), 7.93-8.03 (2H, m).

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-2-phenyl-1,3-thiazole synthesized in Reference Example 29 as starting materials and by an operation similar to that of Example 327.

$^1$H-NMR (CDCl$_3$, 300 MHz) δ: 1.27 (3H, t, J=7.5 Hz), 1.65 (6H, s), 2.61 (2H, q, J=7.5 Hz), 3.28 (2H, t, J=6.3 Hz), 4.46 (2H, t, J=6.3 Hz), 5.08 (2H, s), 7.19 (1H, s), 7.43-7.45 (3H, m), 7.76 (1H, brs), 7.89-7.93 (2H, m), 8.47 (2H, s).

MS: 526 (M$^+$+1).

Example 361

2-{[4-(2-{(5-ethylpyrimidin-2-yl)[(4-methyl-2-phenyl-1,3-oxazol-5-yl)methyl]amino}ethyl)-1,3-thiazol-2-yl]thio}-2-methylpropionic acid hydrochloride

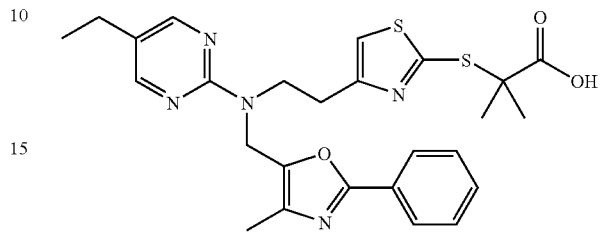

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 5-(chloromethyl)-4-methyl-2-phenyl-1,3-oxazole synthesized in reference to patent reference [WO0100603] and the like as starting materials and by an operation similar to that of Example 327.

$^1$H-NMR (CDCl$_3$, 300 MHz) δ: 1.30 (3H, t, J=7.5 Hz), 1.62 (6H, s), 2.53 (3H, s), 2.67 (2H, q, J=7.5 Hz), 3.42-3.52 (2H, m), 4.31-4.37 (2H, m), 5.27 (2H, s), 7.48-7.57 (3H, m), 7.94 (1H, brs), 8.19-8.22 (2H, m), 8.52 (2H, brs).

MS: 524 (M$^+$+1).

Example 362

2-{[4-(2-{(5-ethylpyrimidin-2-yl)[(4-methyl-2-phenyl-1,3-thiazol-5-yl)methyl]amino}ethyl)-1,3-thiazol-2-yl]thio}-2-methylpropionic acid hydrochloride

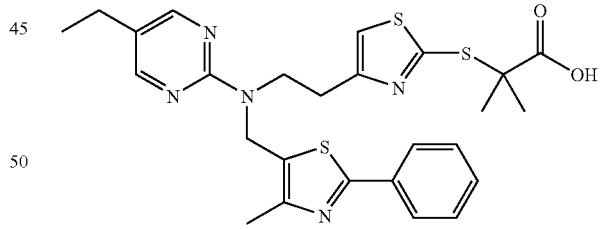

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 5-(chloromethyl)-4-methyl-2-phenyl-1,3-thiazole synthesized in reference to patent reference [WO0100603] and the like as starting materials and by an operation similar to that of Example 327.

$^1$H-NMR (DMSO-d$_6$, 300 MHz) δ: 1.17 (3H, t, J=7.5 Hz), 1.51 (6H, s), 2.44-2.51 (5H, m), 3.02 (2H, t, J=7.5 Hz), 3.90 (2H, t, J=7.5 Hz), 4.88 (2H, s), 7.41-7.49 (4H, m), 7.81-7.85 (2H, m), 8.35 (2H, s).

MS: 540 (M$^+$+1).

Example 363

2-{[4-(2-{(5-ethylpyrimidin-2-yl)[(5-methyl-2-phenyl-1,3-thiazol-4-yl)methyl]amino}ethyl)-1,3-thiazol-2-yl]thio}-2-methylpropionic acid hydrochloride

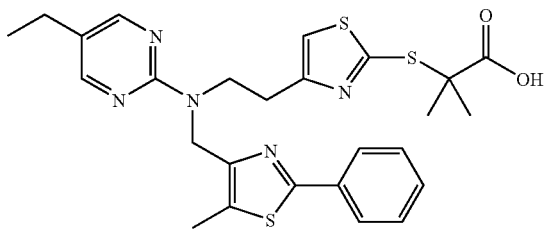

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-5-methyl-2-phenyl-1,3-thiazole as starting materials and by an operation similar to that of Example 327.

$^1$H-NMR (DMSO-$d_6$, 300 MHz) δ: 1.15 (3H, t, J=7.5 Hz), 1.51 (6H, s), 2.47 (2H, q, J=7.5 Hz), 2.53 (3H, s), 3.10 (2H, t, J=7.2 Hz), 4.06 (2H, t, J=7.2 Hz), 4.83 (2H, s), 7.43-7.48 (3H, m), 7.51 (1H, s), 7.78-7.82 (2H, m), 8.36 (2H, s).

MS: 540 (M$^+$+1).

Example 364

2-{[4-(2-{(5-ethylpyrimidin-2-yl)[(2-phenylpyrimidin-5-yl)methyl]amino}ethyl)-1,3-thiazol-2-yl]thio}-2-methylpropionic acid hydrochloride

Reference Example 30

(2-phenylpyrimidin-5-yl)methanol

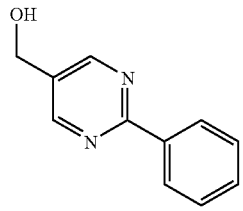

2-Phenylpyrimidine-5-carbaldehyde (2.0 g) was dissolved in ethanol (20 mL), sodium tetrahydroborate (411 mg) was added under ice-cooling, and the mixture was stirred at 0° C. for 1 hr. Water was added to the reaction mixture, and the mixture was extracted with ethyl acetate. The organic layer was washed with saturated aqueous ammonium chloride solution and then saturated brine, and dried over anhydrous sodium sulfate. The solvent was evaporated under reduced pressure to give the title compound (1.75 g) as a white solid.

$^1$H-NMR (CDCl$_3$, 300 MHz) δ: 2.19 (1H, t, J=5.1 Hz), 4.77 (2H, t, J=5.1 Hz), 7.47-7.52 (3H, m), 8.39-8.44 (2H, m), 8.80 (2H, s).

Reference Example 31

5-(chloromethyl)-2-phenylpyrimidine

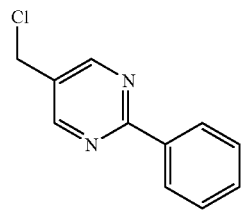

(2-Phenylpyrimidin-5-yl)methanol (1.75 g) synthesized in Reference Example 30 was dissolved in dichloromethane (20 mL) and, after ice-cooling, thionyl chloride (1.45 g) was added thereto, and the mixture was stirred at 0° C. for 2 hr. Saturated aqueous sodium hydrogen carbonate solution was added to the reaction mixture, and the mixture was extracted with dichloromethane. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (1.83 g) as a white solid.

$^1$H-NMR (CDCl$_3$, 300 MHz) δ: 4.61 (2H, s), 7.49-7.53 (3H, m), 8.43-8.47 (2H, m), 8.82 (2H, s).

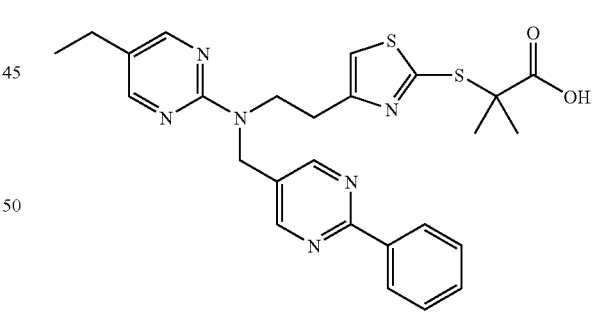

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 5-(chloromethyl)-2-phenoxypyrimidine synthesized in Reference Example 31 as starting materials and by an operation similar to that of Example 327.

$^1$H-NMR (DMSO-$d_6$, 300 MHz) δ: 1.15 (3H, t, J=7.5 Hz), 1.50 (6H, s), 2.46 (2H, q, J=7.5 Hz), 3.08 (2H, t, J=6.6 Hz), 4.02 (2H, t, J=6.6 Hz), 4.77 (2H, s), 7.47-7.53 (4H, m), 8.33-8.37 (4H, m), 8.77 (2H, s).

MS: 521 (M$^+$+1).

Example 365

2-[(4-{2-[(5-ethylpyrimidin-2-yl)(4-phenoxybenzyl)amino]ethyl}-1,3-thiazol-2-yl)thio]-2-methylpropionic acid hydrochloride

Reference Example 32

1-(chloromethyl)-4-phenoxybenzene

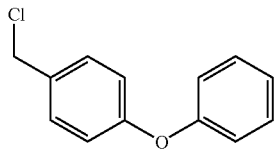

The title compound was obtained using 4-phenoxybenzaldehyde as a starting material, and by operations similar to those of Reference Example 30 and Reference Example 31.

$^1$H-NMR (CDCl$_3$, 300 MHz) δ: 4.61 (2H, s), 7.49-7.53 (3H, m), 8.43-8.47 (2H, m), 8.82 (2H, s).

Example 366

2-[(4-{2-[(5-ethylpyrimidin-2-yl)(quinolin-3-ylmethyl)amino]ethyl}-1,3-thiazol-2-yl)thio]-2-methylpropionic acid hydrochloride

Reference Example 33

3-(chloromethyl)quinoline

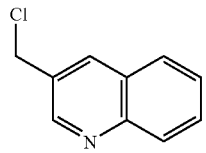

The title compound was obtained using quinoline-3-carbaldehyde as a starting material and by operations similar to those of Reference Example 30 and Reference Example 31.

$^1$H-NMR (CDCl$_3$, 300 MHz) δ: 4.79 (2H, s), 7.58 (1H, t, J=7.2 Hz), 7.71-7.78 (1H, m), 7.83 (1H, d, J=7.2 Hz), 8.10-8.17 (2H, m), 8.94 (1H, d, J=2.1 Hz).

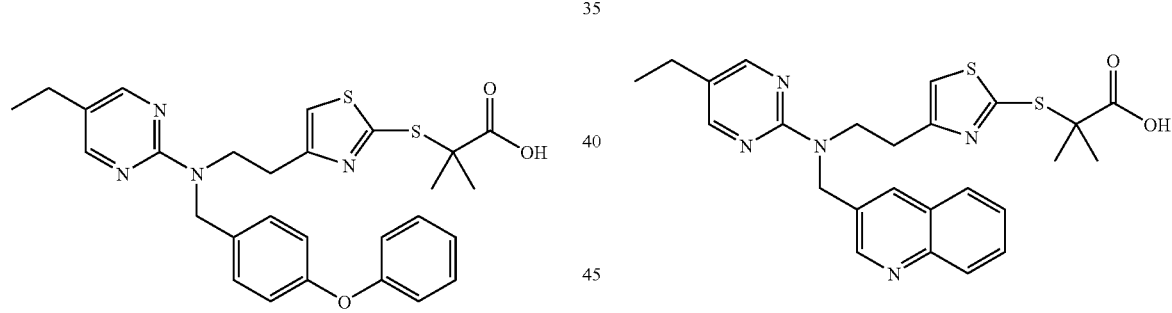

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(chloromethyl)-4-phenoxybenzene synthesized in Reference Example 32 as starting materials and by an operation similar to that of Example 327.

$^1$H-NMR (CDCl$_3$, 300 MHz) δ: 1.28 (3H, t, J=7.5 Hz), 1.61 (6H, s), 2.62 (2H, q, J=7.5 Hz), 3.18 (2H, t, J=7.2 Hz), 4.12 (2H, t, J=7.2 Hz), 4.99 (2H, s), 6.94-7.00 (4H, m), 7.11 (1H, t, J=7.5 Hz), 7.25-7.36 (5H, m), 8.46 (2H, s).

MS: 535 (M$^+$+1).

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 3-(chloromethyl)quinoline synthesized in Reference Example 33 as starting materials and by an operation similar to that of Example 327.

$^1$H-NMR (DMSO-d$_6$, 300 MHz) δ: 1.15 (3H, t, J=7.5 Hz), 1.46 (6H, s), 2.47 (2H, q, J=7.5 Hz), 3.12 (2H, t, J=6.9 Hz), 4.10 (2H, t, J=6.9 Hz), 5.04 (2H, s), 7.50 (1H, s), 7.92 (1H, t, J=7.8 Hz), 8.10 (1H, t, J=7.8 Hz), 8.29-8.43 (4H, m), 8.92 (1H, s), 9.21 (1H, s).

MS: 494 (M$^+$+1).

Example 367

2-[(4-{2-[(5-ethylpyrimidin-2-yl)(quinolin-2-ylmethyl)amino]ethyl}-1,3-thiazol-2-yl)thio]-2-methylpropionic acid hydrochloride Reference Example 34

2-(chloromethyl)quinoline

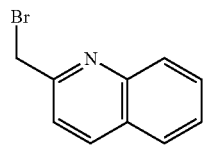

2-Methylquinoline (5.0 g) was dissolved in carbon tetrachloride (25 mL), imide N-bromosuccinate (6.2 g) and 2,2'-azobisisobutyronitrile (AIBN) (57 mg) were added thereto, and the mixture was refluxed for 4 hr. After ice-cooling, the reaction mixture was concentrated under reduced pressure, and the residue was purified by silica gel chromatography (elution solvent; hexane:ethyl acetate=5:1) to give the title compound (3.7 g) as a pale-yellow solid.

$^1$H-NMR (CDCl$_3$, 300 MHz) δ: 4.72 (2H, s), 7.53-7.59 (2H, m), 7.70-7.76 (1H, m), 7.81 (1H, d, J=8.1 Hz), 8.07 (1H, d, J=8.7 Hz), 8.18 (1H, d, J=8.7 Hz).

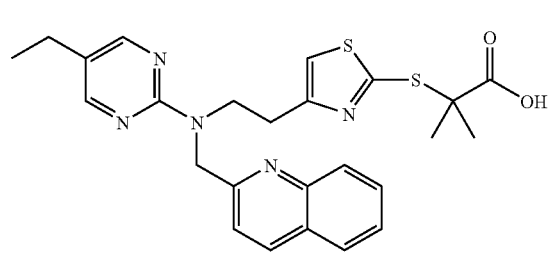

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 2-(chloromethyl)quinoline synthesized in Reference Example 34 as starting materials and by an operation similar to that of Example 327.

$^1$H-NMR (DMSO-d$_6$, 300 MHz) δ: 1.09 (3H, t, J=7.5 Hz), 1.44 (6H, s), 2.40 (2H, q, J=7.5 Hz), 3.11 (2H, t, J=6.9 Hz), 4.12 (2H, t, J=6.9 Hz), 5.18 (2H, s), 7.50 (1H, s), 7.64 (1H, d, J=7.8 Hz), 8.02 (1H, d, J=7.8 Hz), 8.18-8.32 (4H, m), 8.79 (1H, d, J=8.4 Hz).

MS: 494 (M$^+$+1).

Example 368

2-[(4-{2-[[(6-chloroquinolin-2-yl)methyl](5-ethylpyrimidin-2-yl)amino]ethyl}-1,3-thiazol-2-yl)thio]-2-methylpropionic acid hydrochloride Reference Example 35

6-chloro-2-(chloromethyl)quinoline

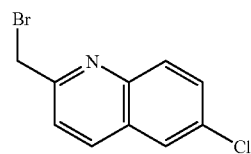

The title compound was obtained using 6-chloro-2-methylquinoline as a starting material and by an operation similar to that of Reference Example 34.

$^1$H-NMR (CDCl$_3$, 300 MHz) δ: 4.69 (2H, s), 7.59 (1H, d, J=8.7 Hz), 7.66 (1H, dd, J=2.4, 9.0 Hz), 7.79 (1H, d, J=2.4 Hz), 8.00 (1H, d, J=9.0 Hz), 8.08 (1H, d, J=8.7 Hz).

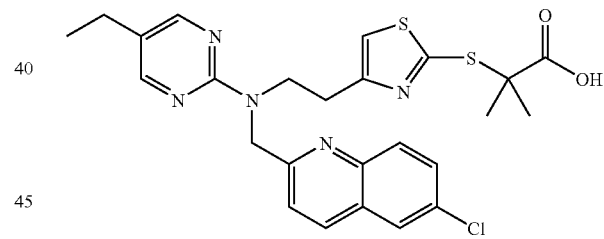

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 6-chloro-2-(chloromethyl)quinoline synthesized in Reference Example 35 as starting materials and by an operation similar to that of Example 327.

$^1$H-NMR (DMSO-d$_6$, 300 MHz) δ: 1.13 (3H, t, J=7.5 Hz), 1.47 (6H, s), 2.45 (2H, q, J=7.5 Hz), 3.12 (2H, t, J=7.2 Hz), 4.10 (2H, t, J=7.2 Hz), 5.12 (2H, s), 7.52 (1H, s), 7.57 (1H, d, J=8.7 Hz), 7.91 (1H, d, J=9.3 Hz), 8.18 (1H, d, J=9.3 Hz), 8.25 (1H, s), 8.30 (2H, s), 8.53 (1H, d, J=8.7 Hz).

MS: 528 (M$^+$+1).

Example 369

2-[(4-{2-[(5-ethylpyrimidin-2-yl)(4-propylbenzyl)amino]ethyl}-1,3-thiazol-2-yl)thio]-2-methylpropionic acid

Reference Example 36

(4-propylphenyl)methanol

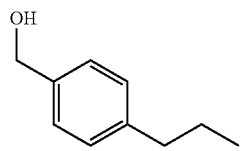

Lithium aluminum hydride (1.16 g) was suspended in diethyl ether (100 mL), a solution (50 mL) of 4-propylbenzoic acid (5.0 g) in diethyl ether was added under ice-cooling, and the mixture was heated under reflux for 2.5 hr. The reaction mixture was ice-cooled, and water (3.0 mL) and aqueous sodium hydroxide solution (1 mol/L, 12 mL) were successively added dropwise. After warming to room temperature, the mixture was stirred for 30 min. The reaction mixture was directly filtered through celite, and the filtrate was evaporated under reduced pressure to give the title compound (4.9 g) as a colorless oil.

$^1$H-NMR (CDCl$_3$, 300 MHz) δ: 0.94 (3H, t, J=7.4 Hz), 1.58-1.70 (3H, m) 2.59 (2H, t, J=7.4 Hz), 4.66 (2H, d, J=5.6 Hz), 7.16-7.19 (2H, m), 7.26-7.30 (2H, m).

Reference Example 37

1-(chloromethyl)-4-propylbenzene

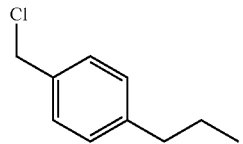

(4-Propylphenyl)methanol (4.93 g) synthesized in Reference Example 36 was dissolved in carbon tetrachloride (65 mL), triphenylphosphine (9.5 g) was added thereto, and the mixture was heated under reflux for 4 hr. The reaction mixture was concentrated under reduced pressure, and the residue was dissolved in hexane. The insoluble material was filtered off, and the filtrate was evaporated under reduced pressure. The residue was purified by silica gel chromatography (elution solvent; hexane) to give the title compound (2.24 g) as a colorless oil.

$^1$H-NMR (CDCl$_3$, 300 MHz) δ: 0.94 (3H, t, J=7.3 Hz), 1.57-1.70 (2H, m), 2.59 (2H, t, J=7.5 Hz), 4.58 (2H, s), 7.16-7.18 (2H, m), 7.29-7.31 (2H, m).

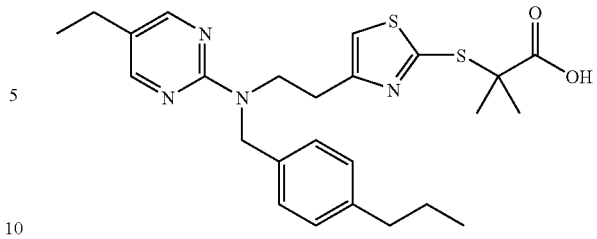

The title compound was obtained using 2-[(4-{2-[(5-Ethylpyrimidin-2-yl)amino]ethyl}-1,3-thiazol-2-yl)thio]-2-methylpropionic acid tert-butyl ester synthesized in Example 265-1 and 1-(chloromethyl)-4-propylbenzene synthesized in Reference Example 37 as starting materials, and by an operation similar to that of Example 326.

$^1$H-NMR (CDCl$_3$, 300 MHz) δ: 0.92 (3H, t, J=7.4 Hz), 1.21 (3H, t, J=7.5 Hz), 1.57-1.63 (8H, m), 2.44-2.56 (4H, m), 3.05 (2H, t, J=7.2 Hz), 3.88 (2H, t, J=7.2 Hz), 4.79 (2H, s), 6.89 (1H, s), 7.07-7.15 (4H, m), 8.19 (2H, s).

MS: 485 (M$^+$+1).

Example 370

2-[(4-{2-[(4-butylbenzyl)(5-ethylpyrimidin-2-yl)amino]ethyl}-1,3-thiazol-2-yl)thio]-2-methylpropionic acid

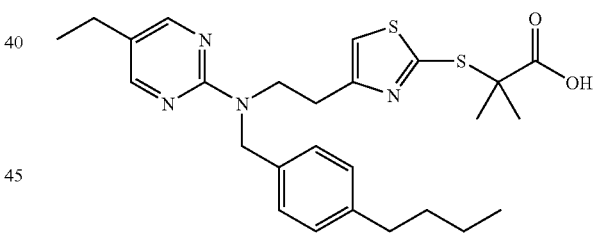

The title compound was obtained using 1-butyl-4-(chloromethyl)benzene, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-butylbenzoic acid as starting materials and by operations similar to those of Reference Examples 36 and 37, and by an operation similar to that of Example 326.

$^1$H-NMR (CDCl$_3$, 300 MHz) δ: 0.90 (3H, t, J=7.3 Hz), 1.21 (3H, t, J=7.5 Hz), 1.26-1.37 (2H, m), 1.53-1.59 (2H, m), 1.63 (6H, s), 2.46-2.59 (4H, m), 3.05 (2H, t, J=7.2 Hz), 3.88 (2H, t, J=7.2 Hz), 4.79 (2H, s), 6.89 (1H, s), 7.07-7.15 (4H, m), 8.19 (2H, s).

MS: 499 (M$^+$+1).

Example 371

2-[(4-{2-[(5-ethylpyrimidin-2-yl)(4-isopropylbenzyl)amino]ethyl}-1,3-thiazol-2-yl)thio]-2-methylpropionic acid

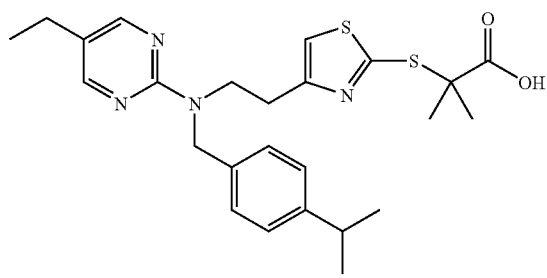

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(chloromethyl)-4-isopropylbenzene as starting materials and by an operation similar to that of Example 326.

$^1$H-NMR (CDCl$_3$, 300 MHz) δ: 1.18-1.23 (9H, m), 1.63 (6H, s), 2.48 (2H, q, J=7.5 Hz), 2.84-2.89 (1H, m), 3.07 (2H, t, J=7.2 Hz), 3.89 (2H, t, J=7.2 Hz), 4.79 (2H, s), 6.90 (1H, s), 7.14 (4H, s), 8.19 (2H, s).

MS: 485 (M$^+$+1).

Example 372

2-[(4-{2-[(4-tert-butylbenzyl)(5-ethylpyrimidin-2-yl)amino]ethyl}-1,3-thiazol-2-yl)thio]-2-methylpropionic acid

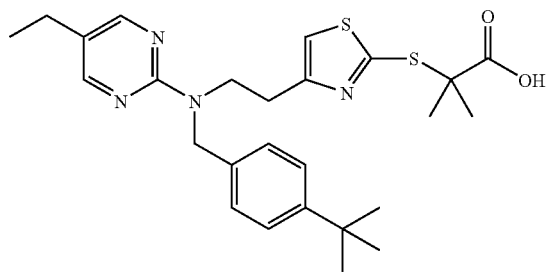

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(bromomethyl)-4-tert-butylbenzene as starting materials and by an operation similar to that of Example 326.

$^1$H-NMR (CDCl$_3$, 300 MHz) δ: 1.21 (3H, t, J=7.5 Hz), 1.29 (9H, s), 1.63 (6H, s), 2.48 (2H, q, J=7.5 Hz), 3.07 (2H, t, J=7.2 Hz), 3.89 (2H, t, J=7.2 Hz), 4.79 (2H, s), 6.90 (1H, s), 7.14-7.16 (2H, m), 7.28-7.31 (2H, m), 8.19 (2H, s).

MS: 499 (M$^+$+1).

Example 373

2-[(4-{2-[(5-ethylpyrimidin-2-yl)(4-isobutylbenzyl)amino]ethyl}-1,3-thiazol-2-yl)thio]-2-methylpropionic acid

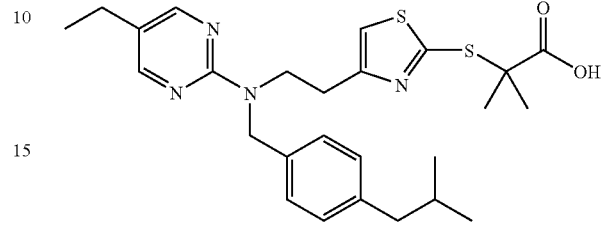

The title compound was obtained using 1-(chloromethyl)-4-isobutylbenzene, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-isobutylbenzoic acid as starting materials and by operations similar to those of Reference Examples 36 and 37, and by an operation similar to that of Example 326.

$^1$H-NMR (CDCl$_3$, 300 MHz) δ: 0.87 (6H, d, J=6.6 Hz), 1.21 (3H, t, J=7.5 Hz), 1.63 (6H, s), 1.77-1.84 (1H, m), 2.41-2.52 (4H, m), 3.05 (2H, t, J=7.2 Hz), 3.88 (2H, t, J=7.2 Hz), 4.79 (2H, s), 6.89 (1H, s), 7.05 (2H, t, J=8.1 Hz), 7.13 (2H, t, J=8.1 Hz), 8.19 (2H, s).

MS: 499 (M$^+$+1).

Example 374

2-[(4-{2-[[4-(ethoxymethyl)benzyl](5-ethylpyrimidin-2-yl)amino]ethyl}-1,3-thiazol-2-yl)thio]-2-methylpropionic acid

Reference Example 38

4-(ethoxymethyl)benzoic acid methyl ester

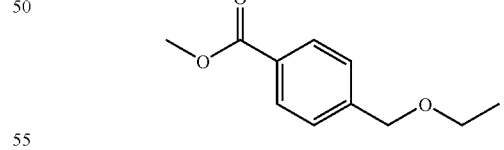

4-(Hydroxymethyl)benzoic acid methyl ester (2.0 g) and ethyl iodide (3.8 g) were dissolved in N,N-dimethylformamide (60 mL), potassium tert-butoxide (2.8 g) was added under ice-cooling, and the mixture was stirred at room temperature for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=10:1 to 5:1) to give the title compound (2.0 g) as a colorless oil.

¹H-NMR (CDCl₃, 300 MHz) δ: 1.27 (3H, t, J=6.9 Hz), 3.57 (2H, q, J=6.9 Hz), 3.92 (3H, s), 4.56 (2H, s), 7.40-7.43 (2H, m), 8.01-8.03 (2H, m).

Reference Example 39

[4-(ethoxymethyl)phenyl]methanol

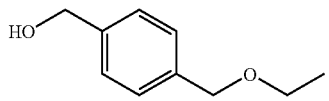

Lithium aluminum hydride (0.39 g) was suspended in tetrahydrofuran (10 mL), a solution of 4-(ethoxymethyl)benzoic acid methyl ester (2.0 g) synthesized in Reference Example 38 in tetrahydrofuran (50 mL) was added under ice-cooling, and the mixture was stirred at room temperature for 12 hr. The reaction mixture was ice-cooled, and water (1.0 mL) and aqueous sodium hydroxide solution (1 mol/L, 4.0 mL) were successively added dropwise. After warming to room temperature, the mixture was stirred for 1 hr. The reaction mixture was filtered through celite, and the filtrate was concentrated under reduced pressure. The residue was purified by silica gel chromatography (elution solvent; hexane:ethyl acetate=1:1) to give the title compound (1.52 g) as a colorless oil.

¹H-NMR (CDCl₃, 300 MHz) δ: 1.24 (3H, t, J=7.1 Hz), 3.54 (2H, q, J=7.1 Hz), 4.51 (2H, s), 4.69 (2H, d, J=5.7 Hz), 7.35 (4H, s).

Reference Example 40

1-(chloromethyl)-4-(ethoxymethyl)benzene

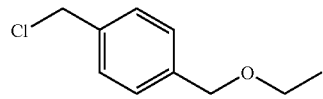

[4-(Ethoxymethyl)phenyl]methanol (1.52 g) synthesized in Reference Example 39 was dissolved in carbon tetrachloride (20 mL), triphenylphosphine (2.64 g) was added thereto, and the mixture was heated under reflux for 2.5 hr. The reaction mixture was concentrated under reduced pressure, the residue was dissolved in hexane, the insoluble material was filtered off, and the filtrate was evaporated under reduced pressure. The residue was purified by silica gel chromatography (elution solvent; hexane:ethyl acetate=20:1) to give the title compound (1.07 g) as a colorless oil.

¹H-NMR (CDCl₃, 300 MHz) δ: 1.25 (3H, t, J=7.0 Hz), 3.54 (2H, q, J=7.0 Hz), 4.50 (2H, s), 4.58 (2H, s), 7.29-7.38 (4H, m).

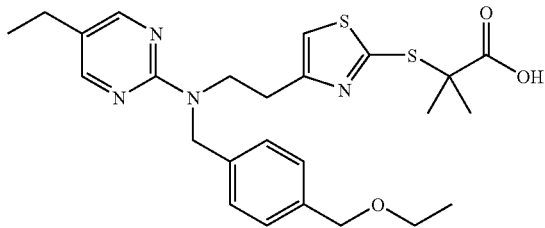

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(chloromethyl)-4-(ethoxymethyl)benzene synthesized in Reference Example 40 as starting materials and by an operation similar to that of Example 326.

¹H-NMR (CDCl₃, 300 MHz) δ: 1.18-1.25 (6H, m), 1.63 (6H, s), 2.48 (2H, q, J=7.5 Hz), 3.05 (2H, t, J=7.2 Hz), 3.52 (2H, q, J=6.9 Hz), 3.88 (2H, t, J=7.2 Hz), 4.47 (2H, s), 4.82 (2H, s), 6.90 (1H, s), 7.19-7.28 (4H, m), 8.20 (2H, s).

MS: 501 (M⁺+1).

Example 375

2-{[4-(2-{(5-ethylpyrimidin-2-yl)[4-(methoxymethyl)benzyl]amino}ethyl)-1,3-thiazol-2-yl]thio}-2-methylpropionic acid

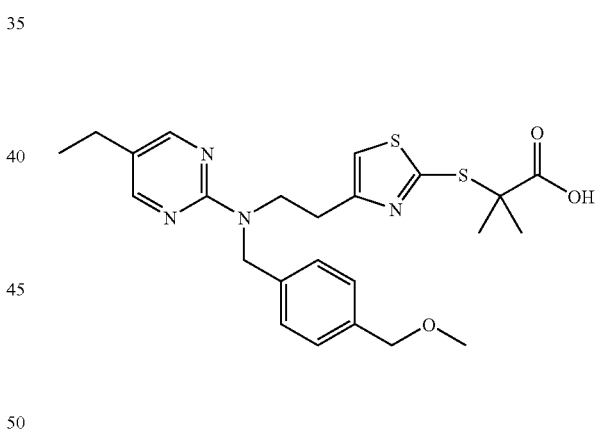

The title compound was obtained using (4-methoxymethyl)phenylmethyl chloride, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and methyl iodide as starting materials and by operations similar to those of Reference Examples 38 to 40, and by an operation similar to that of Example 326.

¹H-NMR (CDCl₃, 400 MHz) δ: 1.21 (3H, t, J=7.8 Hz), 1.63 (6H, s), 2.48 (2H, q, J=7.8 Hz), 3.05 (2H, t, J=7.0 Hz), 3.37 (3H, s), 3.88 (2H, t, J=7.0 Hz), 4.42 (2H, s), 4.82 (2H, s), 6.91 (1H, s), 7.27 (4H, m), 8.20 (2H, s).

MS: 487 (M⁺+1).

Example 376

2-{[4-(2-{(5-ethylpyrimidin-2-yl)[4-(2-methoxy-ethyl)benzyl]amino}ethyl)-1,3-thiazol-2-yl]thio}-2-methylpropionic acid

Reference Example 41

1-bromo-4-(2-methoxyethyl)benzene

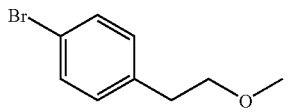

2-(4-Bromophenyl)ethanol (2.0 g) was dissolved in N,N-dimethylformamide (50 mL), and sodium hydride (60% in oil) (0.44 g) was added under ice-cooling. After gradually warming to room temperature, the mixture was stirred for 2 hr, and methyl iodide (2.1 g) was added again under ice-cooling. After gradually warming to room temperature, the mixture was stirred overnight. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=20:1 to 10:1) to give the title compound (1.2 g) as a colorless oil.

$^1$H-NMR (CDCl$_3$, 300 MHz) δ: 2.83 (2H, t, J=6.9 Hz), 3.34 (3H, s), 3.57 (2H, t, J=6.9 Hz), 7.08-7.11 (2H, m), 7.39-7.43 (2H, m).

Reference Example 42

[4-(2-methoxyethyl)phenyl]methanol

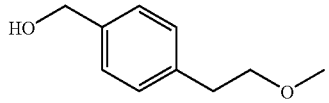

1-Bromo-4-(2-methoxyethyl)benzene (1.15 g) obtained in Reference Example 41 was dissolved in tetrahydrofuran (30 mL), and the mixture was cooled to −78° C. Under a nitrogen atmosphere, n-butyllithium-hexane (1.56 mol/L, 3.6 mL) was added dropwise, and the mixture was directly stirred for 1 hr. N,N-dimethylformamide (0.621 mL) was added dropwise, and the mixture was stirred for 30 min. Saturated aqueous ammonium chloride solution was added, and the reaction solution was concentrated under reduced pressure. The residue was dissolved in ethyl acetate, washed successively with water and saturated brine, and dried over anhydrous sodium sulfate. The solvent was evaporated under reduced pressure to give 4-(2-methoxyethyl)benzaldehyde. The present compound was used in the next step without particular purification. The present compound was dissolved in ethanol (25 mL), sodium tetrahydroborate (0.202 g) was added thereto, and the mixture was stirred for 30 min. Water was added to the reaction mixture, and the solvent was concentrated under reduced pressure. The residue was dissolved in ethyl acetate, washed successively with water and saturated brine, and dried over anhydrous sodium sulfate. The solvent was evaporated under reduced pressure, and the residue was purified by silica gel chromatography (elution solvent; hexane:ethyl acetate=1:1) to give the title compound (0.415 g) as a colorless oil.

$^1$H-NMR (CDCl$_3$, 300 MHz) δ: 2.89 (2H, t, J=6.9 Hz), 3.36 (3H, s), 3.60 (2H, t, J=6.9 Hz), 4.67 (2H, d, J=6.2 Hz), 7.22 (2H, d, J=8.0 Hz), 7.30 (2H, d, J=8.0 Hz).

Reference Example 43

1-(chloromethyl)-4-(2-methoxyethyl)benzene

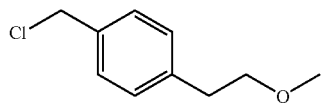

[4-(2-Methoxyethyl)phenyl]methanol (415 mg) synthesized in Reference Example 42 was dissolved in carbon tetrachloride (8 mL), triphenylphosphine (720 mg) was added thereto, and the mixture was heated under reflux for 4 hr. The reaction mixture was concentrated under reduced pressure, the residue was dissolved in hexane, the insoluble material was filtered off, and the filtrate was evaporated under reduced pressure. The residue was purified by silica gel chromatography (elution solvent; hexane:ethyl acetate=20:1) to give the title compound (225 mg) as a colorless oil.

$^1$H-NMR (CDCl$_3$, 300 MHz) δ: 2.89 (2H, t, J=6.9 Hz), 3.35 (3H, s), 3.60 (2H, t, J=6.9 Hz), 4.57 (2H, s), 7.21-7.24 (2H, m), 7.31-7.33 (2H, m).

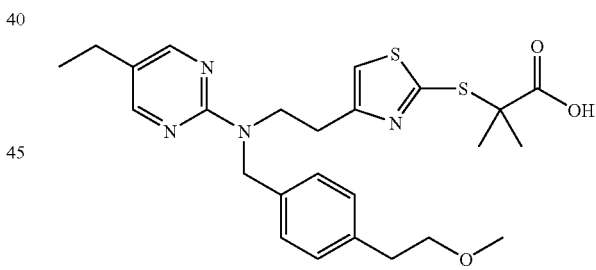

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(chloromethyl)-4-(2-methoxyethyl)benzene obtained in Reference Example 43 as starting materials and by an operation similar to that of Example 326.

$^1$H-NMR (CDCl$_3$, 300 MHz) δ: 1.21 (3H, t, J=7.5 Hz), 1.63 (6H, s), 2.48 (2H, q, J=7.5 Hz), 2.84 (2H, t, J=7.2 Hz), 3.05 (2H, t, J=7.2 Hz), 3.34 (3H, s), 3.57 (2H, t, J=7.2 Hz), 3.88 (2H, t, J=7.2 Hz), 4.79 (2H, s), 6.89 (1H, s), 7.11-7.17 (4H, m), 8.19 (2H, s).

MS: 501 (M$^+$+1).

Example 377

2-[(4-{2-[(5-ethylpyrimidin-2-yl)(4-propoxybenzyl)amino]ethyl}-1,3-thiazol-2-yl)thio]-2-methylpropionic acid hydrochloride

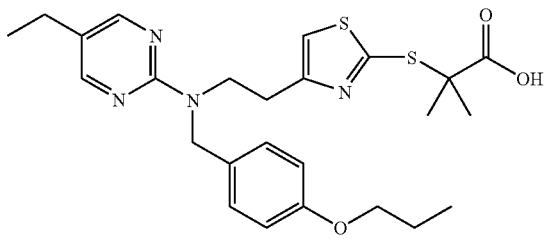

The title compound was obtained using (4-propoxyphenyl)methyl chloride, which is synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-propoxybenzaldehyde as starting materials and by operations similar to those of Reference Examples 42 and 43, and by an operation similar to that of Example 327.

$^1$H-NMR (CDCl$_3$, 400 MHz) δ: 0.95 (3H, t, J=7.3 Hz), 1.15 (3H, t, J=7.8 Hz), 1.50 (6H, s), 1.67-1.75 (2H, m), 2.46 (2H, q, J=7.6 Hz), 2.98 (2H, t, J=7.1 Hz), 3.82 (2H, t, J=7.1 Hz), 3.87 (2H, t, J=7.1 Hz), 4.69 (2H, s), 6.84 (2H, d, J=6.5 Hz), 7.14 (2H, d, J=6.5 Hz), 8.31 (2H, s).

MS: 501 (M$^+$+1).

Example 378

2-[(4-{2-[(4-benzoylbenzyl)(5-ethylpyrimidin-2-yl)amino]ethyl}-1,3-thiazol-2-yl)thio]-2-methylpropionic acid hydrochloride

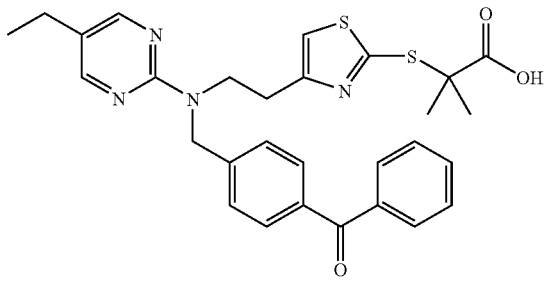

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and [4-(bromomethyl)phenyl](phenyl)methanone as starting materials and by an operation similar to that of Example 327.

$^1$H-NMR (DMSO-d$_6$, 300 MHz) δ: 1.15 (3H, t, J=7.5 Hz), 1.49 (6H, s), 2.44-2.46 (2H, m), 3.04 (2H, brs), 3.92 (2H, brs), 4.84 (2H, s), 7.35 (2H, d, J=8.1 Hz), 7.48 (1H, s), 7.55-7.57 (2H, m), 7.67-7.73 (5H, m), 8.29 (2H, s)

MS: 547 (M$^+$+1).

Example 379

2-[(4-{2-[(3-butoxypropyl)(5-ethylpyrimidin-2-yl)amino]ethyl}-1,3-thiazol-2-yl)thio]-2-methylpropionic acid

Reference Example 44

3-butoxy propan-1-ol

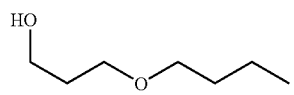

Sodium metal (2.13 g) was added by small portions to 1,3-propanediol (15.75 g) and 1-bromobutane (10.3 g) by reference to non-patent reference [J. Am. Chem. Soc. 249 (1939)]. After the addition, the mixture was stirred at 40° C. for 1 hr and further stirred at 60° C. for 1 hr. The precipitated inorganic compound was filtered off, and the filtrate was distilled away under reduced pressure to give the title compound (3.15 g) as a colorless oil.

$^1$H-NMR (CDCl$_3$, 300 MHz) δ: 0.92 (3H, t, J=7.2 Hz), 1.33-1.40 (2H, m), 1.53-1.58 (2H, m), 1.82-1.87 (2H, m), 3.44 (2H, t, J=6.6 Hz), 3.62 (2H, t, J=5.7 Hz), 3.76-3.81 (2H, m).

Reference Example 45

3-butoxypropyl 4-methylbenzenesulfonic acid

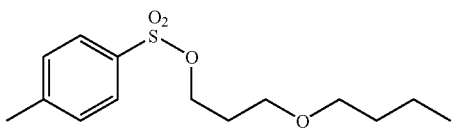

3-Butoxy propan-1-ol (3.15 g) synthesized in Reference Example 44 was dissolved in dichloromethane (80 mL), triethylamine (6.6 mL), p-toluenesulfonyl chloride (6.82 g) and 4-dimethylaminopyridine (0.29 g) were added thereto, and the mixture was stirred at room temperature overnight. Water was added to the reaction solution, and the organic layer was separated and dried over anhydrous sodium sulfate. The solvent was evaporated under reduced pressure, and the residue was purified by silica gel chromatography (elution solvent; hexane:ethyl acetate=3:1) to give the title compound (4.46 g) as a colorless oil.

$^1$H-NMR (CDCl$_3$, 300 MHz) δ: 0.89 (3H, t, J=7.2 Hz), 1.24-1.33 (2H, m), 1.43-1.48 (2H, m), 1.87-1.91 (2H, m), 2.45 (3H, s), 3.31 (2H, t, J=6.6 Hz), 3.41 (2H, t, J=6.0 Hz), 4.13 (2H, t, J=6.3 Hz), 7.33-7.36 (2H, m), 7.77-7.81 (2H, m).

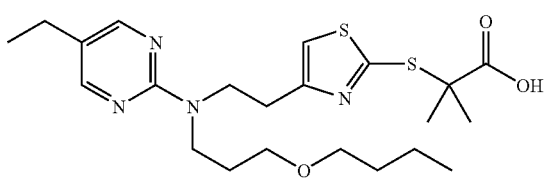

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 3-butoxypropyl 4-methylbenzenesulfonic acid synthesized in Reference Example 45 as starting materials and by an operation similar to that of Example 326.

$^1$H-NMR (CDCl$_3$, 300 MHz) δ: 0.91 (3H, t, J=7.5 Hz), 1.19 (3H, t, J=7.5 Hz), 1.34-1.36 (2H, m), 1.54-1.57 (2H, m), 1.68 (6H, s), 1.75-1.85 (2H, m), 2.44-2.47 (2H, m), 3.08 (2H, t, J=6.6 Hz), 3.44-3.51 (6H, m), 3.91 (2H, t, J=6.6 Hz), 6.87 (1H, s), 8.16 (2H, s).

MS: 467 (M$^+$+1).

Example 380

2-[(4-{2-[(5-ethylpyrimidin-2-yl)(3-propoxypropyl)amino]ethyl}-1,3-thiazol-2-yl)thio]-2-methylpropionic acid

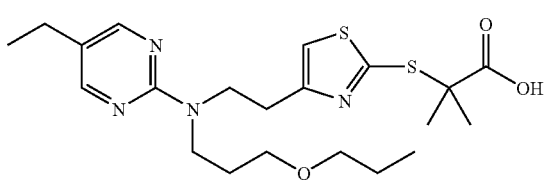

The title compound was obtained using 3-propoxypropyl 4-methylbenzenesulfonic acid synthesized using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-bromopropane as starting materials and by operations similar to those of Reference Examples 44 and 45, and by an operation similar to that of Example 326.

$^1$H-NMR (CDCl$_3$, 300 MHz) δ: 0.91 (3H, t, J=7.2 Hz), 1.19 (3H, t, J=7.5 Hz), 1.57-1.62 (2H, m), 1.68 (6H, s), 1.75-1.85 (2H, m), 2.44-2.47 (2H, m), 3.08 (2H, t, J=6.6 Hz), 3.40-3.51 (6H, m), 3.91 (2H, t, J=6.6 Hz), 6.87 (1H, s), 8.16 (2H, s).

MS: 453 (M$^+$+1).

Example 381

2-[(4-{2-[(5-ethylpyrimidin-2-yl)(2-phenoxyethyl)amino]ethyl}-1,3-thiazol-2-yl)thio]-2-methylpropionic acid

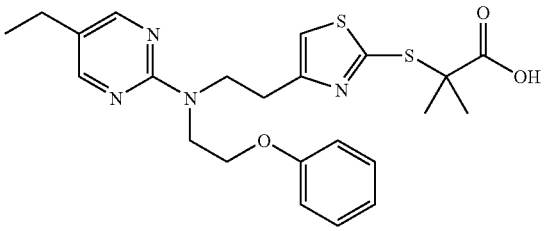

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and (2-bromoethoxy)benzene as starting materials and by an operation similar to that of Example 326.

$^1$H-NMR (CDCl$_3$, 300 MHz) δ: 1.20 (3H, t, J=7.6 Hz), 1.66 (6H, s), 2.48 (2H, q, J=7.6 Hz), 3.17 (2H, t, J=7.1 Hz), 3.90 (2H, t, J=5.5 Hz), 4.06 (2H, t, J=7.1 Hz), 4.17 (2H, t, J=5.5 Hz), 6.88-6.95 (4H, m), 7.23-7.28 (2H, m), 8.19 (2H, s).

MS: 473 (M$^+$+1).

Example 382

2-{[4-(2-{(5-ethylpyrimidin-2-yl)[2-(4-fluorophenoxy)ethyl]amino}ethyl)-1,3-thiazol-2-yl]thio}-2-methylpropionic acid

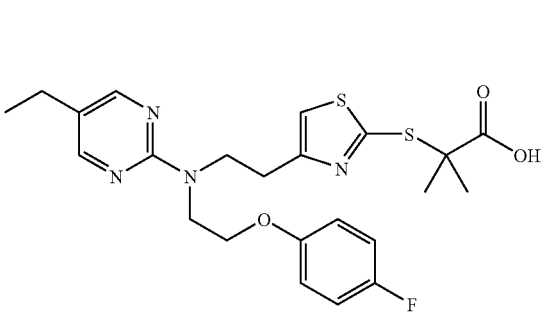

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-fluorobenzene as starting materials and by an operation similar to that of Example 326.

$^1$H-NMR (CDCl$_3$, 300 MHz) δ: 1.20 (3H, t, J=7.5 Hz), 1.66 (6H, s), 2.47 (2H, q, J=7.5 Hz), 3.16 (2H, t, J=7.1 Hz), 3.87 (2H-t, J=5.5 Hz), 4.03 (2H, t, J=7.1 Hz), 4.12 (2H, t, J=5.5 Hz), 6.81-6.86 (2H, m), 6.92-6.97 (3H, m), 8.17 (2H, s).

MS: 491 (M$^+$+1).

Example 383

2-{[4-(2-{(5-ethylpyrimidin-2-yl)[2-(4-methylphenoxy)ethyl]amino}ethyl)-1,3-thiazol-2-yl]thio}-2-methylpropionic acid

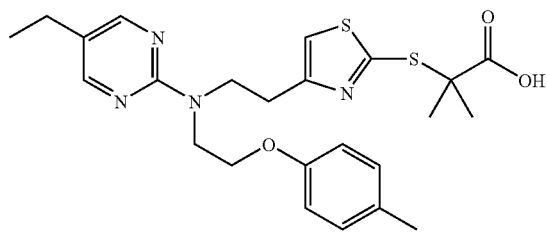

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-methylbenzene synthesized in reference to non-patent reference [Russ. J. Org. Chem. 36, 254 (2000)] as starting materials and by an operation similar to that of Example 326.

$^1$H-NMR (CDCl$_3$, 300 MHz) δ: 1.19 (3H, t, J=7.5 Hz), 1.66 (6H, s), 2.26 (3H, s), 2.46 (2H, q, J=7.5 Hz), 3.16 (2H, t, J=7.2 Hz), 3.87 (2H, t, J=5.4 Hz), 4.04 (2H, t, J=7.2 Hz), 4.13 (2H, t, J=5.4 Hz), 6.79 (2H, d, J=8.4 Hz), 6.94 (1H, s), 7.05 (2H, d, J=8.4 Hz), 8.16 (2H, s).

MS: 487 (M$^+$+1).

Example 384

2-[(4-{2-[[2-(4-chlorophenoxy)ethyl](5-ethylpyrimidin-2-yl)amino]ethyl}-1,3-thiazol-2-yl)thio]-2-methylpropionic acid

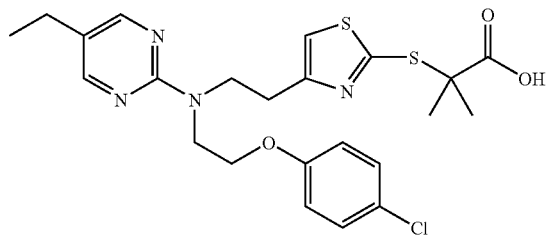

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-chlorobenzene as starting materials and by an operation similar to that of Example 326.

$^1$H-NMR (CDCl$_3$, 300 MHz) δ: 1.20 (3H, t, J=7.5 Hz), 1.65 (6H, s), 2.47 (2H, q, J=7.5 Hz), 3.15 (2H, t, J=7.2 Hz), 3.88 (2H, t, J=5.4 Hz), 4.02 (2H, t, J=7.2 Hz), 4.12 (2H, t, J=5.4 Hz), 6.81-6.84 (2H, m), 6.95 (1H, s), 7.19-7.22 (2H, m), 8.17 (2H, s).

MS: 507 (M$^+$+1).

Example 385

2-{[4-(2-{(5-ethylpyrimidin-2-yl)[2-(4-methoxyphenoxy)ethyl]amino}ethyl)-1,3-thiazol-2-yl]thio}-2-methylpropionic acid

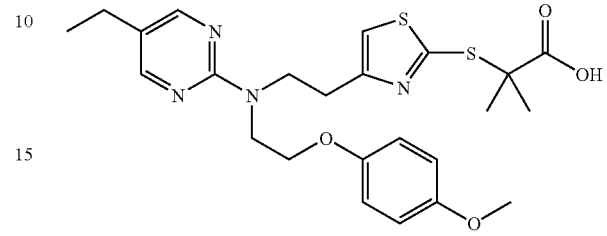

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-methoxybenzene synthesized in reference to non-patent reference [Russ. J. Org. Chem. 36, 254 (2000)] as starting materials and by an operation similar to that of Example 326.

$^1$H-NMR (CDCl$_3$, 300 MHz) δ: 1.19 (3H, t, J=7.5 Hz), 1.66 (6H, s), 2.46 (2H, q, J=7.5 Hz), 3.16 (2H, t, J=7.2 Hz), 3.75 (3H, s), 3.86 (2H, t, J=5.4 Hz), 4.03 (2H, t, J=7.2 Hz), 4.11 (2H, t, J=5.4 Hz), 6.78-6.86 (4H, m), 6.94 (1H, s), 8.17 (2H, s).

MS: 503 (M$^+$+1).

Example 386

2-[(4-{2-[[2-(4-ethylphenoxy)ethyl](5-ethylpyrimidin-2-yl)amino]ethyl}-1,3-thiazol-2-yl)thio]-2-methylpropionic acid

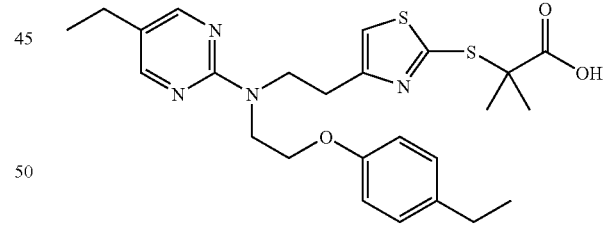

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-ethylbenzene synthesized in reference to non-patent reference [Russ. J. Org. Chem. 36, 254 (2000)] as starting materials and by an operation similar to that of Example 326.

$^1$H-NMR (CDCl$_3$, 300 MHz) δ: 1.16-1.21 (6H, m), 1.66 (6H, s), 2.46 (2H, q, J=7.5 Hz), 2.57 (2H, q, J=7.5 Hz), 3.16 (2H, t, J=7.2 Hz), 3.87 (2H, t, J=5.4 Hz), 4.04 (2H, t, J=7.2 Hz), 4.14 (2H, t, J=5.4 Hz), 6.81-6.85 (2H, m), 6.94 (1H, s), 7.06-7.10 (2H, m), 8.16 (2H, s).

MS: 501 (M$^+$+1).

Example 387

2-{[4-(2-{(5-ethylpyrimidin-2-yl)[2-(4-propylphenoxy)ethyl]amino}ethyl)-1,3-thiazol-2-yl]thio}-2-methylpropionic acid

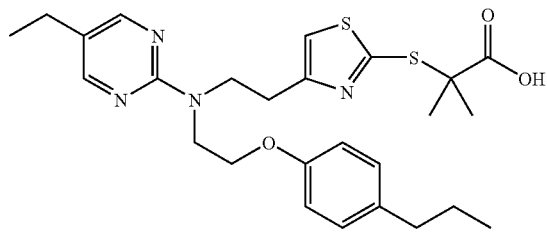

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(2-bromoethoxy)-4-propylbenzene synthesized in reference to non-patent reference [Russ. J. Org. Chem. 36, 254 (2000)] as starting materials and by an operation similar to that of Example 326.

$^1$H-NMR (CDCl$_3$, 300 MHz) δ: 0.91 (3H, t, J=7.5 Hz), 1.19 (3H, t, J=7.5 Hz), 1.54-1.62 (2H, m), 1.66 (6H, s), 2.42-2.53 (4H, m), 3.17 (2H, t, J=7.2 Hz), 3.87 (2H, t, J=5.4 Hz), 4.04 (2H, t, J=7.2 Hz), 4.13 (2H, t, J=5.4 Hz), 6.80-6.84 (2H, m), 6.94 (1H, s), 7.04-7.07 (2H, m), 8.16 (2H, s).

MS: 515 (M$^+$+1).

Example 388

2-[(4-{2-[(5-ethylpyrimidin-2-yl)(3-phenoxypropyl)amino]ethyl}-1,3-thiazol-2-yl)thio]-2-methylpropionic acid

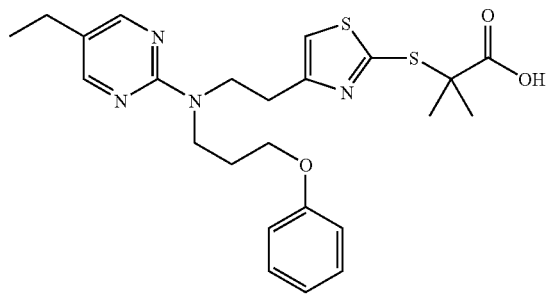

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and (3-bromopropoxy)benzene as starting materials and by an operation similar to that of Example 326.

$^1$H-NMR (CDCl$_3$, 300 MHz) δ: 1.19 (3H, t, J=7.5 Hz), 1.64 (6H, s), 2.04-2.10 (2H, m), 2.45 (2H, q, J=7.5 Hz), 3.11 (2H, t, J=7.2 Hz), 3.68 (2H, t, J=7.2 Hz), 3.91 (2H, t, J=7.2 Hz), 4.00 (2H, t, J=6.0 Hz), 6.88-6.95 (4H, m), 7.24-7.30 (2H, m), 8.15 (2H, s).

MS: 487 (M$^+$+1).

Example 389

2-{[4-(2-{(5-ethylpyrimidin-2-yl)[3-(4-fluorophenoxy)propyl]amino}ethyl)-1,3-thiazol-2-yl]thio}-2-methylpropionic acid

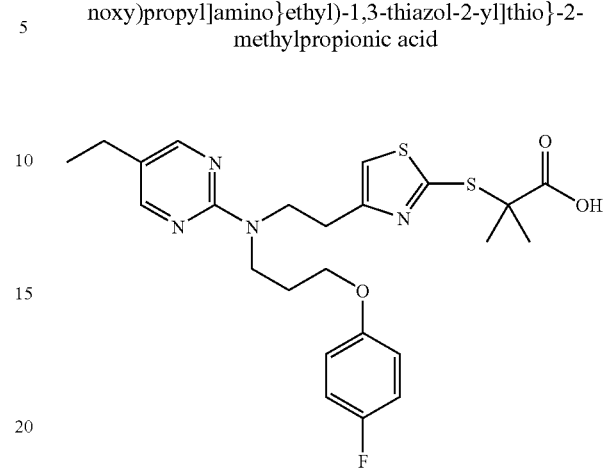

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(3-chloropropoxy)-4-fluorobenzene as starting materials and by an operation similar to that of Example 326.

$^1$H-NMR (CDCl$_3$, 300 MHz) δ: 1.19 (3H, t, J=7.5 Hz), 1.64 (6H, s), 2.02-2.11 (2H, m), 2.45 (2H, q, J=7.5 Hz), 3.11 (2H, t, J=6.9 Hz), 3.67 (2H, t, J=6.9 Hz), 3.88-3.97 (4H, m), 6.80-6.85 (2H, m), 6.93-6.98 (3H, m), 8.15 (2H, s).

MS: 505 (M$^+$+1).

Example 390

2-{[4-(2-{(5-ethylpyrimidin-2-yl)[3-(4-methylphenoxy)propyl]amino}ethyl)-1,3-thiazol-2-yl]thio}-2-methylpropionic acid hydrochloride

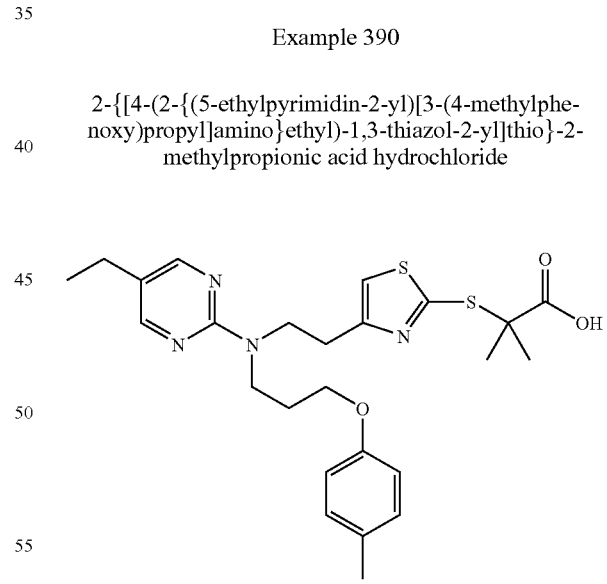

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(3-chloropropoxy)-4-methylbenzene synthesized in reference to non-patent reference [Synthesis, 1069 (1990)] as starting materials and by an operation similar to that of Example 327.

$^1$H-NMR (DMSO-d$_6$, 300 MHz) δ: 1.13 (3H, t, J=7.5 Hz), 1.50 (6H, s), 1.91-1.98 (2H, m), 2.21 (3H, s), 2.45 (2H, q,

J=7.5 Hz), 3.01 (2H, t, J=6.9 Hz), 3.60 (2H, t, J=6.9 Hz), 3.85-3.95 (4H, m), 6.79 (2H, d, J=8.2 Hz), 7.06 (2H, d, J=8.2 Hz), 7.47 (1H, s), 8.30 (2H, s).

MS: 501 (M⁺+1).

Example 391

2-[(4-{2-[[3-(4-chlorophenoxy)propyl](5-ethylpyrimidin-2-yl)amino]ethyl}-1,3-thiazol-2-yl)thio]-2-methylpropionic acid

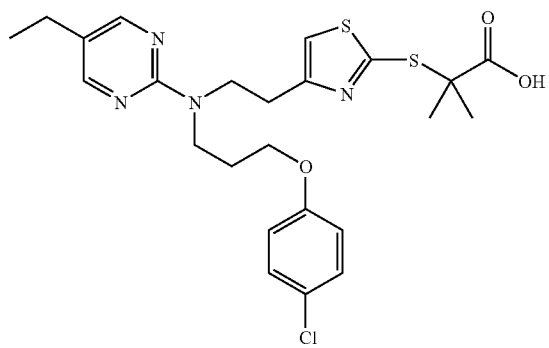

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-chloro-4-(3-chloropropoxy)benzene synthesized in reference to non-patent reference [Synthesis, 1069 (1990)] as starting materials and by an operation similar to that of Example 326.

¹H-NMR (CDCl₃, 300 MHz) δ: 1.19 (3H, t, J=7.8 Hz), 1.64 (6H, s), 2.05-2.09 (2H, m), 2.45 (2H, q, J=7.8 Hz), 3.11 (2H, t, J=7.2 Hz), 3.67 (2H, t, J=6.9 Hz), 3.87-3.98 (4H, m), 6.80-6.83 (2H, m), 6.93 (1H, s), 7.20-7.23 (2H, m), 8.15 (2H, s).

MS: 521 (M⁺+1).

Example 392

2-{[4-(2-{(5-ethylpyrimidin-2-yl)[3-(4-methoxyphenoxy)propyl]amino}ethyl)-1,3-thiazol-2-yl]thio}-2-methylpropionic acid

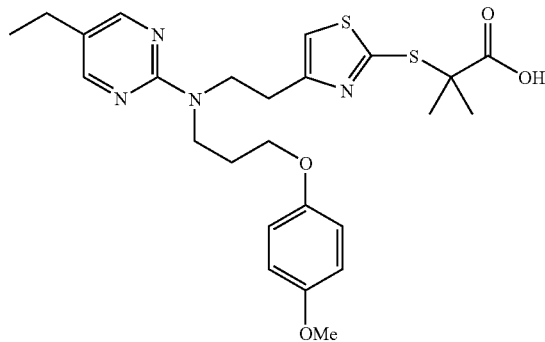

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 1-(3-chloropropoxy)-4-methoxybenzene synthesized in reference to non-patent reference [Synthesis, 1069 (1990)] as starting materials and by an operation similar to that of Example 326.

¹H-NMR (CDCl₃, 300 MHz) δ: 1.19 (3H, t, J=7.5 Hz), 1.64 (6H, s), 2.01-2.10 (2H, m), 2.45 (2H, q, J=7.5 Hz), 3.11 (2H, t, J=7.2 Hz), 3.67 (2H, t, J=7.2 Hz), 3.76 (3H, s), 3.89-3.97 (4H, m), 6.79-6.86 (4H, m), 6.91 (1H, s), 8.15 (2H, s).

MS: 517 (M⁺+1).

Example 393

2-[(4-{2-[[3-(4-cyanophenoxy)propyl](5-ethylpyrimidin-2-yl)amino]ethyl}-1,3-thiazol-2-yl)thio]-2-methylpropionic acid hydrochloride

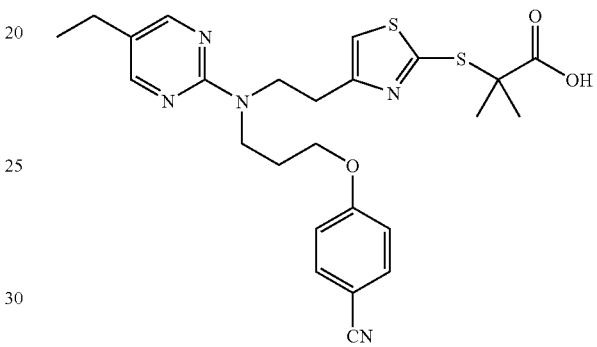

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(3-chloropropoxy)benzonitrile synthesized in reference to non-patent reference [Synthesis, 1069 (1990)] as starting materials and by an operation similar to that of Example 327.

¹H-NMR (DMSO-d₆, 300 MHz) δ: 1.12 (3H, t, J=7.5 Hz), 1.49 (6H, s), 1.99-2.01 (2H, m), 2.43 (2H, q, J=7.5 Hz), 3.00 (2H, t, J=6.6 Hz), 3.60 (2H, t, J=6.6 Hz), 3.86 (2H, t, J=7.5 Hz), 4.07 (2H, t, J=6.0 Hz), 7.07 (2H, d, J=8.7 Hz), 7.46 (1H, s), 7.75 (2H, d, J=8.7 Hz), 8.25 (2H, s).

MS: 512 (M⁺+1).

Example 394

2-[(4-{2-[(5-ethylpyrimidin-2-yl)(3-phenylpropyl)amino]ethyl}-1,3-thiazol-2-yl)thio]-2-methylpropionic acid hydrogen bromide

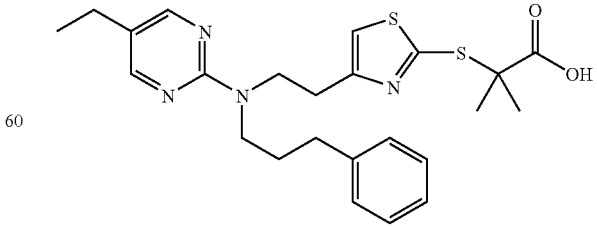

A compound obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and (3-bromopropyl)benzene as starting materials and by an operation similar to that of Example 326 was dissolved in diethyl ether, and reacted with 30% hydrobromic acid-acetic acid to give the title compound.

$^1$H-NMR (DMSO-d$_6$, 300 MHz) δ: 1.16 (3H, t, J=7.5 Hz), 1.51 (6H, s), 1.82-1.85 (2H, m), 2.46-2.61 (4H, m), 3.02 (2H, t, J=7.0 Hz), 3.51 (2H, t, J=7.5 Hz), 3.90 (2H, t, J=7.0 Hz), 7.17-7.29 (5H, m), 7.50 (1H, s), 8.41 (2H, s).

MS: 471 (M$^+$+1).

Example 395

2-[(4-{2-[(5-ethylpyrimidin-2-yl)(4-phenylbutyl)amino]ethyl}-1,3-thiazol-2-yl)thio]-2-methylpropionic acid

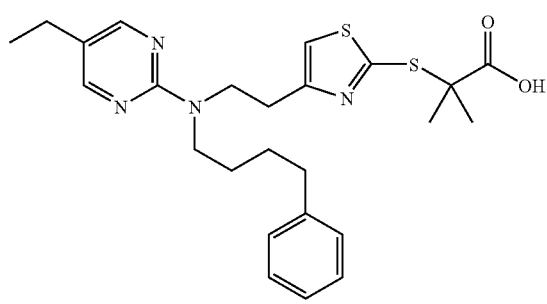

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and (4-chlorobutyl)benzene as starting materials and by an operation similar to that of Example 326.

$^1$H-NMR (CDCl$_3$, 300 MHz) δ: 1.19 (3H, t, J=7.5 Hz), 1.60-1.64 (10H, m), 2.45 (2H, q, J=7.5 Hz), 2.63 (2H, brs), 3.07 (2H, t, J=7.2 Hz), 3.51 (2H, brs), 3.85 (2H, t, J=7.2 Hz), 6.93 (1H, s), 7.16-7.18 (3H, m), 7.24-7.28 (2H, m), 8.16 (2H, s).

MS: 485 (M$^+$+1).

Example 396

2-[(4-{2-[[3-(cyclohexyloxy)propyl](5-ethylpyrimidin-2-yl)amino]ethyl}-1,3-thiazol-2-yl)thio]-2-methylpropionic acid hydrogen bromide Reference Example 46

1,5-dioxaspiro[5,5]undecane

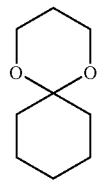

Cyclohexanone (7.94 g) was dissolved in toluene (200 mL), 1,3-propanediol (12.3 g) and p-toluenesulfonic acid monohydrate (0.1 g) were added thereto, and the mixture was heated under reflux for 1.5 hr while removing water being produced. The temperature was allowed to cool to room temperature, and the mixture was washed with saturated aqueous sodium hydrogen carbonate solution and dried over anhydrous sodium sulfate. The solvent was evaporated under reduced pressure to give the title compound (12.4 g) as a colorless oil.

$^1$H-NMR (CDCl$_3$, 300 MHz) δ: 1.38-1.58 (6H, m), 1.69-1.79 (6H, m), 3.89-3.92 (4H, m).

Reference Example 47

3-(cyclohexyloxy)propan-1-ol

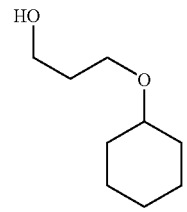

By reference to a non-patent reference [J. Am. Chem. Soc. 2371 (1962)], aluminum chloride (1.71 g) was dissolved in diethyl ether (10 mL), and lithium aluminum hydride (0.121 g) was added thereto under ice-cooling. The mixture was stirred for 20 min, a solution of 1,5-dioxaspiro[5,5]undecane (1.0 g) obtained in Reference Example 46 in diethyl ether (5.0 mL) was added dropwise thereto. After gradually warming to room temperature, the mixture was stirred for 2 hr. Under ice-cooling, 10% sulfuric acid (20 mL) was added, and the mixture was extracted with diethyl ether. The organic layer was dried over anhydrous sodium sulfate, and the solvent was evaporated under reduced pressure to give the title compound (0.82 g) as a colorless oil.

$^1$H-NMR (CDCl$_3$, 300 MHz) δ: 1.21-1.90 (12H, m), 3.25-3.28 (1H, m), 3.66 (2H, t, J=5.5 Hz), 3.79 (2H, t, J=5.5 Hz).

Reference Example 48

3-(cyclohexyloxy)propyl 4-methylbenzenesulfonic acid

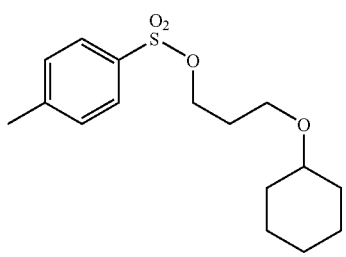

3-(Cyclohexyloxy)propan-1-ol (820 mg) synthesized in Reference Example 47 was dissolved in dichloromethane (20 mL), triethylamine (1.1 mL), p-toluenesulfonyl chloride (1.2 g) and 4-dimethylaminopyridine (63 mg) were added thereto, and the mixture was stirred at room temperature overnight. Water was added to the reaction solution, and the organic layer was separated and dried over anhydrous sodium sulfate. The solvent was evaporated under reduced pressure, and the residue was purified by silica gel chromatography (elution solvent; hexane:ethyl acetate=5:1) to give the title compound (1.0 g) as a colorless oil.

$^1$H-NMR (CDCl$_3$, 300 MHz) δ: 1.12-1.92 (12H, m), 2.45 (3H, s), 3.07-3.10 (1H, m), 3.45 (2H, t, J=6.0 Hz), 4.14 (2H, t, J=6.0 Hz), 7.35 (2H, d, J=8.4 Hz), 7.80 (2H, d, J=8.4 Hz).

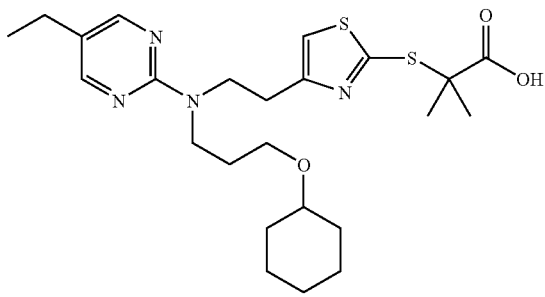

A compound obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 3-(cyclohexyloxy)propyl 4-methylbenzenesulfonic acid synthesized in Reference Example 48 as starting materials and by an operation similar to that of Example 326 was dissolved in diethyl ether, and reacted with 30% hydrobromic acid-acetic acid to give the title compound.

$^1$H-NMR (DMSO-d$_6$, 300 MHz) δ: 1.07-1.20 (9H, m), 1.51 (6H, s), 1.73-1.75 (6H, m), 2.45-2.50 (2H, m), 2.95-3.05 (2H, m), 3.36-3.41 (3H, m), 3.49 (2H, t, J=7.2 Hz), 3.86 (2H, t, J=7.2 Hz), 7.48 (1H, s), 8.33 (2H, s).

MS: 493 (M$^+$+1).

Example 397

2-[(4-{2-[[2-(benzyloxy)ethyl](5-ethylpyrimidin-2-yl)amino]ethyl}-1,3-thiazol-2-yl)thio]-2-methylpropionic acid

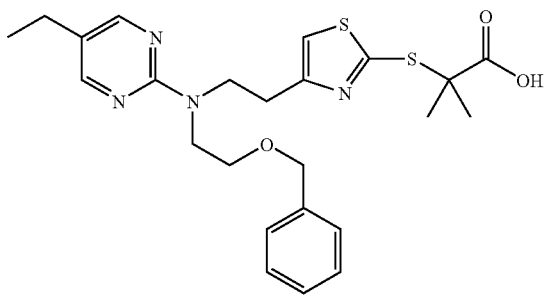

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and [(2-bromoethoxy)methyl]benzene as starting materials and by an operation similar to that of Example 326.

$^1$H-NMR (CDCl$_3$, 300 MHz) δ: 1.19 (3H, t, J=7.5 Hz), 1.66 (6H, s), 2.46 (2H, q, J=7.5 Hz), 3.09 (2H, t, J=6.6 Hz), 3.67 (4H, s), 3.99 (2H, t, J=6.6 Hz), 4.54 (2H, s), 6.84 (1H, s), 7.25-7.31 (5H, m), 8.15 (2H, s).

MS: 487 (M$^+$+1).

Example 398

2-[(4-{2-[[3-(benzyloxy)propyl](5-ethylpyrimidin-2-yl)amino]ethyl}-1,3-thiazol-2-yl)thio]-2-methylpropionic acid

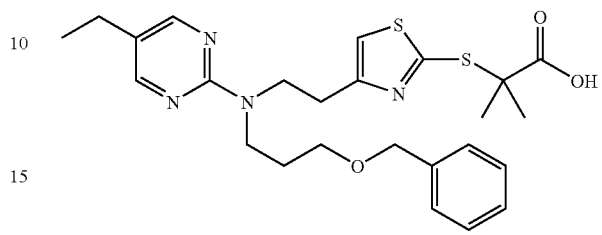

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and [(3-bromopropoxy)methyl]benzene as starting materials and by an operation similar to that of Example 326.

$^1$H-NMR (CDCl$_3$, 300 MHz) δ: 1.86 (3H, t, J=7.5 Hz), 1.65 (6H, s), 1.83-1.92 (2H, m), 2.45 (2H, q, J=7.5 Hz), 3.07 (2H, t, J=6.7 Hz), 3.47-3.54 (4H, m), 3.88 (2H, t, J=6.7 Hz), 4.55 (2H, s), 6.87 (1H, s), 7.26-7.35 (5H, m), 8.15 (2H, s).

MS: 501 (M$^+$+1).

Example 399

2-[(4-{2-[(biphenyl-4-ylmethyl)(5-cyanopyridin-2-yl)amino]ethyl}-1,3-thiazol-2-yl)thio]-2-methylpropionic acid

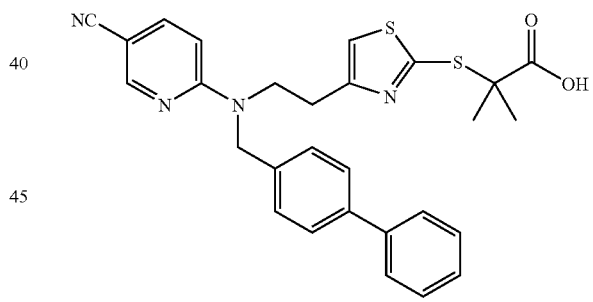

A compound obtained by an operation similar to that of Example 265-1 and using 2-{[4-(2-aminoethyl)-1,3-thiazol-2-yl]thio}-2-methylpropionic acid tert-butyl ester synthesized in Example 7 and 2-chloro-5-cyanopyridine as starting materials, followed by an operation similar to that of Example 265-2 and using biphenyl-4-ylmethyl chloride as starting material was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile) to give the title compound.

$^1$H-NMR (DMSO-d$_6$, 270 MHz) δ: 1.51 (6H, s), 2.95-3.12 (2H, m), 3.80-4.03 (2H, m), 4.79 (2H, s), 6.74 (1H, d, J=8.9 Hz), 7.23-7.71 (10H, m), 7.82 (1H, d, J=8.9 Hz), 8.52 (1H, s).

MS: 515 (M$^+$+1).

Example 400

2-[(4-{2-[(4-bromophenylmethyl)(5-cyanopyridin-2-yl)amino]ethyl}-1,3-thiazol-2-yl)thio]-2-methylpropionic acid hydrochloride

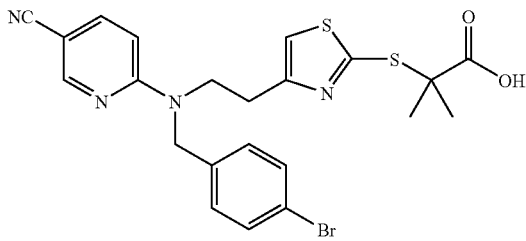

A compound obtained by an operation similar to that of Example 265-1 and using 2-{[4-(2-aminoethyl)-1,3-thiazol-2-yl]thio}-2-methylpropionic acid tert-butyl ester synthesized in Example 7 and 2-chloro-5-cyanopyridine as starting materials, followed by an operation similar to that of Example 265-2 and using 4-bromobenzylbromide as starting material was treated with dichloromethane and trifluoroacetic acid, and the mixture was stirred at room temperature for 12 hr. The reaction solution was concentrated under reduced pressure, and the residue was purified by high performance liquid chromatography (elution solvent; 0.05% trifluoroacetic acid-water:0.05% trifluoroacetic acid-acetonitrile) to give the title compound.

$^1$H-NMR (DMSO-d$_6$, 270 MHz) δ: 1.50 (6H, s), 3.02 (2H, t, J=7.3 Hz), 3.88 (2H, t, J=7.3 Hz), 4.72 (2H, s), 6.71 (1H, d, J=9.2 Hz), 7.14, (1H, d, J=8.4 Hz), 7.40-7.52 (3H, m), 7.82 (1H, dd, J=9.2, 2.0 Hz), 8.50 (1H, d, J=2.0 Hz).

MS: 519 (M$^+$+1).

Example 401

2-[(4-{3-[(biphenyl-4-ylmethyl)(5-ethylpyridin-2-yl)amino]propyl}-1,3-thiazol-2-yl)thio]-2-methylpropionic acid hydrochloride

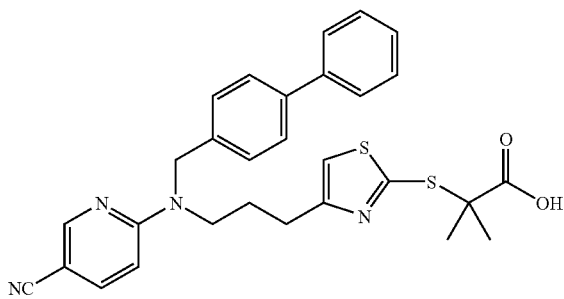

The title compound was obtained by an operation similar to that of Example 265-1 and using 2-{[4-(3-aminopropyl)-1,3-thiazol-2-yl]thio}-2-methylpropionic acid tert-butyl ester synthesized in Example 33 and 2-chloro-5-cyanopyridine as starting materials, followed by an operation similar to that of Example 327 and using biphenyl-4-ylmethyl chloride.

$^1$H-NMR (DMSO-d$_6$, 270 MHz) δ: 1.49 (6H, s), 1.88-2.09 (2H, m), 2.77 (2H, t, J=7.3 Hz), 4.87 (2H, s), 6.75 (1H, d, J=9.2 Hz), 7.21-7.51 (6H, m), 7.58-7.68 (4H, m), 7.81 (1H, dd, J=9.2, 2.4 Hz), 7.50 (1H, d, J=2.4 Hz).

MS: 529 (M$^+$+1).

Example 402

2-[(4-{2-[(4-bromobenzyl)(5-ethylpyrimidin-2-yl)amino]ethyl}-1,3-thiazol-2-yl)thio]-2-methylpropionic acid

Example 402-1

2-[(4-{2-[(4-bromobenzyl)(5-ethylpyrimidin-2-yl)amino]ethyl}-1,3-thiazol-2-yl)thio]-2-methylpropionic acid tert-butyl ester

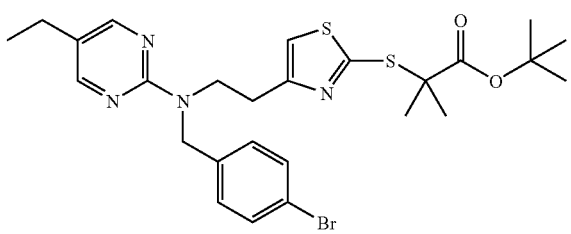

2-[(4-{2-[(5-Ethylpyrimidin-2-yl)amino]ethyl}-1,3-thiazol-2-yl)thio]-2-methylpropionic acid tert-butyl ester (4.0 g) synthesized in Example 265-1 and 1-bromo-4-(bromomethyl)benzene (2.94 g) were dissolved in N,N-dimethylformamide (40 mL), potassium tert-butoxide (1.32 g) was added thereto, and the mixture was stirred at room temperature for 8 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (4.65 g) as a colorless oil.

$^1$H-NMR (CDCl$_3$, 300 MHz) δ: 1.21 (3H, t, J=7.5 Hz), 1.42 (9H, s), 1.56 (6H, s), 2.48 (2H, q, J=7.5 Hz), 3.08 (2H, t, J=6.9 Hz), 3.90 (2H, t, J=6.9 Hz), 4.70 (2H, s), 6.98 (1H, s), 7.09 (2H, d, J=8.1 Hz), 7.38 (2H, d, J=8.1 Hz), 8.19 (2H, s).

Example 402-2

2-[(4-{2-[(4-bromobenzyl)(5-ethylpyrimidin-2-yl)amino]ethyl}-1,3-thiazol-2-yl)thio]-2-methylpropionic acid

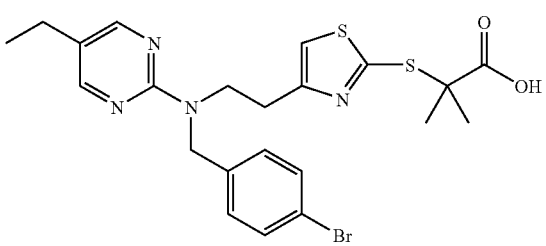

2-[(4-{2-[(4-Bromobenzyl)(5-ethylpyrimidin-2-yl)amino]ethyl}-1,3-thiazol-2-yl)thio]-2-methylpropionic acid tert-butyl ester (350 mg) obtained in Example 402-1 was dissolved in dichloromethane (6 mL), trifluoroacetic acid (2 mL) was added, and the mixture was stirred at room temperature for 20 hr. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (240 mg) as a white solid.

$^1$H-NMR (CDCl$_3$, 300 MHz) δ: 1.21 (3H, t, J=7.5 Hz), 1.63 (6H, s), 2.48 (2H, q, J=7.5 Hz), 3.06 (2H, t, J=6.9 Hz), 3.89 (2H, t, J=6.9 Hz), 4.76 (2H, s), 6.91 (1H, s), 7.11 (2H, d, J=8.4 Hz), 7.39 (2H, d, J=8.4 Hz), 8.20 (2H, s).

MS: 523 (M$^+$+1).

Example 403

2-[(4-{2-[(5-ethylpyrimidin-2-yl)(4-pyrazin-2-ylbenzyl)amino]ethyl}-1,3-thiazol-2-yl)thio]-2-methylpropionic acid hydrochloride Example 403-1

2-[(4-{2-[(5-ethylpyrimidin-2-yl)(4-pyrazin-2-ylbenzyl)amino]ethyl}-1,3-thiazol-2-yl)thio]-2-methylpropionic acid tert-butyl ester

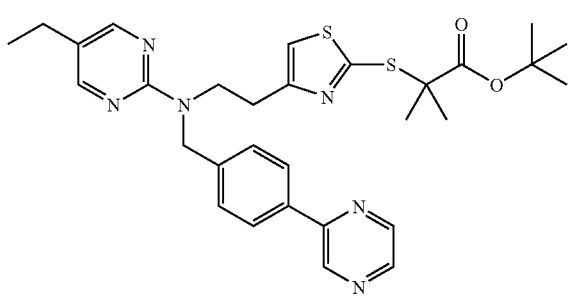

Under nitrogen atmosphere, 2-[(4-{2-[(4-bromobenzyl)(5-ethylpyrimidin-2-yl)amino]ethyl}-1,3-thiazol-2-yl)thio]-2-methylpropionic acid tert-butyl ester (800 mg) synthesized in Example 402-1 and 2-tributylstanylpyrazine (672 mg) were dissolved in dioxane (10 mL), tetrakis(triphenylphosphine)palladium (140 mg) was added, and the mixture was refluxed for 8 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1) to give the title compound (180 mg) as a pale-yellow oil.

$^1$H-NMR (CDCl$_3$, 300 MHz) δ: 1.21 (3H, t, J=7.6 Hz), 1.42 (9H, s), 1.57 (6H, s), 2.48 (2H, q, J=7.6 Hz), 3.13 (2H, t, J=7.0 Hz), 3.98 (2H, t, J=7.0 Hz), 4.85 (2H, s), 7.01 (1H, s), 7.36 (2H, d, J=8.1 Hz), 7.94 (2H, d, J=8.1 Hz), 8.21 (2H, s), 8.47 (1H, s), 8.60 (1H, s), 9.00 (1H, s).

Example 403-2

2-[(4-{2-[(5-ethylpyrimidin-2-yl)(4-pyrazin-2-ylbenzyl)amino]ethyl}-1,3-thiazol-2-yl)thio]-2-methylpropionic acid hydrochloride

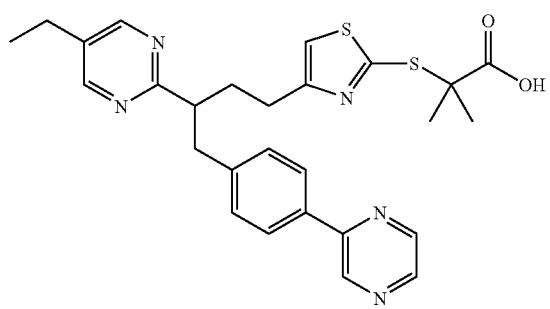

2-[(4-{2-[(5-Ethylpyrimidin-2-yl)(4-pyrazin-2-ylbenzyl)amino]ethyl}-1,3-thiazol-2-yl)thio]-2-methylpropionic acid tert-butyl ester (180 mg) obtained in Example 403-1 was dissolved in dichloromethane (6 mL), trifluoroacetic acid (2 mL) was added, and the mixture was stirred at room temperature for 12 hr. The reaction mixture was concentrated under reduced pressure, and the residue was purified by silica gel chromatography (elution solvent; dichloromethane:methanol=10:1). The obtained compound was dissolved in diethyl ether (5 mL), hydrochloric acid-ethyl acetate (4 mol/L, 1 mL) was added, and the mixture was stirred at room temperature for 1 hr. The precipitated solid was collected by filtration to give the title compound (140 mg) as a white solid.

$^1$H-NMR (DMSO-d$_6$, 300 MHz) δ: 1.30 (3H, t, J=7.6 Hz), 1.62 (6H, s), 2.65 (2H, q, J=7.6 Hz), 3.24 (2H, t, J=7.5 Hz), 4.19 (2H, t, J=7.5 Hz), 5.16 (2H, s), 7.48 (2H, d, J=8.1 Hz), 7.60 (1H, s), 8.00 (2H, d, J=8.1 Hz), 8.50-8.54 (3H, m), 8.66 (1H, s), 9.02 (1H, s).

MS: 521 (M$^+$+1).

Example 404

2-[(4-{2-[(5-ethylpyrimidin-2-yl)(4-pyrimidin-2-ylbenzyl)amino]ethyl}-1,3-thiazol-2-yl)thio]-2-methylpropionic acid hydrochloride

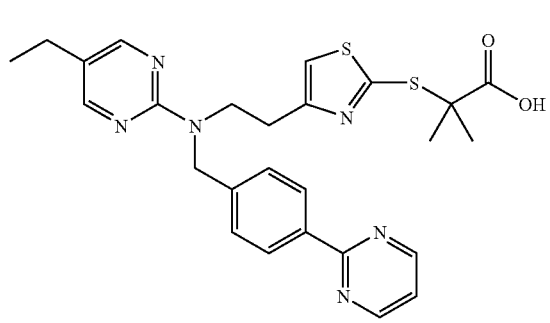

The title compound was obtained using 2-[(4-{2-[(4-bromobenzyl)(5-ethylpyrimidin-2-yl)amino]ethyl}-1,3-thiazol-2-yl)thio]-2-methylpropionic acid tert-butyl ester synthesized in Example 402-1 and 2-tributylstanylpyrimidine as starting materials and by an operation similar to that of Example 403.

¹H-NMR (CDCl₃, 300 MHz) δ: 1.32 (3H, t, J=7.5 Hz), 1.64 (6H, s), 2.67 (2H, q, J=7.5 Hz), 3.39 (2H, brs), 4.21 (2H, brs), 5.29 (2H, s), 7.59-7.63 (3H, m), 8.02 (2H, s), 8.49 (1H, brs), 8.60 (2H, d, J=8.1 Hz), 9.11 (2H, d, J=4.8 Hz).

MS: 521 (M⁺+1).

Example 405

2-{[4-(2-{(5-ethylpyrimidin-2-yl)[4-(1,3-thiazol-2-yl)benzyl]amino}ethyl)-1,3-thiazol-2-yl]thio}-2-methylpropionic acid hydrochloride

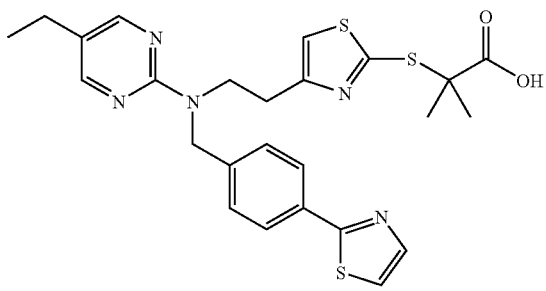

The title compound was obtained using 2-[(4-{2-[(4-bromobenzyl)(5-ethylpyrimidin-2-yl)amino]ethyl}-1,3-thiazol-2-yl)thio]-2-methylpropionic acid tert-butyl ester synthesized in Example 402-1 and 2-tributylstanylthiazole as starting materials and by an operation similar to that of Example 403.

¹H-NMR (DMSO-d₆, 300 MHz) δ: 1.15 (3H, t, J=7.5 Hz), 1.50 (6H, s), 2.46 (2H, q, J=7.5 Hz), 3.03 (2H, t, J=6.6 Hz), 3.91 (2H, t, J=6.6 Hz), 4.81 (2H, s), 7.32 (2H, d, J=8.4 Hz), 7.48 (1H, s), 7.77 (1H, d, J=3.0 Hz), 7.86-7.91 (3H, m), 8.31 (2H, s).

MS: 526 (M⁺+1).

Example 406

2-[(4-{2-[(5-ethylpyrimidin-2-yl)(4-pyridin-2-ylbenzyl)amino]ethyl}-1,3-thiazol-2-yl)thio]-2-methylpropionic acid hydrochloride

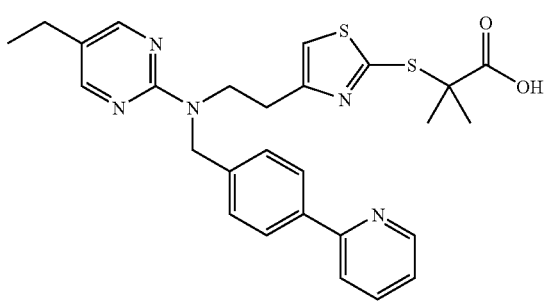

The title compound was obtained using 2-[(4-{2-[(4-bromobenzyl)(5-ethylpyrimidin-2-yl)amino]ethyl}-1,3-thiazol-2-yl)thio]-2-methylpropionic acid tert-butyl ester synthesized in Example 402-1 and 2-tributylstanylpyridine as starting materials and by an operation similar to that of Example 403.

¹H-NMR (CDCl₃, 300 MHz) δ: 1.31 (3H, t, J=7.5 Hz), 1.61 (6H, s), 2.66 (2H, q, J=7.5 Hz), 3.16 (2H, t, J=6.9 Hz), 4.18 (2H, t, J=6.9 Hz), 5.14 (2H, s), 7.45 (1H, brs), 7.63 (2H, d, J=7.8 Hz), 7.80-7.84 (1H, m), 8.16-8.24 (3H, m), 8.41-8.48 (1H, m), 8.93 (1H, d, J=5.7 Hz).

MS: 520 (M⁺+1).

Example 407

2-[(4-{2-[(5-ethylpyrimidin-2-yl)(4-pyridin-3-ylbenzyl)amino]ethyl}-1,3-thiazol-2-yl)thio]-2-methylpropionic acid trifluoroacetate

Example 407-1

2-[(4-{2-[(5-ethylpyrimidin-2-yl)(4-pyridin-3-ylbenzyl)amino]ethyl}-1,3-thiazol-2-yl)thio]-2-methylpropionic acid tert-butyl ester

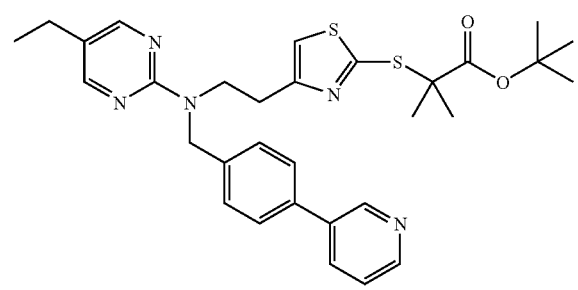

Under nitrogen atmosphere, 2-[(4-{2-[(4-bromobenzyl)(5-ethylpyrimidin-2-yl)amino]ethyl}-1,3-thiazol-2-yl)thio]-2-methylpropionic acid tert-butyl ester (300 mg) synthesized in Example 402-1 and (3-diethylboryl)pyridine (76 mg) were dissolved in dioxane (2.6 mL) and sodium carbonate (2 mol/L, 1.3 mL), tetrakis(triphenylphosphine)palladium (30 mg) was added, and the mixture was refluxed for 2 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=2:1 to 1:1) to give the title compound (223 mg) as a white solid.

¹H-NMR (CDCl₃, 300 MHz) δ: 1.22 (3H, t, J=7.5 Hz), 1.42 (9H, s), 1.57 (6H, s), 2.49 (2H, q, J=7.5 Hz), 3.13 (2H, t, J=7.2 Hz), 3.96 (2H, t, J=7.2 Hz), 4.83 (2H, s), 7.01 (1H, s), 7.31-

7.36 (3H, m), 7.48-7.50 (2H, m), 7.82-7.86 (1H, m), 8.21 (2H, s), 8.55-8.57 (1H, m), 8.81-8.82 (1H, m).

Example 407-2

2-[(4-{2-[(5-ethylpyrimidin-2-yl)(4-pyridin-3-ylbenzyl)amino]ethyl}-1,3-thiazol-2-yl)thio]-2-methylpropionic acid trifluoroacetate

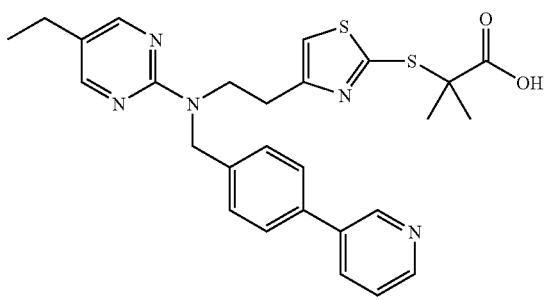

2-[(4-{2-[(5-Ethylpyrimidin-2-yl)(4-pyridin-3-ylbenzyl)amino]ethyl}-1,3-thiazol-2-yl)thio]-2-methylpropionic acid tert-butyl ester synthesized in Example 407-1 was treated with dichloromethane and trifluoroacetic acid. The reaction solution was concentrated under reduced pressure, and the residue was purified by high performance liquid chromatography (elution solvent; 0.05% trifluoroacetic acid-water: 0.05% trifluoroacetic acid-acetonitrile=75:25 to 30:70) to give the title compound.

$^1$H-NMR (CDCl$_3$, 300 MHz) δ: 1.24 (3H, t, J=7.5 Hz), 1.62 (6H, s), 2.53 (2H, q, J=7.5 Hz), 3.10 (2H, t, J=7.2 Hz), 3.98 (2H, t, J=7.2 Hz), 4.91 (2H, s), 6.97 (1H, s), 7.40 (2H, d, J=8.1 Hz), 7.54 (2H, d, J=8.1 Hz), 7.76-7.80 (1H, m), 8.28 (2H, s), 8.34-8.37 (1H, m), 8.70-8.72 (1H, m), 9.04 (1H, brs).

MS: 520 (M$^+$+1).

Example 408

2-[(4-{2-[(5-ethylpyrimidin-2-yl)(4-morpholin-4-ylbenzyl)amino]ethyl}-1,3-thiazol-2-yl)thio]-2-methylpropionic acid Example 408-1

2-[(4-{2-[(5-ethylpyrimidin-2-yl)(4-morpholin-4-ylbenzyl)amino]ethyl}-1,3-thiazol-2-yl)thio]-2-methylpropionic acid tert-butyl ester

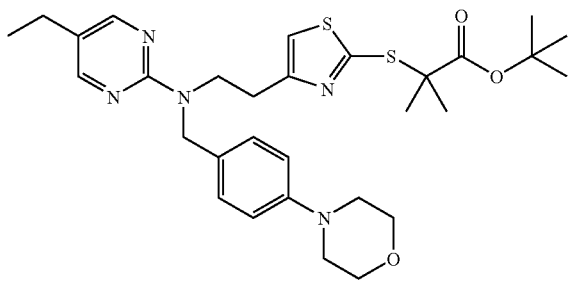

tris(Dibenzylideneacetone)dipalladium (32 mg), 2-(di-tert-butylphosphino)biphenyl (21 mg) and sodium tert-butoxide (73 mg) were added to a 20 mL screw cap test tube substituted with nitrogen, and a solution of 2-[(4-{2-[(4-bromobenzyl)(5-ethylpyrimidin-2-yl)amino]ethyl}-1,3-thiazol-2-yl)thio]-2-methylpropionic acid tert-butyl ester (400 mg) synthesized in Example 402-1 and morpholine (91 mg) in toluene (1.4 mL) was added thereto. The test tube was capped, and stirred at 110° C. for 8 hr. After cooling to room temperature, the solution was directly purified by silica gel chromatography (elution solvent; hexane:ethyl acetate=3:1 to 2:1) to give the title compound (200 mg) as a colorless oil.

$^1$H-NMR (CDCl$_3$, 300 MHz) δ: 1.21 (3H, t, J=7.5 Hz), 1.43 (9H, s), 1.62 (6H, s), 2.47 (2H, q, J=7.5 Hz), 3.05-3.12 (6H, m), 3.83-4.14 (6H, m), 4.70 (2H, s), 6.82 (2H, d, J=8.4 Hz), 6.98 (1H, s), 7.15 (2H, d, J=8.4 Hz), 8.19 (2H, s).

Example 408-2

2-[(4-{2-[(5-ethylpyrimidin-2-yl)(4-morpholin-4-ylbenzyl)amino]ethyl}-1,3-thiazol-2-yl)thio]-2-methylpropionic acid

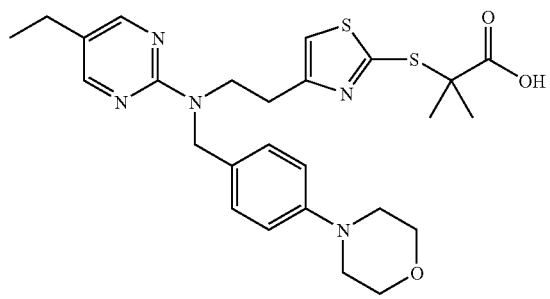

2-[(4-{2-[(5-Ethylpyrimidin-2-yl)(4-morpholin-4-ylbenzyl)amino]ethyl}-1,3-thiazol-2-yl)thio]-2-methylpropionic acid tert-butyl ester (200 mg) synthesized in Example 408-1 was dissolved in dichloromethane (2 mL), trifluoroacetic acid (2 mL) was added, and the mixture was stirred at room temperature for 20 hr. The reaction mixture was concentrated under reduced pressure, ethyl acetate was added, and the organic layer was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; chloroform:methanol=20:1) to give the title compound (111 mg).

$^1$H-NMR (CDCl$_3$, 300 MHz) δ: 1.21 (3H, t, J=7.5 Hz), 1.63 (6H, s), 2.48 (2H, q, J=7.5 Hz), 3.02 (2H, t, J=7.2 Hz), 3.11-3.14 (4H, m), 3.83-3.88 (6H, m), 4.75 (2H, s), 6.84 (2H, d, J=8.4 Hz), 6.90 (1H, s), 7.17 (2H, d, J=8.4 Hz), 8.19 (2H, s).

MS: 528 (M$^+$+1).

Example 409

2-[(4-{2-[[(4'-cyanobiphenyl-4-yl)methyl](5-eth-ylpyrimidin-2-yl)amino]ethyl}-1,3-thiazol-2-yl)thio]-2-methylpropionic acid hydrochloride

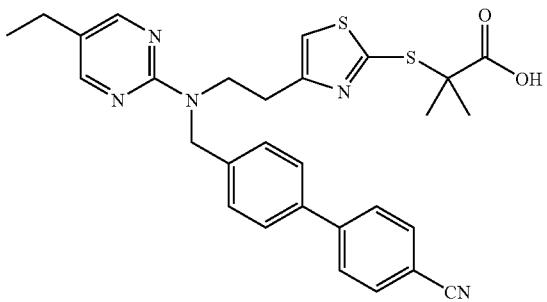

A compound obtained using 2-[(4-{2-[(4-bromobenzyl)(5-ethylpyrimidin-2-yl)amino]ethyl}-1,3-thiazol-2-yl)thio]-2-methylpropionic acid tert-butyl ester synthesized in Example 402-1 and 4-cyanophenylboric acid as starting materials and by an operation similar to that of Example 407 was dissolved in diethyl ether, and reacted with 4 mol/L hydrochloric acid-ethyl acetate to give the title compound.

$^1$H-NMR (DMSO-$d_6$, 300 MHz) δ: 1.15 (3H, t, J=7.5 Hz), 1.50 (6H, s), 2.45 (2H, q, J=7.5 Hz), 3.04 (2H, t, J=7.2 Hz), 3.90 (2H, t, J=7.2 Hz), 4.80 (2H, s), 7.32 (2H, d, J=8.1 Hz), 7.48 (1H, s), 7.68 (2H, d, J=8.1 Hz), 7.85 (2H, d, J=8.4 Hz), 7.91 (2H, d, J=8.4 Hz), 8.29 (2H, s).

MS: 544 (M$^+$+1).

Example 410

2-[(4-{2-[[(3'-cyanobiphenyl-4-yl)methyl](5-eth-ylpyrimidin-2-yl)amino]ethyl}-1,3-thiazol-2-yl)thio]-2-methylpropionic acid hydrochloride

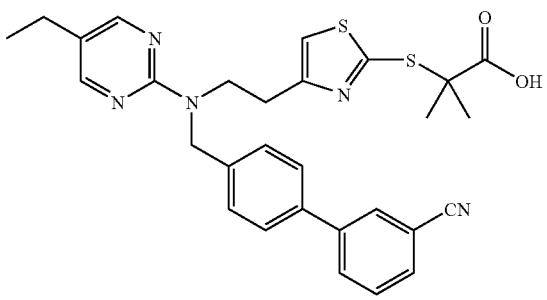

A compound obtained using 2-[(4-{2-[(4-bromobenzyl)(5-ethylpyrimidin-2-yl)amino]ethyl}-1,3-thiazol-2-yl)thio]-2-methylpropionic acid tert-butyl ester synthesized in Example 402-1 and 3-cyanophenylboric acid as starting materials and by an operation similar to that of Example 407 was dissolved in diethyl ether, and reacted with 4 mol/L hydrochloric acid-ethyl acetate to give the title compound.

$^1$H-NMR (DMSO-$d_6$, 300 MHz) δ: 1.15 (3H, t, J=7.5 Hz), 1.50 (6H, s), 2.46 (2H, q, J=7.5 Hz), 3.04 (2H, t, J=6.9 Hz), 3.90 (2H, t, J=6.9 Hz), 4.80 (2H, s), 7.31 (2H, d, J=8.2 Hz), 7.48 (1H, s), 7.62-7.69 (3H, m), 7.81 (1H, d, J=8.8 Hz), 7.99 (1H, d, J=8.0 Hz), 8.12 (1H, s), 8.30 (2H, s).

MS: 544 (M$^+$+1).

Example 411

2-[(4-{2-[(3-bromobenzyl)(5-ethylpyrimidin-2-yl)amino]ethyl}-1,3-thiazol-2-yl)thio]-2-methylpropionic acid

Example 411

2-[(4-{2-[(3-bromobenzyl)(5-ethylpyrimidin-2-yl)amino]ethyl}-1,3-thiazol-2-yl)thio]-2-methylpropionic acid tert-butyl ester

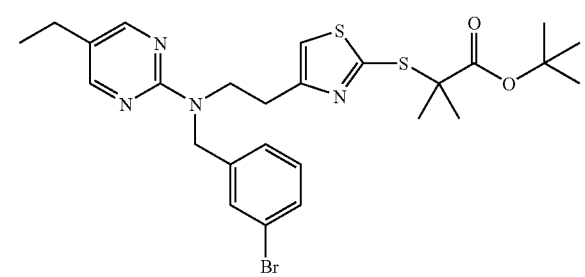

2-[(4-{2-[(5-Ethylpyrimidin-2-yl)amino]ethyl}-1,3-thiazol-2-yl)thio]-2-methylpropionic acid tert-butyl ester (5.5 g) synthesized in Example 265-1 and 1-bromo-3-(bromomethyl)benzene (4.04 g) were dissolved in N,N-dimethylformamide (55 mL), potassium tert-butoxide (1.82 g) was added thereto, and the mixture was stirred at room temperature for 1 hr. Water was added to the reaction mixture, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1) to give the title compound (6.3 g) as a colorless oil.

$^1$H-NMR (CDCl$_3$, 300 MHz) δ: 1.21 (3H, t, J=7.5 Hz), 1.42 (9H, s), 1.57 (6H, s), 2.48 (2H, q, J=7.5 Hz), 3.09 (2H, t, J=6.9 Hz), 3.92 (2H, t, J=6.9 Hz), 4.23 (2H, s), 6.98 (1H, s), 7.11-7.14 (2H, m), 7.31-7.35 (2H, m), 8.19 (2H, s).

Example 411-2

2-[(4-{2-[(3-bromobenzyl)(5-ethylpyrimidin-2-yl)amino]ethyl}-1,3-thiazol-2-yl)thio]-2-methylpropionic acid

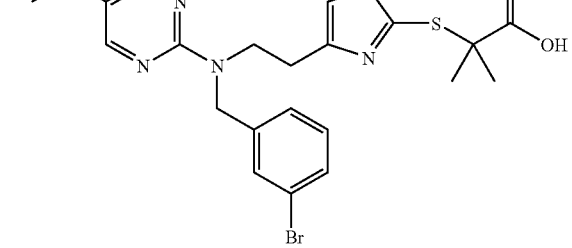

2-[(4-{2-[(3-Bromobenzyl)(5-ethylpyrimidin-2-yl)amino]ethyl}-1,3-thiazol-2-yl)thio]-2-methylpropionic acid tert-butyl ester (300 mg) obtained in Example 411-1 was dissolved in dichloromethane (6 mL), trifluoroacetic acid (2 mL) was added, and the mixture was stirred at room temperature for 20 hr. The reaction mixture was concentrated under reduced pressure, ethyl acetate was added, and the mixture was washed with saturated aqueous sodium hydrogen carbonate solution (at this time point, the object product had been extracted in the ethyl acetate layer). The ethyl acetate layer was washed with aqueous 10% citric acid solution and saturated brine, and dried over anhydrous sodium sulfate. The solvent was evaporated under reduced pressure, and the residue was purified by silica gel chromatography (elution solvent; hexane:ethyl acetate=1:1 to 0:1) to give the title compound (280 mg) as a colorless oil.

$^1$H-NMR (CDCl$_3$, 300 MHz) δ: 1.21 (3H, t, J=7.5 Hz), 1.63 (6H, s), 2.49 (2H, q, J=7.5 Hz), 3.07 (2H, t, J=6.9 Hz), 3.91 (2H, t, J=6.9 Hz), 4.79 (2H, s), 6.93 (1H, s), 7.14-7.17 (2H, m), 7.33-7.35 (2H, m), 8.21 (2H, s).

MS: 523 (M$^+$+1).

Example 412

2-[(4-{2-[(5-ethylpyrimidin-2-yl)(3-pyrimidin-2-ylbenzyl)amino]ethyl}-1,3-thiazol-2-yl)thio]-2-methylpropionic acid hydrochloride

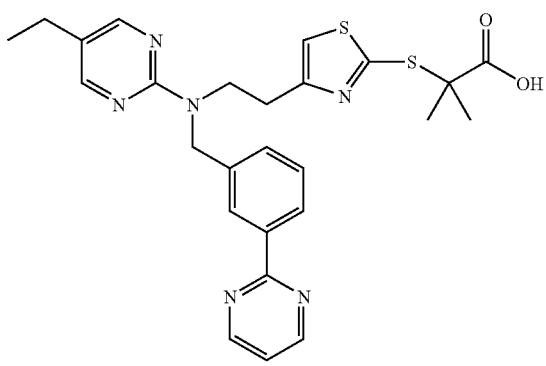

The title compound was obtained using 2-[(4-{2-[(3-bromobenzyl)(5-ethylpyrimidin-2-yl)amino]ethyl}-1,3-thiazol-2-yl)thio]-2-methylpropionic acid tert-butyl ester synthesized in Example 411-1 and 2-tributylstanylpyrimidine as starting materials and by an operation similar to that of Example 403.

$^1$H-NMR (DMSO-d$_6$, 300 MHz) δ: 1.15 (3H, t, J=7.5 Hz), 1.48 (6H, s), 2.46 (2H, q, J=7.5 Hz), 3.04 (2H, t, J=6.3 Hz), 3.90 (2H, t, J=6.3 Hz), 4.78 (2H, s), 7.36 (1H, d, J=7.2 Hz), 7.42-7.49 (3H, m), 8.25-8.27 (2H, m), 8.31 (2H, s), 8.88 (2H, d, J=4.8 Hz).

MS: 521 (M$^+$+1).

Example 413

2-[(4-{2-[(5-ethylpyrimidin-2-yl)(3-pyrazin-2-ylbenzyl)amino]ethyl}-1,3-thiazol-2-yl)thio]-2-methylpropionic acid hydrochloride

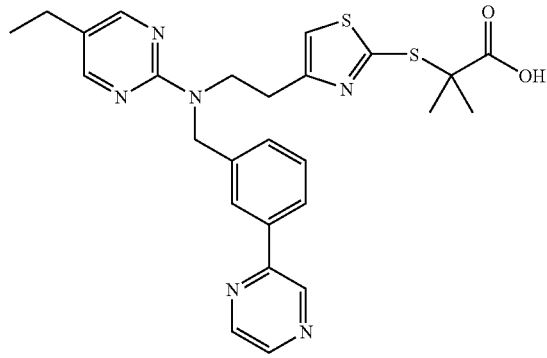

The title compound was obtained using 2-[(4-{2-[(3-bromobenzyl)(5-ethylpyrimidin-2-yl)amino]ethyl}-1,3-thiazol-2-yl)thio]-2-methylpropionic acid tert-butyl ester synthesized in Example 411-1 and 2-tributylstanylpyrazine as starting materials and by an operation similar to that of Example 403.

$^1$H-NMR (DMSO-d$_6$, 300 MHz) δ: 1.16 (3H, t, J=7.5 Hz), 1.48 (6H, s), 2.49 (2H, q, J=7.5 Hz), 3.07 (2H, t, J=7.2 Hz), 3.95 (2H, t, J=7.2 Hz), 4.90 (2H, s), 7.35 (1H, d, J=7.7 Hz), 7.45-7.51 (2H, m), 8.00-8.02 (2H, m), 8.37 (2H, s), 8.62 (1H, d, J=2.5 Hz), 8.70-8.73 (1H, m), 9.22 (1H, d, J=1.4 Hz).

MS: 521 (M$^+$+1).

Example 414

2-{[4-(2-{(5-ethylpyrimidin-2-yl)[3-(1,3-thiazol-2-yl)benzyl]amino}ethyl)-1,3-thiazol-2-yl]thio}-2-methylpropionic acid hydrochloride

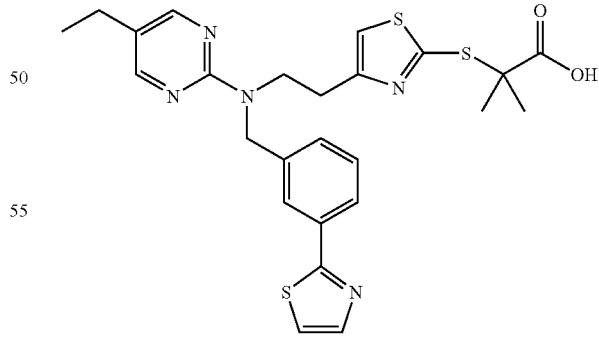

The title compound was obtained using 2-[(4-{2-[(3-bromobenzyl)(5-ethylpyrimidin-2-yl)amino]ethyl}-1,3-thiazol-2-yl)thio]-2-methylpropionic acid tert-butyl ester synthesized in Example 411-1 and 2-tributylstanylthiazole as starting materials and by an operation similar to that of Example 403.

¹H-NMR (DMSO-d₆, 300 MHz) δ: 1.15 (3H, t, J=7.5 Hz), 1.49 (6H, s), 2.46 (2H, q, J=7.5 Hz), 3.04 (2H, t, J=6.9 Hz), 3.91 (2H, t, J=6.9 Hz), 4.84 (2H, s), 7.30 (1H, d, J=7.8 Hz), 7.43 (1H, d, J=7.8 Hz), 7.48 (1H, s), 7.77-7.81 (3H, m), 7.91 (1H, d, J=3.3 Hz), 8.32 (2H, s).
MS: 526 (M⁺+1).

Example 415

2-{[4-(2-{(5-ethylpyrimidin-2-yl)[(1-phenyl-1H-pyrazol-4-yl)methyl]amino}ethyl)-5-methyl-1,3-thiazol-2-yl]thio}-2-methylpropionic acid

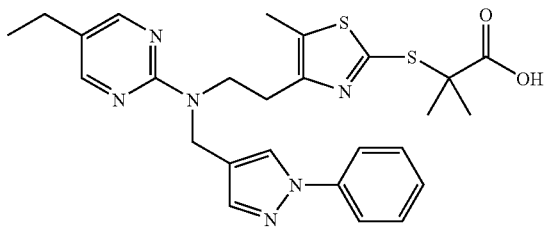

The title compound was obtained by an operation similar to that of Example 265-1 and using 2-{[4-(2-aminoethyl)-5-methyl-1,3-thiazol-2-yl]thio}-2-methylpropionic acid tert-butyl ester synthesized in Example 19 and 2-chloro-ethylpyrimidine as starting materials, followed by an operation similar to that of Example 326.
¹H-NMR (CDCl₃, 300 MHz) δ: 1.22 (3H, t, J=7.5 Hz), 1.61 (6H, s), 2.28 (3H, s), 2.49 (2H, q, J=7.5 Hz), 3.00 (2H, t, J=6.9 Hz), 3.86 (2H, t, J=6.9 Hz), 4.68 (2H, s), 7.22-7.26 (1H, m), 7.39-7.45 (2H, m), 7.65-7.69 (3H, m), 7.95 (1H, s), 8.22 (2H, s).
MS: 523 (M⁺+1).

Example 416

2-{[4-(2-{(5-ethylpyrimidin-2-yl)[(6-phenylpyridin-3-yl)methyl]amino}ethyl)-5-methyl-1,3-thiazol-2-yl]thio}-2-methylpropionic acid

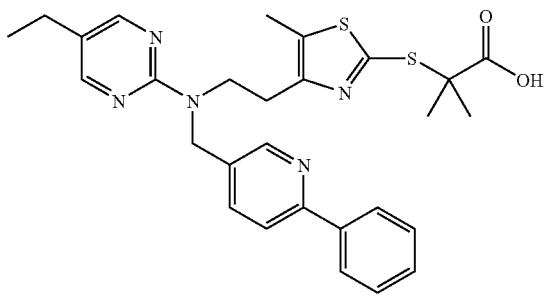

The title compound was obtained by an operation similar to that of Example 265-1 and using 2-{[4-(2-aminoethyl)-5-methyl-1,3-thiazol-2-yl]thio}-2-methylpropionic acid tert-butyl ester synthesized in Example 19 and 2-chloro-ethylpyrimidine as starting materials, followed by operations similar to those of Example 327-1 and 326-2.
¹H-NMR (CDCl₃, 300 MHz) δ: 1.23 (3H, t, J=7.5 Hz), 1.64 (6H, s), 2.19 (3H, s), 2.52 (2H, q, J=7.5 Hz), 3.08 (2H, t, J=6.6 Hz), 3.97 (2H, t, J=6.6 Hz), 4.78 (2H, s), 7.55-7.57 (3H, m), 7.81-7.89 (3H, m), 8.18-8.25 (3H, m), 9.22 (1H, s).
MS: 534 (M⁺+1).

Example 417

2-{[5-(2-{(5-ethylpyrimidin-2-yl)[(1-phenyl-1H-pyrazol-4-yl)methyl]amino}ethyl)-4-methyl-1,3-thiazol-2-yl]thio}-2-methylpropionic acid

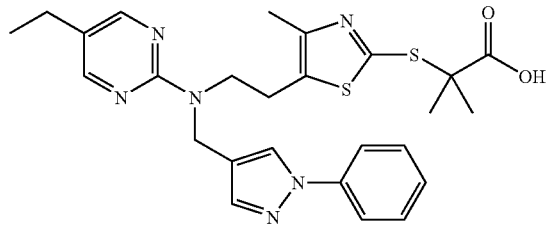

The title compound was obtained by an operation similar to that of Example 265-1 and using 2-{[5-(2-aminoethyl)-4-methyl-1,3-thiazol-2-yl]thio}-2-methylpropionic acid tert-butyl ester synthesized in Example 24 and 2-chloro-ethylpyrimidine as starting materials, followed by an operation similar to that of Example 326.
¹H-NMR (CDCl₃, 300 MHz) δ: 1.23 (3H, t, J=7.5 Hz), 1.60 (6H, s), 2.33 (3H, s), 2.50 (2H, q, J=7.5 Hz), 3.05 (2H, t, J=7.2 Hz), 3.79 (2H, t, J=7.2 Hz), 4.70 (2H, s), 7.24-7.29 (1H, m), 7.29-7.45 (2H, m), 7.61-7.64 (3H, m), 7.85 (1H, s), 8.24 (2H, s).
MS: 523 (M⁺+1).

Example 418

2-{[5-(2-{(5-ethylpyrimidin-2-yl)[(6-phenylpyridin-3-yl)methyl]amino}ethyl)-4-methyl-1,3-thiazol-2-yl]thio}-2-methylpropionic acid

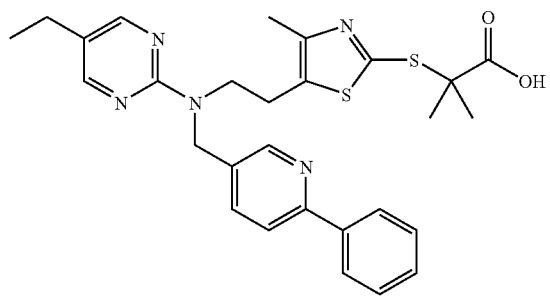

The title compound was obtained by an operation similar to that of Example 265-1 and using 2-{[5-(2-aminoethyl)-4-methyl-1,3-thiazol-2-yl]thio}-2-methylpropionic acid tert-butyl ester synthesized in Example 24 and 2-chloro-ethylpyrimidine as starting materials, followed by operations similar to those of Example 327-1 and 326-2.
¹H-NMR (CDCl₃, 300 MHz) δ: 1.15 (3H, t, J=7.5 Hz), 1.46 (6H, s), 2.24 (3H, s), 2.45 (2H, q, J=7.5 Hz), 3.07 (2H, t, J=7.6 Hz), 3.80 (2H, t, J=7.6 Hz), 4.82 (2H, s), 7.42-7.51 (3H, m), 7.71-7.75 (1H, m), 7.90 (1H, d, J=8.0 Hz), 8.01-8.05 (2H, m), 8.30 (2H, s), 8.56 (1H, s).
MS: 534 (M⁺+1).

Example 419

2-{[5-({(5-ethylpyrimidin-2-yl) [(1-phenyl-1H-pyrazol-4-yl)methyl]amino}methyl)-4-methyl-1,3-thiazol-2-yl]thio}-2-methylpropionic acid

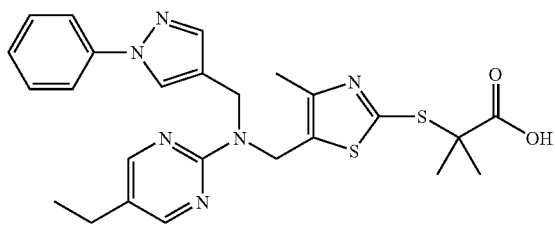

The title compound was obtained by an operation similar to that of Example 265-1 and using 2-{[5-(aminomethyl)-4-methyl-1,3-thiazol-2-yl]thio}-2-methylpropionic acid tert-butyl ester synthesized in Example 30 and 2-chloro-ethylpyrimidine as starting materials, followed by an operation similar to that of Example 326.

$^1$H-NMR (CDCl$_3$, 300 MHz) δ: 1.21 (3H, t, J=7.5 Hz), 1.59 (6H, s), 2.42 (3H, s), 2.53 (2H, q, J=7.5 Hz), 4.77 (2H, s), 4.84 (2H, s), 7.25-7.30 (1H, m), 7.40-7.46 (2H, m), 7.60-7.63 (3H, m), 7.81 (1H, s), 8.27 (2H, s).

MS: 509 (M$^+$+1).

Example 420

2-[(4-{[(biphenyl-4-ylmethyl)(5-ethylpyrimidin-2-yl)amino]methyl}-1,3-thiazol-2-yl)thio]-2-methylpropionic acid hydrochloride

Example 420-1

2-[(4-{[(5-ethylpyrimidin-2-yl)amino]methyl}-1,3-thiazol-2-yl)thio]-2-methylpropionic acid tert-butyl ester

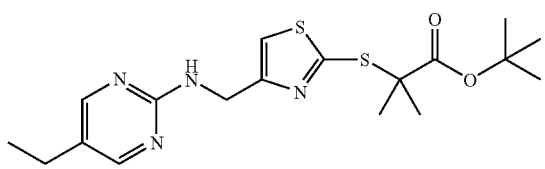

N,N-Diisopropylethylamine (2.24 g) was added to 2-{[4-(aminomethyl)-1,3-thiazol-2-yl]thio}-2-methylpropionic acid tert-butyl ester (5.0 g) synthesized in Example 13 and 2-chloro-5-ethylpyrimidine (2.47 g), and the mixture was stirred at 130° C. for 8 hr. The reaction mixture was directly purified by silica gel chromatography (elution solvent; hexane:ethyl acetate=1:1) to give the title compound (5.0 g) as a slightly yellow oil.

$^1$H-NMR (CDCl$_3$, 300 MHz) δ: 1.19 (3H, t, J=7.5 Hz), 1.42 (9H, s), 1.59 (6H, s), 2.47 (2H, q, J=7.5 Hz), 4.73 (2H, d, J=6.0 Hz), 5.51-5.54 (1H, m), 7.20 (1H, s), 8.16 (2H, s).

Example 420-2

2-[(4-{[(biphenyl-4-ylmethyl)(5-ethylpyrimidin-2-yl)amino]methyl}-1,3-thiazol-2-yl)thio]-2-methylpropionic acid hydrochloride

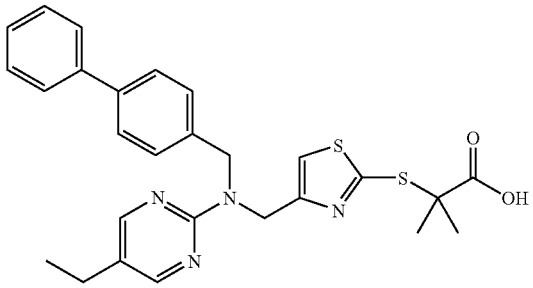

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 4-(bromomethyl)biphenyl as starting materials and by an operation similar to that of Example 326.

$^1$H-NMR (CDCl$_3$, 300 MHz) δ: 1.22 (3H, t, J=7.6 Hz), 1.59 (6H, s), 2.50 (2H, q, J=7.6 Hz), 4.93 (2H, s), 5.01 (2H, s), 7.08 (1H, s), 7.31-7.36 (3H, m), 7.40-7.45 (2H, m), 7.50-7.58 (4H, m), 8.24 (2H, s).

MS: 505 (M$^+$+1).

Example 421

2-{[4-({(5-ethylpyrimidin-2-yl)[4-(trifluoromethyl)benzyl]amino}methyl)-1,3-thiazol-2-yl]thio}-2-methylpropionic acid

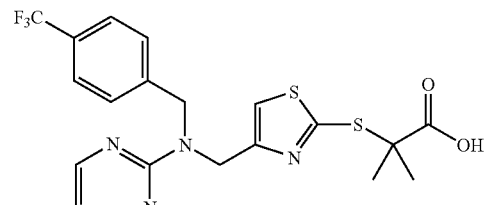

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 1-(bromomethyl)-4-(trifluoromethyl)benzene as starting materials and by an operation similar to that of Example 326.

$^1$H-NMR (CDCl$_3$, 300 MHz) δ: 1.21 (3H, t, J=7.5 Hz), 1.58 (6H, s), 2.50 (2H, q, J=7.5 Hz), 4.90 (2H, s), 5.02 (2H, s), 7.12 (1H, s), 7.36 (2H, d, J=7.8 Hz), 7.54 (2H, d, J=7.8 Hz), 8.22 (2H, s).

MS: 497 (M$^+$+1).

Example 422

2-{[4-({(5-ethylpyrimidin-2-yl)[4-(trifluoromethoxy)benzyl]amino}methyl)-1,3-thiazol-2-yl]thio}-2-methylpropionic acid

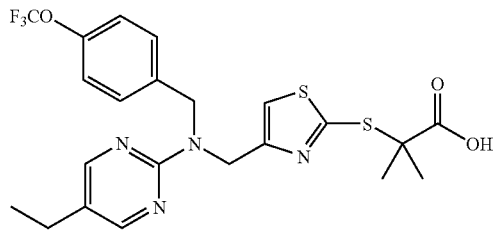

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 1-(bromomethyl)-4-(trifluoromethoxy)benzene as starting materials and by an operation similar to that of Example 326.

$^1$H-NMR (CDCl$_3$, 300 MHz) δ: 1.20 (3H, t, J=7.5 Hz), 1.59 (6H, s), 2.49 (2H, q, J=7.5 Hz), 4.88 (2H, s), 4.96 (2H, s), 7.09 (1H, s), 7.13 (2H, d, J=8.4 Hz), 7.29 (2H, d, J=8.4 Hz), 8.22 (2H, s).

MS: 513 (M$^+$+1).

Example 423

2-{[4-({(5-ethylpyrimidin-2-yl)[(6-phenylpyridin-3-yl)methyl]amino}methyl)-1,3-thiazol-2-yl]thio}-2-methylpropionic acid hydrochloride

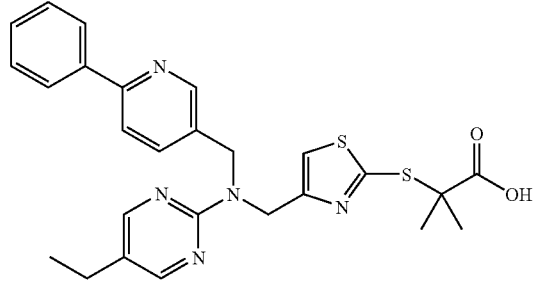

The title compound was obtained using 2-[(4-{[(5-ethylpyrimidin-2-yl)amino]methyl}-1,3-thiazol-2-yl)thio]-2-methylpropionic acid tert-butyl ester synthesized in Example 420-1 and 5-(chloromethyl)-2-phenylpyridine as starting materials and by an operation similar to that of Example 327.

$^1$H-NMR (CDCl$_3$, 300 MHz) δ: 1.29 (3H, t, J=7.5 Hz), 1.57 (6H, s), 2.65 (2H, q, J=7.5 Hz), 5.08 (2H, s), 5.48 (2H, s), 7.62-7.65 (3H, m), 7.80 (1H, s), 8.06 (1H, d, J=8.4 Hz), 8.12-8.16 (2H, m), 8.49 (2H, s), 8.59 (1H, d, J=8.4 Hz), 9.46 (1H, s).

MS: 506 (M$^+$+1).

Example 424

2-{[4-({(5-ethylpyrimidin-2-yl)[(1-phenyl-1H-pyrazol-4-yl)methyl]amino}methyl)-1,3-thiazol-2-yl]thio}-2-methylpropionic acid hydrochloride

Example 483

2-methyl-2-[(4-{2-[(8-methylnonyl)(5-nitropyridin-2-yl)amino]ethyl}-1,3-thiazol-2-yl)thio]propionic acid

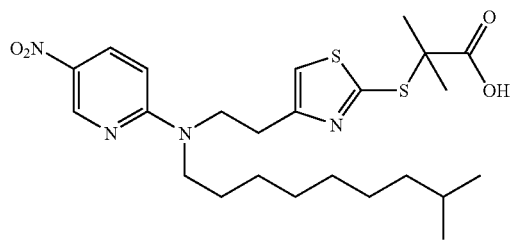

Example 483-1

2-{[4-(2-{[(9H-fluorene-9-ylmethoxy)carbonyl]amino}ethyl)-1,3-thiazol-2-yl]thio}-2-methylpropionic acid tert-butyl ester

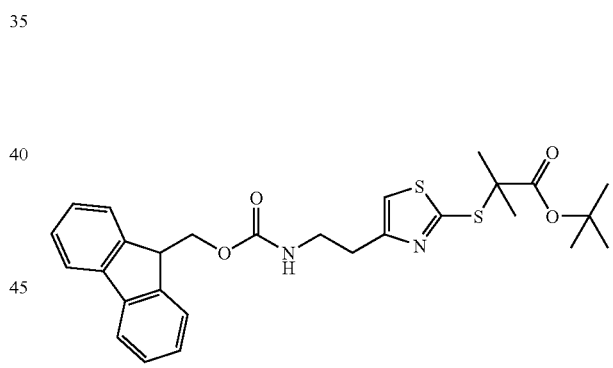

To a solution of 2-{[4-(2-aminoethyl)-1,3-thiazol-2-yl]thio}-2-methylpropionic acid tert-butyl ester (19 g) synthesized in Example 7 in tetrahydrofuran (60 mL) was added N-(9H-fluorene-9-ylmethyloxycarbonyl)succinimide (23 g), and the mixture was stirred at room temperature overnight. Ethyl acetate was added to the reaction mixture, and the mixture was washed with water and saturated brine. The precipitate was filtered and dried over anhydrous sodium sulfate. The solvent was evaporated under reduced pressure and purified by silica gel chromatography (elution solvent; hexane:ethyl acetate=2:1) to give the title compound (33 g) as a pale-brown oil.

$^1$H-NMR (CDCl$_3$, 300 MHz) δ: 1.43 (9H, s), 1.60 (6H, s), 2.96 (2H, dd, J=6.0, 5.4 Hz), 3.59 (2H, q, J=6.0 Hz), 4.21 (1H, t, J=6.9 Hz), 4.37 (2H, d, J=6.9 Hz), 5.50 (1H, bs), 6.98 (1H, s), 7.30 (2H, t, J=7.2 Hz), 7.39 (2H, t, J=7.2 Hz), 7.60 (2H, d, J=7.5 Hz), 7.51 (2H, d, J=7.5 Hz).

Example 483-2

2-{[4-(2-{[(9H-fluorene-9-ylmethoxy)carbonyl]amino}ethyl)-1,3-thiazol-2-yl]thio}-2-methylpropionic acid

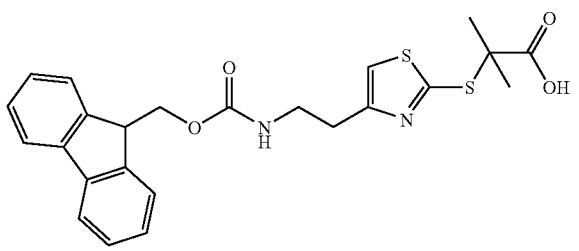

To a solution of 2-{[4-(2-{[(9H-fluorene-9-ylmethoxy)carbonyl]amino}ethyl)-1,3-thiazol-2-yl]thio}-2-methylpropionic acid tert-butyl ester (33 g) synthesized in Example 483-1 in dichloromethane (30 mL) was added trifluoroacetic acid (50 mL), and the mixture was stirred at room temperature overnight. The reaction mixture was poured into water, extracted with ethyl acetate. The organic layer was washed with water and saturated brine, and dried over sodium sulfate. The solvent was concentrated under reduced pressure, and purified by silica gel chromatography (elution solvent; ethyl acetate) to give the title compound (38 g) as a pale-brown oil.

$^1$H-NMR (CDCl$_3$, 300 MHz) δ: 1.64 (6H, s), 2.74-3.07 (2H, m), 3.23-3.65 (2H, m), 4.09-4.32 (1H, m), 4.40-4.59 (2H, m), 6.34 (1H, bs), 6.97 (1H, s), 7.32 (2H, t, J=7.5 Hz), 7.41 (2H, t, J=7.2 Hz), 7.58 (2H, d, J=7.2 Hz), 7.77 (2H, d, J=7.2 Hz).

Example 483-3

2-{[4-(2-aminoethyl)-1,3-thiazol-2-yl]thio}-2-methylpropionic acid resin

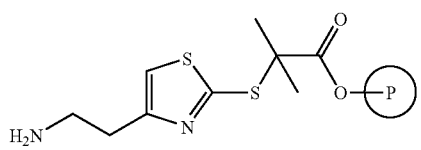

2-{[4-(2-{[(9H-Fluorene-9-ylmethoxy)carbonyl]amino}ethyl)-1,3-thiazol-2-yl]thio}-2-methylpropionic acid resin was obtained using 2-{[4-(2-{[(9H-fluorene-9-ylmethoxy)carbonyl]amino}ethyl)-1,3-thiazol-2-yl]thio}-2-methylpropionic acid synthesized in Example 483-2 as a starting material and by an operation similar to that of Example 461-3.

A part of the resin was cleaved with trifluoroacetic acid and the introduction of the resin was confirmed.

MS: 469 (M$^+$+1).

Then, the title pale-brown resin (44 g) was obtained by an operation similar to that of Example 461-4.

A part of the resin was cleaved with trifluoroacetic acid and the structure was confirmed.

MS: 247 (M$^+$+1).

Example 483-4

2-methyl-2-[(4-{2-[(8-methylnonyl)amino]ethyl}-1,3-thiazol-2-yl)thio]propionic acid resin

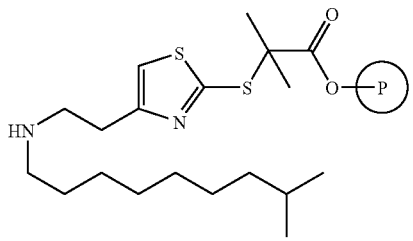

To a suspension of 2-{[4-(2-aminoethyl)-1,3-thiazol-2-yl]thio}-2-methylpropionic acid resin (0.30 g) synthesized in Example 483-3 in dimethylformamide (4.0 mL) were added HOBT monohydrate (0.092 g), diisopropylcarbodiimide (0.10 mL) and 8-methylnonanoic acid (0.10 g), and the mixture was stirred at room temperature overnight. The resin was collected by filtration from the reaction mixture, washed three times each with dimethylformamide, tetrahydrofuran and methanol, and vacuum dried to give 2-methyl-2-[(4-{2-[(8-methylnonanoyl)amino]ethyl}-1,3-thiazol-2-yl)thio]propionic acid resin.

To this resin were added tetrahydrofuran (1.0 mL) and 1 mol/L borane-tetrahydrofuran complex (2.5 ml), and the mixture was stirred at room temperature overnight. The resin was collected by filtration from the reaction mixture, and washed once with tetrahydrofuran, three times with a tetrahydrofuran-methanol (1:1) solution, and twice with methanol. Then, a solution (4.0 mL) of tetrahydrofuran-methanol-piperidine (1:1:2) was added to the resin, and the mixture was stirred at room temperature overnight. After the reaction, the resin was collected by filtration, washed 4 times with tetrahydrofuran, twice with methanol, and vacuum dried to give the title brown resin (0.30 g).

A part of the resin was cleaved with trifluoroacetic acid and the structure was confirmed.

MS: 387 (M$^+$+1).

Example 483-5

2-methyl-2-[(4-{2-[(8-methylnonyl)(5-nitropyridin-2-yl)amino]ethyl}-1,3-thiazol-2-yl)thio]propionic acid

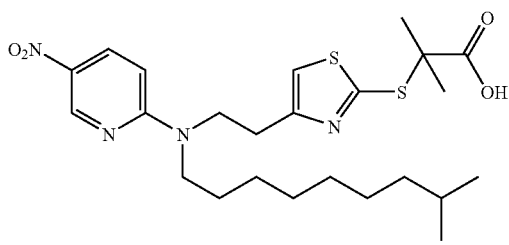

The title compound (30 mg) was obtained as a pale-yellow oil using 2-methyl-2-[(4-{2-[(8-methylnonyl)amino]ethyl}-1,3-thiazol-2-yl)thio]propionic acid resin obtained in Example 483-4 and 2-chloro-5-nitroaniline as starting materials and by an operation similar to that of Example 461-7.

MS: 509 (M$^+$+1).

The following compound was obtained by an operation similar to that of Example 483.

TABLE 3

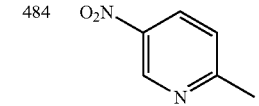

| NO. | Ar | R | MS (M⁺ + 1) | yield (mg) |
|---|---|---|---|---|
| 484 | 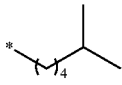 | 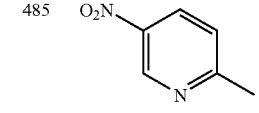 | 467 | 25 |
| 485 | 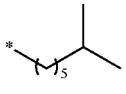 | 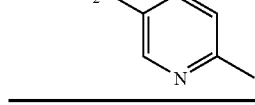 | 481 | 30 |
| 486 | 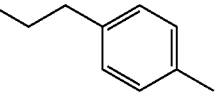 | 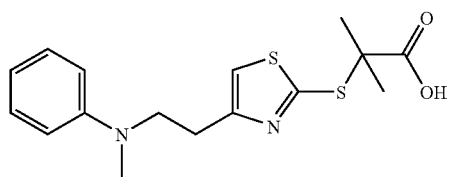 | 515 | 33 |

Example 487

2-methyl-2-[(4-{2-[methyl(phenyl)amino]ethyl}-1,3-thiazol-2-yl)thio]propionic acid

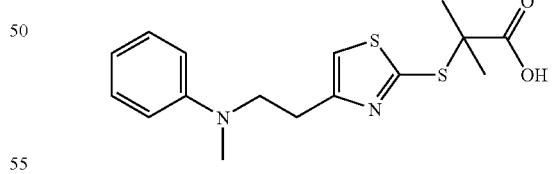

Example 487-1

2-methyl-2-[(4-{2-[methyl(phenyl)amino]-2-oxoethyl}-1,3-thiazol-2-yl)thio]propionic acid resin

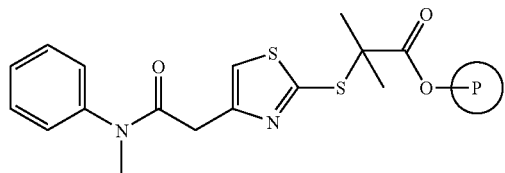

The title yellow resin (2.0 g) was obtained using 2-{[4-(carboxymethyl)-1,3-thiazol-2-yl]thio}-2-methylpropionic acid resin synthesized in Example 461-4 and N-methylaniline (0.52 ml) as starting materials and by an operation similar to that of Example 461-5.

A part of the resin was cleaved with trifluoroacetic acid and the structure was confirmed.

MS: 351 (M⁺+1).

Example 487-2

2-methyl-2-[(4-{2-[methyl(phenyl)amino]ethyl}-1,3-thiazol-2-yl)thio]propionic acid

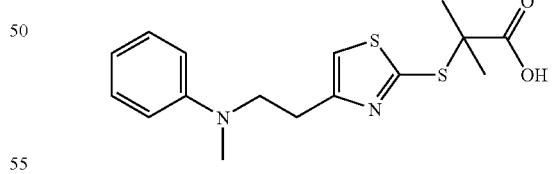

To the resin obtained using 2-methyl-2-[(4-{2-[methyl(phenyl)amino]-2-oxoethyl}-1,3-thiazol-2-yl)thio]propionic acid resin obtained in Example 487-1 as a starting material and by an operation similar to that of Example 461-6 was added trifluoroacetic acid (2.0 mL), and the mixture was left standing as it was for 2 hr. Then the resin was removed by filtration from the reaction mixture, and the filtrate was concentrated by blowing a nitrogen gas, vacuum dried, and purified by preparative HPLC to give the title compound (30 mg) as a pale-brown oil.

MS: 337 (M⁺+1).

Example 488

2-methyl-2-[(4-{2-[phenyl(3-phenylpropyl)amino]ethyl}-1,3-thiazol-2-yl)thio]propionic acid

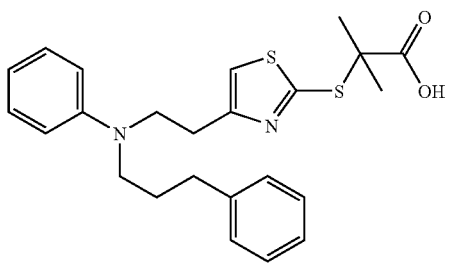

Example 488-1

2-{[4-(2-anilino-2-oxoethyl)-1,3-thiazol-2-yl]thio}-2-methylpropionic acid resin

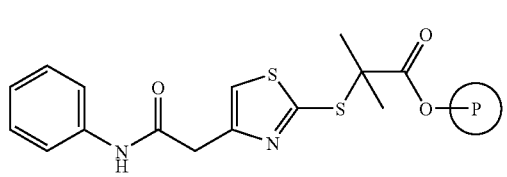

The title yellow resin (2.9 g) was obtained using 2-{[4-(carboxymethyl)-1,3-thiazol-2-yl]thio}-2-methylpropionic acid resin synthesized in Example 461-4 and aniline as starting materials and by an operation similar to that of Example 461-5. A part of the resin was cleaved with trifluoroacetic acid and the structure was confirmed.

MS: 337 (M$^+$+1).

Example 488-2

2-{[4-(2-anilinoethyl)-1,3-thiazol-2-yl]thio}-2-methylpropionic acid resin

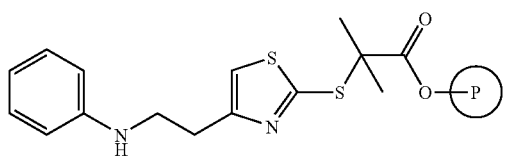

To a suspension of 2-{[4-(2-anilino-2-oxoethyl)-1,3-thiazol-2-yl]thio}-2-methylpropionic acid resin (2.9 g) obtained in Example 488-1 in tetrahydrofuran (30 mL) was added 1 mol/L borane-tetrahydrofuran complex (24 ml), and the mixture was stirred at room temperature overnight. Methanol was gradually added to the reaction mixture, and the mixture was stirred at room temperature overnight. The resin was collected by filtration, washed three times with methanol, and vacuum dried to give the title pale-brown resin (2.4 g).

A part of the resin was cleaved with trifluoroacetic acid and the structure was confirmed.

MS: 323 (M$^+$+1).

Example 488-3

2-methyl-2-[(4-{2-[phenyl(3-phenylpropyl)amino]ethyl}-1,3-thiazol-2-yl)thio]propionic acid

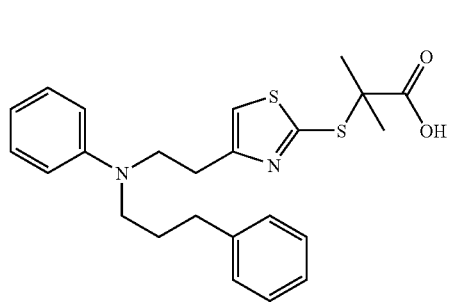

To a solution of 2-{[4-(2-anilinoethyl)-1,3-thiazol-2-yl]thio}-2-methylpropionic acid resin (0.20 g) obtained in Example 488-2 in dichloroethane (3.0 mL) were added 3-phenylpropione aldehyde (0.027 g), sodium tri(acetoxy)borate hydride (0.084 g) and acetic acid (0.22 ml), and the mixture was stirred overnight. The resin was collected by filtration from the reaction solution, washed once each with methanol and dimethylformamide, and twice with methanol.

To the resin was added trifluoroacetic acid (2.0 mL), and the mixture was stood at room temperature for 1 hr. The resin was filtered off, the solution was concentrated by blowing nitrogen gas thereto and purified by preparative HPLC to give the title compound (11 mg) as a colorless oil.

MS: 441 (M$^+$+1).

The following compound was obtained by an operation similar to that of Example 488.

TABLE 4
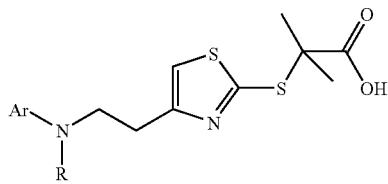
| No. | Ar | R | MS (M+ + 1) | yield (mg) |
|-----|----|----|-------------|------------|
| 489 | phenyl* | *−(CH₂)₂−CH₃ | 365 | 4.5 |
| 490 | phenyl* | *−CH₂−(2-thiazolyl) | 420 | 1.2 |
| 491 | phenyl* | *−(CH₂)₈−CH₃ | 449 | 9.2 |
| 492 | phenyl* | *−CH₂−CH(CH₃)₂ | 379 | 8.6 |
| 493 | phenyl* | *−(CH₂)₂−CH(CH₃)₂ | 393 | 6.8 |
| 494 | phenyl* | *−CH₂−CH=CH−phenyl | 439 | 9.4 |
| 495 | phenyl* | *−(CH₂)₂−O−CH₂−phenyl | 457 | 11 |
| 496 | phenyl* | *−CH₂−(4-biphenyl) | 489 | 5.4 |
| 497 | phenyl* | *−CH₂−(2-furyl) | 403 | 5.4 |

TABLE 5

| No. | Ar | R | MS (M⁺ + 1) | yield (mg) |
|---|---|---|---|---|
| 498 | 2,4-difluorophenyl | *-(CH₂)₂-CH₃ (isopropyl/propyl shown as *⟨⟩₂) | 401 | 2.1 |
| 499 | 2,4-difluorophenyl | *-(CH₂)₂-CH(CH₃)₂ | 429 | 3.9 |
| 500 | 2,4-difluorophenyl | *-CH₂-CH=CH-Ph | 475 | 0.8 |
| 501 | 2,4-difluorophenyl | *-(CH₂)₃-Ph | 477 | 3.7 |
| 502 | 2,4-difluorophenyl | *-CH₂CH₂-O-CH₂-Ph | 493 | 2.6 |
| 503 | 2,4-difluorophenyl | *-CH₂-(4-biphenyl) | 525 | 0.3 |

Example 504

2-[(4-{2-[[4-(2-hydroxyethyl)phenyl](3-phenylpropyl)amino]ethyl}-1,3-thiazol-2-yl)thio]-2-methylpropionic acid

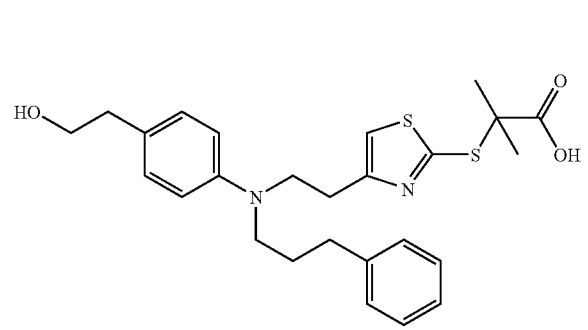

Example 504-1

2-{[4-(2-{[4-(2-ethoxy-2-oxoethyl)phenyl]amino}-2-oxoethyl)-1,3-thiazol-2-yl]thio}-2-methylpropionic acid resin

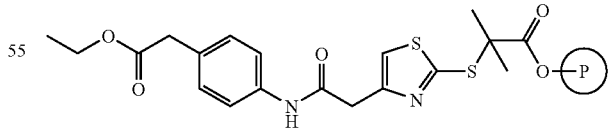

An operation similar to that of Example 461-5 was performed 3 times using 2-{[4-(carboxymethyl)-1,3-thiazol-2-yl]thio}-2-methylpropionic acid resin obtained in Example 461-4 and 4-aminophenylacetic acid ethyl ester. To a suspension of the obtained resin in dimethylformamide (30 mL) were added HOBT monohydrate (0.92 g), diisopropylcarbodiimide (0.93 ml) and 4-aminophenylacetic acid ethyl ester (1.1 g), and the mixture was stirred at room temperature overnight. The resin was collected by filtration from the reaction mixture, washed once each with dimethylformamide and methanol, twice with dimethylformamide, once with methanol, three times with tetrahydrofuran and finally once with methanol, and vacuum dried to give the title pale-brown resin (3.1 g).

A part of the resin was cleaved with trifluoroacetic acid and the structure was confirmed.

MS: 423 ($M^+$+1).

Example 504-2

2-{[4-(2-{[4-(2-hydroxyethyl)phenyl]amino}ethyl)-1,3-thiazol-2-yl]thio}-2-methylpropionic acid resin The title pale-brown resin (2.6 g) was obtained using 2-{[4-(2-{[4-(2-ethoxy-2-oxoethyl)phenyl]amino}-2-oxoethyl)-1,3-thiazol-2-yl]thio}-2-methylpropionic acid resin (2.6 g) obtained in Example 504-1 as a starting material and by an operation similar to that of Example 488-2.

A part of the resin was cleaved with trifluoroacetic acid and the structure was confirmed.

MS: 423 ($M^+$+1).

Example 504-3

2-{[4-(2-{[4-(2-ethoxy-2-oxoethyl)phenyl]amino}-2-oxoethyl)-1,3-thiazol-2-yl]thio}-2-methylpropionic acid resin

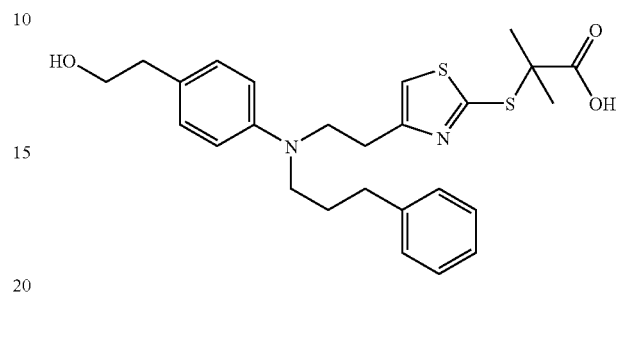

The title compound (8.5 mg) was obtained as a pale-yellow oil using 2-{[4-(2-{[4-(2-hydroxyethyl)phenyl]amino}ethyl)-1,3-thiazol-2-yl]thio}-2-methylpropionic acid resin (0.3 g) obtained in Example 504-2 as a starting material and by an operation similar to that of Example 488-3.

MS: 581 ($M^+$+1).

The following compound was obtained by an operation similar to that of Example 504.

TABLE 6

| No. | Ar | R | MS ($M^+$ + 1) | yield (mg) |
|---|---|---|---|---|
| 505 | 3,4-dimethoxyphenyl | isopropyl-CH2- | 425 | 0.3 |
| 506 | 3,4-dimethoxyphenyl | isobutyl | 439 | 0.4 |
| 507 | 3,4-dimethoxyphenyl | isopentyl | 453 | 0.6 |
| 508 | 3,4-dimethoxyphenyl | cinnamyl | 499 | 1.2 |

TABLE 6-continued
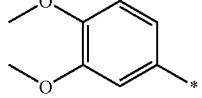
| No. | Ar | R | MS (M+ + 1) | yield (mg) |
|---|---|---|---|---|
| 509 | 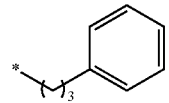 | 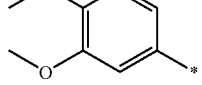 | 501 | 2.0 |
| 510 | 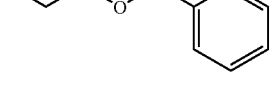 | 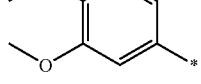 | 517 | 3.0 |
| 511 | 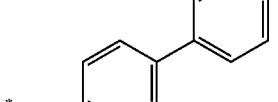 | 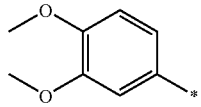 | 549 | 4.4 |
| 512 | 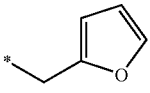 | 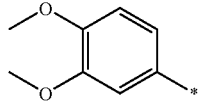 | 463 | 1.9 |
| 513 | 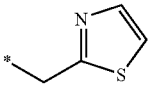 | 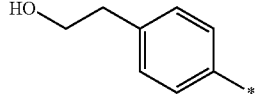 | 480 | 2.4 |
TABLE 7
| No. | Ar | R | MS (M+ + 1) | yield (mg) |
|---|---|---|---|---|
| 514 |  | 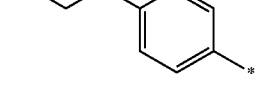 | 493 | 4.0 |
| 515 | 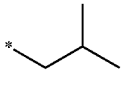 | 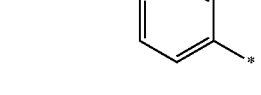 | 423 | 7.7 |
| 516 | 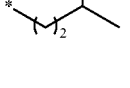 | 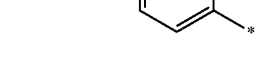 | 437 | 5.0 |
| 517 | 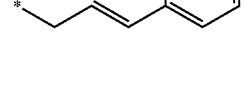 | | 483 | 8.3 |

TABLE 7-continued

| No. | Ar | R | MS (M⁺ + 1) | yield (mg) |
|---|---|---|---|---|
| 518 | HO~~~* (4-(2-hydroxyethyl)phenyl) | *~CH2-biphenyl | 533 | 6.1 |
| 519 | HO~~~* (4-(2-hydroxyethyl)phenyl) | *~CH2-furan-2-yl | 447 | 3.1 |

Example 520

2-[(4-{2-[(4-fluorophenyl)(3-phenylpropyl)amino]ethyl}-1,3-thiazol-2-yl)thio]-2-methylpropionic acid

Example 520-1

2-[(4-{2-[(4-fluorophenyl)amino]-2-oxoethyl}-1,3-thiazol-2-yl)thio]-2-methylpropionic acid resin

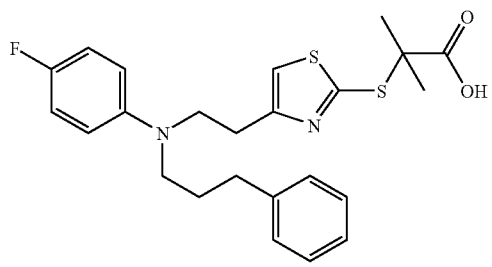

To a suspension of 2-{[4-(carboxymethyl)-1,3-thiazol-2-yl]thio}-2-methylpropionic acid resin (3.0 g) synthesized in Example 461-4 in dimethylformamide (30 mL) were added pyridine (0.35 ml) and hydrochloric acid-dioxane solution (4 mol/L, 1.0 mL) and the mixture was gently stirred at room temperature for 15 min. The resin was collected by filtration, and washed three times with dimethylformamide. To a suspension of the resin in dimethylformamide (30 mL) were added HOBT monohydrate (0.92 g), diisopropylcarbodiimide (0.93 ml) and 4-fluoroaniline (0.57 ml) and the mixture was stirred at room temperature overnight. The resin was collected by filtration from the reaction mixture, washed once each with dimethylformamide and methanol, twice with dimethylformamide, once with methanol, three times with tetrahydrofuran, and finally once with methanol in this order, and vacuum dried to give the title pale-brown resin (3.0 g).

A part of the resin was cleaved with trifluoroacetic acid and the structure was confirmed.
MS: 355 (M⁺+1).

Example 520-2

2-[(4-{2-[(4-fluorophenyl)amino]ethyl}-1,3-thiazol-2-yl)thio]-2-methylpropionic acid resin

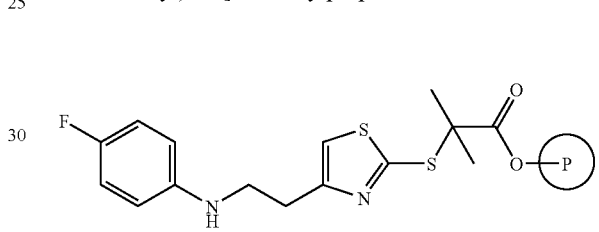

The title yellow resin (2.6 g) was obtained using 2-[(4-{2-[(4-fluorophenyl)amino]-2-oxoethyl}-1,3-thiazol-2-yl)thio]-2-methylpropionic acid resin synthesized in Example 520-1 as a starting material and by an operation similar to that of Example 488-2.

A part of the resin was cleaved with trifluoroacetic acid and the structure was confirmed.
MS: 341 (M⁺+1).

Example 520-3

2-[(4-{2-[(4-fluorophenyl)(3-phenylpropyl)amino]ethyl}-1,3-thiazol-2-yl)thio]-2-methylpropionic acid

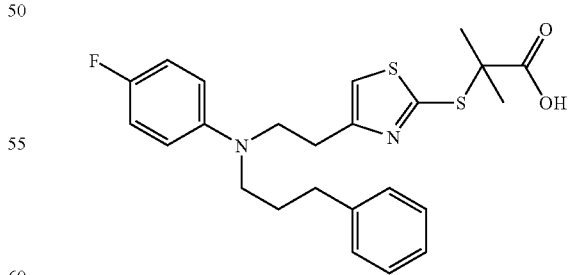

The title compound (13 mg) was obtained as a colorless oil using 2-[(4-{2-[(4-fluorophenyl)amino]ethyl}-1,3-thiazol-2-yl)thio]-2-methylpropionic acid resin synthesized in Example 520-2 as a starting material and by an operation similar to that of Example 488-3.
MS: 459 (M⁺+1).

The following compound was obtained by an operation similar to that of Example 520.

TABLE 8

| No. | Ar | R | MS (M⁺ + 1) | yield (mg) |
|---|---|---|---|---|
| 521 | phenyl | *-(CH₂)₅-CH₃ | 421 | 5.2 |
| 522 | phenyl | *-CH₂-(2-naphthyl) | 463 | 22 |
| 523 | 2,4-difluorophenyl | *-CH₂-(2-naphthyl) | 499 | 5.7 |
| 524 | 3,4-dimethoxyphenyl | *-CH₂-(2-naphthyl) | 523 | 51 |
| 525 | 4-(2-hydroxyethyl)phenyl | *-(CH₂)₅-CH₃ | 465 | 20 |
| 526 | 4-(2-hydroxyethyl)phenyl | *-CH₂-(2-naphthyl) | 507 | 30 |
| 527 | 3-isopropylphenyl | *-(CH₂)₅-CH₃ | 463 | 5.3 |
| 528 | 3-isopropylphenyl | *-CH₂-CH=CH-CH₃ | 419 | 4.5 |
| 529 | 3-isopropylphenyl | *-CH₂CH₂-O-CH₂-phenyl | 499 | 9.9 |

TABLE 9
| No. | Ar | R | MS (M⁺ + 1) | yield (mg) |
|---|---|---|---|---|
| 530 | 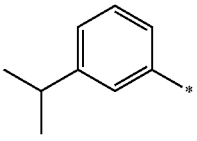 | 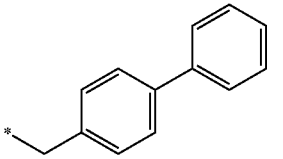 | 531 | 28 |
| 531 | 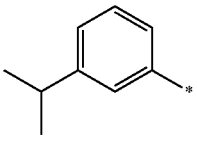 | 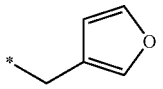 | 445 | 5.3 |
| 532 | 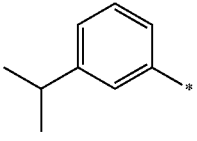 | 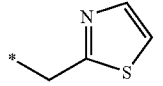 | 462 | 3.6 |
| 533 | 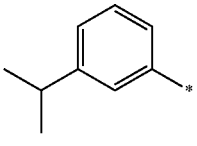 | 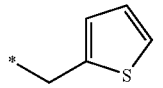 | 461 | 9.6 |
| 534 | 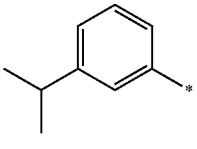 | 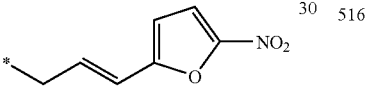 | 516 | 12 |
| 535 | 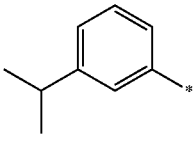 | 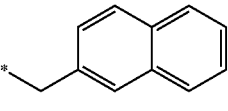 | 505 | 29 |
| 536 | 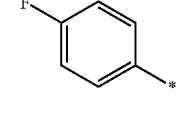 |  | 383 | 4.8 |
| 537 | 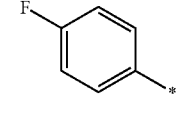 |  | 439 | 3.5 |
| 538 | 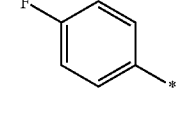 |  | 467 | 8.7 |
| 539 | 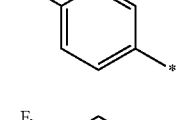 |  | 397 | 7.6 |
| 540 |  |  | 411 | 12 |

TABLE 10
| No. | Ar | R | MS (M+ + 1) | yield (mg) |
|---|---|---|---|---|
| 541 | 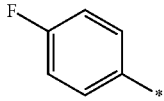 | 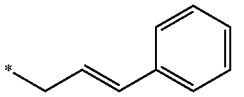 | 457 | 8.7 |
| 542 | 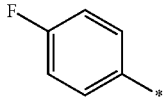 | 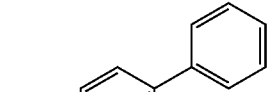 | 507 | 15 |
| 543 | 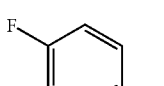 | 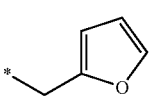 | 421 | 5.8 |
| 544 | 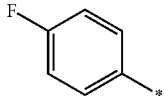 | 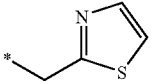 | 438 | 5.7 |
| 545 | 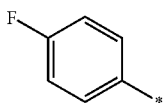 | 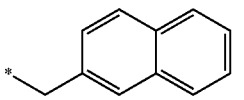 | 481 | 21 |
| 546 | 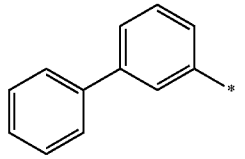 |  | 497 | 1.6 |
| 547 | 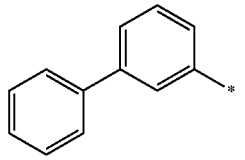 | 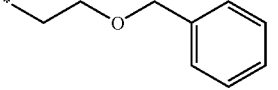 | 533 | 8.3 |
| 548 | 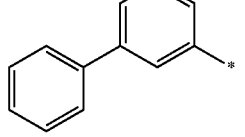 | 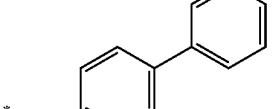 | 565 | 5.7 |
| 549 | 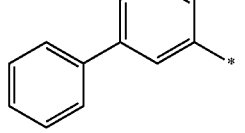 | 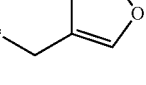 | 479 | 2.3 |
| 550 | 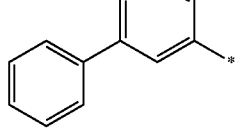 | 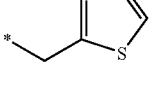 | 495 | 7.1 |

TABLE 10-continued
| No. | Ar | R | MS (M+ + 1) | yield (mg) |
|---|---|---|---|---|
| 551 | 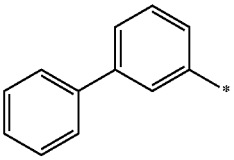 | 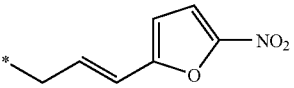 | 549 | 8.6 |
TABLE 11
| No. | Ar | R | MS (M+ + 1) | yield (mg) |
|---|---|---|---|---|
| 552 | 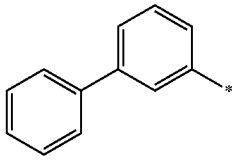 | 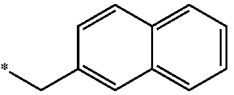 | 539 | 7.0 |
| 553 | 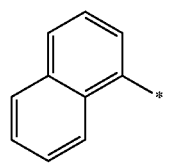 |  | 471 | 14 |
| 554 | 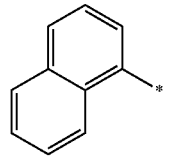 |  | 485 | 26 |
| 555 | 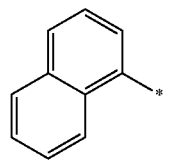 |  | 499 | 3.1 |
| 556 | 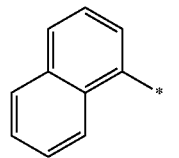 | 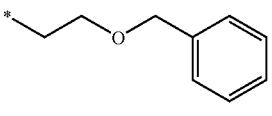 | 507 | 23 |
| 557 | 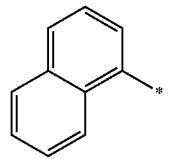 | 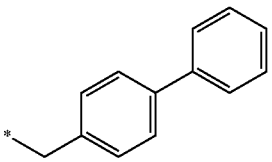 | 539 | 4.5 |
| 558 | 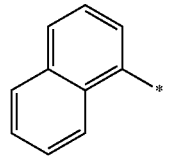 | 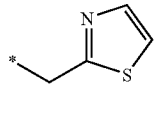 | 470 | 24 |

TABLE 11-continued
| No. | Ar | R | MS (M⁺ + 1) | yield (mg) |
|---|---|---|---|---|
| 559 | 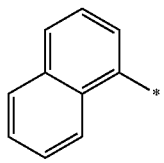 | 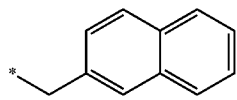 | 513 | 25 |
| 560 | 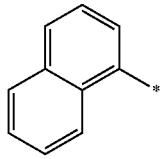 | 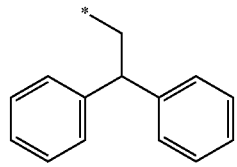 | 553 | 15 |
| 561 | 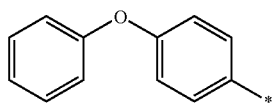 |  | 499 | 17 |
| 562 | 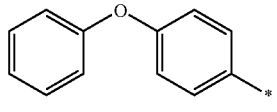 |  | 513 | 34 |
TABLE 12
| No. | Ar | R | MS (M⁺ + 1) | yield (mg) |
|---|---|---|---|---|
| 563 | 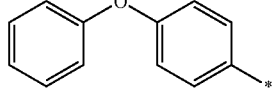 | 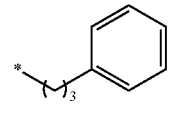 | 533 | 36 |
| 564 | 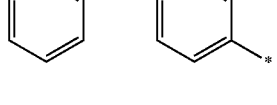 | 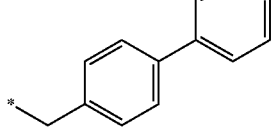 | 581 | 31 |
| 565 | 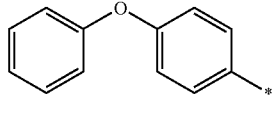 | 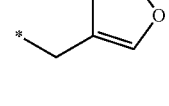 | 495 | 20 |
| 566 | 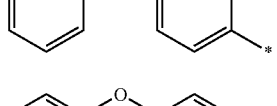 | 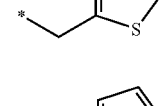 | 511 | 30 |
| 567 | 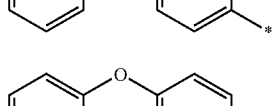 | 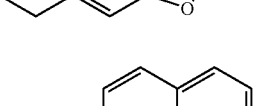 | 566 | 31 |
| 568 | 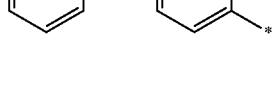 | 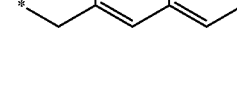 | 555 | 29 |

TABLE 12-continued
| No. | Ar | R | MS (M⁺ + 1) | yield (mg) |
|---|---|---|---|---|
| 569 | 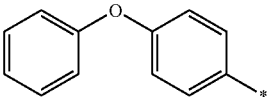 | 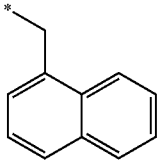 | 555 | 31 |
| 570 | 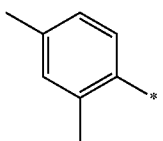 |  | 489 | 48 |
| 571 | 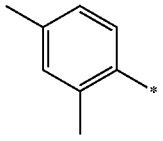 |  | 463 | 47 |
| 572 | 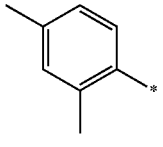 |  | 477 | 41 |
| 573 | 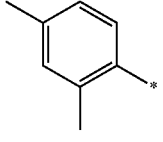 | 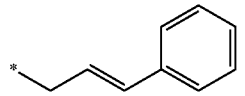 | 467 | 37 |
TABLE 13
| No. | Ar | R | MS (M⁺ + 1) | yield (mg) |
|---|---|---|---|---|
| 574 | 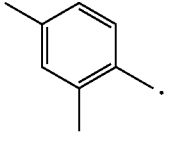 | 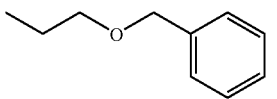 | 485 | 54 |
| 575 | 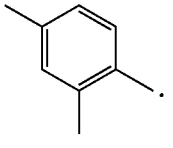 | 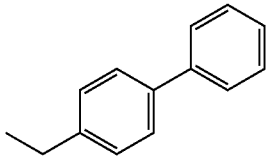 | 517 | 20 |
| 576 | 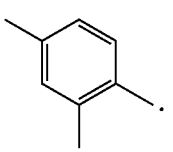 | 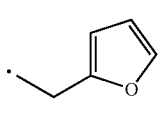 | 431 | 33 |
| 577 | 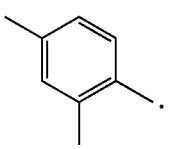 | 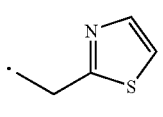 | 448 | 45 |

TABLE 13-continued
| No. | Ar | R | MS (M⁺ + 1) | yield (mg) |
|---|---|---|---|---|
| 578 | 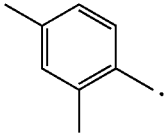 | 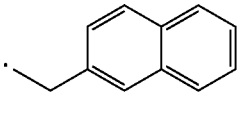 | 491 | 22 |
| 579 | 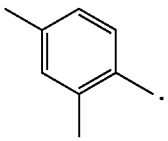 | 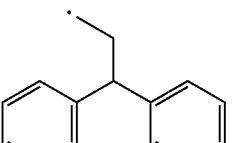 | 531 | 47 |
| 580 | 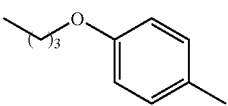 |  | 479 | 44 |
| 581 | 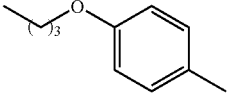 |  | 493 | 40 |
| 582 | 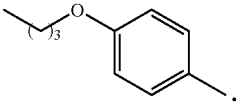 | 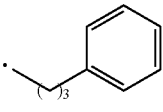 | 513 | 42 |
| 583 | 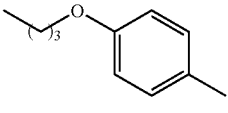 | 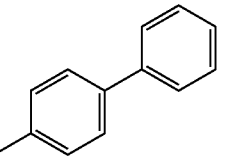 | 561 | 43 |
| 584 | 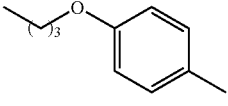 | 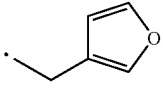 | 475 | 19 |
TABLE 14
| No. | Ar | R | MS (M⁺ + 1) | yield (mg) |
|---|---|---|---|---|
| 585 | 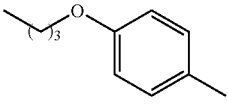 | 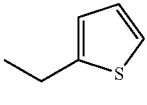 | 491 | 44 |
| 586 | 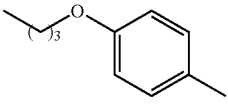 | 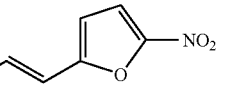 | 546 | 45 |
| 587 | 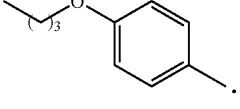 | 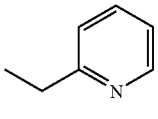 | 486 | 31 |

TABLE 14-continued
| No. | Ar | R | MS (M⁺ + 1) | yield (mg) |
|---|---|---|---|---|
| 588 | 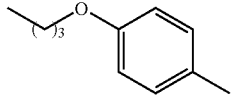 | 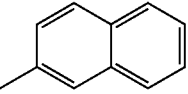 | 535 | 32 |
| 589 | 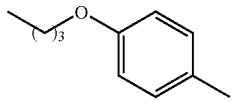 | 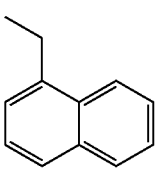 | 535 | 37 |
| 590 | 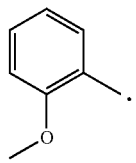 |  | 451 | 21 |
| 591 | 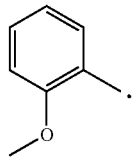 |  | 465 | 40 |
| 592 | 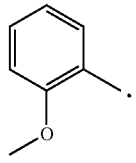 |  | 479 | 29 |
| 593 | 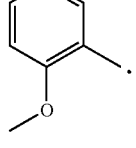 | 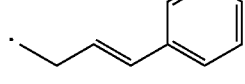 | 469 | 17 |
| 594 | 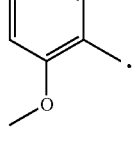 | 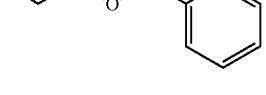 | 487 | 35 |
| 595 | 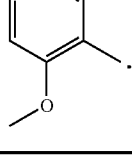 | 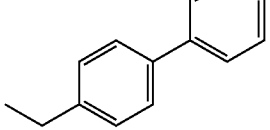 | 519 | 4.9 |

TABLE 15
| No. | Ar | R | MS (M⁺ + 1) | yield (mg) |
|---|---|---|---|---|
| 596 | 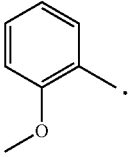 | 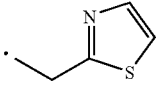 | 450 | 28 |
| 597 | 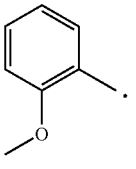 | 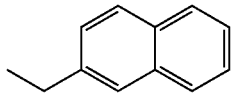 | 493 | 14 |
| 598 | 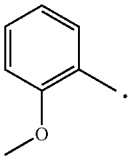 | 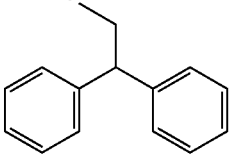 | 533 | 14 |
| 599 | 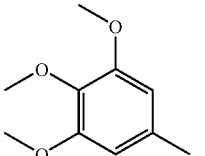 |  | 497 | 54 |
| 600 | 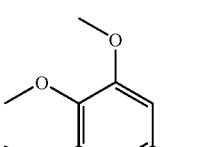 |  | 511 | 59 |
| 601 | 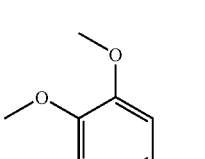 | 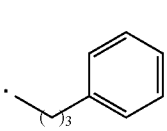 | 531 | 56 |
| 602 | 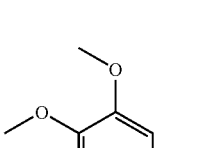 | 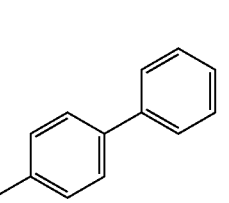 | 579 | 31 |
| 603 | 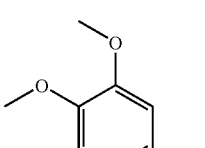 | 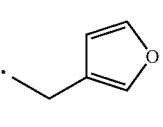 | 493 | 37 |

TABLE 15-continued
| No. | Ar | R | MS (M⁺ + 1) | yield (mg) |
|---|---|---|---|---|
| 604 | 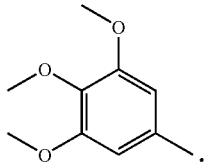 | 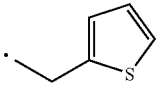 | 509 | 28 |
| 605 | 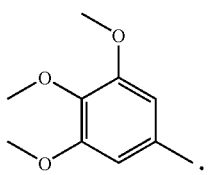 | 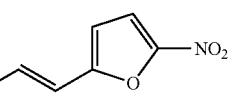 | 564 | 52 |
| 606 | 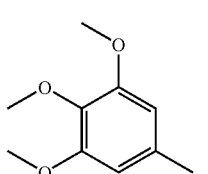 | 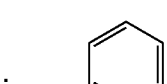 | 504 | 19 |
TABLE 16
| No. | Ar | R | MS (M⁺ + 1) | yield (mg) |
|---|---|---|---|---|
| 607 | 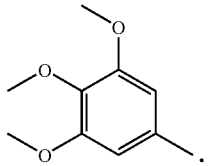 | 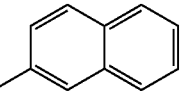 | 553 | 30 |
| 608 | 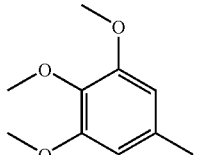 | 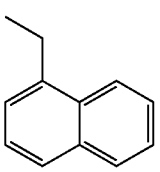 | 553 | 49 |
| 609 | 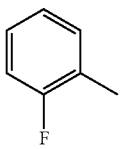 |  | 439 | 9.1 |
| 610 | 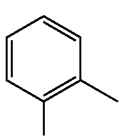 |  | 453 | 2.2 |
| 611 | 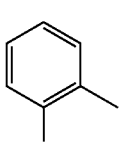 |  | 467 | 7.5 |

TABLE 16-continued
| No. | Ar | R | MS (M⁺ + 1) | yield (mg) |
|---|---|---|---|---|
| 612 | 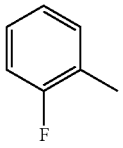 | 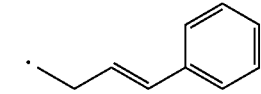 | 457 | 4.0 |
| 613 | 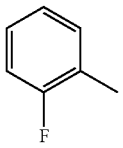 | 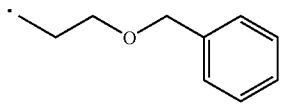 | 475 | 6.9 |
| 614 | 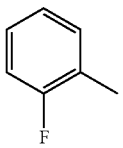 | 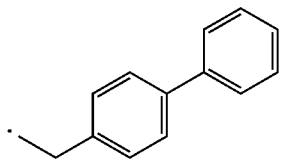 | 507 | 0.9 |
| 615 | 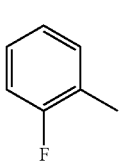 | 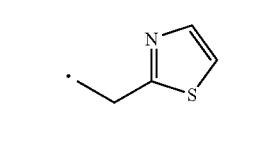 | 438 | 1.1 |
| 616 | 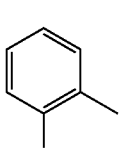 | 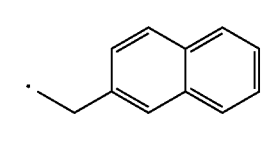 | 481 | 32 |
| 617 | 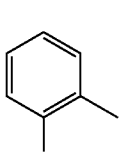 | 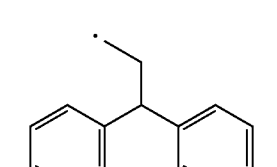 | 521 | 1.1 |
TABLE 17
| No. | Ar | R | MS (M⁺ + 1) | yield (mg) |
|---|---|---|---|---|
| 618 | 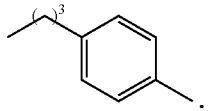 |  | 463 | 31 |
| 619 | 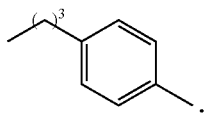 |  | 477 | 37 |
| 620 | 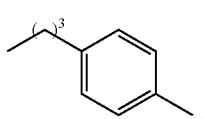 | 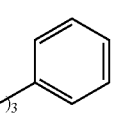 | 497 | 27 |

TABLE 17-continued

| No. | Ar | R | MS (M⁺ + 1) | yield (mg) |
|---|---|---|---|---|
| 621 | | | 545 | 31 |
| 622 | | | 459 | 30 |
| 623 | | | 475 | 45 |
| 624 | | | 530 | 55 |
| 625 | | | 470 | 46 |
| 626 | | | 519 | 39 |
| 627 | | | 519 | 42 |
| 628 | | | 574 | 8.9 |

Example 629

2-[(4-{2-[heptyl(4-phenyl-1,3-thiazol-2-yl)amino]ethyl}-1,3-thiazol-2-yl)thio]-2-methylpropionic acid hydrochloride

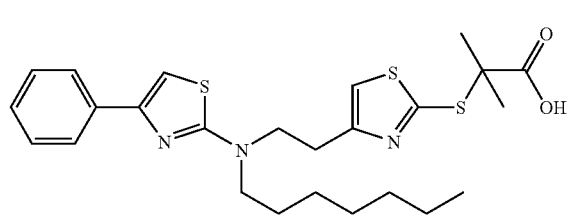

Example 629-1

2-{[4-(2-{3-[(9H-fluorene-9-ylmethoxy)carbonyl]-1-heptylthioureido}ethyl)-1,3-thiazol-2-yl]thio}-2-methylpropionic acid tert-butyl ester

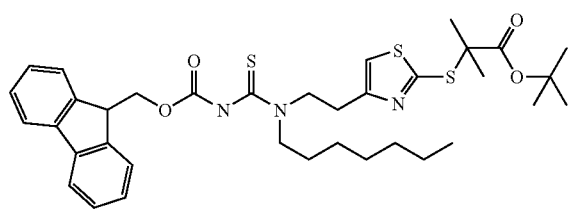

To a solution of 2-({4-[2-(heptylamino)ethyl]-1,3-thiazol-2-yl}thio)-2-methylpropionic acid tert-butyl ester (2.5 g) synthesized in Example 303-2 in dichloromethane (20 mL) was added dropwise 9H-fluorene-9-ylmethyloxycarbonyl-isothiocyanate (2.5 g), and the mixture was stirred at room temperature for 3 hr. The reaction mixture was concentrated under reduced pressure, and subjected to silica gel chromatography (elution solvent; hexane:ethyl acetate=4:1) to give the title compound (3.1 g) as a pale-brown solid.

$^1$H-NMR (CDCl$_3$, 300 MHz) δ: 0.87 (3H, t, J=6.6 Hz), 1.13-1.35 (8H, m), 1.44 (9H, s), 1.44-1.72 (2H, m), 1.56 (6H, s), 3.03-3.40 (4H, m), 3.70-4.00 (2H, m), 4.25 (1H, t, J=6.8 Hz), 4.86 (2H, d, J=6.8 Hz), 7.00-7.20 (1H, m), 7.31 (2H, t, J=7.3 Hz), 7.41 (2H, t, J=7.3 Hz), 7.60 (2H, d, J=7.3 Hz), 7.77 (2H, d, J=7.3 Hz).

MS: 682 (M$^+$+1).

Example 629-2

2-({4-[2-(1-heptylthioureido)ethyl]-1,3-thiazol-2-yl}thio)-2-methylpropionic acid tert-butyl ester

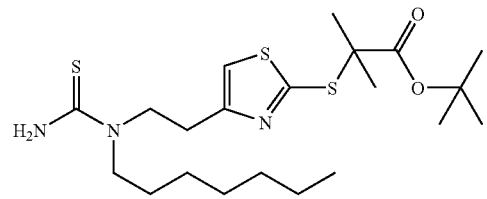

To a solution of 2-{[4-(2-{3-[(9H-fluorene-9-ylmethoxy)carbonyl]-1-heptylthioureido}ethyl)-1,3-thiazol-2-yl]thio}-2-methylpropionic acid tert-butyl ester (3.1 g) synthesized in Example 629-1 in methanol (40 mL) was added piperidine (20 mL), and the mixture was stirred at room temperature overnight. The reaction mixture was concentrated under reduced pressure, and subjected to silica gel chromatography (elution solvent; hexane:ethyl acetate=2:1) to give the title compound (2.0 g) as a colorless oil.

$^1$H-NMR (CDCl$_3$, 300 MHz) δ: 0.88 (3H, t, J=6.6 Hz), 1.21-1.35 (8H, m), 1.43 (9H, s), 1.53-1.75 (2H, m), 1.58 (6H, s), 3.10 (2H, bs), 3.40-4.00 (4H, m), 5.70-6.20 (2H, m), 7.06 (1H, s).

MS: 460 (M$^+$+1).

Example 629-3

2-[(4-{2-[heptyl(4-phenyl-1,3-thiazol-2-yl)amino]ethyl}-1,3-thiazol-2-yl)thio]-2-methylpropionic acid hydrochloride

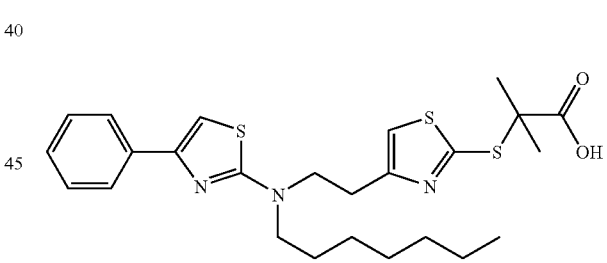

To a solution of 2-({4-[2-(1-heptylthioureido)ethyl]-1,3-thiazol-2-yl}thio)-2-methylpropionic acid tert-butyl ester (1.0 g) synthesized in Example 629-2 in dioxane (20 mL) was added phenacylbromide (0.44 g), and the mixture was stirred at room temperature for 1 hr. The reaction mixture was concentrated under reduced pressure, trifluoroacetic acid (20 mL) was added, and the mixture was stirred at room temperature for 1 hr. The reaction mixture was concentrated under reduced pressure, subjected to silica gel chromatography (elution solvent; chloroform:methanol=12:1), and then subjected to silica gel chromatography (elution solvent; hexane:ethyl acetate=2:1). To the obtained residue were added methanol and 1 mol/L hydrochloric acid-ether, and the mixture was dried under reduced pressure. To the residue were added methanol (35 ml), lithium hydroxide (1.0 g), and water (5 ml), and the mixture was stirred at room temperature overnight. To the reaction mixture was added dil. hydrochloric acid, and the mixture was extracted with ethyl acetate. The organic layer was washed with saturated brine, and dried over sodium sulfate. The solvent was evaporated under reduced pressure. To the residue was added 4 mol/L hydrochloric acid-dioxane, and the mixture was dried under reduced pressure to give the title compound (0.93 g) as a pale-brown amorphous form.

$^1$H-NMR (DMSO-d$_6$, 300 MHz) δ: 0.86 (3H, t, J=6.6 Hz), 1.26-1.40 (8H, m), 1.40-1.70 (2H, m), 1.53 (6H, s), 3.11 (2H, t, J=6.6 Hz), 3.71 (2H, t, J=6.6 Hz), 3.72-3.91 (2H, m), 7.16 (1H, s), 7.30 (1H, t, J=7.2 Hz), 7.40 (2H, t, J=7.2 Hz), 7.54 (1H, s), 7.83 (1H, d, J=7.2 Hz).

MS: 504 (M$^+$+1).

Example 630

2-[(4-{2-[heptyl(4-methyl-1,3-thiazol-2-yl)amino]ethyl}-1,3-thiazol-2-yl)thio]-2-methylpropionic acid hydrochloride

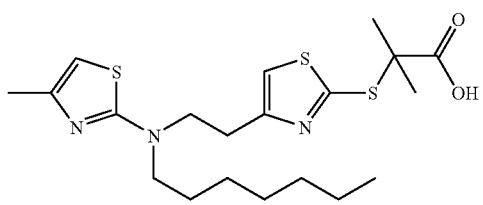

The title compound (0.21 g) was obtained as pale-yellow crystals using 2-({4-[2-(1-heptylthioureido)ethyl]-1,3-thiazol-2-yl}thio)-2-methylpropionic acid tert-butyl ester and bromoacetone synthesized in Example 629-2 as starting materials and by an operation similar to that of Example 629-3.

$^1$H-NMR (DMSO-d$_6$, 300 MHz) δ: 0.88 (3H, t, J=6.6 Hz), 1.15-1.35 (8H, m), 1.58 (2H, t, J=6.9 Hz), 1.65 (6H, s), 2.34 (3H, s), 3.13 (2H, t, J=6.9 Hz), 3.25 (2H, t, J=7.8 Hz), 3.80 (2H, t, J=6.9 Hz), 6.26 (1H, s), 7.00 (1H, s).

MS: 442 (M$^+$+1).

Example 631

2-[(4-{2-[(4-ethyl-1,3-thiazol-2-yl)(heptyl)amino]ethyl}-1,3-thiazol-2-yl)thio]-2-methylpropionic acid hydrochloride

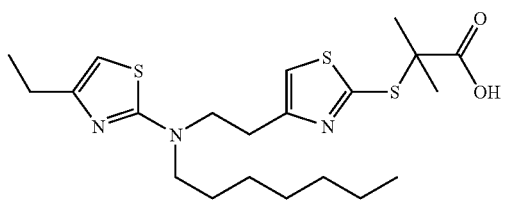

The title compound (0.31 g) was obtained as a pale-yellow oil using 2-({4-[2-(1-heptylthioureido)ethyl]-1,3-thiazol-2-yl}thio)-2-methylpropionic acid tert-butyl ester synthesized in Example 629-2 and 1-bromo-2-butanone as starting materials and by an operation similar to that of Example 629-3.

$^1$H-NMR (DMSO-d$_6$, 300 MHz) δ: 0.88 (3H, t, J=7.2 Hz), 1.22 (3H, t, J=7.5 Hz), 1.22-1.30 (8H, m), 1.58 (2H, t, J=6.3 Hz), 1.60 (6H, s), 2.59 (2H, dq, J=7.2, 0.9 Hz), 3.14 (2H, t, J=6.9 Hz), 3.26 (2H, t, J=7.2 Hz), 3.80 (2H, t, J=7.2 Hz), 6.03 (1H, s), 7.00 (1H, s).

MS: 456 (M$^+$+1).

Example 632

2-[(4-{2-[(4-tert-butyl-1,3-thiazol-2-yl)(heptyl)amino]ethyl}-1,3-thiazol-2-yl)thio]-2-methylpropionic acid hydrochloride

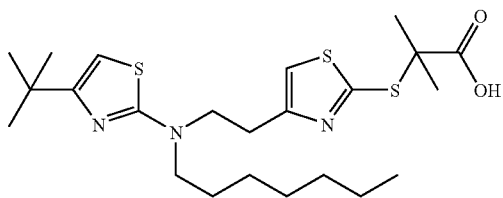

The title compound (0.51 g) was obtained as a pale-purple oil using 2-({4-[2-(1-heptylthioureido)ethyl]-1,3-thiazol-2-yl}thio)-2-methylpropionic acid tert-butyl ester synthesized in Example 629-2 and 1-bromo-3,3-dimethyl-2-propanone as starting materials and by an operation similar to that of Example 629-3.

$^1$H-NMR (DMSO-d$_6$, 300 MHz) δ: 0.84 (3H, t, J=5.4 Hz), 1.32 (9H, s), 1.23-1.35 (8H, m), 1.61-1.78 (2H, m), 1.61 (6H, s), 3.17 (2H, t, J=6.9 Hz), 3.58 (2H, t, J=7.2 Hz), 4.07 (2H, t, J=7.2 Hz), 6.10 (1H, s), 7.26 (1H, s).

MS: 456 (M$^+$+1).

Example 633

2-methyl-2-[(4-{2-[(4-methyl-1,3-thiazol-2-yl)(4-pentylphenyl)amino]ethyl}-1,3-thiazol-2-yl)thio]propionic acid

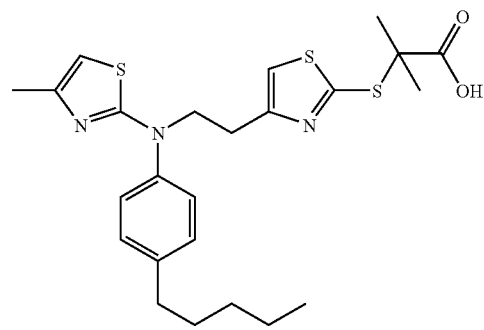

Example 633-1

2-methyl-2-[(4-{2-[(4-pentylphenyl)amino]ethyl}-1,3-thiazol-2-yl)thio]propionic acid resin

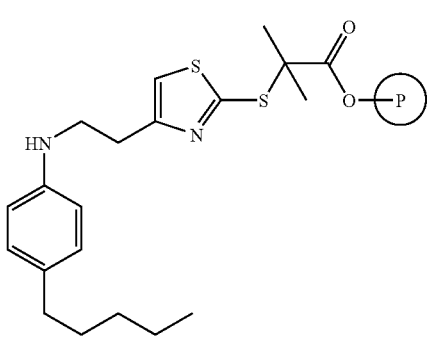

An operation similar to that of Example 520-1 was performed using 2-{[4-(carboxymethyl)-1,3-thiazol-2-yl]thio}-2-methylpropionic acid resin synthesized in Example 461-4 and 4-amylaniline (0.098 g) as starting materials. To the obtained resin were added tetrahydrofuran (2.0 mL) and 1 mol/L borane-tetrahydrofuran complex (2.0 mL), and the mixture was stirred at room temperature overnight. The resin was collected by filtration from the reaction mixture, washed once with tetrahydrofuran, twice with tetrahydrofuran/methanol=1:1 solution, and twice with methanol. Then, a solution (4.0 mL) of tetrahydrofuran-methanol-piperidine (1:1:2) was added to the resin, and the mixture was stirred at room temperature overnight. After completion of the reaction, the resin was collected by filtration, washed four times with tetrahydrofuran and twice with methanol, and vacuum dried to give the title pale-yellow resin (0.30 g).

A part of the resin was cleaved with trifluoroacetic acid and the structure was confirmed.

MS: 393 (M$^+$+1).

Example 633-2

2-methyl-2-[(4-{2-[(4-methyl-1,3-thiazol-2-yl)(4-pentylphenyl)amino]ethyl}-1,3-thiazol-2-yl)thio]propionic acid

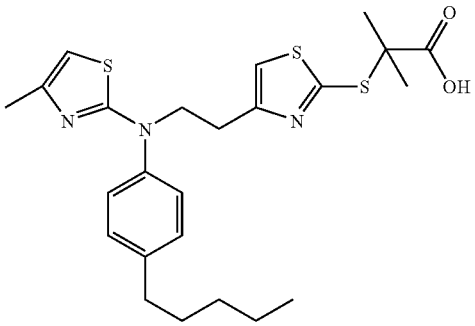

To a suspension of 2-methyl-2-[(4-{2-[(4-pentylphenyl)amino]ethyl}-1,3-thiazol-2-yl)thio]propionic acid resin (0.30 g) synthesized in Example 633-1 in dichloromethane (4.0 mL) was added dropwise 9H-fluorene-9-ylmethyloxycarbonylisothiocyanate (2.5 g), and the mixture was stirred at room temperature overnight. After completion of the reaction, the resin was collected by filtration, washed three times each with dichloromethane, tetrahydrofuran and methanol, and vacuum dried. To the resin was added a solution (3 ml) of piperidine-dimethylformamide (1:2), and the mixture was stood still for 3 hr with occasional stirring. The resin was collected by filtration, washed three times with dimethylformamide, once with methanol, three times with tetrahydrofuran, once with methanol and once with dioxane in this order, and vacuum dried. To the obtained resin were added bromoacetone (0.035 ml) and dioxane (4.0 mL), and the mixture was stirred at room temperature overnight. After completion of the reaction, the resin was collected by filtration, washed three times each with dimethylformamide, tetrahydrofuran and methanol, and vacuum dried. To the resin was added triofluoroacetic acid (2.0 mL), and the mixture was left standing for 1 hr. The resin was filtered off, and the residue was concentrated by blowing nitrogen gas and purified by preparative HPLC to give the title compound (0.029 g) as a pale-brown oil.

MS: 490 (M$^+$+1).

The following compounds were obtained by an operation similar to that of Example 633.

TABLE 18

![structure: Ar-N(R)-CH2CH2-thiazole-S-C(CH3)2-COOH]

| No. | Ar | R | MS (M$^+$ + 1) | yield (mg) |
|---|---|---|---|---|
| 634 | ![4-phenyl-2-thiazolyl] | ![-(CH2)5CH3 pentyl branch] | 490 | 18 |

TABLE 18-continued
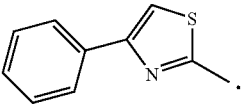
| No. | Ar | R | MS (M⁺ + 1) | yield (mg) |
|---|---|---|---|---|
| 635 |  | 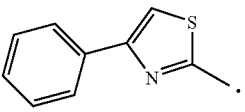 | 532 | 9.0 |
| 636 | 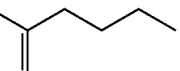 | 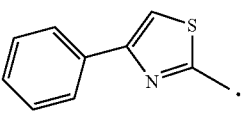 | 552 | 31 |
| 637 |  | 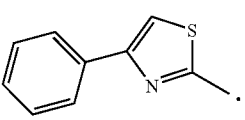 | 496 | 12 |
| 638 |  | 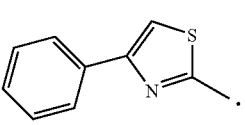 | 510 | 13 |
| 639 |  | 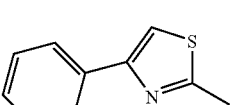 | 524 | 10 |
| 640 |  | 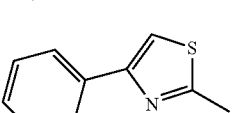 | 538 | 12 |
| 641 |  | 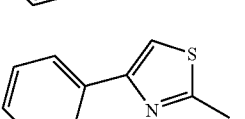 | 552 | 7.9 |
| 642 | 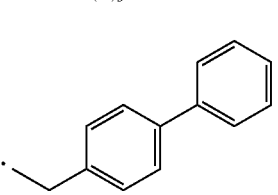 | 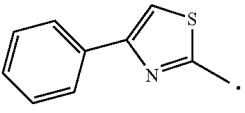 | 572 | 33 |
TABLE 19
| No. | Ar | R | MS (M⁺ + 1) | yield (mg) |
|---|---|---|---|---|
| 643 | 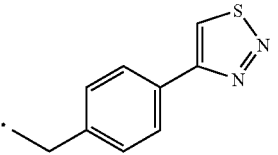 | | 580 | 8.6 |

TABLE 19-continued
| No. | Ar | R | MS (M⁺ + 1) | yield (mg) |
|---|---|---|---|---|
| 644 | 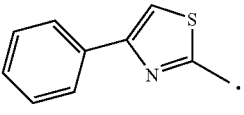 | 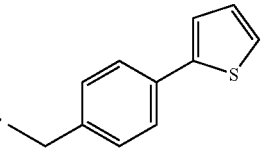 | 578 | 0.6 |
| 645 | 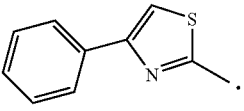 | 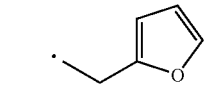 | 486 | 10 |
| 646 | 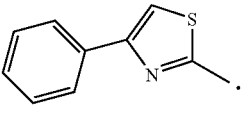 | 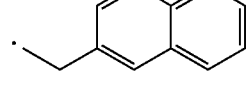 | 546 | 26 |
| 647 | 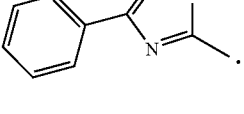 | 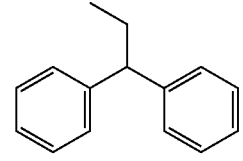 | 586 | 37 |
| 648 | 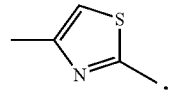 |  | 470 | 22 |
| 649 | 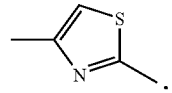 | 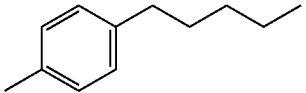 | 490 | 29 |
| 650 | 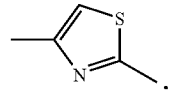 | 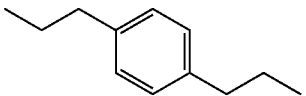 | 490 | 23 |
| 651 | 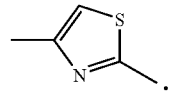 | 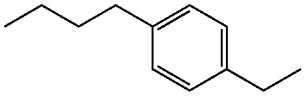 | 490 | 23 |
| 652 | 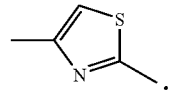 | 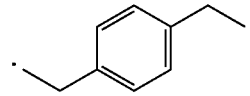 | 462 | 19 |
| 653 | 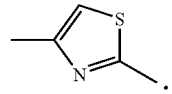 | 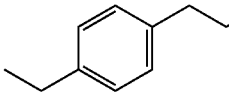 | 476 | 27 |
TABLE 20
| No. | Ar | R | MS (M⁺ + 1) | yield (mg) |
|---|---|---|---|---|
| 654 | 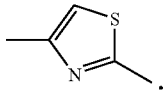 | 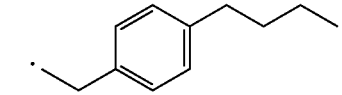 | 490 | 32 |

TABLE 20-continued
| No. | Ar | R | MS (M+ + 1) | yield (mg) |
|---|---|---|---|---|
| 655 | 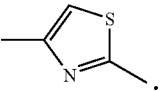 | 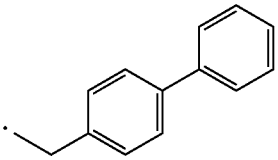 | 510 | 22 |
| 656 | 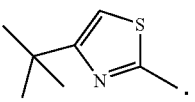 | 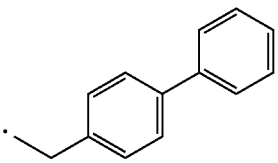 | 552 | 27 |
| 657 | 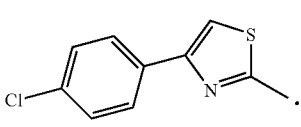 | 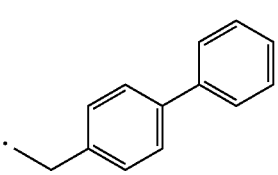 | 606 | 45 |
| 658 | 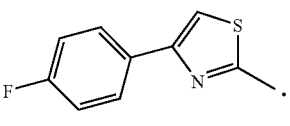 | 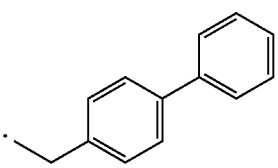 | 590 | 34 |
| 659 | 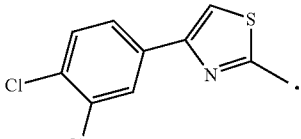 | 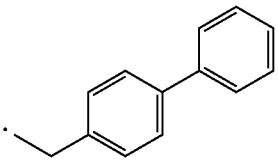 | 940 | 26 |
| 660 | 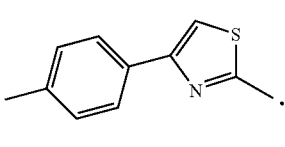 | 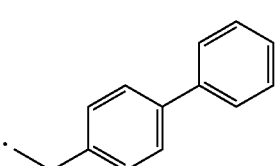 | 586 | 23 |
| 661 | 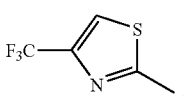 | 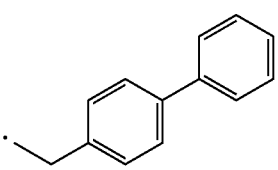 | 564 | 27.2 |
| 662 | 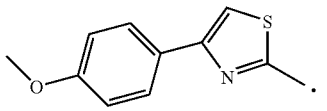 | 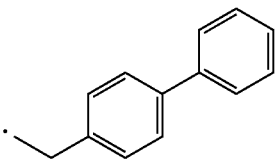 | 602 | 19 |
| 663 | 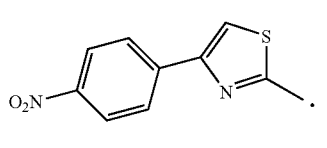 | 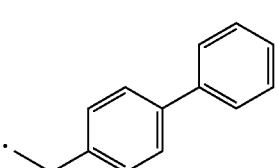 | 617 | 24 |

TABLE 20-continued

| No. | Ar | R | MS (M⁺ + 1) | yield (mg) |
|---|---|---|---|---|
| 664 | (thiophene-thiazole) | (biphenylmethyl) | 578 | 13 |

TABLE 21

| No. | Ar | R | MS (M⁺ + 1) | yield (mg) |
|---|---|---|---|---|
| 665 | (3-thienyl-thiazole) | (biphenylmethyl) | 578 | 14 |
| 666 | (2-nitrophenyl-thiazole) | (biphenylmethyl) | 617 | 24 |
| 667 | (4-trifluoromethylphenyl-thiazole) | (biphenylmethyl) | 640 | 20 |
| 668 | (4-diethylaminophenyl-thiazole) | (biphenylmethyl) | 643 | 21 |
| 669 | (4-pyrrolidinylphenyl-thiazole) | (biphenylmethyl) | 641 | 12 |
| 670 | (3-pyridyl-thiazole) | (biphenylmethyl) | 573 | 21 |
| 671 | (4-pyridyl-thiazole) | (biphenylmethyl) | 573 | 32 |

TABLE 21-continued

| No. | Ar | R | MS (M⁺ + 1) | yield (mg) |
|---|---|---|---|---|
| 672 | 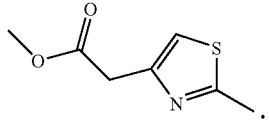 | 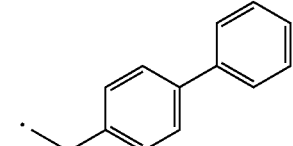 | 568 | 27 |
| 673 | 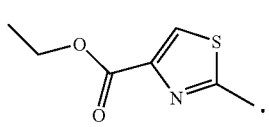 | 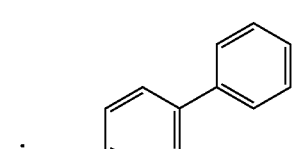 | 568 | 26 |
| 674 | 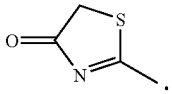 | 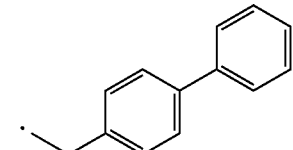 | 512 | 40 |

Example 675

2-methyl-2-[(4-{2-[(8-methylnonyl)(4-methyl-1,3-thiazol-2-yl)amino]ethyl}-1,3-thiazol-2-yl)thio]propionic acid

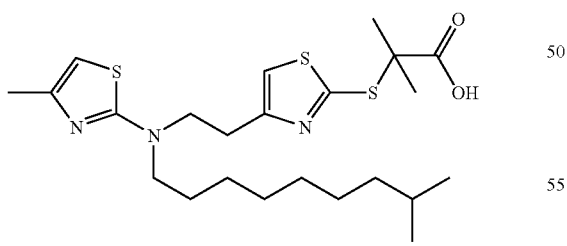

The title compound (0.031 g) was obtained as a pale-yellow oil using 2-methyl-2-[(4-{2-[(8-methylnonyl)amino]ethyl}-1,3-thiazol-2-yl)thio]propionic acid resin (0.3 g) synthesized in Example 483-4 as a starting material and by an operation similar to that of Example 633-2.

MS: 484 (M⁺+1).

The following compounds were obtained by an operation similar to that of Example 675.

TABLE 22

| No. | Ar | R | MS (M⁺ + 1) | yield (mg) |
|---|---|---|---|---|
| 676 | 4-methylthiazol-2-yl | –(CH₂)₄CH(CH₃)₂ | 442 | 30 |
| 677 | 4-methylthiazol-2-yl | –(CH₂)₅CH(CH₃)₂ | 456 | 30 |
| 678 | 4-methylthiazol-2-yl | –(CH₂)₇CH(CH₃)₂ | 484 | 31 |
| 679 | 4-methylthiazol-2-yl | –(CH₂)₄-(4-methylphenyl) | 490 | 33 |

Example 680

2-({4-[2-(biphenyl-3-ylamino)ethyl]-1,3-thiazol-2-yl}thio)-2-methylpropionic acid

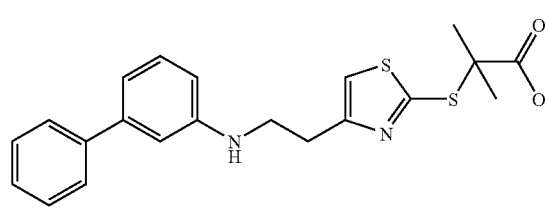

Operations similar to Example 520-1 and Example 488-2 were performed using 2-{[4-(carboxymethyl)-1,3-thiazol-2-yl]thio}-2-methylpropionic acid resin synthesized in Example 461-4 and 3-aminobiphenyl as starting materials. To the obtained resin was added trifluoroacetic acid and the mixture was left standing overnight. The resin was filtered off and the filtrate was concentrated by blowing nitrogen gas thereto, and purified by preparative HPLC to give the title compound (0.015 g) as a pale-brown oil.

MS: 399 (M⁺+1).

The following compounds were obtained by an operation similar to that of Example 680.

TABLE 23

| No. | Ar | MS (M⁺ + 1) | yield (mg) |
|---|---|---|---|
| 681 | 4-pentylphenyl | 393 | 25 |
| 682 | 4'-nitrobiphenyl-4-yl | 444 | 1.9 |
| 683 | 4-(methylthio)phenyl | 369 | 13 |
| 684 | 3-(benzyloxy)phenyl | 429 | 8.2 |

TABLE 23-continued

Ar-NH-CH₂CH₂-[thiazole]-S-C(CH₃)₂-COOH

| No. | Ar | MS (M⁺ + 1) | yield (mg) |
|---|---|---|---|
| 685 | 4-(imidazol-1-yl)phenyl | 389 | 1.0 |
| 686 | 4-tert-butylphenyl | 379 | 20 |
| 687 | 4-isopropylphenyl | 365 | 22 |
| 688 | 4-sec-butylphenyl | 379 | 29 |
| 689 | 4-butoxyphenyl | 295 | 32 |

TABLE 24

| No. | Ar | MS (M⁺ + 1) | yield (mg) |
|---|---|---|---|
| 690 | 4-(1,2,3-thiadiazol-4-yl)phenyl | 407 | 2.3 |
| 691 | 4-methoxy-3-phenyl-phenyl | 429 | 33 |
| 692 | 4-(2-hydroxyethyl)phenyl | 367 | 29 |
| 693 | 4-phenoxyphenyl | 415 | 18 |
| 694 | naphth-1-yl | 373 | 13 |
| 695 | 4-morpholinophenyl | 408 | 12 |
| 696 | 4-butylphenyl | 379 | 38 |
| 697 | benzo[1,3]dioxol-5-yl | 367 | 40 |
| 698 | 4-propylphenyl | 365 | 9.4 |
| 699 | 4-benzyloxyphenyl | 429 | 15.8 |
| 700 | 4-benzylphenyl | 413 | 3.2 |

TABLE 25

| No. | Ar | MS (M⁺ + 1) | yield (mg) |
|---|---|---|---|
| 701 | 4-hexylphenyl | 407 | 12 |
| 702 | 3-isopropylphenyl | 365 | 5.3 |

TABLE 25-continued

| No. | Ar | MS (M⁺ + 1) | yield (mg) |
|-----|----|-----|-----|
| 703 | | 423 | 29 |
| 704 | | 435 | 9.7 |
| 705 | | 421 | 13 |
| 706 | | 405 | 16 |
| 707 | | 381 | 22 |
| 708 | | 409 | 46 |
| 709 | | 414 | 29 |
| 710 | | 369 | 45 |
| 711 | | 399 | 19 |
| 712 | | 413 | 48 |
| 772 | | 387 | 33 |

Example 713

2-({4-[2-(biphenyl-4-yloxy)ethyl]-1,3-thiazol-2-yl}thio)-2-methylpropionic acid

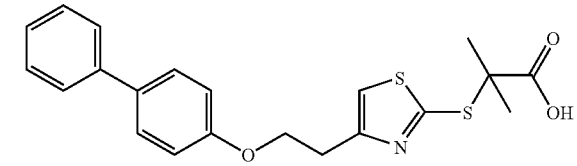

Example 713-1

2-{[4-(2-hydroxyethyl)-1,3-thiazol-2-yl]thio}-2-methylpropionic acid resin

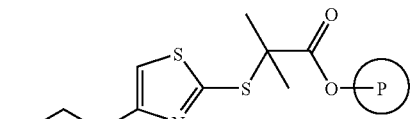

To a suspension of 2-{[4-(carboxymethyl)-1,3-thiazol-2-yl]thio}-2-methylpropionic acid resin (10 g) synthesized in Example 461-4 in tetrahydrofuran (50 mL) was added 1 mol/L borane-tetrahydrofuran complex (25 ml) under ice-cooling, and the mixture was stirred at room temperature overnight. The resin was collected by filtration from the reaction mixture, washed twice with tetrahydrofuran-methanol (1:1) solution, three times with tetrahydrofuran, twice with methanol, once with piperidine, once with tetrahydrofuran and once with methanol in this order, and vacuum dried. To this resin was added 1 mol/L borane-tetrahydrofuran complex (25 ml) again, and the mixture was stirred at room temperature overnight. The resin was collected by filtration from the reaction mixture, washed once each with tetrahydrofuran, tetrahydrofuran-methanol (1:1) solution and tetrahydrofuran-piperidine (1:1) solution, then washed three times each with tetrahydrofuran and methanol, and vacuum dried to give the title pale-yellow resin (8.6 g).

A part of the resin was cleaved with trifluoroacetic acid and the structure was confirmed.
MS: 262 (M⁺+1).

Example 713-2

2-({4-[2-(biphenyl-4-yloxy)ethyl]-1,3-thiazol-2-yl}thio)-2-methylpropionic acid

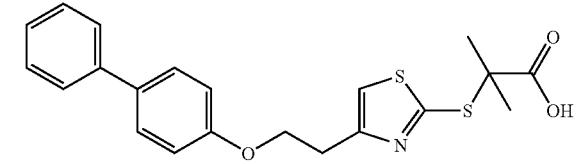

To a suspension of 2-{[4-(2-hydroxyethyl)-1,3-thiazol-2-yl]thio}-2-methylpropionic acid resin (0.3 g) synthesized in Example 713-1 in tetrahydrofuran (3.0 mL) were added triphenylphosphine (0.12 g) and 4-phenylphenol (0.17 g), and the mixture was left standing for 15 min. Thereto was added diisopropyl azodicarboxylate (40% toluene solution, 0.26 ml), and the mixture was stirred at room temperature for 30 min. The resin was collected by filtration from the reaction mixture, and washed three times with tetrahydrofuran. This operation was repeated three times, and the obtained resin was washed three times each with dimethylformamide, tetrahydrofuran and methanol, and vacuum dried. To the resin was added trifluoroacetic acid, and the mixture was left standing at room temperature for 4 hr. The resin was filtered off and the filtrate was concentrated by blowing nitrogen gas thereto, and purified by HPLC to give the title compound (0.012 g) as a colorless oil.

MS: 400 ($M^+$+1).

The following compounds were obtained by an operation similar to that of Example 713.

TABLE 26

| No. | Ar | X | MS ($M^+$ + 1) | yield (mg) |
|---|---|---|---|---|
| 714 | (4-benzylphenyl) | O | 414 | 7.0 |
| 715 | (2-benzylphenyl) | O | 414 | 1.7 |
| 716 | (2-(benzyloxy)phenyl) | O | 430 | 5.9 |
| 717 | (3-biphenyl) | O | 399 | 1.5 |
| 718 | (4-(methylthio)phenyl) | O | 370 | 7.1 |

TABLE 26-continued

| No. | Ar | X | MS ($M^+$ + 1) | yield (mg) |
|---|---|---|---|---|
| 719 | (2-nitro-5-methylphenyl) | O | 383 | 21 |
| 720 | (5-bromo-2-methylphenyl acetyl) | O | 445 | 5.6 |
| 721 | (3-bromophenyl) | O | 403 | 16 |
| 722 | (4-methoxyphenyl) | O | 354 | 10 |

TABLE 27

| No. | Ar | X | MS ($M^+$ + 1) | yield (mg) |
|---|---|---|---|---|
| 723 | (3-(methoxycarbonyl)naphthalen-2-yl) | O | 432 | 17 |
| 724 | (2-tert-butyl-5-methylphenyl) | O | 394 | 4.2 |
| 725 | (4-tert-butylphenyl) | O | 380 | 5.0 |
| 726 | (4-chlorophenyl) | O | 359 | 20 |

TABLE 27-continued

| No. | Ar | X | MS (M⁺ + 1) | yield (mg) |
|---|---|---|---|---|
| 727 | (2-methylquinolin-8-yl) | O | 389 | 25 |
| 728 | (quinolin-4-yl) | O | 375 | 19 |
| 729 | (5-chloro-2-(phenylcarbamoyl)phenyl) | O | 477 | 13 |
| 730 | (4-(3-methoxy-3-oxopropanoyl)phenyl) | O | 424 | 13 |
| 731 | (pyridin-2-yl) | S | 341 | 3.5 |
| 732 | (benzo[d]oxazol-2-yl) | S | 381 | 21.5 |

Example 733

2-methyl-2-[(4-{2-[(4'-nitrobiphenyl-4-yl)oxy]ethyl}-1,3-thiazol-2-yl)thio]propionic acid

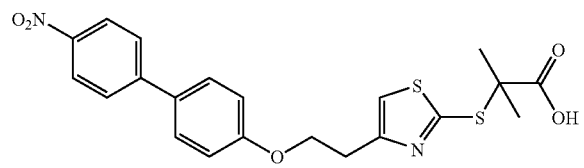

Example 733-1

2-methyl-2-[(4-{2-[(4'-nitrobiphenyl-4-yl)oxy]ethyl}-1,3-thiazol-2-yl)thio]propionic acid tert-butyl ester

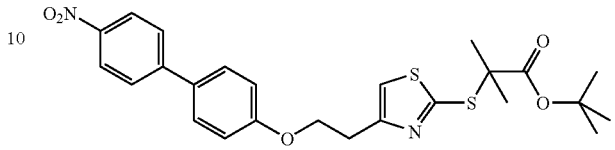

To a solution of 2-{[4-(2-hydroxyethyl)-1,3-thiazol-2-yl]thio}-2-methylpropionic acid tert-butyl ester (2.7 g) synthesized in Example 4 in tetrahydrofuran (15 ml) were added triphenylphosphine (2.5 g) and 4-(4-nitrophenyl)phenol (12.1 g), and the mixture was stirred under ice-cooling for 5 min. To the solution was added diisopropyl azodicarboxylate (40% toluene solution, 4.7 ml), and the mixture was stirred at room temperature overnight. To the solution were further added triphenylphosphine (1.2 g) and diisopropyl azodicarboxylate (40% toluene solution, 2.4 ml), and the mixture was stirred at room temperature for 3.5 hr. The reaction mixture was concentrated, extracted with ethyl acetate. The organic layer was washed with aqueous sodium hydroxide solution and saturated brine, and dried over anhydrous magnesium sulfate. The solvent was evaporated under reduced pressure and the obtained residue was purified by silica gel chromatography (elution solvent; hexane:ethyl acetate=1:1) to give the title compound (3.3 g) as a pale-brown solid.

$^1$H-NMR (CDCl$_3$, 300 MHz) δ: 1.43 (9H, s), 1.58 (6H, s), 3.28 (2H, t, J=6.6 Hz), 4.37 (2H, t, J=6.6 Hz), 7.01 (2H, dd, J=6.8, 2.0 Hz), 7.14 (1H, s), 7.57 (2H, dd, J=6.8, 2.0 Hz), 7.69 (2H, dd, J=7.0, 1.9 Hz), 8.27 (2H, dd, J=7.0, 1.9 Hz).

MS: 501 (M⁺+1).

Example 733-2

2-methyl-2-[(4-{2-[(4'-nitrobiphenyl-4-yl)oxy]ethyl}-1,3-thiazol-2-yl)thio]propionic acid

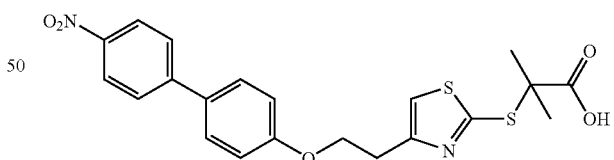

To a solution of 2-methyl-2-[(4-{2-[(4'-nitrobiphenyl-4-yl)oxy]ethyl}-1,3-thiazol-2-yl)thio]propionic acid tert-butyl ester (3.3 g) synthesized in Example 733-1 in dichloromethane (10 mL) was added trifluoroacetic acid (30 mL), and the mixture was stirred at room temperature overnight. The reaction mixture was concentrated, poured into water, and extracted with ethyl acetate. The organic layer was washed with water and saturated brine, and dried over anhydrous magnesium sulfate. The solvent was concentrated under reduced pressure. Thereto was added diisopropyl ether, and the resulting crystals were collected by filtration to give the title compound (2.4 g) as yellow crystals.

¹H-NMR (CDCl₃, 300 MHz) δ: 1.62 (6H, s), 3.30 (2H, t, J=6.0 Hz), 4.36 (2H, t, J=6.0 Hz), 7.01 (2H, ddd, J=9.9, 3.0, 2.0 Hz), 7.13 (1H, s), 7.58 (2H, ddd, J=9.9, 3.0, 2.0 Hz), 7.68 (2H, ddd, J=9.3, 2.7, 2.1 Hz), 8.27 (2H, ddd, J=9.3, 2.7, 2.1 Hz).

MS: 445 (M⁺+1).

Example 734

2-{[4-(2-{[6-(3,4-dichlorophenyl)pyridazin-3-yl]oxy}ethyl)-1,3-thiazol-2-yl]thio}-2-methylpropionic acid

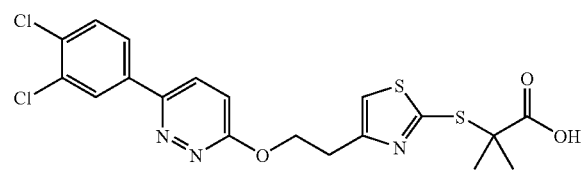

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 3,4-dichlorophenylboric acid as starting materials and by operations similar to those of Example 123-2 and Example 123-3.

¹H-NMR (CDCl₃, 300 MHz) δ: 1.64 (6H, s), 3.36 (2H, t, J=6.0 Hz), 4.90 (2H, t, J=6.0 Hz), 7.08 (1H, s), 7.15 (1H, d, J=9.3 Hz), 7.57 (1H, d, J=8.4 Hz), 7.76 (1H, d, J=9.3 Hz), 7.83 (1H, dd, J=2.1, 8.4 Hz), 8.13 (1H, d, J=2.1 Hz).

MS: 470 (M⁺+1).

Example 735

2-{[4-(2-{[6-(3-chloro-4-fluorophenyl)pyridazin-3-yl]oxy}ethyl)-1,3-thiazol-2-yl]thio}-2-methylpropionic acid

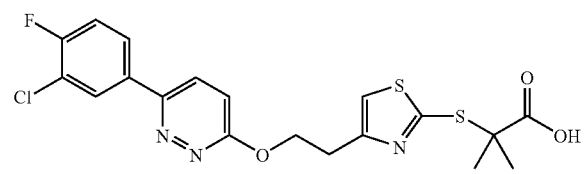

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 3-chloro-4-fluorophenylboric acid as starting materials and by operations similar to those of Example 123-2 and Example 123-3.

¹H-NMR (CDCl₃, 300 MHz) δ: 1.65 (6H, s), 3.36 (2H, t, J=6.0 Hz), 4.89 (2H, t, J=6.0 Hz), 7.08 (1H, s), 7.15 (1H, d, J=9.0 Hz), 7.23-7.29 (1H, m), 7.75 (1H, d, J=9.0 Hz), 7.85-7.89 (1H, m), 8.08-8.11 (1H, m).

MS: 454 (M⁺+1).

Example 736

2-{[4-(2-{[6-(2,4-dichlorophenyl)pyridazin-3-yl]oxy}ethyl)-1,3-thiazol-2-yl]thio}-2-methylpropionic acid

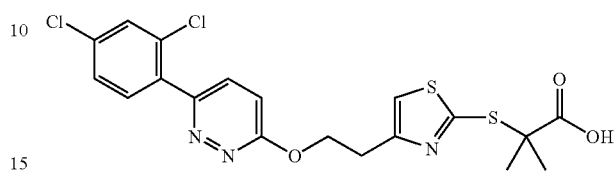

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 2,4-dichlorophenylboric acid as starting materials and by operations similar to those of Example 123-2 and Example 123-3.

¹H-NMR (CDCl₃, 300 MHz) δ: 1.65 (6H, s), 3.36 (2H, t, J=6.0 Hz), 4.90 (2H, t, J=6.0 Hz), 7.08-7.19 (2H, m), 7.37-7.41 (1H, m), 7.51 (1H, brs), 7.65 (1H, d, J=8.4 Hz), 7.76 (1H, d, J=9.3 Hz).

MS: 470 (M⁺+1).

Example 737

2-{[4-(2-{[6-(4-chloro-2-fluorophenyl)pyridazin-3-yl]oxy}ethyl)-1,3-thiazol-2-yl]thio}-2-methylpropionic acid

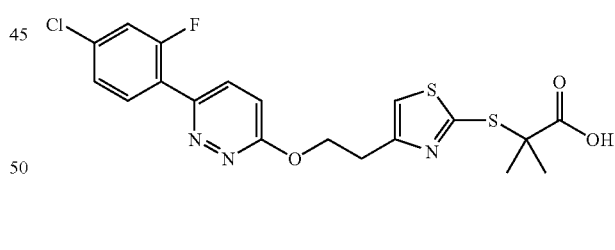

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 4-chloro-2-fluorophenylboric acid as starting materials and by operations similar to those of Example 123-2 and Example 123-3.

¹H-NMR (CDCl₃, 300 MHz) δ: 1.65 (6H, s), 3.36 (2H, t, J=6.0 Hz), 4.90 (2H, t, J=6.0 Hz), 7.08-7.13 (2H, m), 7.20-7.33 (2H, m), 7.83-7.87 (1H, m), 8.06 (1H, t, J=8.4 Hz).

MS: 454 (M⁺+1).

Example 738

2-({4-[2-({6-[2-fluoro-4-(trifluoromethyl)phenyl]pyridazin-3-yl}oxy)ethyl]-1,3-thiazol-2-yl}thio)-2-methylpropionic acid

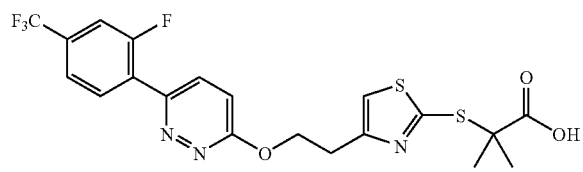

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 2-fluoro-4-(trifluoromethyl)phenylboric acid as starting materials and by operations similar to those of Example 123-2 and Example 123-3.

$^1$H-NMR (CDCl$_3$, 300 MHz) δ: 1.65 (6H, s), 3.37 (2H, t, J=6.0 Hz), 4.92 (2H, t, J=6.0 Hz), 7.09 (1H, s), 7.16 (1H, d, J=9.3 Hz), 7.45-7.48 (1H, m), 7.56-7.59 (1H, m), 7.89-7.93 (1H, m), 8.24 (1H, t, J=8.1 Hz).

MS: 488 (M$^+$+1).

Example 739

2-{[4-(2-{[6-(3,5-dichlorophenyl)pyridazin-3-yl]oxy}ethyl)-1,3-thiazol-2-yl]thio}-2-methylpropionic acid

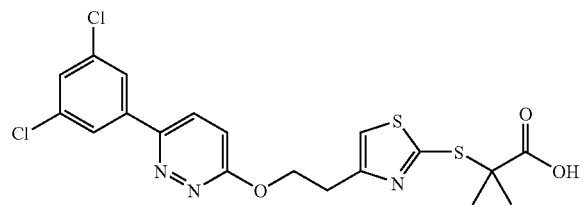

The title compound was obtained using 2-[(4-{2-[(6-chloropyridazin-3-yl)oxy]ethyl}-1,3-thiazol-2-yl)thio]-2-methylpropionic acid tert-butyl ester obtained in Example 123-1 and 3,5-dichlorophenylboric acid as starting materials and by operations similar to those of Example 123-2 and Example 123-3.

$^1$H-NMR (CDCl$_3$, 300 MHz) δ: 1.65 (6H, s), 3.37 (2H, t, J=6.0 Hz), 4.90 (2H, t, J=6.0 Hz), 7.09 (1H, s), 7.16 (1H, d, J=9.0 Hz), 7.44-7.45 (1H, m), 7.76 (1H, d, J=9.0 Hz), 7.90 (2H, brs).

MS: 470 (M$^+$+1).

Example 740

[(4-{2-[(4'-fluorobiphenyl-4-yl)oxy]ethyl}-1,3-thiazol-2-yl)thio]acetic acid

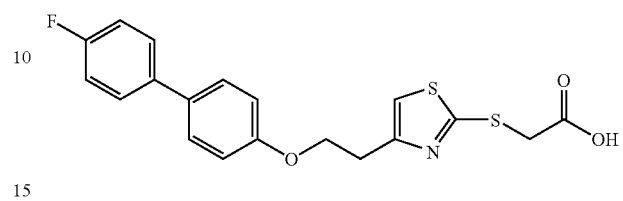

The title compound was obtained by an operation similar to that of Example 2 and using (2-mercapto-1,3-thiazol-4-yl)acetic acid ethyl ester synthesized in Example 1 and bromoacetic acid tert-butyl ester to give {2-[(2-tert-butoxy-2-oxoethyl)thio]-1,3-thiazol-4-yl}acetic acid ethyl ester, followed by sequential operations similar to those of Examples 3, 4 and 34.

$^1$H-NMR (DMSO-d$_6$, 300 MHz) δ: 3.12 (2H, t, J=6.3 Hz), 4.08 (2H, s), 4.31 (2H, t, J=6.3 Hz), 7.03 (2H, d, J=8.7 Hz), 7.25 (2H, t, J=8.7 Hz), 7.36 (1H, s), 7.56 (2H, d, J=8.7 Hz), 7.61-7.66 (2H, m).

MS: 390 (M$^+$+1).

Example 741

{[4-(2-{[5-(4-fluorophenyl)pyridin-2-yl]oxy}ethyl)-1,3-thiazol-2-yl]thio}acetic acid

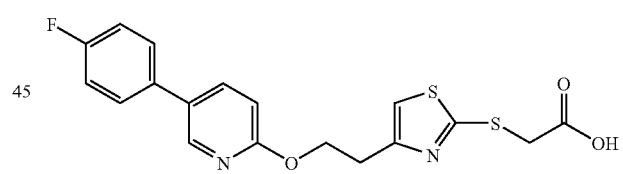

The title compound was obtained by an operation similar to that of Example 2 and using (2-mercapto-1,3-thiazol-4-yl)acetic acid ethyl ester synthesized in Example 1 and bromoacetic acid tert-butyl ester to give {2-[(2-tert-butoxy-2-oxoethyl)thio]-1,3-thiazol-4-yl}acetic acid ethyl ester, followed by sequential operations similar to those of Examples 3, 4 and 100.

$^1$H-NMR (DMSO-d$_6$, 300 MHz) δ: 3.13 (2H, t, J=6.1 Hz), 4.07 (2H, s), 4.58 (2H, t, J=6.1 Hz), 6.88 (1H, d, J=8.4 Hz), 7.30 (2H, t, J=8.8 Hz), 7.34 (1H, s), 7.70 (2H, t, J=8.8 Hz), 7.99 (1H, d, J=11.3 Hz), 8.47 (1H, s).

MS: 391 (M$^+$+1).

Example 742

[(4-{2-[(4'-chlorobiphenyl-4-yl)oxy]ethyl}-1,3-thiazol-2-yl)thio]acetic acid

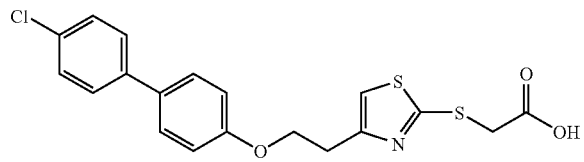

The title compound was obtained by an operation similar to that of Example 2 and using (2-mercapto-1,3-thiazol-4-yl)acetic acid ethyl ester synthesized in Example 1 and bromoacetic acid tert-butyl ester to give {2-[(2-tert-butoxy-2-oxoethyl)thio]-1,3-thiazol-4-yl}acetic acid ethyl ester, followed by operations similar to those of Examples 3, 4 and 38.

$^1$H-NMR (DMSO-$d_6$, 300 MHz) δ: 3.12 (2H, t, J=6.6 Hz), 4.07 (2H, s), 4.31 (2H, t, J=6.6 Hz), 7.04 (2H, d, J=8.1 Hz), 7.36 (1H, s), 7.47 (2H, d, J=8.1 Hz), 7.58-7.66 (4H, m).

MS: 406 (M$^+$+1).

Example 743

({4-[2-({5-[4-(trifluoromethoxy)phenyl]pyrimidin-2-yl}amino)ethyl]-1,3-thiazol-2-yl}thio)acetic acid

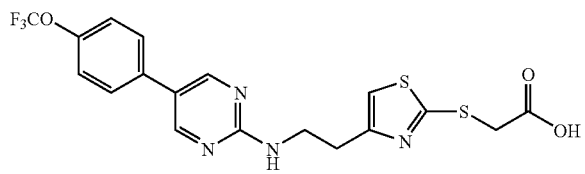

The title compound was obtained by an operation similar to that of Example 2 and using (2-mercapto-1,3-thiazol-4-yl)acetic acid ethyl ester synthesized in Example 1 and bromoacetic acid tert-butyl ester to give {2-[(2-tert-butoxy-2-oxoethyl)thio]-1,3-thiazol-4-yl}acetic acid ethyl ester, followed by sequential operations similar to those of Examples 3, 4, 5, 6, 7 and 162.

$^1$H-NMR (DMSO-$d_6$, 300 MHz) δ: 2.94 (2H, t, J=7.2 Hz), 3.61 (2H, dd, J=6.9 Hz, 13.8 Hz), 4.07 (2H, s), 7.28 (1H, s), 7.41-7.49 (3H, m), 7.75 (2H, t, J=8.7 Hz), 8.65 (2H, s), 13.03 (1H, brs).

MS: 457 (M$^+$+1).

Example 744

({4-[2-({5-[4-(trifluoromethyl)phenyl]pyrimidin-2-yl}amino)ethyl]-1,3-thiazol-2-yl}thio)acetic acid

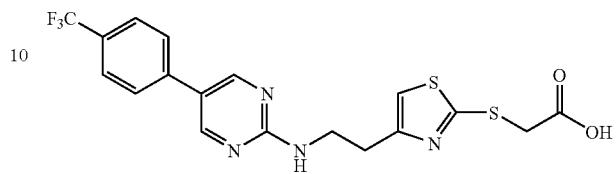

The title compound was obtained by an operation similar to that of Example 2 and using (2-mercapto-1,3-thiazol-4-yl)acetic acid ethyl ester synthesized in Example 1 and bromoacetic acid tert-butyl ester to give {2-[(2-tert-butoxy-2-oxoethyl)thio]-1,3-thiazol-4-yl}acetic acid ethyl ester, followed by sequential operations similar to those of Examples 3, 4, 5, 6, 7 and 165.

$^1$H-NMR (DMSO-$d_6$, 300 MHz) δ: 2.92 (2H, t, J=7.4 Hz), 3.61 (2H, dd, J=6.7 Hz, 13.3 Hz), 4.05 (2H, s), 7.26 (1H, s), 7.54 (1H, t, J=5.7 Hz), 7.75 (2H, d, J=8.3 Hz), 7.85 (2H, d, J=8.3 Hz), 8.70 (2H, s).

MS: 441 (M$^+$+1).

Example 745

2-[(4-{2-[(4'-fluorobiphenyl-4-yl)oxy]ethyl}-1,3-thiazol-2-yl)thio]propionic acid

The title compound was obtained by an operation similar to that of Example 2 and using (2-mercapto-1,3-thiazol-4-yl)acetic acid ethyl ester synthesized in Example 1 and 2-bromopropionic acid tert-butyl ester to give 2-{[4-(2-ethoxy-2-oxoethyl)-1,3-thiazol-2-yl]thio}propionic acid tert-butyl ester, followed by sequential operations similar to those of Examples 3, 4 and 34.

$^1$H-NMR (CDCl$_3$, 300 MHz) δ: 1.59 (3H, d, J=7.4 Hz), 3.26 (2H, d, J=6.1 Hz), 4.08 (1H, q, J=7.4 Hz), 4.32 (2H, d, J=6.1 Hz), 6.96 (2H, d, J=8.7 Hz), 7.07-7.12 (3H, m), 7.44-7.50 (4H, m).

MS: 404 (M$^+$+1).

Example 746

2-[(4-{2-[(4'-fluorobiphenyl-4-yl)oxy]ethyl}-1,3-thiazol-2-yl)thio]-2-butanoic acid

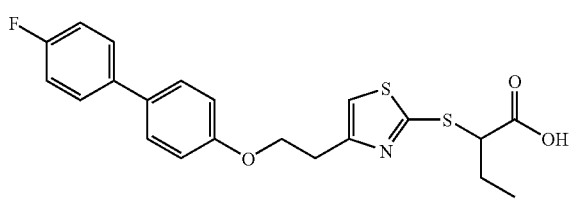

The title compound was obtained by an operation similar to that of Example 2 and using (2-mercapto-1,3-thiazol-4-yl)acetic acid ethyl ester synthesized in Example 1 and 2-bromobutanoic acid tert-butyl ester to give 2-{[4-(2-ethoxy-2-oxoethyl)-1,3-thiazol-2-yl]thio}butanoic acid tert-butyl ester, followed by operations similar to those of Examples 3, 4 and 34.

$^1$H-NMR (CDCl$_3$, 300 MHz) δ: 1.09 (3H, t, J=7.5 Hz), 1.75-1.86 (1H, m), 2.10-2.20 (1H, m), 3.26 (2H, t, J=6.0 Hz), 3.84 (1H, t, J=7.5 Hz), 4.32 (2H, t, J=6.0 Hz), 6.97 (2H, d, J=6.6 Hz), 7.07-7.13 (3H, m), 7.43-7.51 (4H, m).

MS: 418 (M$^+$+1).

Reference Example 51

(2-mercapto-1,3-thiazol-4-yl)acetic acid

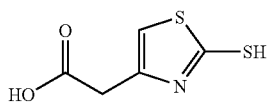

(2-Mercapto-1,3-thiazol-4-yl)ethyl acetate ester (22.6 g) synthesized in Example 1 was dissolved in methanol (200 mL), aqueous sodium hydroxide solution (1 mol/L, 222 mL) was added and the mixture was stirred at room temperature overnight. The reaction mixture was weak-acidified with 1 mol/L hydrochloric acid, methanol was evaporated, and the residue was extracted with ethyl acetate. The organic layer was washed with saturated aqueous sodium chloride solution, the solvent was evaporated and the obtained crystals were washed by suspending in diethyl ether to give the title compound (11.9 g).

$^1$H-NMR (DMSO-d$_6$, 300 MHz) δ: 3.55 (2H, s), 6.72 (1H, s), 13.08 (1H, brs).

Example 747

(2-{[1-(methoxycarbonyl)cyclohexyl]thio}-1,3-thiazol-4-yl)acetic acid

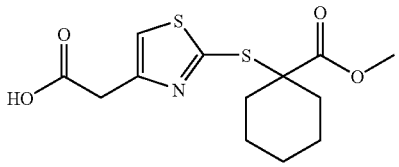

(2-Mercapto-1,3-thiazol-4-yl)acetic acid (3.50 g) synthesized in Reference Example 51 and 2-bromocyclohexanecarboxylic acid methyl ester (4.42 g) were dissolved in methanol (180 mL), sodium methoxide (2.38 g) was added and the mixture was heated under reflux for 22 hr. The solvent was evaporated, and diethyl ether (50 mL) and water (50 mL) were added to the residue. After stirring, the aqueous layer was obtained by partitioning and adjusted to about pH 4 with 1 mol/L hydrochloric acid. The mixture was extracted with ethyl acetate (100 mL), and the organic layer was washed with saturated sodium chloride aqueous solution, and dried over anhydrous sodium sulfate. The solvent was evaporated and the residue was purified by silica gel column chromatography (elution solvent; hexane:ethyl acetate=3:2 to 0:1) and the obtained solid was washed by suspending in hexane-ethyl acetate to give the title compound (663 mg).

$^1$H-NMR (CDCl$_3$, 300 MHz) δ: 1.41-1.50 (4H, m), 1.78-1.86 (4H, m), 2.15-2.22 (2H, m), 3.73 (3H, s), 3.88 (2H, s), 7.26 (1H, s).

Example 748

1-[(4-{2-[(4'-fluorobiphenyl-4-yl)oxy]ethyl}-1,3-thiazol-2-yl)thio]-cyclohexanecarboxylic acid

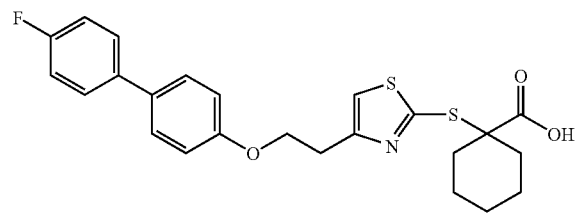

A methyl ester form (892 mg) of the title compound was obtained using (2-{[1-(methoxycarbonyl)cyclohexyl]thio}-1,3-thiazol-4-yl)acetic acid synthesized in Example 747 and by a sequential operation similar to Example 4, 34-1. This was dissolved in methanol (30 mL) and tetrahydrofuran (5 mL), aqueous sodium hydroxide solution (1 mol/L, 2 mL) was added thereto, and the mixture was heated under reflux for 8 hr 30 min. The reaction mixture was allowed to cool, and the solvent was evaporated. Water (10 mL) and diethyl ether were added to the residue and the mixture was stirred and then partitioned. The aqueous layer was adjusted to about pH 2 with 1 mol/L hydrochloric acid. The precipitated solid was

Example 749

2-methyl-2-{[4-(2-{(5-methylpyridin-2-yl)[4-(trifluoromethyl)benzyl]amino}ethyl)-1,3-thiazol-2-yl]thio}propionic acid

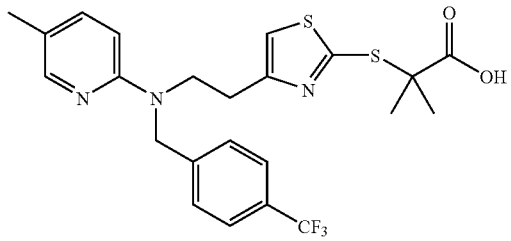

2-[(4-{2-[(5-Methylpyridin-2-yl)amino]ethyl}-1,3-thiazol-2-yl)thio]-2-methylpropionic acid tert-butyl ester was obtained using 2-amino-5-methylpyridine and by operations similar to those of Example 242-1 and Example 242-2. The title compound was obtained using said compound and 1-(bromomethyl)-4-(trifluoromethyl)benzene as starting materials and by an operation similar to that of Example 326.

$^1$H-NMR (DMSO-$d_6$, 300 MHz) δ: 1.50 (6H, s), 2.12 (3H, s), 2.99 (2H, t, J=7.2 Hz), 3.80 (2H, t, J=7.2 Hz), 4.67 (2H, s), 6.53 (1H, d, J=8.7 Hz), 7.27 (4H, s), 7.32 (1H, dd, J=2.4 Hz, 8.7 Hz), 7.44 (1H, s), 7.91 (1H, d, J=2.4 Hz), 12.89 (1H, brs).
MS: 496 (M$^+$+1).

Example 750

2-methyl-2-{[4-(2-{(5-methylpyridin-2-yl)[4-(trifluoromethoxy)benzyl]amino}ethyl)-1,3-thiazol-2-yl]thio}propionic acid

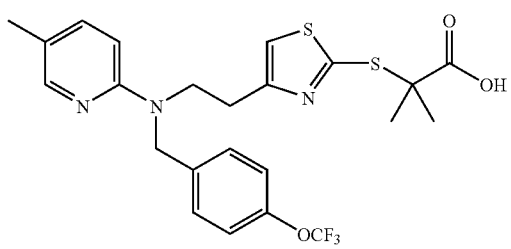

2-[(4-{2-[(5-Methylpyridin-2-yl)amino]ethyl}-1,3-thiazol-2-yl)thio]-2-methylpropionic acid tert-butyl ester was obtained using 2-amino-5-methylpyridine and by operations similar to those of Example 242-1 and Example 242-2. The title compound was obtained using said compound and 1-(bromomethyl)-4-(trifluoromethoxy)benzene as starting materials and by an operation similar to that of Example 326.

$^1$H-NMR (DMSO-$d_6$, 300 MHz) δ: 1.50 (6H, s), 2.13 (3H, s), 3.01 (2H, t, J=7.1 Hz), 3.84 (2H, t, J=7.1 Hz), 4.74 (2H, s), 6.59 (1H, brs), 7.35-7.39 (3H, m), 7.47 (1H, s), 7.65 (2H, d, J=8.1 Hz), 7.91 (1H, d, J=1.8 Hz), 12.91 (1H, brs).
MS: 512 (M$^+$+1).

Example 751

2-methyl-2-{[4-(2-{(5-methylpyridin-2-yl)[(2E)-3-phenylprop-2-en-1-yl]amino}ethyl)-1,3-thiazol-2-yl]thio}propionic acid

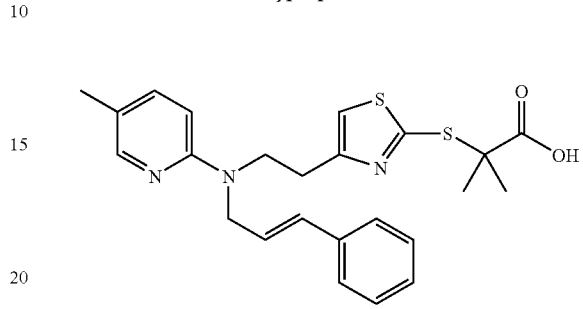

2-[(4-{2-[(5-Methylpyridin-2-yl)amino]ethyl}-1,3-thiazol-2-yl)thio]-2-methylpropionic acid tert-butyl ester was obtained using 2-amino-5-methylpyridine and by operations similar to those of Example 242-1 and Example 242-2. The title compound was obtained using said compound and cinnamyl bromide as starting materials and by an operation similar to that of Example 326.

$^1$H-NMR (DMSO-$d_6$, 300 MHz) δ: 1.49 (6H, s), 2.12 (3H, S), 2.99 (2H, t, J=7.1 Hz), 3.80 (2H, t, J=7.1 Hz), 4.17 (2H, d, J=5.4 Hz), 6.20-6.28 (1H, m), 6.47 (1H, d, J=16 Hz), 6.58 (1H, d, J=8.6 Hz), 7.18-7.39 (7H, m), 7.93 (1H, d, J=1.9 Hz).
MS: 454 (M$^+$+1).

Example 752

2-methyl-2-{[4-(2-{(5-methylpyridin-2-yl)[(1-phenyl-1H-pyrazol-4-yl)methyl]amino}ethyl)-1,3-thiazol-2-yl]thio}propionic acid

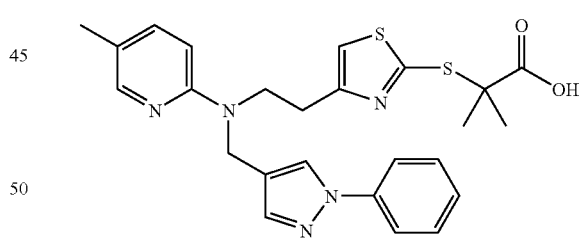

2-[(4-{2-[(5-Methylpyridin-2-yl)amino]ethyl}-1,3-thiazol-2-yl)thio]-2-methylpropionic acid tert-butyl ester was obtained using 2-amino-5-methylpyridine and by operations similar to those of Example 242-1 and Example 242-2. The title compound was obtained using said compound and 4-(chloromethyl)-1-phenyl-1H-pyrazole synthesized in Reference Example 18 as starting materials and by an operation similar to that of Example 326.

$^1$H-NMR (DMSO-$d_6$, 300 MHz) δ: 1.46 (6H, s), 2.27 (3H, s), 2.98 (2H, t, J=7.2 Hz), 3.80 (2H, t, J=7.2 Hz), 4.53 (2H, s), 6.63 (1H, d, J=9.0 Hz), 7.24-7.34 (3H, m), 7.46 (2H, t, J=7.8 Hz), 7.61 (1H, s), 7.77 (2H, d, J=8.4 Hz), 7.95 (1H, s), 8.36 (1H, s).
MS: 494 (M$^+$+1).

--- collected by filtration and recrystallized from hexane and ethyl acetate to give the title compound (591 mg).

$^1$H-NMR (CDCl$_3$, 300 MHz) δ: 1.36-1.66 (6H, m), 1.82-1.88 (2H, m), 2.08-2.18 (2H, m), 3.28 (2H, t, J=6.0 Hz), 4.33 (2H, t, J=6.0 Hz), 6.94 (2H, d, J=6.6 Hz), 7.07-7.13 (3H, m), 7.43-7.51 (4H, m).
MS: 458 (M$^+$+1).

Example 753

2-methyl-2-[(4-{2-[[(2E)-3-phenylprop-2-en-1-yl](pyridin-2-yl)amino]ethyl}-1,3-thiazol-2-yl]thio)propionic acid

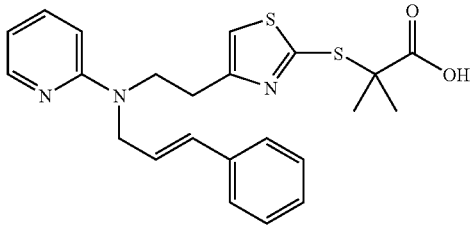

2-[(4-{2-[(Pyridin-2-yl)amino]ethyl}-1,3-thiazol-2-yl)thio]-2-methylpropionic acid tert-butyl ester was obtained using 2-aminopyridine and by operations similar to those of Example 242-1 and Example 242-2. The title compound was obtained using said compound and cinnamyl bromide as starting materials and by an operation similar to that of Example 326.

$^1$H-NMR (DMSO-d$_6$, 300 MHz) δ: 1.49 (6H, s), 3.01 (2H, t, J=7.1 Hz), 3.83 (2H, t, J=7.1 Hz), 4.20 (2H, d, J=5.4 Hz), 6.20-6.28 (1H, m), 6.46 (1H, s), 6.51-6.58 (1H, m), 6.65 (1H, d, J=8.7 Hz), 7.18-7.23 (1H, m), 7.30 (2H, t, J=7.8 Hz), 7.37-7.40 (3H, m), 7.44-7.51 (1H, m), 8.08-8.11 (1H, m).
MS: 440 (M$^+$+1).

Reference Example 52

5-ethylpyridine-2-amine

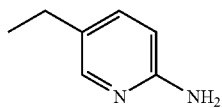

5-Bromopyridine-2-amine (2.51 g) was dissolved in toluene (150 mL), tributylvinyl tin (10.0 g), lithium chloride (1.23 g) and 2,6-di-tert-butyl-4-methylphenol (160 mg) were added and the mixture was heated under reflux for 2 hr 30 min. The resulting solid was removed by filtration, and the solvent was evaporated. The residue was dissolved in ethyl acetate and the insoluble material was removed again by filtration. The filtrate was extracted with 0.2 mol/L hydrochloric acid (100 mL, 50 mL), and the obtained hydrochloric acid solution was basified (pH 12) with 1 mol/L sodium hydroxide, extracted with ethyl acetate (200 mL), and the organic layer was washed with saturated aqueous sodium chloride solution, and dried over anhydrous sodium sulfate. The solvent was evaporated to give 5-vinylpyridine-2-amine (1.00 g). This was dissolved in ethyl acetate (80 mL). Under a nitrogen atmosphere, 10% palladium-carbon (330 mg) was added, and the mixture was stirred under a hydrogen atmosphere for 8 hr. The reaction container was substituted with nitrogen (gas) and 10%-palladium carbon (300 mg) was added. The mixture was stirred under a hydrogen atmosphere for 4 hr. The reaction container was substituted with nitrogen (gas) and the catalyst was filtered off. The solvent was evaporated and the residue was dissolved in 0.4 mol/L hydrochloric acid (20 mL). The obtained hydrochloric acid solution was washed with ethyl acetate, basified (pH 12) with 1 mol/L aqueous sodium hydroxide solution, and extracted with ethyl acetate. The organic layer was washed with saturated sodium chloride aqueous solution, and dried over anhydrous sodium sulfate. The solvent was evaporated to give the title compound (773 mg).

$^1$H-NMR (DMSO-d$_6$, 300 MHz) δ: 1.10 (3H, t, J=7.6 Hz), 2.40 (2H, q, J=7.6 Hz), 5.62 (2H, brs), 6.38 (1H, d, J=8.4 Hz), 7.23 (1H, dd, J=2.3 Hz, 8.4 Hz), 7.74 (1H, d, J=2.3 Hz).

Example 754

2-{[4-(2-{(5-ethylpyridin-2-yl)[(1-phenyl-1H-pyrazol-4-yl)methyl]amino}ethyl)-1,3-thiazol-2-yl]thio}-2-methylpropionic acid

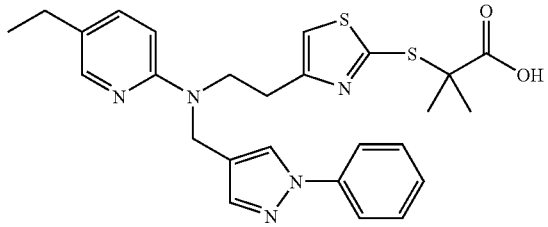

2-[(4-{2-[(5-Ethylpyridin-2-yl)amino]ethyl}-1,3-thiazol-2-yl)thio]-2-methylpropionic acid tert-butyl ester was obtained using 5-ethylpyridine-2-amine synthesized in Reference Example 52 and by operations similar to those of Example 242-1 and Example 242-2. The title compound was obtained using said compound and 4-(chloromethyl)-1-phenyl-1H-pyrazole synthesized in Reference Example 18 as starting materials and by an operation similar to that of Example 326.

$^1$H-NMR (DMSO-d$_6$, 300 MHz) δ: 1.13 (3H, t, J=7.5 Hz), 1.49 (6H, s), 2.45 (2H, q, J=7.5 Hz), 2.99 (2H, t, J=7.1 Hz), 3.81 (2H, t, J=7.1 Hz), 4.53 (2H, s), 6.65 (1H, d, J=8.7 Hz), 7.27 (1H, t, J=7.4 Hz), 7.36 (1H, dd, J=2.4 Hz, 8.7 Hz), 7.41-7.49 (3H, m), 7.63 (1H, m), 7.78 (2H, d, J=8.9 Hz), 7.98 (1H, d, J=2.1 Hz), 8.37 (1H, s).
MS: 508 (M$^+$+1).

Example 755

2-[(4-{2-[(5-ethylpyrimidin-2-yl)({1-[4-(trifluoromethyl)phenyl]-1H-pyrazol-4-yl}methyl)amino]ethyl}-1,3-thiazol-2-yl)thio]-2-methylpropionic acid

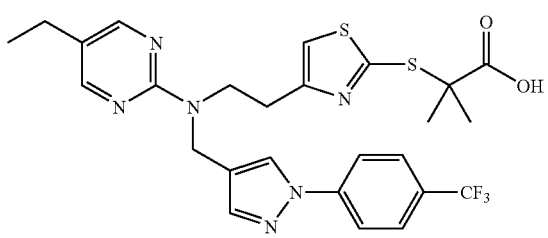

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(4-trifluoromethyl)phenyl-1H-pyrazole synthesized from [4-(trifluoromethyl)phenyl]hydrazine by operations similar to those of Reference Examples 15 to 18 as starting materials, and by an operation similar to that of Example 326.

$^1$H-NMR (CDCl$_3$, 300 MHz) δ: 1.22 (3H, t, J=7.5 Hz), 1.63 (6H, s), 2.50 (2H, q, J=7.5 Hz), 3.10 (2H, t, J=6.6 Hz), 3.92 (2H, t, J=6.6 Hz), 4.70 (2H, s), 6.97 (1H, s), 7.69 (2H, d, J=8.7 Hz), 7.70 (1H, s), 7.84 (2H, d, J=8.7 Hz), 8.07 (1H, s), 8.23 (2H, s).

MS: 577 (M$^+$+1).

Example 756

2-[(4-{2-[(5-ethylpyrimidin-2-yl)({1-[3-(trifluoromethyl)phenyl]-1H-pyrazol-4-yl}methyl)amino]ethyl}-1,3-thiazol-2-yl)thio]-2-methylpropionic acid

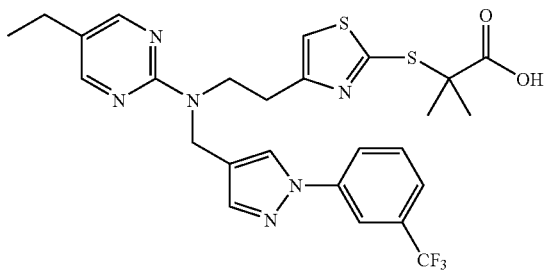

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(3-trifluoromethyl)phenyl-1H-pyrazole synthesized from [3-(trifluoromethyl)phenyl]hydrazine by operations similar to those of Reference Examples 15 to 18 as starting materials, and by an operation similar to that of Example 326.

$^1$H-NMR (CDCl$_3$, 300 MHz) δ: 1.22 (3H, t, J=7.5 Hz), 1.63 (6H, s), 2.50 (2H, q, J=7.5 Hz), 3.10 (2H, t, J=6.6 Hz), 3.93 (2H, t, J=6.9 Hz), 4.70 (2H, s), 6.96 (1H, s), 7.48-7.59 (3H, m), 7.70 (1H, m) 7.88 (2H, d, J=8.1 Hz), 7.98 (1H, s), 8.01 (1H, s), 8.23 (2H, s).

MS: 577 (M$^+$+1).

Example 757

2-[(4-{2-[{[1-(3-chlorophenyl)-1H-pyrazole-4-yl]methyl}(5-ethylpyrimidin-2-yl)amino]ethyl}-1,3-thiazol-2-yl)thio]-2-methylpropionic acid

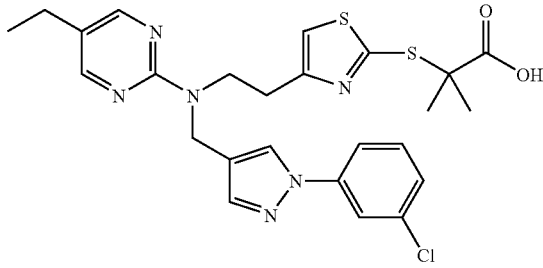

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(3-chlorophenyl)-1H-pyrazole synthesized from (3-chlorophenyl)hydrazine by operations similar to those of Reference Examples 15 to 18 as starting materials, and by an operation similar to that of Example 326.

$^1$H-NMR (CDCl$_3$, 300 MHz) δ: 1.22 (3H, t, J=7.5 Hz), 1.64 (6H, s), 2.50 (2H, q, J=7.5 Hz), 3.09 (2H, t, J=6.9 Hz), 3.93 (2H, t, J=6.9 Hz), 4.69 (2H, s), 6.96 (1H, s), 7.22 (1H, d, J=9.3 Hz), 7.35 (1H, t, J=8.1 Hz), 7.57 (1H, d, J=8.7 Hz), 7.67 (1H, s), 7.72 (1H, s), 7.94 (1H, s), 8.23 (2H, s).

MS: 543 (M$^+$+1).

Example 758

2-[(4-{2-[(5-ethylpyrimidin-2-yl)({1-[4-(trifluoromethoxy)phenyl]-1H-pyrazol-4-yl}methyl)amino]ethyl}-1,3-thiazol-2-yl)thio]-2-methylpropionic acid

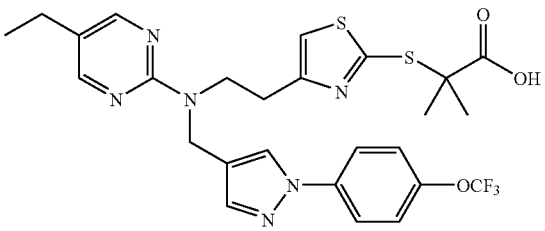

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(4-trifluoromethoxy)phenyl-1H-pyrazole synthesized from [4-(trifluoromethoxy)phenyl]hydrazine by operations similar to those of Reference Examples 15 to 18 as starting materials, and by an operation similar to that of Example 326.

$^1$H-NMR (CDCl$_3$, 300 MHz) δ: 1.22 (3H, t, J=7.5 Hz), 1.63 (6H, s), 2.50 (2H, q, J=7.5 Hz), 3.09 (2H, t, J=7.1 Hz), 3.92 (2H, t, J=7.1 Hz), 4.69 (2H, s), 6.96 (1H, s), 7.28 (2H, d, J=9.0 Hz), 7.67 (1H, s), 7.73 (2H, d, J=9.0 Hz), 7.97 (1H, s), 8.22 (2H, s).

MS: 593 (M$^+$+1).

Example 759

2-({4-[2-((5-ethylpyrimidin-2-yl){[1-(3-fluorophenyl)-1H-pyrazol-4-yl]methyl}amino)ethyl]-1,3-thiazol-2-yl}thio)-2-methylpropionic acid

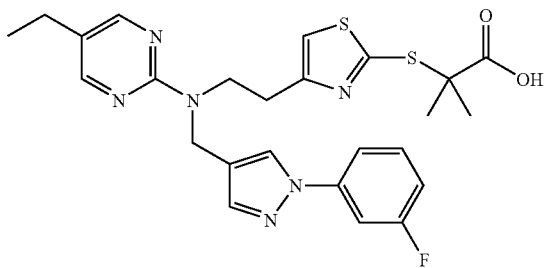

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-1-(3-fluorophenyl)-1H-pyrazole synthesized from (3-fluorophenyl)hydrazine by operations similar to those of Reference Examples 15 to 18 as starting materials, and by an operation similar to that of Example 326.

¹H-NMR (CDCl₃, 300 MHz) δ: 1.22 (3H, t, J=7.5 Hz), 1.63 (6H, s), 2.50 (2H, q, J=7.5 Hz), 3.09 (2H, t, J=7.8 Hz), 3.93 (2H, t, J=7.8 Hz), 4.69 (2H, s), 6.91-6.97 (2H, m), 7.26-7.47 (3H, m), 7.67 (1H, s), 7.95 (1H, s), 8.23 (2H, s).

MS: 527 (M⁺+1).

Example 760

2-{[4-(2-{(5-cyanopyrimidin-2-yl)[(1-phenyl-1H-pyrazol-4-yl)methyl]amino}ethyl)-1,3-thiazol-2-yl]thio}-2-methylpropionic acid

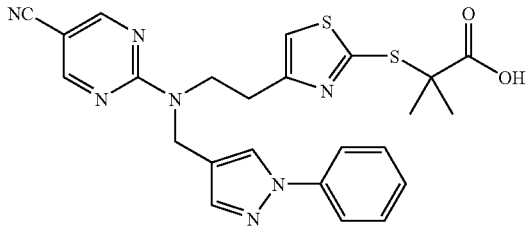

A compound (500 mg) obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(chloromethyl)-1-phenyl-1H-pyrazole synthesized in Reference Example 18 as starting materials and by an operation similar to that of Example 442-1 was dissolved in DMF (2.5 mL), zinc cyanide (100 mg) and tetrakis(triphenylphosphine)palladium (282 mg) were added and the mixture was heated at 100° C. for 6 hr. The reaction mixture was cooled, water was added thereto, and the mixture was extracted with ethyl acetate. The organic layer was washed with saturated brine and dried over anhydrous sodium sulfate. The solvent was evaporated under reduced pressure, and the residue was purified by silica gel chromatography (elution solvent; hexane:ethyl acetate=4:1 to 1:1) to give a compound (300 mg). The obtained compound was subjected to an operation similar to that of Example 442-3 to give the title compound.

¹H-NMR (CDCl₃, 300 MHz) δ: 1.63 (6H, s), 3.08 (2H, t, J=7.5 Hz), 3.98 (2H, t, J=7.5 Hz), 4.77 (2H, s), 6.97 (1H, s), 7.26-7.30 (1H, m), 7.42-7.47 (2H, m), 7.67-7.70 (3H, m), 8.02 (1H, s), 8.57 (2H, bd, J=15.3 Hz).

MS: 506 (M⁺+1).

Example 761

2-{[4-(2-{[5-(dimethylamino)pyrimidin-2-yl][(1-phenyl-1H-pyrazol-4-yl)methyl]amino}ethyl)-1,3-thiazol-2-yl]thio}-2-methylpropionic acid

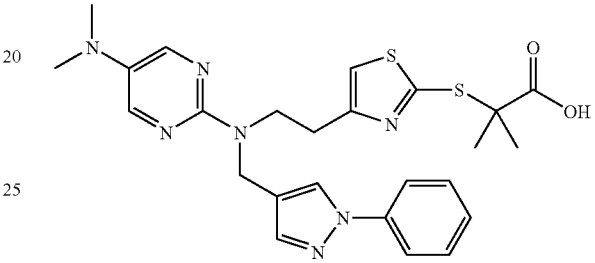

An operation similar to that of Example 442-1 was performed using 2-[(4-{2-[(5-bromopyrimidin-2-yl)amino]ethyl}-1,3-thiazol-2-yl)thio]-2-methylpropionic acid tert-butyl ester synthesized in Example 162-1 and 4-(chloromethyl)-1-phenyl-1H-pyrazole synthesized in Reference Example 18 as starting materials. An operation similar to that of Example 442-2 was performed (solvent was changed to tert-butanol) using the obtained compound and dimethylamine hydrochloride as starting materials. The obtained compound was subjected to an operation similar to that of Example 442-3 to give the title compound.

¹H-NMR (CDCl₃, 300 MHz) δ: 1.62 (6H, s), 2.84 (6H, s), 3.09 (2H, t, J=7.2 Hz), 3.90 (2H, t, J=7.2 Hz), 4.67 (2H, s), 6.94 (1H, s), 7.22-7.28 (1H, m), 7.40-7.45 (2H, m), 7.65-7.68 (3H, m), 7.93 (1H, s), 8.09 (2H, s).

MS: 524 (M⁺+1).

Example 762

2-{[4-(2-{(5-ethylpyrimidin-2-yl)[(3-methyl-5-phenyl-isoxazol-4-yl)methyl]amino}ethyl)-1,3-thiazol-2-yl]thio}-2-methylpropionic acid

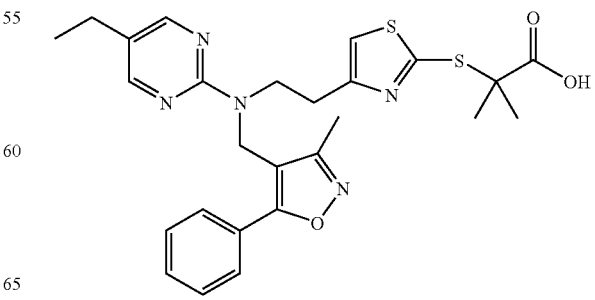

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-3-methyl-5-phenyl-isoxazole as starting materials and by an operation similar to that of Example 326.

$^1$H-NMR (CDCl$_3$, 300 MHz) δ: 1.22 (3H, t, J=7.5 Hz), 1.59 (6H, s), 2.21 (3H, s), 2.50 (2H, q, J=7.5 Hz), 2.85 (2H, t, J=7.4 Hz), 3.66 (2H, t, J=7.4 Hz), 4.92 (2H, s), 6.64 (1H, s), 7.44-7.46 (3H, m), 7.63-7.67 (2H, m), 8.21 (2H, s).

MS: 524 (M$^+$+1).

Example 763

2-{[4-(2-{(5-ethylpyrimidin-2-yl)[(5-phenyl-1,3-oxazol-4-yl)methyl]amino}ethyl)-1,3-thiazol-2-yl]thio}-2-methylpropionic acid

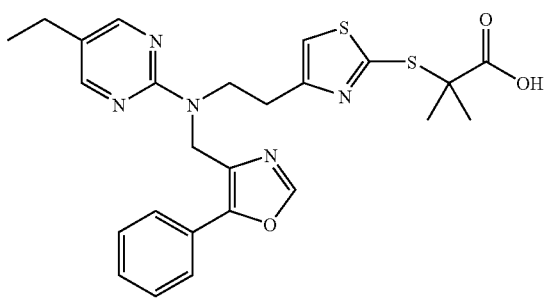

The title compound was obtained using 2-[(4-{2-[(5-ethylpyrimidin-2-yl)amino]ethyl}-1,3-thiazol-2-yl)thio]-2-methylpropionic acid tert-butyl ester synthesized in Example 265-1 and 4-(chloromethyl)-5-phenyl-1,3-oxazole as starting materials and by an operation similar to that of Example 326.

$^1$H-NMR (CDCl$_3$, 300 MHz) δ: 1.19 (3H, t, J=7.5 Hz), 1.65 (6H, s), 2.46 (2H, q, J=7.5 Hz), 3.07 (2H, t, J=6.9 Hz), 3.93 (2H, t, J=6.9 Hz), 4.94 (2H, s), 6.86 (1H, s), 7.32-7.38 (3H, m), 7.65-7.68 (2H, m), 7.95 (1H, s), 8.13 (2H, s).

MS: 510 (M$^+$+1).

Example 764

2-methyl-2-[(4-{2-[(5-morpholin-4-ylpyrimidin-2-yl)(pentyl)amino]ethyl}-1,3-thiazol-2-yl)thio]propionic acid

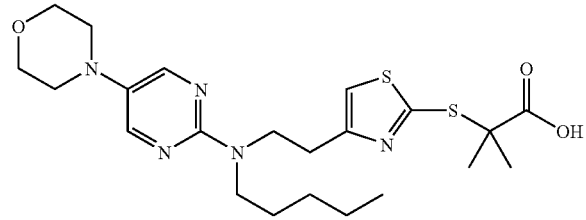

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and pentyl iodide as starting materials and by an operation similar to that of Example 442.

$^1$H-NMR (CDCl$_3$, 300 MHz) δ: 0.89 (3H, t, J=6.6 Hz), 1.26-1.32 (4H, m), 1.55 (2H, brs), 1.65 (6H, s), 2.98-3.00 (4H, m), 3.09 (2H, t, J=7.2 Hz), 3.45 (2H, t, J=7.2 Hz), 3.84-3.88 (6H, m), 6.95 (1H, s), 8.09 (2H, s).

MS: 480 (M$^+$+1).

Example 765

2-[(4-{2-[hexyl(5-morpholin-4-ylpyrimidin-2-yl)amino]ethyl}-1,3-thiazol-2-yl)thio]-2-methylpropionic acid

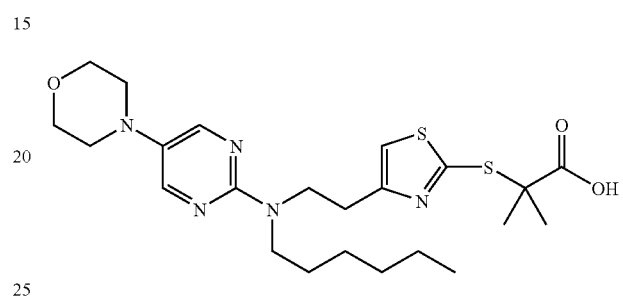

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and hexyl iodide as starting materials and by an operation similar to that of Example 442.

$^1$H-NMR (CDCl$_3$, 300 MHz) δ: 0.85-0.88 (3H, m), 1.28 (6H, brs), 1.54 (2H, brs), 1.65 (6H, s), 2.98-3.01 (4H, m), 3.09 (2H, t, J=7.2 Hz), 3.45 (2H, t, J=7.2 Hz), 3.84-3.87 (6H, m), 6.96 (1H, s), 8.09 (2H, s).

MS: 494 (M$^+$+1).

Example 766

2-methyl-2-[(4-{2-[(5-morpholin-4-ylpyrimidin-2-yl)(octyl)amino]ethyl}-1,3-thiazol-2-yl)thio]propionic acid

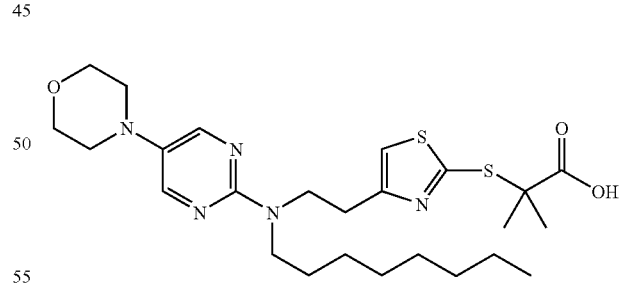

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and octyl iodide as starting materials and by an operation similar to that of Example 442.

$^1$H-NMR (CDCl$_3$, 300 MHz) δ: 0.87 (3H, t, J=6.6 Hz), 1.26-1.27 (10H, m), 1.53-1.58 (2H, m), 1.65 (6H, s), 2.97-3.00 (4H, m), 3.09 (2H, t, J=7.5 Hz), 3.45 (2H, t, J=7.5 Hz), 3.83-3.88 (6H, m), 6.94 (1H, s), 8.09 (2H, s).

MS: 522 (M$^+$+1).

Example 767

2-methyl-2-[(4-{2-[(5-morpholin-4-ylpyrimidin-2-yl)(nonyl)amino]ethyl}-1,3-thiazol-2-yl)thio]propionic acid

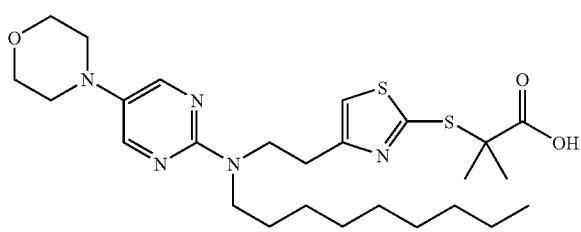

The title compound was obtained using 2-[(4-{2-[(5-bromopyrimidin-2-yl)amino]ethyl}-1,3-thiazol-2-yl)thio]-2-methylpropionic acid tert-butyl ester synthesized in Example 162-1 and nonyl iodide as starting materials and by an operation similar to that of Example 442.

$^1$H-NMR (CDCl$_3$, 300 MHz) δ: 0.87 (3H, t, J=6.6 Hz), 1.26 (12H, brs), 1.54 (2H, brs), 1.65 (6H, s), 2.98-3.01 (4H, m), 3.09 (2H, t, J=7.2 Hz), 3.45 (2H, t, J=7.2 Hz), 3.84-3.88 (6H, m), 6.95 (1H, s), 8.09 (2H, s).

MS: 536 (M$^+$+1).

Example 768

2-[(4-{2-[[5-(dimethylamino)pyrimidin-2-yl](heptyl)amino]ethyl}-1,3-thiazol-2-yl)thio]-2-methylpropionic acid trifluoroacetate

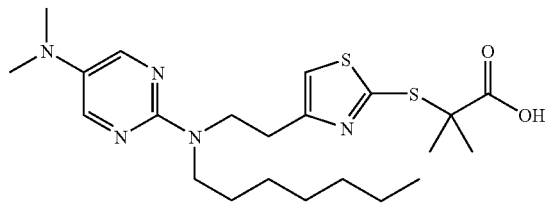

A compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and dimethylamine hydrochloride as starting materials and by an operation similar to that of Example 442-2 (solvent was changed to tert-butanol) was treated with dichloromethane and trifluoroacetic acid. The reaction solution was concentrated under reduced pressure, and the residue was purified by silica gel chromatography (elution solvent; chloroform:methanol=10:1) to give the title compound.

$^1$H-NMR (CDCl$_3$, 300 MHz) δ: 0.88 (3H, t, J=6.6 Hz), 1.26-1.29 (8H, m), 1.57 (2H, brs), 1.62 (6H, s), 2.92 (6H, s), 3.10 (2H, t, J=6.9 Hz), 3.51 (2H, t, J=7.5 Hz), 3.92 (2H, t, J=6.9 Hz), 7.05 (1H, s), 8.21 (2H, s).

MS: 466 (M$^+$+1).

Example 769

2-[(4-{2-[heptyl(5-piperidin-1-ylpyrimidin-2-yl)amino]ethyl}-1,3-thiazol-2-yl)thio]-2-methylpropionic acid trifluoroacetate

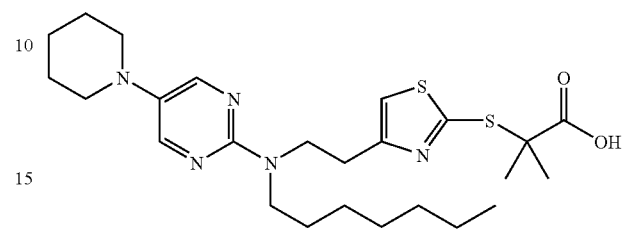

The compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and piperidine as starting materials and by an operation similar to that of Example 442-2 was treated with dichloromethane and trifluoroacetic acid. The reaction solution was concentrated under reduced pressure, and the residue was purified by silica gel chromatography (elution solvent; chloroform:methanol=10:1) to give the title compound.

$^1$H-NMR (CDCl$_3$, 300 MHz) δ: 0.88 (3H, t, J=6.6 Hz), 1.27-1.29 (8H, m), 1.56-1.59 (4H, m), 1.63 (6H, s), 1.85-1.88 (4H, m), 3.10 (2H, t, J=7.2 Hz), 3.19 (4H, t, J=5.4 Hz), 3.50 (2H, t, J=7.7 Hz), 3.91 (2H, t, J=7.2 Hz), 7.03 (1H, s), 8.36 (2H, s).

MS: 506 (M$^+$+1).

Example 770

2-{[4-(2-{heptyl[5-(3-methoxypyrrolidin-1-yl)pyrimidin-2-yl]amino}ethyl)-1,3-thiazol-2-yl]thio}-2-methylpropionic acid trifluoroacetate

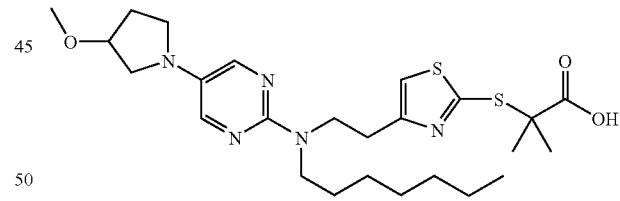

The compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and 3-methoxypyrrolidine as starting materials and by an operation similar to that of Example 442-2 was treated with dichloromethane and trifluoroacetic acid. The reaction solution was concentrated under reduced pressure, and the residue was purified by silica gel chromatography (elution solvent; chloroform:methanol=10:1) to give the title compound.

$^1$H-NMR (CDCl$_3$, 300 MHz) δ: 0.88 (3H, t, J=6.6 Hz), 1.26-1.29 (8H, m), 1.56 (2H, brs), 1.62 (6H, s), 2.05-2.17 (2H, m), 3.09 (2H, t, J=6.9 Hz), 3.28-3.53 (9H, m), 3.91 (2H, t, J=6.9 Hz), 4.10-4.11 (1H, m), 7.06 (1H, s), 8.02 (2H, s).

MS: 522 (M$^+$+1).

Example 771

2-[(4-{2-[[5-(cyclopentylamino)pyrimidin-2-yl](heptyl)amino]ethyl}-1,3-thiazol-2-yl)thio]-2-methylpropionic acid trifluoroacetate

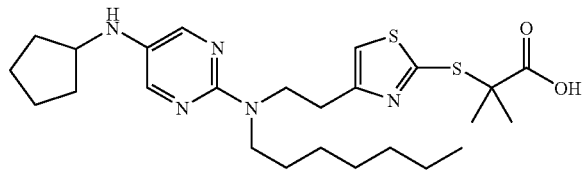

A compound obtained using 2-[(4-{2-[(5-bromopyrimidin-2-yl)(heptyl)amino]ethyl}-1,3-thiazol-2-yl)thio]-2-methylpropionic acid tert-butyl ester synthesized in Example 442-1 and cyclopentylamine as starting materials and by an operation similar to that of Example 442-2 was treated with dichloromethane and trifluoroacetic acid. The reaction solution was concentrated under reduced pressure, and the residue was purified by silica gel chromatography (elution solvent; chloroform:methanol=10:1) to give the title compound.

$^1$H-NMR (CDCl$_3$, 300 MHz) δ: 0.85-0.87 (3H, m), 1.28 (8H, brs), 1.55-1.78 (14H, m), 1.98-2.04 (2H, m), 3.08 (2H, t, J=7.2 Hz), 3.48 (2H, t, J=7.5 Hz), 3.65-3.67 (1H, m), 3.88 (2H, t, J=7.2 Hz), 7.01 (1H, s), 8.11 (2H, s).

MS: 506 (M$^+$+1).

Pharmacological Experimental Example 1

Transcription Activation Test for Human Peroxisome Proliferator-Activated Receptor (PPAR)$_\alpha$ CV-1 cells (CCL-70, manufactured by Dainippon Pharma Co., Ltd.) cultured in Dulbecco's Modified Eagle Medium (DMEM) containing 10% fetal bovine serum (FBS) were transfected, using Lipofectamine 2000 (manufactured by Invitrogen), with pBIND vector (manufactured by Promega) a fusion that expresses protein (GAL4-hPPAR$_\alpha$LBD, manufactured based on Diabetes 47: 1841-1847, 1998) of a DNA binding region of a yeast transcription factor (GAL4) and a human PPAR$_\alpha$ ligand binding region, and an internal standard renilla luciferase, and GAL4 responsive TK vector (manufactured by Promega) that expresses reporter firefly luciferase. 24 hr later, the medium was changed to a serum free medium containing a test compound, and the luciferase activity after 24 hr was measured.

The results are shown in Table 1. The results reveal that the compound of the present invention has a strong transcription activating action on human PPAR$_\alpha$.

From the above, it has been clarified that the compound of the present invention has a human. PPAR$_\alpha$ agonist action.

TABLE 28

| Example | transactivation action (EC50, nmol/l) |
|---|---|
| 34 | 10.4 |
| 100 | 11.2 |
| 162 | 21 |
| 226 | 16.5 |
| 224 | 29.7 |
| 265 | 7.0 |
| 442 | 5.5 |

TABLE 28-continued

| Example | transactivation action (EC50, nmol/l) |
|---|---|
| 326 | 38.8 |
| 346 | 13.6 |

Pharmacological Experimental Example 2

In Vivo Lipid-Lowering Action

1) Blood Triglyceride (TG)-Lowering Action in Normal Rats 7 to 9-week-old male SD rats (manufactured by SEAC Yoshitomi, Ltd.) were used for the test. A test compound and a control compound (GW-9578: J. Med. Chem. 1999, 42, 3785-3788) were dissolved or suspended in 1% ethanol, 0.05% Tween80 (final concentration), and 0.5% hydroxypropylmethyl cellulose (HPMC) was added to adjust to a given concentration. The prepared solution was orally administered once a day for 4 days. After administration for 4 days, blood samples were collected from the jugular vein under non-fasting condition and blood TG was measured by an enzyme method. The lowering rate was calculated by determining the rate of a value obtained by subtracting the average blood TG of a drug administration group from the average blood TG of a vehicle administration group, to the average blood TG of the vehicle administration group.

The results are shown in Table 2. The results reveal that the compound of the present invention has a superior blood hypotriglyceridemic action.

2) Influence on Serum Lipid of High Cholesterol Diet-Treated Rat 8-week-old male SD rats (manufactured by SEAC Yoshitomi, Ltd.) were raised on a standard diet CE-2 (manufactured by Japan Clea, Inc.) added with 1% cholesterol, 2% olive oil and 0.2% cholic acid, from one week before test compound administration to the last day of the administration. A test compound and a control compound (GW-9578) were dissolved or suspended in 1% ethanol, 0.05% Tween80 (final concentration), and 0.5% hydroxypropylmethyl cellulose (HPMC) was added to adjust to a given concentration. The prepared solution was orally administered once a day for 5 days. After administration for 5 days, blood samples were collected from the jugular vein under non-fasting condition and blood lipid was measured by an enzyme method. The lowering rate was calculated by determining the rate of a value obtained by subtracting the average blood TG (or average blood TC) of a drug administration group from the average blood triglyceride (TG) (or average blood total cholesterol (TC)) of a vehicle administration group, to the average blood TG (or average blood TC) of the vehicle administration group.

The results are shown in Table 3. The results reveal that the compound of the present invention has a superior blood hypolipidemic (TG, TC) action.

From the above results, it has been clarified that the compound of the present invention has a superior hypolipidemic action.

TABLE 29

| Example | hypotriglyceridemic rate (%, 0.3 mg/kg, p.o.) |
|---|---|
| GW-9578 | 50-60 |
| 34 | 62 |

441

TABLE 29-continued

| Example | hypotriglyceridemic rate (%, 0.3 mg/kg, p.o.) |
|---|---|
| 100 | 61 |
| 162 | 65 |
| 226 | 64 |
| 224 | 63 |
| 265 | 69 |
| 442 | 65 |
| 326 | 59 |
| 346 | 63 |

TABLE 30

| | lowering rate (%, 0.3 mg/kg, p.o.) | |
|---|---|---|
| Example | TG | TC |
| GW-9578 | 30-50 | 30-50 |
| 34 | 45 | 43 |
| 100 | 38 | 35 |
| 162 | 48 | 31 |
| 226 | 56 | 38 |
| 224 | 57 | 31 |
| 265 | 63 | 31 |
| 442 | 39 | 38 |
| 326 | 43 | 31 |
| 346 | 47 | 31 |

INDUSTRIAL APPLICABILITY

According to the present invention, a compound useful as an agent for the prophylaxis and/or treatment of hyperlipidemia and an intermediate therefor can be provided.

This application has been filed claiming priority benefit based on a patent application No. 2004-321347 filed in Japan.

The invention claimed is:

1. A carboxylic acid derivative containing a thiazole ring represented by formula (I):

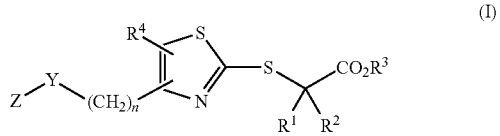

(I)

wherein $R^1$ and $R^2$ are the same or different and each is a hydrogen atom or an alkyl group, or $R^1$ and $R^2$ are bonded to each other to form a cycloalkyl group;
$R^3$ is a hydrogen atom or an alkyl group;
$R^4$ is a hydrogen atom, an alkyl group or an aryl group;
n is an integer of 1 to 5;
Y is an oxygen atom, a sulfur atom, —$NR^5$—, —$CONR^5$—, —$NR^5CO$— or —$NHCONR^5$—, wherein $R^5$ is a hydrogen atom, an alkyl group, a cycloalkylalkyl group, an aryl group, an arylalkyl group, an arylalkenyl group, an aryloxyalkyl group, a heteroaryl group or a heteroarylalkyl group; and
Z is a cycloalkyl group, an aryl group, an arylalkyl group, an arylalkenyl group, an aryloxyalkyl group, a heteroaryl group or a heteroarylalkyl group,
wherein, in the aforementioned groups, an alkyl group, a cycloalkyl group, a cycloalkylalkyl group, an aryl group, an arylalkyl group, an arylalkenyl group, an aryloxyalkyl group, a heteroaryl group and a heteroarylalkyl group each optionally have substituent, or a pharmaceutically acceptable salt thereof.

2. The carboxylic acid derivative containing the thiazole ring of claim 1, which is represented by formula (I'):

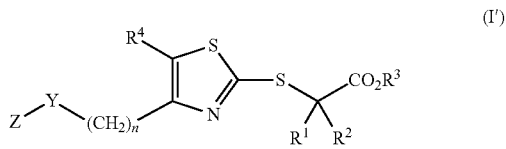

(I')

wherein $R^1$, $R^2$, $R^3$, $R^4$, n, Y and Z are as defined above, or a pharmaceutically acceptable salt thereof.

3. The carboxylic acid derivative containing the thiazole ring of claim 1, wherein, in the formula (I), n is an integer of 1 to 3, Y is an oxygen atom, a sulfur atom, —$NR^6$—, —$CONR^6$—, —$NR^6CO$— or —$NHCONR^6$—, wherein $R^6$ is a hydrogen atom, an alkyl group, a cycloalkylalkyl group, an arylalkyl group, an arylalkenyl group, an aryloxyalkyl group or a heteroarylalkyl group, wherein, in the aforementioned groups, an alkyl group, an arylalkyl group, an arylalkenyl group, an aryloxyalkyl group and a heteroarylalkyl group each optionally have substituent, and Z is an optionally substituted cycloalkyl group, an optionally substituted aryl group, an optionally substituted arylalkyl group or an optionally substituted heteroaryl group, or a pharmaceutically acceptable salt thereof.

4. The carboxylic acid derivative containing the thiazole ring of claim 1, wherein, in the formula (I), Y is an oxygen atom, a sulfur atom or —$NR^7$—, wherein $R^7$ is a hydrogen atom, an alkyl group or —$CH_2$—W, wherein W is an aryl group or a heteroaryl group, wherein, in the aforementioned groups, an alkyl group, an aryl group and a heteroaryl group each optionally have, and Z is represented by a substituent selected from formula (II):

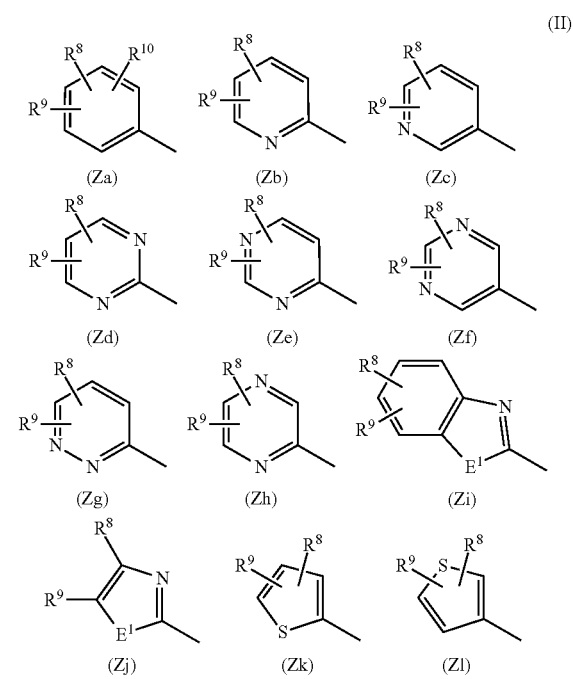

(II)

-continued

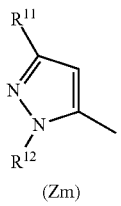 and 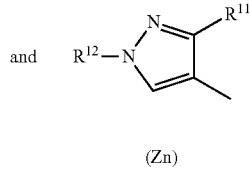

(Zm)  (Zn)

wherein $R^8$, $R^9$ and $R^{10}$ are the same or different and each is a hydrogen atom, an alkyl group, an aryl group, a heteroaryl group, a halogen atom, a haloalkyl group, a haloalkyloxy group, a cyano group, a nitro group, $-NR^{13}R^{14}$, $-NR^{15}COR^{16}$, $-CONR^{17}R^{18}$, wherein $R^{13}$, $R^{14}$, $R^{15}$, $R^{16}$, $R^{17}$ and $R^{18}$ are the same or different and each is independently a hydrogen atom, an alkyl group, a cycloalkyl group, an aryl group, an arylalkyl group, a heteroaryl group or a heteroarylalkyl group, or $R^{13}$ and $R^{14}$ can be bonded to each other to form a heterocyclic ring wherein the heterocyclic ring comprises a total of 2 to 10 carbon atoms and 1 to 3 heteroatoms selected from the group consisting of oxygen atom, sulfur atom and nitrogen atom, and $R^{15}$ and $R^{16}$ can be bonded to each other to form a heterocyclic ring wherein the heterocyclic ring comprises a total of 2 to 10 carbon atoms and 1 to 3 heteroatoms selected from the group consisting of oxygen atom, sulfur atom and nitrogen atom, $-OR^{19}$, $-COR^{20}$ or $-C\equiv R^{21}$, wherein $R^{19}$, $R^{20}$ and $R^{21}$ are each independently a hydrogen atom, an alkyl group, a cycloalkyl group, an aryl group, an arylalkyl group, a heteroaryl group or a heteroarylalkyl group;

$R^{11}$ is a hydrogen atom, an alkyl group, a cycloalkyl group, an aryl group, a heteroaryl group, a halogen atom, a haloalkyl group, a cyano group or a nitro group;

$R^{12}$ is a hydrogen atom, an alkyl group, a cycloalkyl group, a cycloalkylalkyl group, an aryl group, an arylalkyl group, a heteroaryl group or a heteroarylalkyl group;

$E^1$ is an oxygen atom, a sulfur atom or $-NR^{22}-$, wherein $R^{22}$ is a hydrogen atom, an alkyl group, a cycloalkyl group, a cycloalkylalkyl group, an aryl group, an arylalkyl group or a heteroarylalkyl group, wherein, in the aforementioned groups, an alkyl group, a cycloalkyl group, a cycloalkylalkyl group, an aryl group, an arylalkyl group, a heteroaryl group, a heteroarylalkyl group and a heterocycle each optionally have substituent, or a pharmaceutically acceptable salt thereof.

5. The carboxylic acid derivative containing the thiazole ring of claim 1, wherein, in the formula (I), Y is an oxygen atom, a sulfur atom or $-NR^{23}-$, wherein $R^{23}$ is a hydrogen atom, an optionally substituted alkyl group, or a substituent selected from formula (III):

(III)

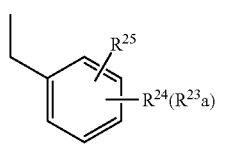 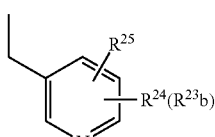

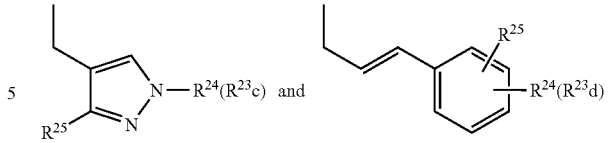

wherein $R^{24}$ and $R^{25}$ are the same or different and each is a hydrogen atom, an alkyl group, a cycloalkyl group, an aryl group, an arylcarbonyl group, a heteroaryl group, a halogen atom, a haloalkyl group, a haloalkyloxy group, $-NR^{26}R^{27}$, $-NR^{28}COR^{29}$, $-CONR^{30}R^{31}$, wherein $R^{26}$, $R^{27}$, $R^{28}$, $R^{29}$, $R^{30}$ and $R^{31}$ are the same or different and each is independently a hydrogen atom, an alkyl group, an aryl group or a heteroaryl group, or $R^{26}$ and $R^{27}$, and $R^{30}$ and $R^{31}$ are bonded to each other to form a heterocycle, or $-OR^{32}$, wherein $R^{32}$ is a hydrogen atom, an alkyl group, a cycloalkyl group, an aryl group, an arylalkyl group, a heteroaryl group or a heteroarylalkyl group, wherein, in the aforementioned groups, an alkyl group, a cycloalkyl group, an aryl group, an arylalkyl group, a heteroaryl group, a heteroarylalkyl group and a heterocycle each optionally have substituent, and Z is a substituent selected from formula (IV):

(IV)

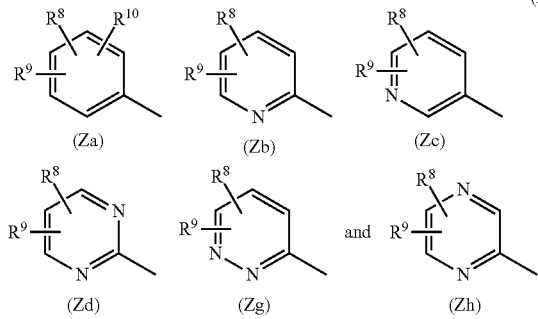

(Za)  (Zb)  (Zc)

(Zd)  (Zg) and (Zh)

wherein $R^8$, $R^9$ and $R^{10}$ are as defined above, or a pharmaceutically acceptable salt thereof.

6. The carboxylic acid derivative containing the thiazole ring of claim 1, which is selected from the group consisting of

(34) 2-[(4-[2-[(4'-fluorobiphenyl-4-yl)oxy]ethyl]-1,3-thiazol-2-yl)thio]-2-methylpropionic acid

(38) 2-[(4-{2-[(4'-chlorobiphenyl-4-yl)oxy]ethyl}-1,3-thiazol-2-yl)thio]-2-methylpropionic acid

(68) 2-[(4-{2-[(3'-fluorobiphenyl-4-yl)oxy]ethyl}-1,3-thiazol-2-yl)thio]-2-methylpropionic acid

(76) 2-[(4-{2-[(4'-fluorobiphenyl-4-yl)thio]ethyl}-1,3-thiazol-2-yl)thio]-2-methylpropionic acid

(79) 2-[(4-[2-[(3,4'-difluorobiphenyl-4-yl)oxy]ethyl]-1,3-thiazol-2-yl)thio]-2-methylpropionic acid (100) 2-{[4-(2-{[5-(4-fluorophenyl)pyridin-2-yl]oxy}ethyl)-1,3-thiazol-2-yl]thio-2-methylpropionic acid (102) 2-methyl-2-({4-[2-({5-[4-(trifluoromethyl)phenyl]pyridin-2-yl}oxy)ethyl]-1,3-thiazol-2-yl}thio)propionic acid (103) 2-methyl-2-({4-[2-({5-[3-(trifluoromethyl)phenyl]pyridin-2-yl}oxy)ethyl]-1,3-thiazol-2-yl}thio)propionic acid (104) 2-methyl-2-({4-[2-({5-[4-(trifluoromethoxy)phenyl]pyridin-2-yl}oxy)ethyl]-1,3-thiazol-2-yl}thio)propionic acid (106)  2-{[4-(2-{[5-(4-chlorophenyl)pyridin-2-yl]oxy}ethyl)-1,3-thiazol-2-yl]thio}-2-methylpropionic acid
(107)  2-{[4-(2-{[5-(3-chlorophenyl)pyridin-2-yl]oxy}ethyl)-1,3-thiazol-2-yl]thio}-2-methylpropionic acid
(108)  2-{[4-(2-{[5-(3,4-dichlorophenyl)pyridin-2-yl]oxy}ethyl)-1,3-thiazol-2-yl]thio}-2-methylpropionic acid
(109)  2-{[4-(2-{[5-(3-chloro-4-fluorophenyl)pyridin-2-yl]oxy}ethyl)-1,3-thiazol-2-yl]thio}-2-methylpropionic acid
(152)  2-methyl-2-{[4-({[4'-(trifluoromethyl)biphenyl-4-yl]methoxy}methyl)-1,3-thiazol-2-yl]thio}propionic acid
(162)  2-methyl-2-({4-[2-({5-[4-(trifluoromethoxy)phenyl]pyrimidin-2-yl}amino)ethyl]-1,3-thiazol-2-yl}thio)propionic acid
(220)  2-{[4-(2-{[6-(4-chloro-2-fluorophenyl)pyridazin-3-yl]amino}ethyl)-1,3-thiazol-2-yl]thio}-2-methylpropionic acid
(224)  2-({4-[2-({6-[2-fluoro-4-(trifluoromethyl)phenyl]pyridazin-3-yl}amino)ethyl]-1,3-thiazol-2-yl}thio)-2-methylpropionic acid
(226)  2-{[4-(2-{[5-(4-chlorophenyl)pyrazin-2-yl]amino}ethyl)-1,3-thiazol-2-yl]thio}-2-methylpropionic acid
(227)  2-[(4-{2-[[5-(4-chlorophenyl)pyrazin-2-yl](methyl)amino]ethyl}-1,3-thiazol-2-yl)thio]-2-methylpropionic acid
(229)  2-methyl-2-({4-[2-(methyl{5-[4-(trifluoromethyl)phenyl]pyrazin-2-yl}amino)ethyl]-1,3-thiazol-2-yl}thio)propionic acid
(231)  2-methyl-2-({4-[2-(methyl{5-[4-(trifluoromethoxy)phenyl]pyrazin-2-yl}amino)ethyl]-1,3-thiazol-2-yl}thio)propionic acid
(232)  2-({4-[2-({5-[2-fluoro-4-(trifluoromethyl)phenyl]pyrazin-2-yl}amino)ethyl]-1,3-thiazol-2-yl}thio)-2-methylpropionic acid
(243)  2-methyl-2-({4-[2-({5-[4-(trifluoromethyl)phenyl]pyridin-2-yl}amino)ethyl]-1,3-thiazol-2-yl}thio)propionic acid
(260)  2-{[4-(2-{[6-(4-chlorophenyl)pyridin-3-yl]amino}ethyl)-1,3-thiazol-2-yl]thio}-2-methylpropionic acid
(261)  2-methyl-2-({4-[2-({6-[4-(trifluoromethyl)phenyl]pyridin-3-yl}amino)ethyl]-1,3-thiazol-2-yl}thio)propionic acid
(265)  2-[(4-{2-[(5-ethylpyrimidin-2-yl)(heptyl)amino]ethyl}-1,3-thiazol-2-yl)thio]-2-methylpropionic acid
(267)  2-[(4-{2-[heptyl(5-propylpyrimidin-2-yl)amino]ethyl}-1,3-thiazol-2-yl)thio]-2-methylpropionic acid
(319)  2-[(4-{2-[3-(2,4-difluorophenyl)-1-heptylureido]ethyl}-1,3-thiazol-2-yl)thio]-2-methylpropionic acid
(320)  2-({4-[2-(3-cyclohexyl-1-heptylureido)ethyl]-1,3-thiazol-2-yl}thio)-2-methylpropionic acid
(326)  2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid
(329)  2-[(4-{2-[(5-ethylpyrimidin-2-yl)(hexyl)amino]ethyl}-1,3-thiazol-2-yl)thio]-2-methylpropionic acid
(346)  2-{[4-(2-{(5-ethylpyrimidin-2-yl)[(2E)-3-phenylprop-2-en-1-yl]amino}ethyl)-1,3-thiazol-2-yl]thio}-2-methylpropionic acid
(379)  2-[(4-{2-[(3-butoxypropyl)(5-ethylpyrimidin-2-yl)amino]ethyl}-1,3-thiazol-2-yl)thio]-2-methylpropionic acid
(430)  2-methyl-2-[(4-{2-[[(1-phenyl-1H-pyrazol-4-yl)methyl](5-propylpyrimidin-2-yl)amino]ethyl}-1,3-thiazol-2-yl)thio]propionic acid
(442)  2-[(4-{2-[heptyl(5-morpholin-4-ylpyrimidin-2-yl)amino]ethyl}-1,3-thiazol-2-yl)thio]-2-methylpropionic acid
(449)  2-[(4-{2-[(3-ethyl-1H-pyrazol-5-yl)(heptyl)amino]ethyl}-1,3-thiazol-2-yl)thio]-2-methylpropionic acid, and
(450)  2-[(4-{2-[heptyl(3-propyl-1H-pyrazol-5-yl)amino]ethyl}-1,3-thiazol-2-yl)thio]-2-methylpropionic acid,
or a pharmaceutically acceptable salt thereof.

7. The carboxylic acid derivative containing the thiazole ring of claim 1, wherein, in the formula (I), Y is an oxygen atom and Z is an aryl group or a heteroaryl group, or a pharmaceutically acceptable salt thereof.

8. The carboxylic acid derivative containing the thiazole ring of claim 1, wherein, in the formula (I), Y is an oxygen atom and Z is an aryl group, or a pharmaceutically acceptable salt thereof.

9. The carboxylic acid derivative containing the thiazole ring of claim 1, which is selected from the group consisting of

(34)  2-[(4-{2-[(4'-fluorobiphenyl-4-yl)oxy]ethyl}-1,3-thiazol-2-yl)thio]-2-methylpropionic acid
(38)  2-[(4-{2-[(4'-chlorobiphenyl-4-yl)oxy]ethyl}-1,3-thiazol-2-yl)thio]-2-methylpropionic acid
(68)  2-[(4-{2-[(3'-fluorobiphenyl-4-yl)oxy]ethyl}-1,3-thiazol-2-yl)thio]-2-methylpropionic acid
(76)  2-[(4-{2-[(4'-fluorobiphenyl-4-yl)thio]ethyl}-1,3-thiazol-2-yl)thio]-2-methylpropionic acid
(79)  2-[(4-{2-[(3,4'-difluorobiphenyl-4-yl)oxy]ethyl}-1,3-thiazol-2-yl)thio]-2-methylpropionic acid
(100)  2-{[4-(2-{[5-(4-fluorophenyl)pyridin-2-yl]oxy}ethyl)-1,3-thiazol-2-yl]thio-2-methylpropionic acid
(102)  2-methyl-2-({4-[2-({5-[4-(trifluoromethyl)phenyl]pyridin-2-yl}oxy)ethyl]-1,3-thiazol-2-yl}thio)propionic acid
(103)  2-methyl-2-({4-[2-({5-[3-(trifluoromethyl)phenyl]pyridin-2-yl}oxy)ethyl]-1,3-thiazol-2-yl}thio)propionic acid
(104)  2-methyl-2-({4-[2-({5-[4-(trifluoromethoxy)phenyl]pyridin-2-yl}oxy)ethyl]-1,3-thiazol-2-yl}thio)propionic acid
(106)  2-{[4-(2-{[5-(4-chlorophenyl)pyridin-2-yl]oxy}ethyl)-1,3-thiazol-2-yl]thio}-2-methylpropionic acid
(107)  2-{[4-(2-{[5-(3-chlorophenyl)pyridin-2-yl]oxy}ethyl)-1,3-thiazol-2-yl]thio}-2-methylpropionic acid
(108)  2-{[4-(2-{[5-(3,4-dichlorophenyl)pyridin-2-yl]oxy}ethyl)-1,3-thiazol-2-yl]thio}-2-methylpropionic acid
(109)  2-{[4-(2-{[5-(3-chloro-4-fluorophenyl)pyridin-2-yl]oxy}ethyl)-1,3-thiazol-2-yl]thio}-2-methylpropionic acid
(152)  2-methyl-2-{[4-({[4'-(trifluoromethyl)biphenyl-4-yl]methoxy}methyl)-1,3-thiazol-2-yl]thio}propionic acid
(162)  2-methyl-2-({4-[2-({5-[4-(trifluoromethoxy)phenyl]pyrimidin-2-yl}amino)ethyl]-1,3-thiazol-2-yl}thio)propionic acid
(220)  2-{[4-(2-{[6-(4-chloro-2-fluorophenyl)pyridazin-3-yl]amino}ethyl)-1,3-thiazol-2-yl]thio}-2-methylpropionic acid, and (224) 2-({4-[2-({6-[2-fluoro-4-(trifluoromethyl)phenyl]pyridazin-3-yl}amino)ethyl]-1,3-thiazol-2-yl}thio)-2-methylpropionic acid, or a pharmaceutically acceptable salt thereof.

10. The carboxylic acid derivative containing the thiazole ring of claim 1, wherein, in the formula (I), Y is —NR$^{5a}$—, wherein R$^{5a}$ is an alkyl group having 4 to 10 carbon atoms, and Z is a heteroaryl group, or a pharmaceutically acceptable salt thereof.

11. The carboxylic acid derivative containing the thiazole ring of claim 1, wherein, in the formula (I), Y is —NR$^{5b}$—, wherein R$^{5b}$ is alkyl group having 6 to 9 carbon atoms, and Z is a heteroaryl group, or a pharmaceutically acceptable salt thereof.

12. The carboxylic acid derivative containing the thiazole ring of claim 1, which is selected from the group consisting of (265) 2-[(4-{2-[(5-ethylpyrimidin-2-yl)(heptyl)amino]ethyl}-1,3-thiazol-2-yl)thio]-2-methylpropionic acid (267) 2-[(4-{2-[heptyl(5-propylpyrimidin-2-yl)amino]ethyl}-1,3-thiazol-2-yl)thio]-2-methylpropionic acid (329) 2-[(4-{2-[(5-ethylpyrimidin-2-yl)(hexyl)amino]ethyl}-1,3-thiazol-2-yl)thio]-2-methylpropionic acid (442) 2-[(4-{2-[heptyl(5-morpholin-4-ylpyrimidin-2-yl)amino]ethyl}-1,3-thiazol-2-yl)thio]-2-methylpropionic acid (449) 2-[(4-{2-[(3-ethyl-1H-pyrazol-5-yl)(heptyl)amino]ethyl}-1,3-thiazol-2-yl)thio]-2-methylpropionic acid, and (450) 2-[(4-{2-[heptyl(3-propyl-1H-pyrazol-5-yl)amino]ethyl}-1,3-thiazol-2-yl)thio]-2-methylpropionic acid, or a pharmaceutically acceptable salt thereof.

13. The carboxylic acid derivative containing the thiazole ring of claim 1, wherein, in the formula (I), Y is —NR$^{5c}$—, wherein R$^{5c}$ is an arylalkyl group or an heteroarylalkyl group, and Z is a heteroaryl group, or a pharmaceutically acceptable salt thereof.

14. The carboxylic acid derivative containing the thiazole ring of claim 1, wherein, in the formula (I), Y is —NR$^{5d}$—, wherein R$^{5d}$ is a heteroarylalkyl group, and Z is a heteroaryl group, or a pharmaceutically acceptable salt thereof.

15. The carboxylic acid derivative containing the thiazole ring of claim 1, which is a compound selected from the group consisting of (326) 2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid, and (430) 2-methyl-2-[(4-{2-[[(1-phenyl-1H-pyrazol-4-yl)methyl](5-propylpyrimidin-2-yl)amino]ethyl}-1,3-thiazol-2-yl)thio]propionic acid, or a pharmaceutically acceptable salt thereof.

16. A carboxylic acid derivative containing a thiazole ring, which is

(34) 2-[(4-{2-[(4'-fluorobiphenyl-4-yl)oxy]ethyl}-1,3-thiazol-2-yl)thio]-2-methylpropionic acid, or a pharmaceutically acceptable salt thereof.

17. A carboxylic acid derivative containing a thiazole ring, which is (442) 2-[(4-{2-[heptyl(5-morpholin-4-ylpyrimidin-2-yl)amino]ethyl}-1,3-thiazol-2-yl)thio]-2-methylpropionic acid, or a pharmaceutically acceptable salt thereof.

18. A carboxylic acid derivative containing a thiazole ring, which is (326) 2-{[4-(2-{(5-ethylpyrimidin-2-yl)[(1-phenyl-1H-pyrazol-4-yl)methyl]amino}ethyl)-1,3-thiazol-2-yl]thio}-2-methylpropionic acid, or a pharmaceutically acceptable salt thereof.

19. A carboxylic acid derivative containing a thiazole ring selected from the group consisting of:

(40) 2-[(4-{2-[(4'-cyanobiphenyl-4-yl)oxy]ethyl}-1,3-thiazol-2-yl)thio]-2-methylpropionic acid, (60-2) 4-(2-{2-[(2-tert-butoxy-1,1-dimethyl-2-oxoethyl)thio]-1,3-thiazol-4-yl}ethoxy)benzoic acid,

(66) 2-methyl-2-[(4-{2-[4-(morpholin-4-ylcarbonyl)phenoxy]ethyl}-1,3-thiazol-2-yl)thio]propionic acid,

(73) 2-{[4-(2-{[4'-(acetylamino)biphenyl-4-yl]oxy}ethyl)-1,3-thiazol-2-yl]thio}-2-methylpropionic acid,

(74) 2-{[4-(2-{[4'-(dimethylamino)biphenyl-4-yl]oxy}ethyl)-1,3-thiazol-2-yl]thio}-2-methylpropionic acid, (92-3) 2-{[4-(2-{[4'-fluoro-3-(methoxycarbonyl)biphenyl-4-yl]oxy}ethyl)-1,3-thiazol-2-yl]thio}-2-methylpropionic acid, (93-1) 4'-fluoro-4-(2-{2-[(2-tert-butoxy-1,1-dimethyl-2-oxoethyl)thio]-1,3-thiazol-4-yl}ethoxy)biphenyl-3-carboxylic acid, (93-3) 2-{[4-(2-{[4'-fluoro-3-(morpholin-4-ylcarbonyl)biphenyl-4-yl]oxy}ethyl)-1,3-thiazol-2-yl]thio}-2-methylpropionic acid, (149) 2-{[4-(2-{4-[4-(4-fluorophenyl)piperazin-1-yl]phenoxy}ethyl)-1,3-thiazol-2-yl]thio}-2-methylpropionic acid, (150) 2-methyl-2-({4-[2-(4-{4-[4-(trifluoromethyl)phenyl]piperazin-1-yl}phenoxy)ethyl]-1,3-thiazol-2-yl}thio)propionic acid, (152-3) 2-methyl-2-{[4-({[4'-(trifluoromethyl)biphenyl-4-yl]methoxy}methyl)-1,3-thiazol-2-yl]thio}propionic acid, (153) 2-[(4-{[(4'-fluorobiphenyl-4-yl)methoxy]methyl}-1,3-thiazol-2-yl)thio]-2-methylpropionic acid, (154) 2-[(4-{[(4'-chlorobiphenyl-4-yl)methoxy]methyl}-1,3-thiazol-2-yl)thio]-2-methylpropionic acid, (155-4) 2-[(4-{2-[(4'-fluorobiphenyl-4-yl)methoxy]ethyl}-1,3-thiazol-2-yl)thio]-2-methylpropionic acid, (156) 2-[(4-{2-[(4'-chlorobiphenyl-4-yl)methoxy]ethyl}-1,3-thiazol-2-yl)thio]-2-methylpropionic acid, (157) 2-methyl-2-{[4-(2-{[4'-(trifluoromethyl)biphenyl-4-yl]methoxy}ethyl)-1,3-thiazol-2-yl]thio}propionic acid, (391) 2-[(4-{2-[[3-(4-chlorophenoxy)propyl](5-ethylpyrimidin-2-yl)amino]ethyl}-1,3-thiazol-2-yl)thio]-2-methylpropionic acid, (392) 2-{[4-(2-{(5-ethylpyrimidin-2-yl)[3-(4-methoxyphenoxy)propyl]amino}ethyl)-1,3-thiazol-2-yl]thio}-2-methylpropionic acid, (397) 2-[(4-{2-[[2-(benzyloxy)ethyl](5-ethylpyrimidin-2-yl)amino]ethyl}-1,3-thiazol-2-yl)thio]-2-methylpropionic acid, (398) 2-[(4-{2-[[3-(benzyloxy)propyl](5-ethylpyrimidin-2-yl)amino]ethyl}-1,3-thiazol-2-yl)thio]-2-methylpropionic acid, (437-2) 4-{[(2-{2-[(2-tert-butyl-1,1-dimethyl-2-oxoethyl)thio]-1,3-thiazol-4-yl}ethyl)(5-ethylpyrimidin-2-yl)amino]methyl}benzoic acid, (437-4) 2-[(4-{2-[{4-[(ethylamino)carbonyl]benzyl}(5-ethylpyrimidin-2-yl)amino]ethyl}-1,3-thiazol-2-yl)thio]-2-methylpropionic acid, (438) 2-{[4-(2-{(5-ethylpyrimidin-2-yl)[4-(pyrrolidin-1-ylcarbonyl)benzyl]amino}ethyl)-1,3-thiazol-2-yl]thio}-2-methylpropionic acid, (455-3) 2-methyl-2-({4-[({[4'-(trifluoromethyl)biphenyl-4-yl]carbonyl}amino)ethyl]-1,3-thiazol-2-yl}thio)propionic acid, (456) 2-{[4-({[(4'-fluorobiphenyl-4-yl)carbonyl]amino}methyl)-1,3-thiazol-2-yl]thio}-2-methylpropionic acid,
(457) 2-{[4-({[(4'-chlorobiphenyl-4-yl)carbonyl]amino}methyl)-1,3-thiazol-2-yl]thio}-2-methylpropionic acid,
(458-3) 2-methyl-2-{[4-(2-oxo-2-{[4'-(trifluoromethyl)biphenyl-4-yl]amino}ethyl)-1,3-thiazol-2-yl]thio}propionic acid,
(459) 2-[(4-{2-[(4'-fluorobiphenyl-4-yl)amino]-2-oxoethyl}-1,3-thiazol-2-yl)thio]-2-methylpropionic acid,
(460) 2-[(4-{2-[(4'-chlorobiphenyl-4-yl)amino]-2-oxoethyl}-1,3-thiazol-2-yl)thio]-2-methylpropionic acid,
(495) 2-((4-(2-((2-(benzyloxy)ethyl)(phenyl)amino)ethyl)thiazol-2-yl)thio)-2-methylpropionic acid,
(502) 2-((4-(2-((2-(benzyloxy)ethyl)(2,4-difluorophenyl)amino)ethyl)thiazol-2-yl)thio)-2-methylpropionic acid,
(504) 2-[(4-{2-[[4-(2-hydroxyethyl)phenyl] (3-phenylpropyl)amino]ethyl}-1,3-thiazol-2-yl)thio]-2-methylpropionic acid,
(510) 2-((4-(2-((2-(benzyloxy)ethyl)(3,4-dimethoxyphenyl)amino)ethyl)thiazol-2-yl)thio)-2-methylpropionic acid,
(514) 2-((4-(2-((4-(2-hydroxyethyl)phenyl)(nonyl)amino)ethyl)thiazol-2-yl)thio)-2-methylpropionic acid,
(515) 2-((4-(2-((4-(2-hydroxyethyl)phenyl)(isobutyl)amino)ethyl)thiazol-2-yl)thio)-2-methylpropionic acid,
(516) 2-((4-(2-((4-(2-hydroxyethyl)phenyl)(isopentyl)amino)ethyl)thiazol-2-yl)thio)-2-methylpropionic acid,
(517) (E)-2-((4-(2-(cinnamyl(4-(2-hydroxyethyl)phenyl)amino)ethyl)thiazol-2-yl)thio)-2-methylpropionic acid,
(518) 2-((4-(2-((biphenyl-4-ylmethyl)(4-(2-hydroxyethyl)phenyl)amino)ethyl)thiazol-2-yl)thio)-2-methylpropionic acid,
(519) 2-((4-(2-((furan-2-ylmethyl)(4-(2-hydroxyethyl)phenyl)amino)ethyl)thiazol-2-yl)thio)-2-methylpropionic acid,
(525) 2-((4-(2-(heptyl(4-(2-hydroxyethyl)phenyl)amino)ethyl)thiazol-2-yl)thio)-2-methylpropionic acid,
(526) 2-((4-(2-((4-(2-hydroxyethyl)phenyl)(2-naphthylmethyl)amino)ethyl)thiazol-2-yl)thio)-2-methylpropionic acid,
(528) (E)-2-((4-(2-(but-2-enyl(3-isopropylphenyl)amino)ethyl)thiazol-2-yl)thio)-2-methylpropionic acid,
(529) 2-((4-(2-((2-(benzyloxy)ethyl)(3-isopropylphenyl)amino)ethyl)thiazol-2-yl)thio)-2-methylpropionic acid,
(534) (E)-2-((4-(2-((3-isopropylphenyl)(3-(5-nitrofuran-2-yl)propen-2-yl)amino)ethyl)thiazol-2-yl)thio)-2-methylpropionic acid,
(547) 2-((4-(2-(biphenyl-3-yl(2-(benzyloxy)ethyl)amino)ethyl)thiazol-2-yl)thio)-2-methylpropionic acid,
(551) (E)-2-((4-(2-(biphenyl-3-yl(3-(5-nitrofuran-2-yl)propen-2-yl)amino)ethyl)thiazol-2-yl)thio)-2-methylpropionic acid,
(556) 2-((4-(2-((2-(benzyloxy)ethyl)(1-naphthyl)amino)ethyl)thiazol-2-yl)thio)-2-methylpropionic acid,
(567) (E)-2-methyl-2-((4-(2-((3-(5-nitrofuran-2-yl)propen-2-yl)(4-phenoxyphenyl)amino)ethyl)thiazol-2-yl)thio) propionic acid,
(574) 2-((4-(2-((2-(benzyloxy)ethyl)(2,4-dimethylphenyl)amino)ethyl)thiazol-2-yl)thio)-2-methylpropionic acid,
(586) (E)-2-((4-(2-((4-butoxyphenyl)(3-(5-nitrofuran-2-yl)propen-2-yl)amino)ethyl)thiazol-2-yl)thio)-2-methylpropionic acid,
(594) 2-((4-(2-((2-(benzyloxy)ethyl)(2-methoxyphenyl)amino)ethyl)thiazol-2-yl)thio)-2-methylpropionic acid,
(605) (E)-2-methyl-2-((4-(2-((3-(5-nitrofuran-2-yl)propen-2-yl)(3,4,5-trimethoxyphenyl)amino)ethyl)thiazol-2-yl)thio) propionic acid,
(613) 2-((4-(2-((2-(benzyloxy)ethyl)(2-fluorophenyl)amino)ethyl)thiazol-2-yl)thio)-2-methylpropionic acid,
(624) (E)-2-((4-(2-((4-butylphenyl)(3-(5-nitrofuran-2-yl)propen-2-yl)amino)ethyl)thiazol-2-yl)thio)-2-methylpropionic acid,
(668) 2-((4-(2-((biphenyl-4-ylmethyl)(4-(4-(diethylamino)phenyl)thiazol-2-yl)amino)ethyl)thiazol-2-yl)thio)-2-methylpropionic acid,
(669) 2-((4-(2-((biphenyl-4-ylmethyl)(4-(4-(pyrrolidin-1-yl)phenyl)thiazol-2-yl)amino)ethyl)thiazol-2-yl)thio)-2-methylpropionic acid,
(672) 2-((4-(2-((biphenyl-4-ylmethyl)(4-(methoxycarbonylmethyl)thiazol-2-yl)amino)ethyl)thiazol-2-yl)thio)-2-methylpropionic acid,
(673) 2-((4-(2-((biphenyl-4-ylmethyl)(4-(ethoxycarbonyl)thiazol-2-yl)amino)ethyl)thiazol-2-yl)thio)-2-methylpropionic acid,
(674) 2-((4-(2-((biphenyl-4-ylmethyl)(4-oxo-4,5-dihydrothiazol-2-yl)amino)ethyl)thiazol-2-yl)thio)-2-methylpropionic acid,
(682) 2-methyl-2-((4-(2-((4'-nitro-biphenyl-4-yl)amino)ethyl)thiazol-2-yl)thio) propionic acid,
(683) 2-methyl-2-((4-(2-((4-(methylthio)phenyl)amino)ethyl)thiazol-2-yl)thio) propionic acid,
(692) 2-((4-(2-((4-(2-hydroxyethyl)phenyl)amino)ethyl)thiazol-2-yl)thio)-2-methylpropionic acid,
(697) 2-((4-(2-(3,4-methylenedioxyphenylamino)ethyl)thiazol-2-yl)thio)-2-methylpropionic acid,
(718) 2-methyl-2-((4-(2-(4-(methylthio)phenoxy)ethyl)thiazol-2-yl)thio) propionic acid,
(723) 2-((4-(2-((3-(methoxycarbonyl)napht-2-yl)oxy)ethyl)thiazol-2-yl)thio)-2-methylpropionic acid,
(730) 2-((4-(2-(4-(3-methoxy-3-oxopropionyl)phenoxy)ethyl)thiazol-2-yl)thio)-2-methylpropionic acid, and
(733-2) 2-methyl-2-[(4-{2-[(4'-nitrobiphenyl-4-yl)oxy]ethyl}-1,3-thiazol-2-yl)thio]propionic acid,
or a pharmaceutically acceptable salt thereof.

20. A carboxylic acid derivative containing a thiazole ring selected from the group consisting of:
(50-1) benzoic acid 4-(2-{2-[(2-tert-butoxy-1,1-dimethyl-2-oxyethyl)thio]-1,3-thiazol-4-yl}ethoxy)phenyl ester,
(60-1) 4-(2-{2-[(2-tert-butoxy-1,1-dimethyl-2-oxoethyl)thio]-1,3-thiazol-4-yl}ethoxy)benzoic acid methyl ester,
(92-1) 2-(2-{2-[(2-tert-butoxy-1,1-dimethyl-2-oxoethyl)thio]-1,3-thiazol-4-yl}ethoxy)-5-iodobenzoic acid methyl ester,
(92-2) 4-(2-{2-[(2-tert-butoxy-1,1-dimethyl-2-oxoethyl)thio]-1,3-thiazol-4-yl}ethoxy)-4'-fluoro-biphenyl-3-carboxylic acid methyl ester,
(93-2) 2-{[4-(2-{[4'-fluoro-3-(morpholin-4-ylcarbonyl)biphenyl-4-yl]oxy}ethyl)-1,3-thiazol-2-yl]thio}-2-methylpropionic acid tert-butyl ester,
(152-2) 2-methyl-2-{[4-({[4'-(trifluoromethyl)biphenyl-4-yl]methoxy}methyl)-1,3-thiazol-2-yl]thio}propionic acid tert-butyl ester,
(155-3) 2-[(4-{2-[(4'-fluorobiphenyl-4-yl)methoxy]ethyl}-1,3-thiazol-2-yl)thio]-2-methylpropionic acid ethyl ester,
(281-1) 2-[(4-{2-[(3-chloro-5-methoxycarbonylpyridin-2-yl)(heptyl)amino]ethyl}-1,3-thiazol-2-yl)thio]-2-methylpropionic acid tert-butyl ester, (437-1) 4-{[(2-{2-[(2-tert-butyl-1,1-dimethyl-2-oxoethyl)thio]-1,3-thiazol-4-yl}ethyl)(5-ethylpyrimidin-2-yl)amino]methyl}benzoic acid methyl ester, (437-3) 2-[(4-{2-[{4-[(ethylamino)carbonyl]benzyl}(5-ethylpyrimidin-2-yl)amino]ethyl}-1,3-thiazol-2-yl)thio]-2-methylpropionic acid tert-butyl ester, (439-1) 2-[(4-{2-[{4-[(tert-butoxycarbonyl)amino]benzyl}(5-ethylpyrimidin-2-yl)amino]ethyl}-1,3-thiazol-2-yl)thio]-2-methylpropionic acid tert-butyl ester, (439-3) 2-{[4-(2-{(5-ethylpyrimidin-2-yl)[4-(propionylamino)benzyl]amino}ethyl)-1,3-thiazol-2-yl]thio}-2-methylpropionic acid tert-butyl ester, (455-2) 2-methyl-2-({4-[({[4'-(trifluoromethyl)biphenyl-4-yl]carbonyl}amino)methyl]-1,3-thiazol-2-yl}thio)propionic acid tert-butyl ester, (458-2) 2-methyl-2-{[4-(2-oxo-2-{[4'-(trifluoromethyl)biphenyl-4-yl]amino}ethyl)-1,3-thiazol-2-yl]thio}propionic acid tert-butyl ester, and (733-1) 2-methyl-2-[(4-{2-[(4'-nitrobiphenyl-4-yl)oxy]ethyl}-1,3-thiazol-2-yl)thio]propionic acid tert-butyl ester, or a pharmaceutically acceptable salt thereof.

21. A carboxylic acid derivative containing a thiazole ring selected from the group consisting of:

(358) 2-({4-[2-((5-ethylpyrimidin-2-yl) {[2-(4-methylphenyl)-1,3-oxazol-4-yl]methyl}amino)ethyl]-1,3-thiazol-2-yl}thio)-2-methylpropionic acid hydrochloride, (359) 2-({4-[2-((5-ethylpyrimidin-2-yl){[2-(4-fluorophenyl)-1,3-oxazol-4-yl]methyl}amino)ethyl]-1,3-thiazol-2-yl}thio)-2-methylpropionic acid hydrochloride, (390) 2-{[4-(2-{(5-ethylpyrimidin-2-yl)[3-(4-methylphenoxy)propyl]amino}ethyl)-1,3-thiazol-2-yl]thio}-2-methylpropionic acid hydrochloride, (393) 2-[(4-{2-[[3-(4-cyanophenoxy)propyl](5-ethylpyrimidin-2-yl)-amino]ethyl}-1,3-thiazol-2-yl)thio]-2-methylpropionic acid hydrochloride, (396) 2-[(4-{2-[[3-(cyclohexyloxy)propyl](5-ethylpyrimidin-2-yl)amino]ethyl}-1,3-thiazol-2-yl)thio]-2-methylpropionic acid hydrogen bromide, (409) 2-[(4-{2-[[(4'-cyanobiphenyl-4-yl)methyl](5-ethylpyrimidin-2-yl)amino]ethyl}-1,3-thiazol-2-yl)thio]-2-methylpropionic acid hydrochloride, (410) 2-[(4-{2-[[(3'-cyanobiphenyl-4-yl)methyl](5-ethylpyrimidin-2-yl)amino]ethyl}-1,3-thiazol-2-yl)thio]-2-methylpropionic acid hydrochloride, (427) 2-({4-[((5-ethylpyrimidin-2-yl) {[2-(4-fluorophenyl)-1,3-oxazol-4-yl]methyl}amino)methyl]-1,3-thiazol-2-yl}thio)-2-methylpropionic acid hydrochloride, (439-4) 2-{[4-(2-{(5-ethylpyrimidin-2-yl)[4-(propionylamino)benzyl]amino}ethyl)-1,3-thiazol-2-yl]thio}-2-methylpropionic acid hydrochloride, and (440) 2-[(4-{2-[{4-[(cyclopentylcarbonyl)amino]benzyl}(5-ethylpyrimidin-2-yl)amino]ethyl}-1,3-thiazol-2-yl)thio]-2-methylpropionic acid hydrochloride.

22. A composition comprising a carboxylic acid derivative containing a thiazole ring of claim 1, or a pharmaceutically acceptable salt thereof, and at least one additive selected from the group consisting of a pharmacologically acceptable carrier, an excipient, and a diluent.

23. A method of treating hyperlipidemia in a subject in need thereof comprising administering to said subject an effective amount of a carboxylic acid derivative containing a thiazole ring of claim 1, or a pharmaceutically acceptable salt thereof.

24. A method of treating arteriosclerosis in a subject in need thereof comprising administering to said subject an effective amount of a carboxylic acid derivative containing a thiazole ring of claim 1, or a pharmaceutically acceptable salt thereof.

25. A method of treating ischemic cardiac disease in a subject in need thereof comprising administering to said subject an effective amount of a carboxylic acid derivative containing a thiazole ring of claim 1, or a pharmaceutically acceptable salt thereof.

\* \* \* \* \*

UNITED STATES PATENT AND TRADEMARK OFFICE
CERTIFICATE OF CORRECTION

PATENT NO. : 8,026,370 B2
APPLICATION NO. : 11/667006
DATED : September 27, 2011
INVENTOR(S) : Takashi Tozawa et al.

It is certified that error appears in the above-identified patent and that said Letters Patent is hereby corrected as shown below:

Column 442, lines 38-39, "each optionally have, and Z is represented by a substituent selected from formula (II):"

Should read --each optionally have substituent, and Z is represented by a substituent selected from formula (II):--

Column 444, lines 54-55, "(79) 2-[(4-[2-[(3,4'-difluorobiphenyl-4-yl)oxy]ethyl]-1,3-thiazol-2-yl)thio]-2-methylpropionic acid"

Should read --(79) 2-[(4-{2-[(3,4'-difluorobiphenyl-4-yl)oxy]ethyl}-1,3-thiazol-2-yl)thio]-2-methylpropionic acid--

Column 451, lines 37-39, "(393) 2-[(4-{2-[[3-(4-cyanophenoxy)propyl](5-ethylpyrimidin-2-yl)-amino]ethyl}-1,3-thiazol-2-yl)thio]-2-methylpropionic acid hydrochloride,"

Should read --(393) 2-[(4-{2-[[3-(4-cyanophenoxy)propyl](5-ethylpyrimidin-2-yl)amino]ethyl}-1,3-thiazol-2-yl)thio]-2-methylpropionic acid hydrochloride,--

Signed and Sealed this
Sixth Day of March, 2012

David J. Kappos
*Director of the United States Patent and Trademark Office*